US010266549B2

(12) United States Patent
Shaw et al.

(10) Patent No.: US 10,266,549 B2
(45) Date of Patent: Apr. 23, 2019

(54) ULK1 INHIBITORS AND METHODS USING SAME

(71) Applicants: SALK INSTITUTE FOR BIOLOGICAL STUDIES, La Jolla, CA (US); SANFORD BURNHAM PREBYS MEDICAL DISCOVERY INSTITUTE, La Jolla, CA (US); YALE UNIVERSITY, New Haven, CT (US)

(72) Inventors: Reuben J. Shaw, La Jolla, CA (US); Daniel F. Egan, La Jolla, CA (US); Nicholas Cosford, La Jolla, CA (US); Benjamin Turk, New Haven, CT (US); Mitchell Vamos, La Jolla, CA (US); Dhanya Raveendra Panickar, La Jolla, CA (US); Matthew Chun, La Jolla, CA (US); Douglas Sheffler, La Jolla, CA (US)

(73) Assignees: SALK INSTITUTE FOR BIOLOGICAL STUDIES, La Jolla, CA (US); SANFORD BURNHAM PREBYS MEDICAL DISCOVERY INSTITUTE, La Jolla, CA (US); YALE UNIVERSITY, New Haven, CT (US)

( * ) Notice: Subject to any disclaimer, the term of this patent is extended or adjusted under 35 U.S.C. 154(b) by 0 days.

(21) Appl. No.: 15/505,532

(22) PCT Filed: Aug. 25, 2015

(86) PCT No.: PCT/US2015/046777
§ 371 (c)(1),
(2) Date: Feb. 21, 2017

(87) PCT Pub. No.: WO2016/033100
PCT Pub. Date: Mar. 3, 2016

(65) Prior Publication Data

US 2017/0342088 A1 Nov. 30, 2017

Related U.S. Application Data

(60) Provisional application No. 62/041,559, filed on Aug. 25, 2014, provisional application No. 62/184,212, filed on Jun. 24, 2015.

(51) Int. Cl.

| | |
|---|---|
| ***C07D 239/42*** | (2006.01) |
| ***C07D 417/04*** | (2006.01) |
| ***A61K 31/505*** | (2006.01) |
| ***A61K 31/506*** | (2006.01) |
| ***C07D 498/04*** | (2006.01) |
| ***C07D 403/12*** | (2006.01) |
| ***C07D 401/14*** | (2006.01) |
| ***C07D 405/14*** | (2006.01) |
| ***C07D 413/14*** | (2006.01) |
| ***C07D 401/12*** | (2006.01) |
| ***C07D 405/12*** | (2006.01) |
| ***C07D 239/48*** | (2006.01) |

(Continued)

(52) U.S. Cl.
CPC .......... *C07D 498/04* (2013.01); *A61K 31/505* (2013.01); *A61K 31/506* (2013.01); *A61K 31/5377* (2013.01); *A61K 31/5383* (2013.01); *A61K 45/06* (2013.01); *C07D 239/34* (2013.01); *C07D 239/42* (2013.01); *C07D 239/47* (2013.01); *C07D 239/48* (2013.01); *C07D 239/557* (2013.01); *C07D 401/12* (2013.01); *C07D 401/14* (2013.01); *C07D 403/12* (2013.01); *C07D 405/12* (2013.01); *C07D 405/14* (2013.01); *C07D 413/14* (2013.01); *C07D 417/04* (2013.01); *C07D 417/12* (2013.01); *C07D 417/14* (2013.01); *C07D 471/04* (2013.01); *C07K 7/08* (2013.01); *C12Q 1/485* (2013.01); *C12Y 207/11001* (2013.01); *G01N 2333/912* (2013.01); *G01N 2500/04* (2013.01); *G01N 2500/20* (2013.01); *G01N 2800/52* (2013.01)

(58) Field of Classification Search
CPC .. C07D 417/04; C07D 239/42; A61K 31/505; A61K 31/506
See application file for complete search history.

(56) References Cited

U.S. PATENT DOCUMENTS 4,652,441 A 3/1987 Okada et al.
4,675,189 A 6/1987 Kent et al.

(Continued)

FOREIGN PATENT DOCUMENTS

DE 102007010801 A1 9/2008
WO WO-03078404 A1 9/2003

(Continued)

OTHER PUBLICATIONS

Egan et al. Small Molecule Inhibition of the Autophagy Kinase ULK1 and Identification of ULK1 Substrates. Mol Cell 59(2):285-297 (2015).

(Continued)

*Primary Examiner* — Zohreh A Fay
(74) *Attorney, Agent, or Firm* — Wilson Sonsini Goodrich & Rosati

(57) ABSTRACT

In certain aspects, the invention provides a method for treating a disease or condition in a subject, the method comprising co-administering to a subject in need thereof a therapeutically effective amount of at least one ULK1-inhibiting pyrimidine, and a therapeutically effective amount of an mTOR inhibitor.

20 Claims, 34 Drawing Sheets

Specification includes a Sequence Listing.

(51) Int. Cl.

| | |
|---|---|
| ***C07D 239/557*** | (2006.01) |
| ***C07D 471/04*** | (2006.01) |
| ***A61K 45/06*** | (2006.01) |
| ***A61K 31/5383*** | (2006.01) |
| ***A61K 31/5377*** | (2006.01) |
| ***C07D 239/34*** | (2006.01) |
| ***C07D 239/47*** | (2006.01) |
| ***C07D 417/12*** | (2006.01) |
| ***C07D 417/14*** | (2006.01) |
| ***C07K 7/08*** | (2006.01) |
| ***C12Q 1/48*** | (2006.01) |

(56) References Cited

U.S. PATENT DOCUMENTS

| | | | |
|---|---|---|---|
| 4,677,191 | A | 6/1987 | Tanaka et al. |
| 4,728,721 | A | 3/1988 | Yamamoto et al. |
| 4,917,893 | A | 4/1990 | Okada et al. |
| 2010/0249092 | A1 | 9/2010 | Singh et al. |
| 2012/0196870 | A1 | 8/2012 | Arbiser |
| 2013/0040310 | A1 | 2/2013 | Shaw et al. |

FOREIGN PATENT DOCUMENTS

| | | | |
|---|---|---|---|
| WO | 2005049021 | A1 | 6/2005 |
| WO | 2009083185 | A2 | 7/2009 |
| WO | 2010129622 | A1 | 11/2010 |
| WO | WO-2010146132 | A1 | 12/2010 |
| WO | 2011084108 | A1 | 7/2011 |
| WO | 2011133668 | A2 | 10/2011 |
| WO | 2012119095 | A1 | 9/2012 |
| WO | 2012120048 | A1 | 9/2012 |
| WO | 2013072392 | A1 | 5/2013 |
| WO | 2013173506 | A2 | 11/2013 |
| WO | 2014062621 | A1 | 4/2014 |
| WO | 2014071109 | A1 | 5/2014 |
| WO | 2014098932 | A1 | 6/2014 |
| WO | 2014116973 | A1 | 7/2014 |
| WO | WO-2016033100 | A1 | 3/2016 |

OTHER PUBLICATIONS

Lazarus et al. Discovery and structure of a new inhibitor scaffold of the autophagy initiating kinase ULK1. Bioorg Med Chem 23(17)5483-5488 (2015).

Berge et al. Pharmaceutical Salts. Journal of Pharmaceutical Sciences 66(1):1-19 (Jan. 1977).

Chan et al. MTORC1 phosphorylates the ULK1-mAtg13-FIP200 autophagy regulatory complex. Science Signaling 2(84):pe51 (2009).

Egan et al. Phosphorylation of ULK1 (hATG1) by AMP-activated protein kinase connects energy sensing to mitophagy. Science 331:456-461 (2011b).

Egan et al. The autophagy initiating kinase ULK1 is regulated via opposing phosphorylation by AMPK and mTOR. Autophagy 7:643-644 (2011a).

Fabian et al. A small molecule-kinase interaction map for clinical kinase inhibitors. Nature Biotechnology, 23(3): 329-336 (2005).

Fichert et al. A new strategy for the preparation of secondary amines via o-(tetrahydropyranyloxymethyl)-benzamides. Tetrahedron Letters 39:5017-5018 (1998).

Green et al. To be or not to be? How selective autophagy and cell death govern cell fate. Cell 157:65-75 (2014).

Guo et al. Activated Ras requires autophagy to maintain oxidative metabolism and tumorigenesis. Genes Dev. 25:460-470 (2011).

Guo et al. Autophagy-mediated tumor promotion. Cell 155:1216-1219 (2013).

Gwinn et al. AMPK Phosphorylation of Raptor Mediates a Metabolic Checkpoint. Molecular Cell 30(2):214-226 (2008).

Hara et al. FIP200, a ULK-interacting protein, is required for autophagosome formation in mammalian cells. J Cell Biol 181(3):497-510 (2008).

Hornbeck et al. PhosphoSite: A bioinformatics resource dedicated to physiological protein phosphorylation. Proteomics 4(6):1551-1561 (2004).

Hosokawa et al. Atg101, a novel mammalian autophagy protein interacting with Atg13. Autophagy 5:973-979 (2009).

Jaber et al. Class III PI3K Vps34 plays an essential role in autophagy and in heart and liver function. PNAS USA 109:2003-2008 (2012).

Jung et al. ULK-Atg13-FIP200 Complexes Mediate mTOR Signaling to the Autophagy Machinery. Mol Biol Cell 20(7):1992-2003 (2009).

Kang et al. mTORC1 phosphorylation sites encode their sensitivity to starvation and rapamycin. Science 341:1236566 (2013).

Karaman et al. A quantitative analysis of kinase inhibitor selectivity. Nat. Biotechnol. 26:127-132 (2008).

Kim et al. AMPK and mTOR regulate autophagy through direct phosphorylation of Ulk1. Nat. Cell Biol. 13:132-141 (2011).

Kim et al. Differential regulation of distinct Vps34 complexes by AMPK in nutrient stress and autophagy. Cell 152:290-303 (2013).

Kinoshita et al. Phosphate-binding tag, a new tool to visualize phosphorylated proteins. Mol. Cell. Proteomics 5:749-757 (2006).

Mercer et al. A novel, human Atg13 binding protein, Atg101, interacts with ULK1 and is essential for macroautophragy. Autophagy 5:649-662 (2009).

Michel et al. The effect of site of administration in the gastrointestinal tract on the absorption of insulin from nanocapsules in diabetic rats. J Pharm Pharmacol 43:1-5 (1991).

Obenauer et al. Scansite 2.0: Proteome-wide prediction of cell signaling interactions using short sequence motifs. Nucleic Acids Res. 31:3635-3641 (2003).

Papinski et al. Early steps in autophagy depend on direct phosphorylation of Atg9 by the Atg1 kinase. Mol. Cell 53:471-483 (2014).

PCT/US2015/046777 International Preliminary Report on Patentability dated Mar. 9, 2017.

Rajesh et al. Binding to syntenin-1 protein defines a new mode of ubiquitin-based interactions regulated by phos-phorylation. J Biol Chem 286:39606-39614 (2011).

Russell et al. ULK1 induces autophagy by phosphorylating Beclin-1 and activating VPS34 lipid kinase. Nat. Cell Biol. 15:741-750 (2013).

Tsukada et al. Isolation and characterization of autophagy-defective mutants of *Saccharomyces cerevisiae*. FEBS Lett. 333:169-174 (1993).

Ubersax et al. Mechanisms of specificity in protein phosphorylation. Nat Rev Mol Cell Biol 8(7):530-541 (2007).

Molhoek, K.R., et al., "Synergistic inhibition of human melanoma proliferation by combination treatment of B-Raf inhibitor BAY43-9006 and mTORinhibitor Rapamycin," Journal of Transitional Medicine, 2005, vol. 3, article 39, published Oct. 28, 2005, (online journal) [retrieved from internet Nov. 12, 2015] <URL: http://www.translational-medicine.com/content/3/1/39> figure 4.

Written Opinion of the International Searching Authority for corresponding PCT Patent Application No. PCT/US2015/046777, dated Nov. 24, 2015 (12 pages).

International Search Report for corresponding PCT Patent Application No. PCT/US2015/046777, dated Nov. 24, 2015 (12 pages).

Beclin1 with WT ULK1

Beclin1 with KI ULK1

```
Human Beclin1
Ser15      NNST QVs VCQ
Ser30      QPLK DTs KILD
Ser96      MSTESANs TLIG
Ser337     LVPYGNHs LESL
            (Y)   (G)  (P)    (R) highlighted
                                  positions
```

FIG. 5C (CON'T)
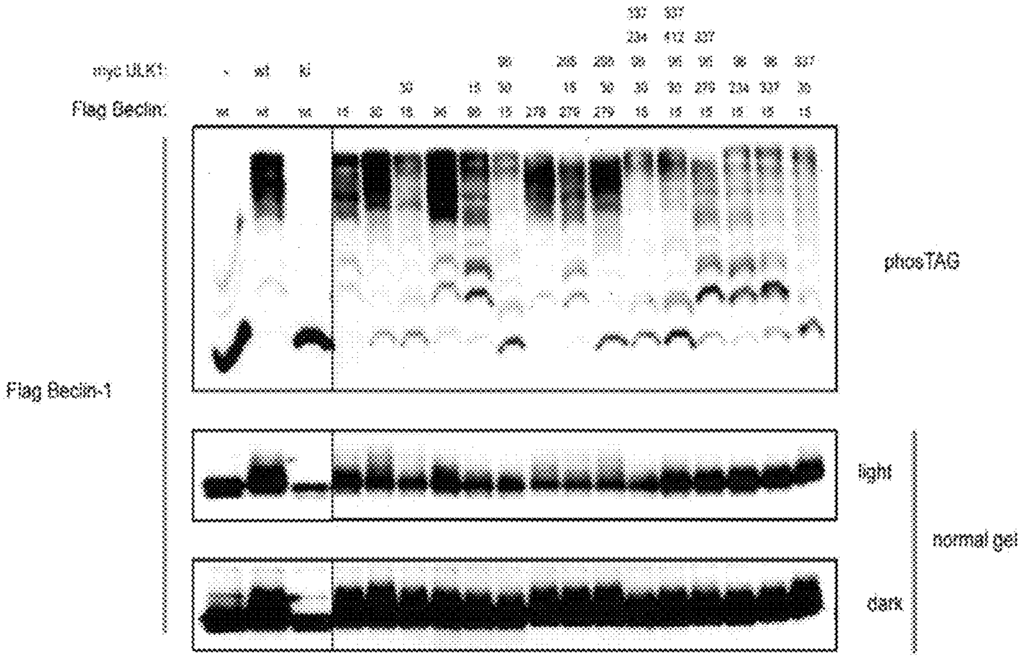

FIG. 5F

| | | |
|---|---|---|
| Ambra1 | Ser465 | SQASVYTsATEGR |
| Ambra1 | Ser635 | SSSRLELsSSASP |
| Atg13 | Ser389 | INQVTLTsIDIPF |
| Atg101 | Ser11 | RSEVLEVsVEGRQ |
| Atg101 | Ser203 | ITDALGTsVTTTM |
| Beclin1 | Ser15 | NNSTMQVsFVCQR |
| Beclin1 | Ser30 | QPLKLDTsFKILD |
| Beclin1 | Ser96 | MSTESANsFTLIG |
| Beclin1 | Ser279 | ATFHIWHsGQFGT |
| Beclin1 | Ser337 | LVPYGNHsYLESL |
| FIP200 | Ser943 | EMENIMHsQNCEI |
| FIP200 | Ser986 | ELQSLEQsHLKEL |
| FIP200 | Ser1323 | EMQNVRTsIIAEQ |
| STING | Ser366 | QEPELLIsGMEKP |
| Syntenin1 | Ser6 | __MSLYPsLEDLK |
| Syntenin1 | Ser61 | LSQYMGLsINEAE |
| VPS34 | Ser249 | ESSPILTsFELVK |

highlighted positions a b (Y)

Vps34 co-expressed with KI ULK1

Vps34 co-expressed with WT ULK1

S249

Candidate ULK1 site in VPS34

| | | |
|---|---|---|
| Human | Ser249 | S LTsFE K |
| Mouse | Ser249 | S LTsFE K |
| Xenopus | Ser249 | T STsSE R |
| Zebrafish | Ser248 | S PTsSD K |
| Apis mellifera | Ser685 | P KLsKE E |
| Drosophila | Ser843 | P KLsKE E |
| C. elegans | Ser253 | MR STsVNGGV |
| C. albicans | Ser274 | NI INsID PM |
| S. cerevisiae | Ser239 | NNPGLsTD RE |
| Arabidopsis | Thr240 | A GStNEF T |

highlighted positions  (B) (Y) (G)
                      (G)     (G)

Compound 14 (also referred to as "0296965" or "6965")

| *KINASE:* | Relative IC50 | Fold vs ULK1 |
|---|---|---|
| FAK | 4.122E-08 | 0.4 |
| c-Src | 5.674E-07 | 5.7 |
| JAK3 | 5.854E-07 | 6.0 |
| ULK1 | 1.08E-07 | 1.0 |
| ABL1 (T315I) | 2.352E-06 | 23.5 |
| BLK | 2.128E-06 | 21.3 |
| ULK2 | 7.110E-07 | 6.6 |
| FLT3 | 7.932E-08 | 0.8 |
| IRAK1 | 9.313E-07 | 9.3 |
| ERK2/MAPK1 | 8.338E-06 | 83.4 |

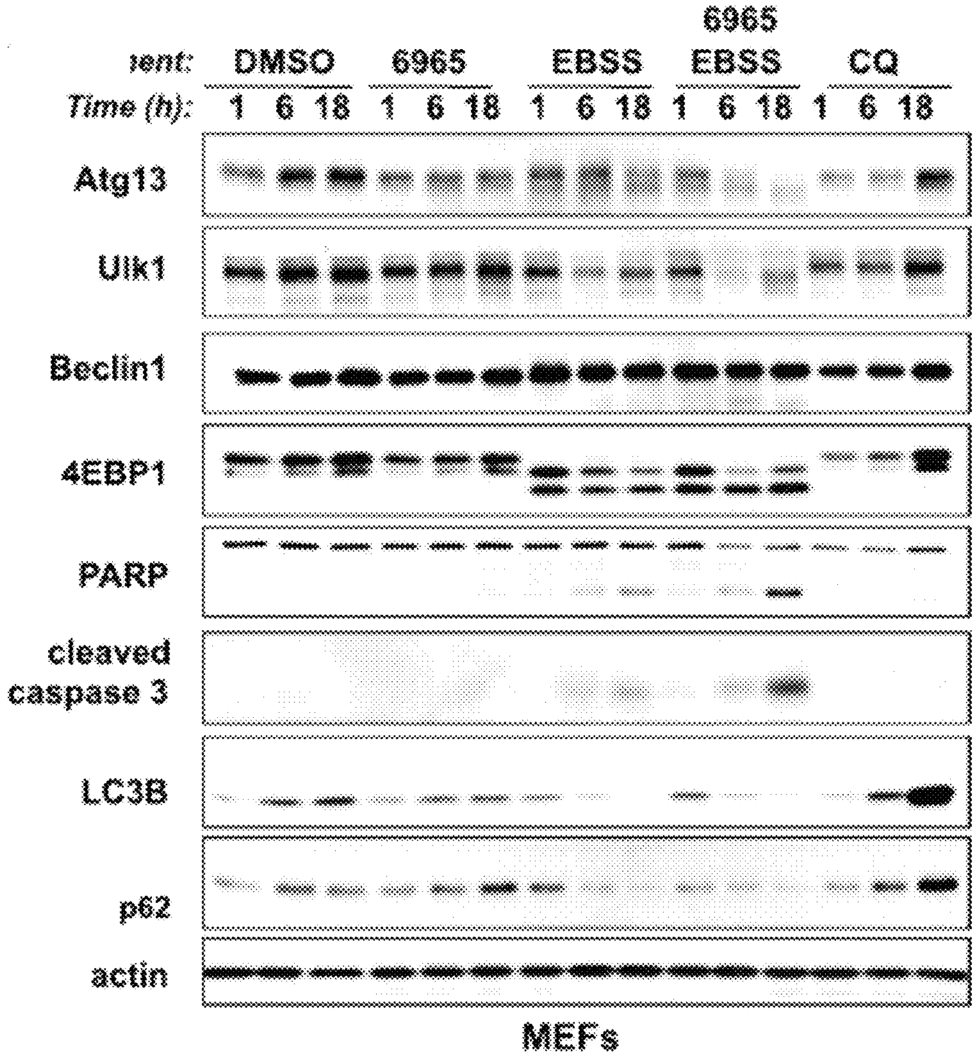
ent:
DMSO
6965
EBSS
6965 EBSS
CQ
Time (h):
1 6 18 1 6 18 1 6 18 1 6 18 1 6 18
Atg13
Ulk1
Beclin1
4EBP1
PARP
cleaved caspase 3
LC3B
p62
actin
MEFs

A549 siRNA pools

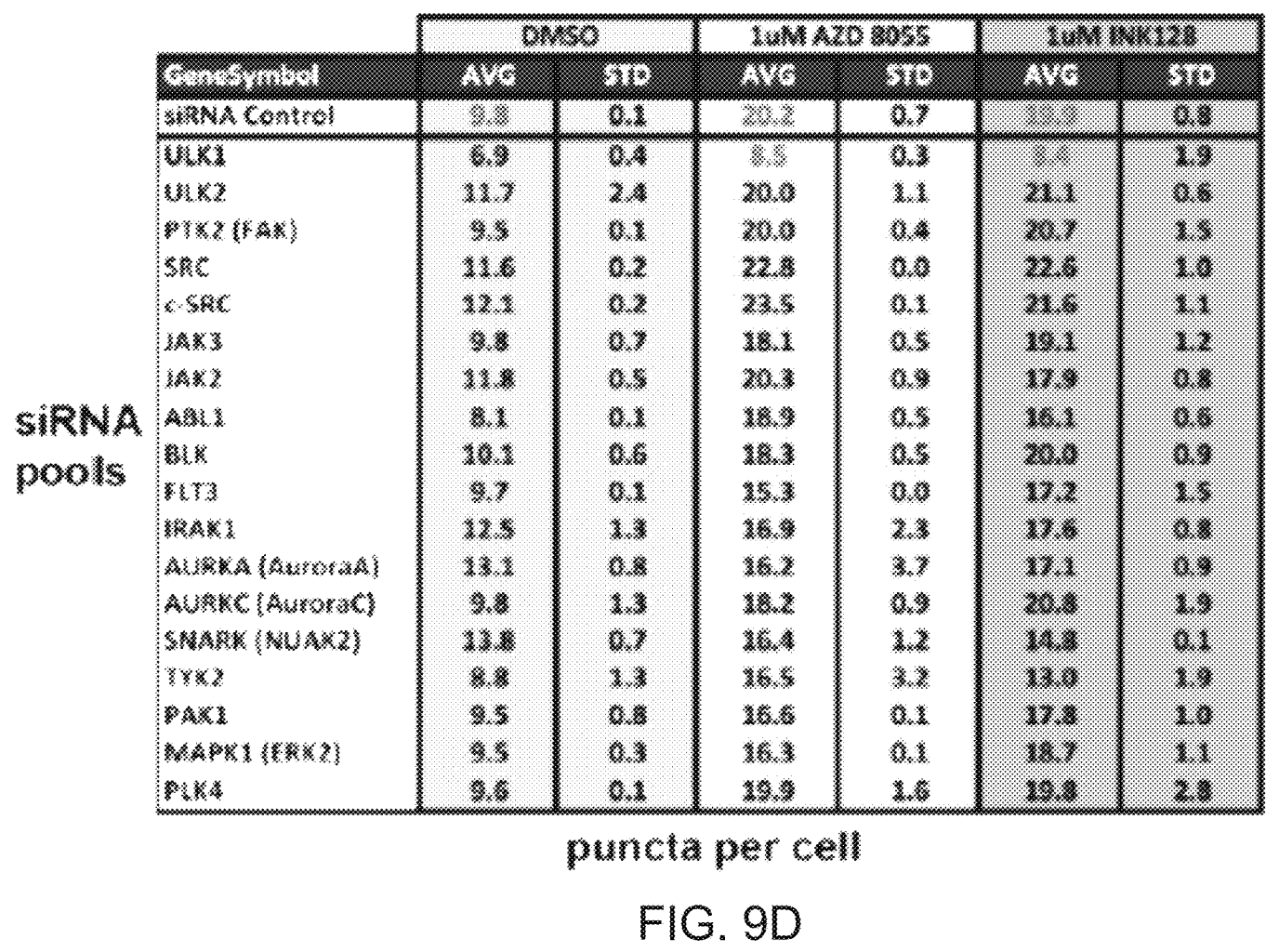

| | DMSO | | 1uM AZD 8055 | | 1uM INK128 | |
|---|---|---|---|---|---|---|
| GeneSymbol | AVG | STD | AVG | STD | AVG | STD |
| siRNA Control | 9.8 | 0.1 | 20.2 | 0.7 | [illegible] | 0.8 |
| ULK1 | 6.9 | 0.4 | 8.5 | 0.3 | [illegible] | 1.9 |
| ULK2 | 11.7 | 2.4 | 20.0 | 1.1 | 21.1 | 0.6 |
| PTK2 (FAK) | 9.5 | 0.1 | 20.0 | 0.4 | 20.7 | 1.5 |
| SRC | 11.6 | 0.2 | 22.8 | 0.0 | 22.6 | 1.0 |
| c-SRC | 12.1 | 0.2 | 23.5 | 0.1 | 21.6 | 1.1 |
| JAK3 | 9.8 | 0.7 | 18.1 | 0.5 | 19.1 | 1.2 |
| JAK2 | 11.8 | 0.5 | 20.3 | 0.9 | 17.9 | 0.8 |
| ABL1 | 8.1 | 0.1 | 18.9 | 0.5 | 16.1 | 0.6 |
| BLK | 10.1 | 0.6 | 18.3 | 0.5 | 20.0 | 0.9 |
| FLT3 | 9.7 | 0.1 | 15.3 | 0.0 | 17.2 | 1.5 |
| IRAK1 | 12.5 | 1.3 | 16.9 | 2.3 | 17.6 | 0.8 |
| AURKA (AuroraA) | 13.1 | 0.8 | 16.2 | 3.7 | 17.1 | 0.9 |
| AURKC (AuroraC) | 9.8 | 1.3 | 18.2 | 0.9 | 20.8 | 1.9 |
| SNARK (NUAK2) | 13.8 | 0.7 | 16.4 | 1.2 | 14.8 | 0.1 |
| TYK2 | 8.8 | 1.3 | 16.5 | 3.2 | 13.0 | 1.9 |
| PAK1 | 9.5 | 0.8 | 16.6 | 0.1 | 17.8 | 1.0 |
| MAPK1 (ERK2) | 9.5 | 0.3 | 16.3 | 0.1 | 18.7 | 1.1 |
| PLK4 | 9.6 | 0.1 | 19.9 | 1.6 | 19.8 | 2.8 |

puncta per cell

FIG. 9D

FIP200 with WT ULK1

*FIP200 with KI ULK1*

| Compound Name | Selectivity Score Type | Number of Hits | Number of Non-Mutant Kinases | Screening Concentration (nM) | Selectivity Score |
|---|---|---|---|---|---|
| SBI-0206965.0003 | S(35) | 49 | 397 | 1000 | 0.123 |
| SBI-0206965.0003 | S(10) | 19 | 397 | 1000 | 0.048 |
| SBI-0206965.0003 | S(1) | 4 | 397 | 1000 | 0.010 |

ULK1 INHIBITORS AND METHODS USING SAME

CROSS REFERENCE TO RELATED APPLICATIONS

This application is the U.S. national phase application, pursuant to 35 U.S.C. § 371, of PCT International Application No.: PCT/US2015/046777, filed Aug. 25, 2015, designating the United States and published in English, which claims priority under 35 U.S.C. § 119(e) to U.S. Provisional Application No. 62/041,559, filed Aug. 25, 2014 and No. 62/184,212, filed Jun. 24, 2015, all of which applications are incorporated herein by reference in their entireties.

STATEMENT REGARDING FEDERALLY SPONSORED RESEARCH OR DEVELOPMENT

This invention was made with government support under grants R01 CA172229, R01 CA188694, and R01 GM104047 awarded by the National Institutes of Health, and W81XWH-13-1-0043 awarded by the Department of Defense. The government has certain rights in the invention.

BACKGROUND OF THE INVENTION

Autophagy is a central cellular mechanism for elimination of damaged proteins, protein complexes, and organelles. This conserved process plays crucial roles in the cellular response to nutrient deprivation and other stresses, in addition to being required for proper cellular and tissue homeostasis during embryonic development and in defense against pathogens. Defects in autophagy pathways are associated with certain human pathologies, including infectious diseases, neurodegenerative disorders, and cancer. In spite of these highly conserved fundamental cellular functions, the molecular and biochemical details of how autophagy is initiated for different cargoes, and the coordination of steps starting from autophagosome initiation to ultimate fusion with the lysosome remain poorly understood.

Pioneering studies in budding yeast first defined 36 core autophagy ("ATG") genes required for this process, most of which are conserved with mammals. One of the most upstream components of the pathway in yeast is the Atg1 gene, which is notable for being the only core ATG gene to encode a serine/threonine kinase. Atg1 forms a complex with multiple regulatory subunits, including Atg13 and Atg17. In mammals, there appear to be two Atg1 homologs, ULK1 (unc-51 like kinase 1) and ULK2, which similarly bind to an Atg13 homolog and an Atg17 like protein, FIP200. The ULK1 kinase complex is activated in response to nutrient deprivation and is thought to serve as a critical initiator of starvation-induced autophagy. Whether the ULK1 complex is needed for bulk steady-state autophagy that some cell types undergo remains unclear, as well as whether certain forms of selective autophagy may also proceed without involvement of the ULK1 complex. In the context of starvation induced autophagy, ULK1 receives inputs from the cellular energy sensor AMP-activated protein kinase (AMPK), which is activated following cellular stresses that lower intracellular ATP levels, including glucose or oxygen deprivation as well as following mitochondrial insults. Another critical input to ULK1 is the mechanistic target of rapamycin complex 1 (mTORC1). Some nutrient stresses such as amino acid withdrawal do not result in acute AMPK activation, but do trigger rapid mTORC1 inactivation, thereby resulting in ULK1 activation even without the stimulatory input from AMPK. ULK1 is directly phosphorylated on at least one serine, Ser757, by mTORC1, and is phosphorylated on at least four different serines by AMPK to activate it. As most of the aforementioned stresses result in both AMPK activation and mTOR inhibition, starvation should result in an increase in phosphorylation of the AMPK sites in ULK1 and loss of the mTORC1 site. In addition, a recent study suggests that AMPK may directly phosphorylate both Beclin-1 and Vps34, the two central components of the Vps34/Beclin complex which is responsible for localized PI3P production required for autophagosome biogenesis, thus positively mediating autophagic flux. The relative requirements for AMPK phosphorylation of components of the Beclin complex versus phosphorylation the Ulk1 complex in various forms of autophagy remains to be investigated.

There is a need in the art for novel compounds that inhibit ULK1 and can be used to treat ULK1-associated diseases or disorders. The present invention addresses this need.

BRIEF SUMMARY OF THE INVENTION

As disclosed herein, the invention provides compounds and methods for treating a disease or condition in a subject, comprising co-administering to a subject in need thereof: a therapeutically effective amount of a compound, or a pharmaceutically acceptable salt thereof, having a structure of Formula A, and a therapeutically effective amount of an mTOR inhibitor.

The invention further provides a method of treating an anticancer agent-resistant disease in a subject, the method comprising selecting a subject having an anticancer agent-resistant disease, and administering to the subject a therapeutically effective amount of a compound, or a pharmaceutically acceptable salt thereof, having a structure of Formula A.

Additionally the invention provides a method of treating an autophagy-mediated disease or condition in a subject, the method comprising administering to a subject in need thereof a therapeutically effective amount of a compound, or a pharmaceutically acceptable salt thereof, having a structure of formula A, wherein the autophagy-mediated disease or condition comprises diseases or conditions arising out of mutations in the genes STK11, PTEN, TSC1, TSC2, and/or PIK3CA, or diseases or conditions indicated by an mTOR substrate biomarker Phospho-S6K or Phospho-4ebp1.

In certain embodiments, the compound of formula A is:

Formula A

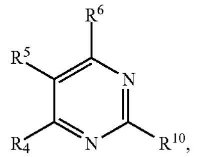

or a pharmaceutically acceptable salt thereof, wherein in Formula A: $R^{10}$ is selected from the group consisting of: halogen; —$OR^{11}$ wherein $R^{11}$ is H, optionally substituted aryl, or optionally substituted heteroaryl; —$NR^1R^2$ wherein $R^1$ and $R^2$ are each individually selected from the group consisting of H, optionally substituted aryl, optionally substituted heteroaryl, optionally substituted cycloalkyl, and optionally substituted alkyl, or $NR^1R^2$ together form a heterocycle; or $R^4$ and $R^{10}$ together form a cyclic structure;

$R^4$ is selected from the group consisting of optionally substituted amino, optionally substituted aryloxy, optionally substituted heteroaryloxy, optionally substituted alkoxy, N-heterocyclic, optionally substituted thiol, optionally substituted alkyl, hydroxyl and halogen; $R^5$ is selected from the group consisting of H, hydroxyl, optionally substituted alkyl, halo, optionally substituted alkoxy, or optionally substituted aryl, optionally substituted carboxyl, cyano, and nitro, or $R^5$ and $R^6$ together form a cyclic structure; and $R^6$ is H or haloalkyl.

The invention further provides a method of treating a disease or condition in a subject, the method comprising co-administering to a subject in need thereof: a therapeutically effective amount of a compound, or a pharmaceutically acceptable salt thereof, having a structure of Formula I, and a therapeutically effective amount of an mTOR inhibitor.

The invention further provides a method of treating a disease or condition in a subject, the method comprising co-administering to a subject in need thereof: a therapeutically effective amount of a ULK1 inhibitor selected from the group consisting of a 2-(substituted)amino-4-(substituted) amino-5-halo-pyrimidine, 2-(substituted)amino-4-(substituted)amino-5-(halo)alkyl-pyrimidine, 2-(substituted) amino-4-(substituted)oxo-5-halo-pyrimidine, 2-(substituted)amino-4-(substituted)oxo-5-(halo)alkyl-pyrimidine, 2-(substituted)amino-4-(substituted)thio-5-halo-pyrimidine, and 2-(substituted)amino-4-(substituted)thio-5-(halo)alkyl-pyrimidine; and a therapeutically effective amount of an mTOR inhibitor.

The invention further provides a method of treating an anticancer agent-resistant disease in a subject, the method comprising selecting a subject having an anticancer agent-resistant disease, and administering to the subject a therapeutically effective amount of a compound, or a pharmaceutically acceptable salt thereof, having a structure of Formula I.

The invention further provides a method of treating an autophagy-mediated disease or condition in a subject, the method comprising administering to a subject in need thereof a therapeutically effective amount of a compound, or a pharmaceutically acceptable salt thereof, having a structure of Formula I, wherein the autophagy-mediated disease or condition comprises diseases or conditions arising out of mutations in the genes STK11, PTEN, TSC1, TSC2, and/or PIK3CA, or diseases or conditions indicated by an mTOR substrate biomarker Phospho-S6K or Phospho-4ebp1.

In certain embodiments, the compound of Formula I is:

Formula I

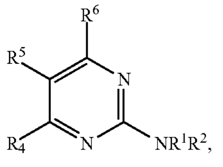

wherein in Formula I: $R^1$ and $R^2$ are each individually selected from the group consisting of H, optionally substituted aryl, optionally substituted heteroaryl, optionally substituted cycloalkyl, and optionally substituted alkyl, or $NR^1R^2$ together form a heterocycle; $R^4$ is selected from the group consisting of optionally substituted amino, optionally substituted aryloxy, optionally substituted heteroaryloxy, optionally substituted alkoxy, N-heterocyclic, optionally substituted thiol, and optionally substituted alkyl; $R^5$ is selected from the group consisting of H, hydroxyl, optionally substituted alkyl, halo, optionally substituted alkoxy, and optionally substituted aryl; and $R^6$ is H; or a pharmaceutically acceptable salt thereof.

The invention further provides a method of determining the effectiveness of an mTOR inhibitor treatment, the method comprising: performing one or more assays that detect the level of at least one of mTOR substrates Phospho-S6K and Phospho-4ebp1 in a biological sample from a subject administered an mTOR inhibitor; and comparing the level of at least one of the mTOR substrates Phospho-S6K and Phospho-4ebp1 to a respective control level found in a normal tissue.

The invention further provides compounds, or a pharmaceutically acceptable salt thereof, having a structure

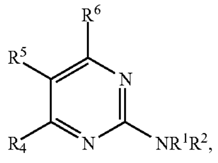

wherein: $R^1$ is H; $R^2$ is selected from the group consisting of

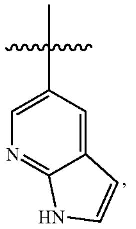
,
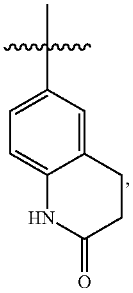
, and
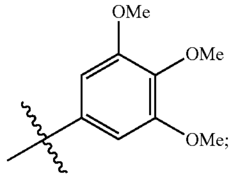
;

$R^4$ is selected from the group consisting of optionally substituted amino, optionally substituted aryloxy, optionally substituted heteroaryloxy, optionally substituted alkoxy, N-heterocyclic, optionally substituted thiol, and optionally substituted alkyl; $R^5$ is selected from the group consisting of H, hydroxy, optionally substituted alkyl, halo, optionally substituted alkoxy, and optionally substituted aryl; and $R^6$ is H.

The invention further provides compounds, or a pharmaceutically acceptable salt thereof, having a structure of

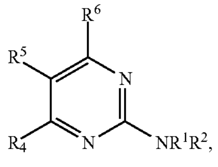

wherein: $R^1$ is H; $R^2$ is selected from the group consisting of optionally substituted aryl, optionally substituted heteroaryl, optionally substituted cycloalkyl, and optionally substituted alkyl, or $NR^1R^2$ together form a heterocycle; $R^4$ is selected from the group consisting of optionally substituted aryloxy, optionally substituted heteroaryloxy, and optionally substituted alkoxy; $R^5$ is selected from the group consisting of H, hydroxyl, optionally substituted alkyl, halo, optionally substituted alkoxy, and optionally substituted aryl; and $R^6$ is H.

The invention further provides compounds, or a pharmaceutically acceptable salt thereof, having a structure

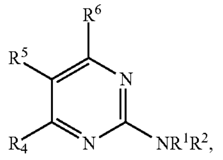

wherein: $R^1$ is H; $R^2$ is an optionally substituted heteroaryl fused ring; $R^4$ is —$NR^7R^8$, wherein $R^7$ is H and $R^8$ is an optionally substituted heteroaryl fused ring; $R^5$ is H, hydroxyl, optionally substituted alkyl, halo, optionally substituted alkoxy, or optionally substituted aryl; and $R^6$ is H.

The invention further provides compounds, or a pharmaceutically acceptable salt thereof, having a structure

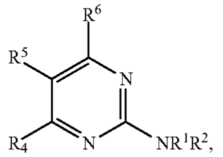

wherein $R^1$ is H; $R^2$ is selected from the group consisting of

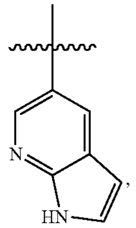, 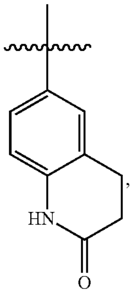, 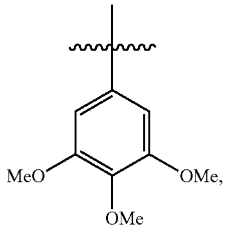

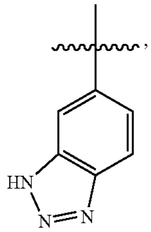, 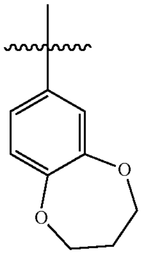, 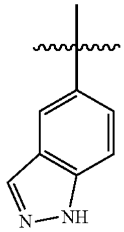, and

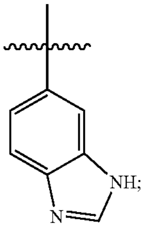

$R^4$ is selected from the group consisting of optionally substituted amino, optionally substituted aryloxy, optionally substituted heteroaryloxy, optionally substituted alkoxy, N-heterocyclic, optionally substituted thiol, and optionally substituted alkyl; $R^5$ is selected from the group consisting of H, hydroxy, optionally substituted alkyl, halo, optionally substituted alkoxy, and optionally substituted aryl; and $R^6$ is H.

The invention further provides pharmaceutical compositions, comprising:

(a) a compound, or pharmaceutically acceptable salt thereof, having a structure of Formula I:

Formula I

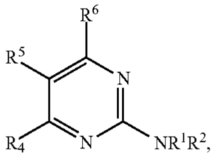

wherein in Formula I: $R^1$ and $R^2$ are each individually selected from the group consisting of H, optionally substituted aryl, optionally substituted heteroaryl, optionally substituted cycloalkyl, and optionally substituted alkyl, or $NR^1R^2$ together form a heterocycle; $R^4$ is selected from the group consisting of optionally substituted amino, optionally substituted aryloxy, optionally substituted heteroaryloxy, optionally substituted alkoxy, N-heterocyclic, optionally substituted thiol, and optionally substituted alkyl; $R^5$ is selected from the group consisting of H, hydroxyl, optionally substituted alkyl, halo, optionally substituted alkoxy, and optionally substituted aryl; and $R^6$ is H;

(b) an mTOR inhibitor; and (c) at least one pharmaceutically acceptable additive.

The invention further provides a recombinant peptide comprising the sequence YANWLAASIYLDGKKK (SEQ ID NO: 1).

The invention further provides a screening method to identify compounds that inhibit kinase activity of ULK1, the method comprising: contacting a candidate compound, ULK1 and the recombinant peptide of the invention; detecting phosphorylation of the recombinant peptide in the presence and absence of the candidate compound; and identifying a compound that inhibits kinase activity of ULK1 if phosphorylation of the recombinant peptide is decreased in the presence of the candidate compound compared to in the absence of the candidate compound.

The foregoing embodiments, and other features and advantages will be apparent from the following detailed description, which proceeds with reference to the accompanying figures.

BRIEF DESCRIPTION OF THE DRAWINGS

FIG. 2A is a series of images illustrating IP-kinase assays using GST-Atg101 as a substrate.

FIG. 2B is a series of images illustrating endogenous LC3 puncta formation.

FIG. 2C is a series of images illustrating autophagic flux and regulation of p62 and LC3 processing.

FIG. 2D is a series of images illustrating TEM quantification of mitochondrial content.

FIG. 2E is a series of images illustrating effects on apoptosis detected by AnnexinV FACS. ULK1/2 or Atg5 RNAi increase cells death under conditions of nutrient deprivation.

FIG. 3A is a scheme illustrating the hypothesis wherein newly identified ULK1 substrate sites increase after treatment of TSC cells and TSC patients with mTOR inhibitors and can be tested as markers of efficacy of mTOR inhibition.

FIG. 3B is a scheme illustrating the hypothesis wherein ULK1 inhibition combined with mTOR inhibitor converts cytostatic response into cytotoxic response.

FIGS. 5A-5F illustrate identification of novel ULK1-dependent phosphorylation sites in vivo.

FIG. 5A: Myc-tagged WT ULK1 (WT ULK1; top) or Myc-tagged kinase-inactive ULK1 (KI ULK1; bottom) was transfected into HEK293T cells along with WT Flag-tagged Atg101 (Flag-Atg101) and immunoprecipitated with M2 agarose. The immunoprecipitate was run out on an SDS-PAGE gel and stained with coomassie, and the band corresponding to Flag-Atg101 was cut out, isolated, and subjected to tryptic digest and LC/MS/MS analysis. The phosphorylated sites that conform to the optimal ULK1 phosphorylation motif that were identified by this analysis are boxed. Green bars, indicated as (G), indicate peptide coverage, and purple, indicated as (P), highlights indicate phosphorylation events. (Y)=yellow.

FIG. 5B: WT ULK1 or KI ULK1 was transfected into HEK293T cells along with Flag-Atg101 or Flag-Atg101 serine-to-alanine point mutants. The specific mutants used in this analysis are indicated by the position(s) of the substituted amino acid (top). Cellular lysates were isolated 24-hr post-transfection, run out on an SDS-PAGE gel containing the Phos-Tag reagent (middle) or a standard SDS-PAGE gel lacking the Phos-Tag reagent (bottom), and transferred to PVDF membranes, which were subsequently immunoblotted with the indicated antibodies.

FIG. 5C: Same as FIG. 5A except using WT Flag-tagged Beclin1 as a substrate. (Y)=yellow; (G)=green; (P)=purple; (B)=blue; (R)=red.

FIG. 5D: Same as FIG. 5A except using WT Flag-tagged Ambra1 as a substrate. (B)=blue; (P)=purple.

FIG. 5E: Same as FIG. 5B except using WT Flag-tagged Syntenin-1 (Flag-Syntenin-1) or Flag-tagged Syntenin-1 serine-to-alanine point mutants. The specific mutants used in this analysis are indicated by the position(s) of the substituted amino acid (top). Cellular lysates were isolated 24-hr post-transfection, run out on an SDS-PAGE gel containing the Phos-Tag reagent (middle) or a standard SDS-PAGE gel lacking the Phos-Tag reagent (bottom), and transferred to PVDF membranes, which were subsequently immunoblotted with the indicated antibodies. (B)=blue; (Y)=yellow; (G)=green; (R)=red.

FIG. 5F: Alignment of all novel ULK1 phosphorylation sites identified in this analysis, alongside the STING phosphorylation site, which is a ULK1 site. Phosphorylation sites that contain residues conforming to the optimal ULK1 phosphorylation motif at the −3 (green), +1 (green), and +2 (yellow) positions are highlighted. For position a: (G) for all highlighted positions except (B) for Atg13 (Ser389), Beclin1 (Ser96), Beclin1 (ser337). For position b: (G) for Atg13 (Ser389), Atg101 (ser11), Atg101 (Ser203), FIP200 (Ser1323), Syntenin 1 (ser 6), Syntenin1 (Ser61), and (P) for the remaining highlighted positions. (G)=green; (P)=purple.

FIG. 6A: Either Myc-tagged WT ULK1 (WT ULK1; right) or Myc-tagged kinase-inactive ULK1 (KI ULK1; left) was transfected into HEK293T cells along with WT Flag-tagged Vps34 (WT Vps34) and immunoprecipitated with M2 agarose. The immunoprecipitate was run out on an SDS-PAGE gel and stained with coomassie, and the band corresponding to WT Vps34 was cut out, isolated, and subjected to tryptic digest and LC/MS/MS analysis. Green bars indicate peptide coverage, and purple highlights indicate phosphorylation events. Arrow indicates serine 249.

FIG. 6B: Clustal alignment of Vps34 serine 249 across species shows that it is conserved throughout evolution and conforms to the optimal ULK1 phosphorylation motif. (B)=blue; (G)=green; (Y)=yellow.

FIG. 6C: An in vitro kinase assay was performed using Flag-tagged WT Vps34 (Vps34 WT) or a Flag-tagged serine-to-alanine point mutant Vps34 (Vps34 S249A) as substrates for either WT ULK1 or KI ULK1. The in vitro kinase assay was performed in the presence of radiolabeled γ-$^{32}$P-ATP (top). Vps34 WT, Vps34 S249A, WT ULK1, and KI ULK1 were produced in HEK293T cells (bottom).

FIG. 6D: Vps34 WT or Vps34 S249A and WT ULK1 or KI ULK1 were transfected into HEK293T cells. Cellular lysates were isolated 24-hr posttransfection, run out on an SDS-PAGE gel, and transferred to PVDF membranes, which were subsequently probed with the indicated antibodies. Arrow indicates a mobility shift representative of phosphorylation that only occurs with the Vps34 WT and WT ULK1 combination.

FIG. 6E: HEK293T cells were transfected with Vps34 WT or Vps34 S249A and WT ULK1, WT Myc-tagged ULK2 (ULK2), or WT Myc-tagged ULK3 (ULK3). Cellular lysates were isolated 24-hr post-transfection and immunoblotted with the indicated antibodies.

FIG. 6F shows a comparison of the phosphor-Ser249 Vps34 antibody to a commercial available phospho-Ser15 Beclin antibody, demonstrating parallel induction of each site when wild-type but not kinase ULK1 was co-expressed in HEK293T cells. (P)=purple; (G)=green; (Y)=yellow; (R)=red.

FIG. 7A: The $IC_{50}$ value for compound 14 against WT ULK1 and ULK2 was determined using an in vitro kinase assay ($IC_{50}$ of 107 nM for ULK1 and 711 nM for ULK2). WT ULK1 (left) and WT ULK2 (right) were assayed using 10-μM MBP in the presence of 30-μM radiolabeled γ-$^{32}$P-ATP. Compound 14 was tested in triplicate in a ten-dose $IC_{50}$ mode with 3-fold serial dilution and a starting dose of 1 μM.

FIG. 7B: Human embryonic kidney cells (HEK293T) were transfected with WT or kinase inactive (KI) Myc-tagged ULK1 and WT Flag-tagged Vps34 (WT Vps34). At 24-hr post-transfection, cells were treated with a panel of putative ULK1 competitive inhibitors in a dose-response manner (1, 10, 50 μM). Cellular lysates were isolated after 1 hr of treatment and immunoblotted with the indicated antibodies. Representative results for compound 14 are shown.

FIG. 7C: HEK293T cells were transfected with WT or KI ULK1 and WT Vps34 (left) or WT Flag-tagged Beclin1 (WT Beclin1; right). At 24-hr post-transfection, cells were treated with compound 14 (10 μM) or DMSO. Cellular lysates were isolated after 1 hr of treatment and immunoblotted with the indicated antibodies.

FIG. 7D: WT or Ulk1/Ulk2 double knockout mouse embryonic fibroblasts (MEFs) were treated with fresh media (Dulbecco's modified Eagle medium [DMEM] containing 10% FBS) containing 1-μM INK128, 1-μM AZD8055, or DMSO or with starvation media (EBSS) in the presence or absence of 10 μM compound 14. Cellular lysates were isolated after 1 hr of treatment and immunoblotted with the indicated antibodies. Asterisk denotes non-specific band.

FIG. 7E: (top) The kinase selectivity profile for compound 14 was determined using the DiscoveRx KINOMEscan profiling service. Briefly, compound 14 was screened at a 1-μM dose for its ability to impair binding of a panel of 456 kinases to substrate in an in vitro binding assay. Scores for the primary screen hits are reported as a percent of the DMSO control (% Control). Lower scores reflect stronger inhibitory effects of compound 14 on the target kinase. Compound 14 was very selective, only inhibiting 8 kinases >95% and 19 kinases >90% when tested at 10 μM. (bottom) In vitro kinase assays were performed for selected kinases. These assays were performed in the presence of compound 14 in a dose-response manner to identify the $IC_{50}$ value for compound 14 for each of these individual kinases. Kinases which $IC_{50}$ value was less than 1-fold difference than ULK1 are highlighted in yellow. Of the remaining kinases, those kinases which IC50 value was less than what was identified from ULK2 are highlighted in brown.

FIG. 7F: A TREEspot interaction map was generated to visually represent the selectivity profile for compound 14 against the panel of kinases tested in 5 A. Kinases whose binding was inhibited by compound 14 are marked with red circles, with larger circles indicating stronger inhibitory effects. Kinases tested in this analysis are arrayed according to their phylogenetic groupings in the human kinome.

FIG. 8B is a set of images that show that an immunoblot timecourse analysis of amino-acid starved cells revealed that active cleaved caspase-3 and the cleavage of its target PARP was observed only appreciably in starved, compound 14 co-treated cells, which was paralleled by apoptotic markers by immunocytochemistry (FIG. 8C).

FIG. 9D is a table that shows that RNAi to ULK1 completely ablated the ability of AZD8055 to induce LC3 puncta, whereas RNAi to FAK, Src, AuroraA or JAK3 had no effect. PC3 human prostate cells that stably express a construct encoding LC3 fused to green fluorescent protein (GFP-LC3) were transfected with siRNAs against the top 18 kinases whose binding was shown to be inhibited by compound 14. At 48 hr after RNAi transfection, the cells were treated with 1 μM of the catalytic mTOR inhibitors AZD8055 or INK128 for 4 hr and assessed for the presence of GFP-LC3 puncta. The average number of GFPLC3 puncta and SD for each siRNA and drug treatment are shown. SRC, c-Src; c-Src kinase, CSK.

DETAILED DESCRIPTION OF THE INVENTION

Autophagy is a cellular response to loss of nutrients in which cells catabolize various proteins and organelles to provide building blocks and critical metabolites needed for cell survival. In addition, autophagy plays a critical homeostatic role in many tissues by removing protein aggregates and defective organelles that accumulate with cellular damage over time. While genetics first defined the core components of autophagy conserved across all eukaryotes, the molecular details of how the different autophagy complexes regulate one another and the precise temporal and spatial ordering of biochemical events involved in autophagy induction are poorly understood currently.

Much progress has been made in decoding the molecular function of the TSC1-TSC2 complex, which is encoded by genes inactivated in tumors and lesions in patients with Tuberous Sclerosis Complex. The TSC tumor suppressor proteins are central regulators of cell growth through effects on a kinase complex composed of the mammalian-target of rapamycin (mTOR) kinase and its regulatory subunit Raptor and other components (mTORC1). The TSC complex receives signals from a variety of cellular inputs including from the NF1, PTEN, and LKB1 tumor suppressors, and in response, the TSC complex downregulates mTORC1.

Patients inheriting or acquiring mutations in the TSC1 or TSC2 gene exhibit elevated mTORC1 activity, which drives cellular overgrowth. LKB1 tumor suppressor and its downstream target, the AMP-activated Protein Kinase (AMPK), directly regulate the phosphorylation of the TSC2 tumor suppressor and Raptor to downregulate mTORC1 activity under conditions when intracellular energy is low, such as following nutrient deprivation.

The best-studied output of mTORC1 activity is control of cell growth, which is achieved by mTORC1 phosphorylation of downstream substrates including the translation regulators 6K1 and 4ebp1. While the role of mTORC1 in cell growth is widely appreciated, more recently a conserved role for mTORC1 in the cellular process of autophagy has become appreciated. Genetic studies first defined the genes involved in autophagy and the most upstream complex controlling the initiation of autophagy is composed of kinase ATG1 in budding yeast (ULK1 in mammals), whose activity is stimulated when nutrients are low.

Figure 1:
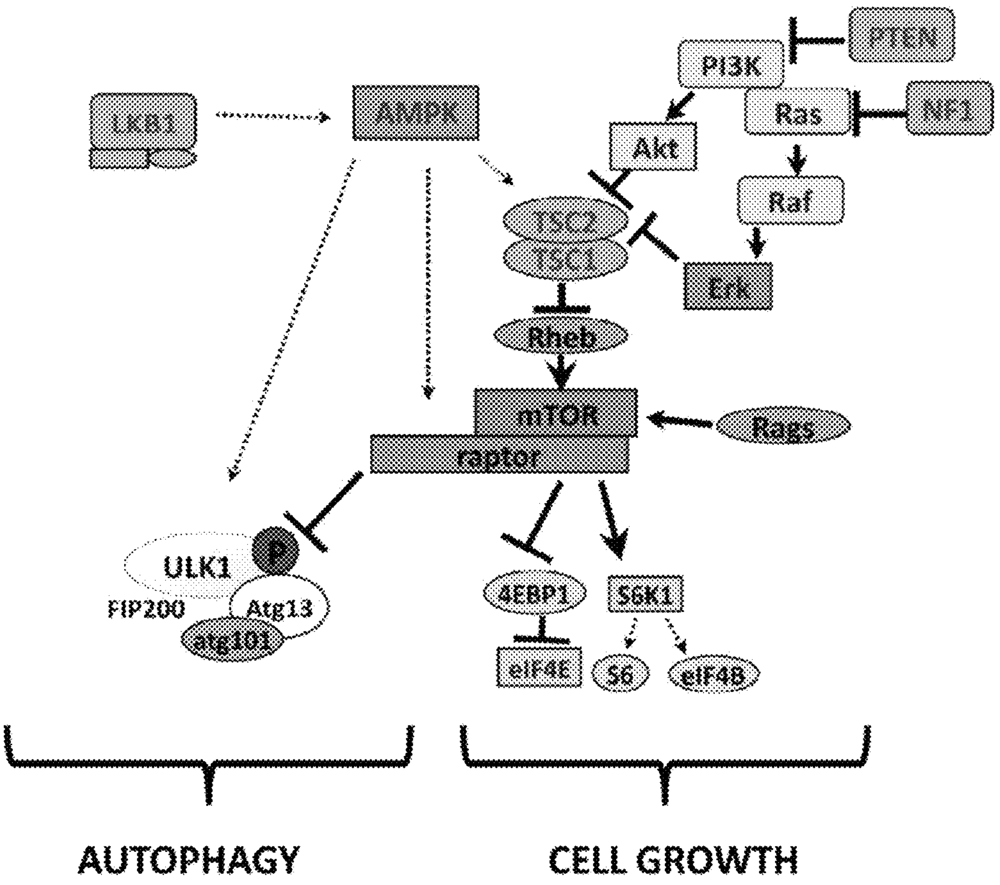
FIG. 1 is an exemplary scheme illustrating that signals from various tumor suppressors and oncogenes converge on the TSC1-TSC2 complex and onto the mTOR-raptor (mTORC1) complex to control cell growth and autophagy through the substrates shown therein.
Figure 2A:
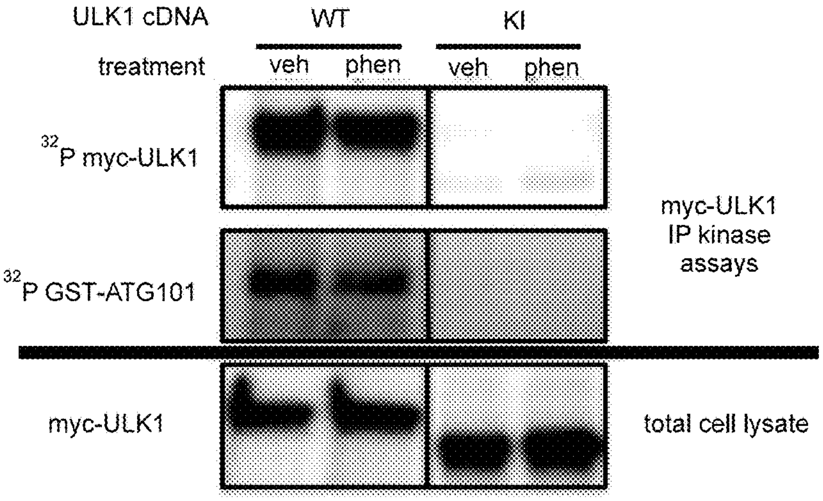
FIGS. 2A-2E illustrate assays developed for analyzing ULK1 function.
Figure 2B:
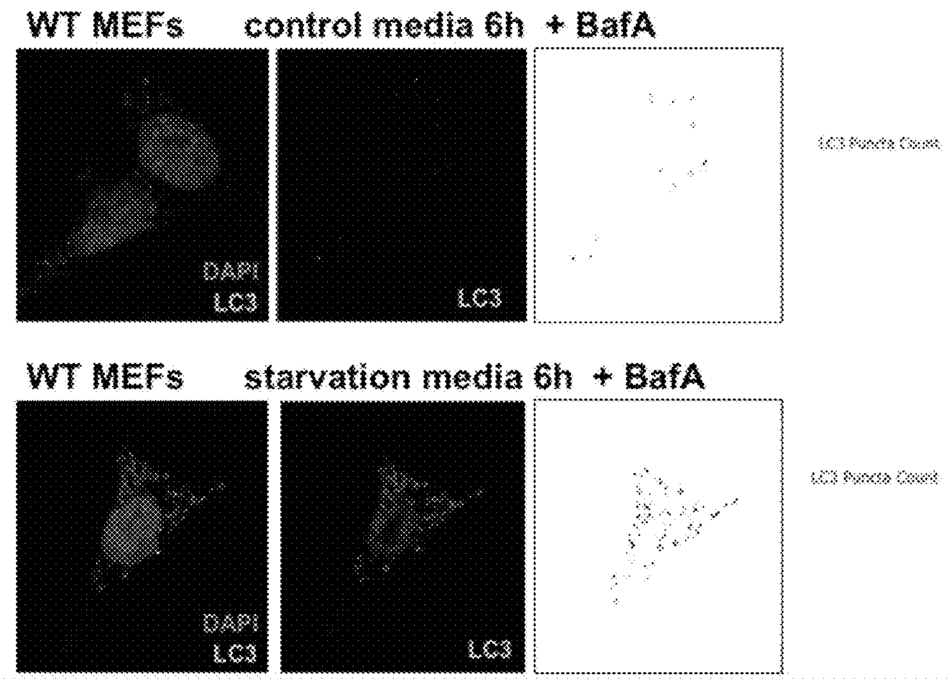
Figure 2C:
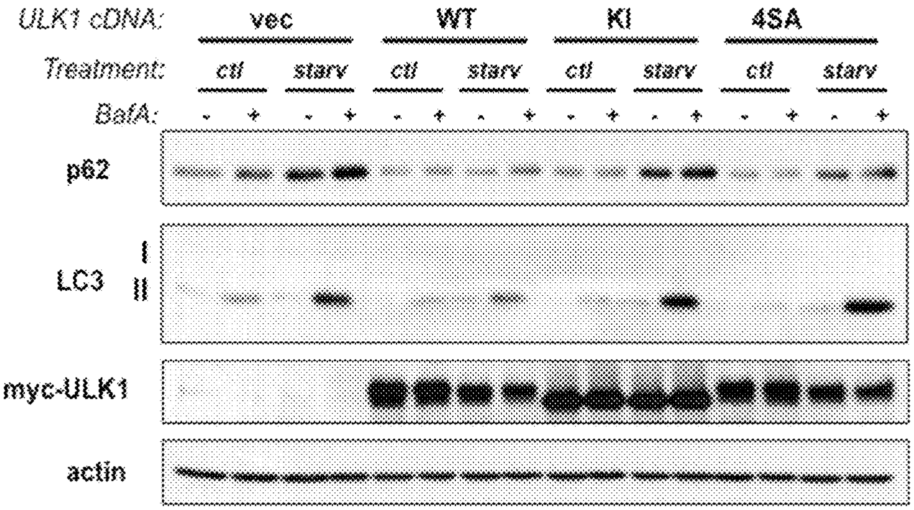
Figure 2D:
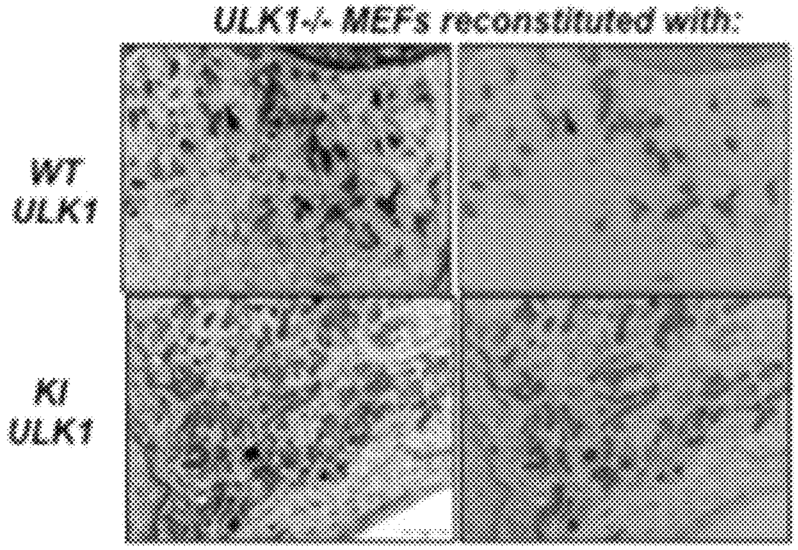
Figure 2E:
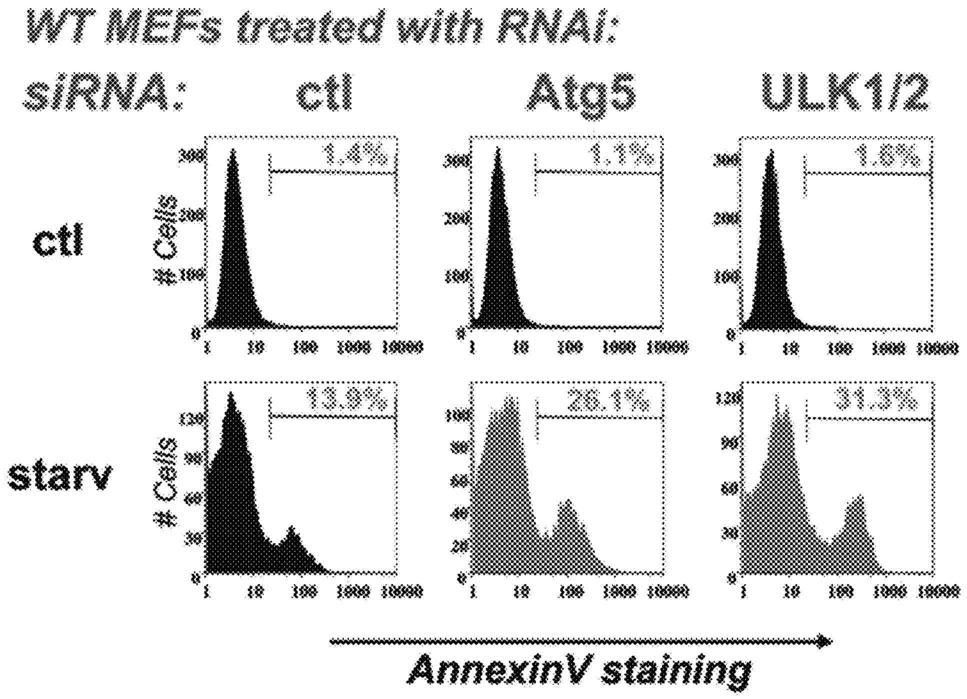

ULK1 is directly phosphorylated on several residues by AMPK, which activates ULK1 (Ser467, Ser555, Thr575, Ser638). In contrast, direct phosphorylation of ULK1 by mTORC1 on a distinct site (Ser757) results in ULK1 inactivation (FIG. 1), consistent with studies demonstrating that mTORC1 inhibits the ULK1 complex in mammalian cells, paralleling how TOR inhibits Ulk1/Atg1 orthologs in lower eukaryotes. Without wishing to be limited by any theory, in cells and tumors with TSC mutations and hyperactive mTORC1, ULK1 may be highly phosphorylated on Serine 757 by mTORC1 and held in the inactive state. In certain embodiments, in TSC-deficient cells, the process of autophagy is suppressed. While AMPK phosphorylation of ULK1 is required for proper autophagy following starvation, the induction of autophagy by treatment of cells with mTOR inhibitors does not require AMPK, but does require ULK1 and mTOR regulation of ULK1. This indicates that pharmacological mTOR inhibition is sufficient to activate ULK1 and that ULK1 is in fact activated following treatment with mTOR inhibitors even though AMPK is not on.

These findings have important implications for the origin and treatment of TSC. Restoration of ULK1 function and ULK1-dependent autophagy may have significant benefits on different pathologies involved in TSC. Accordingly, mTOR inhibitor treatment of TSC-deficient cells and tumors results in upregulation of ULK1 activity and autophagy. While autophagy is generally beneficial, in the context of treating tumors it is a double-edged sword that also promotes cell survival. ULK1 and other core autophagy components promote cell survival under conditions of cellular stress (FIG. 2). This cell biological prediction (treatment with mTOR inhibitors curtails cell growth but also promotes cell survival of the treated cells due to elevated autophagy) is consistent with recent clinical observations. While rapalogs exhibit some efficacy against specific clinical manifestations of TSC, the effect of the drugs appears transient, as upon withdrawal tumors rapidly return to their pre-treatment size. This suggests that these agents are largely cytostatic, and while causing regression and shrinkage of tumor cells, do not lead to death and elimination of the tumor cells.

Given that mTOR inhibition is directly regulating ULK1, the induction of autophagy and cell survival by rapalogs and other mTOR inhibitors may be in part due to ULK1 activation. One result is that combining inhibition of ULK1 with rapalog treatment converts the standard cytostatic effect of rapamycin into a cytotoxic effect once the survival benefit from ULK1-autophagy is removed. This result is demonstrated in cell culture using ULK1 siRNA and newly developed direct ULK1 kinase inhibitors described herein. Inhibition of ULK1 in the context of treatment with mTOR inhibitors in fact led to dramatic increases in cell death of tumor cells, converting a more cytostatic response from mTOR inhibitors to into cell death. In certain embodiments, catalytic inhibitors of ULK1 are clinically useful in the treatment of TSC.

ULK1 is the only core conserved component of the autophagy pathway which is a serine/threonine kinase, making it a particularly unique target of opportunity for development of compounds to control autophagy and more specifically, mTOR-dependent autophagy. Equally importantly for a clinical therapeutic index for agents inhibiting ULK1, mice genetically engineered to completely lack ULK1 are viable without significant pathology.

Thus, a ULK1 selective kinase inhibitor can be well-tolerated by normal tissues, but not by tumor cells that have become reliant on autophagy for survival in the face of therapeutic enforcement of autophagy induction.

While the entire process of autophagy promotes cell survival, currently the best-established agents to pharmacologically inhibit autophagy are lysotropic agents such as chloroquine or bafilomycin. Indeed, chloroquine has anti-tumoral activity when combined with targeted therapeutics and rin the context of TSC-deficiency. However, extended exposure to such agents that alter lysosome flux in all tissues may have more clinical complications than potentially observed with a ULK1 selective kinase inhibitor, making ULK1 inhibition an extremely selective and particularly attractive target for TSC tumor where mTOR activation is central to the pathology.

Given that the most upstream component of the conserved autophagy cascade encodes the only serine/threonine kinase in the cascade, ULK1-dependent phosphorylation of other components of the pathway may instruct and provide proper temporal and spatial cues. While a detailed understanding of how ULK1 is controlled by opposing phosphorylation events by AMPK and mTORC1 has become appreciated, the absolute requirement for ULK1/2 in different forms of mammalian autophagy has become less clear given recent findings that AMPK and mTOR also regulate multiple components of the downstream Beclin-Vps34 complex which directly initiates the PI3P lipid formation which incorporates into the omegasome and is held to represent a direct physical initiation of autophagosomes.

The induction of ULK1 kinase activity following catalytic mTORC1 inhibition alone (FIG. 7D) is consistent with amino acid deprivation induction of ULK1 kinase activity, which does not appear to involve AMPK. mTORC1 phosphorylates and inhibits ULK1 via at least one well-established serine site in ULK1, Ser757. mTOR inhibitors are being widely testing in clinical trials for oncology, and rapamycin analogs are the approved standard of care for advanced kidney cancer and other solid tumors. Given that ULK1 is a kinase inhibited by mTORC1, further delineation of ULK1 substrate phosphorylation sites may yield important biomarkers for mTOR inhibitors as their signal will increase under the exact conditions when mTORC1-substrates phosphorylation is decreasing.

Figure 9A:
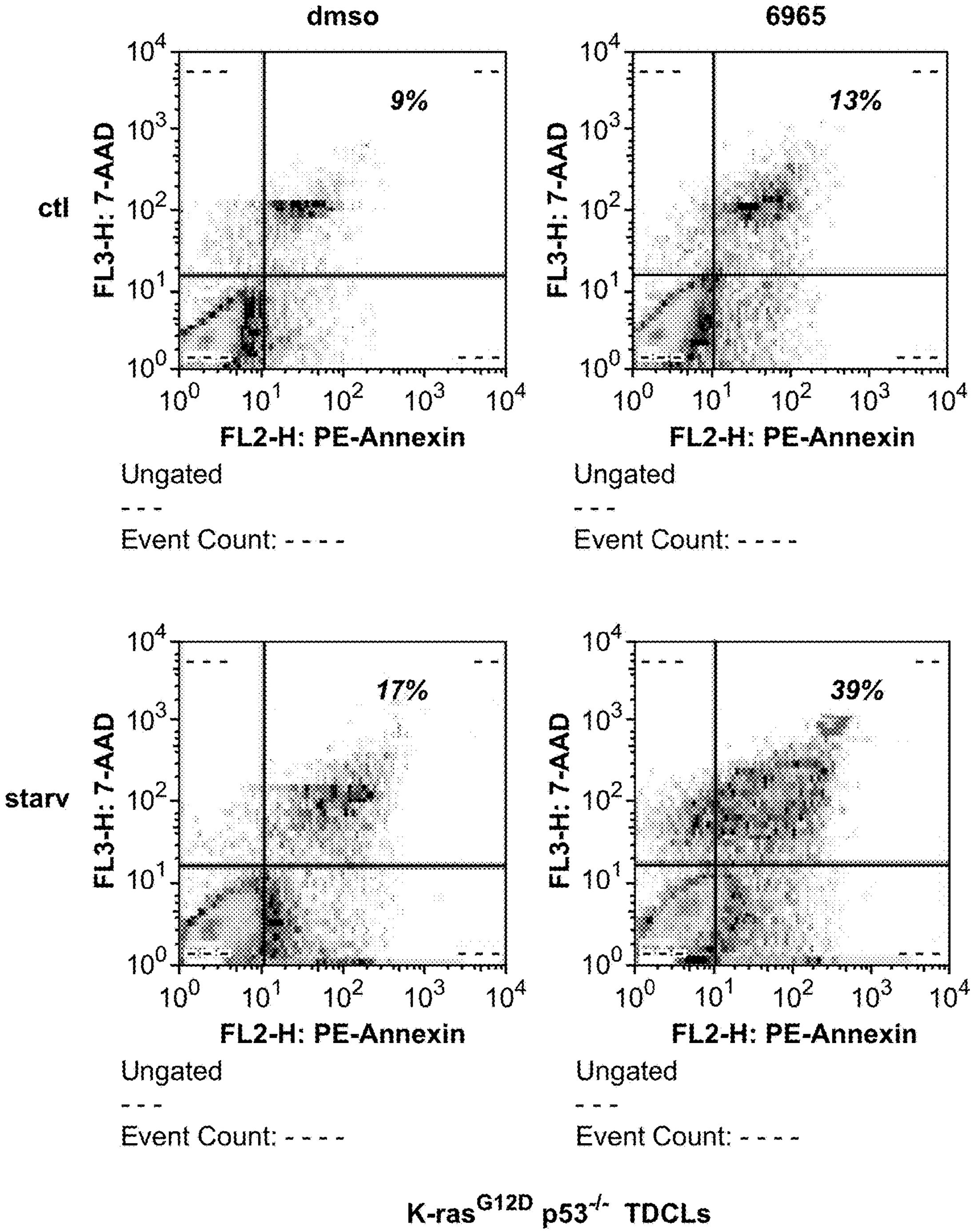
FIG. 9A is a set of images that show that in U87MG glioblastoma cells and murine Kras p53 lung carcinoma cells, compound 14 promoted apoptosis (AnnexinV+ cells) selectively in the nutrient-starved state.
Figure 9B:
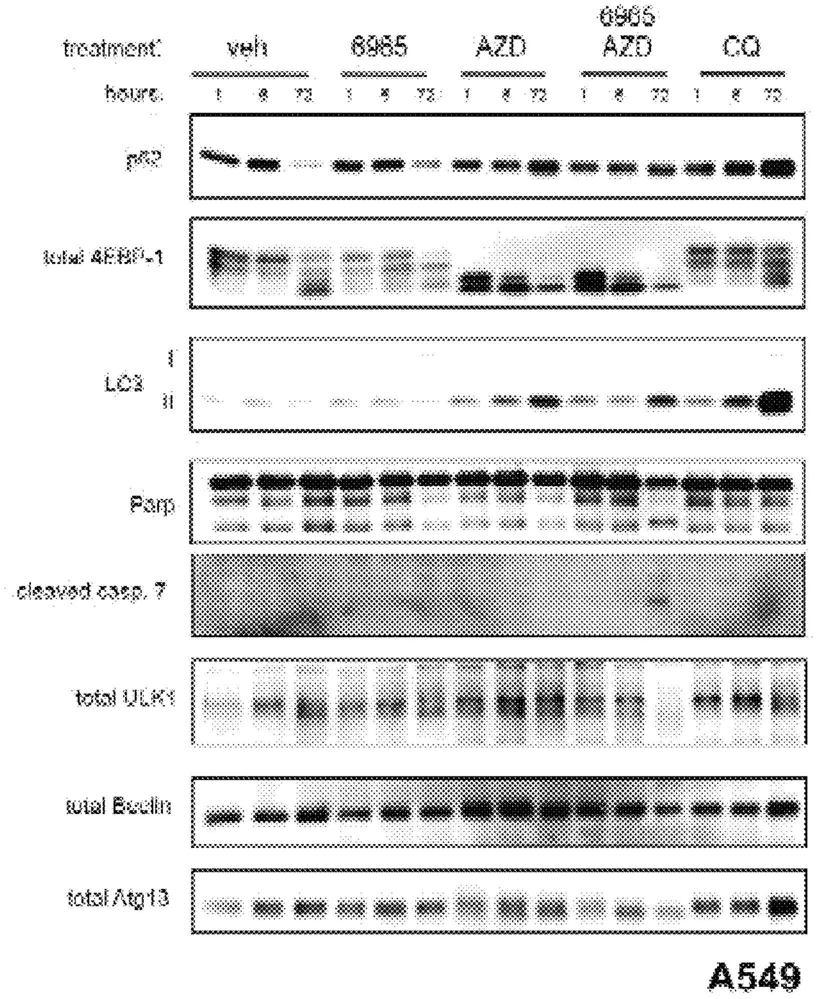
FIG. 9B is a set of images that show that, as observed in MEFs with nutrient deprivation combined with the ULK1 inhibitor, immunoblot analysis revealed that only the combination of ULK1 and mTOR inhibitors triggered caspase activation in A549 cells, paralleling the FACS analysis of cell death.
Figure 9C:
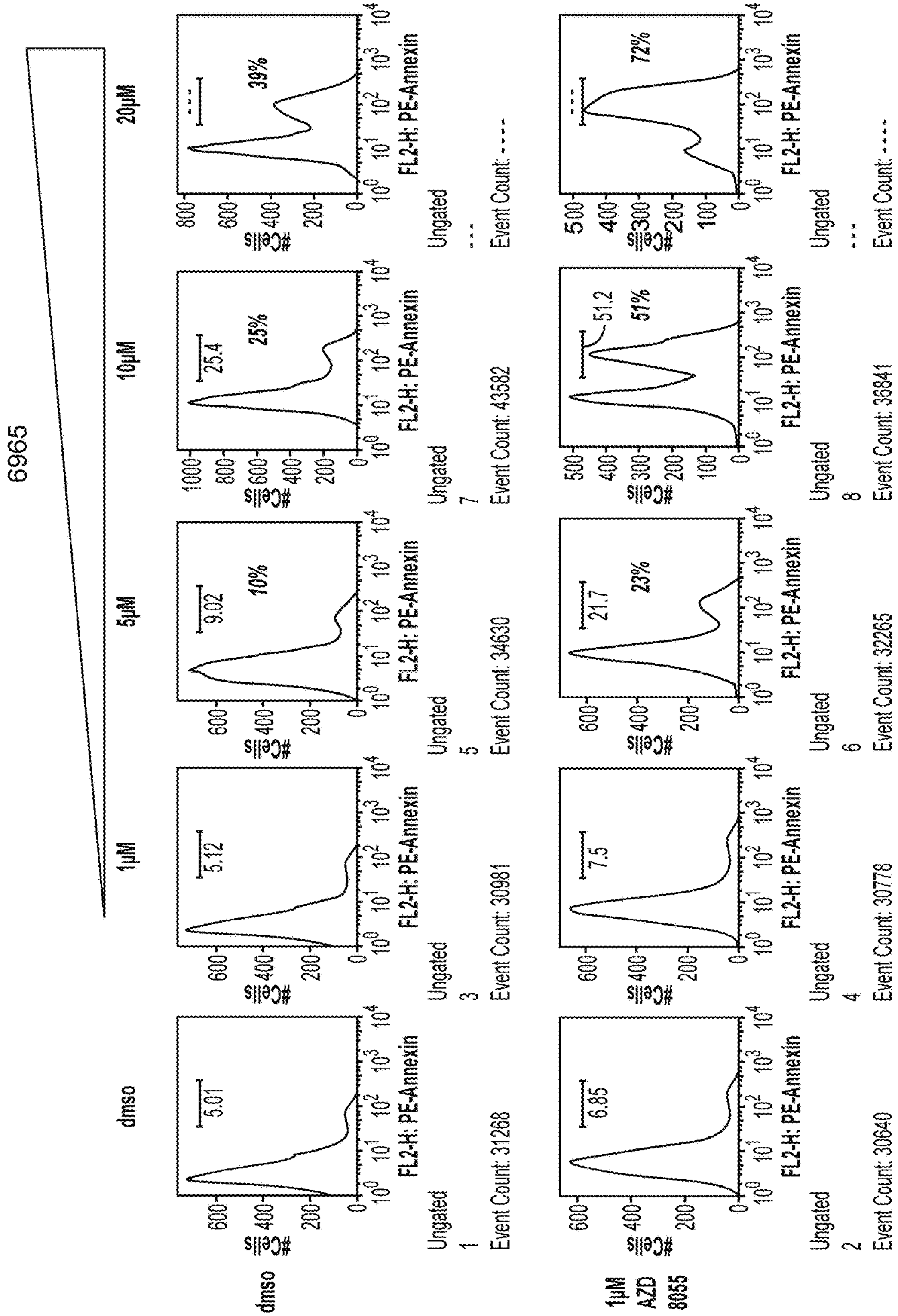
FIG. 9C is a set of images that show that the induction of Annexin-V+ apoptotic A549 cells was even more dramatically heightened at 10 or 20 μM dosing of compound 14.

Moreover, autophagy provides a survival signal to cells faced with mTORC1 inhibition and this effect may greatly rely on ULK1 as the primary mechanism by which mTORC1 suppresses autophagy, unlike board nutrient loss which may engage the autophagy pathways via ULK1-dependent and ULK1-independent means (including direct phosphorylation of Beclin-Vps34 complexes by stress kinases like AMPK and p38, and so forth). ULK1 inhibition converts the cytostatic response to mTOR inhibition to a cytotoxic response due to loss of ability of autophagy to promote cell survival, as demonstrated in A549 NSCLC cells (FIG. 9C).

Despite the flurry of studies identifying molecular details of how nutrients regulate ULK1 via opposing effects from mTORC1 and AMPK, the critical targets of the ULK1 kinase complex in the initiation of autophagy remain largely unknown. In spite of a lack of molecular details of how ULK1 mediates initiation of autophagy, genetic disruption of ULK1, similar to genetic disruption of any core autophagy gene results in loss of cell viability under nutrient-poor conditions. The ability of autophagy to promote cell survival following a variety of cellular stresses has led to the direct examination of autophagy inhibitors for the treatment of cancer. To date, however, potent and selective autophagy inhibitors have remained elusive as most of the core autophagy proteins are not druggable enzymes. As ULK1 is the only conserved serine/threonine kinase in the autophagy pathway, disclosed herein are the first small molecule ATP-competitive kinase inhibitors to ULK1. Described herein is the ability of these compounds to ameliorate cell survival following different stresses, including therapeutic treatment of cancer cells.

The fact that ULK1 is the only conserved serine/threonine kinase in the autophagy cascade makes it a very unique and attractive target for therapeutic development. The finding disclosed herein that compound 14 potently synergizes with nutrient deprivation to trigger cell death in tumor cells, yet has minimal effects on cells growing in full media, corroborates findings with genetic loss of ULK1/2. The finding that ULK1 and its binding partner Atg13 are selectively degraded by co-treatment of starvation and compound 14, but not following either alone, indicates that the active pool of the ULK1 kinase complex may be uniquely sensitive to compound 14-induced degradation. This provides additional biomarkers for ULK1 inhibition in vivo, as it suggests that when cells rely on ULK1 for survival, their ULK1 will be degraded when effectively inhibited by on-target ATP-competitive inhibitors. In certain embodiments, total ULK1 or total Atg13 levels can serve as a biomarker for effective targeting and suppression of ULK1 in contexts where it is turned on to act as a survival promoting mechanism.

Collectively the data indicate that chemical suppression of ULK1 leads to a block in the ability of mTOR inhibitors to induce autophagy, which triggers rapid apoptosis in tumor cells addicted to mTOR signaling, such as tumors lacking Pten, LKB1, TSC1, TSC2, or NF1 or bearing oncogenic mutations in Kras, Rheb, p110a or other components of the Pi3K-mTOR pathway. As mTOR kinase inhibitors or rapalogs are in widespread clinical oncology trials, the data suggest that combining ULK1 inhibitors like compound 14 with mTOR inhibitors converts their largely cytostatic effects observed in the clinic into more cytotoxic effects, making ULK1 inhibition an exciting new therapeutic route to avoid therapeutic resistance in the many patients treated with mTOR inhibitors.

Also disclosed herein is a new set of biochemical signals that are deranged in cells altered in TSC patients. The signals form a circuit called the ULK1 signal, which is normally active in cells of our body to provide a quality control mechanism to ensure the health and recycling of cellular parts. In cells defective in the TSC genes such as found in the lesions, tubers, and tumors of TSC patients, this ULK1 signal is blocked due to elevations in the activity of a protein complex called mTORC1, which is the major thing the TSC genes serve to do in cells: shut off mTORC1. So when TSC genes are defective, mTORC1 activity is high and it shuts off ULK1. This results in a loss of cellular quality control and recycling, which contributes to the aberrant growth and cellular behavior of TSC-deficient cells. These new findings make a number of predictions for better ways to treat and diagnose TSC, from the current use of mTOR inhibitors to their combination with ULK1 inhibitors, and using markers of ULK1 activity to determine when and where mTOR is getting effectively shut off in TSC patients during therapy.

The best available treatments for TSC currently are drugs that can suppress the elevated mTOR found in these patients' cells, such as the drug rapamycin and its analogs (called "rapalogs"). Treatment with rapalogs and newer direct mTOR inhibiting drugs will lead to an activation of ULK1 once its blockage by mTOR is relieved. This means that markers of ULK1 activity may be able to be used in biopsies and blood samples from TSC-patients to determine how well the mTOR blockade from rapalogs or other mTOR-inhibitors are, as the signal from ULK1 will go "up" proportional to how much mTOR goes down.

Disclosed herein are markers that increase when mTOR is being effectively blocked from therapy. All the current markers are all lowered when mTOR is blocked, but it may be easier to quantify a signal that is low in the starting state and then increased with treatment, proportional to how effective treatment is. For the therapeutic combination of ULK1 and mTOR inhibitors, the benefit can be far more durable and lasting responses, meaning complete eradication of the tumor cells or restored function to TSC-deficient cell types that are not tumorous (e.g. brain tubers), without patients needing to keep rapamycin for the rest of their lives.

Figure 5A:
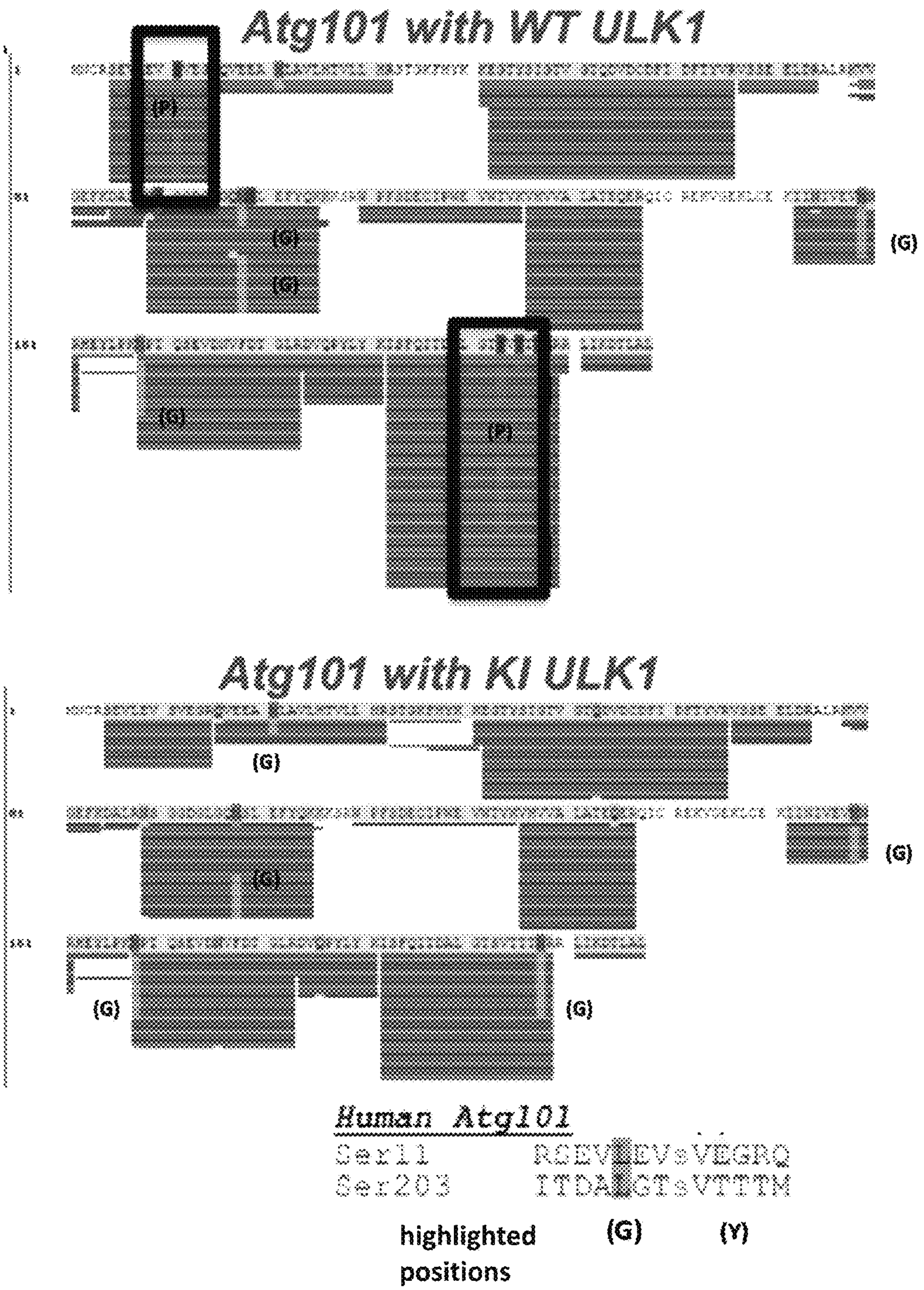
Figure 5B:
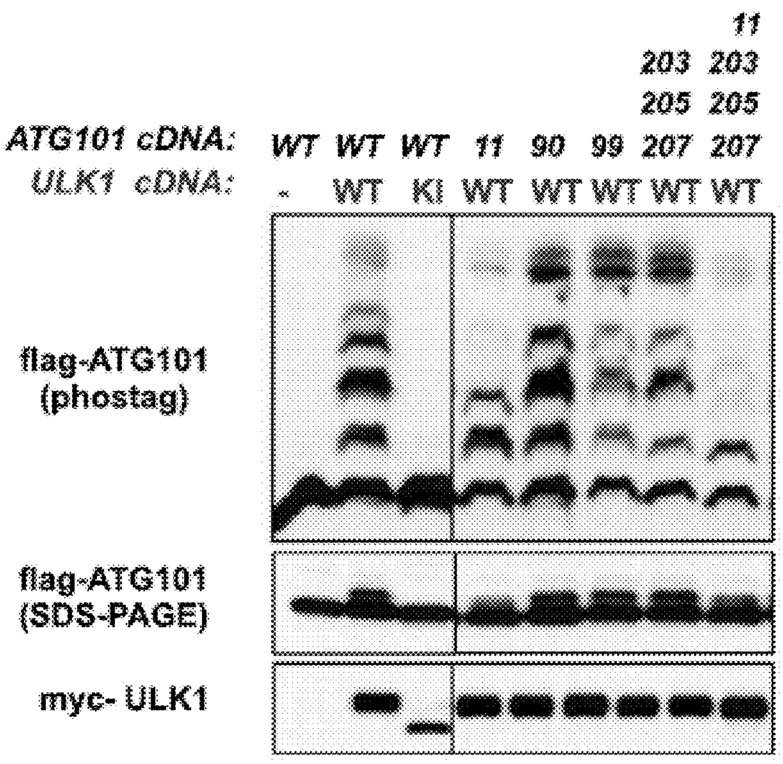
Figure 5C:
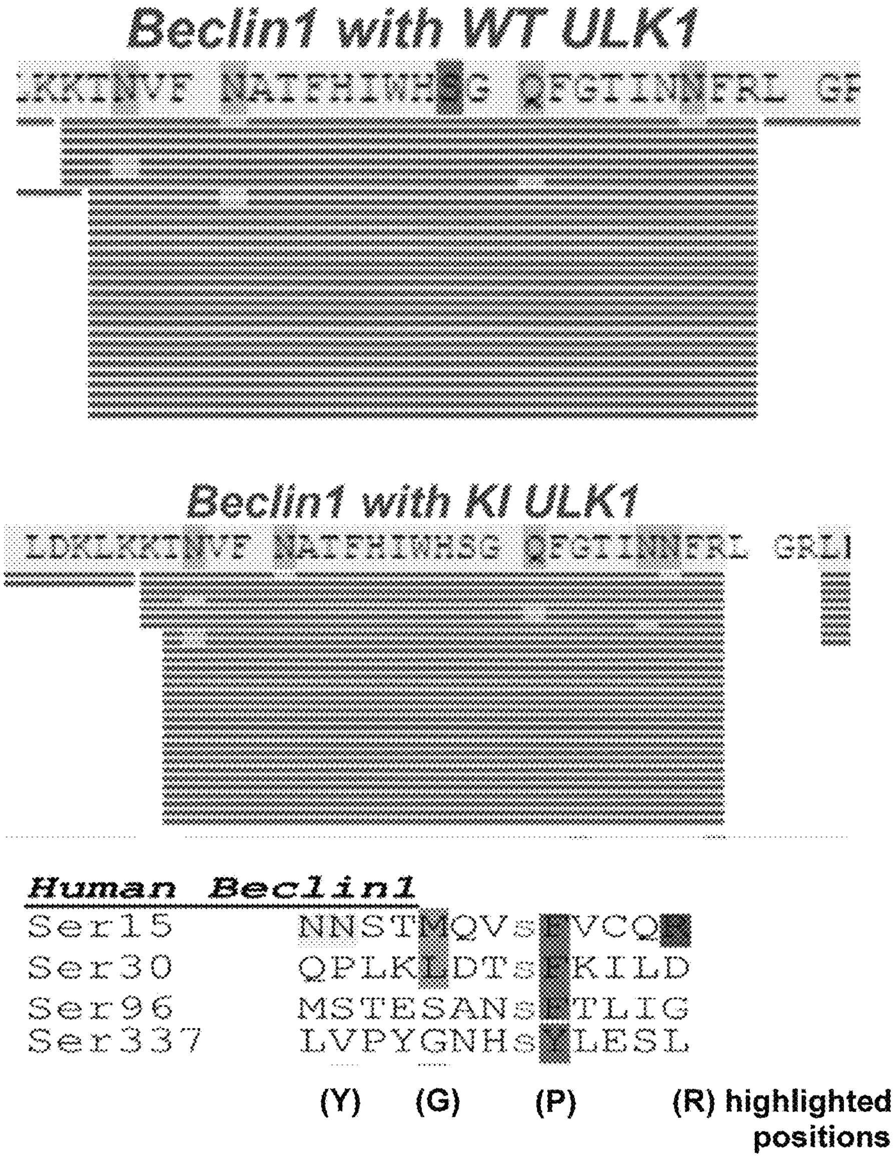
Figure 5D:
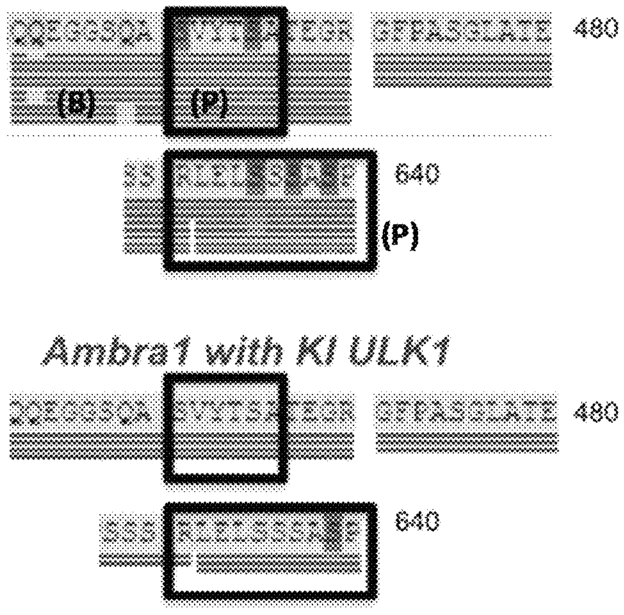
Figure 5E:
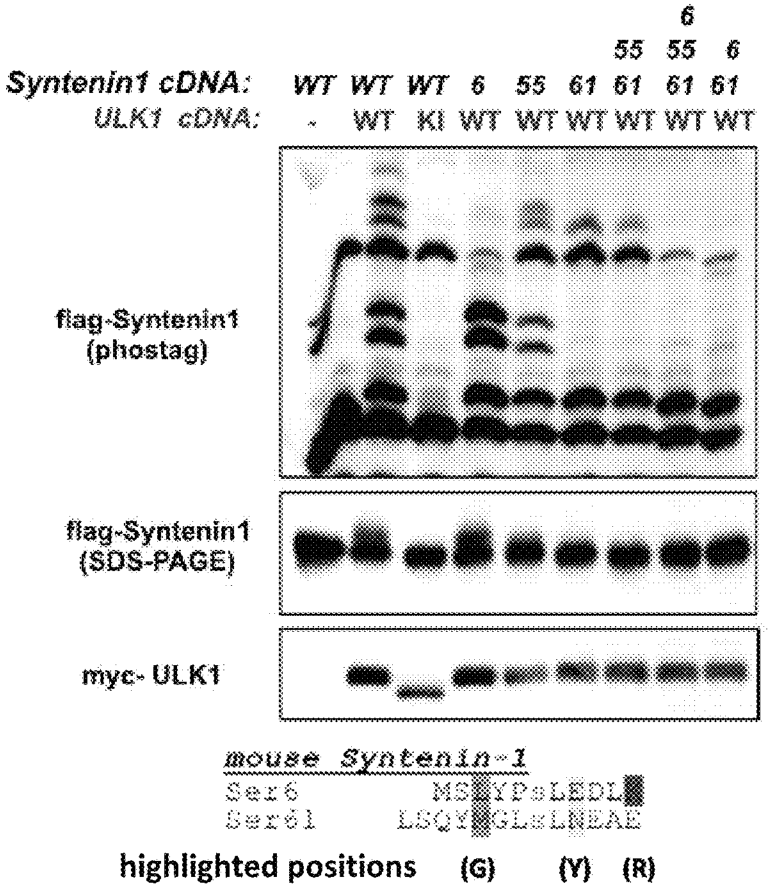

In the process of decoding how ULK1 is regulated by phosphorylation, a number of assays of ULK1 function have been developed. First, ULK1 antibodies capable of immunoprecipitating endogenous ULK1 were characterized, allowing for performing kinase activity assays on ULK1 isolated in this fashion from cells (FIG. 5A). The regulation of autophagy and autophagic flux in different cell types when ULK1 function is perturbed has also been characterized. The best established markers and assays on which the effects of ULK1-deficiency have been characterized are the autophagosome component LC3b, which forms aggregated puncta upon autophagy induction and which undergoes a covalent lipidation and processing when it localizes into mature autophagosomes. Thus one can monitor endogenous LC3b lipidation by immunoblotting and puncta formation by indirect immunoflourescence on endogenous LC3b and puncta quantification using morphometric software and NIH Image J (FIGS. 5C, 5E). A commercial lipophilic dye to autophagosomes (CytoID autophagy, Enzo Lifesciences) has been validated as being a reliable readout of autophagosomes (FIG. 10). Another widely used marker of autophagy is the p62 Sequestrosome-1 protein, whose turnover is selectively induced by autophagy. Thus under conditions of pharmacological or genetic blockage of autophagy, p62 levels are elevated (FIG. 5C). One of the cellular organelles critically dependent on autophagy for selective removal upon damage is the mitochondria. The autophagic destruction of damaged mitochondria is known as mitophagy, and defects in mitophagy are characterized by the accumulation of mitochondria defective in appearance by Transmission Electron Microscopy (TEM) and in mitochondrial membrane potential as assayed by the molecular dye JC-1.

Another cellular process controlled by ULK1 under conditions of cell stress is cell survival. Suppression of ULK function by RNAi results in elevated rates of apoptosis in cells subjected to nutrient deprivation.

Figure 6A:
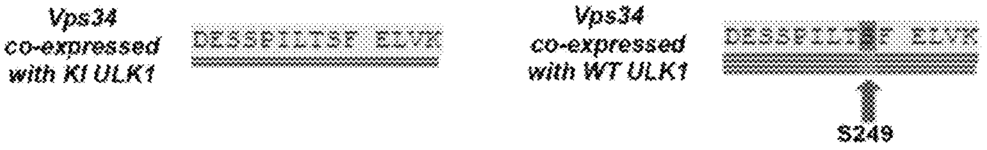
FIGS. 6A-6F illustrate the finding that Vps34 Ser249 is a novel ULK1 phosphorylation site in vivo.
Figure 6B:
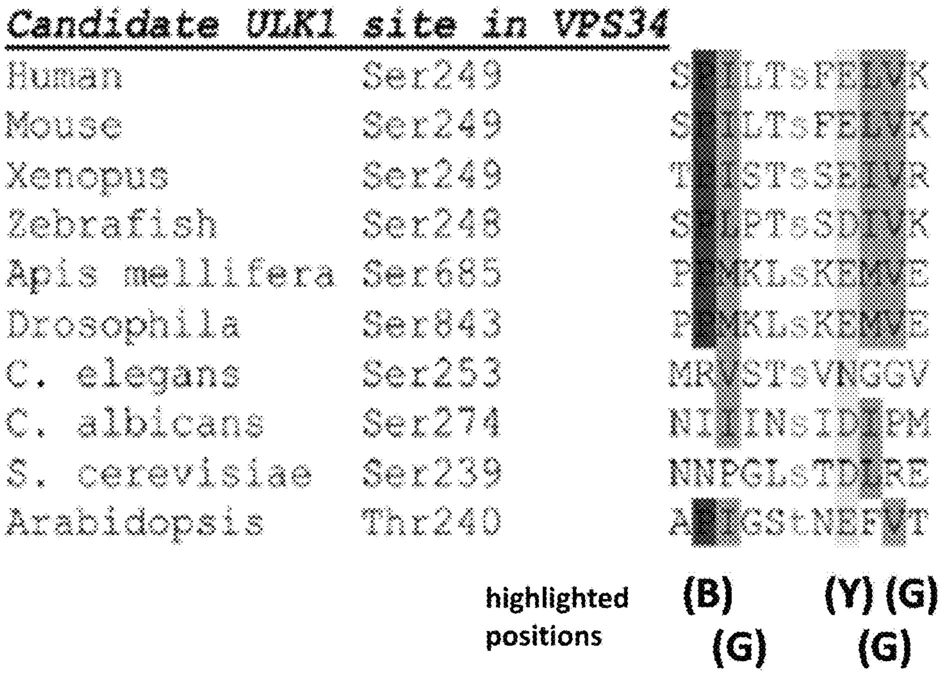
Figure 6C:
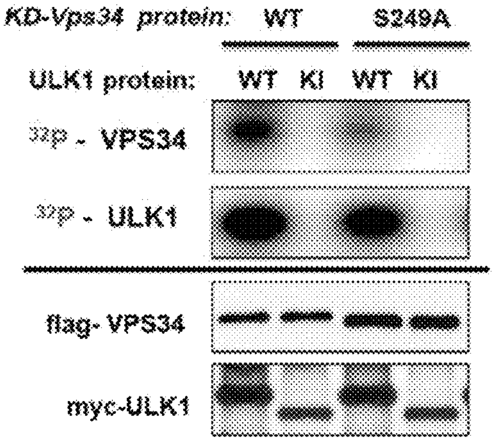
Figure 6D:
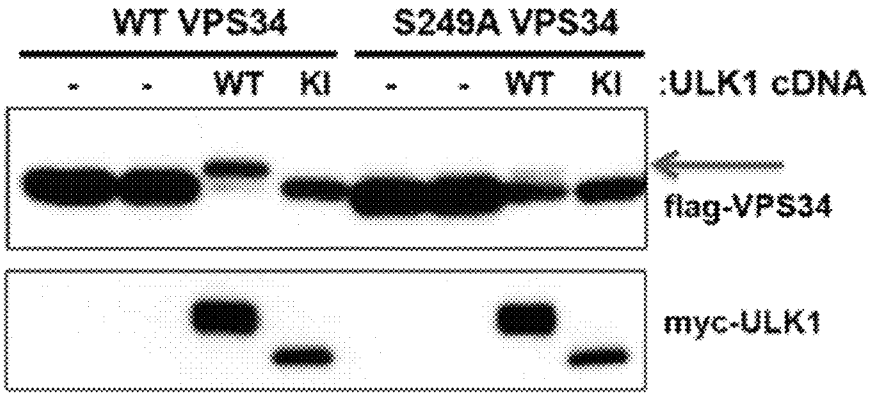
Figure 6E:
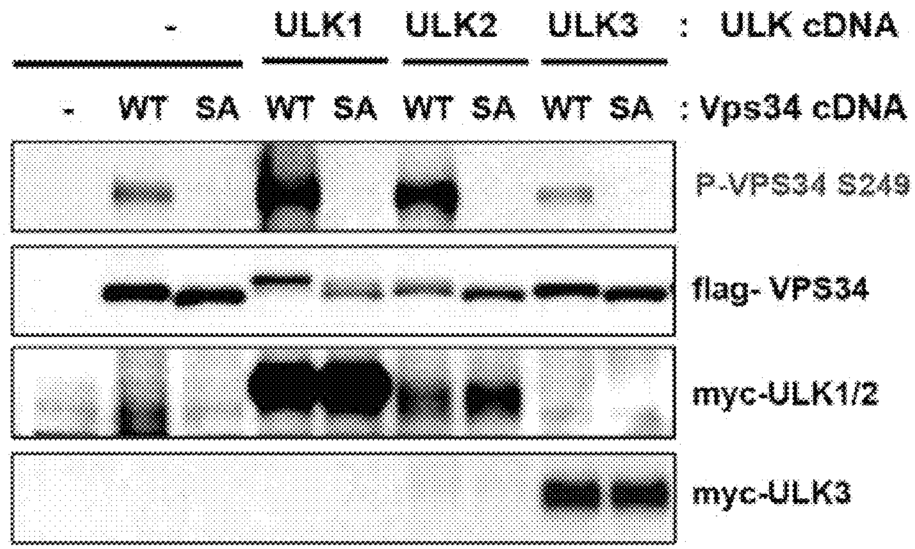

In addition to these assays of ULK1 function, the sequence specificity of what amino acids ULK1 prefers in peptide substrates phosphorylated in in vitro kinase assays were profiled. This method revealed that ULK1 is an odd kinase that does not prefer charged residues at any particular positions, rather favoring hydrophobic residues at several positions, most notably the −3, +1, and +3 position relative to the phospho-acceptor site (FIG. 6A). In the course of evaluating ULK1 interactions with other core autophagy components, it was discovered that overexpression of wild-type but not kinase-dead ULK1 with the Vps34/Beclin complex led to a dramatic mobility shift of these complex components on SDS-PAGE. Analysis of the sequence of Vps34 led to the identification of a highly conserved serine in Vps34 that matched the optimal ULK1 substrate motif (FIG. 6B). Consistent with Vps34 serving a direct substrate for ULK1, increasing amounts of purified ULK1 kinase led to a mobility shift of Vps34 after in vitro kinase assay (FIG. 6B). Mass spectrometry on Vps34 purified from cells expressing wild-type or kinase-inactive ULK1 was utilized to identify phosphorylation events whose abundance was regulated in an ULK1-dependent manner in vivo. Vps34 Serine 249 was fully phosphorylated in the sample isolated from cells expressing wild-type ULK1 but not kinase-dead ULK1 (FIG. 6E). In addition, this was the only site stoichiometrically phosphorylated in the ULK1 activated cells, suggesting Vps34 Ser249 phosphorylation is extremely sensitive to ULK1 kinase activity in vivo relative to other sites in Vps34. Finally, it was tested whether Ser249 phosphorylation was involved in the bandshift Vps34 undergoes on SDS-PAGE. Indeed, the non-phosphorylatable Vps34 Ser249Ala mutant fails to undergo a mobility shift in the presence of active ULK1 (FIG. 6D). Collectively, these data suggest that Vps34 Ser249 is a direct target of ULK1 phosphorylation.

Phosphorylation of specific sites in Vps34, Beclin, and Ambra1 by ULK1 can serve as biomarkers of therapeutic efficacy of mTOR inhibition. These sites are Vps34 Serine 249, Beclin Serine 15, 30, 96, and 337, and Ambra1 Serine 465 and 635 (FIG. 5F). All the current markers of mTOR activity are lowered when mTOR is blocked (Phospho-S6, Phospho-S6K1, Phospho-4ebp1), whereas phosphorylation of these substrates of ULK1 increases when mTOR is inhibited, and thus should serve as useful alternative readouts of mTOR activity.

Definitions

Unless defined otherwise, all technical and scientific terms used herein generally have the same meaning as commonly understood by one of ordinary skill in the art to which this invention belongs. The following references provide one of skill with a general definition of many of the terms used in this invention: Singleton et al., Dictionary of Microbiology and Molecular Biology ($2^{nd}$ Ed. 1994); The Cambridge Dictionary of Science and Technology (Walker, Ed., 1988); The Glossary of Genetics, 5th Ed., R. Rieger, et al. (Eds.), Springer Verlag (1991); and Hale & Marham, The Harper Collins Dictionary of Biology (1991). Generally, the nomenclature used herein and the laboratory procedures in medicine, organic chemistry and polymer chemistry are those well known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

"Acyl" refers to a group having the structure —C(O)R, where R may be, for example, optionally substituted alkyl, optionally substituted aryl, or optionally substituted heteroaryl. "Lower acyl" groups are those that contain one to six carbon atoms.

"Acyloxy" refers to a group having the structure —OC(O)R—, where R may be, for example, optionally substituted alkyl, optionally substituted aryl, or optionally substituted heteroaryl. "Lower acyloxy" groups contain one to six carbon atoms.

The term "addition salt" as used hereinabove also comprises the solvates that the compounds described herein are able to form. Such solvates are for example hydrates, alcoholates and the like.

"Administration" as used herein is inclusive of administration by another person to the subject or self-administration by the subject.

The term "alkoxy" refers to a straight, branched or cyclic hydrocarbon configuration and combinations thereof, including from 1 to 20 carbon atoms, preferably from 1 to 6 carbon atoms (referred to as a "lower alkoxy"), more preferably from 1 to 4 carbon atoms, that include an oxygen atom at the point of attachment. An example of an "alkoxy group" is represented by the formula —OR, where R can be an alkyl group, optionally substituted with an alkenyl, alkynyl, aryl, aralkyl, cycloalkyl, halogenated alkyl, alkoxy or heterocycloalkyl group. Suitable alkoxy groups include methoxy, ethoxy, n-propoxy, i-propoxy, n-butoxy, i-butoxy, sec-butoxy, tert-butoxy cyclopropoxy, cyclohexyloxy, and the like.

"Alkoxycarbonyl" refers to an alkoxy substituted carbonyl radical, —C(O)OR, wherein R represents an optionally substituted alkyl, aryl, aralkyl, cycloalkyl, cycloalkylalkyl or similar moiety.

The term "alkyl" refers to a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. A "lower alkyl" group is a saturated branched or unbranched hydrocarbon having from 1 to 6 carbon atoms. Preferred alkyl groups have 1 to 4 carbon atoms. Alkyl groups may be "substituted alkyls" wherein one or more hydrogen atoms are substituted with a substituent such as halogen, cycloalkyl, alkoxy, amino, hydroxyl, aryl, alkenyl, or carboxyl. For example, a lower alkyl or ($C_1$-$C_6$)alkyl can be methyl, ethyl, propyl, isopropyl, butyl, iso-butyl, sec-butyl, pentyl, 3-pentyl, or hexyl; ($C_3$-$C_6$)cycloalkyl can be cyclopropyl, cyclobutyl, cyclopentyl, or cyclohexyl; ($C_3$-$C_6$)cycloalkyl($C_1$-$C_6$)alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; halo($C_1$-$C_6$)alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; or hydroxy($C_1$-$C_6$)alkyl can be hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 1-hydroxypentyl, 5-hydroxypentyl, 1-hydroxyhexyl, or 6-hydroxyhexyl.

As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease.

The term "amide" or "amido" is represented by the formula —C(O)NRR', where R and R' independently can be a hydrogen, alkyl, alkenyl, alkynyl, aryl, aralkyl, cycloalkyl, halogenated alkyl, or heterocycloalkyl group.

The term "amine" or "amino" refers to a group of the formula —NRR', where R and R' can be, independently, hydrogen or an alkyl, acyl, alkenyl, alkynyl, aryl, aralkyl, cycloalkyl, halogenated alkyl, or heterocycloalkyl group. For example, an "alkylamino" or "alkylated amino" refers to —NRR', wherein at least one of R or R' is an alkyl. An carbonylamino group may be —N(R)—C(O)—R (wherein R is a substituted group or H). A suitable amino group is acetamido.

As used herein, an "amino acid" is represented by the full name thereof, by the three-letter code, as well as the one-letter code corresponding thereto, as indicated in the following table. The structure of amino acids and their abbreviations can also be found in the chemical literature, such as in Stryer, 1988, "Biochemistry", $3^{rd}$ Ed., W. H. Freeman and Co., New York.

The term "aminoalkyl" refers to alkyl groups as defined above where at least one hydrogen atom is replaced with an amino group (e.g, $—CH_2—NH_2$).

"Aminocarbonyl" alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like.

An "analog" is a molecule that differs in chemical structure from a parent compound, for example a homolog (differing by an increment in the chemical structure or mass, such as a difference in the length of an alkyl chain or the inclusion of one of more isotopes), a molecular fragment, a structure that differs by one or more functional groups, or a change in ionization. An analog is not necessarily synthesized from the parent compound. A derivative is a molecule derived from the base structure.

An "animal" refers to living multi-cellular vertebrate organisms, a category that includes, for example, mammals and birds. The term mammal includes both human and non-human mammals. Similarly, the term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

The term "aralkyl" refers to an alkyl group wherein an aryl group is substituted for a hydrogen of the alkyl group. An example of an aralkyl group is a benzyl group.

"Aryl" refers to a monovalent unsaturated aromatic carbocyclic group having a single ring (e.g., phenyl) or multiple condensed or fused rings (e.g., naphthyl or anthryl), which can optionally be unsubstituted or substituted. A "heteroaryl group," is defined as an aromatic group that has at least one heteroatom incorporated within the ring or fused rings of the aromatic group. Examples of heteroatoms include, but are not limited to, nitrogen, oxygen, sulfur, and phosphorous. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl, and the like. The aryl or heteroaryl group can be substituted with one or more groups including, but not limited to, alkyl, alkynyl, alkenyl, aryl, halide, nitro, amino, ester, ketone, aldehyde, hydroxy, carboxylic acid, or alkoxy, or the aryl or heteroaryl group can be unsubstituted.

"Aryloxy" or "heteroaryloxy" refers to a group of the formula —OAr, wherein Ar is an aryl group or a heteroaryl group, respectively.

As used herein, the term "AZD8055" refers to (5-(2,4-bis((S)-3-methylmorpholino) pyrido[2,3-d]pyrimidin-7-yl)-2-methoxyphenyl)methanol, or a salt or solvate thereof.

The term "carboxylate" or "carboxyl" refers to the group $—COO^-$ or —COOH. The carboxyl group can form a carboxylic acid. "Substituted carboxyl" refers to —COOR where R is alkyl, alkenyl, alkynyl, aryl, aralkyl, cycloalkyl, halogenated alkyl, or heterocycloalkyl group. For example, a substituted carboxyl group could be a carboxylic acid ester or a salt thereof (e.g., a carboxylate).

The term "co-administration" or "co-administering" refers to administration of a compound disclosed herein with at least one other therapeutic or diagnostic agent within the same general time period, and does not require administration at the same exact moment in time (although co-administration is inclusive of administering at the same exact moment in time). Thus, co-administration may be on the same day or on different days, or in the same week or in different weeks. In certain embodiments, a plurality of therapeutic and/or diagnostic agents may be co-administered by combining the agents in a single dosage unit or form. The term "conjugated" refers to two molecules that are bonded together, for example by covalent bonds. An example of a conjugate is a molecule (such as a peptide) conjugated to a detectable label, such as a fluorophore.

A as used herein, the terms "compound 14", "SBI-0206965", "0206965", "SBI-6965" and "6965" are used interchangeably to refer to compound 2-(5-bromo-2-(3,4,5-trimethoxy phenylamino)pyrimidin-4-yl amino)-N-methylbenzamide, or a salt or solvate thereof (Table 1).

The term "contacting" refers to placement in direct physical association; includes both in solid and liquid form.

The term "cycloalkyl" refers to a non-aromatic carbon-based ring composed of at least three carbon atoms. Examples of cycloalkyl groups include, but are not limited to, cyclopropyl, cyclobutyl, cyclopentyl, cyclohexyl, and the like. The term "heterocycloalkyl group" is a cycloalkyl group as defined above where at least one of the carbon atoms of the ring is substituted with a heteroatom such as, but not limited to, nitrogen, oxygen, sulfur, or phosphorous.

By "decreases" is meant a negative alteration of at least about 10%, 25%, 50%, 75%, 100%, or more.

A "detectable label" is a compound or composition that is conjugated directly or indirectly to another molecule (such as an oligonucleotide) to facilitate detection of that molecule. Specific, non-limiting examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

By "disease" or "disorder" is meant any condition that damages or interferes with the normal function of a cell, tissue, or organ.

By "effective amount" is meant the amount of a compound that is required to ameliorate the symptoms of a disease relative to an untreated patient. The effective amount of active compound(s) used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

The term "ester" refers to a carboxyl group-containing moiety having the hydrogen replaced with, for example, a $C_{1-6}$alkyl group ("carboxyl$C_{1-6}$alkyl" or "alkylester"), an aryl or aralkyl group ("arylester" or "aralkylester") and so on. $CO_2C_{1-3}$alkyl groups are preferred, such as for example, methylester ($CO_2Me$), ethylester ($CO_2Et$) and propylester ($CO_2Pr$) and includes reverse esters thereof (e.g. —OCOMe, —OCOEt and —OCOPr).

By "fragment" is meant a portion of a polypeptide or nucleic acid molecule. This portion contains, preferably, at least about 10%, 20%, 30%, 40%, 50%, 60%, 70%, 80%, or 90% of the entire length of the reference nucleic acid molecule or polypeptide. A fragment may contain about 10, 20, 30, 40, 50, 60, 70, 80, 90, or 100, 200, 300, 400, 500, 600, 700, 800, 900, or 1,000 nucleotides or amino acids.

The terms "halogenated alkyl" or "haloalkyl group" refer to an alkyl group with one or more hydrogen atoms present on these groups substituted with a halogen (F, Cl, Br, I).

The term "hydroxyl" is represented by the formula —OH.

The term "hydroxyalkyl" refers to an alkyl group that has at least one hydrogen atom substituted with a hydroxyl group. The term "alkoxyalkyl group" is defined as an alkyl group that has at least one hydrogen atom substituted with an alkoxy group described above.

By "identity" is meant the amino acid or nucleic acid sequence identity between a sequence of interest and a reference sequence. Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

"Inhibiting" refers to inhibiting the full development of a disease or condition. "Inhibiting" also refers to any quantitative or qualitative reduction in biological activity or binding, relative to a control.

As used herein, the term "INK128" refers to 3-(2-amino-5-benzoxazolyl)-1-(1-methyl ethyl)-1H-pyrazolo[3,4-d]pyrimidin-4-amine, or a salt or solvate thereof.

As used herein, the term "instructional material" includes a publication, a recording, a diagram, or any other medium of expression that may be used to communicate the usefulness of the compositions and methods of the invention. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; instructions for use of the compositions; or instructions for use of a formulation of the compositions.

An "isolated" biological component is a component that has been substantially separated or purified away from other biological components in the cell of the organism in which the component naturally occurs, i.e., other chromosomal and extra-chromosomal DNA and RNA, proteins, lipids, and organelles. "Isolated" does not require absolute purity. For example, the desired isolated biological component may represent at least 50%, particularly at least about 75%, more particularly at least about 90%, and most particularly at least about 98%, of the total content of the preparation. Isolated biological components as described herein can be isolated by many methods such as salt fractionation, phenol extraction, precipitation with organic solvents (for example, hexadecyltrimethylammonium bromide or ethanol), affinity chromatography, ion-exchange chromatography, hydrophobic chromatography, high performance liquid chromatography, gel filtration, iso-electric focusing, physical separation (e.g., centrifugation or stirring), and the like.

"N-Heterocyclic" refers to mono or bicyclic rings or ring systems that include at least one nitrogen heteroatom. The rings or ring systems generally include 1 to 9 carbon atoms in addition to the heteroatom(s) and may be saturated, unsaturated or aromatic (including pseudoaromatic). The term "pseudoaromatic" refers to a ring system which is not strictly aromatic, but which is stabilized by means of delocalization of electrons and behaves in a similar manner to aromatic rings. Aromatic includes pseudoaromatic ring systems, such as pyrrolyl rings.

Examples of 5-membered monocyclic N-heterocycles include pyrrolyl, H-pyrrolyl, pyrrolinyl, pyrrolidinyl, oxazolyl, oxadiazolyl, (including 1,2,3 and 1,2,4 oxadiazolyls) isoxazolyl, furazanyl, thiazolyl, isothiazolyl, pyrazolyl, pyrazolinyl, pyrazolidinyl, imidazolyl, imidazolinyl, triazolyl (including 1,2,3 and 1,3,4 triazolyls), tetrazolyl, thiadiazolyl (including 1,2,3 and 1,3,4 thiadiazolyls), and dithiazolyl. Examples of 6-membered monocyclic N-heterocycles include pyridyl, pyrimidinyl, pyridazinyl, pyrazinyl, piperidinyl, morpholinyl, thiomorpholinyl, piperazinyl, and triazinyl. The heterocycles may be optionally substituted with a broad range of substituents, and preferably with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. The N-heterocyclic group may be fused to a carbocyclic ring such as phenyl, naphthyl, indenyl, azulenyl, fluorenyl, and anthracenyl.

Examples of 8, 9 and 10-membered bicyclic heterocycles include 1H thieno[2,3-c]pyrazolyl, indolyl, isoindolyl, benzoxazolyl, benzothiazolyl, benzisoxazolyl, benzisothiazolyl, benzimidazolyl, indazolyl, isoquinolinyl, quinolinyl, quinoxalinyl, purinyl, cinnolinyl, phthalazinyl, quinazolinyl, quinoxalinyl, benzotriazinyl, and the like. These heterocycles may be optionally substituted, for example with $C_{1-6}$ alkyl, $C_{1-6}$ alkoxy, $C_{2-6}$ alkenyl, $C_{2-6}$ alkynyl, halo, hydroxy, mercapto, trifluoromethyl, amino, cyano or mono or di($C_{1-6}$alkyl)amino. Unless otherwise defined optionally substituted N-heterocyclics includes pyridinium salts and the N-oxide form of suitable ring nitrogens.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic has a N-terminus and a C-terminus. The N-terminus has an amino group, which may be free (i.e., as a $NH_2$ group) or appropriately protected (e.g., with a BOC or a Fmoc group). The C-terminus has a carboxylic group, which may be free (i.e., as a COOH group) or appropriately protected (e.g., as a benzyl or a methyl ester). A cyclic peptide does not necessarily have free N- or C-termini, since they are covalently bonded through an amide bond to form the cyclic structure.

"Pharmaceutical compositions" are compositions that include an amount (for example, a unit dosage) of one or more of the disclosed compounds together with one or more non-toxic pharmaceutically acceptable additives, including carriers, diluents, and/or adjuvants, and optionally other biologically active ingredients. Such pharmaceutical compositions can be prepared by standard pharmaceutical formulation techniques such as those disclosed in Remington's Pharmaceutical Sciences, Mack Publishing Co., Easton, Pa. (19th Edition).

The terms "pharmaceutically acceptable salt or ester" refers to salts or esters prepared by conventional means that include salts, e.g., of inorganic and organic acids, including but not limited to hydrochloric acid, hydrobromic acid, sulfuric acid or phosphoric acid, s organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid.

"Pharmaceutically acceptable salts" of the presently disclosed compounds also include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. Particular examples of suitable amine bases (and their corresponding ammonium ions) for use in the present compounds include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine, tris(hydroxymethyl)methylamine, N,N-dimethyl-N-(2-hydroxyethyl)amine, tri-(2-hydroxyethyl)amine and N-methyl-D-glucamine. For additional examples of "pharmacologically acceptable salts," see Berge et al., J. Pharm. Sci. 66:1 (1977). These salts may be prepared by standard procedures, for example by reacting the free acid with a suitable organic or inorganic base. Any chemical compound recited in this specification may alternatively be administered as a pharmaceutically acceptable salt thereof.

"Pharmaceutically acceptable salts" are also inclusive of the free acid, base, and zwitterionic forms. Descriptions of suitable pharmaceutically acceptable salts can be found in *Handbook of Pharmaceutical Salts, Properties, Selection and Use*, Wiley VCH (2002). When compounds disclosed herein include an acidic function such as a carboxy group, then suitable pharmaceutically acceptable cation pairs for the carboxy group are well known to those skilled in the art and include alkaline, alkaline earth, ammonium, quaternary ammonium cations and the like. Such salts are known to those of skill in the art. For additional examples of "pharmacologically acceptable salts," see Berge et al., J. Pharm. Sci. 66:1 (1977).

"Pharmaceutically acceptable esters" includes those derived from compounds described herein that are modified to include a carboxyl group. An in vivo hydrolysable ester is an ester, which is hydrolysed in the human or animal body to produce the parent acid or alcohol. Representative esters thus include carboxylic acid esters in which the non-carbonyl moiety of the carboxylic acid portion of the ester grouping is selected from straight or branched chain alkyl (for example, methyl, n-propyl, t-butyl, or n-butyl), cycloalkyl, alkoxyalkyl (for example, methoxymethyl), aralkyl (for example benzyl), aryloxyalkyl (for example, phenoxymethyl), aryl (for example, phenyl, optionally substituted by, for example, halogen, $C_{1-4}$ alkyl, or $C_{1-4}$ alkoxy) or amino); sulphonate esters, such as alkyl- or aralkylsulphonyl (for example, methanesulphonyl); or amino acid esters (for example, L-valyl or L-isoleucyl). A "pharmaceutically acceptable ester" also includes inorganic esters such as mono-, di-, or tri-phosphate esters. In such esters, unless otherwise specified, any alkyl moiety present advantageously contains from 1 to 18 carbon atoms, particularly from 1 to 6 carbon atoms, more particularly from 1 to 4 carbon atoms. Any cycloalkyl moiety present in such esters advantageously contains from 3 to 6 carbon atoms. Any aryl moiety present in such esters advantageously comprises a phenyl group, optionally substituted as shown in the definition of carbocycylyl above. Pharmaceutically acceptable esters thus include $C_1$-$C_{22}$ fatty acid esters, such as acetyl, t-butyl or long chain straight or branched unsaturated or omega-6 monounsaturated fatty acids such as palmoyl, stearoyl and the like. Alternative aryl or heteroaryl esters include benzoyl, pyridylmethyloyl and the like any of which may be substituted, as defined in carbocyclyl above. Additional pharmaceutically acceptable esters include aliphatic L-amino acid esters such as leucyl, isoleucyl and especially valyl.

For therapeutic use, salts of the compounds are those wherein the counter-ion is pharmaceutically acceptable. However, salts of acids and bases which are non-pharmaceutically acceptable may also find use, for example, in the preparation or purification of a pharmaceutically acceptable compound. The pharmaceutically acceptable acid and base addition salts as mentioned hereinabove are meant to comprise the therapeutically active non-toxic acid and base addition salt forms which the compounds are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form. The compounds containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

"Preventing" a disease or condition refers to prophylactic administering a composition to a subject who does not exhibit signs of a disease or exhibits only early signs for the purpose of decreasing the risk of developing a pathology or condition, or diminishing the severity of a pathology or condition.

The term "purified" does not require absolute purity; rather, it is intended as a relative term. Thus, for example, a purified peptide preparation is one in which the peptide or protein is more enriched than the peptide or protein is in its natural environment within a cell. For example, a compound preparation is purified such that the desired polysaccharide protein conjugate represents at least 50%, more particularly at least about 90%, and most particularly at least about 98%, of the total content of the preparation.

The term "quaternary amine" as used hereinbefore defines the quaternary ammonium salts which the compounds are able to form by reaction between a basic nitrogen of a compound and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

A "recombinant" protein is one that has a sequence that is not naturally occurring or has a sequence that is made by an artificial combination of two otherwise separated segments of sequence.

The term "subject" includes both human and non-human subjects, including birds and non-human mammals, such as non-human primates, companion animals (such as dogs and cats), livestock (such as pigs, sheep, cows), as well as non-domesticated animals, such as the big cats. The term subject applies regardless of the stage in the organism's life-cycle. Thus, the term subject applies to an organism in utero or in ovo, depending on the organism (that is, whether the organism is a mammal or a bird, such as a domesticated or wild fowl).

"Substituted" or "substitution" refers to replacement of a hydrogen atom of a molecule or an R-group with one or more additional R-groups. Unless otherwise defined, the term "optionally-substituted" or "optional substituent" as used herein refers to a group which may or may not be further substituted with 1, 2, 3, 4 or more groups, preferably 1, 2 or 3, more preferably 1 or 2 groups. The substituents may be selected, for example, from $C_{1-6}$alkyl, $C_{2-6}$ alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$ and $CHF_2$), $C_{1-6}$alkoxyhalo (such as $OCF_3$ and $OCHF_2$), carboxyl, esters, cyano, nitro, amino, substituted amino, disubstituted amino, acyl, ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case N-heterocycles may also include but are not limited to $C_{1-6}$alkyl i.e. N—$C_{1-3}$alkyl, more preferably methyl particularly N-methyl.

A "therapeutically effective amount" refers to a quantity of a specified agent sufficient to achieve a desired effect in a subject being treated with that agent. For example, a therapeutically amount may be an amount of a ULK1 inhibitor that is sufficient to inhibit autophagy in a desired cell in a subject. Ideally, a therapeutically effective amount of an agent is an amount sufficient to inhibit or treat the disease or condition without causing a substantial cytotoxic, or other substantially deleterious, effect in the subject. The therapeutically effective amount of an agent will be dependent on the subject being treated, the severity of the affliction, and the manner of administration of the therapeutic composition.

"Thiol" refers to the group —SH. The term "substituted thiol" refers to a thiol group having the hydrogen replaced with, for example a $C_{1-6}$alkyl group ("—S($C_{1-6}$alkyl)"), an aryl ("—S(aryl)"), or an aralkyl ("—S(alkyl)(aryl)") and so on.

The phrase "treating a disease" refers to inhibiting the full development of a disease, for example, in a subject who is at risk for a disease such as diabetes.

"Treatment" refers to a therapeutic intervention that ameliorates a sign or symptom of a disease or pathological condition after it has begun to develop, or administering a compound or composition to a subject who does not exhibit signs of a disease or exhibits only early signs for the purpose of decreasing the risk of developing a pathology or condition, or diminishing the severity of a pathology or condition.

Compounds

In one aspect, disclosed herein are compounds that function as ULK1 inhibitors.

In certain embodiments, the ULK1 inhibitor is at least one selected from the group consisting of a 2-(substituted) amino-4-(substituted)amino-5-halo-pyrimidine; 2-(substituted)amino-4-(substituted) amino-5-(halo)alkyl-pyrimidine; 2-(substituted)amino-4-(substituted)oxo-5-halo-pyrimidine; 2-(substituted)amino-4-(substituted)oxo-5-(halo)alkyl-pyrimidine; 2-(substituted)amino-4-(substituted)thio-5-halo-pyrimidine; and 2-(substituted) amino-4-(substituted)thio-5-(halo)alkyl-pyrimidine; or a pharmaceutically acceptable salt thereof.

Also disclosed herein are compounds, or pharmaceutically acceptable salts thereof, having a structure of:

Formula A

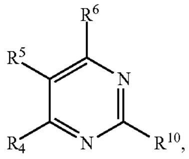

wherein in Formula A:

$R^{10}$ is selected from the group consisting of: halogen; —$OR^{11}$ wherein $R^{11}$ is H, optionally substituted aryl, or optionally substituted heteroaryl; —$NR^1R^2$ wherein $R^1$ and $R^2$ are each individually selected from the group consisting of H, optionally substituted aryl, optionally substituted heteroaryl, optionally substituted cycloalkyl, and optionally substituted alkyl, or $NR^1R^2$ together form a heterocycle; or $R^4$ and $R^{10}$ together form a cyclic structure;

$R^4$ is selected from the group consisting of optionally substituted amino, optionally substituted aryloxy, optionally substituted heteroaryloxy, optionally substituted alkoxy, N-heterocyclic, optionally substituted thiol, optionally substituted alkyl, hydroxyl and halogen;

$R^5$ is selected from the group consisting of H, hydroxyl, optionally substituted alkyl, halo, optionally substituted alkoxy, or optionally substituted aryl, optionally substituted carboxyl, cyano, and nitro, or $R^5$ and $R^6$ together form a cyclic structure; and $R^6$ is H or haloalkyl.

Also disclosed herein are compounds, or pharmaceutically acceptable salts thereof, having a structure of:

Formula I

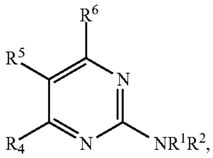

wherein in Formula I:

$R^1$ and $R^2$ are each individually selected from the group consisting of H, optionally substituted aryl, optionally substituted heteroaryl, optionally substituted cycloalkyl, and optionally substituted alkyl, or $NR^1R^2$ together form a heterocycle;

$R^4$ is selected from the group consisting of optionally substituted amino, optionally substituted aryloxy, optionally substituted heteroaryloxy, optionally substituted alkoxy, N-heterocyclic, optionally substituted thiol, and optionally substituted alkyl;

$R^5$ is selected from the group consisting of H, hydroxyl, optionally substituted alkyl, halo, optionally substituted alkoxy, and optionally substituted aryl; and $R^6$ is H; or a pharmaceutically acceptable salt thereof.

In certain embodiments, $R^1$ is H and $R^2$ is not H. In other embodiments, $R^1$ is H and $R^2$ is an optionally substituted fused heteroaryl or an optionally substituted aryl. The optionally substituted fused heteroaryl, for example, may be a bicyclic fused ring system that include at least one nitrogen heteroatom. In certain embodiments, $R^1$ is H and $R^2$ is an optionally substituted bicyclic fused ring system that includes at least one heteroatom. In certain embodiments, $R^1$ is H and $R^2$ is an optionally substituted bicyclic fused ring system that includes at least one nitrogen heteroatoms. In certain embodiments, $R^1$ is H and $R^2$ is an optionally substituted bicyclic fused ring system that includes at least two nitrogen heteroatoms. In certain embodiments, $R^1$ is H and $R^2$ is an optionally substituted bicyclic fused ring system that includes at least two oxygen heteroatoms. The optionally substituted aryl, for example, may be a substituted or unsubstituted phenyl. The phenyl, for example, may be substituted with at least one alkoxy, preferably ($C_1$-$C_6$) alkoxy.

In certain embodiments, $R^1$ is H and $R^2$ is selected from the group consisting of:

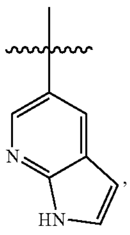
,
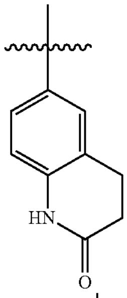
,
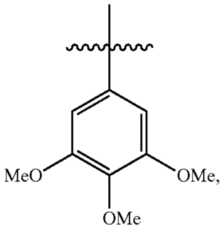
,
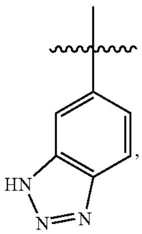
,
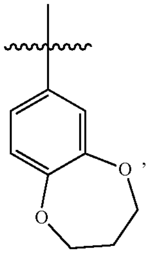
,
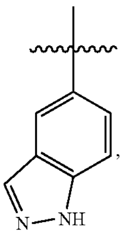
,

-continued and 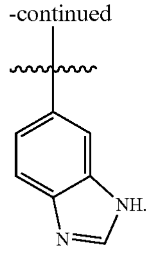

In certain embodiments, $R^4$ is selected from the group consisting of optionally substituted amino, optionally substituted aryloxy, optionally substituted heteroaryloxy, and optionally substituted alkoxy.

In certain embodiments, $R^4$ is selected from the group consisting of optionally substituted aryloxy, optionally substituted heteroaryloxy, and optionally substituted alkoxy. In particular embodiments, $R^4$ is selected from the group consisting of optionally substituted phenoxy and optionally substituted alkoxy. In particular embodiments, $R^4$ is selected from the group consisting of phenoxy, $(C_1\text{-}C_6)$alkoxy, and —O—(N-alkylbenzamide), particularly —O—(N—$(C_1\text{-}C_6)$alkylbenzamide). In particular embodiments, $R^4$ is

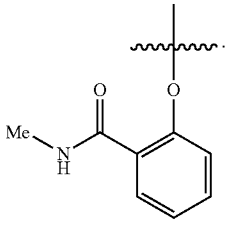 [SMILES: *Oc1ccccc1C(=O)NC]

In certain embodiments, $R^4$ is —$NR^7R^8$, wherein $R^7$ and $R^8$ are each individually selected from the group consisting of H, optionally substituted aryl, optionally substituted heteroaryl, cycloalkyl, and optionally substituted alkyl, or $NR^7R^8$ together form a heterocycle. In certain embodiments, $R^7$ is H and $R^8$ is N-alkylbenzamide, particularly N—$(C_1\text{-}C_6)$alkylbenzamide. In certain embodiments, $R^7$ is H and $R^8$ is phenyl. In certain embodiments, $R^7$ is H and $R^8$ is alkoxy-substituted phenyl, particularly $(C_1\text{-}C_6)$alkoxy. In certain embodiments, $R^7$ is H and $R^8$ is cyclopropyl. In certain embodiments, $R^7$ is H and $R^8$ is cyclobutyl. In certain embodiments, $R^7$ is H and $R^8$ is alkoxyalkyl, particularly $(C_1\text{-}C_6)$alkoxy$(C_1\text{-}C_6)$alkyl. In certain embodiments, $R^7$ is H and $R^8$ is haloalkyl. In certain embodiments, $R^7$ is H and $R^8$ is optionally substituted acyl. In certain embodiments, $R^4$ is —$NH_2$. In certain embodiments, $R^4$—OH.

In certain embodiments, $R^5$ is haloalkyl, particularly $CF_3$. In certain embodiments, $R^5$ is Br. In certain embodiments, $R^5$ is Cl.

In certain embodiments, $R^2$ is a fused heteroaryl ring and $R^4$ is —$NR^7R^8$, wherein $R^7$ is H and $R^8$ is a fused heteroaryl ring. In particular embodiments, $R^2$ is selected from the group consisting of:

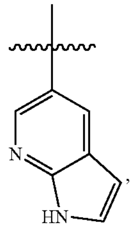 , and 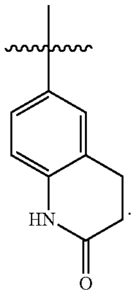

In particular embodiments, $R^8$ is

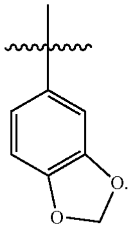 [SMILES: *c1ccc2c(c1)OCO2]

Illustrative compounds are shown in Table 1 (along with their respective $IC_{50}$ values for ULK1 inhibition assay). $IC_{50}$s are presented in µM, with A representing $IC_{50}<0.2$ µM, B representing 0.2 µM$<IC_{50}<$2 µM, and C representing $IC_{50}>2$ µM. An * notes tested as a mixture of regioisomers.

TABLE 1

| Example | Structure | $IC_{50}$ |
| --- | --- | --- |
| 12 | 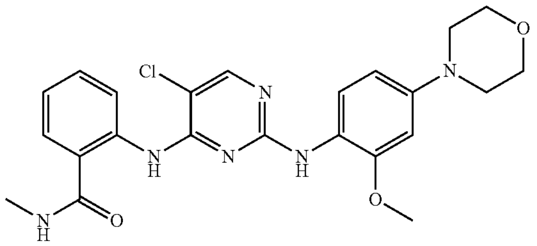 [SMILES: CNC(=O)c1ccccc1Nc1nc(Nc2ccc(N3CCOCC3)cc2OC)ncc1Cl] | A |

TABLE 1-continued
| Example | Structure | $IC_{50}$ |
|---|---|---|
| 13 | 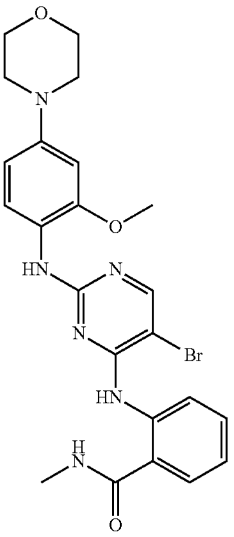 [SMILES: CNC(=O)c1ccccc1Nc1nc(Nc2ccc(N3CCOCC3)cc2OC)ncc1Br] | B |
| 14 | 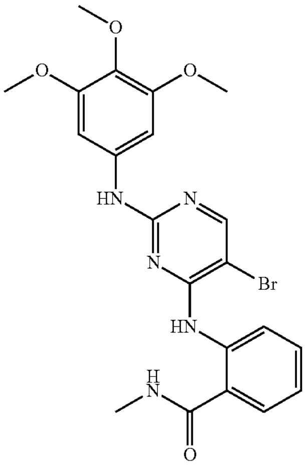 [SMILES: CNC(=O)c1ccccc1Nc1nc(Nc2cc(OC)c(OC)c(OC)c2)ncc1Br] | A |
| 15 | 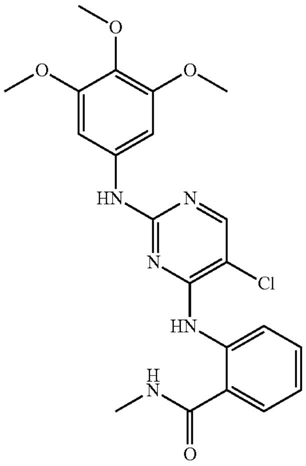 [SMILES: CNC(=O)c1ccccc1Nc1nc(Nc2cc(OC)c(OC)c(OC)c2)ncc1Cl] | A |

TABLE 1-continued
| Example | Structure | $IC_{50}$ |
|---|---|---|
| 16 | 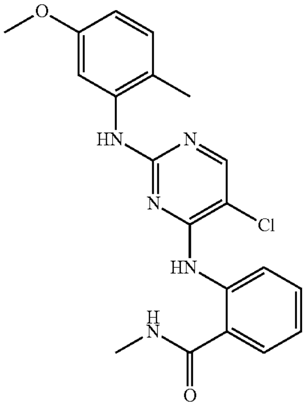 [SMILES: CNC(=O)c1ccccc1Nc1nc(Nc2cc(OC)ccc2C)ncc1Cl] | A |
| 17 | 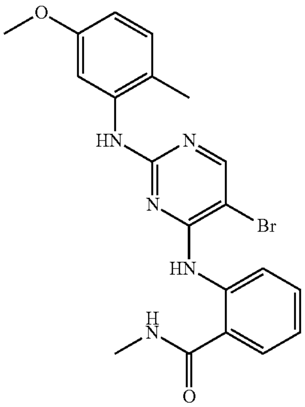 [SMILES: CNC(=O)c1ccccc1Nc1nc(Nc2cc(OC)ccc2C)ncc1Br] | A |
| 18 | 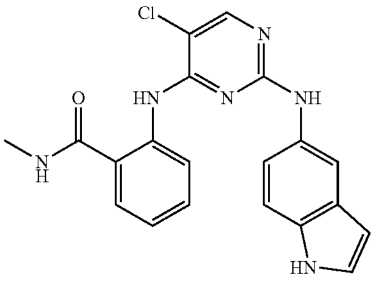 [SMILES: CNC(=O)c1ccccc1Nc1nc(Nc2ccc3[nH]ccc3c2)ncc1Cl] | B |
| 19 | 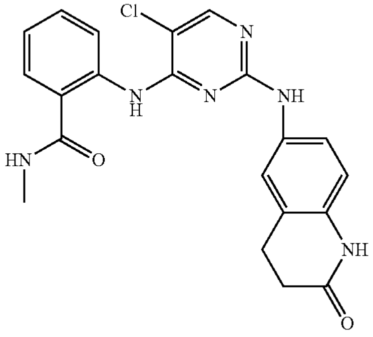 [SMILES: CNC(=O)c1ccccc1Nc1nc(Nc2ccc3c(c2)CCC(=O)N3)ncc1Cl] | A |

TABLE 1-continued
| Example | Structure | IC$_{50}$ |
|---|---|---|
| 20 | 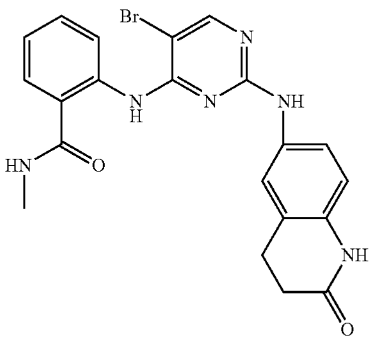 [SMILES: CNC(=O)c1ccccc1Nc1nc(Nc2ccc3c(c2)CCC(=O)N3)ncc1Br] | A |
| 21 | 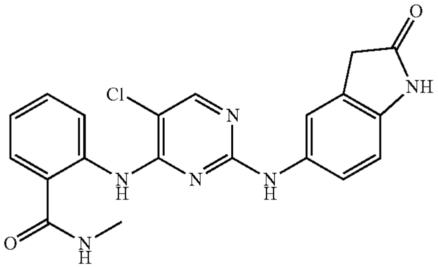 [SMILES: CNC(=O)c1ccccc1Nc1nc(Nc2ccc3c(c2)CC(=O)N3)ncc1Cl] | A |
| 22 | 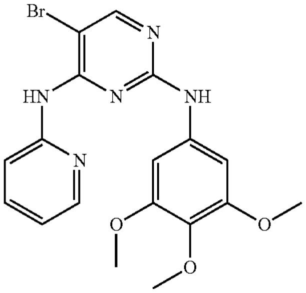 [SMILES: COc1cc(Nc2ncc(Br)c(Nc3ccccn3)n2)cc(OC)c1OC] | A |
| 23 | 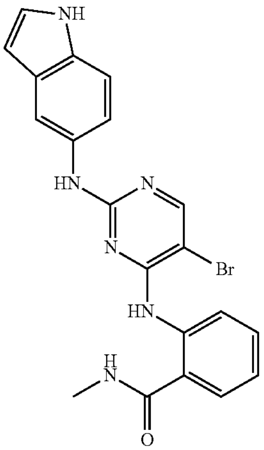 [SMILES: CNC(=O)c1ccccc1Nc1nc(Nc2ccc3[nH]ccc3c2)ncc1Br] | A |

TABLE 1-continued
| Example | Structure | $IC_{50}$ |
| --- | --- | --- |
| 24 | 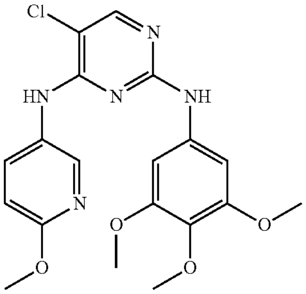 | A |
| 25 | 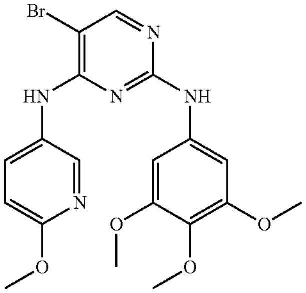 [SMILES: COc1ccc(Nc2nc(Nc3cc(OC)c(OC)c(OC)c3)ncc2Cl)cn1] | A |
| 26 | 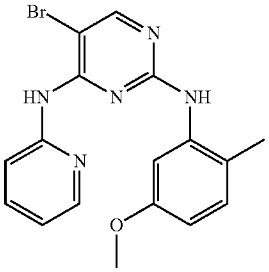 [SMILES: COc1ccc(C)c(Nc2ncc(Br)c(Nc3ccccn3)n2)c1] | B |
| 27 | 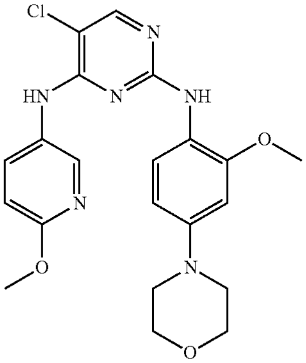 [SMILES: COc1ccc(Nc2nc(Nc3ccc(N4CCOCC4)cc3OC)ncc2Cl)cn1] | C |
| 28 | 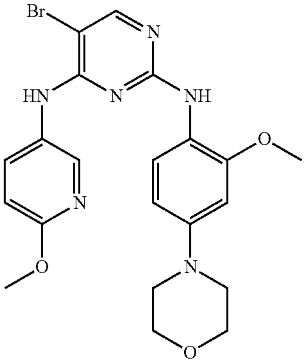 | B |

TABLE 1-continued
| Example | Structure | $IC_{50}$ |
|---|---|---|
| 29 | 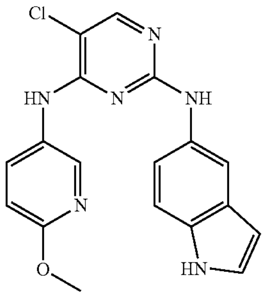 | B |
| 30 | 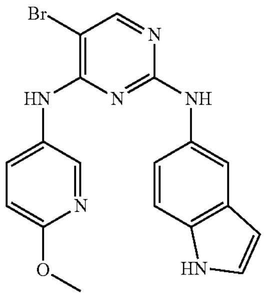 [SMILES: COc1ccc(Nc2nc(Nc3ccc4[nH]ccc4c3)ncc2Br)cn1] | A |
| 31 | 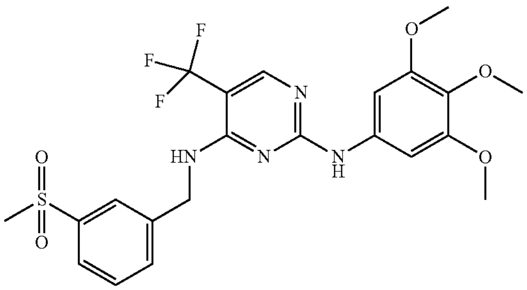 | A |
| 32 | 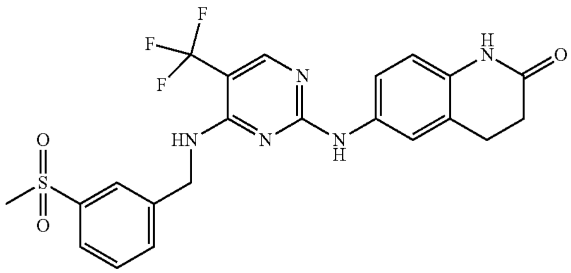 [SMILES: CS(=O)(=O)c1cccc(CNc2nc(Nc3ccc4c(c3)CCC(=O)N4)ncc2C(F)(F)F)c1] | B |
| 33 | 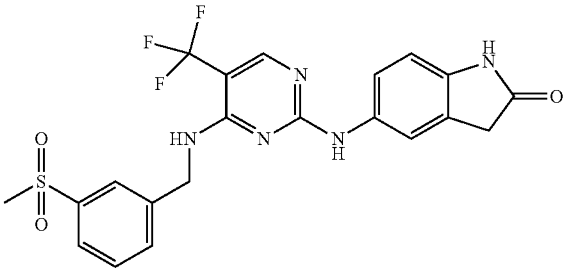 [SMILES: CS(=O)(=O)c1cccc(CNc2nc(Nc3ccc4c(c3)CC(=O)N4)ncc2C(F)(F)F)c1] | B |

TABLE 1-continued
| Example | Structure | $IC_{50}$ |
|---|---|---|
| 34 | 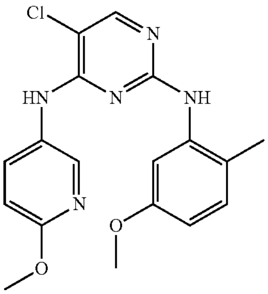 | C |
| 35 | 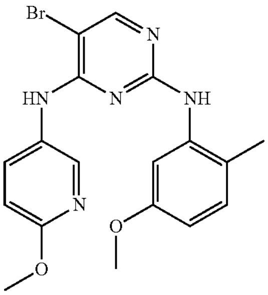 [SMILES: COc1ccc(C)c(Nc2ncc(Br)c(Nc3ccc(OC)nc3)n2)c1] | |
| 36 | 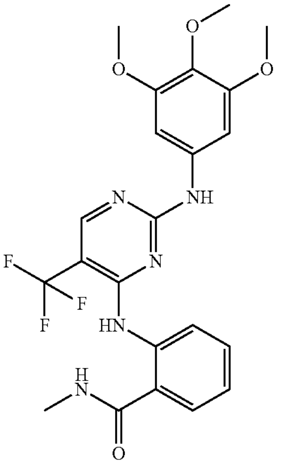 [SMILES: CNC(=O)c1ccccc1Nc1nc(Nc2cc(OC)c(OC)c(OC)c2)ncc1C(F)(F)F] | C |
| 37 | 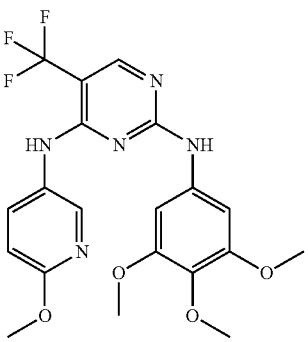 [SMILES: COc1ccc(Nc2nc(Nc3cc(OC)c(OC)c(OC)c3)ncc2C(F)(F)F)cn1] | A |

TABLE 1-continued
| Example | Structure | $IC_{50}$ |
|---|---|---|
| 38 | 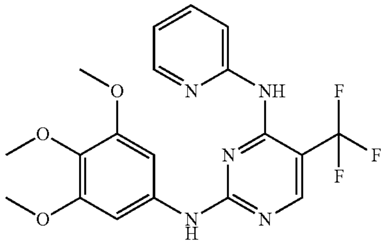 [SMILES: COc1cc(Nc2ncc(C(F)(F)F)c(Nc3ccccn3)n2)cc(OC)c1OC] | B |
| 39 | 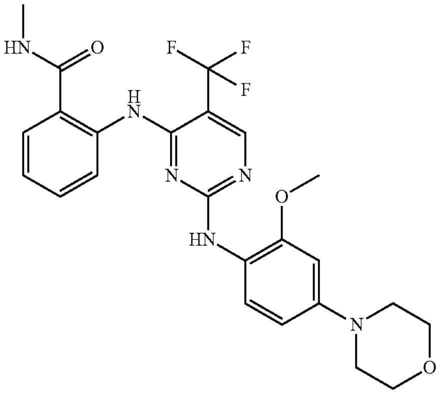 [SMILES: CNC(=O)c1ccccc1Nc1nc(Nc2ccc(N3CCOCC3)cc2OC)ncc1C(F)(F)F] | A |
| 40 | 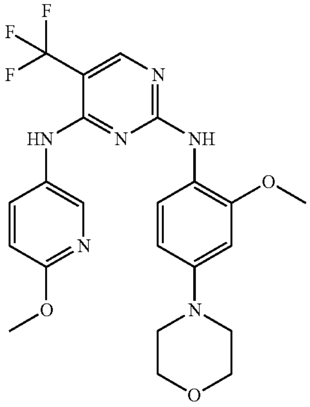 [SMILES: COc1ccc(Nc2nc(Nc3ccc(N4CCOCC4)cc3OC)ncc2C(F)(F)F)cn1] | C |
| 41 | 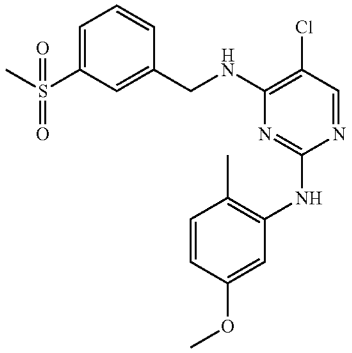 [SMILES: COc1ccc(C)c(Nc2ncc(Cl)c(NCc3cccc(S(C)(=O)=O)c3)n2)c1] | C |

TABLE 1-continued
| Example | Structure | $IC_{50}$ |
| --- | --- | --- |
| 42 | 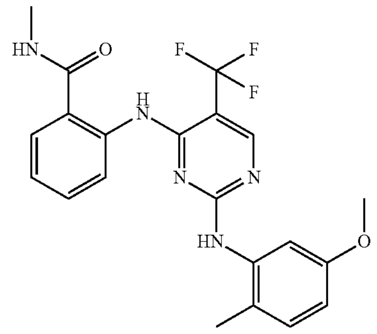 [SMILES: CNC(=O)c1ccccc1Nc1nc(Nc2cc(OC)ccc2C)ncc1C(F)(F)F] | A |
| 43 | 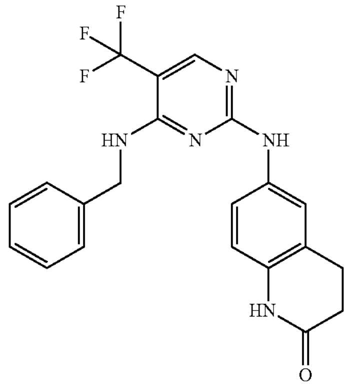 [SMILES: O=C1CCc2cc(Nc3ncc(C(F)(F)F)c(NCc4ccccc4)n3)ccc2N1] | A |
| 44 | 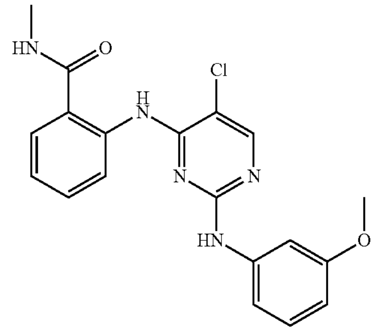 [SMILES: CNC(=O)c1ccccc1Nc1nc(Nc2cccc(OC)c2)ncc1Cl] | A |
| 45 | 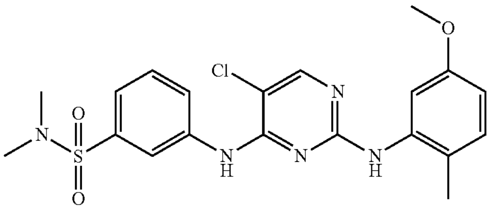 [SMILES: COc1ccc(C)c(Nc2ncc(Cl)c(Nc3cccc(S(=O)(=O)N(C)C)c3)n2)c1] | C |

TABLE 1-continued
| Example | Structure | $IC_{50}$ |
| --- | --- | --- |
| 46 | 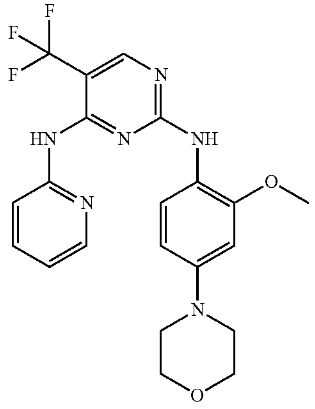 [SMILES: COc1cc(N2CCOCC2)ccc1Nc1ncc(C(F)(F)F)c(Nc2ccccn2)n1] | B |
| 48 | 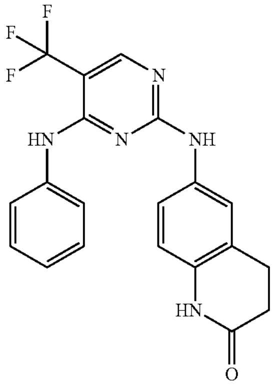 [SMILES: O=C1CCc2cc(Nc3ncc(C(F)(F)F)c(Nc4ccccc4)n3)ccc2N1] | A |
| 49 | 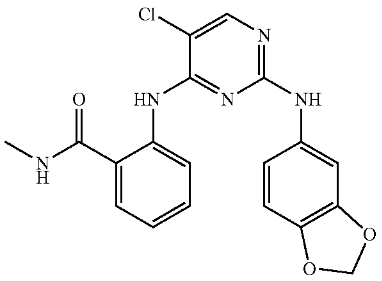 [SMILES: CNC(=O)c1ccccc1Nc1nc(Nc2ccc3c(c2)OCO3)ncc1Cl] | A |
| 50 | 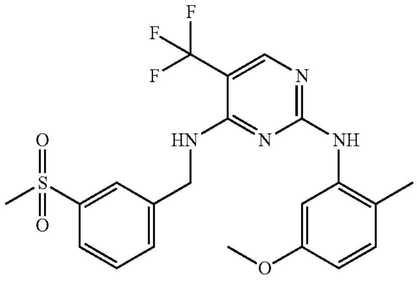 | C |

TABLE 1-continued
| Example | Structure | $IC_{50}$ |
|---|---|---|
| 51 | 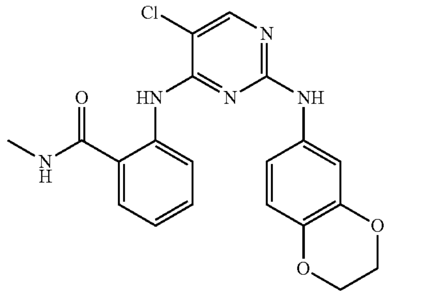 [SMILES: CNC(=O)c1ccccc1Nc1nc(Nc2ccc3c(c2)OCCO3)ncc1Cl] | A |
| 52 | 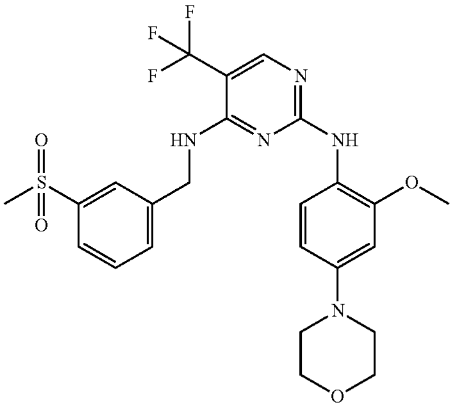 | C |
| 53 | 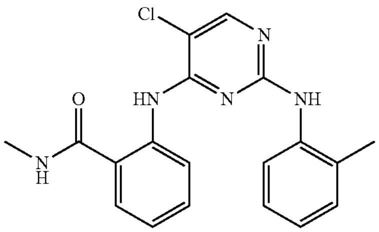 | C |
| 54 | 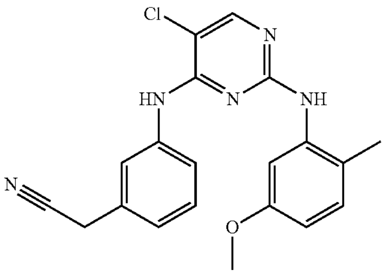 [SMILES: COc1ccc(C)c(Nc2ncc(Cl)c(Nc3cccc(CC#N)c3)n2)c1] | C |
| 55 | 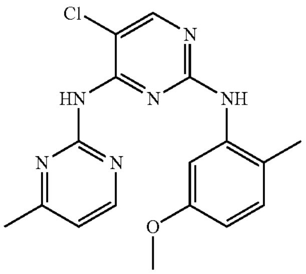 | C |

TABLE 1-continued
| Example | Structure | $IC_{50}$ |
|---|---|---|
| 56 | 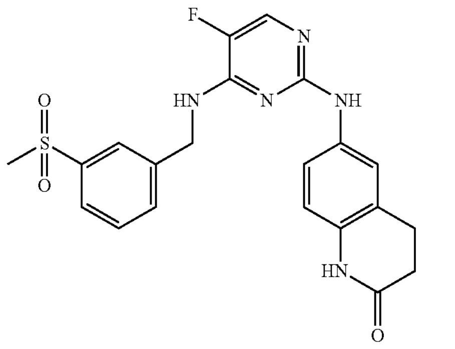 [SMILES: CS(=O)(=O)c1cccc(CNc2nc(Nc3ccc4c(c3)CCC(=O)N4)ncc2F)c1] | C |
| 57 | 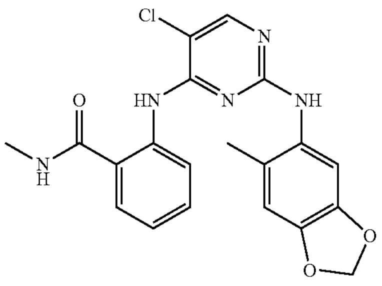 [SMILES: CNC(=O)c1ccccc1Nc1nc(Nc2cc3c(cc2C)OCO3)ncc1Cl] | A |
| 58 | 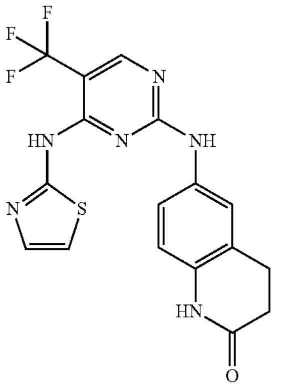 [SMILES: O=C1CCc2cc(Nc3ncc(C(F)(F)F)c(Nc4nccs4)n3)ccc2N1] | C |
| 60 | 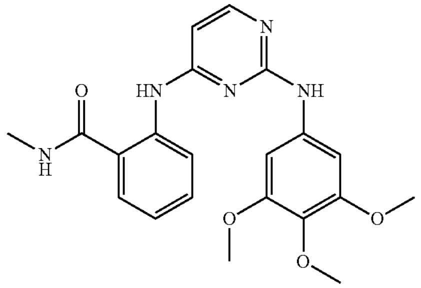 | A |

TABLE 1-continued
| Example | Structure | $IC_{50}$ |
|---|---|---|
| 61 | 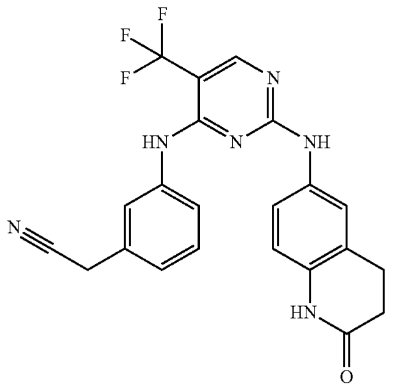 [SMILES: N#CCc1cccc(Nc2nc(Nc3ccc4c(c3)CCC(=O)N4)ncc2C(F)(F)F)c1] | A |
| 62 | 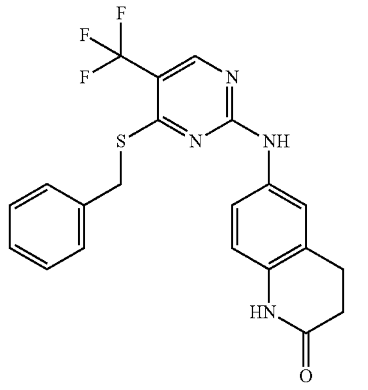 [SMILES: O=C1CCc2cc(Nc3ncc(C(F)(F)F)c(SCc4ccccc4)n3)ccc2N1] | A |
| 64 | 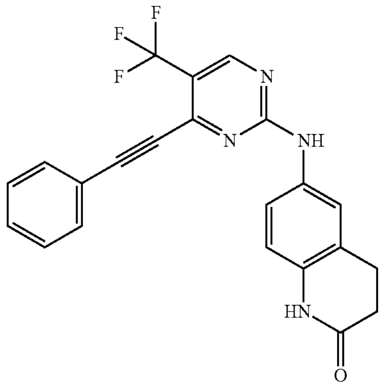 [SMILES: O=C1CCc2cc(Nc3ncc(C(F)(F)F)c(C#Cc4ccccc4)n3)ccc2N1] | C |
| 66 | 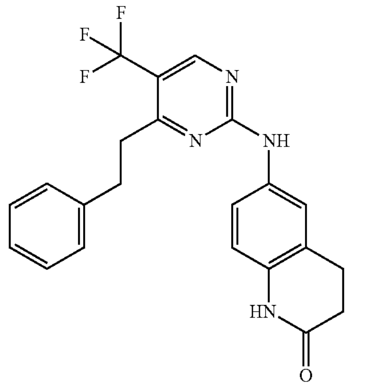 [SMILES: O=C1CCc2cc(Nc3ncc(C(F)(F)F)c(CCc4ccccc4)n3)ccc2N1] | B |

TABLE 1-continued
| Example | Structure | $IC_{50}$ |
| --- | --- | --- |
| 67 | 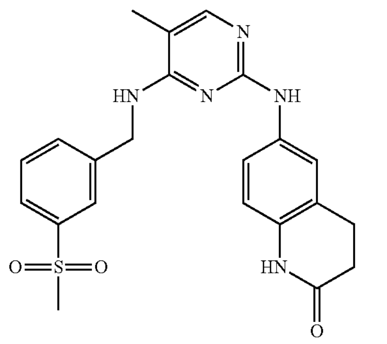 [SMILES: Cc1cnc(Nc2ccc3c(c2)CCC(=O)N3)nc1NCc1cccc(S(C)(=O)=O)c1] | C |
| 69 | 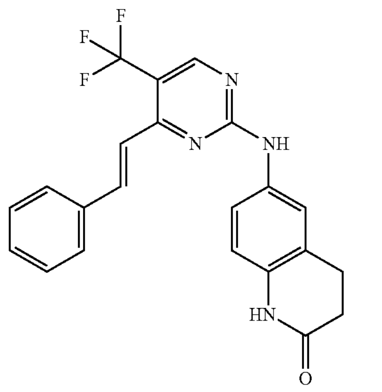 [SMILES: O=C1CCc2cc(Nc3ncc(C(F)(F)F)c(/C=C/c4ccccc4)n3)ccc2N1] | A |
| 71 | 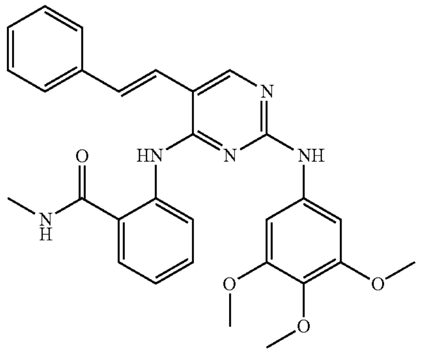 [SMILES: CNC(=O)c1ccccc1Nc1nc(Nc2cc(OC)c(OC)c(OC)c2)ncc1/C=C/c1ccccc1] | A |
| 72 | 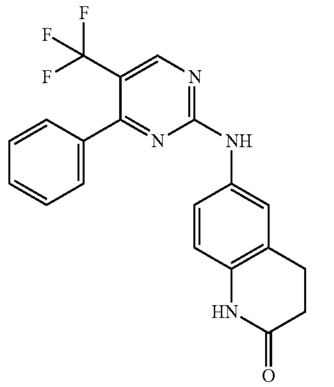 [SMILES: O=C1CCc2cc(Nc3ncc(C(F)(F)F)c(-c4ccccc4)n3)ccc2N1] | C |

TABLE 1-continued
| Example | Structure | $IC_{50}$ |
|---|---|---|
| 73 | 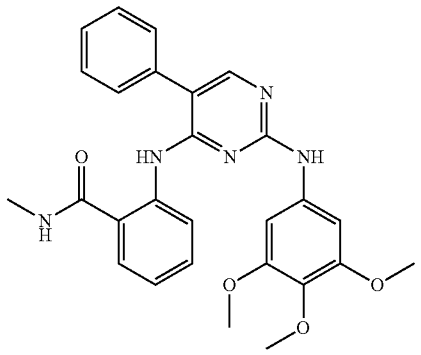 | A |
| 74 | 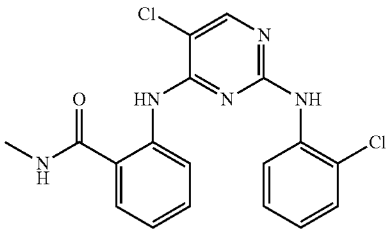 [SMILES: CNC(=O)c1ccccc1Nc1nc(Nc2ccccc2Cl)ncc1Cl] | B |
| 75 | 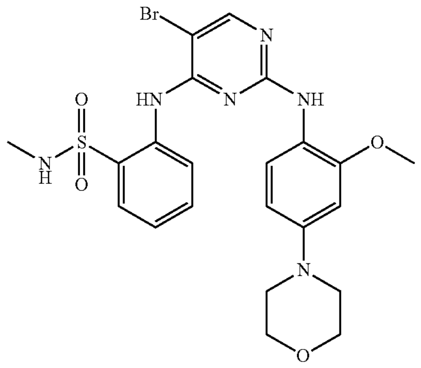 | B |
| 76 | 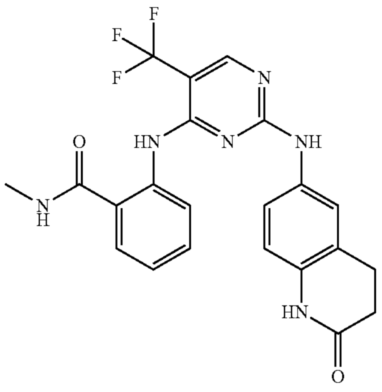 [SMILES: CNC(=O)c1ccccc1Nc1nc(Nc2ccc3c(c2)CCC(=O)N3)ncc1C(F)(F)F] | A |

TABLE 1-continued
| Example | Structure | $IC_{50}$ |
|---|---|---|
| 78 | 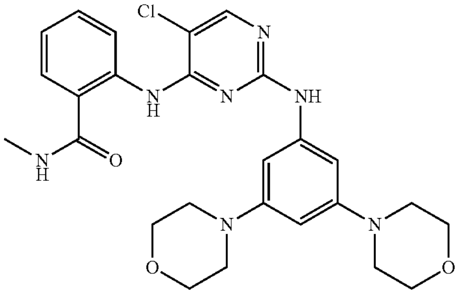 [SMILES: CNC(=O)c1ccccc1Nc1nc(Nc2cc(N3CCOCC3)cc(N3CCOCC3)c2)ncc1Cl] | B |
| 80 | 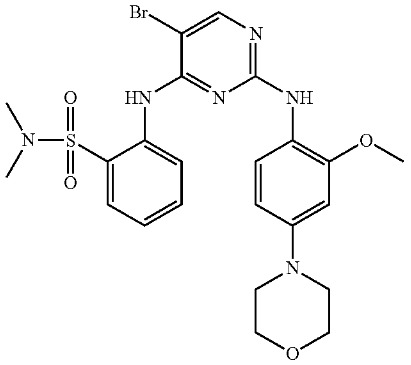 | A |
| 81 | 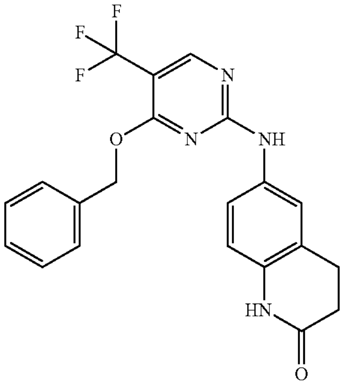 [SMILES: O=C1CCc2cc(Nc3ncc(C(F)(F)F)c(OCc4ccccc4)n3)ccc2N1] | A |
| 82 | 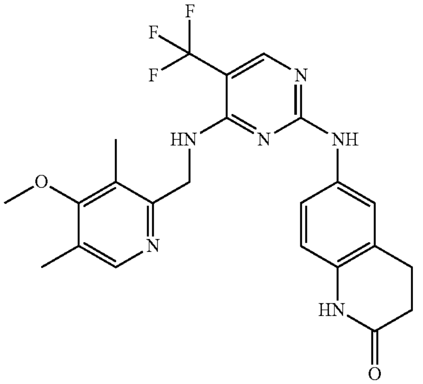 [SMILES: COc1c(C)cnc(CNc2nc(Nc3ccc4c(c3)CCC(=O)N4)ncc2C(F)(F)F)c1C] | A |

TABLE 1-continued
| Example | Structure | $IC_{50}$ |
|---|---|---|
| 83 | 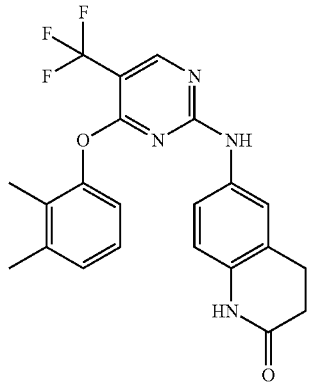 [SMILES: Cc1cccc(Oc2nc(Nc3ccc4c(c3)CCC(=O)N4)ncc2C(F)(F)F)c1C] | A |
| 87 | 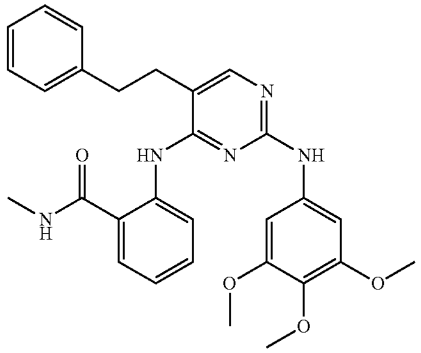 | B |
| 88 | 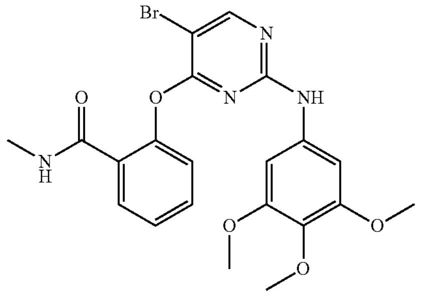 | A |
| 89 | 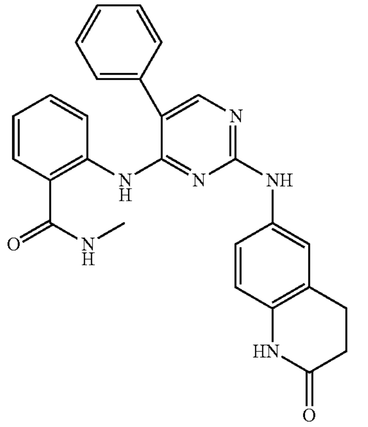 [SMILES: CNC(=O)c1ccccc1Nc1nc(Nc2ccc3c(c2)CCC(=O)N3)ncc1-c1ccccc1] | A |

TABLE 1-continued
| Example | Structure | $IC_{50}$ |
| --- | --- | --- |
| 90 | 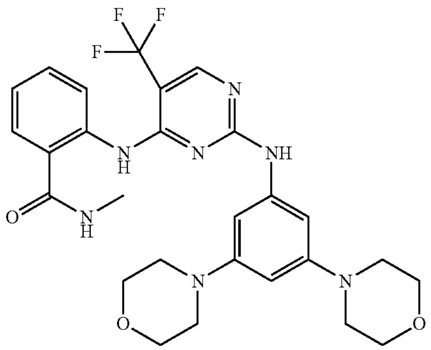 [SMILES: CNC(=O)c1ccccc1Nc1nc(Nc2cc(N3CCOCC3)cc(N3CCOCC3)c2)ncc1C(F)(F)F] | A |
| 92 | 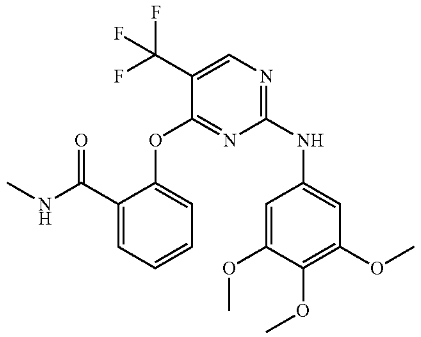 | A |
| 99 | 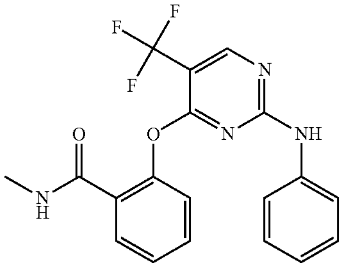 [SMILES: CNC(=O)c1ccccc1Oc1nc(Nc2ccccc2)ncc1C(F)(F)F] | C |
| 100 | 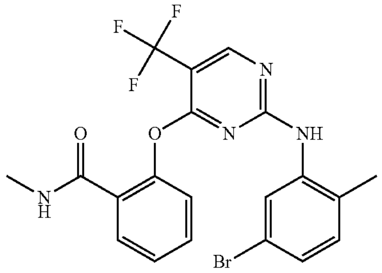 | C |
| 101 | 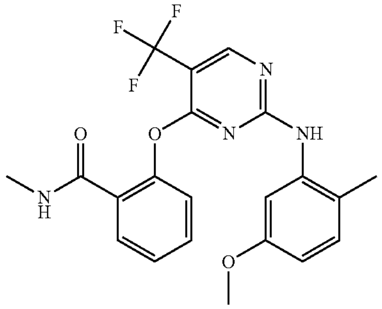 | C |

TABLE 1-continued
| Example | Structure | $IC_{50}$ |
|---|---|---|
| 102 | 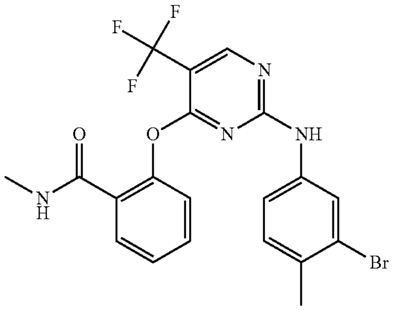 [SMILES: CNC(=O)c1ccccc1Oc1nc(Nc2ccc(C)c(Br)c2)ncc1C(F)(F)F] | C |
| 103 | 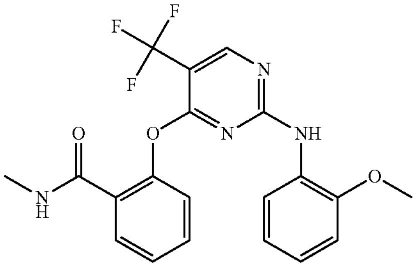 | C |
| 104 | 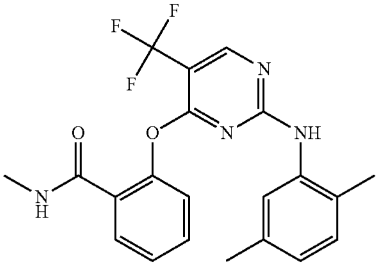 | C |
| 105a | 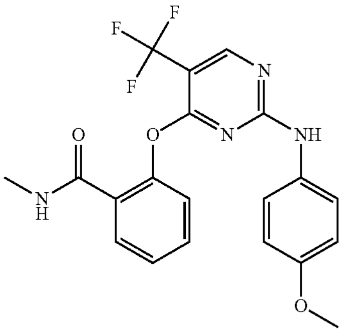 | C |
| 105b | 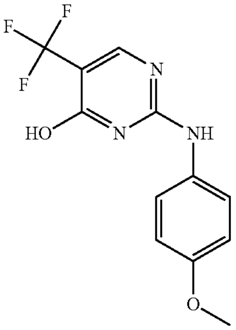 [SMILES: COc1ccc(Nc2ncc(C(F)(F)F)c(O)n2)cc1] | C |

TABLE 1-continued
| Example | Structure | IC50 |
|---|---|---|
| 106 | 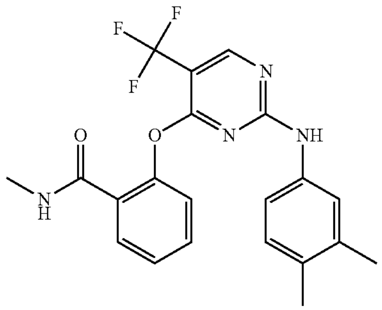 | B |
| 107 | 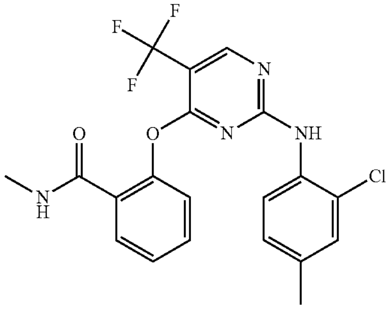 [SMILES: CNC(=O)c1ccccc1Oc1nc(Nc2ccc(C)cc2Cl)ncc1C(F)(F)F] | C |
| 108a | 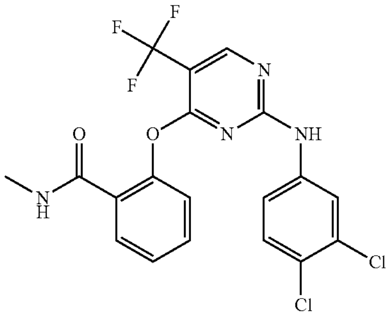 [SMILES: CNC(=O)c1ccccc1Oc1nc(Nc2ccc(Cl)c(Cl)c2)ncc1C(F)(F)F] | C |
| 108b | 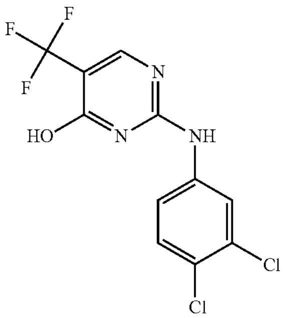 [SMILES: Oc1nc(Nc2ccc(Cl)c(Cl)c2)ncc1C(F)(F)F] | C |
| 109a | 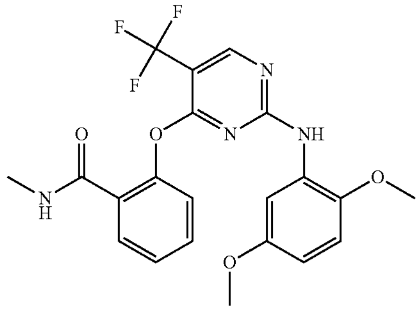 | C |

TABLE 1-continued
| Example | Structure | $IC_{50}$ |
|---|---|---|
| 109b | 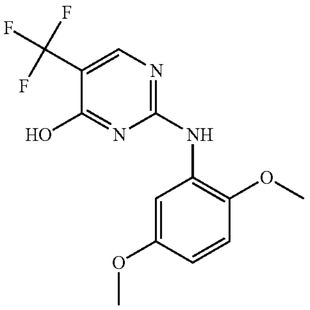 [SMILES: COc1ccc(OC)c(Nc2ncc(C(F)(F)F)c(O)n2)c1] | C |
| 110 | 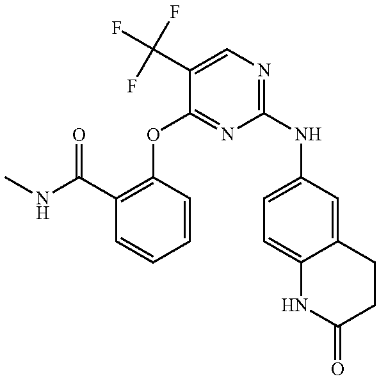 [SMILES: CNC(=O)c1ccccc1Oc1nc(Nc2ccc3c(c2)CCC(=O)N3)ncc1C(F)(F)F] | B |
| 111 | 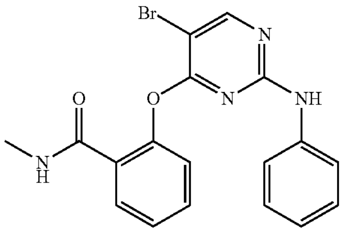 [SMILES: CNC(=O)c1ccccc1Oc1nc(Nc2ccccc2)ncc1Br] | C |
| 112 | 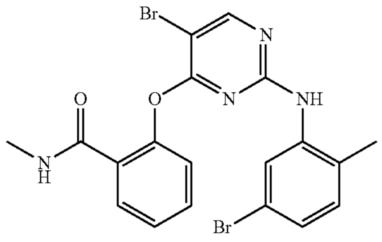 | C |
| 113 | 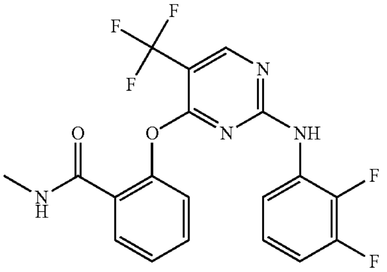 [SMILES: CNC(=O)c1ccccc1Oc1nc(Nc2cccc(F)c2F)ncc1C(F)(F)F] | C |

TABLE 1-continued
| Example | Structure | $IC_{50}$ |
| --- | --- | --- |
| 114 | 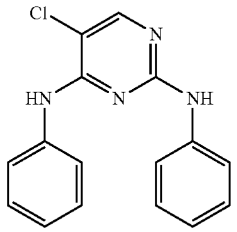 [SMILES: Clc1cnc(Nc2ccccc2)nc1Nc1ccccc1] | C |
| 115a | 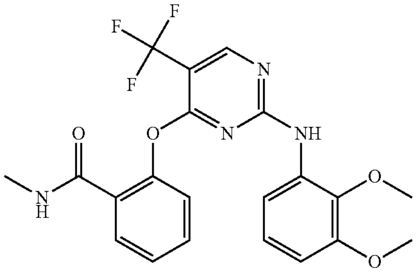 | C |
| 115b | 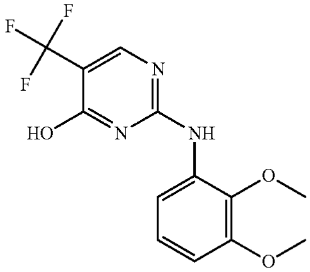 [SMILES: COc1cccc(Nc2ncc(C(F)(F)F)c(O)n2)c1OC] | C |
| 116a | 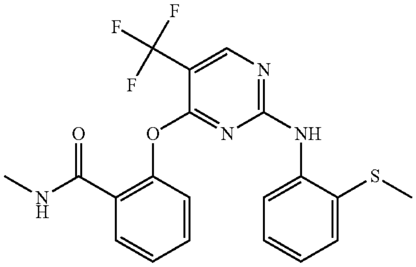 | C |
| 116b | 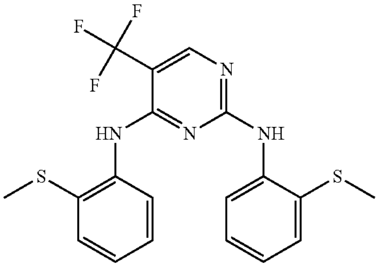 | C |

TABLE 1-continued
| Example | Structure | $IC_{50}$ |
|---|---|---|
| 117 | 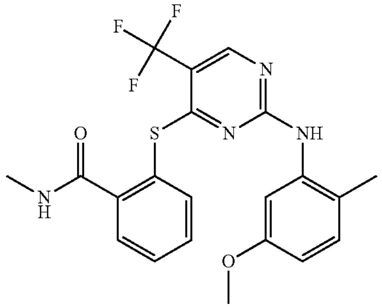 | C |
| 118a | 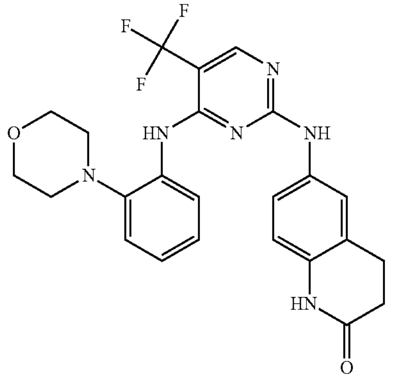 [SMILES: O=C1CCc2cc(Nc3ncc(C(F)(F)F)c(Nc4ccccc4N4CCOCC4)n3)ccc2N1] | A |
| 118b | 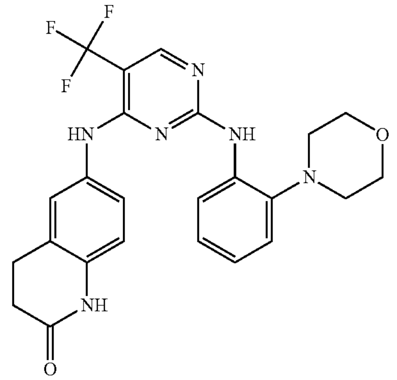 [SMILES: O=C1CCc2cc(Nc3nc(Nc4ccccc4N4CCOCC4)ncc3C(F)(F)F)ccc2N1] | C |
| 118c | 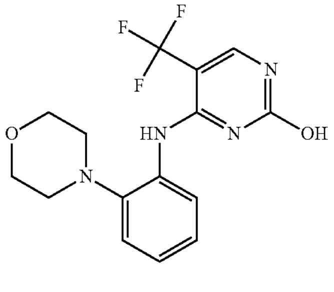 [SMILES: Oc1ncc(C(F)(F)F)c(Nc2ccccc2N2CCOCC2)n1] | C |

TABLE 1-continued
| Example | Structure | $IC_{50}$ |
| --- | --- | --- |
| 119 | 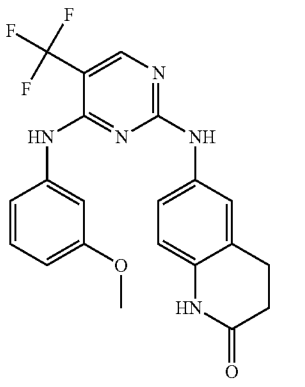 [SMILES: COc1cccc(Nc2nc(Nc3ccc4c(c3)CCC(=O)N4)ncc2C(F)(F)F)c1] | A |
| 120a | 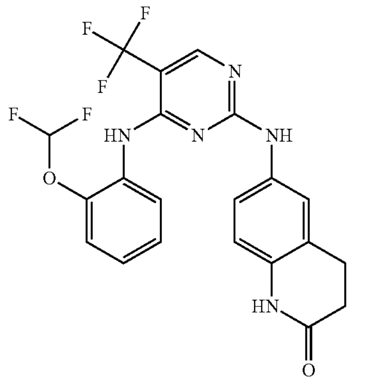 [SMILES: O=C1CCc2cc(Nc3ncc(C(F)(F)F)c(Nc4ccccc4OC(F)F)n3)ccc2N1] | A |
| 120b | 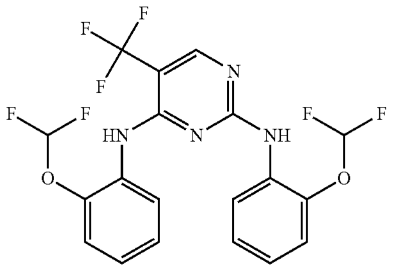 [SMILES: FC(F)Oc1ccccc1Nc1ncc(C(F)(F)F)c(Nc2ccccc2OC(F)F)n1] | B |
| 120c | 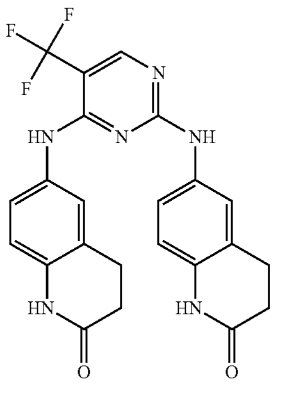 [SMILES: O=C1CCc2cc(Nc3ncc(C(F)(F)F)c(Nc4ccc5c(c4)CCC(=O)N5)n3)ccc2N1] | A |

TABLE 1-continued
| Example | Structure | IC50 |
| --- | --- | --- |
| 121 | 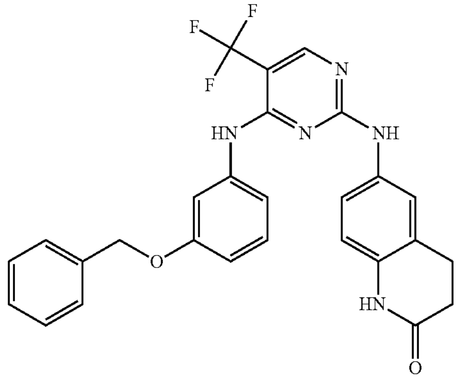 [SMILES: O=C1CCc2cc(Nc3ncc(C(F)(F)F)c(Nc4cccc(OCc5ccccc5)c4)n3)ccc2N1] | B |
| 122 | 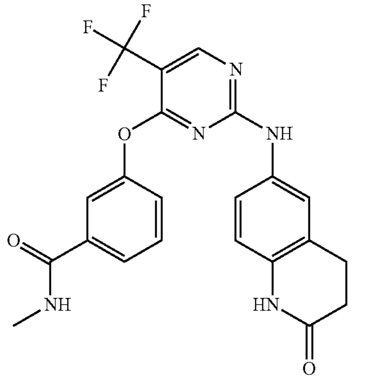 [SMILES: CNC(=O)c1cccc(Oc2nc(Nc3ccc4c(c3)CCC(=O)N4)ncc2C(F)(F)F)c1] | B |
| 123a | 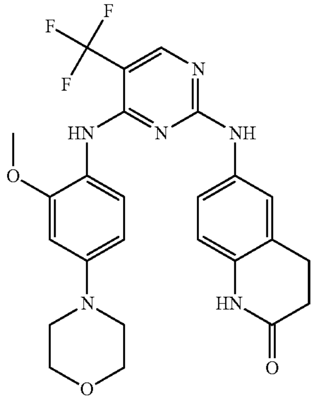 [SMILES: COc1cc(N2CCOCC2)ccc1Nc1nc(Nc2ccc3c(c2)CCC(=O)N3)ncc1C(F)(F)F] | A |
| 123b | 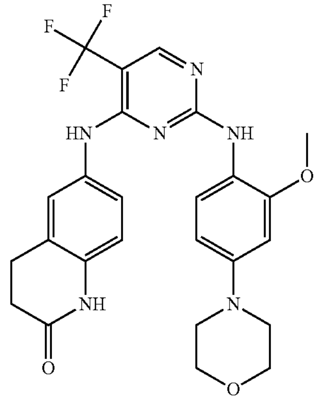 [SMILES: COc1cc(N2CCOCC2)ccc1Nc1ncc(C(F)(F)F)c(Nc2ccc3c(c2)CCC(=O)N3)n1] | A |

TABLE 1-continued
| Example | Structure | $IC_{50}$ |
| --- | --- | --- |
| 124* | 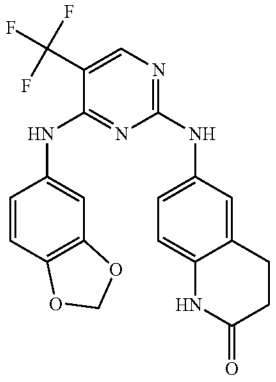 [SMILES: O=C1CCc2cc(Nc3ncc(C(F)(F)F)c(Nc4ccc5c(c4)OCO5)n3)ccc2N1] | A |
| 124c | 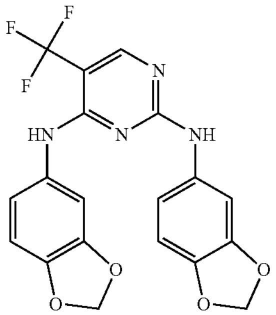 [SMILES: FC(F)(F)c1cnc(Nc2ccc3c(c2)OCO3)nc1Nc1ccc2c(c1)OCO2] | A |
| 125 | 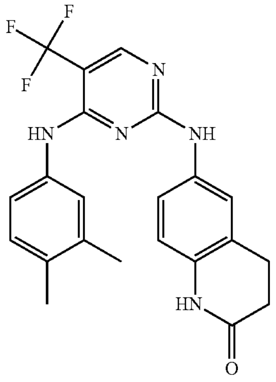 [SMILES: Cc1ccc(Nc2nc(Nc3ccc4c(c3)CCC(=O)N4)ncc2C(F)(F)F)cc1C] | A |
| 126a | 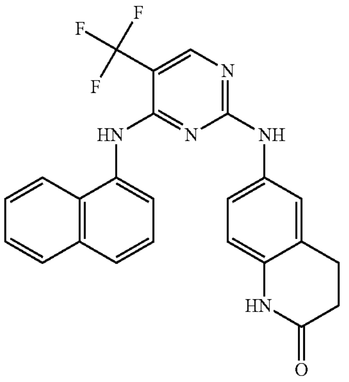 [SMILES: O=C1CCc2cc(Nc3ncc(C(F)(F)F)c(Nc4cccc5ccccc45)n3)ccc2N1] | B |

TABLE 1-continued
| Example | Structure | $IC_{50}$ |
|---|---|---|
| 126b | 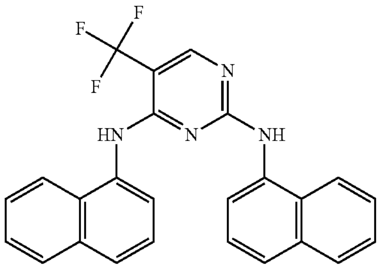 [SMILES: FC(F)(F)c1cnc(Nc2cccc3ccccc23)nc1Nc1cccc2ccccc12] | B |
| 127 | 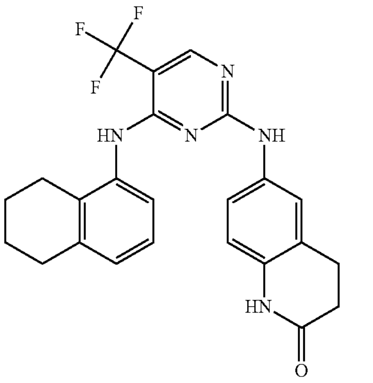 [SMILES: O=C1CCc2cc(Nc3ncc(C(F)(F)F)c(Nc4cccc5c4CCCC5)n3)ccc2N1] | B |
| 128 | 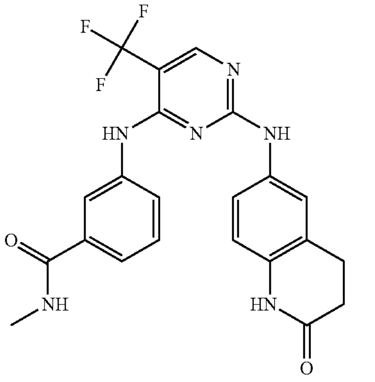 [SMILES: CNC(=O)c1cccc(Nc2nc(Nc3ccc4c(c3)CCC(=O)N4)ncc2C(F)(F)F)c1] | A |
| 129 | 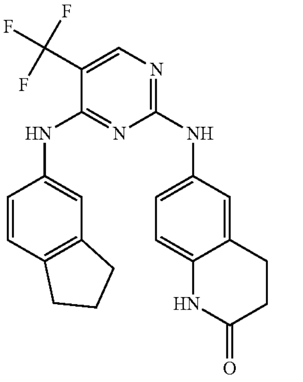 [SMILES: O=C1CCc2cc(Nc3ncc(C(F)(F)F)c(Nc4ccc5c(c4)CCC5)n3)ccc2N1] | A |

TABLE 1-continued
| Example | Structure | $IC_{50}$ |
| --- | --- | --- |
| 130a | 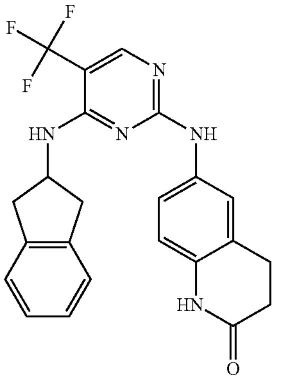 [SMILES: O=C1CCc2cc(Nc3ncc(C(F)(F)F)c(NC4Cc5ccccc5C4)n3)ccc2N1] | A |
| 130b | 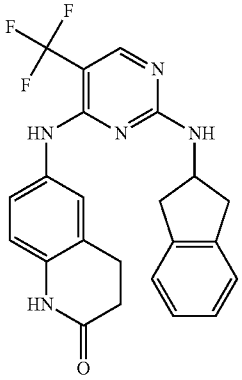 [SMILES: O=C1CCc2cc(Nc3nc(NC4Cc5ccccc5C4)ncc3C(F)(F)F)ccc2N1] | C |
| 131a | 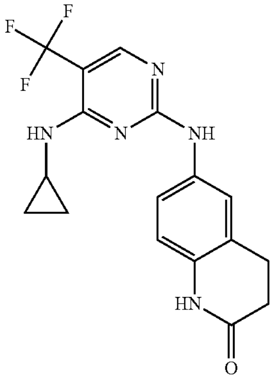 [SMILES: O=C1CCc2cc(Nc3ncc(C(F)(F)F)c(NC4CC4)n3)ccc2N1] | A |
| 131b | 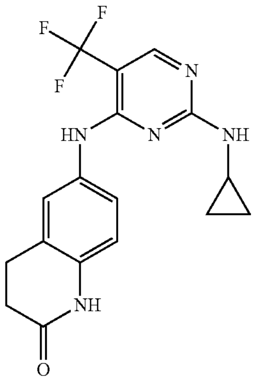 [SMILES: O=C1CCc2cc(Nc3nc(NC4CC4)ncc3C(F)(F)F)ccc2N1] | A |

TABLE 1-continued
| Example | Structure | $IC_{50}$ |
| --- | --- | --- |
| 132 | 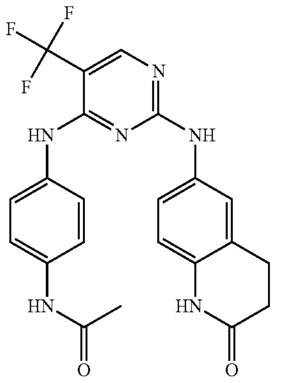 [SMILES: CC(=O)Nc1ccc(Nc2nc(Nc3ccc4c(c3)CCC(=O)N4)ncc2C(F)(F)F)cc1] | A |
| 133 | 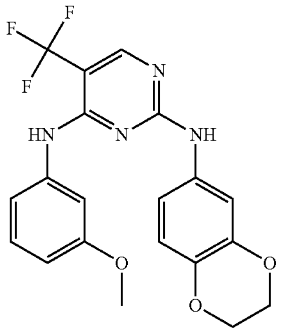 [SMILES: COc1cccc(Nc2nc(Nc3ccc4c(c3)OCCO4)ncc2C(F)(F)F)c1] | A |
| 134 | 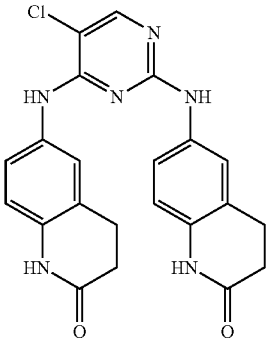 [SMILES: O=C1CCc2cc(Nc3ncc(Cl)c(Nc4ccc5c(c4)CCC(=O)N5)n3)ccc2N1] | A |
| 135 | 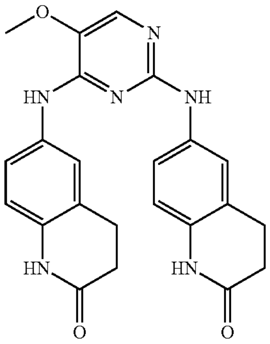 [SMILES: COc1cnc(Nc2ccc3c(c2)CCC(=O)N3)nc1Nc1ccc2c(c1)CCC(=O)N2] | C |

TABLE 1-continued
| Example | Structure | $IC_{50}$ |
| --- | --- | --- |
| 136* | 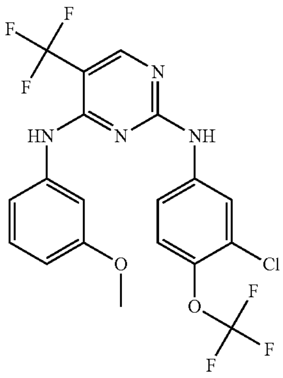 [SMILES: COc1cccc(Nc2nc(Nc3ccc(OC(F)(F)F)c(Cl)c3)ncc2C(F)(F)F)c1] | C |
| 137* | 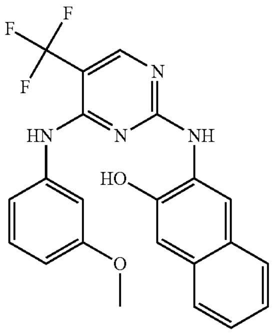 [SMILES: COc1cccc(Nc2nc(Nc3cc4ccccc4cc3O)ncc2C(F)(F)F)c1] | B |
| 138* | 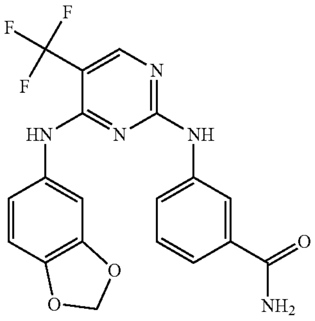 [SMILES: NC(=O)c1cccc(Nc2ncc(C(F)(F)F)c(Nc3ccc4c(c3)OCO4)n2)c1] | A |
| 139* | 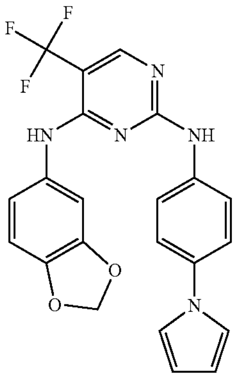 [SMILES: FC(F)(F)c1cnc(Nc2ccc(-n3cccc3)cc2)nc1Nc1ccc2c(c1)OCO2] | A |

TABLE 1-continued
| Example | Structure | IC50 |
| --- | --- | --- |
| 140* | 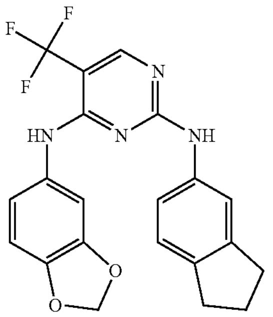 [SMILES: FC(F)(F)c1cnc(Nc2ccc3c(c2)CCC3)nc1Nc1ccc2c(c1)OCO2] | A |
| 141a | 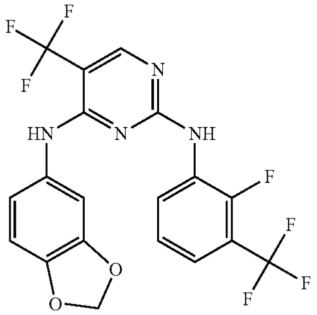 [SMILES: Fc1c(Nc2ncc(C(F)(F)F)c(Nc3ccc4c(c3)OCO4)n2)cccc1C(F)(F)F] | C |
| 141b | 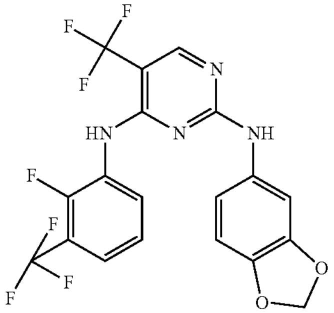 [SMILES: Fc1c(Nc2nc(Nc3ccc4c(c3)OCO4)ncc2C(F)(F)F)cccc1C(F)(F)F] | A |
| 142 | 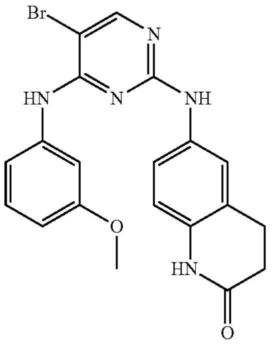 | A |

TABLE 1-continued
| Example | Structure | $IC_{50}$ |
|---|---|---|
| 143a | 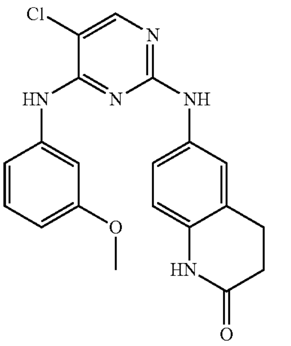 [SMILES: COc1cccc(Nc2nc(Nc3ccc4c(c3)CCC(=O)N4)ncc2Cl)c1] | A |
| 143b | 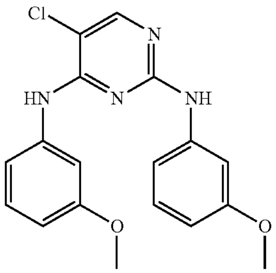 [SMILES: COc1cccc(Nc2ncc(Cl)c(Nc3cccc(OC)c3)n2)c1] | A |
| 144* | 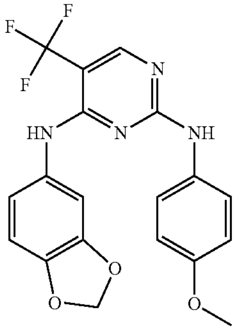 [SMILES: COc1ccc(Nc2ncc(C(F)(F)F)c(Nc3ccc4c(c3)OCO4)n2)cc1] | A |
| 145* | 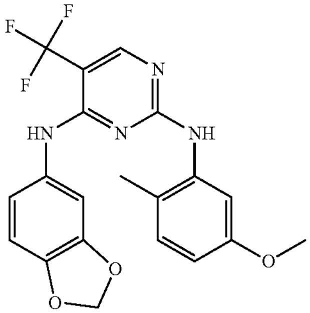 [SMILES: COc1ccc(C)c(Nc2ncc(C(F)(F)F)c(Nc3ccc4c(c3)OCO4)n2)c1] | B |
| 146* | 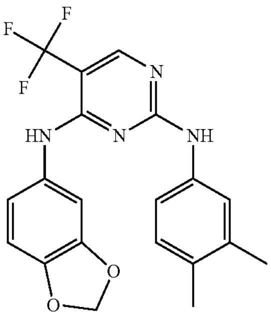 [SMILES: Cc1ccc(Nc2ncc(C(F)(F)F)c(Nc3ccc4c(c3)OCO4)n2)cc1C] | B |

TABLE 1-continued
| Example | Structure | $IC_{50}$ |
| --- | --- | --- |
| 147* | 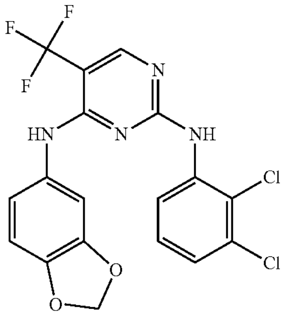 [SMILES: FC(F)(F)c1cnc(Nc2cccc(Cl)c2Cl)nc1Nc1ccc2c(c1)OCO2] | C |
| 148* | 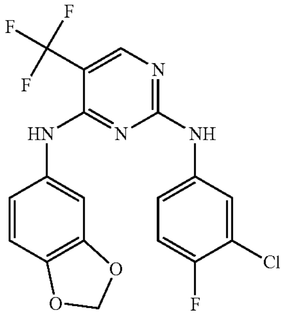 [SMILES: Fc1ccc(Nc2ncc(C(F)(F)F)c(Nc3ccc4c(c3)OCO4)n2)cc1Cl] | B |
| 149* | 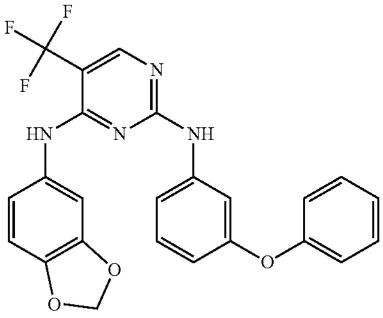 [SMILES: FC(F)(F)c1cnc(Nc2cccc(Oc3ccccc3)c2)nc1Nc1ccc2c(c1)OCO2] | C |
| 150a | 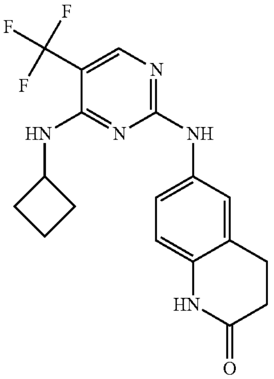 | A |

TABLE 1-continued
| Example | Structure | $IC_{50}$ |
|---|---|---|
| 150b | 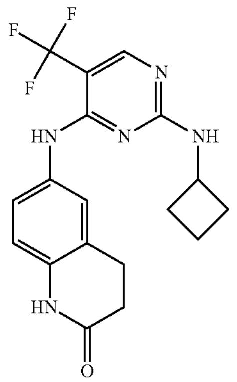 [SMILES: O=C1CCc2cc(Nc3nc(NC4CCC4)ncc3C(F)(F)F)ccc2N1] | A |
| 151a | 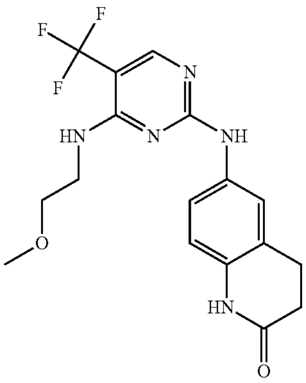 [SMILES: COCCNc1nc(Nc2ccc3c(c2)CCC(=O)N3)ncc1C(F)(F)F] | A |
| 151b | 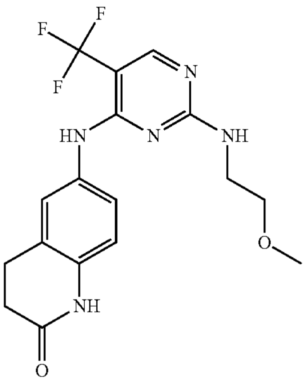 [SMILES: COCCNc1ncc(C(F)(F)F)c(Nc2ccc3c(c2)CCC(=O)N3)n1] | A |
| 152a | 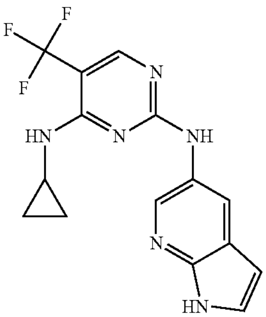 [SMILES: FC(F)(F)c1cnc(Nc2cnc3[nH]ccc3c2)nc1NC1CC1] | A |

TABLE 1-continued
| Example | Structure | $IC_{50}$ |
|---|---|---|
| 152b | 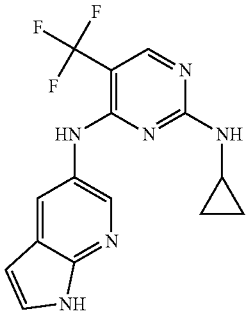 [SMILES: FC(F)(F)c1cnc(NC2CC2)nc1Nc1cnc2[nH]ccc2c1] | B |
| 153 | 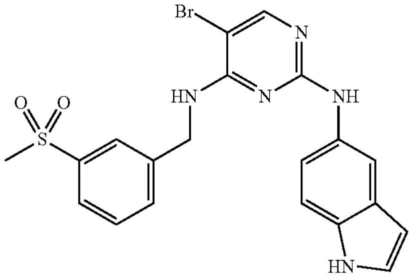 [SMILES: CS(=O)(=O)c1cccc(CNc2nc(Nc3ccc4[nH]ccc4c3)ncc2Br)c1] | C |
| 154 | 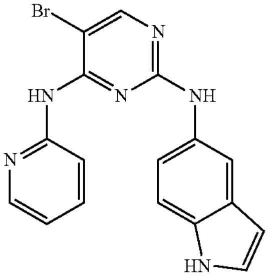 [SMILES: Brc1cnc(Nc2ccc3[nH]ccc3c2)nc1Nc1ccccn1] | A |
| 155 | 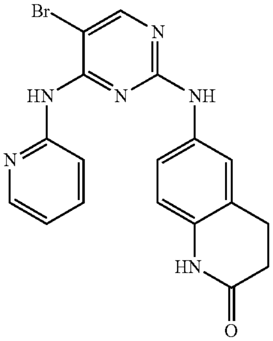 [SMILES: O=C1CCc2cc(Nc3ncc(Br)c(Nc4ccccn4)n3)ccc2N1] | A |
| 156 | 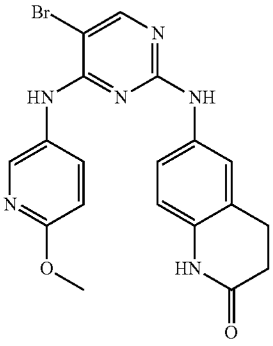 [SMILES: COc1ccc(Nc2nc(Nc3ccc4c(c3)CCC(=O)N4)ncc2Br)cn1] | A |

TABLE 1-continued
| Example | Structure | $IC_{50}$ |
|---|---|---|
| 157* | 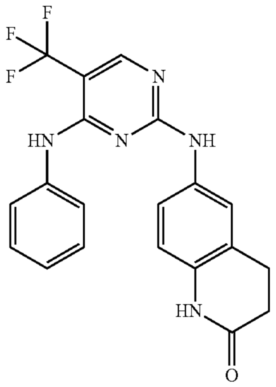 [SMILES: O=C1CCc2cc(Nc3ncc(C(F)(F)F)c(Nc4ccccc4)n3)ccc2N1] | A |
| 158a | 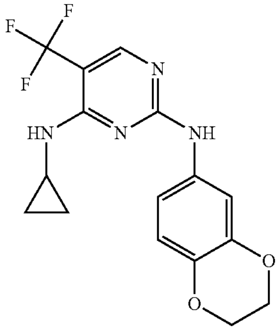 [SMILES: FC(F)(F)c1cnc(Nc2ccc3c(c2)OCCO3)nc1NC1CC1] | A |
| 158b | 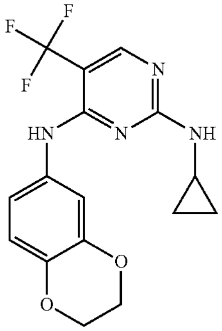 [SMILES: FC(F)(F)c1cnc(NC2CC2)nc1Nc1ccc2c(c1)OCCO2] | A |
| 159 | 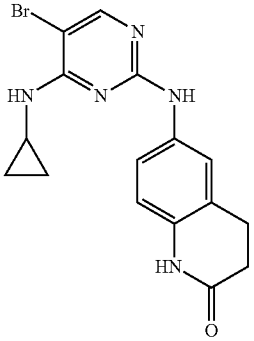 [SMILES: O=C1CCc2cc(Nc3ncc(Br)c(NC4CC4)n3)ccc2N1] | A |

TABLE 1-continued
| Example | Structure | $IC_{50}$ |
|---|---|---|
| 160a | 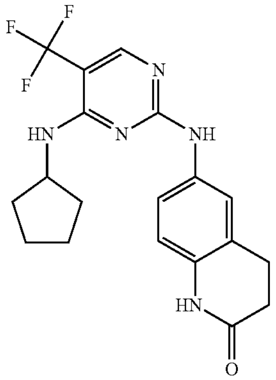 [SMILES: O=C1CCc2cc(Nc3ncc(C(F)(F)F)c(NC4CCCC4)n3)ccc2N1] | A |
| 160b | 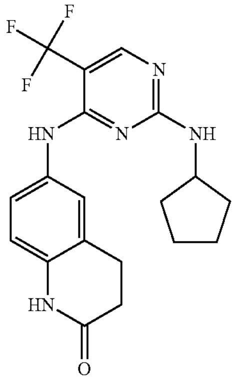 [SMILES: O=C1CCc2cc(Nc3nc(NC4CCCC4)ncc3C(F)(F)F)ccc2N1] | B |
| 161a | 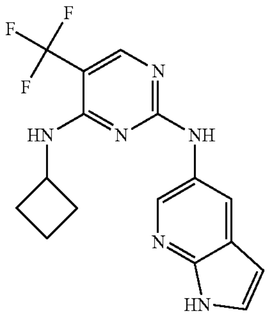 [SMILES: FC(F)(F)c1cnc(Nc2cnc3[nH]ccc3c2)nc1NC1CCC1] | A |
| 161b | 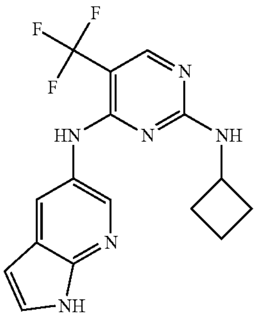 [SMILES: FC(F)(F)c1cnc(NC2CCC2)nc1Nc1cnc2[nH]ccc2c1] | A |

TABLE 1-continued
| Example | Structure | $IC_{50}$ |
| --- | --- | --- |
| 163a | 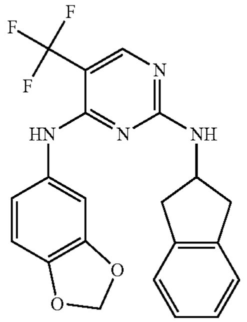 [SMILES: FC(F)(F)c1cnc(NC2Cc3ccccc3C2)nc1Nc1ccc2c(c1)OCO2] | C |
| 163b | 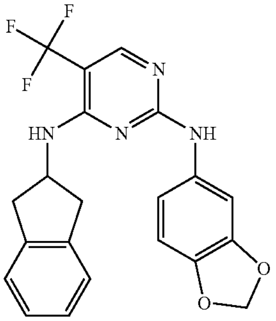 [SMILES: FC(F)(F)c1cnc(Nc2ccc3c(c2)OCO3)nc1NC1Cc2ccccc2C1] | C |
| 164a | 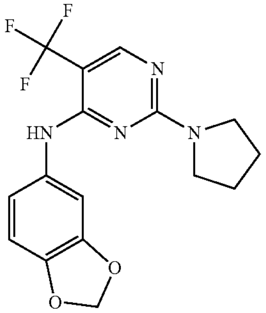 [SMILES: FC(F)(F)c1cnc(N2CCCC2)nc1Nc1ccc2c(c1)OCO2] | C |
| 164b | 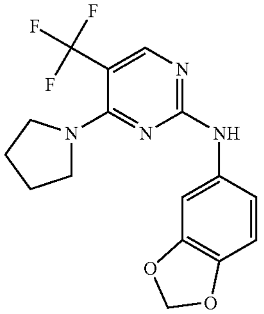 [SMILES: FC(F)(F)c1cnc(Nc2ccc3c(c2)OCO3)nc1N1CCCC1] | B |
| 165a | 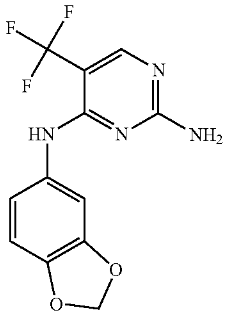 [SMILES: Nc1ncc(C(F)(F)F)c(Nc2ccc3c(c2)OCO3)n1] | B |

TABLE 1-continued
| Example | Structure | $IC_{50}$ |
|---|---|---|
| 165b | 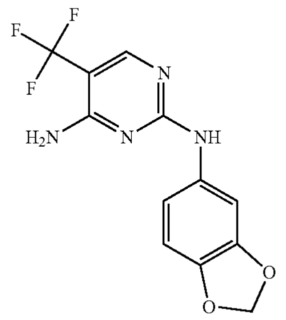 [SMILES: Nc1nc(Nc2ccc3c(c2)OCO3)ncc1C(F)(F)F] | B |
| 166a | 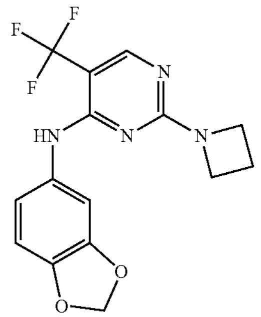 [SMILES: FC(F)(F)c1cnc(N2CCC2)nc1Nc1ccc2c(c1)OCO2] | C |
| 166b | 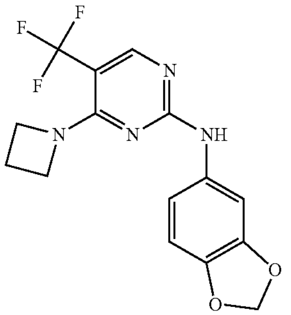 [SMILES: FC(F)(F)c1cnc(Nc2ccc3c(c2)OCO3)nc1N1CCC1] | A |
| 167a | 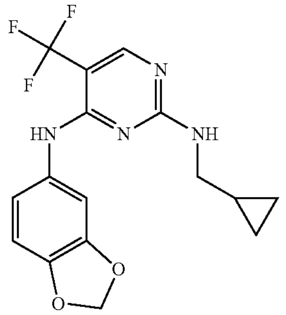 [SMILES: FC(F)(F)c1cnc(NCC2CC2)nc1Nc1ccc2c(c1)OCO2] | A |
| 167b | 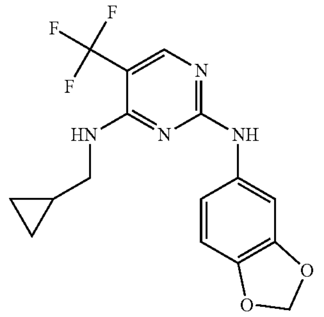 [SMILES: FC(F)(F)c1cnc(Nc2ccc3c(c2)OCO3)nc1NCC1CC1] | A |

TABLE 1-continued
| Example | Structure | $IC_{50}$ |
|---|---|---|
| 168a | 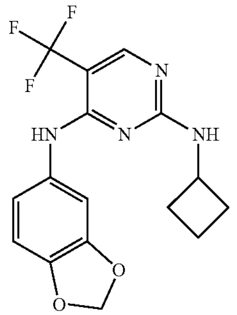 [SMILES: FC(F)(F)c1cnc(NC2CCC2)nc1Nc1ccc2c(c1)OCO2] | A |
| 168b | 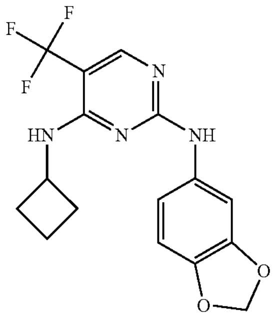 [SMILES: FC(F)(F)c1cnc(Nc2ccc3c(c2)OCO3)nc1NC1CCC1] | B |
| 168c | 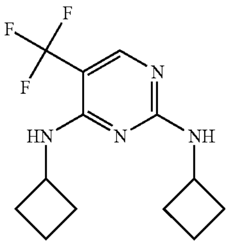 [SMILES: FC(F)(F)c1cnc(NC2CCC2)nc1NC1CCC1] | B |
| 169 | 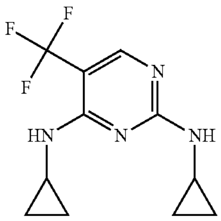 [SMILES: FC(F)(F)c1cnc(NC2CC2)nc1NC1CC1] | C |
| 170 | 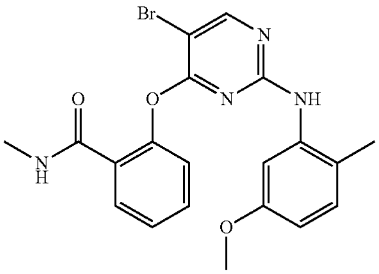 | C |

TABLE 1-continued
| Example | Structure | $IC_{50}$ |
|---|---|---|
| 171a | 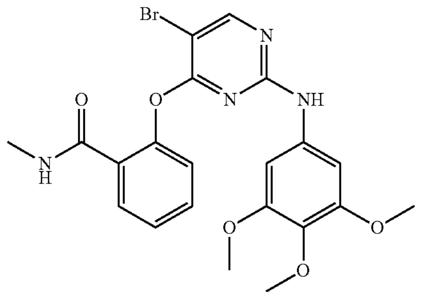 | A |
| 171b | 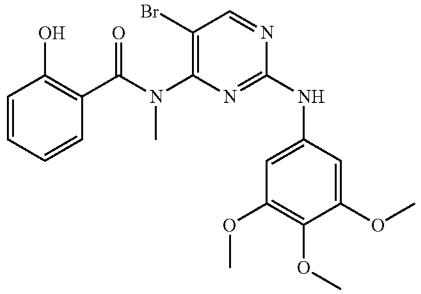 | A |
| 172 | 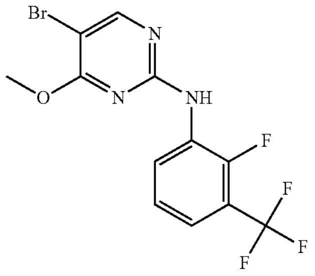 [SMILES: COc1nc(Nc2cccc(C(F)(F)F)c2F)ncc1Br] | B |
| 173 | 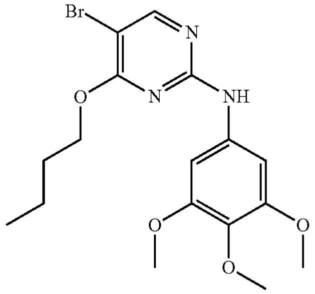 [SMILES: CCCCOc1nc(Nc2cc(OC)c(OC)c(OC)c2)ncc1Br] | A |
| 174 | 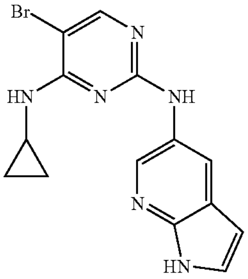 [SMILES: Brc1cnc(Nc2cnc3[nH]ccc3c2)nc1NC1CC1] | A |

TABLE 1-continued
| Example | Structure | IC<sub>50</sub> |
|---|---|---|
| 175 | 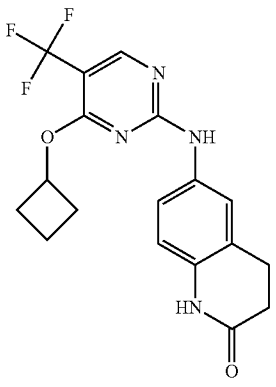 [SMILES: O=C1CCc2cc(Nc3ncc(C(F)(F)F)c(OC4CCC4)n3)ccc2N1] | A |
| 177 | 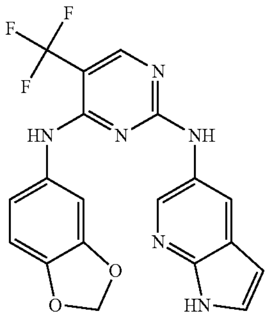 [SMILES: FC(F)(F)c1cnc(Nc2cnc3[nH]ccc3c2)nc1Nc1ccc2c(c1)OCO2] | A |
| 178a | 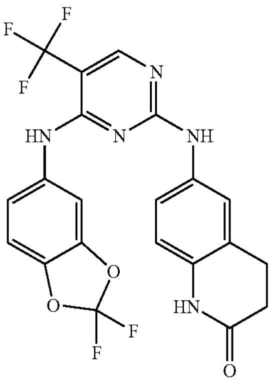 [SMILES: O=C1CCc2cc(Nc3ncc(C(F)(F)F)c(Nc4ccc5c(c4)OC(F)(F)O5)n3)ccc2N1] | A |
| 178b | 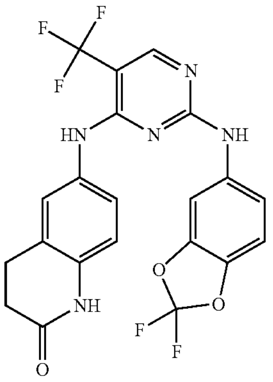 [SMILES: O=C1CCc2cc(Nc3nc(Nc4ccc5c(c4)OC(F)(F)O5)ncc3C(F)(F)F)ccc2N1] | A |

TABLE 1-continued
| Example | Structure | $IC_{50}$ |
|---|---|---|
| 179 | 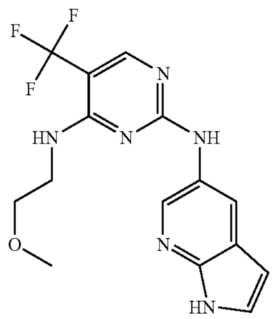 [SMILES: COCCNc1nc(Nc2cnc3[nH]ccc3c2)ncc1C(F)(F)F] | B |
| 180a | 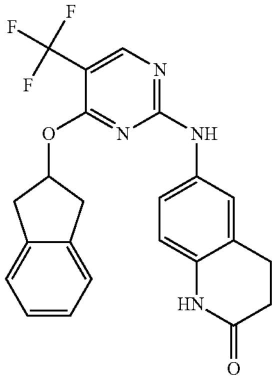 [SMILES: O=C1CCc2cc(Nc3ncc(C(F)(F)F)c(OC4Cc5ccccc5C4)n3)ccc2N1] | A |
| 180b | 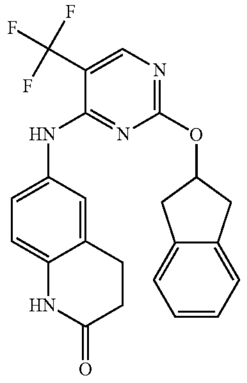 [SMILES: O=C1CCc2cc(Nc3nc(OC4Cc5ccccc5C4)ncc3C(F)(F)F)ccc2N1] | C |
| 181a | 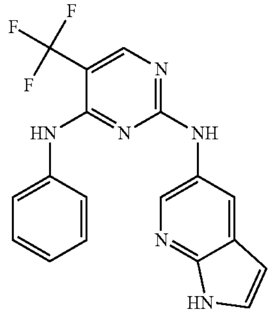 [SMILES: FC(F)(F)c1cnc(Nc2cnc3[nH]ccc3c2)nc1Nc1ccccc1] | A |

TABLE 1-continued
| Example | Structure | IC$_{50}$ |
| --- | --- | --- |
| 181b | 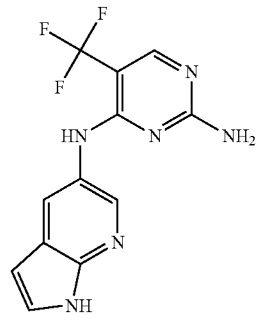 [SMILES: Nc1ncc(C(F)(F)F)c(Nc2cnc3[nH]ccc3c2)n1] | B |
| 182a | 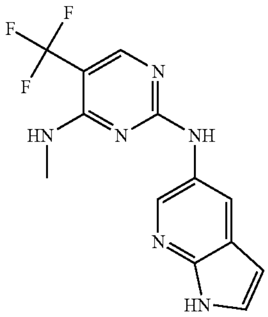 [SMILES: CNc1nc(Nc2cnc3[nH]ccc3c2)ncc1C(F)(F)F] | A |
| 182b | 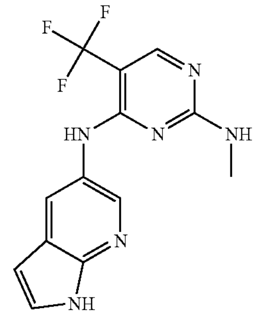 [SMILES: CNc1ncc(C(F)(F)F)c(Nc2cnc3[nH]ccc3c2)n1] | B |
| 183a | 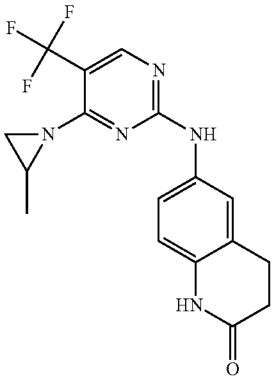 [SMILES: CC1CN1c1nc(Nc2ccc3c(c2)CCC(=O)N3)ncc1C(F)(F)F] | C |

TABLE 1-continued
| Example | Structure | $IC_{50}$ |
| --- | --- | --- |
| 183b | 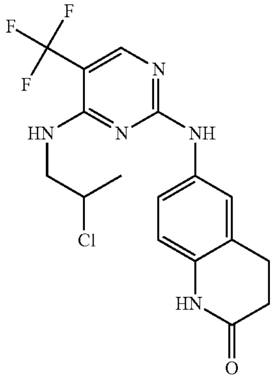 [SMILES: CC(Cl)CNc1nc(Nc2ccc3c(c2)CCC(=O)N3)ncc1C(F)(F)F] | A |
| 183c | 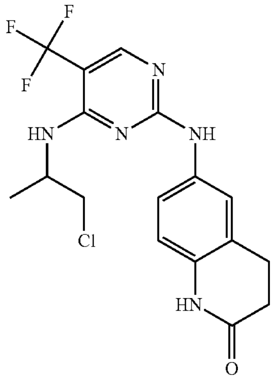 [SMILES: CC(CCl)Nc1nc(Nc2ccc3c(c2)CCC(=O)N3)ncc1C(F)(F)F] | C |
| 184a | 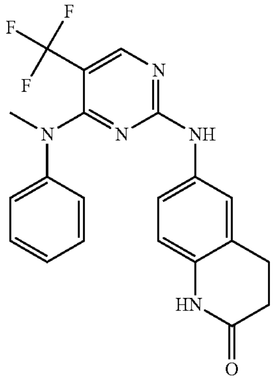 [SMILES: CN(c1ccccc1)c1nc(Nc2ccc3c(c2)CCC(=O)N3)ncc1C(F)(F)F] | B |
| 184b | 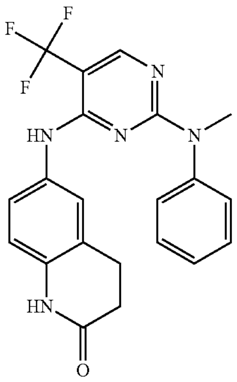 [SMILES: CN(c1ccccc1)c1ncc(C(F)(F)F)c(Nc2ccc3c(c2)CCC(=O)N3)n1] | A |

TABLE 1-continued
| Example | Structure | IC50 |
| --- | --- | --- |
| 185 | 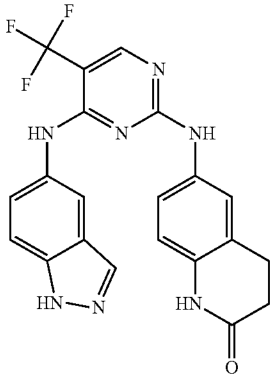 [SMILES: O=C1CCc2cc(Nc3ncc(C(F)(F)F)c(Nc4ccc5[nH]ncc5c4)n3)ccc2N1] | A |
| 186 | 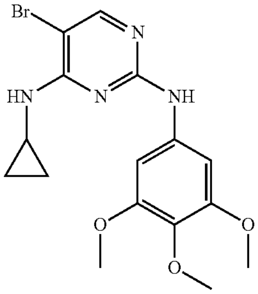 [SMILES: COc1cc(Nc2ncc(Br)c(NC3CC3)n2)cc(OC)c1OC] | A |
| 187 | 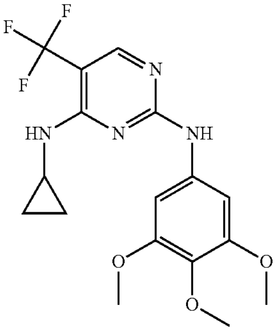 [SMILES: COc1cc(Nc2ncc(C(F)(F)F)c(NC3CC3)n2)cc(OC)c1OC] | A |
| 188 | 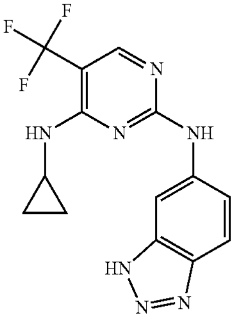 [SMILES: FC(F)(F)c1cnc(Nc2ccc3nn[nH]c3c2)nc1NC1CC1] | A |
| 189 | 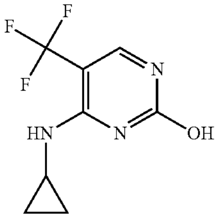 [SMILES: Oc1ncc(C(F)(F)F)c(NC2CC2)n1] | C |

TABLE 1-continued
| Example | Structure | $IC_{50}$ |
|---|---|---|
| 190 | 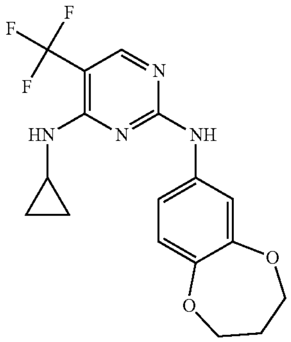 [SMILES: FC(F)(F)c1cnc(Nc2ccc3c(c2)OCCCO3)nc1NC1CC1] | A |
| 192 | 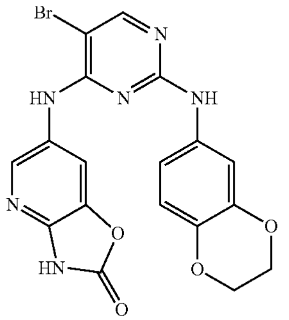 [SMILES: O=c1[nH]c2ncc(Nc3nc(Nc4ccc5c(c4)OCCO5)ncc3Br)cc2o1] | A |
| 193 | 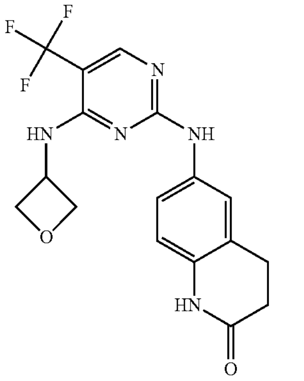 [SMILES: O=C1CCc2cc(Nc3ncc(C(F)(F)F)c(NC4COC4)n3)ccc2N1] | C |
| 194 | 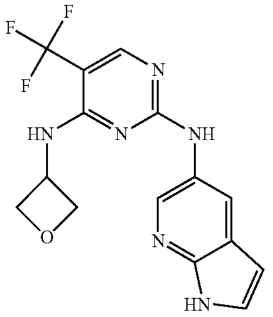 [SMILES: FC(F)(F)c1cnc(Nc2cnc3[nH]ccc3c2)nc1NC1COC1] | A |

TABLE 1-continued
| Example | Structure | IC$_{50}$ |
| --- | --- | --- |
| 195 | 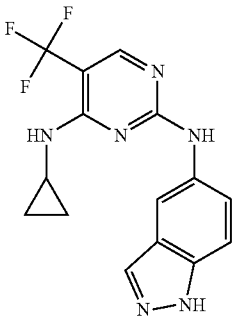 [SMILES: FC(F)(F)c1cnc(Nc2ccc3[nH]ncc3c2)nc1NC1CC1] | A |
| 196 | 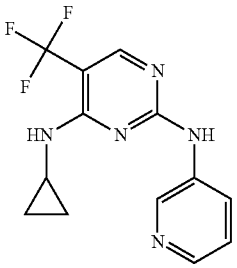 [SMILES: FC(F)(F)c1cnc(Nc2cccnc2)nc1NC1CC1] | C |
| 197 | 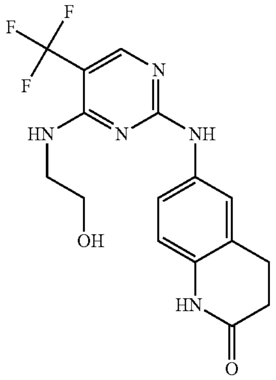 [SMILES: O=C1CCc2cc(Nc3ncc(C(F)(F)F)c(NCCO)n3)ccc2N1] | A |
| 198a | 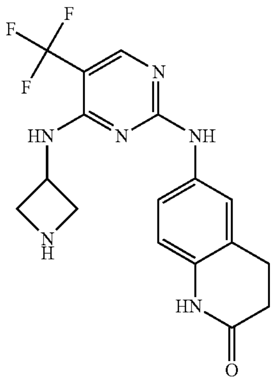 [SMILES: O=C1CCc2cc(Nc3ncc(C(F)(F)F)c(NC4CNC4)n3)ccc2N1] | B |

TABLE 1-continued
| Example | Structure | $IC_{50}$ |
|---|---|---|
| 198b | 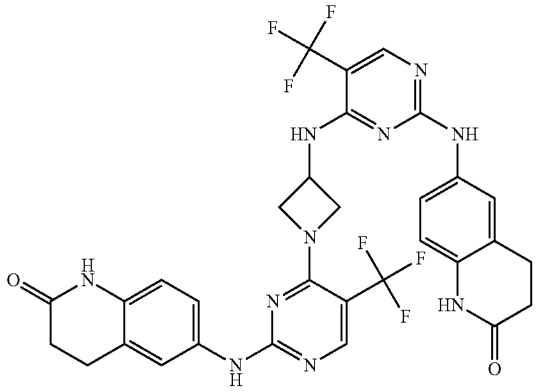 [SMILES: O=C1CCc2cc(Nc3ncc(C(F)(F)F)c(NC4CN(c5nc(Nc6ccc7c(c6)CCC(=O)N7)ncc5C(F)(F)F)C4)n3)ccc2N1] | C |
| 199 | 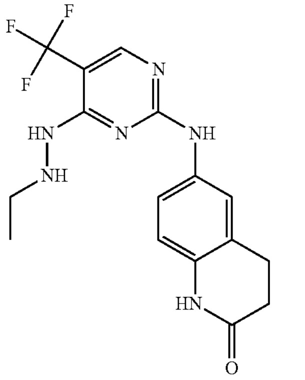 [SMILES: CCNNc1nc(Nc2ccc3c(c2)CCC(=O)N3)ncc1C(F)(F)F] | A |
| 200 | 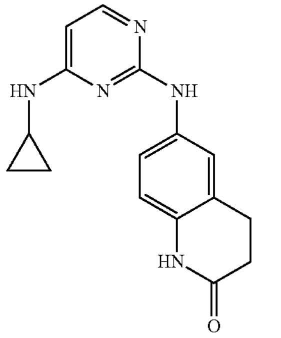 [SMILES: O=C1CCc2cc(Nc3nccc(NC4CC4)n3)ccc2N1] | C |
| 201 | 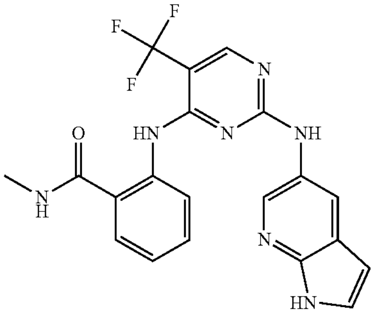 [SMILES: CNC(=O)c1ccccc1Nc1nc(Nc2cnc3[nH]ccc3c2)ncc1C(F)(F)F] | A |

TABLE 1-continued
| Example | Structure | $IC_{50}$ |
|---|---|---|
| 202 | 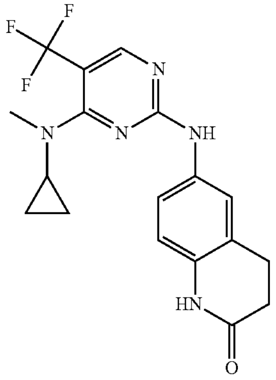 [SMILES: CN(c1nc(Nc2ccc3c(c2)CCC(=O)N3)ncc1C(F)(F)F)C1CC1] | A |
| 203 | 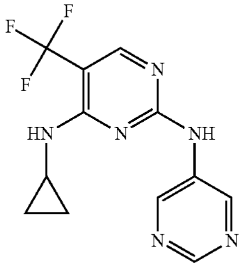 [SMILES: FC(F)(F)c1cnc(Nc2cncnc2)nc1NC1CC1] | A |
| 204 | 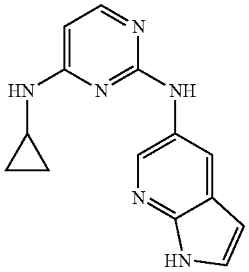 [SMILES: c1cc(NC2CC2)nc(Nc2cnc3[nH]ccc3c2)n1] | C |
| 205 | 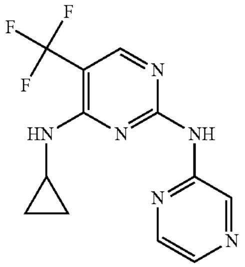 [SMILES: FC(F)(F)c1cnc(Nc2cnccn2)nc1NC1CC1] | C |
| 206 | 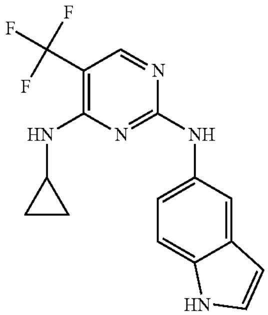 [SMILES: FC(F)(F)c1cnc(Nc2ccc3[nH]ccc3c2)nc1NC1CC1] | A |

TABLE 1-continued
| Example | Structure | IC<sub>50</sub> |
|---|---|---|
| 207 | 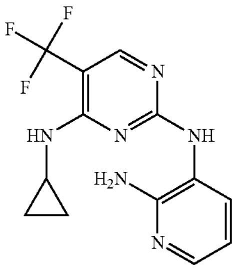 [SMILES: Nc1ncccc1Nc1ncc(C(F)(F)F)c(NC2CC2)n1] | C |
| 208a | 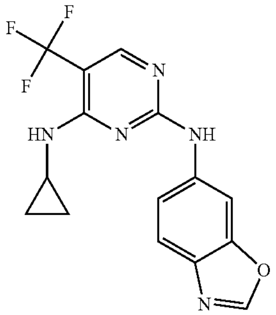 [SMILES: FC(F)(F)c1cnc(Nc2ccc3ncoc3c2)nc1NC1CC1] | A |
| 208b | 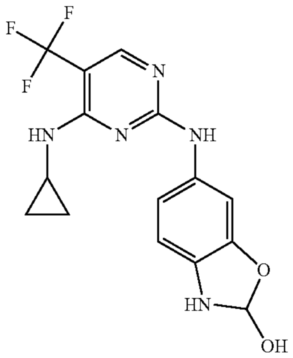 [SMILES: OC1Nc2ccc(Nc3ncc(C(F)(F)F)c(NC4CC4)n3)cc2O1] | A |
| 209 | 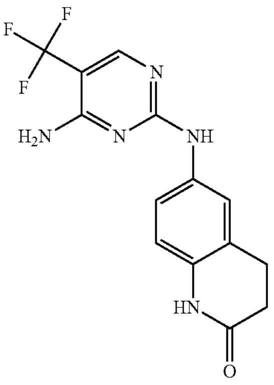 [SMILES: Nc1nc(Nc2ccc3c(c2)CCC(=O)N3)ncc1C(F)(F)F] | B |
| 210 | 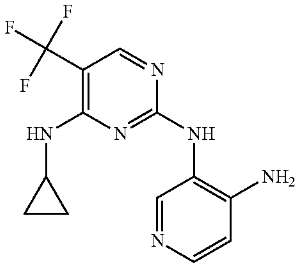 [SMILES: Nc1ccncc1Nc1ncc(C(F)(F)F)c(NC2CC2)n1] | B |

TABLE 1-continued
| Example | Structure | IC50 |
|---|---|---|
| 211 | 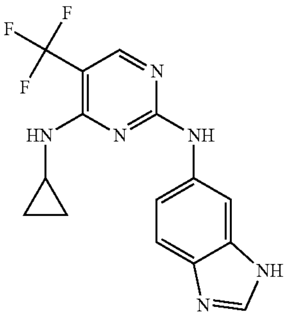 [SMILES: FC(F)(F)c1cnc(Nc2ccc3nc[nH]c3c2)nc1NC1CC1] | A |
| 212a | 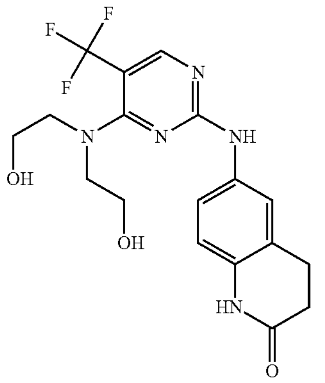 [SMILES: O=C1CCc2cc(Nc3ncc(C(F)(F)F)c(N(CCO)CCO)n3)ccc2N1] | C |
| 212b | 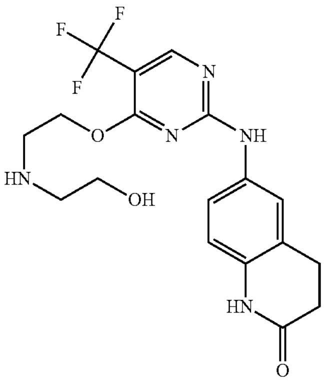 [SMILES: O=C1CCc2cc(Nc3ncc(C(F)(F)F)c(OCCNCCO)n3)ccc2N1] | B |
| 213 | 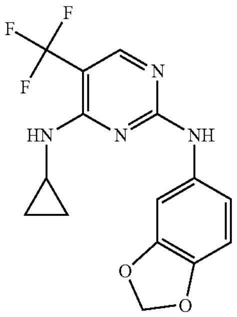 [SMILES: FC(F)(F)c1cnc(Nc2ccc3c(c2)OCO3)nc1NC1CC1] | A |

TABLE 1-continued
| Example | Structure | $IC_{50}$ |
| --- | --- | --- |
| 214a | 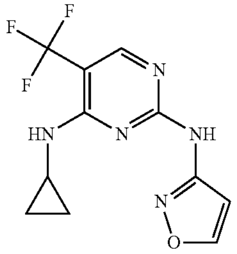 [SMILES: FC(F)(F)c1cnc(Nc2ccon2)nc1NC1CC1] | B |
| 214b | 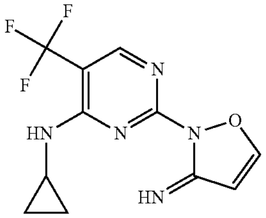 [SMILES: N=c1ccon1-c1ncc(C(F)(F)F)c(NC2CC2)n1] | C |
| 215 | 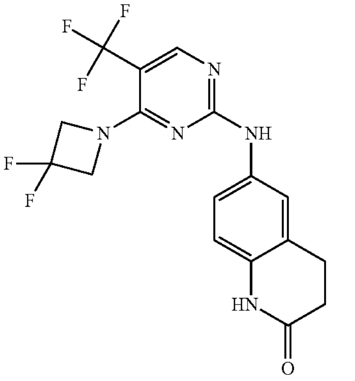 [SMILES: O=C1CCc2cc(Nc3ncc(C(F)(F)F)c(N4CC(F)(F)C4)n3)ccc2N1] | A |
| 216 | 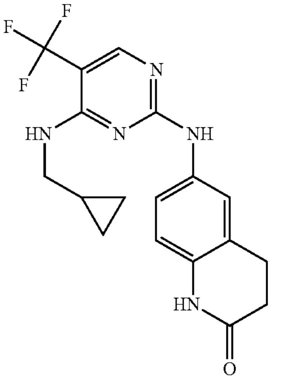 [SMILES: O=C1CCc2cc(Nc3ncc(C(F)(F)F)c(NCC4CC4)n3)ccc2N1] | A |
| 217 | 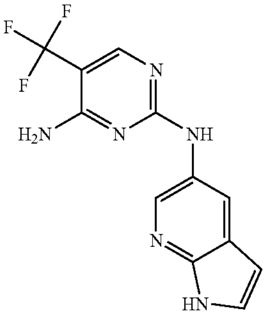 | C |

TABLE 1-continued
| Example | Structure | $IC_{50}$ |
|---|---|---|
| 218 | 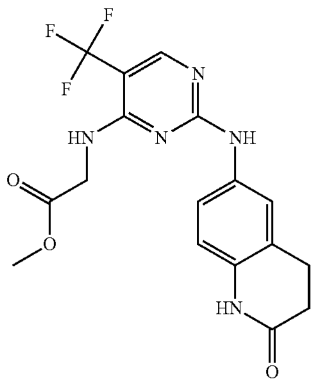 [SMILES: COC(=O)CNc1nc(Nc2ccc3c(c2)CCC(=O)N3)ncc1C(F)(F)F] | C |
| 219 | 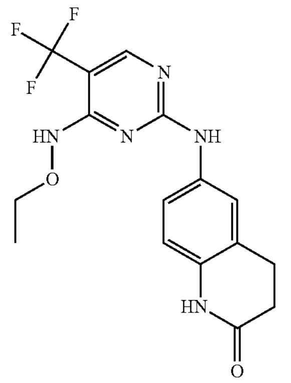 [SMILES: CCONc1nc(Nc2ccc3c(c2)CCC(=O)N3)ncc1C(F)(F)F] | C |
| 220a | 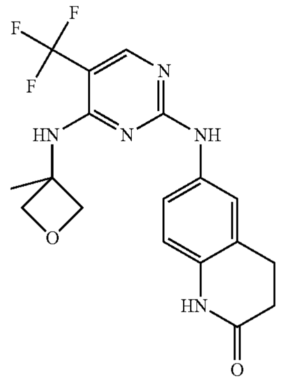 [SMILES: CC1(Nc2nc(Nc3ccc4c(c3)CCC(=O)N4)ncc2C(F)(F)F)COC1] | C |
| 220b | 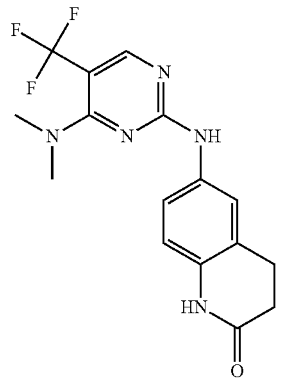 [SMILES: CN(C)c1nc(Nc2ccc3c(c2)CCC(=O)N3)ncc1C(F)(F)F] | A |

TABLE 1-continued
| Example | Structure | $IC_{50}$ |
|---|---|---|
| 220c | 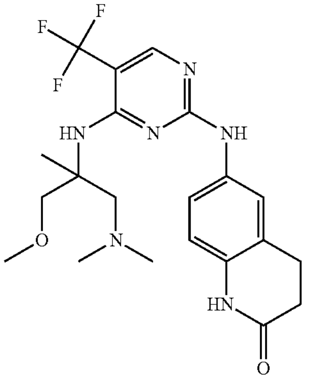 [SMILES: COCC(C)(CN(C)C)Nc1nc(Nc2ccc3c(c2)CCC(=O)N3)ncc1C(F)(F)F] | C |
| 221a | 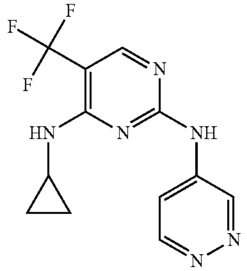 [SMILES: FC(F)(F)c1cnc(Nc2ccnnc2)nc1NC1CC1] | A |
| 222 | 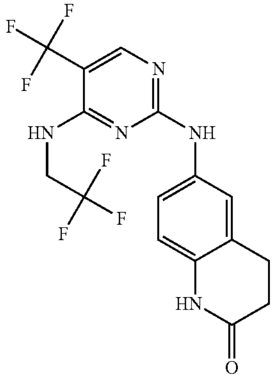 [SMILES: O=C1CCc2cc(Nc3ncc(C(F)(F)F)c(NCC(F)(F)F)n3)ccc2N1] | A |
| 223 | 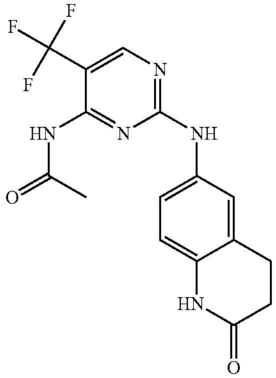 [SMILES: CC(=O)Nc1nc(Nc2ccc3c(c2)CCC(=O)N3)ncc1C(F)(F)F] | C |

TABLE 1-continued
| Example | Structure | IC50 |
| --- | --- | --- |
| 224 | 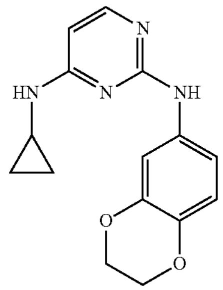 [SMILES: c1cc(NC2CC2)nc(Nc2ccc3c(c2)OCCO3)n1] | C |
| 225 | 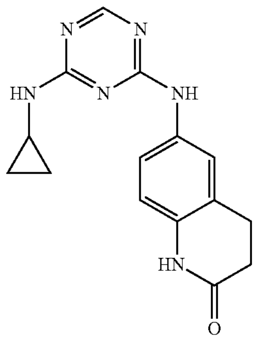 [SMILES: O=C1CCc2cc(Nc3ncnc(NC4CC4)n3)ccc2N1] | C |
| 226 | 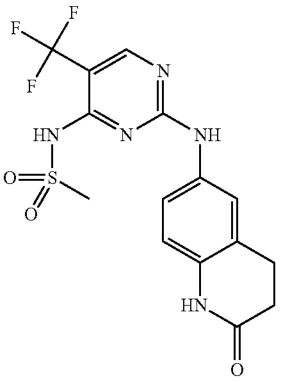 [SMILES: CS(=O)(=O)Nc1nc(Nc2ccc3c(c2)CCC(=O)N3)ncc1C(F)(F)F] | C |
| 227 | 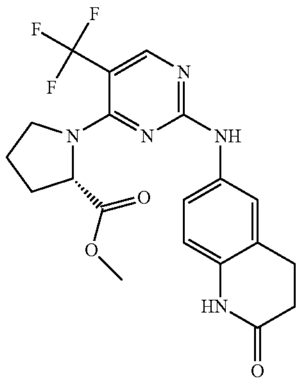 [SMILES: COC(=O)[C@@H]1CCCN1c1nc(Nc2ccc3c(c2)CCC(=O)N3)ncc1C(F)(F)F] | B |

TABLE 1-continued
| Example | Structure | $IC_{50}$ |
|---|---|---|
| 228 | 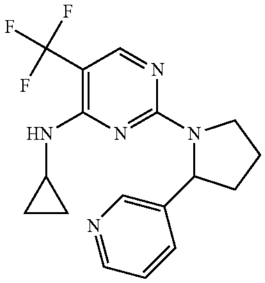 [SMILES: FC(F)(F)c1cnc(N2CCCC2c2cccnc2)nc1NC1CC1] | C |
| 229 | 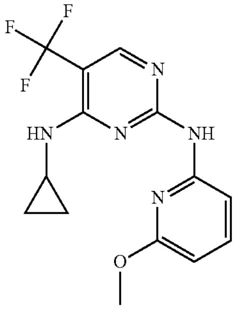 [SMILES: COc1cccc(Nc2ncc(C(F)(F)F)c(NC3CC3)n2)n1] | A |
| 230 | 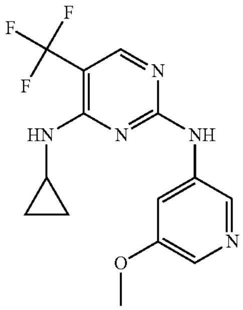 [SMILES: COc1cncc(Nc2ncc(C(F)(F)F)c(NC3CC3)n2)c1] | A |
| 231a | 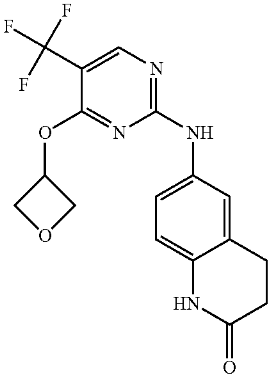 [SMILES: O=C1CCc2cc(Nc3ncc(C(F)(F)F)c(OC4COC4)n3)ccc2N1] | A |

TABLE 1-continued
| Example | Structure | $IC_{50}$ |
|---|---|---|
| 231b | 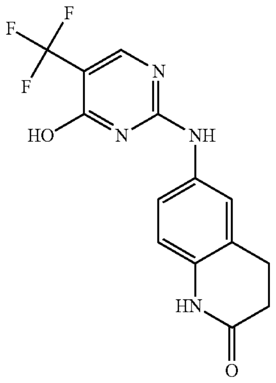 [SMILES: O=C1CCc2cc(Nc3ncc(C(F)(F)F)c(O)n3)ccc2N1] | C |
| 232 | 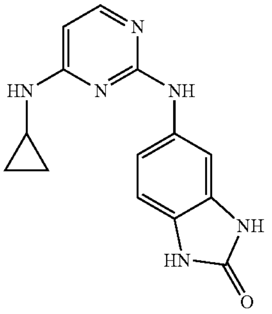 [SMILES: O=c1[nH]c2ccc(Nc3nccc(NC4CC4)n3)cc2[nH]1] | C |
| 233 | 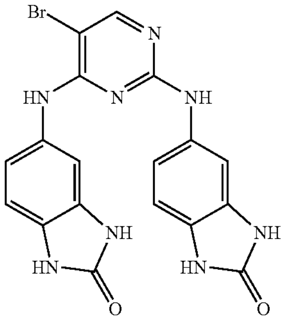 [SMILES: O=c1[nH]c2ccc(Nc3ncc(Br)c(Nc4ccc5[nH]c(=O)[nH]c5c4)n3)cc2[nH]1] | A |
| 234a | 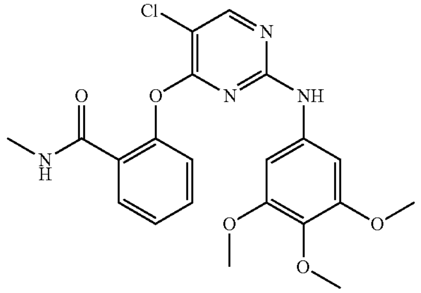 | C |

TABLE 1-continued
| Example | Structure | $IC_{50}$ |
|---|---|---|
| 234b | 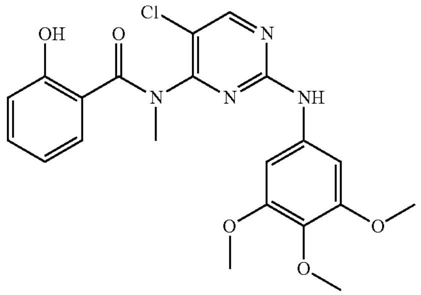 [SMILES: COc1cc(Nc2ncc(Cl)c(N(C)C(=O)c3ccccc3O)n2)cc(OC)c1OC] | B |
| 235 | 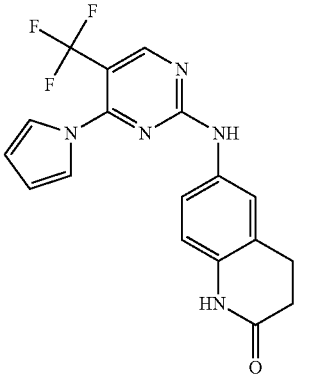 [SMILES: O=C1CCc2cc(Nc3ncc(C(F)(F)F)c(-n4cccc4)n3)ccc2N1] | C |
| 236 | 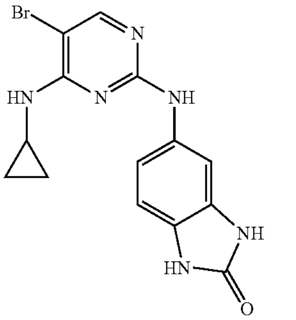 [SMILES: O=c1[nH]c2ccc(Nc3ncc(Br)c(NC4CC4)n3)cc2[nH]1] | A |
| 237 | 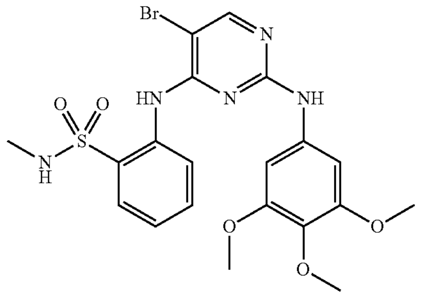 | B |
| 239 | 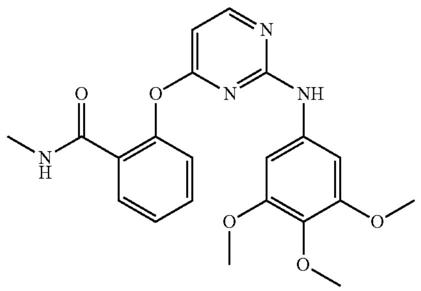 | C |

TABLE 1-continued
| Example | Structure | $IC_{50}$ |
| --- | --- | --- |
| 240 | 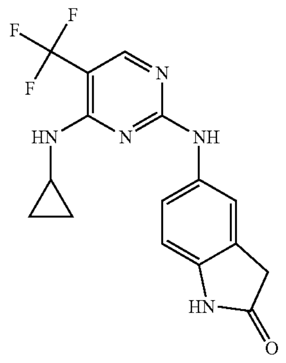 [SMILES: O=C1Cc2cc(Nc3ncc(C(F)(F)F)c(NC4CC4)n3)ccc2N1] | A |
| 242 | 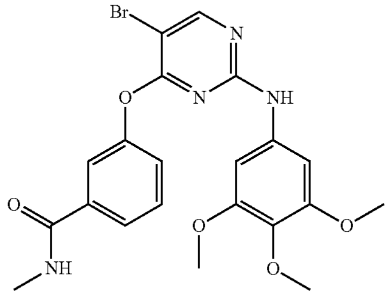 [SMILES: CNC(=O)c1cccc(Oc2nc(Nc3cc(OC)c(OC)c(OC)c3)ncc2Br)c1] | B |
| 243 | 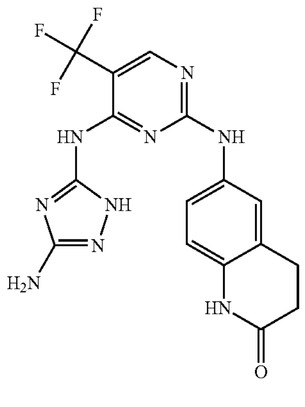 [SMILES: Nc1n[nH]c(Nc2nc(Nc3ccc4c(c3)CCC(=O)N4)ncc2C(F)(F)F)n1] | B |
| 245 | 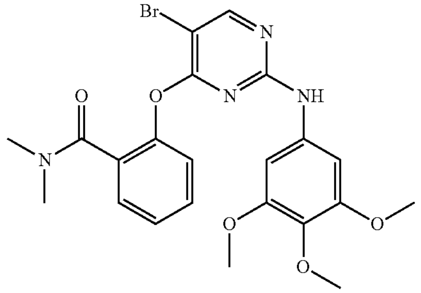 | A |

TABLE 1-continued
| Example | Structure | IC50 |
| --- | --- | --- |
| 246 | 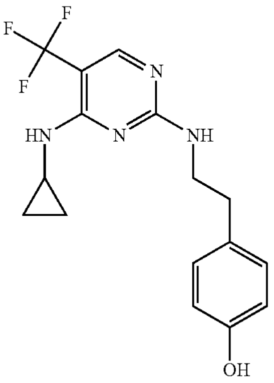 [SMILES: Oc1ccc(CCNc2ncc(C(F)(F)F)c(NC3CC3)n2)cc1] | B |
| 247 | 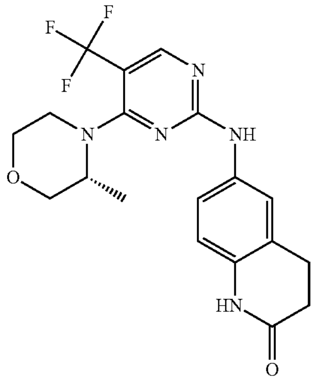 [SMILES: C[C@@H]1COCCN1c1nc(Nc2ccc3c(c2)CCC(=O)N3)ncc1C(F)(F)F] | A |
| 249 | 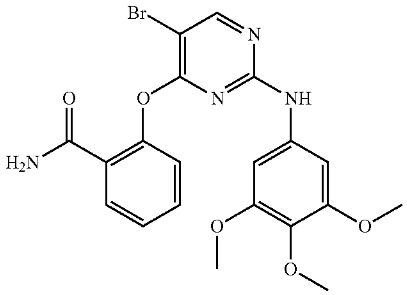 [SMILES: COc1cc(Nc2ncc(Br)c(Oc3ccccc3C(N)=O)n2)cc(OC)c1OC] | A |
| 250 | 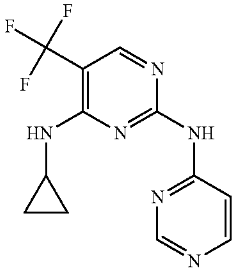 [SMILES: FC(F)(F)c1cnc(Nc2ccncn2)nc1NC1CC1] | C |

TABLE 1-continued
| Example | Structure | $IC_{50}$ |
| --- | --- | --- |
| 252 | 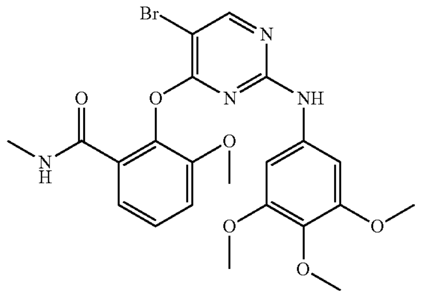 | A |
| 254a | 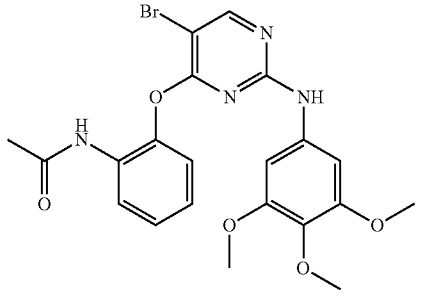 [SMILES: COc1cc(Nc2ncc(Br)c(Oc3ccccc3NC(C)=O)n2)cc(OC)c1OC] | A |
| 254b | 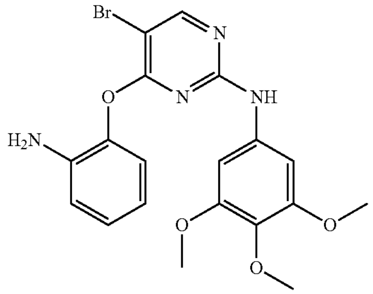 [SMILES: COc1cc(Nc2ncc(Br)c(Oc3ccccc3N)n2)cc(OC)c1OC] | A |
| 255 | 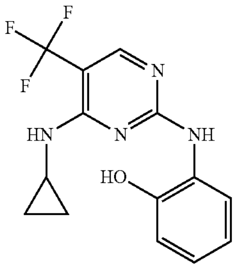 [SMILES: Oc1ccccc1Nc1ncc(C(F)(F)F)c(NC2CC2)n1] | A |
| 257 | 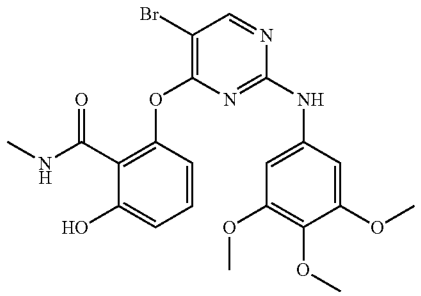 | A |

TABLE 1-continued
| Example | Structure | $IC_{50}$ |
|---|---|---|
| 258 | 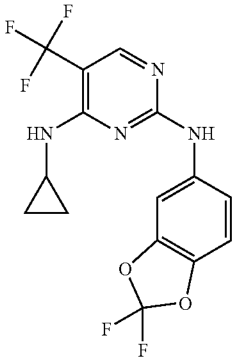 [SMILES: FC1(F)Oc2ccc(Nc3ncc(C(F)(F)F)c(NC4CC4)n3)cc2O1] | C |
| 260 | 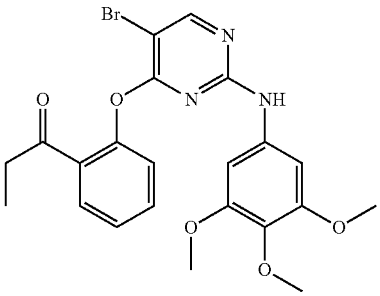 [SMILES: CCC(=O)c1ccccc1Oc1nc(Nc2cc(OC)c(OC)c(OC)c2)ncc1Br] | A |
| 261 | 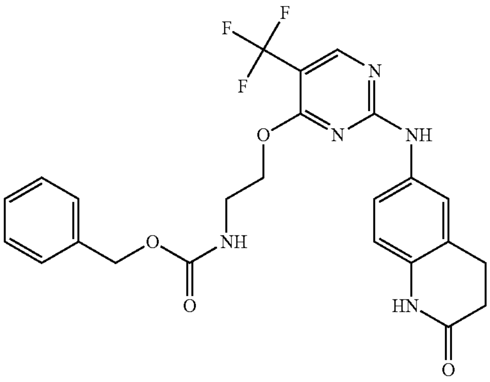 [SMILES: O=C1CCc2cc(Nc3ncc(C(F)(F)F)c(OCCNC(=O)OCc4ccccc4)n3)ccc2N1] | C |
| 262 | 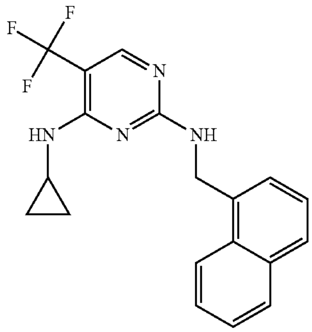 [SMILES: FC(F)(F)c1cnc(NCc2cccc3ccccc23)nc1NC1CC1] | C |

TABLE 1-continued
| Example | Structure | $IC_{50}$ |
| --- | --- | --- |
| 263 | 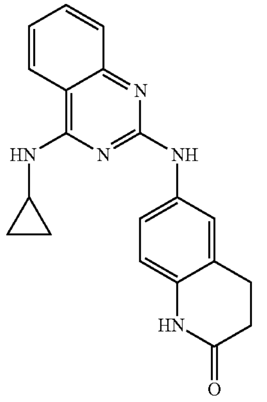 [SMILES: O=C1CCc2cc(Nc3nc(NC4CC4)c4ccccc4n3)ccc2N1] | C |
| 264 | 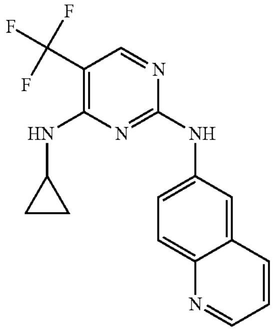 [SMILES: FC(F)(F)c1cnc(Nc2ccc3ncccc3c2)nc1NC1CC1] | A |
| 266 | 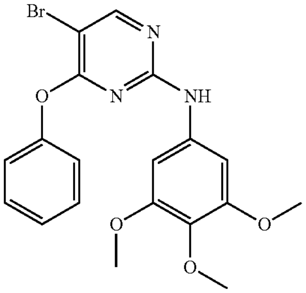 [SMILES: COc1cc(Nc2ncc(Br)c(Oc3ccccc3)n2)cc(OC)c1OC] | A |
| 268 | 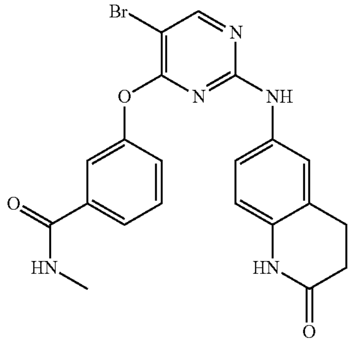 [SMILES: CNC(=O)c1cccc(Oc2nc(Nc3ccc4c(c3)CCC(=O)N4)ncc2Br)c1] | B |

TABLE 1-continued
| Example | Structure | $IC_{50}$ |
|---|---|---|
| 270 | 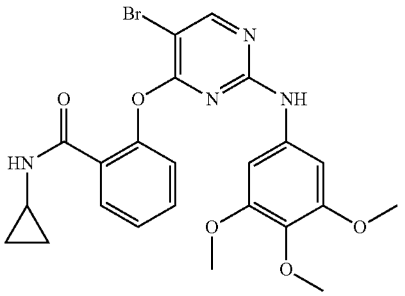 [SMILES: COc1cc(Nc2ncc(Br)c(Oc3ccccc3C(=O)NC3CC3)n2)cc(OC)c1OC] | B |
| 271 | 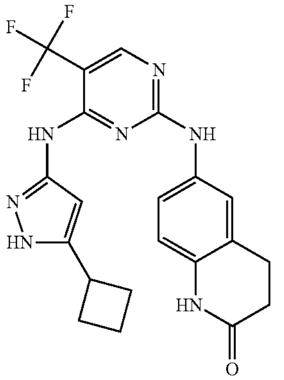 [SMILES: O=C1CCc2cc(Nc3ncc(C(F)(F)F)c(Nc4cc(C5CCC5)[nH]n4)n3)ccc2N1] | A |
| 274 | 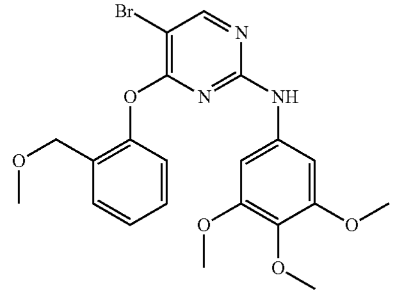 [SMILES: COCc1ccccc1Oc1nc(Nc2cc(OC)c(OC)c(OC)c2)ncc1Br] | A |
| 275 | 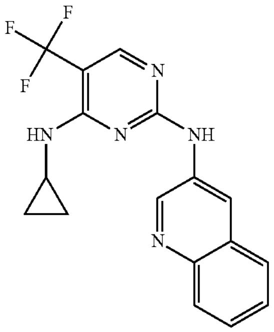 [SMILES: FC(F)(F)c1cnc(Nc2cnc3ccccc3c2)nc1NC1CC1] | A |
| 277 | 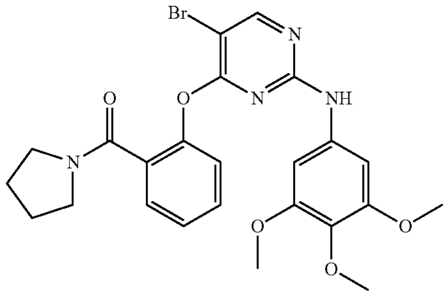 [SMILES: COc1cc(Nc2ncc(Br)c(Oc3ccccc3C(=O)N3CCCC3)n2)cc(OC)c1OC] | A |

TABLE 1-continued
| Example | Structure | IC50 |
|---|---|---|
| 278 | 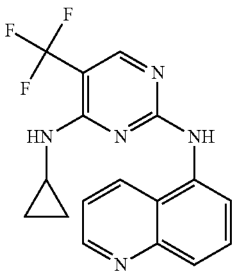 [SMILES: FC(F)(F)c1cnc(Nc2cccc3ncccc23)nc1NC1CC1] | C |
| 281 | 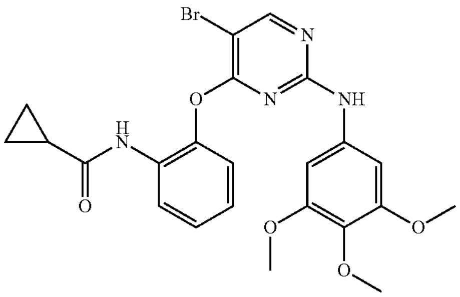 [SMILES: COc1cc(Nc2ncc(Br)c(Oc3ccccc3NC(=O)C3CC3)n2)cc(OC)c1OC] | A |
| 283 | 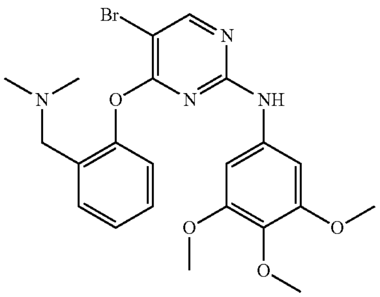 | C |
| 286 | 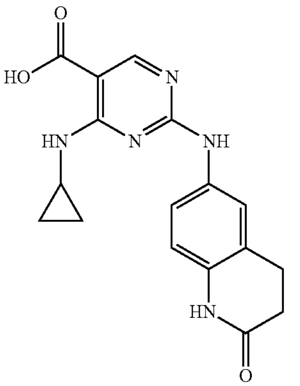 [SMILES: O=C1CCc2cc(Nc3ncc(C(=O)O)c(NC4CC4)n3)ccc2N1] | C |

TABLE 1-continued
| Example | Structure | $IC_{50}$ |
| --- | --- | --- |
| 287 | 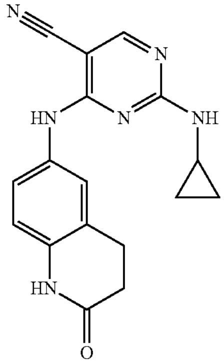 [SMILES: N#Cc1cnc(NC2CC2)nc1Nc1ccc2c(c1)CCC(=O)N2] | C |
| 288 | 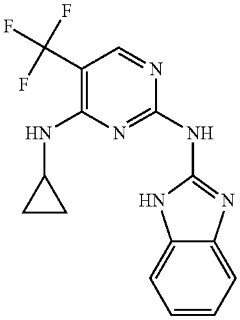 [SMILES: FC(F)(F)c1cnc(Nc2nc3ccccc3[nH]2)nc1NC1CC1] | C |
| 290 | 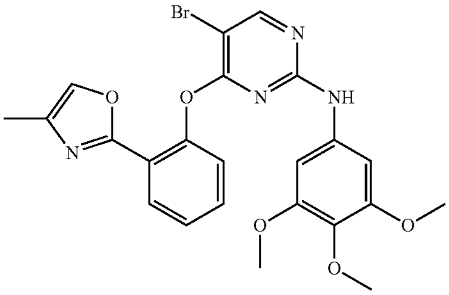 | C |
| 291b | 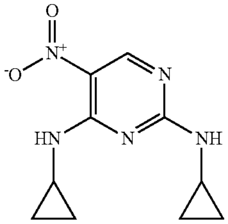 | C |
| 293 | 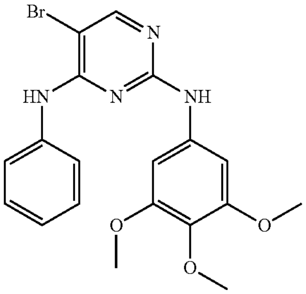 | A |

TABLE 1-continued
| Example | Structure | $IC_{50}$ |
|---|---|---|
| 294 | 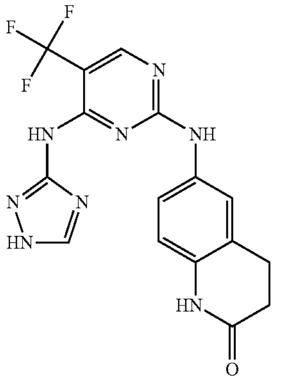 [SMILES: O=C1CCc2cc(Nc3ncc(C(F)(F)F)c(Nc4nc[nH]n4)n3)ccc2N1] | C |
| 296 | 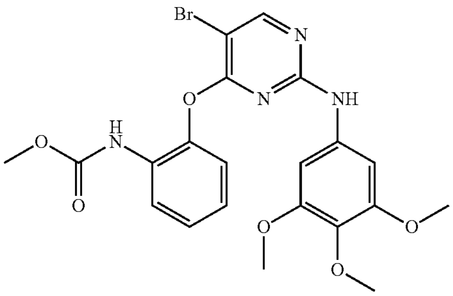 | A |
| 297 | 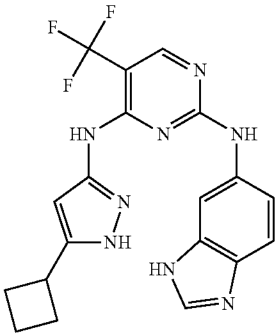 [SMILES: FC(F)(F)c1cnc(Nc2ccc3nc[nH]c3c2)nc1Nc1cc(C2CCC2)[nH]n1] | A |
| 299 | 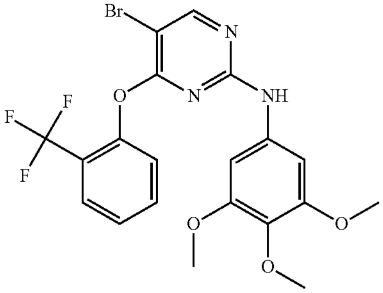 [SMILES: COc1cc(Nc2ncc(Br)c(Oc3ccccc3C(F)(F)F)n2)cc(OC)c1OC] | A |

TABLE 1-continued
| Example | Structure | IC50 |
| --- | --- | --- |
| 300a | 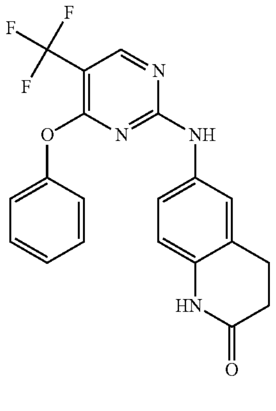 [SMILES: O=C1CCc2cc(Nc3ncc(C(F)(F)F)c(Oc4ccccc4)n3)ccc2N1] | C |
| 300b | 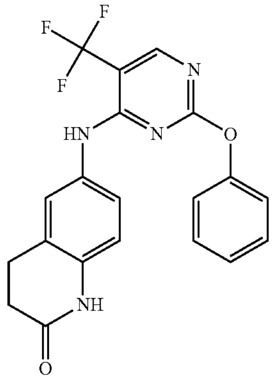 [SMILES: O=C1CCc2cc(Nc3nc(Oc4ccccc4)ncc3C(F)(F)F)ccc2N1] | C |
| 301 | 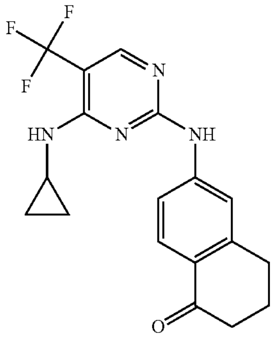 [SMILES: O=C1CCCc2cc(Nc3ncc(C(F)(F)F)c(NC4CC4)n3)ccc21] | A |
| 303 | 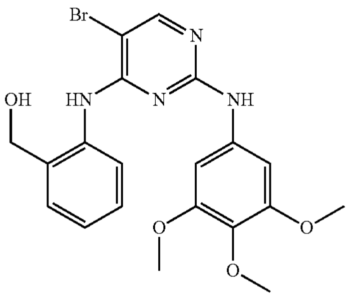 [SMILES: COc1cc(Nc2ncc(Br)c(Nc3ccccc3CO)n2)cc(OC)c1OC] | A |

TABLE 1-continued
| Example | Structure | $IC_{50}$ |
|---|---|---|
| 304a | 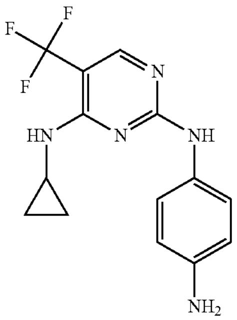 [SMILES: Nc1ccc(Nc2ncc(C(F)(F)F)c(NC3CC3)n2)cc1] | A |
| 304b | 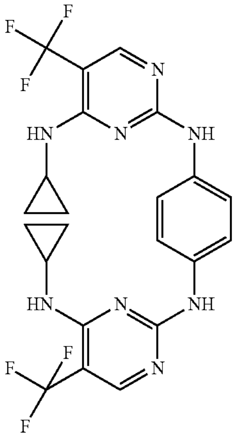 [SMILES: FC(F)(F)c1cnc(Nc2ccc(Nc3ncc(C(F)(F)F)c(NC4CC4)n3)cc2)nc1NC1CC1] | C |
| 305 | 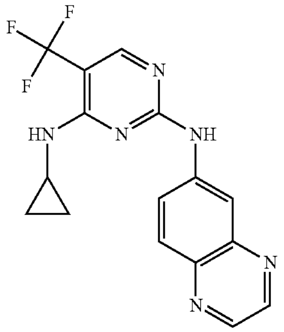 [SMILES: FC(F)(F)c1cnc(Nc2ccc3nccnc3c2)nc1NC1CC1] | A |
| 307 | 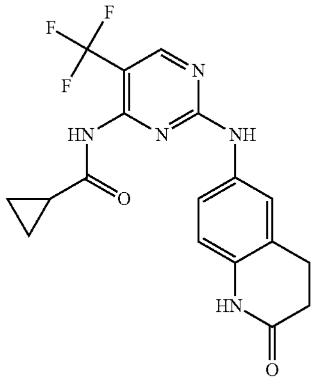 [SMILES: O=C1CCc2cc(Nc3ncc(C(F)(F)F)c(NC(=O)C4CC4)n3)ccc2N1] | C |

TABLE 1-continued
| Example | Structure | $IC_{50}$ |
| --- | --- | --- |
| 308 | 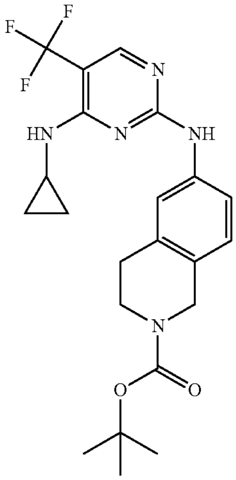 [SMILES: CC(C)(C)OC(=O)N1CCc2cc(Nc3ncc(C(F)(F)F)c(NC4CC4)n3)ccc2C1] | A |
| 309 | 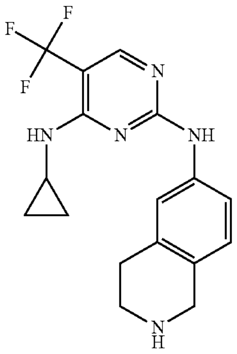 [SMILES: FC(F)(F)c1cnc(Nc2ccc3c(c2)CCNC3)nc1NC1CC1] | A |
| 310 | 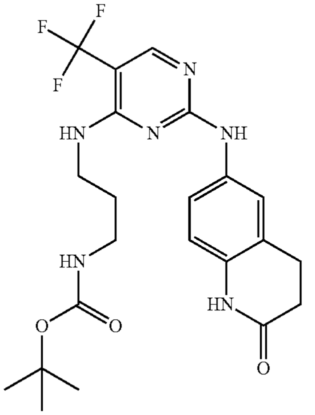 [SMILES: CC(C)(C)OC(=O)NCCCNc1nc(Nc2ccc3c(c2)CCC(=O)N3)ncc1C(F)(F)F] | A |

TABLE 1-continued
| Example | Structure | $IC_{50}$ |
|---|---|---|
| 311 | 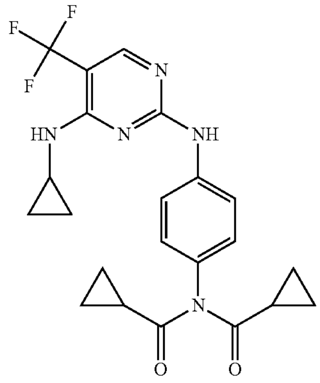 [SMILES: O=C(C1CC1)N(C(=O)C1CC1)c1ccc(Nc2ncc(C(F)(F)F)c(NC3CC3)n2)cc1] | A |
| 312 | 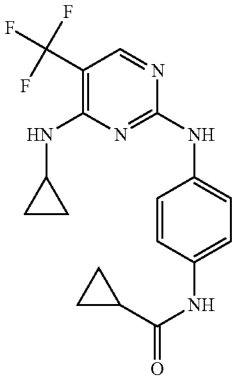 [SMILES: O=C(Nc1ccc(Nc2ncc(C(F)(F)F)c(NC3CC3)n2)cc1)C1CC1] | A |
| 313 | 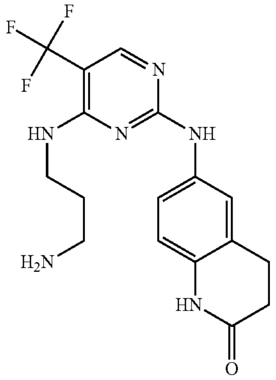 [SMILES: NCCCNc1nc(Nc2ccc3c(c2)CCC(=O)N3)ncc1C(F)(F)F] | A |
| 314 | 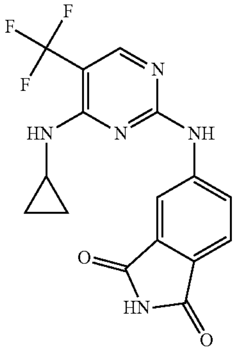 [SMILES: O=C1NC(=O)c2cc(Nc3ncc(C(F)(F)F)c(NC4CC4)n3)ccc21] | A |

TABLE 1-continued
| Example | Structure | $IC_{50}$ |
| --- | --- | --- |
| 316 | 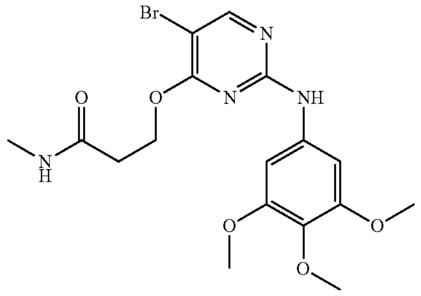 | A |
| 317 | 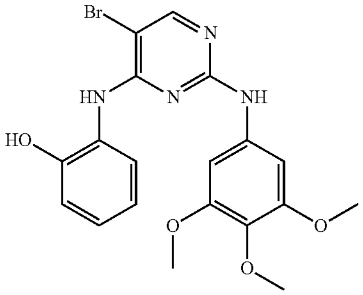 [SMILES: COc1cc(Nc2ncc(Br)c(Nc3ccccc3O)n2)cc(OC)c1OC] | A |
| 318a | 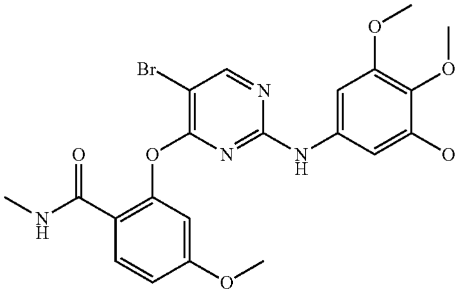 [SMILES: CNC(=O)c1ccc(OC)cc1Oc1nc(Nc2cc(O)c(OC)c(OC)c2)ncc1Br] | C |
| 318b | 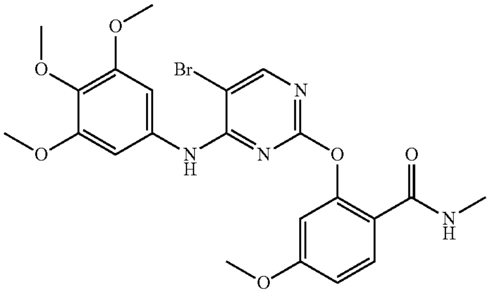 | C |
| 320 | 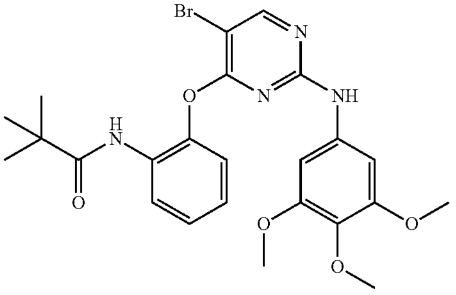 [SMILES: COc1cc(Nc2ncc(Br)c(Oc3ccccc3NC(=O)C(C)(C)C)n2)cc(OC)c1OC] | C |

TABLE 1-continued
| Example | Structure | IC50 |
|---|---|---|
| 321a | 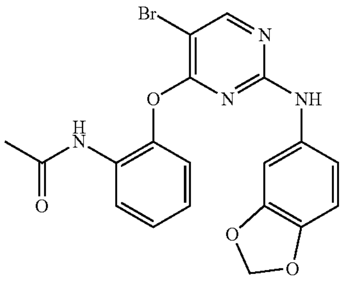 [SMILES: CC(=O)Nc1ccccc1Oc1nc(Nc2ccc3c(c2)OCO3)ncc1Br] | C |
| 321b | 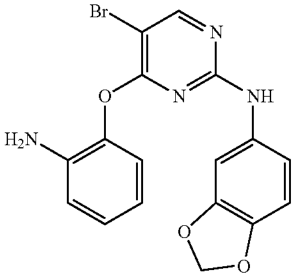 [SMILES: Nc1ccccc1Oc1nc(Nc2ccc3c(c2)OCO3)ncc1Br] | A |
| 323 | 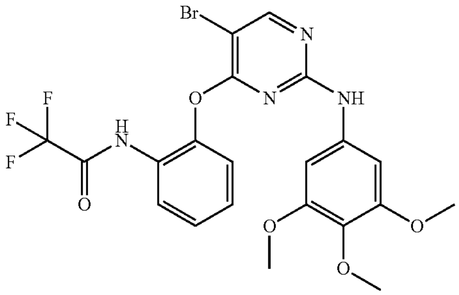 [SMILES: COc1cc(Nc2ncc(Br)c(Oc3ccccc3NC(=O)C(F)(F)F)n2)cc(OC)c1OC] | A |
| 324a | 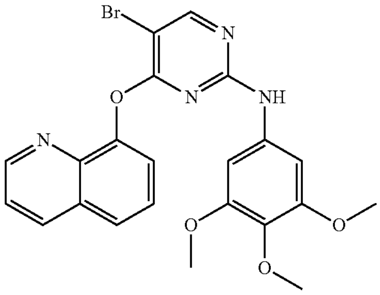 [SMILES: COc1cc(Nc2ncc(Br)c(Oc3cccc4cccnc34)n2)cc(OC)c1OC] | C |
| 324b | 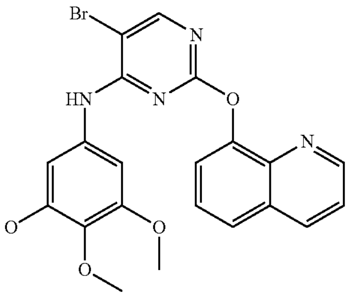 [SMILES: COc1cc(Nc2nc(Oc3cccc4cccnc34)ncc2Br)cc(O)c1OC] | A |

TABLE 1-continued
| Example | Structure | $IC_{50}$ |
|---|---|---|
| 325 | 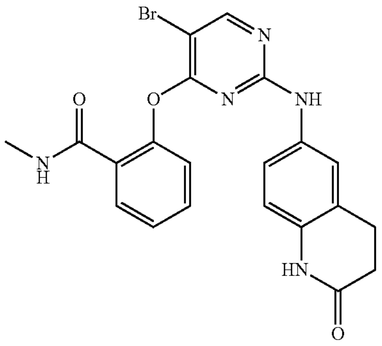 [SMILES: CNC(=O)c1ccccc1Oc1nc(Nc2ccc3c(c2)CCC(=O)N3)ncc1Br] | C |
| 326 | 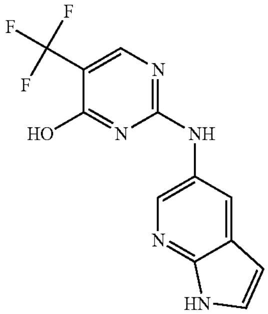 [SMILES: Oc1nc(Nc2cnc3[nH]ccc3c2)ncc1C(F)(F)F] | C |
| 327 | 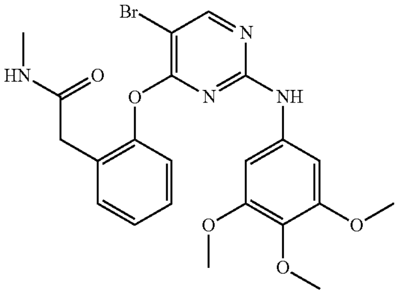 [SMILES: CNC(=O)Cc1ccccc1Oc1nc(Nc2cc(OC)c(OC)c(OC)c2)ncc1Br] | C |
| 328 | 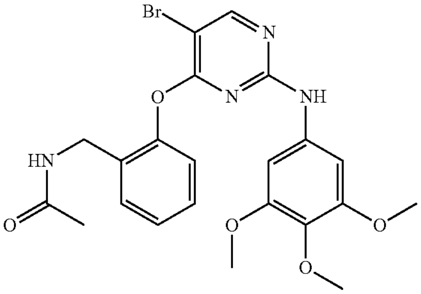 [SMILES: COc1cc(Nc2ncc(Br)c(Oc3ccccc3CNC(C)=O)n2)cc(OC)c1OC] | C |
| 329a | 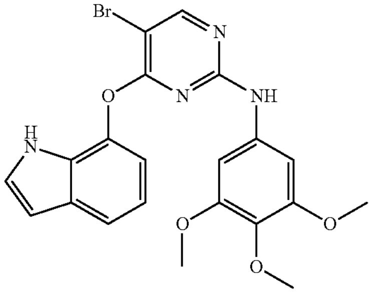 [SMILES: COc1cc(Nc2ncc(Br)c(Oc3cccc4cc[nH]c34)n2)cc(OC)c1OC] | C |

TABLE 1-continued
| Example | Structure | IC50 |
|---|---|---|
| 329b | 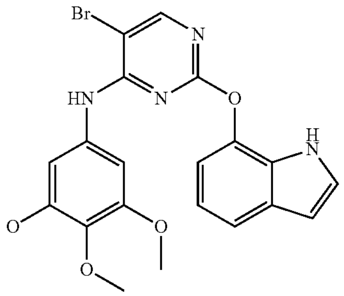 [SMILES: COc1cc(Nc2nc(Oc3cccc4cc[nH]c34)ncc2Br)cc(O)c1OC] | C |
| 330a | 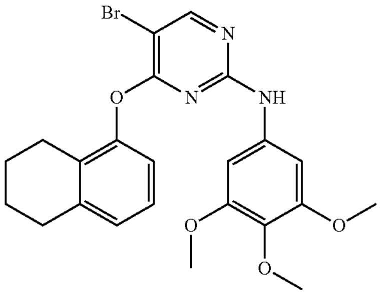 [SMILES: COc1cc(Nc2ncc(Br)c(Oc3cccc4c3CCCC4)n2)cc(OC)c1OC] | C |
| 330b | 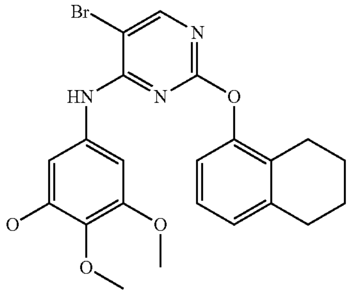 [SMILES: COc1cc(Nc2nc(Oc3cccc4c3CCCC4)ncc2Br)cc(O)c1OC] | C |
| 331a | 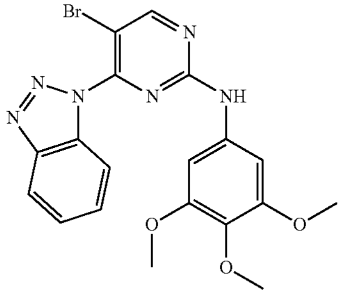 [SMILES: COc1cc(Nc2ncc(Br)c(-n3nnc4ccccc43)n2)cc(OC)c1OC] | C |
| 331b | 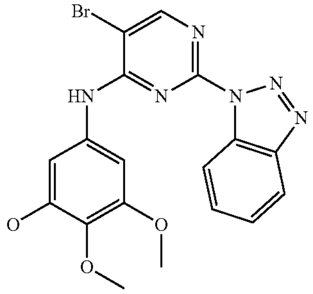 [SMILES: COc1cc(Nc2nc(-n3nnc4ccccc43)ncc2Br)cc(O)c1OC] | B |

TABLE 1-continued
| Example | Structure | $IC_{50}$ |
| --- | --- | --- |
| 332 | 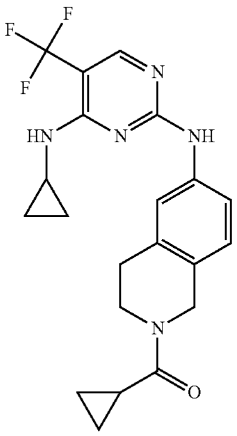 [SMILES: O=C(C1CC1)N1CCc2cc(Nc3ncc(C(F)(F)F)c(NC4CC4)n3)ccc2C1] | A |
| 333 | 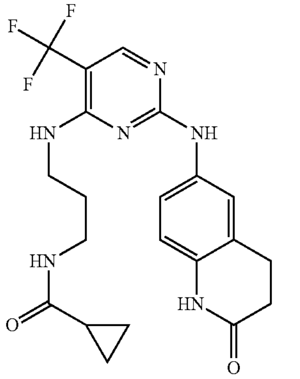 [SMILES: O=C1CCc2cc(Nc3ncc(C(F)(F)F)c(NCCCNC(=O)C4CC4)n3)ccc2N1] | A |
| 334 | 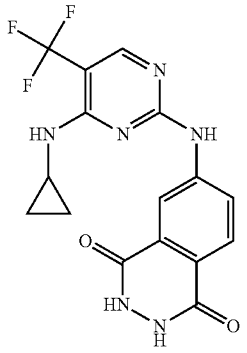 [SMILES: O=c1[nH][nH]c(=O)c2cc(Nc3ncc(C(F)(F)F)c(NC4CC4)n3)ccc12] | A |
| 335a | 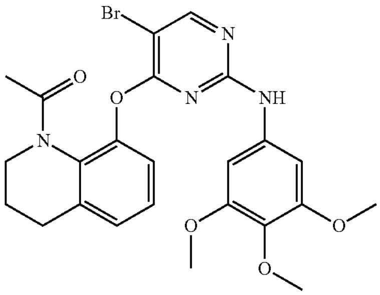 [SMILES: COc1cc(Nc2ncc(Br)c(Oc3cccc4c3N(C(C)=O)CCC4)n2)cc(OC)c1OC] | C |

TABLE 1-continued
| Example | Structure | $IC_{50}$ |
|---|---|---|
| 335b | 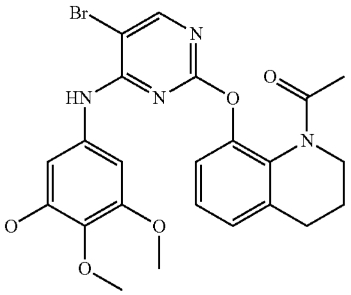 [SMILES: COc1cc(Nc2nc(Oc3cccc4c3N(C(C)=O)CCC4)ncc2Br)cc(O)c1OC] | A |
| 336 | 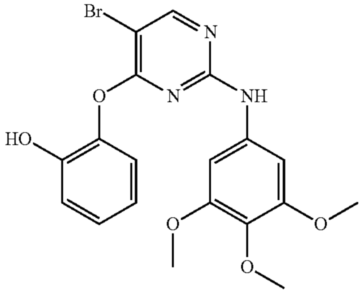 [SMILES: COc1cc(Nc2ncc(Br)c(Oc3ccccc3O)n2)cc(OC)c1OC] | C |
| 338 | 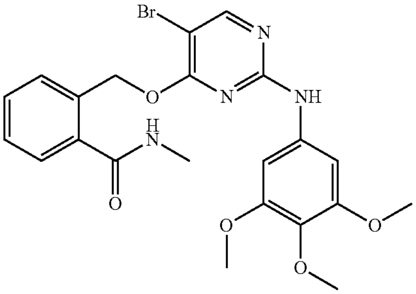 [SMILES: CNC(=O)c1ccccc1COc1nc(Nc2cc(OC)c(OC)c(OC)c2)ncc1Br] | C |
| 343 | 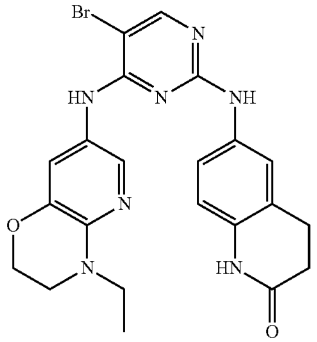 [SMILES: CCN1CCOc2cc(Nc3nc(Nc4ccc5c(c4)CCC(=O)N5)ncc3Br)cnc21] | A |
| 344 | 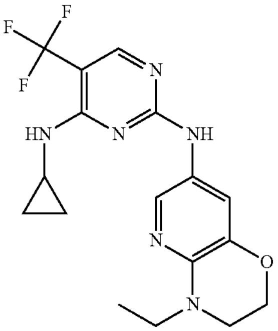 [SMILES: CCN1CCOc2cc(Nc3ncc(C(F)(F)F)c(NC4CC4)n3)cnc21] | A |

TABLE 1-continued
| Example | Structure | $IC_{50}$ |
|---|---|---|
| 345 | 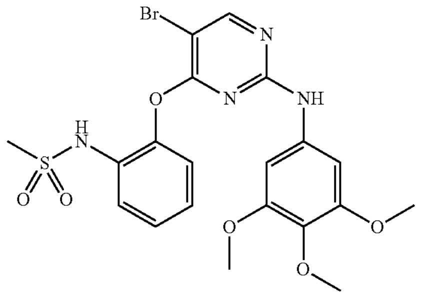 | C |
| 346 | 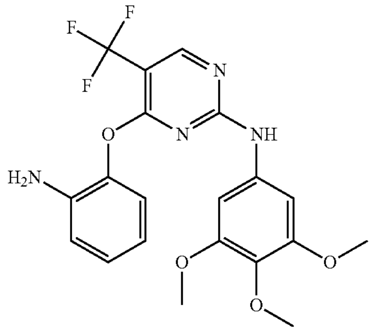 [SMILES: COc1cc(Nc2ncc(C(F)(F)F)c(Oc3ccccc3N)n2)cc(OC)c1OC] | A |
| 347 | 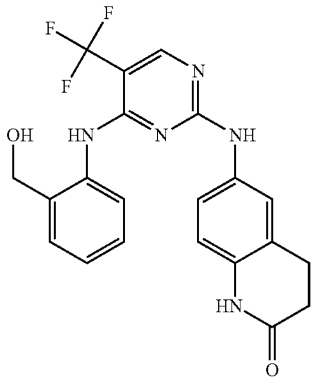 [SMILES: O=C1CCc2cc(Nc3ncc(C(F)(F)F)c(Nc4ccccc4CO)n3)ccc2N1] | A |
| 348 | 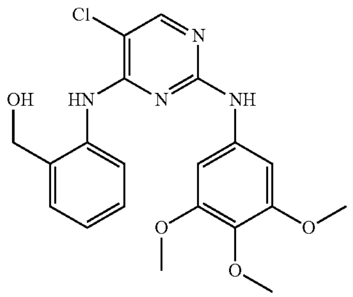 [SMILES: COc1cc(Nc2ncc(Cl)c(Nc3ccccc3CO)n2)cc(OC)c1OC] | C |

TABLE 1-continued
| Example | Structure | $IC_{50}$ |
| --- | --- | --- |
| 349 | 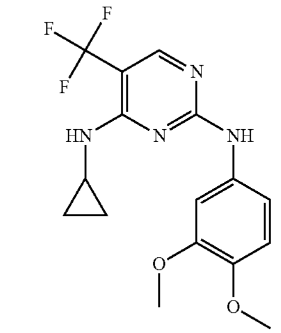 [SMILES: COc1ccc(Nc2ncc(C(F)(F)F)c(NC3CC3)n2)cc1OC] | A |
| 350 | 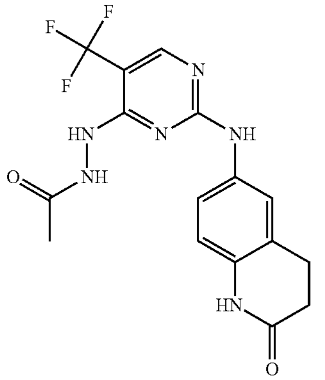 [SMILES: CC(=O)NNc1nc(Nc2ccc3c(c2)CCC(=O)N3)ncc1C(F)(F)F] | C |
| 351 | 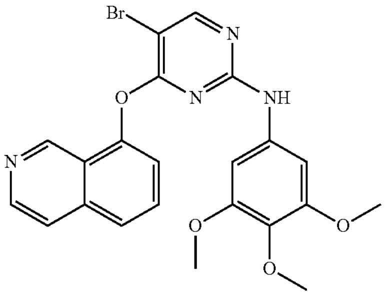 [SMILES: COc1cc(Nc2ncc(Br)c(Oc3cccc4ccncc34)n2)cc(OC)c1OC] | C |
| 352 | 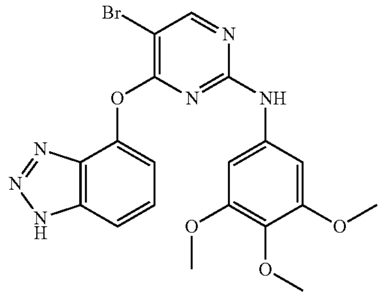 [SMILES: COc1cc(Nc2ncc(Br)c(Oc3cccc4[nH]nnc34)n2)cc(OC)c1OC] | C |
| 353 | 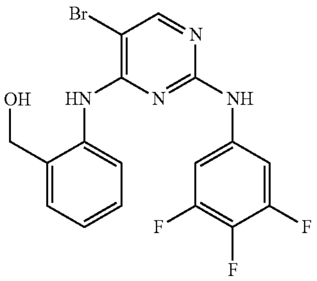 [SMILES: OCc1ccccc1Nc1nc(Nc2cc(F)c(F)c(F)c2)ncc1Br] | C |

TABLE 1-continued
| Example | Structure | $IC_{50}$ |
|---|---|---|
| 354 | 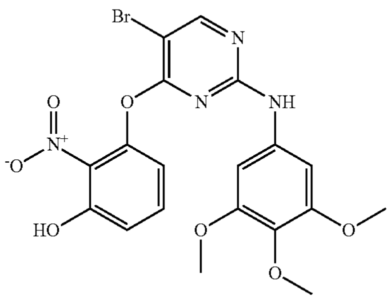 | C |
| 355 | 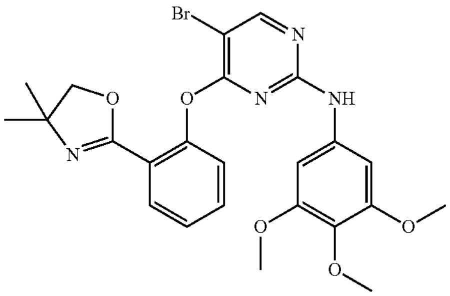 | C |
| 356 | 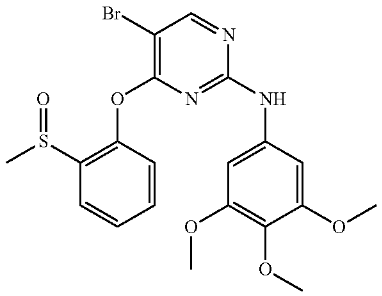 | C |
Exemplary compounds are illustrated in a non-limiting manner below:
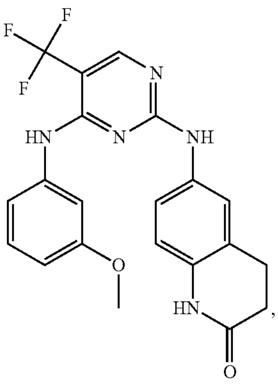
,
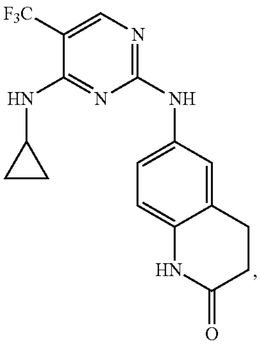
,
-continued
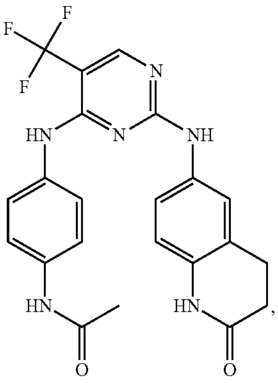
,
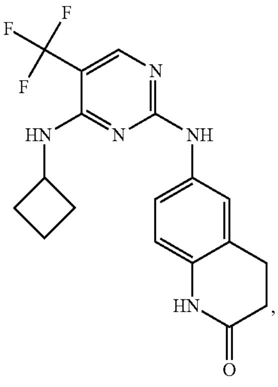
, -continued
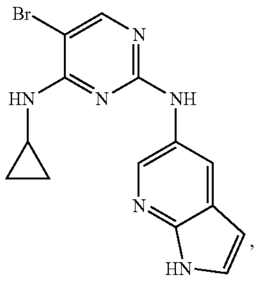
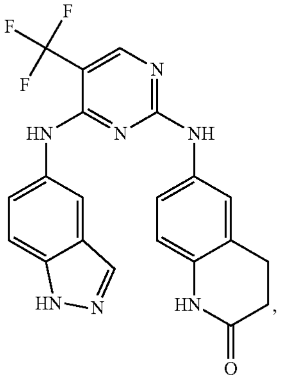
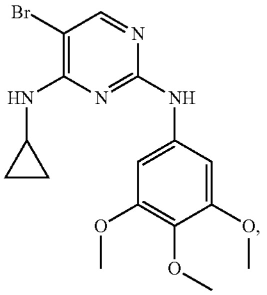
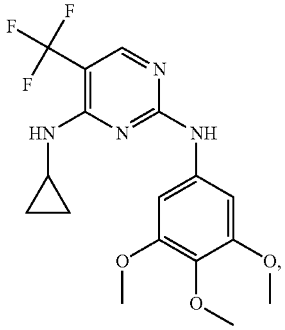
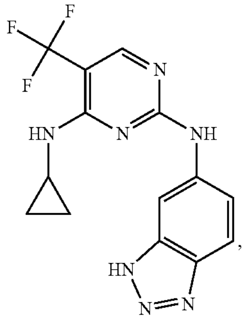
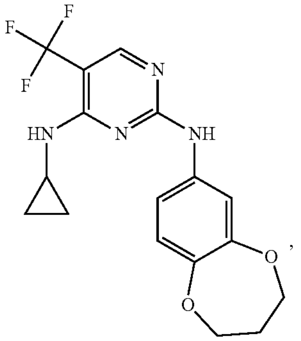
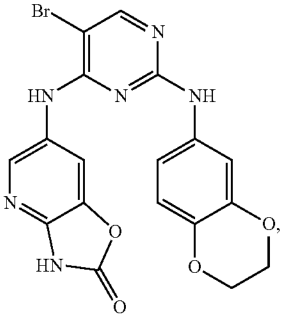
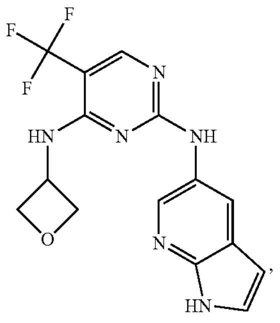
-continued
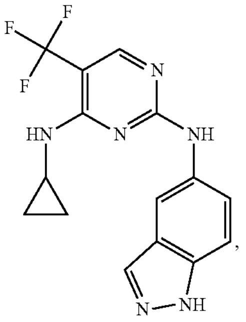
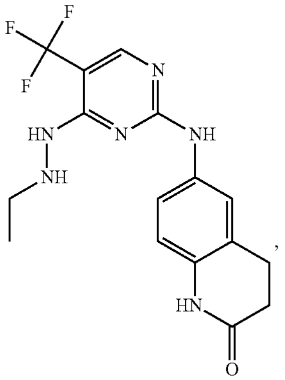
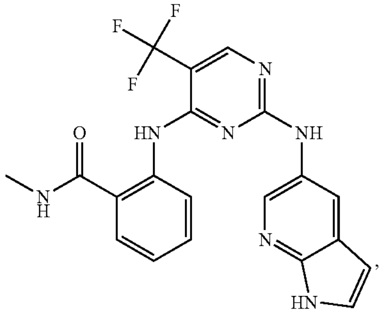
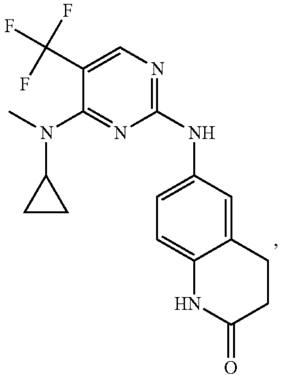
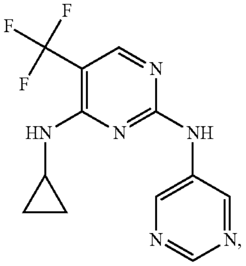
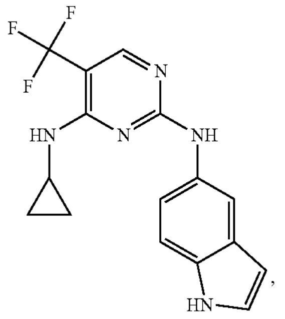
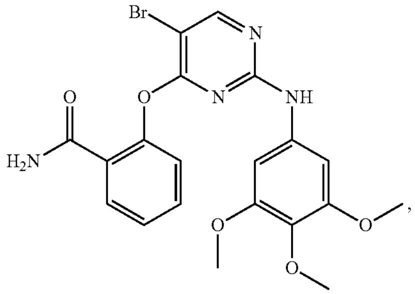

-continued
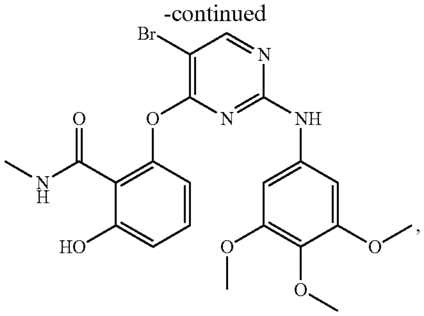
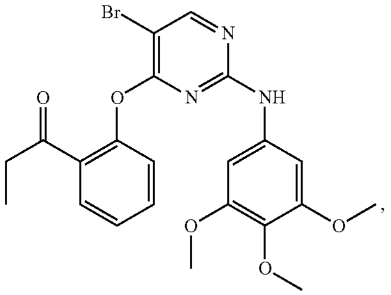
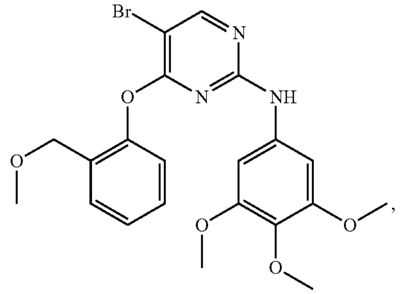
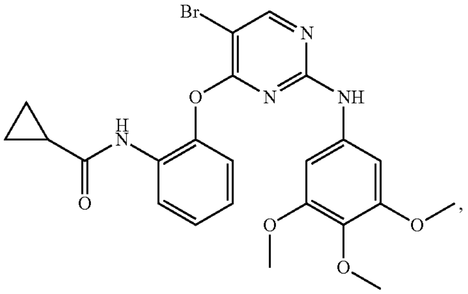
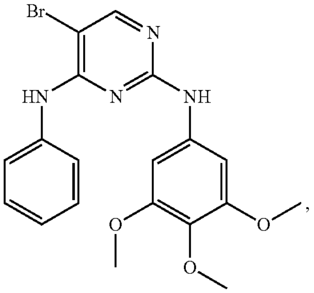
-continued
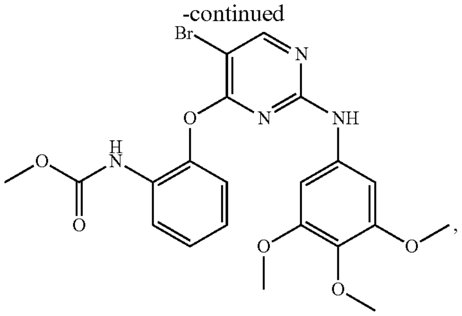
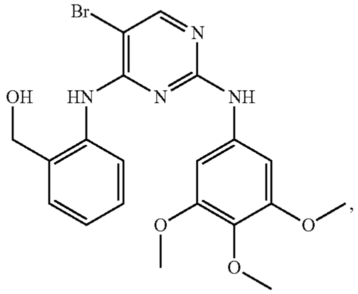
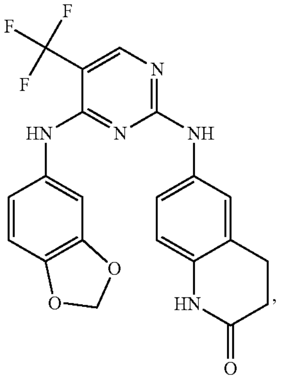
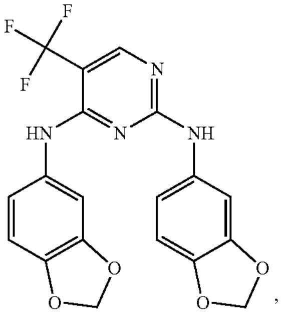
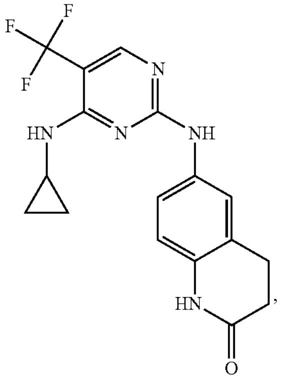
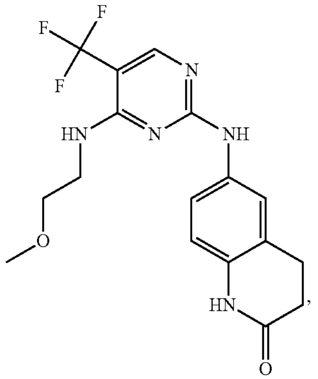

-continued
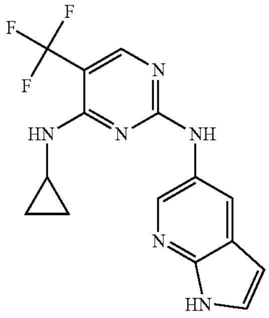
,
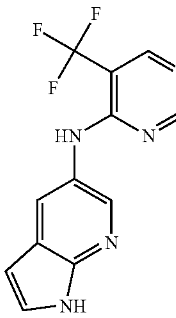
,
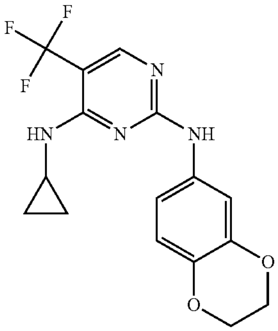
,
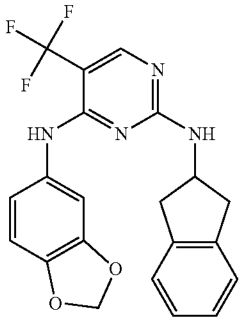
,
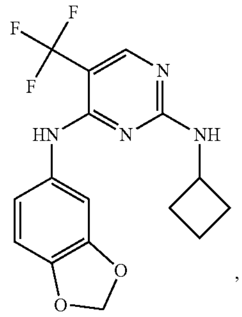
,
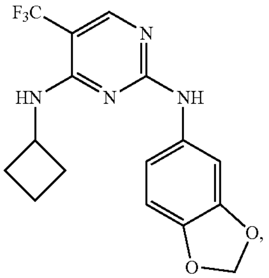
,
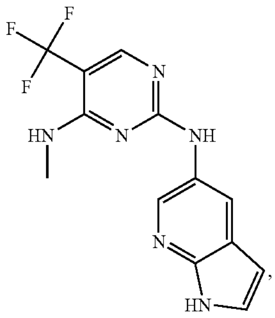
,
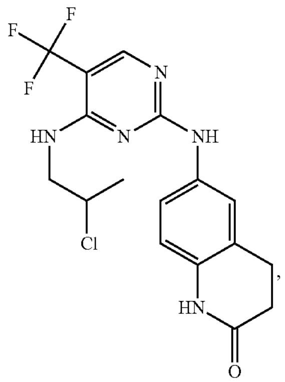
,
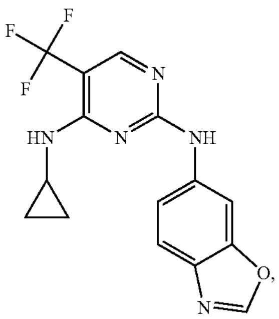
,
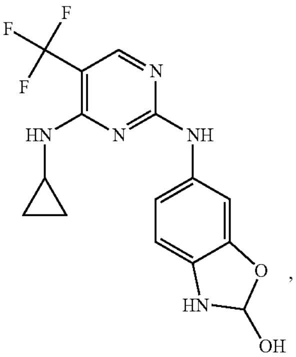
,
-continued
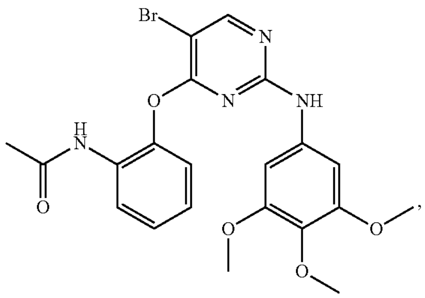
,
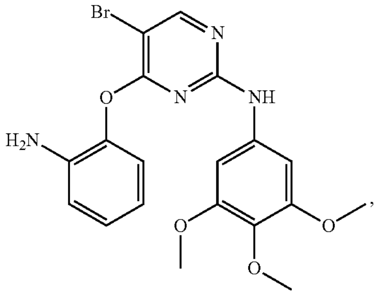
,
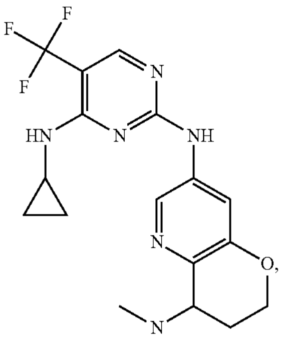
,
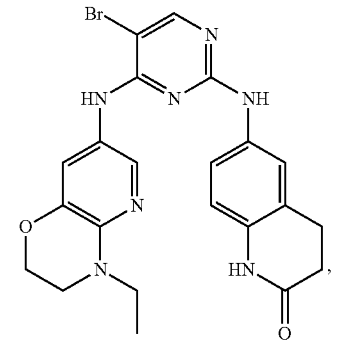
,
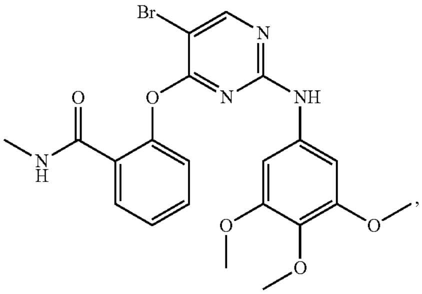
, and -continued

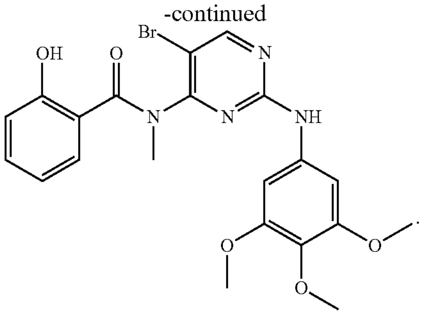

Particular examples of the presently disclosed compounds include one or more asymmetric centers; thus these compounds can exist in different stereoisomeric forms. Accordingly, compounds and compositions may be provided as individual pure enantiomers or as stereoisomeric mixtures, including racemic mixtures. In certain embodiments the compounds disclosed herein are synthesized, or are purified to be, in substantially enantiopure form, such as in a 90% enantiomeric excess, a 95% enantiomeric excess, a 97% enantiomeric excess or even in greater than a 99% enantiomeric excess, such as in enantiopure form.

Also provided herein is a recombinant peptide that serves as a substrate for the ULK1 enzyme, referred to as "ULKtide." The ULKtide peptide can be used as a surrogate marker for ULK1 kinase activity in vitro. In certain embodiments, provided is a recombinant peptide comprising the amino acid sequence YANWLAASIYLDGKKK (SEQ ID NO: 1). In some embodiments, a variant of the ULKtide peptide is provided. For example, the variant peptide has any hydrophobic residue at the −3 position (which corresponds to residue 5 of SEQ ID NO: 1), such as a leucine. In other examples, the peptide has any hydrophobic residue at the +1 position (which corresponds to residue 9 of SEQ ID NO: 1), such as a phenylalanine or a tyrosine. In certain embodiments, the peptide has any hydrophobic residue at the +2 position (corresponding to residues 10 of SEQ ID NO: 1). In certain embodiments, the recombinant peptide comprises one of the following sequences:

(SEQ ID NO: 2)
EANWLAASIYLDGKKK (SEQ ID NO: 3)
YANWLAASIYLDKKKK (SEQ ID NO: 4)
YANWMAASIYLDGKKK (SEQ ID NO: 5)
YANWRAASIYLDGKKK (SEQ ID NO: 6)
YANWLAASDYLDGKKK (SEQ ID NO: 7)
YANWLAASIDLDGKKK

In certain embodiments, the recombinant peptide is conjugated to a detecatable label, such as, but not limited to, a fluorophore or a radioisotope.

The presently disclosed compounds can have at least one asymmetric center or geometric center, cis-trans center (C═C, C═N). All chiral, diasteromeric, racemic, meso, rotational and geometric isomers of the structures are intended unless otherwise specified. The compounds can be isolated as a single isomer or as mixture of isomers. All tautomers of the compounds are also considered part of the disclosure. The presently disclosed compounds also includes all isotopes of atoms present in the compounds, which can include, but are not limited to, deuterium, tritium, $^{18}F$, and so forth.

"Prodrugs" of the disclosed compounds also are contemplated herein. A prodrug is an active or inactive compound that is modified chemically through in vivo physiological action, such as hydrolysis, metabolism and the like, into an active compound following administration of the prodrug to a subject. The term "prodrug" as used throughout this text means the pharmacologically acceptable derivatives such as esters, amides and phosphates, such that the resulting in vivo biotransformation product of the derivative is the active drug as defined in the compounds described herein. Prodrugs preferably have excellent aqueous solubility, increased bioavailability and are readily metabolized into the active inhibitors in vivo. Prodrugs of a compounds described herein may be prepared by modifying functional groups present in the compound in such a way that the modifications are cleaved, either by routine manipulation or in vivo, to the parent compound. The suitability and techniques involved in making and using prodrugs are well known by those skilled in the art. For a general discussion of prodrugs involving esters see Svensson and Tunek, Drug Metabolism Reviews 165 (1988) and Bundgaard, Design of Prodrugs, Elsevier (1985).

The term "prodrug" also is intended to include any covalently bonded carriers that release an active parent drug of the present invention in vivo when the prodrug is administered to a subject. Since prodrugs often have enhanced properties relative to the active agent pharmaceutical, such as, solubility and bioavailability, the compounds disclosed herein can be delivered in prodrug form. Thus, also contemplated are prodrugs of the presently disclosed compounds, methods of delivering prodrugs and compositions containing such prodrugs. Prodrugs of the disclosed compounds typically are prepared by modifying one or more functional groups present in the compound in such a way that the modifications are cleaved, either in routine manipulation or in vivo, to yield the parent compound. Prodrugs include compounds having a phosphonate and/or amino group functionalized with any group that is cleaved in vivo to yield the corresponding amino and/or phosphonate group, respectively. Examples of prodrugs include, without limitation, compounds having an acylated amino group and/or a phosphonate ester or phosphonate amide group. In particular examples, a prodrug is a lower alkyl phosphonate ester, such as an isopropyl phosphonate ester.

Protected derivatives of the disclosed compounds also are contemplated. A variety of suitable protecting groups for use with the disclosed compounds are disclosed in Greene and Wuts, *Protective Groups in Organic Synthesis;* 3rd Ed.; John Wiley & Sons, New York, 1999.

In general, protecting groups are removed under conditions that will not affect the remaining portion of the molecule. These methods are well known in the art and include acid hydrolysis, hydrogenolysis and the like. One preferred method involves the removal of an ester, such as cleavage of a phosphonate ester using Lewis acidic conditions, such as in TMS-Br mediated ester cleavage to yield the free phosphonate. A second preferred method involves removal of a protecting group, such as removal of a benzyl group by hydrogenolysis utilizing palladium on carbon in a suitable solvent system such as an alcohol, acetic acid, and the like or mixtures thereof. A t-butoxy-based group, including t-butoxy carbonyl protecting groups can be removed utilizing an inorganic or organic acid, such as HCl or trifluoroacetic acid, in a suitable solvent system, such as water, dioxane and/or methylene chloride. Another exemplary protecting group, suitable for protecting amino and hydroxy functions amino is trityl. Other conventional protecting groups are known and suitable protecting groups can be selected by those of skill in the art in consultation with Greene and Wuts, *Protective Groups in Organic Synthesis;* 3rd Ed.; John Wiley & Sons, New York, 1999. When an amine is deprotected, the resulting salt can readily be neutralized to yield the free amine. Similarly, when an acid moiety, such as a phosphonic acid moiety is unveiled, the compound may be isolated as the acid compound or as a salt thereof.

Compounds disclosed herein can be crystallized and can be provided in a single crystalline form or as a combination of different crystal polymorphs. As such, the compounds can be provided in one or more physical form, such as different crystal forms, crystalline, liquid crystalline or non-crystalline (amorphous) forms. Such different physical forms of the compounds can be prepared using, for example different solvents or different mixtures of solvents for recrystallization. Alternatively or additionally, different polymorphs can be prepared, for example, by performing recrystallizations at different temperatures and/or by altering cooling rates during recrystallization. The presence of polymorphs can be determined by X-ray crystallography, or in some cases by another spectroscopic technique, such as solid phase NMR spectroscopy, IR spectroscopy, or by differential scanning calorimetry.

Methods

The compounds disclosed herein may be useful in treating or inhibiting diseases that are mediated by aberrant or abnormal autophagy. In such diseases the compounds disclosed herein may inhibit excessive or undesired autophagy that is inducing, exacerbating, or maintaining the disease. Illustrative diseases include diseases or conditions arising out of mutations in the genes STK11, PTEN, TSC1, TSC2, and/or PIK3CA, or that are indicated by an mTOR substrate biomarker Phospho-S6K or Phospho-4ebp1. Illustrative diseases include, but are not limited to, tuberous sclerosis complex (TSC), cancer, neoplasms, Crohn's disease, Parkinson's disease, Alzheimer's disease, and static encephalopathy of childhood with neurodegeneration in adulthood (SENDA). Illustrative cancers include, but are not limited to, glioblastoma, metastatic solid tumors, breast cancer, prostate cancer, non-small cell lung cancer, colorectal cancer, pancreatic cancer, renal cell carcinoma, B Cell chronic lymphocytic leukemia, melanoma, adenocarcinoma, colorectal, and kidney cancer.

In certain embodiments, the compounds ameliorate conditions or diseases in which undesired autophagy has been therapeutically initiated or enhanced. In such diseases or conditions, administration of a ULK1 inhibitor in a combined therapy inhibits the undesired autophagy. Such therapy includes mTOR inhibitor administration. Non-limiting illustrative mTOR inhibitors include rapamycin, sirolimus, temsirolimus, everolimus, ridaforolimus, NVP-BEZ235, BGT226, XL765, GDC0980, SF1126, PKI587, PFO4691502, GSK2126458, INK128, TORKiCC223, OSI027, AZD8055, AZD2014, and Palomid 529. Illustrative indirect mTOR inhibitors include metformin and AICAR (5-amino-1-β-D-ribofuranosyl-imidazole-4-carboxamide). Illustrative diseases or conditions for treatment with an mTOR inhibitor, and thus amenable to co-administration treatment with a ULK1 inhibitor, include immunosuppression (such as for preventing graft rejection), anti-restenosis (for example, following angioplasty), cancer (for example, renal cell carcinoma, pancreatic, TSC, lymphoma, endometrial, breast, colon, prostate, glioblastoma, astrocytoma, multiple myeloma, hepatocellular carcinoma), Cowden's syndrome, Peutz-Jegher's syndrome, Tuberous Sclerosis Complex, LAM (lymphoangiomyoleiomatosis), and age-related macular degeneration.

The compounds disclosed herein may also be administered to a subject having a refractory disease, such as, for example, an mTOR inhibitor-resistant disease. Non-limiting illustrative refractory diseases include glioblastoma, metastatic solid tumors, breast cancer, prostate cancer, non-small cell lung cancer, colorectal cancer, pancreatic cancer, renal cell carcinoma, B Cell chronic lymphocytic leukemia, melanoma, adenocarcinoma, colorectal, and kidney cancer.

In certain embodiments, the subject is in need of, or has been recognized as being in need of, treatment with a ULK1 inhibitor. The subject may be selected as being amenable to treatment with a ULK1 inhibitor. For example, the subject may be in need of an agent that inhibits undesired autophagy in tumor cells caused by administration of an mTOR inhibitor.

In certain embodiments, autophagy inhibition provided by the compounds disclosed herein stimulates clearance of damaged cells and expedites resolution of damaged and tumorigenic cells.

Available treatments for TSC currently are drugs that can suppress the elevated mTOR found in these patients' cells, such as the drug rapamycin, its analogs (called "rapalogs") and other mTOR inhibitors. Treatment with rapalogs and newer direct mTOR inhibiting drugs leads to activation of ULK1 once its blockage by mTOR is relieved. Moreover, ULK1 normally provides a survival signal to cells to stay alive during times of stress by allowing them to recycle their own parts and metabolites. These findings suggest that in patients treated with rapamycin or other mTOR inhibitors, the activation of ULK1 by these drugs actually keeps the tumor cells and other TSC-deficient cells alive during the treatment, preventing the full eradication of the tumor cells. Combining mTOR inhibitors with ULK1 inhibitors as described herein may convert the modest but positive effects seen in TSC and lymphangioleiomyomatosis ("LAM") with mTOR inhibitors into a much more sustained and robust response. Indeed, the synergistic combination in culture in LKB1-deficient tumor cells showed dramatic synergy on therapeutic killing. In certain embodiments, the ULK1 inhibitors disclosed herein help all TSC patients as well as any patients with spontaneously arising LAM or AML (angiomyolipomas). Because the ULK1 components are expressed in all cells of the body, combining ULK1 and mTOR drugs benefits all organs affected by TSC: brain (tubers, SEGAs), kidney (AML), skin fibromas, heart rhabdomyosarcomas, and lung LAM lesions.

In certain embodiments, the therapeutic combination of ULK1 and mTOR inhibitors provides more durable and lasting responses, which may mean complete eradication of the tumor cells or restored function to TSC-deficient cell types that are not tumorous (e.g. brain tubers), without patients needing to keep taking an mTOR inhibitor for the rest of their lives. The discovery that ULK1 is blocked by mTOR in all cell types and the fact that ULK1 small molecular inhibitors have been discovered makes this one of the broadest possible new therapeutic options to rationally combine with mTOR drugs.

Treatment with rapalogs and newer direct mTOR inhibiting drugs leads to an activation of ULK1 once its inhibition by mTOR is relieved. This means that markers of ULK1 activity can be able to be used in biopsies and blood samples from TSC-patients to determine the efficacy of the mTOR blockade from rapalogs or other mTOR-inhibitors, as the signal from ULK1 will go "up" proportional to how much mTOR goes down. Importantly, mTOR inhibition is sufficient to activate ULK1, and that AMPK phosphorylation of ULK1 is not needed in this condition.

All the current markers of mTOR activity are lowered when mTOR is blocked (Phospho-S6, Phospho-S6K1, Phospho-4ebp1), which is also useful, but sometimes it is easier to quantify a signal that is low basally and then increased with treatment, proportional to how effective treatment is. Thus using a combination of the two sets of antibodies (mTOR substrate phosphorylation sites & ULK1 substrate phosphorylation sites) should provide a fruitful panel of antibodies that can then be tested against human clinical samples.

Methods are also disclosed for determining the likelihood that an mTOR inhibitor is effective for treatment of a disease. In some embodiments, the methods include performing one or more assays that detect the level of at least one of the mTOR substrates Phospho-S6K or Phospho-4ebp1 in a biological sample from a subject administered an mTOR inhibitor, and comparing the level of at least one of the mTOR substrates Phospho-S6K or Phospho-4ebp1 to a respective control level of a normal corresponding tissue. Detection of an increase in the level of at least one of the mTOR substrates Phospho-S6K or Phospho-4ebp1 as compared to the respective control indicates that the mTOR inhibitor is effective for the treatment of a disease in the subject.

In certain embodiments, the inhibitors are selective autophagy mediators, in the sense that they inhibit an ATG gene in the autophagy pathway, as compared to the far more widespread use of lysomotropic agents like chloroqine and chloroquine derivatives, which stop autophagy by virtue of disrupting lysosome function but also cause other potential complications since they are very nonspecific to autophagy.

In certain embodiments, the compounds disclosed herein are ATP-competitive binding agents which bind into the catalytic ATP-binding pocket of ULK1. In certain embodiments, the compounds disclosed herein are reversible inhibitors.

Further provided is a screening assay to identify compounds that inhibit kinase activity of ULK1 using the ULKtide peptide. In some embodiments, the method contacting a candidate compound, ULK1 and a recombinant ULKtide peptide (or variant thereof); detecting phosphorylation of the recombinant peptide in the presence and absence of the candidate compound; and identifying a compound that inhibits kinase activity of ULK1 if phosphorylation of the recombinant peptide is decreased in the presence of the candidate compound compared to in the absence of the candidate compound.

Compositions

Another aspect of the disclosure includes pharmaceutical compositions prepared for administration to a subject and which include a therapeutically effective amount of one or more of the compounds disclosed herein. The therapeutically effective amount of a disclosed compound will depend on the route of administration, the species of subject and the physical characteristics of the subject being treated. Specific factors that can be taken into account include disease severity and stage, weight, diet and concurrent medications. The relationship of these factors to determining a therapeutically effective amount of the disclosed compounds is understood by those of skill in the art. The pharmaceutical composition may include both a ULK1 inhibitor and an mTOR inhibitor in a single dosage unit or form.

Pharmaceutical compositions for administration to a subject can include at least one further pharmaceutically acceptable additive such as carriers, thickeners, diluents, buffers, preservatives, surface active agents and the like in addition to the molecule of choice. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds herein disclosed.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed compounds. The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the compound can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The compound can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The compound can be combined with the base or vehicle according to a variety of methods, and release of the compound can be by diffusion, disintegration of the vehicle, or associated formation of water channels. In some circumstances, the compound is dispersed in microcapsules (microspheres) or nanocapsules (nanospheres) prepared from a suitable polymer, for example, isobutyl 2-cyanoacrylate (see, for example, Michael et al., J. Pharmacy Pharmacol. 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the compound can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the compound can be brought about by including in the composition an agent which delays absorption, for example, monostearate salts and gelatin.

In certain embodiments, the compound can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the compound and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-aprolactone-CO-lactic acid), poly(epsilon.-aprolactone-CO-glycolic acid), poly (beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, Sustained and Controlled Release Drug Delivery Systems, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675, 189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the compound can be delivered to a subject in a manner consistent with conventional methodologies associated with management of the disorder for which treatment or prevention is sought. In accordance with the disclosure herein, a prophylactically or therapeutically effective amount of the compound and/or other biologically active agent is administered to a subject in need of such treatment for a time and under conditions sufficient to prevent, inhibit, and/or ameliorate a selected disease or condition or one or more symptom(s) thereof.

The administration of the compound of the disclosure can be for either prophylactic or therapeutic purpose. When provided prophylactically, the compound is provided in advance of any symptom. The prophylactic administration of the compound serves to prevent or ameliorate any subsequent disease process. When provided therapeutically, the compound is provided at (or shortly after) the onset of a symptom of disease or infection.

For prophylactic and therapeutic purposes, the compound can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the compound can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, dog, sheep, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the compound (for example, amounts that are effective to alleviate one or more symptoms of a targeted disease). In alternative embodiments, an effective amount or effective dose of the compound may simply inhibit or enhance one or more selected biological activities correlated with a disease or condition, as set forth herein, for either therapeutic or diagnostic purposes.

The actual dosage of the compound will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum prophylactic or therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, intraosseous, or intranasal delivery versus intravenous or subcutaneous or intramuscular delivery. Dosage can also be adjusted based on the release rate of the administered formulation, for example, of an intrapulmonary spray versus powder, sustained release oral versus injected particulate or transdermal delivery formulations, and so forth.

The compounds disclosed herein may also be co-administered with an additional therapeutic agent, particularly an mTOR inhibitor as described above. Additional agents for co-administration include, but are not limited to, an antidiabetic agent, a cholesterol-lowering agent, an anti-inflammatory agent, an antimicrobial agent, a matrix metalloprotease inhibitor, a lipoxygenase inhibitor, a cytokine antagonist, an immunosuppressant, an anticancer agent, an anti-viral agent, a cytokine, a growth factor, an immunomodulator, a prostaglandin or an anti-vascular hyperproliferation compound.

The instant disclosure also includes kits, packages and multi-container units containing the herein described pharmaceutical compositions, active ingredients, and/or means for administering the same for use in the prevention and treatment of diseases and other conditions in mammalian subjects. Kits for diagnostic use are also provided. In certain embodiments, these kits include a container or formulation that contains one or more of the compounds described herein. In one example, this component is formulated in a pharmaceutical preparation for delivery to a subject. The compound is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples are put forth so as to provide those of ordinary skill in the art with a complete disclosure and description of how to make and use the assay, screening, and therapeutic methods of the invention, and are not intended to limit the scope of what the inventor(s) regard(s) as the invention.

EXAMPLES

The invention is now described with reference to the following Examples. These Examples are provided for the purpose of illustration only, and the invention is not limited to these Examples, but rather encompasses all variations that are evident as a result of the teachings provided herein. Unless noted otherwise, the starting materials for the synthesis described herein were obtained from commercial sources or known synthetic procedures and were used without further purification. All solvents were used as purchased from commercial sources.

Methods

Reactions conducted under microwave irradiation were performed in a CEM Discover microwave reactor using either CEM 10 mL reaction vessels or a ChemGlass heavy wall pressure vessel (100 mL, 38 mm×190 mm). Reaction progress was monitored by reverse-phase HPLC and/or thin-layer chromatography (TLC). Liquid chromatography-mass spectrometry was performed using either Waters or Shimadzu HPLC instruments using water and acetonitrile or methanol doped with 0.1% formic acid. Reverse phase purifications were conducted using water and acetonitrile or methanol doped with 0.1% formic acid. TLC was performed using silica gel 60 F254 pre-coated plates (0.25 mm). Flash chromatography was performed using silica gel (32-63 μm particle size) or aluminum oxide (activated, basic, ~150 mesh size). All products were purified to homogeneity by TLC analysis (single spot, unless stated otherwise), using a UV lamp and/or iodine and/or CAM or basic $KMnO_4$ for detection purposes. NMR spectra were recorded on 400 MHz spectrometers at ambient temperature. $^{1}H$ and $^{13}C$ NMR chemical shifts are reported as δ using residual solvent as an internal standard; $CDCl_3$: 7.26, 77.16 ppm; $CD_3OD$: 3.31, 49.00 ppm; DMSO-d6: 2.50, 39.52 ppm, $CD_3CN$: 1.94 ($^{1}H$), 1.32 ($^{13}C$) ppm. Abbreviations used: mass spectrometry (MS), palladium on carbon (Pd—C), acetonitrile (MeCN), dichloromethane (DCM), diethyl ether ($Et_2O$), ethyl acetate (EtOAc), ethanol (EtOH), methanol (MeOH), tetrahydrofuran (THF).

Example 1

Synthesis of 5-halo-2,4-(diaryl amino/oxo/thio)-pyrimidine Derivatives

SCHEME 1

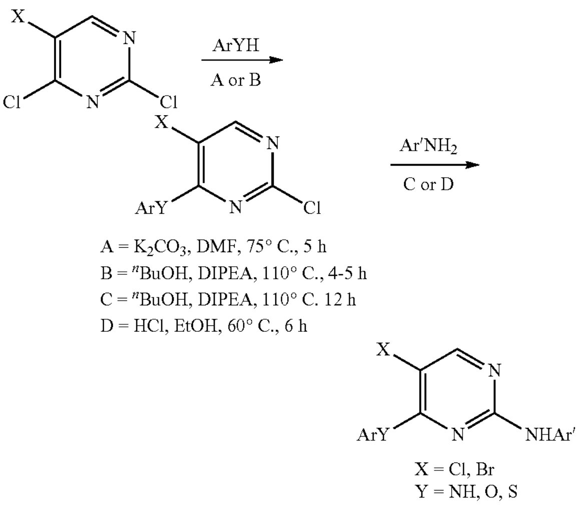

Example 2

Synthesis of 5-halo-$N^2$,$N^4$-diarylpyrimidine-2,4-diamine Derivatives (using Reaction Conditions A and C, Method 1)

To a solution of appropriate amine (10 mmol, 1 equiv.) in DMF (30 mL) were added 2,4,5-trichloro pyrimidine (13 mmol, 1.3 equiv.) and $K_2CO_3$ (13 mmol, 1.3 equiv.). The reaction mixture was stirred at 75° C. for 5 h. It was then cooled to room temperature and poured into water (300 mL). The resulting precipitate was collected by filtration followed by washing with 50% aqueous acetonitrile and dried to provide the desired 2,5-dihalo-N-arylpyrimidin-4-amine derivative. The crude product was used for next step without further purification (Method 1a). A mixture of 2,5-dichloro-N-arylpyrimidin-4-amine (1 mmol, 1 equiv.) and appropriate aniline (2 mmol, 2 equiv.) were taken in $^{n}$BuOH (10 mL) and heated at 110° C. for 12 h. The reaction mixture was cooled to room temperature and excess solvent was reduced under reduced pressure. The crude residue was purified using automated prep-HPLC to yield the desired 5-halo-$N^2$,$N^4$-diarylpyrimidine-2,4-diamine derivatives (Method 1b).

Example 3

Synthesis of 2,5-dichloro-N-aryl pyrimidin-4-amine Derivatives (using Reaction Conditions B and C, Method 2)

To a solution of appropriate amine (1 mmol, 1 equiv.) in $^{n}$BuOH (10 mL) were added 2,4,5-trichloro pyrimidine (1 mmol, 1 equiv.) and DIPEA (1 mmol, 1 equiv.). The resulting mixture was stirred at 110° C. for 4-5 (Method 2a). Reaction mixture was cooled to room temperature and to the same reaction mixture added appropriate aniline (1 mmol, 1 equiv) and DIPEA (1 mmol, 1 equiv.) heated at 110° C. for 12 h. The reaction mixture was cooled to room temperature and excess solvent was reduced under reduced pressure. The crude residue was purified using automated prep-HPLC to yield the desired 5-halo-$N^2$,$N^4$-diarylpyrimidine-2,4-diamine derivatives (Method 2b).

Example 4

Synthesis of 2,5-dichloro-N-aryl pyrimidin-4-amine Derivatives (using Reaction Condition D from the Intermediate Obtained using Reaction Conditions A or B, Method 3)

To a solution of 2,5-dihalo-N-arylpyrimidin-4-amine derivative (1 mmol, 1 equiv.) in EtOH (10 mL), were added appropriate amine (1 mmol, 1 equiv.) and few drops of HCl. The reaction mixture was stirred at 60° C. for 4-5 h (Method 3a). Reaction mixture was then cooled to room temperature diluted with water (25 mL) and neutralized with 1N NaOH solution and extracted with ethyl acetate (3×20 mL). The combined organic layers were washed with water, brine and dried over anhydrous $Na_2SO_4$. Removal off the solvent under reduced pressure afforded the crude product. The crude residue was purified using automated prep-HPLC to yield the desired 5-halo-$N^2$,$N^4$-diarylpyrimidine-2,4-diamine derivatives (Method 3b).

Example 5

Synthesis of 2-(5-trifluoromethyl-2-(arylamino/oxo/thio)pyrimidin-4-ylamino)-N-methylbenzamide Derivatives

SCHEME 2

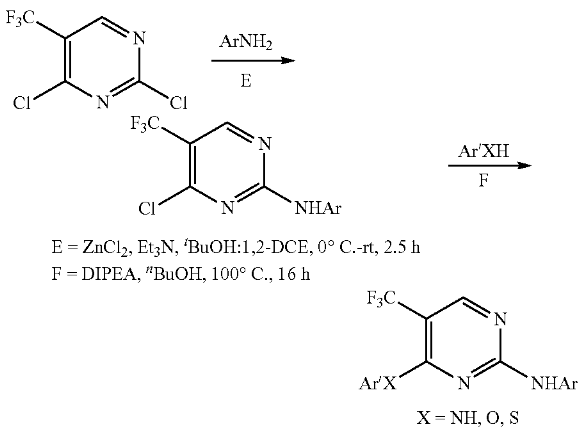

Example 6

Synthesis of $N^2$,$N^4$-diaryl-5-(trifluoromethyl)pyrimidine-2,4-diamine Derivatives (using Reaction Conditions E and F, Method 4)

To a solution of 5-trifluromethyl-2,4-dichloropyrimidine (4.6 mmol, 1 equiv.) in DCE:$^t$BuOH (1:1, 40 mL) was added $ZnCl_2$ (5.5 mmol, 1.2 equiv.) at 0° C. After 1 h, appropriate aniline (1 equiv.) and triethylamine (4.6 mmol, 1.2 equiv) in DCE:$^t$BuOH (4 mL) was added to the reaction mixture. After stirring for 1.5 h, the reaction mixture was concentrated to get the crude product. The crude product was triturated with MeOH, filtered and dried to yield the desired 5-trifluromethyl-4-chloro-N-arylpyrimidin-2-amine derivative (Method 4a). To a solution of 5-trifluromethyl-4-chloro-N-arylpyrimidin-2-amine derivative (1 mmol, 1 equiv) in $^n$BuOH (10 mL), were added appropriate aniline (1 mmol, 1 equiv.) and DIPEA (1 mmol, 1 equiv.). The reaction mixture was stirred at 100° C. for 16 h. It was then cooled to room temperature excess solvent was reduced under reduced pressure. The crude residue was purified using automated prep-HPLC to yield the desired 5-trifluromethyl-$N^2$,$N^4$-diarylpyrimidine-2,4-diamine derivatives (Method 4b).

Example 7

Preparation of 2-(2,5-Dichloropyrimidin-4-ylamino)-N-methylbenzamide

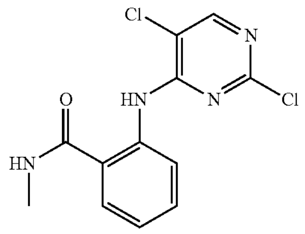

Prepared according to method 1a using 2-amino-N-methyl benzamide (1.5 g, 10 mmol), 2,4,5-trichloro pyrimidine (2.38 g, 13 mmol) and $K_2CO_3$ (1.79 g, 13 mmol). White solid (2.6 g, 89%). $^1$H NMR (400 MHz, DMSO-$d_6$): δ 12.15 (s, 1H), 8.82 (brs, 1H), 8.48 (d, J=7.3 Hz, 1H), 8.43 (s, 1H), 7.76 (d, J=7.3 Hz, 1H), 7.57 (t, J=8.2 Hz, 1H), 7.18 (t, J=7.8 Hz, 1H), 2.76 (d, J=2.3 Hz, 3H). LC-MS (ESI) calcd. for $C_{12}H_{10}Cl_2N_4O$ $[M+H]^+$: 297.02; found: 297.00.

Example 8

Preparation of 2-(5-Bromo-2-chloropyrimidin-4-ylamino)-N-methylbenzamide

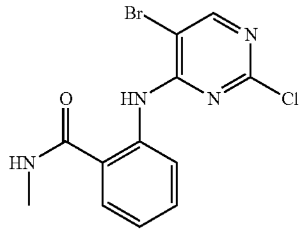 [SMILES: CNC(=O)c1ccccc1Nc1nc(Cl)ncc1Br]

Prepared according to method 1a using 2-amino-N-methyl benzamide (1.5 g, 10 mmol), 5-bromo-2,4-dichloropyrimidine (2.75 g, 13 mmol) and $K_2CO_3$ (1.79 g, 13 mmol). Yellow solid (4.5 g, 66%). $^1$H NMR (400 MHz, DMSO-$d_6$): δ 11.93 (s, 1H), 8.50 (brs, 1H), 8.48 (d, J=7.3 Hz, 1H), 8.41 (s, 1H), 7.75 (d, J=7.3 Hz, 1H), 7.54 (t, J=8.2 Hz, 1H), 7.17

(t, J=7.8 Hz, 1H), 2.76 (d, J=2.3 Hz, 3H). LC-MS (ESI) calcd. for $C_{12}H_{10}BrClN_4O$ $[M+H]^+$: 342.97; found: 342.85.

Example 9

Preparation of 6-(4-Chloro-5-(trifluoromethyl)pyrimidin-2-ylamino)-3,4-dihydroquinolin-2(1H)-one (Method 4a)

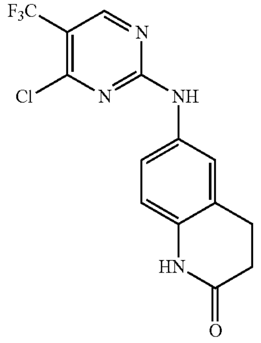 [SMILES: O=C1CCc2cc(Nc3ncc(C(F)(F)F)c(Cl)n3)ccc2N1]

To a solution of 5-trifluromethyl-2,4-dichloropyrimidine (1 g, 4.6 mmol) in DCE:$^t$BuOH (1:1, 40 mL) was added $ZnCl_2$ (5.5 mL, 5.5 mmol) at 0° C. After 1 h, 6-amino-3,4-dihydroquinolin-2(1H)-one hydrochloride (0.938 g, 4.6 mmol) and triethylamine (1 g, 5.5 mmol) in DCE:$^t$BuOH (4 mL) was added to the reaction mixture. After stirring for 1.5 h, the reaction mixture was concentrated to get the crude product. The crude product was triturated with methanol and filterd and dried in vacuuo to afford the compound. Yellow solid (1 g, 64%). $^1$H NMR (400 MHz, DMSO-$d_6$): δ 10.51 (s, 1H), 10.04 (s, 1H), 8.79 (s, 1H), 7.40 (s, 1H), 7.39 (d, J=8.2 Hz, 1H), 6.82 (d, J=12.6 Hz, 1H), 2.76 (t, J=7.2 Hz, 2H), 2.39 (t, J=7.3 Hz, 2H). LC-MS (ESI) calcd. for $C_{14}H_{10}ClF_3N_4O$ $[M+H]^+$: 343.05; found: 342.90.

Example 10

Preparation of 4-Chloro-5-(trifluoromethyl)-N-(3,4,5-trimethoxyphenyl) pyrimidin-2-amine

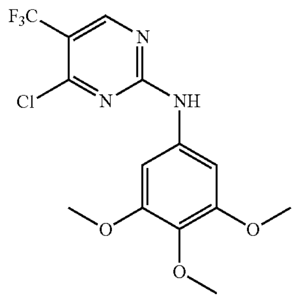 [SMILES: COc1cc(Nc2ncc(C(F)(F)F)c(Cl)n2)cc(OC)c1OC]

The title compound was prepared by the reaction of 5-trifluromethyl-2,4-dichloro pyrimidine (1 g, 4.6 mmol), $ZnCl_2$ (5.5 mL, 5.5 mmol), 3,4,5-trimethoxyaniline (0.841 g, 4.6 mmol) and triethylamine (1 g, 5.5 mmol) according to method 4a. Pale yellow solid (1.38 g, 82%). $^1$H NMR (400 MHz, DMSO-$d_6$): δ 10.45 (s, 1H), 8.75 (s, 1H), 7.06 (s, 2H), 3.85 (s, 6H), 3.68 (s, 3H). LC-MS (ESI) calcd. for $C_{14}H_{13}ClF_3N_3O_3$ $[M+H]^+$: 364.06; found: 363.95.

Example 11

Preparation of 4-Chloro-N-(5-methoxy-2-methylphenyl)-5-(trifluoromethyl) pyrimidin-2-amine

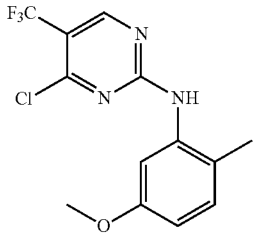 [SMILES: COc1ccc(C)c(Nc2ncc(C(F)(F)F)c(Cl)n2)c1]

The title compound was prepared by the reaction of 5-trifluromethyl-2,4-dichloro pyrimidine (1 g, 4.6 mmol), $ZnCl_2$ (5.5 mL, 5.5 mmol), 5-methoxy-2-methylaniline (0.60 g, 4.6 mmol) and triethylamine (1 g, 5.5 mmol) according to Method 4a. Colorless solid (0.800 g, 53%). $^1$H NMR (400 MHz, DMSO-$d_6$): δ 8.04 (s, 1H), 7.20 (d, J=2.8 Hz, 1H), 7.19 (d, J=8.2 Hz, 1H), 6.68 (dd, J=8.9 Hz, 2.8 Hz, 1H), 3.70 (s, 3H), 2.11 (s, 3H). LC-MS (ESI) calcd. for $C_{13}H_{11}ClF_3N_2O$ $[M+H]^+$: 318.05; found: 318.00.

Example 12

Preparation of 2-(5-Chloro-2-(2-methoxy-4-morpholinophenylamino) pyrimidin-4-ylamino)-N-methylbenzamide

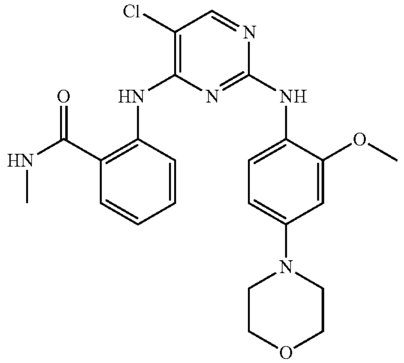 [SMILES: CNC(=O)c1ccccc1Nc1nc(Nc2ccc(N3CCOCC3)cc2OC)ncc1Cl]

2-(2,5-Dichloropyrimidin-4-ylamino)-N-methylbenzamide (0.148 g, 0.5 mmol), 2-methoxy-4-morpholinoaniline (0.208 g, 1 mmol) and few drops of HCl were processed according to method 3. Brown solid (0.150, 64%). $^1$H NMR (400 MHz, DMSO-$d_6$): 11.56 (s, 1H), 8.68 (d, J=4.6 Hz, 2H), 8.56 (d, J=7.8 Hz, 1H), 8.14 (s, 1H), 7.68 (d, J=9.2 Hz, 1H), 7.39 (d, J=8.7 Hz, 1H), 7.29 (t, J=7.8 Hz, 1H), 7.03 (t, J=15.0 Hz, 1H), 6.61 (d, J=2.3 Hz, 1H), 6.46 (dd, J=11.5, 2.8 Hz, 1H), 3.73-3.64 (overlapping singlet and triplet, 7H), 3.09 (t, J=4.6 Hz, 4H), 2.75 (d, J=4.6 Hz, 3H). LC-MS (ESI) calcd. for $C_{23}H_{25}ClN_6O_6$$[M+H]^+$: 469.17; found: 469.10. HRMS (ESI) Calcd for $C_{23}H_{25}ClN_6O_6$$[M+H]^+$: 469.1749; found: 469.1749.

Example 13

Preparation of 2-(5-Bromo-2-(2-methoxy-4-morpholinophenylamino) pyrimidin-4-ylamino)-N-methylbenzamide

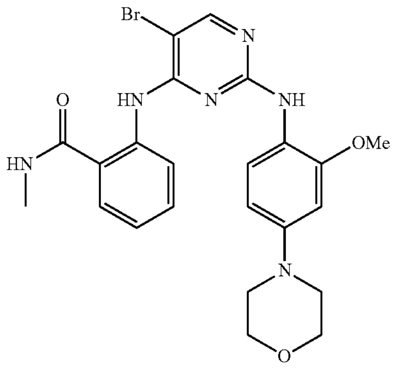 [SMILES: CNC(=O)c1ccccc1Nc1nc(Nc2ccc(N3CCOCC3)cc2OC)ncc1Br]

2-(5-Bromo-2-chloropyrimidin-4-ylamino)-N-methylbenzamide (0.341 g, 1 mmol), 2-methoxy-4-morpholinoaniline (0.208 g, 1 mmol) and HCl were processed according to method 3. Tan solid (0.258 g, 50%). $^1$H NMR (400 MHz, DMSO-$d_6$): δ 11.33 (s, 1H), 8.80 (brs, 1H), 8.50 (brs, 1H), 8.01 (s, 1H), 7.64 (d, J=7.3 Hz, 1H), 7.34 (d, J=8.2 Hz, 1H), 7.27 (t, J=7.2 Hz, 1H), 7.03 (t, J=7.3 Hz, 1H), 6.61 (s, 1H), 6.43 (d, J=8.7 Hz, 1H), 5.71 (s, 1H), 3.72-3.68 (overlapping singlet and triplet, 7H), 3.06 (t, J=7.3 Hz, 4H), 2.75 (d, J=4.3 Hz, 3H). LC-MS (ESI) calcd. for $C_{23}H_{25}BrN_6O_3$ $[M+H]^+$: 515.12; found: 515.05. HRMS (ESI) calcd. for $C_{23}H_{25}BrN_6O_3$ $[M+H]^+$: 515.1227; found: 515.1226.

Example 14

Preparation of 2-(5-Bromo-2-(3,4,5-trimethoxyphenylamino)pyrimidin-4-yl amino)-N-methylbenzamide

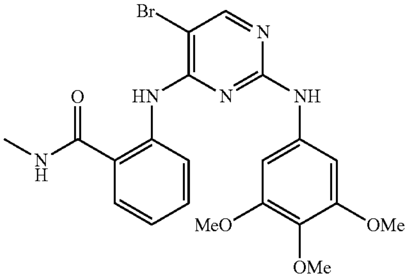 [SMILES: CNC(=O)c1ccccc1Nc1nc(Nc2cc(OC)c(OC)c(OC)c2)ncc1Br]

2-(5-Bromo-2-chloropyrimidin-4-ylamino)-N-methylbenzamide (0.341 g, 1 mmol) and 3,4,5-trimethoxyaniline (0.366 g, 2 mmol) were processed according to method 1b. Tan solid (0.325 g, 67%). $^1$H NMR (400 MHz, DMSO-$d_6$): δ 11.39 (s, 1H), 9.26 (s, 1H), 8.69-8.65 (m, 2H), 8.25 (s, 1H), 7.68 (d, J=7.8 Hz, 1H), 7.37 (t, J=7.8 Hz, 1H), 7.08 (t, J=7.8 Hz, 1H), 6.97 (s, 2H), 3.61 (s, 6H), 3.59 (s, 3H), 7.76 (d, J=4.4 Hz, 3H). LC-MS (ESI) calcd. for $C_{21}H_{22}BrN_5O_4$ $[M+H]^+$: 490.09; found: 490.00. HRMS (ESI) calcd. for $C_{21}H_{22}BrN_5O_4$ $[M+H]^+$: 490.0910; found: 490.0912.

Example 15

Preparation of 2-(5-Chloro-2-(3,4,5-trimethoxyphenylamino)pyrimidin-4-yl amino)-N-methylbenzamide

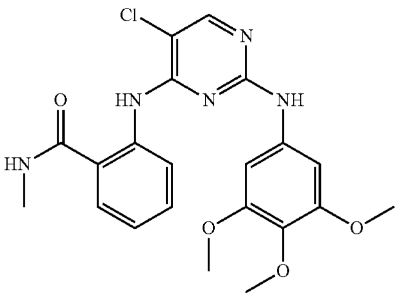 [SMILES: CNC(=O)c1ccccc1Nc1nc(Nc2cc(OC)c(OC)c(OC)c2)ncc1Cl]

A mixture of 2-(2,5-dichloropyrimidin-4-ylamino)-N-methylbenzamide (0.296 g, 1 mmol) and 3,4,5-trimethoxyaniline (0.366 g, 2 mmol) were processed according to method 1b. Colorless solid (0.160, 73%). $^1$H NMR (400 MHz, DMSO-$d_6$): δ 11.63 (s, 1H), 9.27 (s, 1H), 8.27-8.71 (m, 2H), 8.18 (s, 1H), 7.70 (d, J=9.2 Hz, 1H), 7.69 (t, J=7.8 Hz, 1H), 7.08 (t, J=7.3 Hz, 1H), 6.98 (s, 2H), 3.62 (s, 3H), 3.59 (s, 6H), 2.76 (d, J=4.6 Hz, 3H). LC-MS (ESI) calcd. for $C_{21}H_{22}ClN_5O_4$ $[M+H]^+$: 444.13; found: 444.05. HRMS (ESI) calcd. for $C_{21}H_{22}ClN_5O_4$ $[M+H]^+$: 444.1433; found: 444.1431.

Example 16

Preparation of 2-(5-Chloro-2-(5-methoxy-2-methylphenylamino)pyrimidin-4-ylamino)-N-methylbenzamide

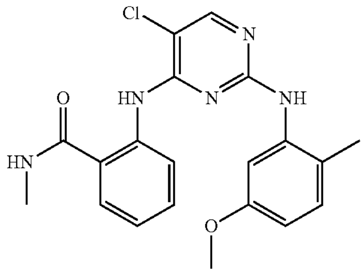 [SMILES: CNC(=O)c1ccccc1Nc1nc(Nc2cc(OC)ccc2C)ncc1Cl]

2-(2,5-Dichloropyrimidin-4-ylamino)-N-methylbenzamide (0.296 g, 1 mmol) and 5-methoxy-2-methylaniline (0.274 g, 2 mmol) were processed according to method 1b. Yellow solid (0.232 g, 58%). $^1$H NMR (400 MHz, DMSO-$d_6$): δ 11.44 (s, 1H), 8.48 (s, 1H), 8.66 (d, J=8.7 Hz, 1H), (d, J=8.7 Hz, 1H), 8.16 (s, 1H), 7.64 (d, J=7.8 Hz, 1H), 7.09-7.04 (m, 4H), 6.65 (d, J=8.2 Hz, 1H), 3.65 (s, 3H), 2.77 (d, J=4.6 Hz, 3H), 2.11 (s, 3H). LC-MS (ESI) calcd. for $C_{20}H_{20}ClN_5O_2$ $[M+H]^+$: 398.13; found: 398.00. HRMS (ESI) calcd. for $C_{20}H_{20}ClN_5O_2$ $[M+H]^+$: 398.1378; found: 398.1366.

Example 17

Preparation of 2-(5-Bromo-2-(5-methoxy-2-methylphenylamino)pyrimidin-4-ylamino)-N-methylbenzamide

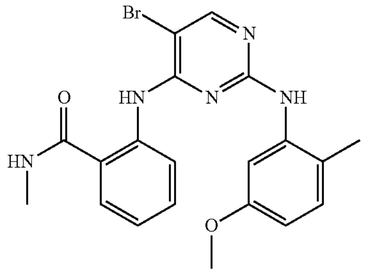 [SMILES: CNC(=O)c1ccccc1Nc1nc(Nc2cc(OC)ccc2C)ncc1Br]

2-(5-Bromo-2-chloropyrimidin-4-ylamino)-N-methylbenzamide (0.341 g, 1 mmol) and 5-methoxy-2-methylaniline (0.274 g, 2 mmol) were processed according to method 1b. Tan solid (0.298 g, 67%). $^1$H NMR (400 MHz, DMSO-$d_6$): δ 11.61 (s, 1H), 9.40 (s, 1H), 8.73-8.72 (m, 2H), 8.20 (s, 1H), 7.72 (d, J=7.8 Hz, 1H), 7.44 (t, J=7.4 Hz, 1H), 7.30-7.10 (m, 3H), 6.51 (d, J=7.8 Hz, 1H), 3.65 (s, 3H), 2.77 (d, J=4.1 Hz, 3H), 2.11 (s, 3H). LC-MS (ESI) calcd. for $C_{20}H_{20}BrN_5O_2$[M+H]$^+$: 444.08; found: 443.95. HRMS (ESI) calcd. for $C_{20}H_{20}BrN_5O_2$[M+H]$^+$: 444.0855; found: 444.0849.

Example 18

Preparation of 2-(2-(1H-indol-5-ylamino)-5-chloropyrimidin-4-ylamino)-N-methylbenzamide

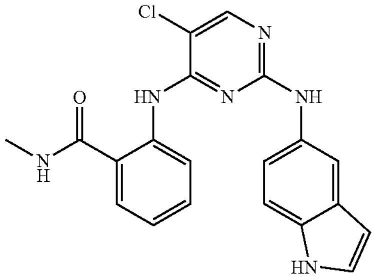 [SMILES: CNC(=O)c1ccccc1Nc1nc(Nc2ccc3[nH]ccc3c2)ncc1Cl]

The title compound was prepared from 2-(2,5-dichloropyrimidin-4-ylamino)-N -methylbenzamide (0.148 g, 0.5 mmol) and 1H-indol-5-amine (0.132 g, 1 mmol) were processed according to method 1b. Tan solid (0.172 g, 84%). $^1$H NMR (400 MHz, DMSO -$d_6$): δ 11.03 (s, 1H), 9.66 (s, 1H), 8.63-8.51 (m, 1H), 7.85 (s, 1H), 7.70 (s, 1H), 7.53-7.38 (m, 1H), 7.14 (d, J=7.8 Hz, 1H), 7.24 (s, 1H), 7.15-7.09 (m, 3H), 7.00-6.96 (m, 1H), 6.81 (t, J=7.8 Hz, 1H), 6.21 (s, 1H), 2.77 (d, J=4.2 Hz, 3H). LC-MS (ESI) calcd. for $C_{20}H_{17}ClN_6O$ [M+H]$^+$: 393.12; found: 392.95. HRMS (ESI) calcd. for $C_{20}H_{17}ClN_6O$ [M+H]$^+$: 393.1152; found: 393.1213.

Example 19

Preparation of 2-(5-Chloro-2-(2-oxo-1,2,3,4-tetrahydroquinolin-6-ylamino) pyrimidin-4-ylamino)-N-methylbenzamide

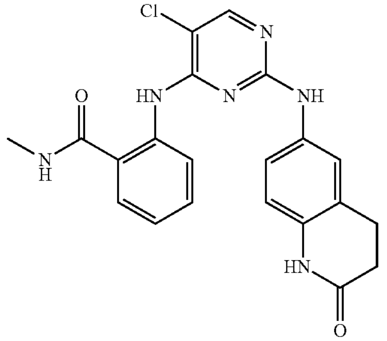 [SMILES: CNC(=O)c1ccccc1Nc1nc(Nc2ccc3c(c2)CCC(=O)N3)ncc1Cl]

2-(2,5-Dichloropyrimidin-4-ylamino)-N-methylbenzamide (0.148 g, 0.5 mmol) and 6-amino-3,4-dihydroquinolin-2(1H)-one (0.162 g, 1 mmol) were processed according to method 1b to afford the desired compound as a tan solid (0.154 g, 73%). $^1$H NMR (400 MHz, DMSO-$d_6$): δ 11.87 (s, 1H), 9.99 (s, 1H), 9.74 (s, 1H), 8.80 (d, J=4.1 Hz, 1H), 8.56 (brs, 1H), 8.22 (s, 1H), 7.74 (d, J=7.3 Hz, 1H), 7.40-7.38 (m, 2H), 7.24 (d, J=7.8 Hz, 1H), 7.15 (t, J=7.3 Hz, 1H), 677 (d, J=8.7 Hz, 1H), 2.72-2.76 (overlapping doublet and triplet, 5H), 2.39 (t, J=7.3 Hz, 2H). LC-MS (ESI) calcd. for $C_{21}H_{19}ClN_6O_2$ [M+H]$^+$: 423.13; found: 423.00. HRMS (ESI) calcd. for $C_{21}H_{19}ClN_6O_2$ [M+H]$^+$: 423.1331; found: 423.1303.

Example 20

Preparation of 2-((5-Bromo-2-((2-oxo-1,2,3,4-tetrahydroquinolin-6-yl)amino) pyrimidin-4-yl)amino)-N-methylbenzamide

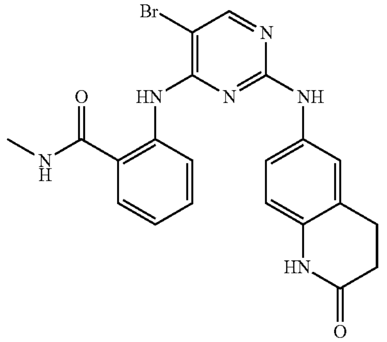

2-(5-Bromo-2-chloropyrimidin-4-ylamino)-N-methylbenzamide (0.171 g, 0.5 mmol) and 6-amino-3,4-dihydroquinolin-2(1H)-one (0.162 g, 1 mmol) were processed according to method 1b to afford the desired compound. Yellow solid (0.193 g, 83%). $^1$H NMR (400 MHz, DMSO-$d_6$): δ 11.27 (s, 1H), 9.90 (s, 1H), 9.27 (s, 1H), 8.68 (d, J=4.1 Hz, 1H), 8.56 (s, 1H), 8.20 (s, 1H), 7.67 (d, J=7.3 Hz, 1H), 7.44-7.08 (m, 4H), 672 (d, J=8.7 Hz, 1H), 2.72-2.76 (overlapping doublet and triplet, 5H), 2.39 (t, J=7.3 Hz, 2H). LC-MS (ESI) calcd. for $C_{21}H_{19}BrN_6O_2$ $[M+H]^+$: 467.08; found: 467.00.

Example 21

Preparation of 2-(5-Chloro-2-(2-oxoindolin-5-ylamino)pyrimidin-4-ylamino)-N-methylbenzamide

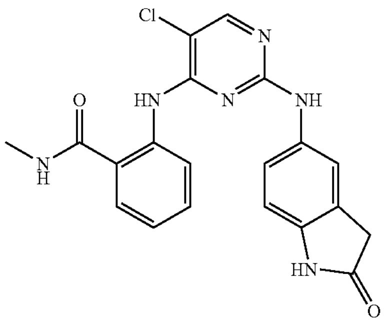 [SMILES: CNC(=O)c1ccccc1Nc1nc(Nc2ccc3c(c2)CC(=O)N3)ncc1Cl]

2-(2,5-Dichloropyrimidin-4-ylamino)-N-methylbenzamide (0.148 g, 0.5 mmol) and 5-aminoindolin-2-one (0.148 g, 1 mmol) were taken in ⁿBuOH. It was then processed according to the general procedure (method 1 b) to afford the desired compound as a tan solid (0.147 g, 73%). $^1H$ NMR (400 MHz, DMSO-$d_6$): δ 11.50 (s, 1H), 10.23 (s, 1H), 9.29 (s, 1H), 8.71-8.70 (overlapping singlet and doubletet, 2H), 8.13 (s, 1H), 7.70 (d, J=7.8 Hz, 1H), 7.56 (s, 1H), 7.43 (t, J=7.3 Hz, 1H), 7.30 (d, J=7.8 Hz, 1H), 7.10 (t, J=7.3 Hz, 1H), 6.70 (d, J=8.2 Hz, 1H), 3.39 (s, 2H), 2.76 (d, J=3.2 Hz, 3H). LC-MS (ESI) calcd. for $C_{20}H_{17}ClN_6O_2$ $[M+H]^+$: 409.11; found: 409.05.

Example 22

Preparation of Bromo-$N^4$-(pyridin-2-yl)-$N^2$-(3,4,5-trimethoxyphenyl) pyrimidine-2,4-diamine

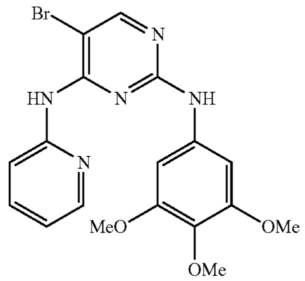 [SMILES: COc1cc(Nc2ncc(Br)c(Nc3ccccn3)n2)cc(OC)c1OC]

5-Bromo-2,4-dichloropyrimidine (0.227 g, 1 mmol), 2-aminopyridine (0.094 g, 1 mmol) 3,4,5-trimethoxyaniline (0.183 g, 1 mmol) and disopropylethylamine (0.258 g, 2 mmol) were processed according to method 2 to afford the desired compound as a colorless solid (0.240 g, 56%). $^1H$ NMR (400 MHz, DMSO-$d_6$): 9.37 (s, 1H), 8.30-8.29 (overlapping singlet and multiplets, 4H), 8.16 (s, 1H), 7.71 (t, J=6.9 Hz, 1H), 7.10 (t, J=6.4 Hz, 1H), 6.98 (s, 1H), 3.70 (s, 3H), 3.63 (s, 6H). LC-MS (ESI) calcd. for $C_{18}H_{18}BrN_5O_3$ $[M+H]^+$: 434.05; found: 433.95. HRMS (ESI) calcd. for $C_{18}H_{18}BrN_5O_3$ $[M+H]^+$: 434.0647; found: 434.0650.

Example 23

Preparation of 2-(2-(1H-indol-5-ylamino)-5-bromopyrimidin-4-ylamino)-N-methylbenzamide

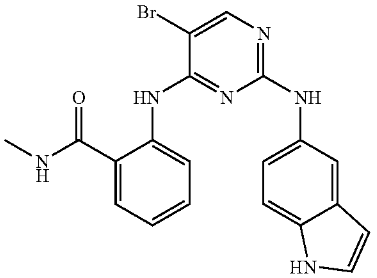 [SMILES: CNC(=O)c1ccccc1Nc1nc(Nc2ccc3[nH]ccc3c2)ncc1Br]

2-(5-Bromo-2-chloropyrimidin-4-ylamino)-N-methylbenzamide (0.341 g, 1 mmol) 1H-indol-5-amine (0.264 g, 2 mmol) were processed according to method 1b to afford the desired compound as a tan solid (0.296 g, 68%). $^1H$ NMR (400 MHz, DMSO-$d_6$): δ 11.28 (s, 1H), 10.91 (s, 1H), 9.18 (s, 1H), 8.68-8.67 (m, 2H), 8.19 (s, 1H), 7.83 (s, 1H), 7.66 (d, J=7.8 Hz, 1H), 7.27-7.18 (m, 4H), 7.06 (t, J=7.3 Hz, 1H), 6.29 (s, 1H), 2.76 (d, J=4.6 Hz, 3H). LC-MS (ESI) calcd. for $C_{20}H_{17}BrN_6O$ $[M+H]^+$: 439.06; found: 439.00. HRMS (ESI) calcd. for $C_{20}H_{17}BrN_6O$ $[M+H]^+$: 439.0702; found: 439.0693.

Example 24

Preparation of 5-Chloro-$N^4$-(6-methoxypyridin-3-yl)-$N^2$-(3,4,5-trimethoxy phenyl)pyrimidine-2,4-diamine

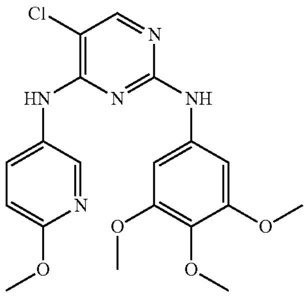 [SMILES: COc1ccc(Nc2nc(Nc3cc(OC)c(OC)c(OC)c3)ncc2Cl)cn1]

5-Chloro-2,4-dichloropyrimidine (0.183 g, 1 mmol), 6-methoxy-pyridine-3-amine (0.124 g, 1 mmol) 3,4,5-trimethoxyaniline (0.183 g, 1 mmol) and disopropylethylamine (0.258 g, 2 mmol) were processed according to method 2 to afford the desired compound as a colorless solid (0.272 g, 65%). $^1H$ NMR (400 MHz, DMSO-$d_6$): δ 9.13 (s, 1H), 8.84 (s, 1H), 8.37 (s, 1H), 8.08 (s, 1H), 7.82 (dd, J=8.7 Hz, 2.8 Hz, 1H), 6.91 (s, 2H), 6.75 (d, J=8.7 Hz, 1H), 3.98 (s, 3H), 3.72 (s, 6H), 3.54 (s, 3H). LC-MS (ESI) calcd. for $C_{19}H_{20}ClN_5O_4$ $[M+H]^+$: 418.12; found: 418.00. HRMS-MS (ESI) calcd. for $C_{19}H_{20}ClN_5O_4$ $[M+H]^+$: 418.1277; found: 418.1275.

Example 25

Preparation of 5-Bromohloro-$N^4$-(6-methoxypyridin-3-yl)-$N^2$-(3,4,5-trimethoxyphenyl)pyrimidine-2,4-diamine

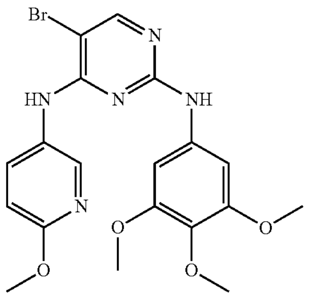

5-Bromo-2,4-dichloropyrimidine (0.227 g, 1 mmol), 6-methoxypyridin-3-amine (0.124 g, 1 mmol), diisopropylethylamine (0.258 g, 2 mmol) and 3,4,5-trimethoxy aniline (0.183 g, 1 mmol) were processed according to the general procedure (method 2) to afford the desired compound as a colorless solid (0.232 g, 50%). $^1$H NMR (400 MHz, DMSO-$d_6$): δ 9.10 (s, 1H), 8.60 (s, 1H), 8.33 (s, 1H), 8.16 (s, 1H), 7.79 (d, J=8.7 Hz, 1H), 6.89 (s, 1H), 6.74 (d, J=8.8 Hz, 1H), 3.81 (s, 3H), 3.54 (s, 3H), 3.49 (s, 3H), 3.31 (s, 3H). LC -MS (ESI) calcd. for $C_{19}H_{20}BrN_5O_4$ $[M+H]^+$: 463.07; found: 463.15.

Example 26

Preparation of 5-Bromo-$N^2$-(5-methoxy-2-methylphenyl)-$N^4$-(pyridin-2-yl) pyrimidine-2,4-diamine

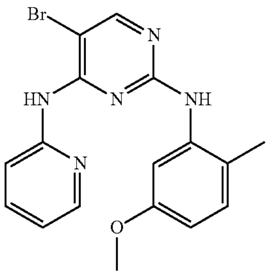 [SMILES: COc1ccc(C)c(Nc2ncc(Br)c(Nc3ccccn3)n2)c1]

2-Amino-pyridine (0.094 g, 1 mmol), 5-bromo-2,4-dichloropyrimidine (0.227 g, 1 mmol) diisopropylethylamine (0.258 g, 2 mmol) and 5-methoxy-2-methylaniline (0.137 g, 2 mmol) were taken in $^n$BuOH (10 mL). It was then processed according to method 2 to yield the desired compound as a colorless solid (0.120 g, 31%). $^1$H NMR (400 MHz, DMSO-$d_6$): δ 8.86 (s, 1H), 8.25-8.24 (m, 1H), 8.23 (s, 1H), 8.01 (d, J=8.2 Hz, 1H), 7.97 (s, 1H), 7.88 (t, J=8.7 Hz, 1H), 7.11 (d, J=8.7 Hz, 1H), 7.03-7.00 (m, 1H), 6.96 (s, 1H), 6.70 (d, J=2.8 Hz, 1H), 3.65 (s, 3H), 2.08 (s, 3H). LC-MS (ESI) calcd. for $C_{17}H_{16}BrN_5O$ $[M+H]^+$:386.05; found: 385.85.

Example 27

Preparation of 5-Chloro-$N^2$-(2-methoxy-4-morpholinophenyl)-$N^4$-(6-methoxy pyridin-3-yl)pyrimidine-2,4-diamine

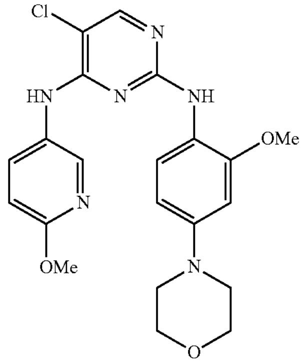

6-Methoxypyridin-3-amine (0.124 g, 1 mmol), 2,4,5-trichlorochloropyrimidine (0.208 g, 1 mmol) diisopropylethylamine (0.258 g, 2 mmol), and 2-methoxy-4-morpholinoaniline (0.127 g, 1 mmol) were taken in $^n$BuOH (10 mL). It was then processed according to method 2 to yield the desired compound as a colorless solid (0.289 g, 65%). $^1$H NMR (400 MHz, DMSO-$d_6$): δ 8.76 (s, 1H), 8.28 (s, 1H), 7.98 (s, 1H), 7.67-7.72 (m, 2H), 7.86 (d, J=6.9 Hz, 1H), 7.74 (s, 1H), 7.43 (d, J=8.2 Hz, 1H), 6.70 (d, J=8.2 Hz, 1H), 6.30 (s, 1H), 7.43 (d, J=7.8 Hz, 1H), 3.80 (s, 3H), 3.73-3.72 (overlapping singlet and triplet, 8H), 3.02 (t, J=4.6 Hz, 4H). LC-MS (ESI) calcd. for $C_{21}H_{23}ClN_6O_3[M+H]^+$: 443.15; found: 443.05.

Example 28

Preparation of 5-Bromo-$N^2$-(2-methoxy-4-morpholinophenyl)-$N^4$-(6-methoxy pyridin-3-yl)pyrimidine-2,4-diamine

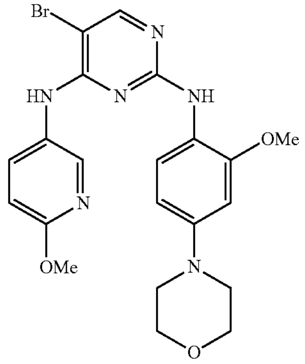 [SMILES: COc1ccc(Nc2nc(Nc3ccc(N4CCOCC4)cc3OC)ncc2Br)cn1]

5-Bromo-2,4-dichloropyrimidine (0.227 g, 1 mmol), 6-methoxypyridin-3-amine (0.124 g, 1 mmol), diisopropylethylamine (0.258 g, 2 mmol), and 2-methoxy-4-morpholinoaniline (0.208 g, 1 mmol) were processed according to method 2 to yield the desired compound as a colorless solid (0.258 g, 53%). $^1$H NMR (400 MHz, DMSO-$d_6$): δ 8.53 (s, 1H), 8.24 (s, 1H), 8.05 (s, 1H), 7.83 (d, J=8.7 Hz, 1H), 7.73 (s, 1H), 7.41 (d, J=8.7 Hz, 1H), 6.71 (d, J=8.7 Hz, 1H), 6.56 (s, 1H), 6.28 (d, J=8.7 Hz, 1H), 3.80 (s, 3H), 3.72 (s, 3H), 3.60 (t, J=4.6 Hz, 4H), 3.02 (t, J=5.0 Hz, 4H). LC-MS (ESI) calcd. for $C_{21}H_{23}BrN_6O_3$ $[M+H]^+$:487.11, found: 487.00.

Example 29

Preparation of 5-Chloro-$N^2$-(1H-indol-5-yl)-$N^4$-(6-methoxypyridin-3-yl) pyrimidine-2,4-diamine

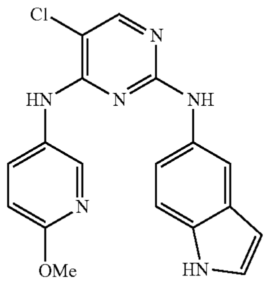 [SMILES: COc1ccc(Nc2nc(Nc3ccc4[nH]ccc4c3)ncc2Cl)cn1]

5-Chloro-2,4-dichloropyrimidine (0.183 g, 1 mmol), 6-methoxypyridin-3-amine (0.124 g, 1 mmol), diisopropylethylamine (0.258 g, 2 mmol) and 1H-indol-5-amine (0.132 g, 1 mmol) were processed according to method 2. Pale yellow solid (0.158 g, 42%). $^1H$ NMR (400 MHz, DMSO-$d_6$): δ 10.77 (s, 1H), 8.99 (s, 1H), 8.47 (s, 1H), 8.07 (s, 1H), 7.86 (s, 1H), 7.83 (d, J=8.4 Hz, 1H), 7.72 (s, 1H), 7.16-7.12 (m, 3H), 6.73 (d, J=8.7 Hz, 1H), 6.15 (s, 1H), 3.84 (s, 3H). LC-MS (ESI) calcd. for $C_{18}H_{15}ClN_6O$ $[M+H]^+$: 367.10; found: 367.45.

Example 30

Preparation of 5-Bromo-$N^2$-(1H-indol-5-yl)-$N^4$-(6-methoxypyridin-3-yl) pyrimidine-2,4-diamine

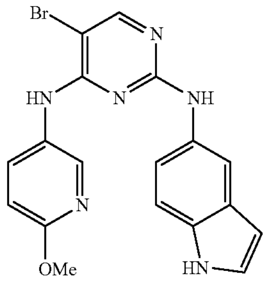 [SMILES: COc1ccc(Nc2nc(Nc3ccc4[nH]ccc4c3)ncc2Br)cn1]

5-Bromo-2,4-dichloropyrimidine (0.227 g, 1 mmol), 6-methoxypyridin-3-amine (0.124 g, 1 mmol), diisopropylethylamine (0.258 g, 2 mmol) and 1H-indol-5-amine (0.132 g, 1 mmol) were processed according to general method 2. Colorless solid (0.172 g, 42%). $^1H$ NMR (400 MHz, DMSO-$d_6$): δ 10.77 (s, 1H), 8.99 (s, 1H), 8.47 (s, 1H), 8.07 (s, 1H), 7.86 (s, 1H), 7.83 (d, J=8.4 Hz, 1H), 7.72 (s, 1H), 7.16-7.12 (m, 3H), 6.73 (d, J=8.7 Hz, 1H), 6.15 (s, 1H), 3.84 (s, 3H). LC-MS (ESI) calcd. for $C_{18}H_{15}BrN_6O$ $[M+H]^+$: 411.05; found: 411.00.

Example 31

Preparation of $N^4$-(3-(Methylsulfonyl)benzyl)-5-(trifluoromethyl)-$N^2$-(3,4,5-trimethoxyphenyl)pyrimidine-2,4-diamine

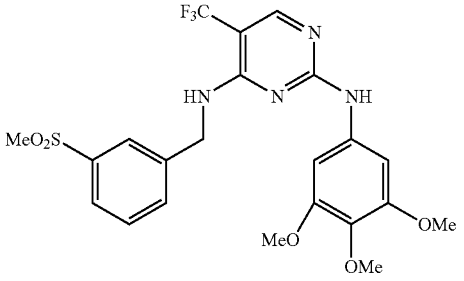 [SMILES: COc1cc(Nc2ncc(C(F)(F)F)c(NCc3cccc(S(C)(=O)=O)c3)n2)cc(OC)c1OC]

4-Chloro-5-(trifluoromethyl)-N-(3,4,5-trimethoxyphenyl)pyrimidin-2-amine (0.036 g, 0.1 mmol), (3-(methylsulfonyl)phenyl)methanamine hydrochloride (0.022 g, 0.1 mmol) and disopropylethyl amine (0.013 g, 0.1 mmol) were processed according to method 4b. Colorless solid (0.039 g, 76%). $^1H$ NMR (400 MHz, DMSO-$d_6$): δ 9.44 (s, 1H), 8.42 (s, 1H), 7.84 (s, 1H), 7.76 (d, J=6.8 HZ, 1H), 7.55-7.52 (m, 2H), 6.99 (s, 2H), 4.78 (d, J=5.5 Hz, 2H), 3.56 (s, 3H), 3.54 (s, 6H), 3.10 (s, 3H). LC-MS (ESI) calcd. for $C_{22}H_{23}F_3N_4O_5S$ $[M+H]^+$: 513.14; found: 513.10. HRMS (ESI) calcd. for $C_{22}H_{23}F_3N_4O_5S$ $[M+H]^+$: 513.1414; found: 513.1405.

Example 32

Preparation of 6-(4-(3-(Methylsulfonyl)benzylamino)-5-(trifluoromethyl) pyrimidin-2-ylamino)-3,4-dihydroquinolin-2(1H)-one

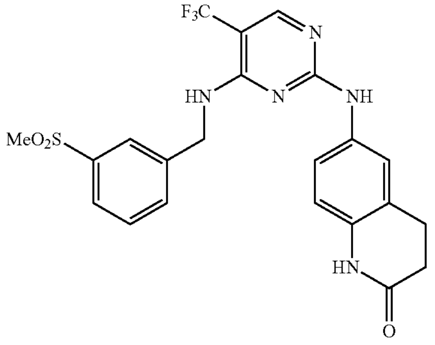 [SMILES: CS(=O)(=O)c1cccc(CNc2nc(Nc3ccc4c(c3)CCC(=O)N4)ncc2C(F)(F)F)c1]

6-(4-Chloro-5-(trifluoromethyl)pyrimidin-2-ylamino)-3,4-dihydroquinolin-2(1H)-one (0.034 g, 0.1 mmol), (3-(methylsulfonyl)phenyl)methanamine hydrochloride (0.022 g, 0.1 mmol) and disopropylethyl amine (0.013 g, 0.1 mmol) were processed according to method 4b. Colorless solid (0.035 g, 71%). $^1H$ NMR (400 MHz, DMSO-$d_6$): δ 9.89 (s, 1H), 9.43 (brs, 1H), 8.16 (s, 1H), 7.82-7.75 (m, 3H), 7.56-7.54 (m, 2H), 7.34 (s, 1H), 7.19 (d, J=7.3 Hz, 1H), 6.64 (d, J=8.7 Hz, 1H), 4.70 (d, J=5.5 Hz, 2H), 3.34 (s, 3H), 2.63 (t, J=7.3 Hz, 2H), 2.34 (t, J=11.0 Hz, 2H). LC-MS (ESI)

calcd. for $C_{22}H_{20}F_3N_5O_3S$ $[M+H]^+$: 492.12; found: 492.05. HRMS (ESI) calcd. for $C_{22}H_{20}F_3N_5O_3S$ $[M+H]^+$: 492.1312; found: 492.1197.

Example 33

Preparation of 5-((4-((3-(Methylsulfonyl)benzyl) amino)-5-(trifluoromethyl) pyrimidin-2-yl)amino) indolin-2-one

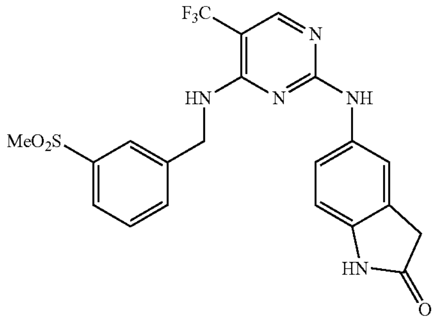 [SMILES: CS(=O)(=O)c1cccc(CNc2nc(Nc3ccc4c(c3)CC(=O)N4)ncc2C(F)(F)F)c1]

5-((4-Chloro-5-(trifluoromethyl)pyrimidin-2-yl)amino) indolin-2-one (0.164 g, 0.5 mmol), (3-(methylsulfonyl)phenyl)methanamine hydrochloride (0.100 g, 0.5 mmol) and disopropylethylamine (0.065 g, 0.5 mmol) were processed according to method 4b. Colorless solid (0.190 g, 80%). $^1$H NMR (400 MHz, DMSO-$d_6$): δ 10.23 (s, 1H), 9.45 (s, 1H), 8.08 (s, 1H), 7.84-7.56 (m, 5H), 7.42 (s, 1H), 7.26 (d, J=8.2 Hz, 1H), 6.64 (d, J=8.2 Hz, 1H), 4.71 (d, J=5.5 Hz, 2H), 3.36 (s, 2H), 3.10 (s, 3H). LC-MS (ESI) calcd. for $C_{22}H_{18}F_3N_5O_3S$ $[M+H]^+$: 478.11; found: 477.60.

Example 34

Preparation of 5-Chloro-N$^2$-(5-methoxy-2-methylphenyl)-N$^4$-(6-methoxy pyridin-3-yl)pyrimidine-2,4-diamine

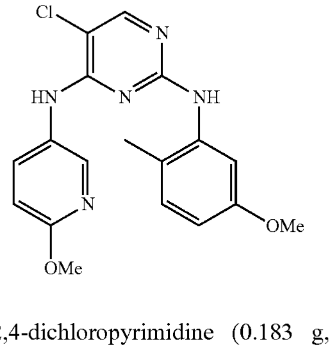

5-Chloro-2,4-dichloropyrimidine (0.183 g, 1 mmol), 6-methoxypyridin-3-amine (0.124 g, 1 mmol), diisopropylethy amine (0.258 g, 2 mmol) and 5-methoxy-2-methylaniline (0.137 g, 1 mmol) were processed according to method 2. Colorless solid (0.171 g, 46%). $^1$H NMR (400 MHz, DMSO-$d_6$): δ 8.74 (s, 1H), 8.40 (s, 1H), 8.29 (s, 1H), 8.00 (s, 1H), 7.82 (d, J=8.7 Hz, 1H), 6.99 (d, J=8.2 Hz, 1H), 6.95 (d, J=2.8 Hz, 1H), 6.60 (d, J=9.2 Hz, 1H), 6.56 (d, J=8.2 Hz, 1H), 3.82 (s, 3H), 3.57 (s, 3H), 2.05 (s, 3H). LC-MS (ESI) calcd. for $C_{18}H_{18}ClN_5O_2$ $[M+H]^+$: 372.11; found: 372.00.

Example 35

Preparation of 5-Bromo-N$^2$-(5-methoxy-2-methylphenyl)-N$^4$-(6-methoxy pyridin-3-yl)pyrimidine-2,4-diamine

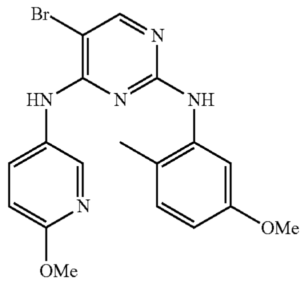 [SMILES: COc1ccc(C)c(Nc2ncc(Cl)c(Nc3ccc(OC)nc3)n2)c1]

5-Bromo-2,4-dichloropyrimidine (0.227 g, 1 mmol), 6-methoxypyridin-3-amine (0.124 g, 1 mmol), diisopropylethyamine (0.258 g, 2 mmol) and 5-methoxy-2-methylaniline (0.137 g, 1 mmol) were processed according to method 2. Colorless solid (0.241 g, 58%). $^1$H NMR (400 MHz, DMSO-$d_6$): δ 8.51 (s, 1H), 8.39 (s, 1H), 8.26 (s, 1H), 8.07 (s, 1H), 7.82 (d, J=8.7 Hz, 1H), 6.99 (d, J=8.2 Hz, 1H), 6.95 (d, J=2.8 Hz, 1H), 6.60 (d, J=9.2 Hz, 1H), 6.56 (d, J=8.2 Hz, 1H), 3.77 (s, 3H), 3.57 (s, 3H), 2.05 (s, 3H). LC-MS (ESI) calcd. for $C_{18}H_{18}BrN_5O_2$ $[M+H]^+$:417.06; found: 417.00.

Example 36

Preparation of N-Methyl-2-(5-(trifluoromethyl)-2-(3,4,5-trimethoxy phenylamino) pyrimidin-4-ylamino)benzamide

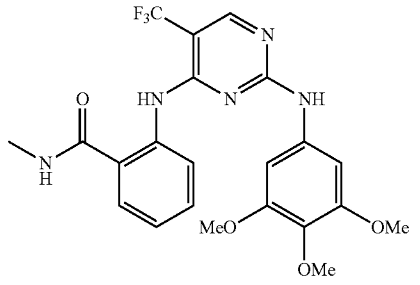

4-Chloro-5-(trifluoromethyl)-N-(3,4,5-trimethoxyphenyl)pyrimidin-2-amine (0.363 g, 1 mmol), 2-amino-N-methylbenzamide and disopropylethylamine (0.129 g, 1 mmol) were processed according to method 4b to afford the title compound as a colorless solid (0.232 g, 59%). $^1$H NMR (400 MHz, DMSO-$d_6$): δ 11.43 (s, 1H), 9.65 (s, 1H), 8.72 (d, J=4.0 Hz, 1H), 8.42-8.40 (2H), 7.67 (d, J=7.8 Hz, 1H), 7.31 (s, 1H), 7.10 (t, J=7.3 Hz, 1H), 6.95 (s, 2H), 3.68 (s, 6H), 3.58 (s, 3H), 2.75 (d, J=4.6 Hz, 3H). LC-MS (ESI) calcd. for $C_{22}H_{22}F_3N_5O_4$ $[M+H]^+$: 478.16; found: 478.10. HRMS (ESI) calcd. for $C_{22}H_{22}F_3N_5O_4$ $[M+H]^+$: 478.1683; found: 478.1683.

Example 37

Preparation of $N^4$-(6-Methoxypyridin-3-yl)-5-(trifluoromethyl)-$N^2$-(3,4,5-trimethoxyphenyl)pyrimidine-2,4-diamine

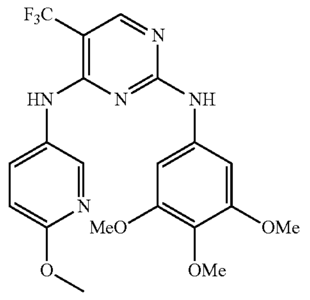 [SMILES: COc1ccc(Nc2nc(Nc3cc(OC)c(OC)c(OC)c3)ncc2C(F)(F)F)cn1]

4-Chloro-5-(trifluoromethyl)-N-(3,4,5-trimethoxyphenyl)pyrimidin-2-amine (0.363 g, 1 mmol), 6-methoxy-pyridine-3-amine (0.124 g, 1 mmol) and disopropylethyl amine (0.129 g, 1 mmol) were processed according to method 4b to afford the title compound. Yellow solid (0.330 g, 73%). $^1$H NMR (400 MHz, DMSO-$d_6$): δ 8.30 (s, 1H), 8.22 (s, 1H), 7.66 (dd, J=8.4 Hz, 2.8 Hz, 1H), 7.56 (brs, 1H), 6.72-6.65 (m, 4H), 3.92 (s, 3H), 3.79 (s, 3H), 3.61 (s, 6H). LC-MS (ESI) calcd. for $C_{20}H_{20}F_3N_5O_4$ $[M+H]^+$: 452.15; found: 452.05. HRMS (ESI) calcd. for $C_{20}H_{20}F_3N_5O_4$ $[M+H]^+$: 452.1540; found: 452.1526.

Example 38

Preparation of $N^4$-(Pyridin-2-yl)-5-(trifluoromethyl)-$N^2$-(3,4,5-trimethoxy phenyl)pyrimidine-2,4-diamine

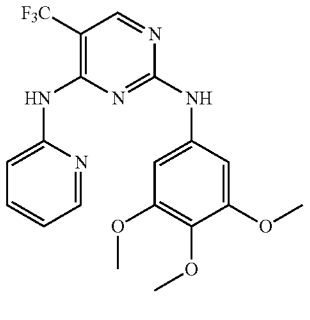 [SMILES: COc1cc(Nc2ncc(C(F)(F)F)c(Nc3ccccn3)n2)cc(OC)c1OC]

4-Chloro-5-(trifluoromethyl)-N-(3,4,5-trimethoxyphenyl)pyrimidin-2-amine (0.181 g, 0.5 mmol), 2-aminopyridine (0.0.047 g, 0.5 mmol) and disopropylethylamine (0.065 g) were processed according to method 4b to afford the title compound as a colorless solid (0.132 g, 63%). $^1$H NMR (400 MHz, DMSO-$d_6$): δ 11.83 (s, 1H), 10.20 (s, 1H), 8.86 (d, J=4.6 Hz, 2H), 8.47 (s, 1H), 7.73 (d, J=6.9 Hz, 1H), 7.17 (t, J=7.8 Hz, 1H), 6.99 (s, 2H), 3.77 (s, 6H), 3.60 (s, 3H). LC-MS (ESI) calcd. for $C_{19}H_{18}F_3N_5O_3$ $[M+H]^+$: 422.37; found: 422.05.

Example 39

Preparation of 2-(2-(2-Methoxy-4-morpholinophenylamino)-5-(trifluoromethyl)pyrimidin-4-ylamino)-N-methylbenzamide

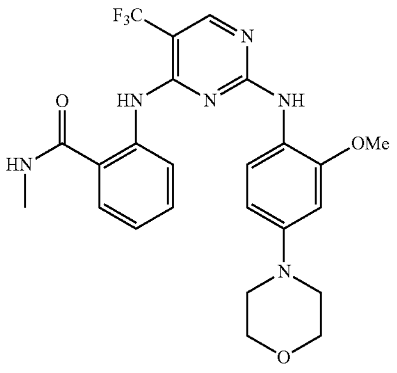

4-Chloro-N-(2-methoxy-4-morpholinophenyl)-5-(trifluoromethyl)pyrimidin-2-amine (0.194 g, 0.5 mmol), 2-amino-N-methylbenzamide and disopropylethylamine (0.065 g, 0.5 mmol) were processed according to method 4b to afford the title compound as a colorless solid (0.125 g, 50%). $^1$H NMR (400 MHz, DMSO-$d_6$): δ 11.40 (s, 1H), 8.65 (s, 1H), 8.64 (s, 2H), 8.27 (s, 1H), 7.62 (d, J=7.8 Hz, 1H), 7.26-7.24 (m, 2H), 7.03 (t, J=7.7 Hz, 1H), 6.62 (d, J=2.3 Hz, 1H), 6.45 (dd, J=10.0 Hz, J=2.8 Hz, 1H), 3.73-3.71 (overlapping singlet and triplet, 7H), 3.09 (t, J=5.2 Hz, 4H), 2.73 (d, J=4.6 Hz, 3H). LC-MS (ESI) calcd. for $C_{24}H_{25}F_3N_6O_3$ $[M+H]^+$: 503.19; found: 503.05. HRMS (ESI) calcd. for $C_{24}H_{25}F_3N_6O_3$ $[M+H]^+$: 503.2013; found: 503.2001.

Example 40

Preparation of $N^2$-(2-methoxy-4-morpholinophenyl)-$N^4$-(6-methoxypyridin-3-yl)-5-(trifluoromethyl) pyrimidine-2,4-diamine

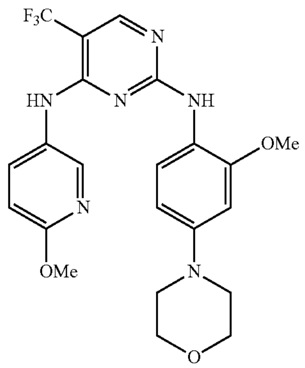 [SMILES: COc1ccc(Nc2nc(Nc3ccc(N4CCOCC4)cc3OC)ncc2C(F)(F)F)cn1]

4-Chloro-N-(2-methoxy-4-morpholinophenyl)-5-(trifluoromethyl)pyrimidin-2-amine (0.194 g, 0.5 mmol), 6-methoxypyridin-3-amine (0.062 g, 0.5 mmol) and disopropylethyl amine (0.065 g, 0.5 mmol) were processed according to general method 2. Tan solid (0.125 g, 50%). $^1$H NMR (400 MHz, DMSO-$d_6$): δ 8.55 (s, 1H), 8.21-8.11 (m, 3H), 7.17 (s, 1H), 7.25 (s, 1H), 6.70 (d, J=6.9 Hz, 1H), 6.54

(s, 1H), 6.24 (s, 1H), 3.80 (s, 3H), 3.72 (s, 3H), 3.32 (t, J=4.2 Hz, 4H), 3.03 (t, J=4.6 Hz, 4H). LC-MS (ESI) calcd. for $C_{22}H_{23}F_3N_6O_3$ $[M+H]^+$: 477.45; found: 477.00.

Example 41

Preparation of 5-Chloro-$N^2$-(5-methoxy-2-methylphenyl)-$N^4$-(3-(methyl sulfonyl)benzyl)pyrimidine-2,4-diamine

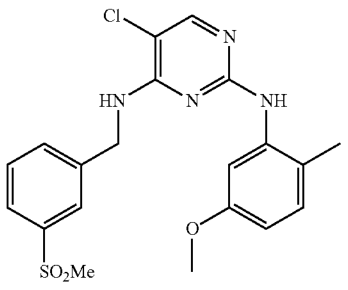 [SMILES: COc1ccc(C)c(Nc2ncc(Cl)c(NCc3cccc(S(C)(=O)=O)c3)n2)c1]

5-Chloro-2,4-dichloropyrimidine (0.109 g, 0.6 mmol), (3-(methylsulfonyl)phenyl) methanamine hydrochloride (0.110 g, 0.5 mmol), 6-methoxypyridin-3-amine (0.082 g, 0.6 mmol) and disopropylethyl amine (0.129 g, 1 mmol) were processed according to general method 2. Yellow solid (0.100 g, 46%). $^1$H NMR (400 MHz, DMSO-$d_6$): δ 9.35 (s, 1H), 8.77 (s, 1H), 8.04 (s, 1H), 7.81 (s, 1H), 7.76 (d, J=7.8 Hz, 2H), 7.75 (d, J=8.7 Hz, 1H), 7.46-7.43 (m, 1H), 7.12 (d, J=10.1 Hz, 1H), 6.98 (s, 1H), 4.53 (d, J=5.9 Hz, 2H), 3.67 (s, 3H), 3.12 (s, 3H), 2.02 (s, 3H). LC-MS (ESI) calcd. for $C_{20}H_{21}ClN_4O_3S$ $[M+H]^+$: 433.10; found: 433.00.

Example 42

Preparation of 2-(2-(5-Methoxy-2-methylphenylamino)-5-(trifluoromethyl) pyrimidin-4-ylamino)-N-methylbenzamide

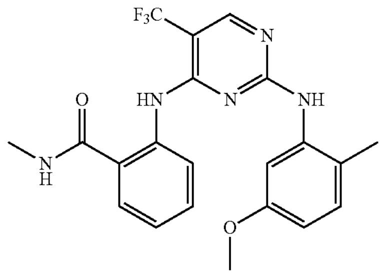

4-Chloro-N-(5-methoxy-2-methylphenyl)-5-(trifluoromethyl)pyrimidin-2-amine (0.158 g, 0.5 mmol), 2-amino-N-methylbenzamide (0.075 g, 0.5 mmol) and disopropylethyl amine (0.065 g, 0.5 mmol) were processed according to method 4b to afford the title compound as a colorless solid (0.186 g, 86%). $^1$H NMR (400 MHz, DMSO-$d_6$): δ 11.53 (s, 1H), 9.26 (s, 2H), 8.67-8.66 (m, 2H), 8.32 (s, 1H), 7.63 (dd, J=7.8 Hz, 1.7 Hz, 1H), 7.11 (d, J=8.2 Hz, 1H), 7.01 (t, J=7.3 Hz, 1H), 6.92 (d, J=2.3 Hz, 1H), 6.73 (dd, J=8.2 Hz, 2.8 Hz, 1H), 3.62 (s, 3H), 2.71 (d, J=4.6 Hz, 3H), 2.05 (s, 3H). LC-MS (ESI) calcd. for $C_{21}H_{20}F_3N_5O_2$ $[M+H]^+$: 432.15; found: 432.05. HRMS (ESI) calcd. for $C_{21}H_{20}F_3N_5O_2$ $[M+H]^+$: 432.1642; found: 432.1631.

Example 43

Preparation of 6-(4-(Benzylamino)-5-(trifluoromethyl)pyrimidin-2-ylamino)-3,4-dihydroquinolin-2 (1H)-one

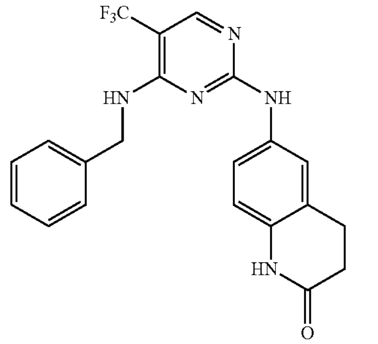 [SMILES: O=C1CCc2cc(Nc3ncc(C(F)(F)F)c(NCc4ccccc4)n3)ccc2N1]

6-(4-Chloro-5-(trifluoromethyl)pyrimidin-2-ylamino)-3,4-dihydroquinolin-2(1H)-one (0.050 g, 0.15 mmol), benzylamine (0.031 g, 0.29 mmol) and disopropylethyl amine (0.019 g, 0.15 mmol) were processed according to method 4b. Colorless solid (0.038 g, 62%). $^1$H NMR (400 MHz, DMSO-$d_6$): δ 9.95 (s, 1H), 8.21 (s, 1H), 8.01 (s, 1H), 7.25-7.17 (m, 7H), 6.68 (J=8.8 Hz, 1H), 4.36 (d, J=5.9 Hz, 2H), 2.65 (t, J=7.0 Hz, 2H), 2.33 (t, J=7.3 Hz, 2H). LC-MS (ESI) calcd. for $C_{21}H_{18}F_3N_5O$ $[M+H]^+$: 414.15; found: 414.00.

Example 44

Preparation of 2-(5-Chloro-2-(3-methoxyphenylamino)pyrimidin-4-ylamino)-N-methylbenzamide

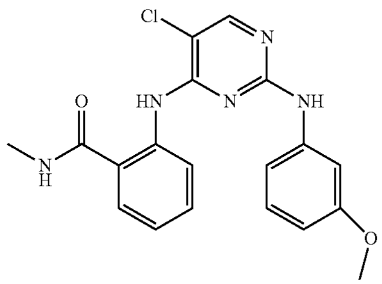 [SMILES: CNC(=O)c1ccccc1Nc1nc(Nc2cccc(OC)c2)ncc1Cl]

2-(2,5-Dichloropyrimidin-4-ylamino)-N-methylbenzamide (0.297 g, 1 mmol) and 3-methoxyaniline (0.246 g, 2 mmol) were taken in $^n$BuOH (10 mL). It was then processed according to the general method 1b to afford the desired compound as a colorless solid (0.253 g, 66%). $^1$H NMR (400 MHz, DMSO-$d_6$): δ 11.6 (s, 1H), 9.40 (s, 1H), 8.73-8.72 (m, 2H), 8.19 (s, 1H), 7.29 (d, J=8.8 Hz, 1H), 7.14 (t, J=7.3 Hz, 1H), 7.12-7.10 (m, 4H), 6.51 (d, J=7.8 Hz, 1H), 3.65 (s, 3H), 2.77 (d, J=4.1 Hz, 3H). LC-MS (ESI) calcd. for $C_{19}H_{18}ClN_5O_2$ $[M+H]^+$: 384.11; found: 384.00. HRMS (ESI) calcd. for $C_{19}H_{18}ClN_5O_2$ $[M+H]^+$: 384.1222; found: 384.1210.

Example 45

Preparation of 2-(5-Chloro-2-(5-methoxy-2-methylphenylamino)pyrimidin-4-ylamino)-N,N-dimethylbenzenesulfonamide

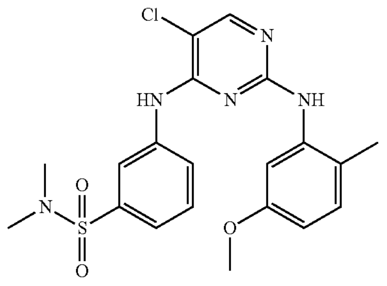

5-Chloro-2,4-dichloropyrimidine (0.92 g, 0.5 mmol), 3-amino-N,N-dimethylbenzene sulfonamide (0.100 g, 0.5 mmol), diisopropylethylamine (0.129 g, 1 mmol) and 5-methoxy-2-methylaniline (0.068 g, 0.5 mmol) were processed according to general method 2 to afford the desired compound as an yellow solid (0.098 g, 44%). $^1$H NMR (400 MHz, DMSO-$d_6$): δ 9.14 (s, 1H), 8.66 (s, 1H), 8.21-8.18 (m, 1H), 8.18 (s, 1H), 7.85-7.84 (m, 1H), 7.33-7.27 (m, 2H), 7.06 (d, J=8.7 Hz, 1H), 6.98 (d, J=2.3 Hz, 1H), 6.65 (d, J=8.7 Hz, 1H), 3.53 (s, 3H), 2.45 (s, 6H), 2.39 (s, 3H). LC-MS (ESI) calcd. for $C_{20}H_{22}ClN_5O_3S$ $[M+H]^+$: 448.11; found: 448.00.

Example 46

Preparation of $N^2$-(2-Methoxy-4-morpholinophenyl)-$N^4$-(pyridin-2-yl)-5-(trifluoromethyl) pyrimidine-2,4-diamine

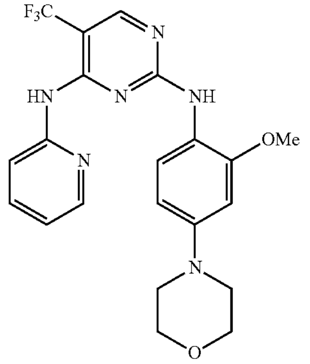 [SMILES: COc1cc(N2CCOCC2)ccc1Nc1ncc(C(F)(F)F)c(Nc2ccccn2)n1]

4-Chloro-N-(2-methoxy-4-morpholinophenyl)-5-(trifluoromethyl)pyrimidin-2-amine (0.097 g, 0.25 mmol), 2-aminopyridine (0.023 g, 0.25 mmol) and disopropylethyl amine (0.032 g, 0.25 mmol) were processed according to general method 2b. Brown solid (0.045 g, 41%).%). $^1$H NMR (400 MHz, DMSO-$d_6$): δ 8.93 (s, 1H), 8.33 (s, 1H), 8.24 (s, 1H), 8.05 (s, 1H), 7.90-7.85 (m, 1H), 7.23 (s, 1H), 7.11-6.92 (m, 1H), 6.98-6.94 (m, 1H), 6.84 (t, J=6.9 Hz, 1H), 6.46 (dd, J=2.3 Hz, 8.7 Hz, 1H), 3.79-3.70 (overlapping singlet and doublet, 7H), 3.11 (t, J=5.6 Hz, 4H). LC-MS (ESI) calcd. for $C_{21}H_{21}F_3N_6O_3$ $[M+H]^+$: 447.17; found: 447.00.

Example 47

Preparation of $N^2$-(2-Methoxy-4-morpholinophenyl)-$N^4$-(pyridin-3-yl)-5-(trifluoromethyl)pyrimidine-2,4-diamine

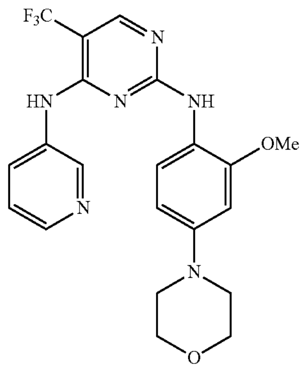 [SMILES: COc1cc(N2CCOCC2)ccc1Nc1ncc(C(F)(F)F)c(Nc2cccnc2)n1]

4-Chloro-N-(2-methoxy-4-morpholinophenyl)-5-(trifluoromethyl)pyrimidin-2-amine (0.097 g, 0.25 mmol), 3-aminopyridine (0.023 g, 0.25 mmol), and disopropylethyl amine (0.032 g, 0.25 mmol) were processed according to general method 4b. Brown solid (0.037 g, 33%). LC-MS (ESI) calcd. for $C_{21}H_{21}F_3N_6O_3$ $[M+H]^+$: 447.12; found: 447.00.

Example 48

Preparation of 6-(4-(Phenylamino)-5-(trifluoromethyl)pyrimidin-2-ylamino)-3,4-dihydroquinolin-2(1H)-one

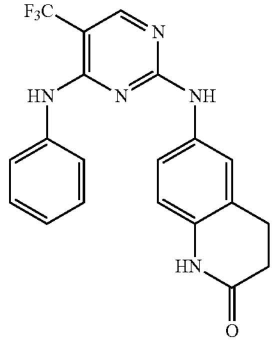 [SMILES: O=C1CCc2cc(Nc3ncc(C(F)(F)F)c(Nc4ccccc4)n3)ccc2N1]

6-(4-Chloro-5-(trifluoromethyl)pyrimidin-2-ylamino)-3,4-dihydroquinolin-2(1H)-one (0.050 g, 0.15 mmol), aniline (0.014 g, 0.15 mmol) and disopropylethyl amine (0.019 g, 0.15 mmol) were processed according to method 4b. Colorless solid (0.022 g, 37%). $^1$H NMR (400 MHz, DMSO-$d_6$): δ 9.58 (s, 1H), 9.51 (brs, 1H), 8.57 (brs, 1H), 8.26 (s, 1H) 7.42-7.12 (m, 7H), 6.75 (d, J=8.2 Hz, 1H), 3.31 (t, J=7.3 Hz, 2H), 2.46 (t, J=6.9 Hz, 2H). LC-MS (ESI) calcd. for $C_{20}H_{16}F_3N_5O$ $[M+H]^+$:400.13; found: 400.00.

Example 49

Preparation of 2-(2-(Benzo[d][1,3]dioxol-5-ylamino)-5-chloropyrimidin-4-yl amino)-N-methylbenzamide

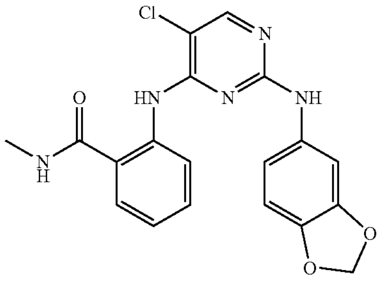 [SMILES: CNC(=O)c1ccccc1Nc1nc(Nc2ccc3c(c2)OCO3)ncc1Cl]

2-(2,5-Dichloropyrimidin-4-ylamino)-N-methylbenzamide (0.296 g, 1 mmol) and benzo[d][1,3]dioxol-5-amine (0.274 g, 2 mmol) were taken in $^{n}$BuOH (10 mL). It was then processed according to method 1b to afford the desired compound as a tan solid (0.162 g, 41%). $^{1}$H NMR (400 MHz, DMSO-$d_6$): δ 11.70 (s, 1H), 9.47 (s, 1H), 8.73 (d, J=4.2 Hz, 1H), 8.64 (d, J=7.8 Hz, 1H), 8.17 (s, 1H), 7.39 (dd, J=8.2 Hz, J=1.3 Hz, 1H), 7.43 (t, J=8.2 Hz, 1H), 7.28 (d, J=1.8 Hz, 1H), 7.13 (t, J=7.3 Hz, 1H), 6.96-6.94 (m, 1H), 6.8 (d, J=8.4 Hz, 1H), 5.99 (s, 2H), 2.77 (d, J=4.6 Hz, 3H). LC-MS (ESI) calcd. for $C_{19}H_{16}ClN_5O_3$ [M+H]$^+$: 398.09; found: 398.00.

Example 50

Preparation of N2-(2-methoxy-5-methylphenyl)-N4-(3-(methylsulfonyl) benzyl)-5-(trifluoromethyl)pyrimidine-2,4-diamine

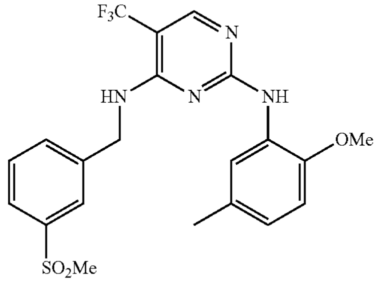 [SMILES: COc1ccc(C)cc1Nc1ncc(C(F)(F)F)c(NCc2cccc(S(C)(=O)=O)c2)n1]

4-Chloro-N-(5-methoxy-2-methylphenyl)-5-(trifluoromethyl)pyrimidin-2-amine (0.080 g, 0.25 mmol), (3-(methylsulfonyl)phenyl)methanamine hydrochloride (0.110 g, 0.5 mmol) and disopropylethylamine (0.065 g, 0.5 mmol) were processed according to method 4b to afford the title compound. Yellow solid (0.046 g, 39%). $^{1}$H NMR (400 MHz, DMSO-$d_6$): δ 8.85 (s, 1H), 8.38 (s, 1H), 8.14 (s, 1H), 7.83 (s, 1H), 7.76 (d, J=7.8 Hz, 2H), 7.75 (d, J=8.7 Hz, 1H), 7.46-7.43 (m, 1H), 7.12 (d, J=10.1 Hz, 1H), 6.95 (s, 1H), 4.53 (d, J=5.5 Hz, 2H), 3.65 (s, 3H), 3.15 (s, 3H), 2.04 (s, 3H). LC-MS (ESI) calcd. for $C_{21}H_{21}F_3N_4O_3S$ [M+H]$^+$: 467.14; found: 467.00. HRMS (ESI) calcd. for $C_{21}H_{21}F_3N_4O_3S$ [M+H]$^+$: 467.1359; found: 467.1348.

Example 51

Preparation of 2-(5-Chloro-2-(2,3-dihydrobenzo[b][1,4]dioxin-6-ylamino) pyrimidin-4-ylamino)-N-methylbenzamide

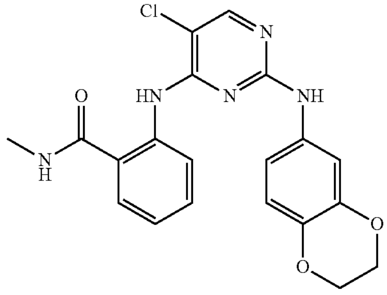 [SMILES: CNC(=O)c1ccccc1Nc1nc(Nc2ccc3c(c2)OCCO3)ncc1Cl]

2-(2,5-Dichloropyrimidin-4-ylamino)-N-methylbenzamide (0.148 g, 0.5 mmol) and 2,3-dihydrobenzo[b][1,4]dioxin-6-amine (0.151 g, 1 mmol) were taken in $^{n}$BuOH. It was then processed according to method 1b to afford the desired compound as a tan solid (0.172 g, 84%). $^{1}$H NMR (400 MHz, DMSO-$d_6$): δ 11.56 (s, 1H), 9.22 (s, 1H), 8.71-8.70 (m, 2H), 8.14 (s, 1H), 7.70 (d, J=7.3 Hz, 1H), 7.43 (t, J=7.8 Hz, 1H), 7.23 (s, 1H), 7.08 (t, J=7.3 Hz, 1H), 7.00 (s, 1H), 6.71 (d, J=8.7 Hz, 1H), 4.18 (t, J=5.5 Hz, 4H), 2.77 (d, J=4.6 Hz, 3H). LC-MS (ESI) calcd. for $C_{20}H_{18}ClN_5O_3$ [M+H]$^+$: 412.11; found: 412.00. HRMS (ESI) calcd. for $C_{20}H_{18}ClN_5O_3$[M+H]$^+$: 412.1171; found: 412.1151.

Example 52

Preparation of $N^2$-(2-Methoxy-4-morpholinophenyl)-$N^4$-(3-(methylsulfonyl) benzyl)-5-(trifluoromethyl)pyrimidine-2,4-diamine

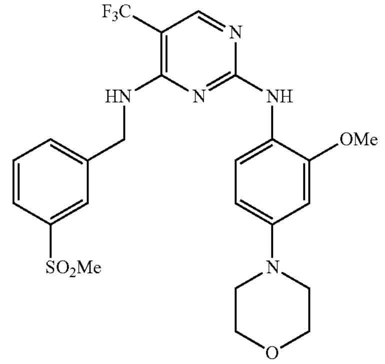 [SMILES: COc1cc(N2CCOCC2)ccc1Nc1ncc(C(F)(F)F)c(NCc2cccc(S(C)(=O)=O)c2)n1]

4-Chloro-N-(2-methoxy-4-morpholinophenyl)-5-(trifluoromethyl)pyrimidin-2-amine (0.097 g, 0.25 mmol), (3-(methylsulfonyl)phenyl)methanamine hydrochloride (0.066 g, 0.3 mmol), and disopropylethyl amine (0.040 g, 0.3 mmol) were processed according to general method 2b. Yellow solid (0.068 g, 51%). $^{1}$H NMR (400 MHz, DMSO-$d_6$): δ 9.01 (s, 1H), 8.56 (s, 1H), 8.21 (s, 1H), 7.85 (s, 1H), 7.78 (d, J=7.3 Hz, 2H), 7.53 (t, J=7.8 Hz, 1), 7.51 (s, 1H), 6.61 (s, 1H), 6.42 (d, J=8.2 Hz, 1H), 4.62 (s, 2H), 3.75 (s, 3H), 3.70 (t, J=5.0 Hz, 4H), 3.23 (s, 3H), 3.10 (t, J=7.3 Hz, 4H). LC-MS (ESI) calcd. for $C_{24}H_{26}F_3N_5O_4S$ $[M+H]^+$: 538.16; found: 538.00.

Example 53

Preparation of 2-(5-Chloro-2-(o-tolylamino)pyrimidin-4-ylamino)-N-methylbenzamide

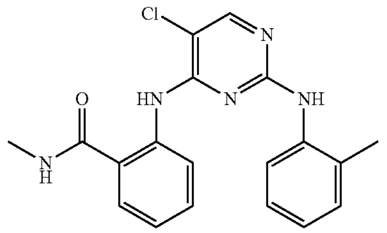

2-(2,5-Dichloropyrimidin-4-ylamino)-N-methylbenzamide (0.148 g, 0.5 mmol) and 2-methyl aniline (0.107 g, 1 mmol) were taken in $^n$BuOH (5 mL). It was then processed according to method 1b to afford the desired compound as a tan solid (0.159 g, 88%). $^1$H NMR (400 MHz, DMSO-$d_6$): δ 11.76 (s, 1H), 8.92 (s, 1H), 8.70 (brs, 1H), 8.44 (d, J=8.7 Hz, 1H), 8.11 (s, 1H), 7.68 (d, J=7.8 Hz, 1H), 7.36 (d, J=6.9 Hz, 1H), 7.23-7.08 (m, 4H), 6.99 (t, J=6.9 Hz, 1H), 2.75 (d, J=4.6 Hz, 3H), 2.16 (s, 3H). LC-MS (ESI) calcd. for $C_{19}H_{18}ClN_5O$ $[M+H]^+$: 368.12; found: 368.00. HRMS (ESI) calcd. for $C_{19}H_{18}ClN_5O$ $[M+H]^+$: 368.1273; found: 368.1268.

Example 54

Preparation of 2-(3-(5-Chloro-2-(5-methoxy-2-methylphenylamino)pyrimidin-4-ylamino)phenyl) acetonitrile

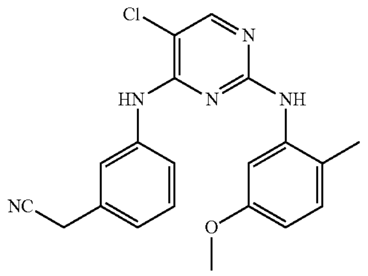 [SMILES: COc1ccc(C)c(Nc2ncc(Cl)c(Nc3cccc(CC#N)c3)n2)c1]

5-Chloro-2,4-dichloropyrimidine (0.183 g, 1 mmol), 2-(3-aminophenyl)acetonitrile (0.130 g, 1 mmol), diisopropylamine (0.258 g, 1 mmol) and 5-methoxy-2-methylaniline (0.136 g, 1 mmol) were processed according to method 2 to afford the desired compound as tan solid (0.168 g, 44%). $^1$H NMR (400 MHz, DMSO-$d_6$): δ 8.97 (s, 1H), 8.77 (s, 1H), 8.14 (s, 1H), 7.60-7.58 (m, 2H), 7.16 (t, J=7.3 Hz, 1H), 7.08 (d, J=8.2 Hz, 1H), 6.98-6.96 (m, 2H), 6.66 (dd, J=8.3 Hz, 2.8 Hz, 1H), 3.99 (2H), 3.66 (s, 3H), 2.07 (s, 3H). LC -MS (ESI) calcd. for $C_{20}H_{18}ClN_5O$ $[M+H]^+$: 381.12; found: 381.00.

Example 55

Preparation of 5-Chloro-$N^2$-(5-methoxy-2-methylphenyl)-$N^4$-(4-methyl pyrimidin-2-yl)pyrimidine-2,4-diamine

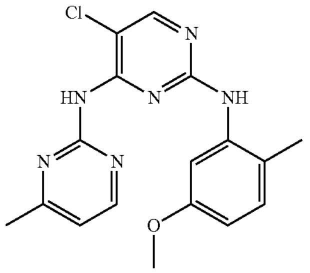

2,4,5-Trichloropyrimidine (0.091 g, 0.5 mmol), 4-methylpyrimidin-2-amine (0.055 g, 0.5 mmol) 2-methoxy-5-methylaniline (0.069 g, 0.5 mmol) and disopropylethylamine (0.129 g, 1 mmol) were processed according to method 2 to afford the desired compound. Yellow solid (0.020 g, 11%). $^1$H NMR (400 MHz, DMSO-$d_6$): δ. LC-MS (ESI) calcd. for $C_{17}H_{17}ClN_6O$ $[M+H]^+$: 357.12; found: 357.00.

Example 56

Preparation of 6-((5-Fluoro-4-((3-(methylsulfonyl)benzyl)amino)pyrimidin-2-yl)amino)-3,4-dihydroquinolin-2(1H)-one

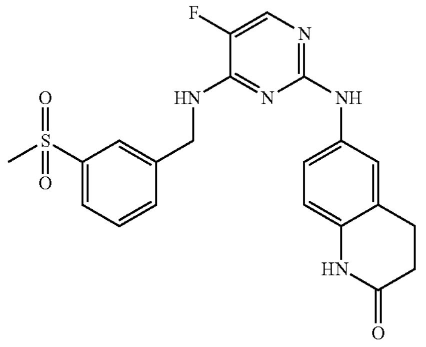 [SMILES: CS(=O)(=O)c1cccc(CNc2nc(Nc3ccc4c(c3)CCC(=O)N4)ncc2F)c1]

2,4-Dichloro-5-fluoropyrimidine (0.091 g, 0.5 mmol), (3-(methylsulfonyl)phenyl) methanamine hydrochloride (0.110 g, 0.5 mmol), 6-amino-3,4-dihydroquinolin-2(1H)-one (0.075 g, 0.55 mmol) and disopropylethylamine (0.129 g, 1 mmol) were processed according to method 2 to afford the desired compound. Tan solid (0.128 g, 58%). $^1$H NMR (400 MHz, DMSO-$d_6$): δ 10.00 (s, 1H), 9.71 (s, 1H), 9.09 (s, 1H), 8.04-8.03 (m, 1H), 7.86 (s, 1H), 7.82 (d, J=7.8 Hz, 1H), 7.64-7.57 (m, 2H), 7.29 (s, 1H), 7.17 (d, J=8.2 Hz, 1H), 6.75 (dd, J=2.3 Hz, 8.7 Hz, 1H), 4.69 (d, J=5.0 Hz, 2H), 3.10 (s, 3H), 2.72 (t, J=7.8 Hz, 2H), 2.39 (t, J=8.2 Hz, 2H). LC-MS (ESI) calcd. for $C_{21}H_{20}FN_5O_3S$ $[M+H]^+$: 442.13; found: 442.00.

Example 57

Preparation of 2-(5-Chloro-2-(6-methylbenzo[d][1,3]dioxol-5-ylamino) pyrimidin-4-ylamino)-N-methylbenzamide

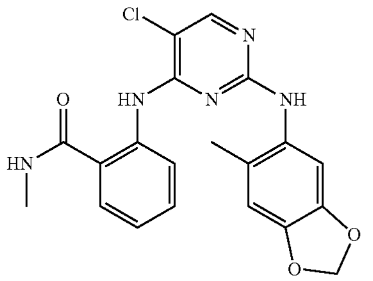 [SMILES: CNC(=O)c1ccccc1Nc1nc(Nc2cc3c(cc2C)OCO3)ncc1Cl]

2-(5-Chloro-2-chloropyrimidin-4-ylamino)-N-methylbenzamide (0.296 g, 1 mmol) and 6-methylbenzo[d][1,3]dioxol-5-amine (0.151 g, 1 mmol) were processed according to method 2b. brown solid (0.286 g, 69%). $^1$H NMR (400 MHz, DMSO-$d_6$): δ 11.62 (s, 1H), 8.68-8.67 (m, 1H), 8.62 (s, 1H), 8.52 (d, J=6.4 Hz, 1H), 8.05 (s, 1H), 7.65 (dd, J=7.8 Hz, 1.8 Hz, 1H), 7.20 (t, J=8.7 Hz, 1H), 7.02 (t, J=7.8 Hz, 1H), 6.89 (s, 1H), 6.79 (s, 1H), 5.90 (s, 2H), 2.75 (d, J=4.6 Hz, 3H), 2.10 (s, 3H). HRMS (ESI) calcd. for $C_{20}H_{18}ClN_5O_3$ [M+H]$^+$: 412.1171; found: 413.1158.

Example 58

Preparation of 6-(4-(Thiazol-2-ylamino)-5-(trifluoromethyl)pyrimidin-2-yl amino)-3,4-dihydroquinolin-2(1H)-one

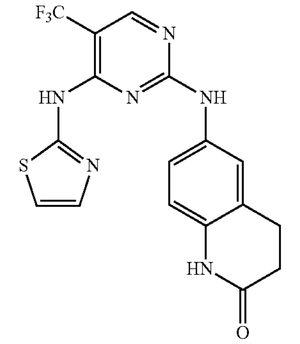 [SMILES: O=C1CCc2cc(Nc3ncc(C(F)(F)F)c(Nc4nccs4)n3)ccc2N1]

6-(4-Chloro-5-(trifluoromethyl)pyrimidin-2-ylamino)-3,4-dihydroquinolin-2(1H)-one (0.086 g, 0.25 mmol), thiazol-2-amine (0.025 g, 0.25 mmol) and disopropylethyl amine (0.033 g, 0.25 mmol) were processed according to method 4b. Yellow solid (0.035 g, 32%). $^1$H NMR (400 MHz, DMSO-$d_6$): δ 10.47 (s, 1H), 10.02 (s, 1H), 8.69 (s, 1H), 7.37-7.35 (m, 3H), 6.78 (d, J=8.7 Hz, 1H), 2.79 (t, J=7.8 Hz, 2H), 2.39 (t, J=7.6 Hz, 2H). LC-MS (ESI) calcd. for $C_{17}H_{13}F_3N_6OS$ [M+H]$^+$: 407.08; found: 407.00.

Example 59

General Scheme for the Synthesis of N-Methyl-2-(2-(3,4,5-trimethoxyphenyl amino) pyrimidin-4-ylamino)benzamide

SCHEME 3

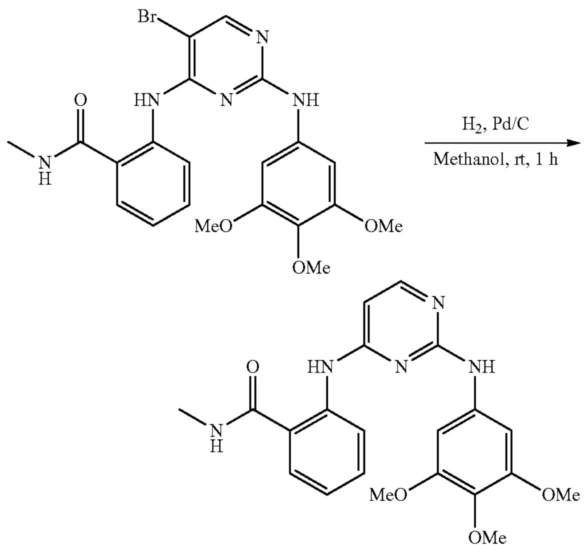

Example 60

Preparation of N-Methyl-2-(2-(3,4,5-trimethoxyphenylamino)pyrimidin-4-ylamino)benzamide

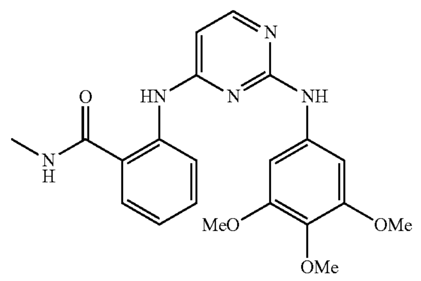 [SMILES: CNC(=O)c1ccccc1Nc1ccnc(Nc2cc(OC)c(OC)c(OC)c2)n1]

2-(5-Bromo-2-(3,4,5-trimethoxyphenylamino)pyrimidin-4-ylamino)-N-methylbenzamide (0.050 g, 0.1 mmol) was taken in methanol and Pd/C (cat) was added to it and stirred at room temperature under an atmosphere of $H_2$ for 1 h. Reaction mixture was then passed through a short pad of celite and washed with methanol. Romoval of the solvent under reduced pressure yielded the crude product which was then purified by automated Prep-HPLC to give the title compound as a colorless solid (0.036 g, 88%). $^1$H NMR (400 MHz, DMSO-$d_6$): δ 11.55 (s, 1H), 10.11 (brs, 1H), 8.55 (d, J=4.6 Hz, 1H), 8.08 (d, J=7.8 Hz, 1H), 7.93 (d, J=6.5 Hz, 1H), 7.63 (d, J=7.8 Hz, 1H), 7.36 (t, J=7.8 Hz, 1H), 7.20 (t, J=8.6 Hz, 1H), 6.42 (d, J=6.5 Hz, 1H), 3.63 (s, 3H), 3.61 (s, 9H), 2.73 (d, J=4.6 Hz, 3H). LC-MS (ESI) calcd. for $C_{21}H_{23}N_5O_4$ $[M+H]^+$: 410.18; found: 410.05. HRMS (ESI) calcd. for $C_{21}H_{23}N_5O_4$ $[M+H]^+$: 410.1823; found: 410.1813.

Example 61

Preparation of 2-(3-(2-(2-Oxo-1,2,3,4-tetrahydroquinolin-6-ylamino)-5-(trifluoromethyl)pyrimidin-4-ylamino)phenyl)acetonitrile

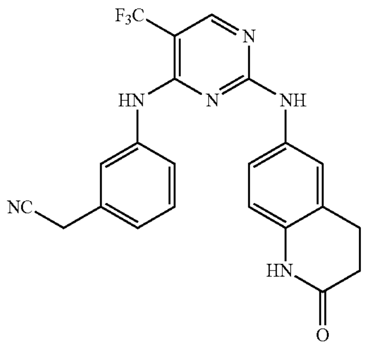 [SMILES: N#CCc1cccc(Nc2nc(Nc3ccc4c(c3)CCC(=O)N4)ncc2C(F)(F)F)c1]

6-(4-Chloro-5-(trifluoromethyl)pyrimidin-2-ylamino)-3,4-dihydroquinolin-2(1H)-one (0.342, 1 mmol), 2-(3-aminophenyl)acetonitrile (0.168 g, 1 mmol) and disopropylethyl amine (0.129 g, 1 mmol) were processed according to method 4b to afford the title compound as a pale yellow solid (0.289 g, 66%). $^1$H NMR (400 MHz, DMSO-$d_6$): δ 9.87 (s, 1H), 9.63 (brs, 1H), 8.86 (brs, 1H), 8.32 (s, 1H), 7.37-7.15 (m, 6H), 6.60 (d, J=7.8 Hz, 1H), 3.98 (s, 2H), 2.62 (t, J=7.3 Hz, 2H), 2.45 (t, J=7.4 Hz, 2H). LC-MS (ESI) calcd. for $C_{22}H_{17}F_3N_6O$ $[M+H]^+$: 439.14; found: 439.09. HRMS (ESI) calcd. for $C_{22}H_{17}F_3N_6O$ $[M+H]^+$: 439.1489; found: 439.1484.

Example 62

Preparation of 6-(4-(Benzylthio)-5-(trifluoromethyl)pyrimidin-2-ylamino)-3,4-dihydroquinolin-2(1H)-one

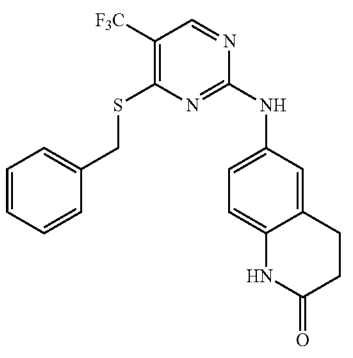

6-(4-Chloro-5-(trifluoromethyl)pyrimidin-2-ylamino)-3,4-dihydroquinolin-2(1H)-one (0.162 g, 0.5 mmol), phenylmethanethiol (0.062 g, 0.5 mmol) and disopropylethyl amine (0.065 g, 0.5 mmol) were processed according to method 4b to afford the title compound. Pale yellow solid (0.136 g, 63%). $^1$H NMR (400 MHz, DMSO-$d_6$): δ 10.04 (s, 1H), 9.98 (s, 1H), 8.45 (s, 1H), 7.45 (s, 1H), 7.34-7.20 (m, 6H), 6.76 (d, J=8.7 Hz, 1H), 4.51 (s, 2H), 2.48 (t, J=6.9 Hz, 2H), 2.34 (t, J=6.9 Hz, 2H). LC-MS (ESI) calcd. for $C_{21}H_{17}F_3N_4OS$ $[M+H]^+$: 431.10; found: 431.00.

Example 63

General Scheme for the Synthesis of 6-(4-(Phenylethynyl)-5-(trifluoromethyl) pyrimidin-2-ylamino)-3,4-dihydroquinolin-2(1H)-one

SCHEME 4

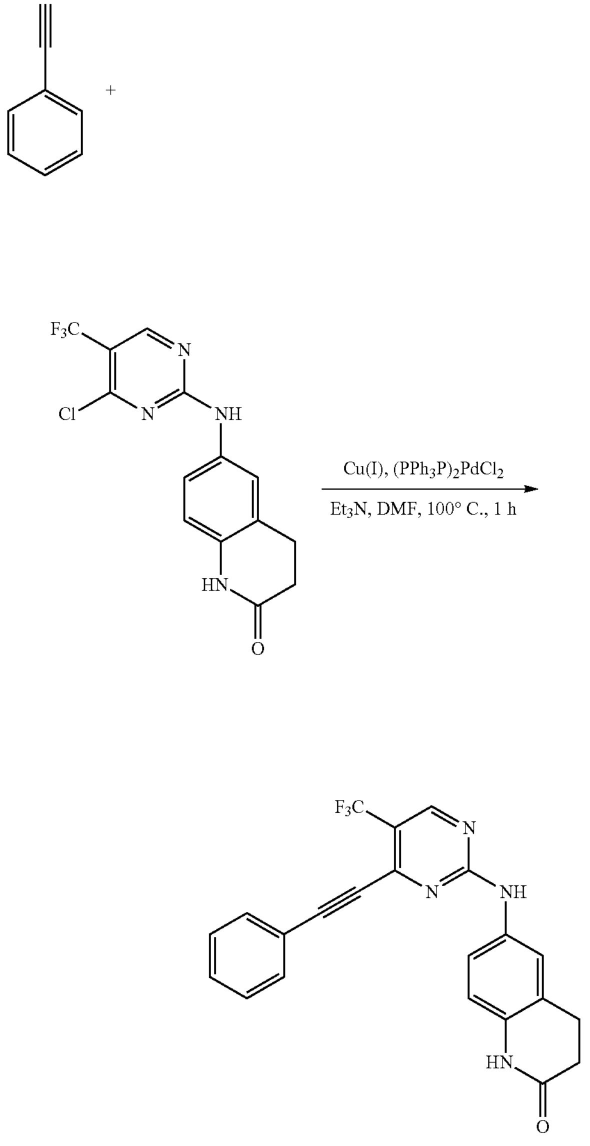

Example 64

Preparation of 6-(4-(Phenylethynyl)-5-(trifluoromethyl)pyrimidin-2-ylamino)-3,4-dihydroquinolin-2(1H)-one

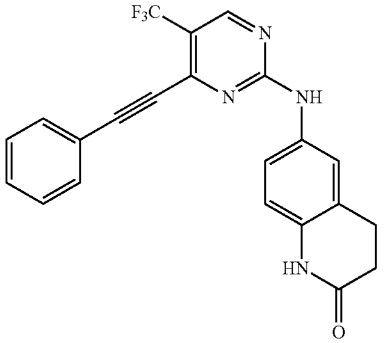 [SMILES: O=C1CCc2cc(Nc3ncc(C(F)(F)F)c(C#Cc4ccccc4)n3)ccc2N1]

To a solution of 6-(4-chloro-5-(trifluoromethyl)pyrimidin-2-ylamino)-3,4-dihydroquinolin-2(1H)-one (0.171 g, 0.5 mmol) in dry DMF (2.5 mL) were added bistriphenylphosphine palladiumdichloride (0.018 g, 0.025 mmol), copper (I)iodide (0.005 g, 0.025 mmol) and triethylamine (0.202 g, 2 mmol). The resulting mixture was heated at 100° C. under an atmosphere of $N_2$ for 1 h. After filtration through a short pad of celite and evaporation of the solvent yiled the crude product which was purified by reverse-phase HPLC. Yellow solid (0.188 g, 92%). $^1$H NMR (400 MHz, DMSO-$d_6$): δ 10.28 (s, 1H), 10.00 (s, 1H), 8.74 (s, 1H), 7.57-7.48 (m, 7H), 6.68 (d, J=8.7 Hz, 1H), 2.82 (t, J=7.3 Hz, 2H), 2.40 (t, J=7.4 Hz, 2H). LC-MS (ESI) calcd. for $C_{22}H_{15}F_3N_4O$ $[M+H]^+$:409.12; found: 409.00.

Example 65

General Scheme for the Synthesis of 6-((4-Phenethyl-5-(trifluoromethyl)pyrimidin-2-yl)amino)-3,4-dihydroquinolin-2(1H)-one

SCHEME 5

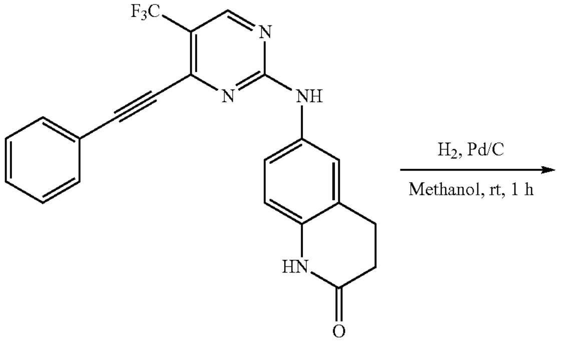

-continued

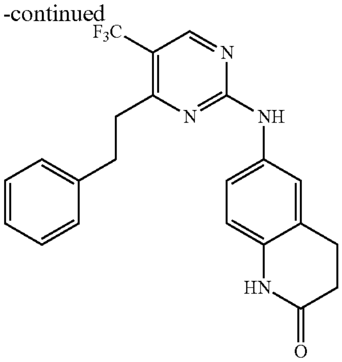

Example 66

Preparation of 6-((4-Phenethyl-5-(trifluoromethyl)pyrimidin-2-yl)amino)-3,4-dihydroquinolin-2(1H)-one

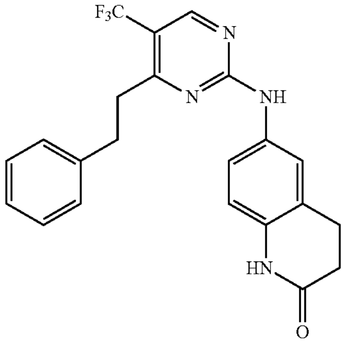 [SMILES: O=C1CCc2cc(Nc3ncc(C(F)(F)F)c(CCc4ccccc4)n3)ccc2N1]

6-(4-(Phenylethynyl)-5-(trifluoromethyl)pyrimidin-2-ylamino)-3,4-dihydroquinolin-2(1H)-one (0.010 g, 0.025 mmol) was taken in 2 mL of MeOH. Pd/C (cat) was added to it and stirred at room temperature under an atmosphere of $H_2$ for 1 h. Reaction mixture was then passed through a short pad of celite washed with methanol. Romoval of the solvent under reduced pressure yielded the crude product which was purified by automated prep-HPLC to give the title compound as a colorless solid (0.008 g, 80%). $^1$H NMR (400 MHz, DMSO-$d_6$): δ 10.04 (s, 1H), 9.97 (s, 1H), 8.58 (s, 1H), 7.52 (s, 1H), 7.42 (dd, J=2.8 Hz, 8.7 Hz, 1H), 7.27-7.13 (m, 5H), 6.77 (d, J=8.2 Hz, 1H), 3.01-3.00 (m, 4H), 2.81 (t, J=6.8 Hz, 2H), 2.39 (t, J=7.8 Hz, 2H). LC-MS (ESI) calcd. for $C_{22}H_{19}F_3N_4O$ $[M+H]^+$: 413.41; found: 413.00.

Example 67

Preparation of 6-((5-Methyl-4-((3-(methylsulfonyl) benzyl)amino)pyrimidin-2-yl)amino)-3,4-dihydro-quinolin-2(1H)-one

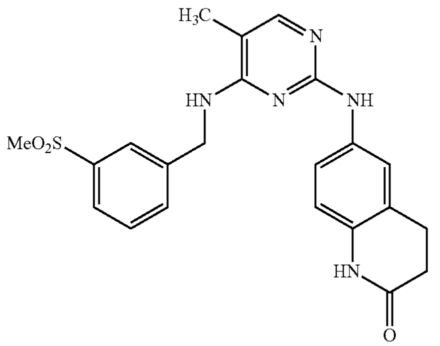

2,4-Dichloro-5-methylpyrimidine (0.089 g, 0.55 mmol), 6-amino-3,4-dihydroquinolin-2(1H)-one (0.081, 0.5 mmol), (3-(methylsulfonyl)phenyl)methanamine hydrochloride (0.111 g, 0.5 mmol), and disopropylethylamine (0.129 g, 1 mmol) were processed according to method 2 to afford the desired compound as a tan solid (0.153 g, 70%). $^1$H NMR (400 MHz, DMSO-$d_6$): δ 10.12 (s, 1H), 10.03 (s, 1H), 8.87 (s, 1H), 7.82 (s, 1H), 7.78 (d, J=6.9 Hz, 1H), 7.70 (s, 1H), 7.56-7.55 (m, 2H), 7.20 (s, 1H), 7.11 (d, J=8.2 Hz, 1H), 6.73 (d, J=8.2 Hz, 1H), 4.69 (d, J=5.5 Hz, 2H), 3.10 (s, 3H), 2.67 (t, J=7.3 Hz, 2H), 2.35 (t, J=7.3 Hz, 2H), 2.10 (s, 3H). LC-MS (ESI) calcd. for $C_{22}H_{23}N_5OS$ $[M+H]^+$:438.15; found: 438.00.

Example 68

General Scheme for the Synthesis of (E)-6-(4-aryl-5-(trifluoromethyl) pyrimidin-2-ylamino)-3,4-dihyd-roquinolin-2(1H)-one

SCHEME 6

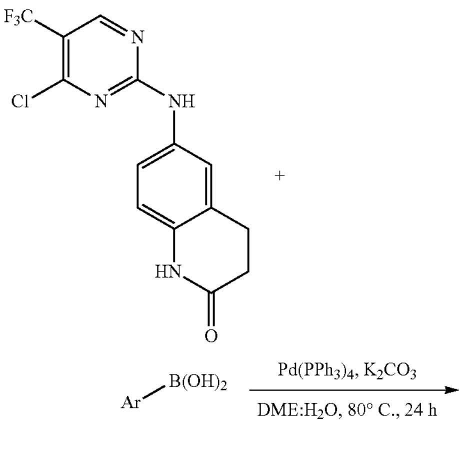

-continued

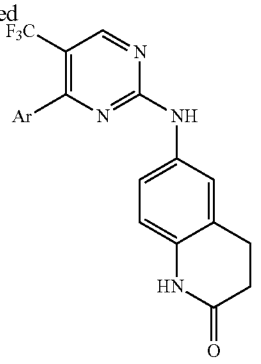

Ar = Ph, 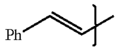

Example 69

Preparation of (E)-6-(4-Styryl-5-(trifluoromethyl) pyrimidin-2-ylamino)-3,4-dihydroquinolin-2(1H)-one

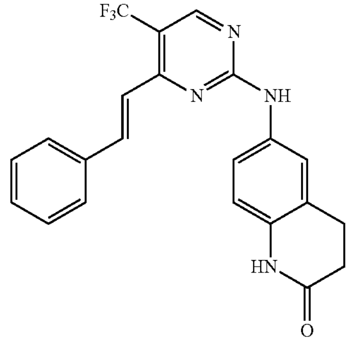 [SMILES: O=C1CCc2cc(Nc3ncc(C(F)(F)F)c(/C=C/c4ccccc4)n3)ccc2N1]

A two necked flask equipped with a condensor, nitrogen inlet and stirring bar charged with 6-(4-chloro-5-(trifluoromethyl)pyrimidin-2-ylamino)-3,4--dihydroquinolin-2(1H)-one (0.171 g, 0.5 mmol) and palladiumtetrakistriphenylphosphine (0.023 g, 0.02 mmol) in in dry DME (3 mL). The resulting mixture was stitted at room temperature for 20 min. To this potassium carbonate (0.138 g, 1 mmol) dissolved in water (1.2 mL) was added followed by the addition of trans-phenylvinyl boronic acid (0.088 g, 0.6 mmol). The mixture was heated to reflux for 24 h, cooled and diluted with water (10 mL) and extracted with ethylacetate. The combined organic layer was washed with brine and dried over anhydrous sodium sulfate. Evaporation of the solvent under reduced pressure and followed by reverse phase HPLC afforded the title compound. Yellow solid (0.098 g, 48%). $^1$H NMR (400 MHz, DMSO-$d_6$): δ 10.03 (s, 1H), 9.98 (s, 1H), 8.67 (s, 1H), 8.02 (d, J=15.0 Hz, 1H), 7.65-7.63 (m, 3 H), 7.62-7.42 (m, 4 H), 7.19 (d, J=17.0 Hz, 1H), 6.80 (d, J=8.4 Hz, 1H), 2.71 (t, J=7.3 Hz, 2H), 2.45 (t, J=7.3 Hz, 2H). LC-MS (ESI) calcd. for $C_{22}H_{17}F_3N_4O$ $[M+H]^+$:411.14; found: 411.00.

Example 70

General Scheme for the Synthesis of (E)-N-Methyl-2-((aryl-2-((3,4,5-trimethoxyphenyl)amino)pyrimidin-4-yl)amino)benzamide

SCHEME 7

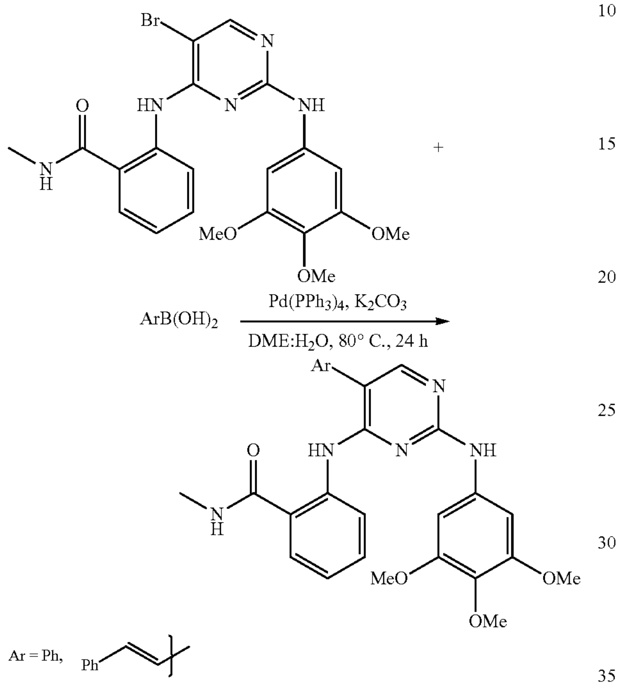

Example 71

Preparation of (E)-N-Methyl-2-((5-styryl-2-((3,4,5-trimethoxyphenyl)amino) pyrimidin-4-yl)amino) benzamide

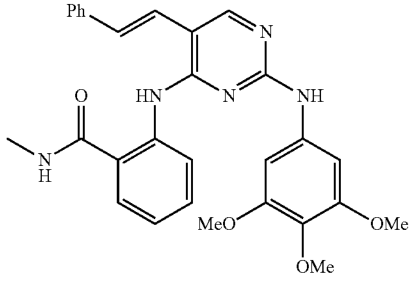 [SMILES: CNC(=O)c1ccccc1Nc1nc(Nc2cc(OC)c(OC)c(OC)c2)ncc1/C=C/c1ccccc1]

A two necked flask equipped with a condensor, nitrogen inlet and stirring bar charged with 2-(5-bromo-2-(3,4,5-trimethoxyphenylamino)pyrimidin-4-ylamino)-N-methylbenzamide (0.048 g, 0.1 mmol), and palladiumtetrakistriphenylphosphine (0.005 g, 0.004 mmol) in in dry DME (2 mL). The resulting mixture was stitted at room temperature for 20 min. To this potassium carbonate (0.0276 g, 0.2 mmol) in water (0.5 mL) was added followed by the addition of trans-phenylvinyl boronic acid (0.018 g, 0.12 mmol). The mixture was heated to reflux for 12 h, cooled and diluted with water (5 mL) and extracted with ethylacetate (3×10 mL). The combined organic layer was washed with brine and dried over anhydrous sodium sulfate. Evaporation of the solvent under reduced pressure and followed by reverse phase HPLC afforded the title compound. White solid (0.024 g, 47%). LC-MS (ESI) calcd. for $C_{29}H_{29}N_5O_4$ $[M+H]^+$: 512.22; found: 512.10.

Example 72

Preparation of 6-(4-Phenyl-5-(trifluoromethyl)pyrimidin-2-ylamino)-3,4-dihydroquinolin-2(1H)-one

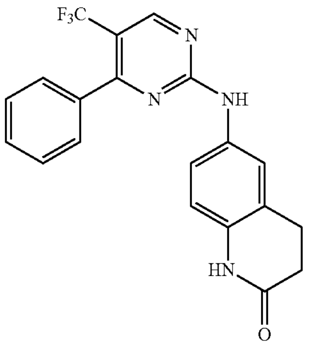 [SMILES: O=C1CCc2cc(Nc3ncc(C(F)(F)F)c(-c4ccccc4)n3)ccc2N1]

Prepared according to a similar procedure described for (E)-6-(4-styryl-5-(trifluoro methyl)pyrimidin-2-ylamino)-3,4-dihydroquinolin-2(1H)-one using appropriate starting materials (Scheme 5). Yellow solid (0.122 g, 63%). $^1H$ NMR (400 MHz, DMSO-$d_6$): δ 10.19 (s, 1H), 9.97 (s, 1H), 8.78 (s, 1H), 7.49-7.48 (m, 7H), 6.75 (d, J=8.2 Hz, 1H), 2.79 (t, J=7.3 Hz, 2H), 2.38 (t, J=6.9 Hz, 2H). LC-MS (ESI) calcd. for $C_{20}H_{15}F_3N_4O$ $[M+H]^+$: 385.11; found: 384.96.

Example 73

Preparation of N-Methyl-2-(5-phenyl-2-(3,4,5-trimethoxyphenylamino) pyrimidin-4-ylamino)benzamide

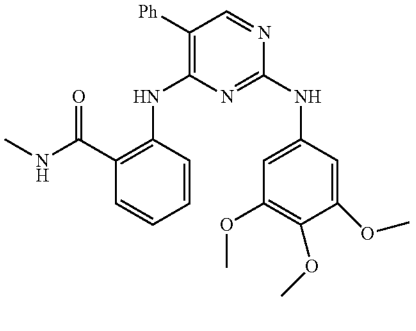

Prepared according to a similar procedure described for (E)-N-Methyl-2-((5-styryl-2-((3,4,5-trimethoxyphenyl) amino)pyrimidin-4-yl)amino)benzamide using appropriate starting materials. Yellow solid (0.041 g, 85%). $^1H$ NMR (400 MHz, DMSO-$d_6$): δ 11.01 (s, 1H), 9.79 (s, 1H), 8.55 (d, J=4.1 Hz, 1H), 8.48 (d, J=7.3 Hz, 1H), 7.94 (s, 1H), 7.58 (dd, J=1.4 Hz, 7.8 Hz, 1H), 7.51-7.42 (m, 5H), 7.30 (t, J=8.2 Hz, 1H), 7.30 (t, J=7.3 Hz, 1H), 6.91 (s, 2H), 3.62 (s, 3H), 3.61

(s, 6H), 2.58 (d, J=4.6 Hz, 3H). LC-MS (ESI) calcd. for $C_{27}H_{27}N_5O_4$ $[M+H]^+$: 486.20; found: 486.00.

Example 74

Preparation of 2-(5-Chloro-2-(2-chlorophenylamino) pyrimidin-4-ylamino)-N-methylbenzamide

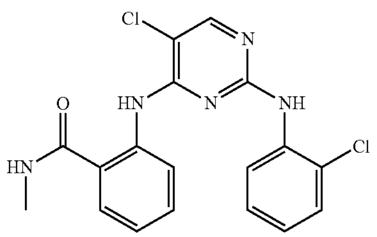 [SMILES: CNC(=O)c1ccccc1Nc1nc(Nc2ccccc2Cl)ncc1Cl]

2-(2,5-Dichloropyrimidin-4-ylamino)-N-methylbenzamide (0.148 g, 0.5 mmol) and 2-chloro aniline (0.127 g, 1 mmol) were taken in $^n$BuOH (5 mL). It was then processed according to the general procedure (method 1b) to afford the desired compound as a tan solid (0.109 g, 56%). $^1$H NMR (400 MHz, DMSO-$d_6$): δ 11.7 (s, 1H), 8.9 (s, 1H), 8.69 (d, J=4.5 Hz, 1H), 8.43 (d, J=7.8 Hz, 1H), 8.1 (s, 1H), 7.68 (d, 0.1=9.6 Hz, 1H), 7.61 (d, J=9.6 Hz, 1H), 7.50 (d, J=9.6 Hz, 1H), 7.32-7.18 (m, 3H), 7.02 (t, J=7.8 Hz, 1H), 2.75 (d, J=4.6 Hz, 3H). LC-MS (ESI) calcd. for $C_{18}H_{15}Cl_2N_5O$ $[M+H]^+$: 388.06; found: 386.00.

Example 75

Preparation of 2-(5-Bromo-2-(2-methoxy-4-morpholinophenylamino) pyrimidin-4-ylamino)-N-methylbenzenesulfonamide

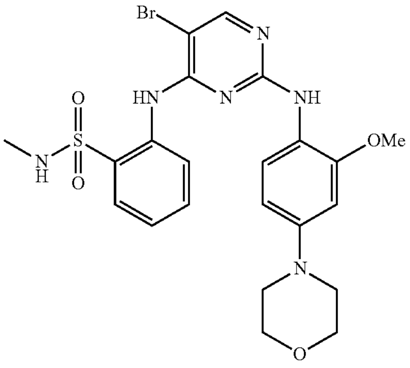 [SMILES: CNS(=O)(=O)c1ccccc1Nc1nc(Nc2ccc(N3CCOCC3)cc2OC)ncc1Br]

5-Bromo-2,4-dichloropyrimidine (0.227 g, 1 mmol), 2-amino-N-methylbenzene sulfonamide (0.186 g, 1 mmol) 2-methoxy-4-morpholinoaniline (0.202 g, 1 mmol) and disopropylethylamine (0.258 g, 2 mmol) were processed according to method 2 to afford the desired compound as a tan solid (0.220 g, 40%). $^1$H NMR (400 MHz, DMSO-$d_6$): δ 9.44 (s, 1H), 8.75-8.73 (m, 1H), 8.27-8.22 (overlapping singlet and multiplet, 2H), 7.67-7.72 (m, 2H), 7.49 (t, J=7.8 Hz, 1H), 7.30-7.27 (m, 2H), 6.64 (s, 1H), 6.42 (d, J=8.2 Hz, 1H), 3.73-3.72 (overlapping singlet and triplet, 7H), 3.10 (t, J=4.6 Hz, 4H), 2.39 (s, 3H). LC-MS (ESI) calcd. for $C_{22}H_{25}BrN_6O_4S$ $[M+H]^+$: 551.08; found: 551.10. HRMS (ESI) calcd. for $C_{22}H_{25}BrN_6O_4S$ $[M+H]^+$: 551.0896; found: 551.0895.

Example 76

Preparation of N-Methyl-2-(2-(2-oxo-1,2,3,4-tetrahydroquinolin-6-ylamino)-5-(trifluoromethyl)pyrimidin-4-ylamino)benzamide

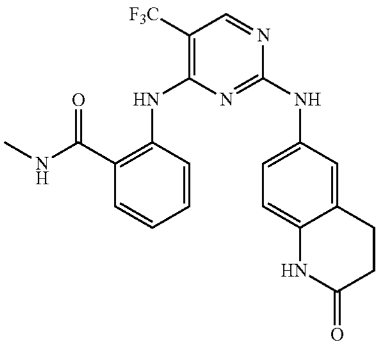 [SMILES: CNC(=O)c1ccccc1Nc1nc(Nc2ccc3c(c2)CCC(=O)N3)ncc1C(F)(F)F]

6-(4-Chloro-5-(trifluoromethyl)pyrimidin-2-ylamino)-3,4-dihydroquinolin-2(1H)-one (0.085, 0.25 mmol), 2-amino-N-methyl benzamide (0.037 g, 0.25 mmol) and disopropylethylamine were processed according to method 4b to afford the title compound as a colorless solid (0.085 g, 75%). $^1$H NMR (400 MHz, DMSO-$d_6$): 11.32 (s, 1H), 9.95 (s, 1H), 9.73 (s, 1H), 8.70 (s, 1H), 8.37 (s, 1H), 7.67 (d, J=7.8 Hz, 1H), 7.52-7.23 (m, 4H), 7.12 (t, J=7.8 Hz, 1H), 6.72 (d, J=8.7 Hz, 1H), 2.74-2.73 (overlapping doublets and triplets, 5H), 2.46 (t, J=7.3H, 2H). LC-MS (ESI) calcd. for $C_{22}K_9F_3N_6O_2$ $[M+H]^+$: 457.15; found: 457.05. HRMS (ESI) calcd. for $C_{22}H_{19}F_3N_6O_2$ $[M+H]^+$: 457.1594; found: 457.1585.

Example 77

Preparation of N-methyl-2-((2-((2-oxo-1,2,3,4-tetrahydroquinolin-6-yl)amino)-5-(trifluoromethyl)pyrimidin-4-yl)amino)benzenesulfonamide

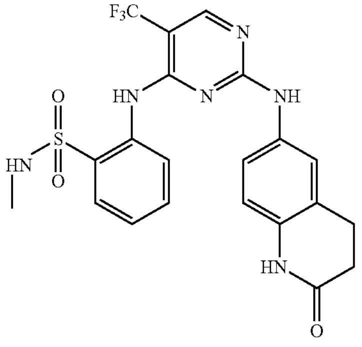 [SMILES: CNS(=O)(=O)c1ccccc1Nc1nc(Nc2ccc3c(c2)CCC(=O)N3)ncc1C(F)(F)F]

6-(4-Chloro-5-(trifluoromethyl)pyrimidin-2-ylamino)-3,4-dihydroquinolin-2(1H)-one (0.085 g, 0.25 mmol), 2-aminobenzenesulfonamide (0.051 g, 0.275 mmol) and disopropylethylamine (0.035 g, 0.275 mmol) were processed according to method 4b to afford the title compound as a colorless solid (0.068 g, 55%). LC-MS (ESI) calcd. for $C_{21}H_{19}F_3N_6O_2S$ $[M+H]^+$: 493.12; found: 493.00.

Example 78

Preparation of 2-(5-Chloro-2-(3,5-dimorpholinophenylamino)pyrimidin-4-ylamino)-N-methylbenzamide

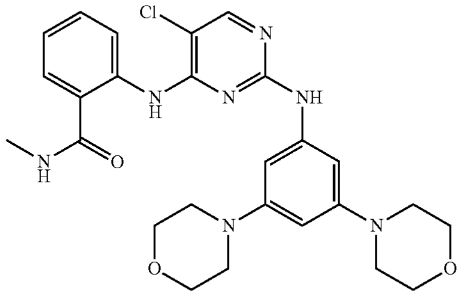 [SMILES: CNC(=O)c1ccccc1Nc1nc(Nc2cc(N3CCOCC3)cc(N3CCOCC3)c2)ncc1Cl]

2-(2,5-Dichloropyrimidin-4-ylamino)-N-methylbenzamide (0.148 g, 0.5 mmol) and 3,5-dimorpholinoaniline (0.263 g, 2 mmol) were processed according to method 3 to afford the title compound as a brownish solid (0.170 g, 65%). $^1H$ NMR (400 MHz, DMSO-$d_6$): δ 11.77 (s, 1H), 9.35 (s, 1H), 8.77-8.76 (m, 2H), 8.22 (s, 1H), 7.72 (dd, J=8.2 Hz, 1.3 Hz, 1H), 7.41 (t, J=7.3 Hz, 1H), 7.10 (t, J=7.8 Hz, 1H), 6.78 (s, 2H), 6.23 (s, 1H), 3.71 (t, J=4.6 Hz, 8H), 3.01 (t, J=5.0 Hz, 8H), 2.77 (d, J=4.6 Hz, 3H). LC-MS (ESI) calcd. for $C_{26}H_{30}ClN_7O_3$ $[M+H]^+$: 524.20; found: 524.20. HRMS (ESI) calcd. for $C_{26}H_{30}ClN_7O_3$ $[M+H]^+$: 524.2171; found: 524.2158.

Example 79

General Scheme for the Synthesis of 2-(5-Bromo-2-(2-methoxy-4-morpholino phenylamino) pyrimidin-4-ylamino)-N—N-dimethylbenzenesulfonamide

SCHEME 8

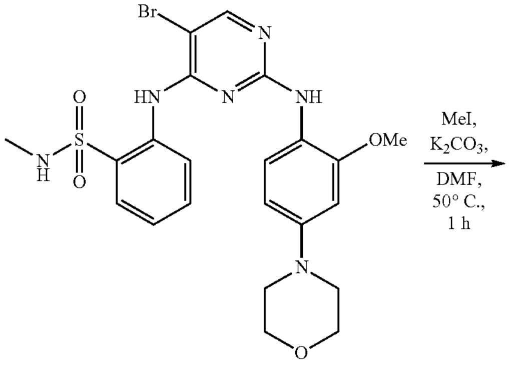

-continued

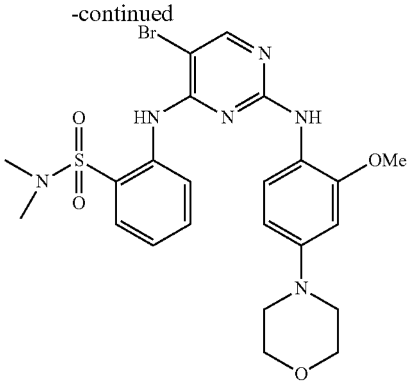

Example 80

Preparation of 2-(5-Bromo-2-(2-methoxy-4-morpholinophenylamino) pyrimidin-4-ylamino)-N—N-dimethylbenzenesulfonamide

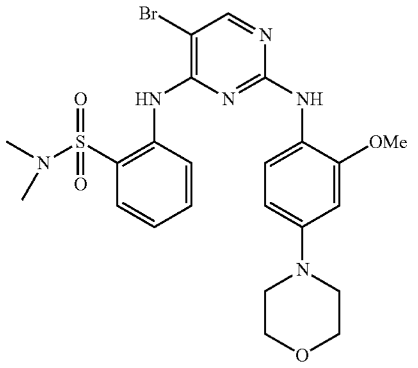 [SMILES: COc1cc(N2CCOCC2)ccc1Nc1ncc(Br)c(Nc2ccccc2S(=O)(=O)N(C)C)n1]

To a solution of 2-(5-bromo-2-(2-methoxy-4-morpholinophenylamino)pyrimidin-4-ylamino)-N-methylbenzenesulfonamide (0.055 g, 0.1 mmol) in DMF, were added potassiun carbonate (0.069 g, 0.15 mmol) and methyl iodide (0.021 g, 0.15 mmol). The resulting mixtute was stirred at 50° C. for 1 h. Cooled and the crude mixture was passed through a short pad of celite and washed with methanol. Removal of the solvent under reduced pressure afforded the crude product which was was purified by automated prep-HPLC to yield the title compound as a brown solid (0.039 g, 72%). $^1H$ NMR (400 MHz, DMSO-$d_6$): δ 9.36 (s, 1H), 8.53 (s, 1H), 8.38 (d, J=6.0 Hz, 1H), 8.22 (s, 1H), 7.75 (dd, J=9.6 Hz, 1.8 Hz, 1H), 7.53 (t, J=8.2 Hz, 1H), 7.31-7.26 (m, 2H), 6.62 (d, J=2.2 Hz, 1H), 6.44 (dd, J=11.4 Hz, 5.7 Hz, 1H), 3.73-3.69 (overlapping triplet and singlet, 7H), 3.10 (t, J=7.3 Hz, 4H), 2.60 (s, 6H). LC-MS (ESI) calcd. for $C_{23}H_{27}BrN_6O_4S$ $[M+H]^+$: 565.10; found: 565.10. HRMS (ESI) calcd. for $C_{26}H_{30}ClN_7O_3$ $[M+H]^+$: 565.1053; found: 565.1048.

Example 81

Preparation of 6-(4-(Benzyloxy)-5-(trifluoromethyl)pyrimidin-2-ylamino)-3,4-dihydroquinolin-2(1H)-one

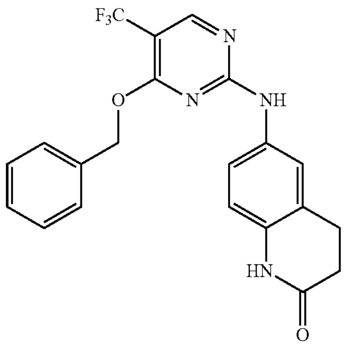 [SMILES: O=C1CCc2cc(Nc3ncc(C(F)(F)F)c(OCc4ccccc4)n3)ccc2N1]

6-(4-Chloro-5-(trifluoromethyl)pyrimidin-2-ylamino)-3,4-dihydroquinolin-2(1H)-one (0.103 g, 0.3 mmol), benzylalcohol (0.065 g, 0.6 mmol) and disopropylethylamine (0.077 g, 0.6 mmol) were processed according to method 4b to afford the title compound. Yellow solid (0.081 g, 65%). $^1$H NMR (400 MHz, DMSO-$d_6$): δ 9.99 (s, 1H), 8.47 (s, 1H), 7.37-7.29 (m, 8H), 6.76 (d, J=8.7 Hz, 1H), 5.49 (s, 2H), 2.79 (t, J=7.3 Hz, 2H), 2.41 (t, J=6.8 Hz, 2H). LC-MS (ESI) calcd. for $C_{21}H_{17}F_3N_4O_2$ $[M+H]^+$: 415.13; found: 415.00.

Example 82

Preparation of 6-((4-(((4-Methoxy-3,5-dimethylpyridin-2-yl)methyl)amino)-5-(trifluoromethyl)pyrimidin-2-yl)amino)-3,4-dihydroquinolin-2(1H)-one

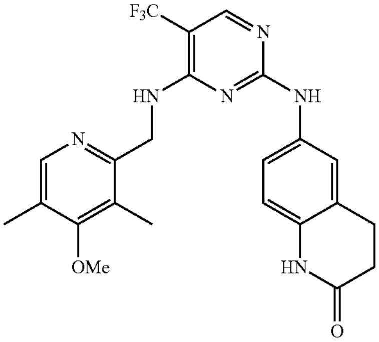 [SMILES: COc1c(C)cnc(CNc2nc(Nc3ccc4c(c3)CCC(=O)N4)ncc2C(F)(F)F)c1C]

6-(4-Chloro-5-(trifluoromethyl)pyrimidin-2-ylamino)-3,4-dihydroquinolin-2(1H)-one (0.103 g, 0.3 mmol), (2,6-dimethylpyridin-4-yl)methanamine (0.050 g, 0.3 mmol) and disopropylethylamine (0.039 g, 0.3 mmol) were processed according to method 4b to afford the title compound. White solid (0.083 g, 58%). LC-MS (ESI) calcd. for $C_{23}H_{23}F_3N_6O_2$ $[M+H]^+$: 473.18; found: 473.00.

Example 83

Preparation of 6-((4-(2,3-Dimethylphenoxy)-5-(trifluoromethyl)pyrimidin-2-yl)amino)-3,4-dihydroquinolin-2(1H)-one

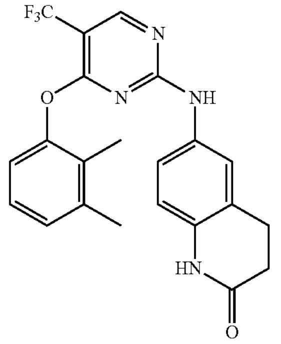 [SMILES: Cc1cccc(Oc2nc(Nc3ccc4c(c3)CCC(=O)N4)ncc2C(F)(F)F)c1C]

6-(4-Chloro-5-(trifluoromethyl)pyrimidin-2-ylamino)-3,4-dihydroquinolin-2(1H)-one (0.171 g, 0.5 mmol), 2,3-dimethylphenol (0.122 g, 1 mmol) and disopropylethylamine (0.129 g, 1 mmol) were processed according to method 4b to afford the title compound. Yellow solid (0.128 g, 60%). LC-MS (ESI) calcd. for $C_{22}H_{19}F_3N_4O_2$ $[M+H]^+$: 429.15; found: 429.05.

Example 84

General Scheme for the Synthesis of N-Methyl-2-((5-(phenylethynyl)-2-((3,4,5-trimethoxyphenyl)amino)pyrimidin-4-yl)amino)benzamide

SCHEME 9

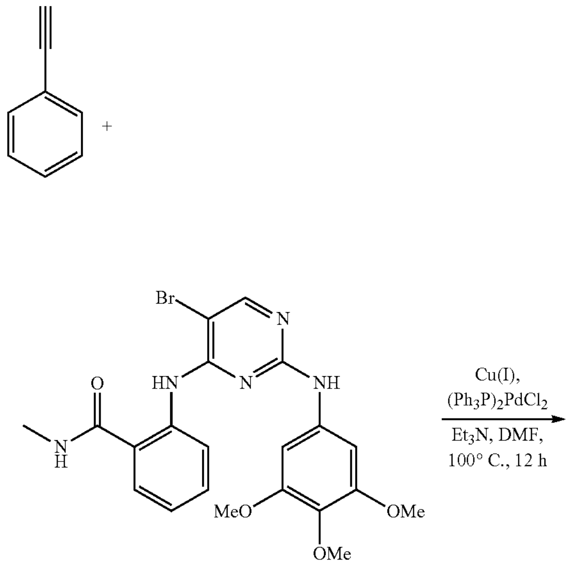

-continued

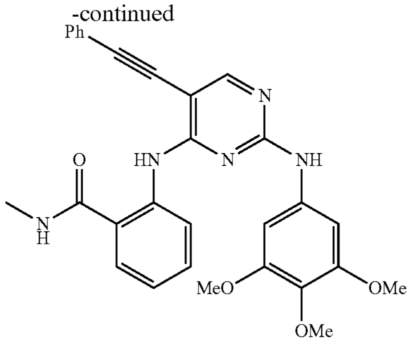

Example 85

Preparation of N-Methyl-2-((5-(phenylethynyl)-2-((3,4,5-trimethoxyphenyl) amino)pyrimidin-4-yl) amino)benzamide

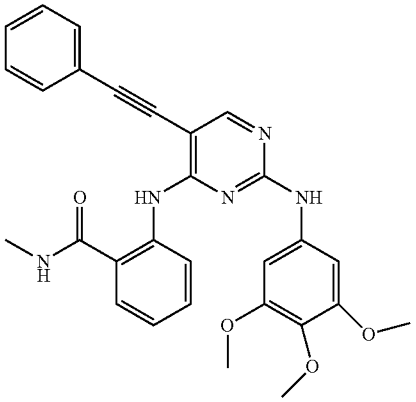

To a stirred mixture of bistriphenylphosphinepalladium-dichloride (0.018 g, 0.025 mmol), 2-(5-bromo-2-(3,4,5-trimethoxyphenylamino)pyrimidin-4-ylamino)-N-methyl-benzamide (0.244 g, 0.5 mmol) and triethylamine (0.202 g, 2 mmol) in 3 mL dry DMF was added Cu(I)I (0.005 g, 0.25 mmol). Phenylacetylene (0.056 g, 0.55 mmol) was added to the above reaction mixture and heated at 100° C. for 12 h. The reaction mixture was cooled to room temperature and diluted with water (20 mL) and extracted with ethylacetate (3×20 mL). The combined organic layers were washed with brine and dried over anhydrous sodium sulfate. Evaporation of the solvent followed by reverse phase HPLC purification of the crude material yielded the desired compound. White solid (0.050 g, 19%). LC-MS (ESI) calcd. for $C_{29}H_{27}N_5O_4$ $[M+H]^+$: 510.21; found: 510.00.

Example 86

General Scheme for the Synthesis of N-Methyl-2-((5-phenethyl-2-((3,4,5-trimethoxyphenyl)amino) pyrimidin-4-yl)amino)benzamide

SCHEME 10

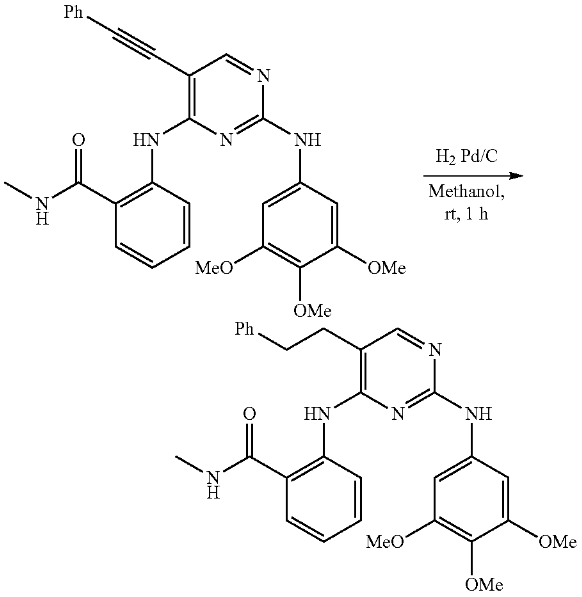

Example 87

Preparation of N-Methyl-2-((5-phenethyl-2-((3,4,5-trimethoxyphenyl)amino) pyrimidin-4-yl)amino) benzamide

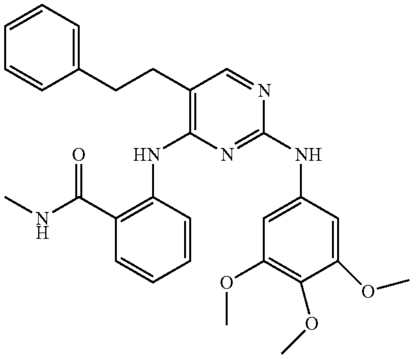

N-Methyl-2-((5-(phenylethynyl)-2-((3,4,5-trimethoxy-phenyl)amino)pyrimidin-4-yl) amino)benzamide (0.030 g, 0.059 mmol) was taken in 2 mL of MeOH. Pd/C (cat) was added to it and the resulting mixture was stirred at room temperature under an atmosphere of $H_2$ for 1 h. Reaction mixture was then passed through a short pad of celite washed with methanol. Romoval of the solvent under reduced pressure yielded the crude product which was purified by automated prep-HPLC to give the title compound as a colorless solid (0.026 g, 87%). LC-MS (ESI) calcd. for $C_{29}H_{31}N_5O_4$ $[M+H]^+$: 514.24; found: 514.20.

Example 88

Preparation of 2-(5-Bromo-2-(3,4,5-trimethoxyphenylamino)pyrimidin-4-yloxy)-N-methylbenzamide

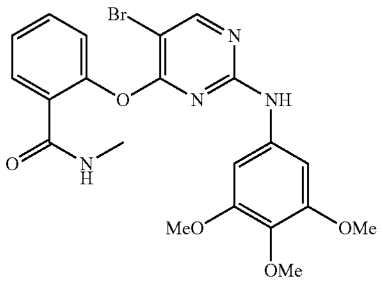 [SMILES: CNC(=O)c1ccccc1Oc1nc(Nc2cc(OC)c(OC)c(OC)c2)ncc1Br]

5-Bromo-2,4-dichloropyrimidine (0.227 g, 1 mmol), 2-hydroxy-N-methylbenzamide (0.151 g, 1 mmol) 3,4,5-trimethoxyaniline (0.183 g, 1 mmol) and disopropylethylamine (0.258 g, 2 mmol) were processed according to method 2 to afford the desired compound as a brown solid (0.100 g, 20%). $^1$H NMR (400 MHz, DMSO-$d_6$): δ 9.41 (s, 1H), 8.47 (s, 1H), 8.50-8.03 (m, 1H), 7.56 (dd, J=7.8 Hz, 1.8 Hz, 1H), 7.50 (t, J=7.8 Hz, 1H), 7.32-7.29 (m, 2H), 6.80 (s, 2H), 3.62 (s, 9H), 2.60 (d, J=4.5 Hz, 3H). LC-MS (ESI) calcd. for $C_{21}H_{21}BrN_4O_5$ $[M+H]^+$: 491.07; found: 491.0. HRMS (ESI) calcd. for $C_{21}H_{21}BrN_4O_5$ $[M+H]^+$: 491.0751; found: 491.0761.

Example 89

Preparation of N-Methyl-2-((2-((2-oxo-1,2,3,4-tetrahydroquinolin-6-yl) amino)-5-phenylpyrimidin-4-yl) amino)benzamide

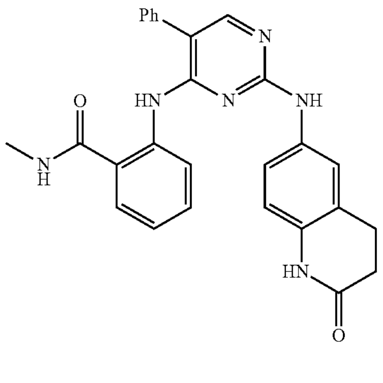 [SMILES: CNC(=O)c1ccccc1Nc1nc(Nc2ccc3c(c2)CCC(=O)N3)ncc1-c1ccccc1]

A two necked flask equipped with a condensor, nitrogen inlet and stirring bar charged with 2-(5-bromo-2-(3,4,5-trimethoxyphenylamino)pyrimidin-4-ylamino)-N-methylbenzamide (0.100 g, 0.21 mmol), and palladiumtetrakistriphenylphosphine (0.010 g, 0.0084 mmol) in in dry DME (5 mL). The resulting mixture was stitted at room temperature for 20 min. To this potassium carbonate (0.056 g, 0.42 mmol) in water (1 mL) was added followed by phenylboronic acid (0.032 g, 0.25 mmol). The mixture was heated to reflux for 12 h, cooled and diluted with water (5 mL) and extracted with ethylacetate (3×10 mL). The combined organic layer was washed with brine and dried over anhydrous sodium sulfate. Evaporation of the solvent under reduced pressure and followed by reverse phase HPLC afforded the title compound. Pale yellow solid (0.030 g, 31%). LC-MS (ESI) calcd. for $C_{27}H_{24}N_6O_2$ $[M+H]^+$: 465.20; found: 465.15.

Example 90

Preparation of 2-(2-(3,5-dimorpholinophenylamino)-5-(trifluoromethyl) pyrimidin-4-ylamino)-N-methylbenzamide

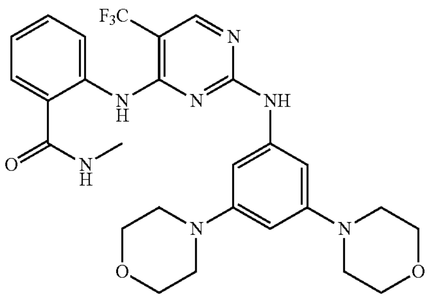 [SMILES: CNC(=O)c1ccccc1Nc1nc(Nc2cc(N3CCOCC3)cc(N3CCOCC3)c2)ncc1C(F)(F)F]

4-Chloro-N-(3,5-dimorpholinophenyl)-5-(trifluoromethyl)pyrimidin-2-amine (0.110 g, 0.25 mmol), 2-amino-N-methyl benzamide and HCl (0.041 g, 0.275 mmol) were processed according to method 3 to afford the title compound as a brown solid (0.097 g, 70%). $^1$H NMR (400 MHz, DMSO-$d_6$): δ 11.48 (s, 1H), 9.60 (s, 1H), 8.71 (s, 1H), 8.40 (s, 1H), 7.69 (d, J=7.8 Hz, 2H), 7.36 (s, 1H), 7.10 (t, J=7.3 Hz, 1H), 6.77 (s, 1H), 6.24 (s, 2H), 3.63 (brs, 8H), 2.96 (brs, 8H), 2.75 (d, =4.7 Hz, 3H). LC-MS (ESI) calcd. for $C_{27}H_{30}F_3N_7O_3$ $[M+H]^+$: 558.24; found: 558.20. HRMS (ESI) calcd. for $C_{27}H_{30}F_3N_7O_3$ $[M+H]^+$: 558.2435; found: 558.2424.

Example 91

Preparation of 2-((5-Bromo-2-((3,5-dimorpholinophenyl)amino)pyrimidin-4-yl)amino)-N-methylbenzamide

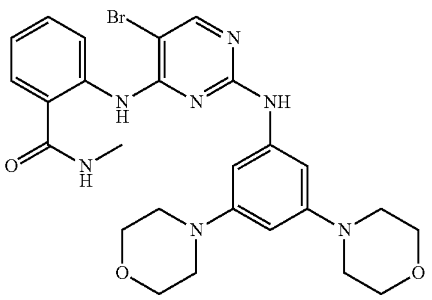 [SMILES: CNC(=O)c1ccccc1Nc1nc(Nc2cc(N3CCOCC3)cc(N3CCOCC3)c2)ncc1Br]

2-(5-Bromo-2-chloropyrimidin-4-ylamino)-N-methylbenzamide (0.071 g, 0.21 mmol) and 3,5-dimorpholinoaniline (0.055 g, 0.21 mmol) were processed according to method 3 to afford the title compound as a brownish solid (0.081 g, 68%). LC-MS (ESI) calcd. for $C_{26}H_{30}BrN_7O_3$ $[M+H]^+$: 568.16; found: 5678.00.

Example 92

Preparation of N-Methyl-2-(5-(trifluoromethyl)-2-(3,4,5-trimethoxy phenylamino) pyrimidin-4-yloxy) benzamide

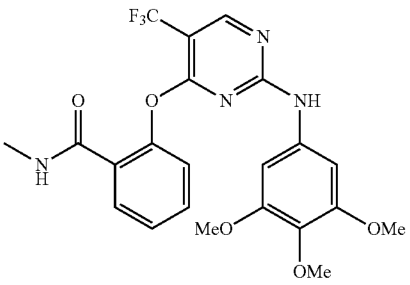 [SMILES: CNC(=O)c1ccccc1Oc1nc(Nc2cc(OC)c(OC)c(OC)c2)ncc1C(F)(F)F]

4-Chloro-5-(trifluoromethyl)-N-(3,4,5-trimethoxyphenyl)pyrimidin-2-amine (0.1 g, 0.3 mmol), 2-hydroxy-N-methylbenzamide (0.054 g, 0.36 mmol) and disopropylethyl amine were processed according to method 4b to afford the title compound. White solid (0.075 g, 76%). $^1H$ NMR (400 MHz, DMSO-$d_6$): δ 10.06 (brs, 1H), 8.66 (s, 1H), 8.08 (d, J=4.6 Hz, 1H), 7.62-7.55 (m, 2H), 7.37-7.35 (m, 2H), 6.87 (s, 2H), 3.66 (s, 6H), 3.64 (s, 3H), 2.62 (d, J=4.6 Hz, 3H). LC-MS (ESI) calcd. for $C_{24}H_{26}F_3N_5O_4S$ $[M+H]^+$: 479.15; found: 479.00. HRMS (ESI) calcd. for $C_{22}H_{21}F_3N_4O_5[M+H]^+$: 479.1537; found: 479.1541.

Example 93

Preparation of 2-hydroxy-N-methylbenzamide

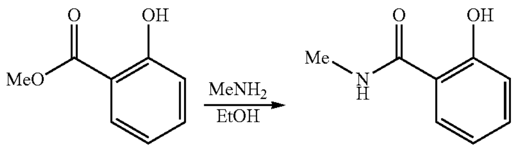 [SMILES: "MeNH2" ; "EtOH" ; COC(=O)c1ccccc1O ; CNC(=O)c1ccccc1O]

Methyl salicylate (8.7 g, 57.2 mmol, 1.0 equiv) and methylamine (33 wt % in ethanol, 37.37 mL, 300 mmol, 5.25 equiv) were stirred at 0° C. The mixture was warmed to 21° C. over 3 h and then stirred at that temperature for 14 h. The mixture was concentrated in vacuo and then recrystallized from hot MeOH to yield 7.08 g of product. MS calcd for $[C_8H_9NO_2+H]^+$: 152.07, found 152.16.

Example 94

Preparation of 3-hydroxy-N-methylbenzamide

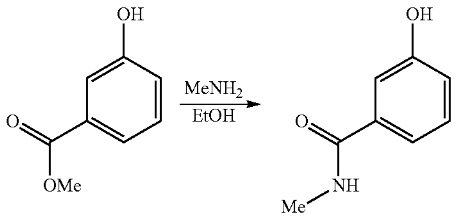 [SMILES: "MeNH2" ; "EtOH" ; COC(=O)c1cccc(O)c1 ; CNC(=O)c1cccc(O)c1]

Methyl salicylate (8.7 g, 57.2 mmol, 1.0 equiv) and methylamine (33 wt % in ethanol, 12.36 mL, 171.6 mmol, 3.0 equiv) were stirred at 21° C. The mixture was heated to 35° C. for 14 h. An additional 6 mL of methylamine in EtOH was added and heating was continued at 50° C. for 5 h. The mixture was concentrated in vacuo and then purified by flash chromatography (10% EtOAc in DCM to 100% EtOAc in DCM over 30 min gradient) to yield 6.09 g of product. MS calcd for $[C_8H_9NO_2+H]^+$: 152.07, found 152.22.

Example 95

Preparation of 2-mercapto-N-methylbenzamide

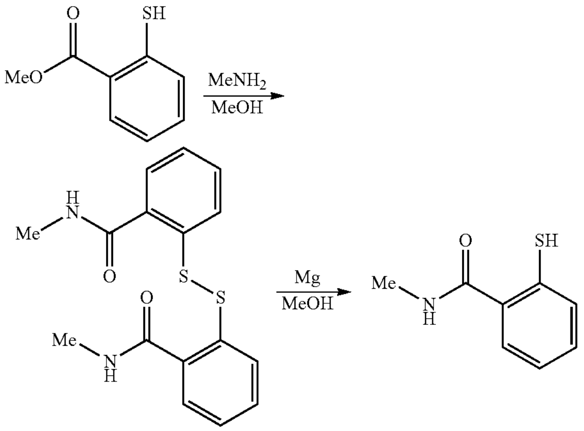

Methyl thiosalicylate (5.07 g, 30.1 mmol, 1.0 equiv) and methylamine (33 wt % in ethanol, 19.69 mL, 158 mmol, 5.25 equiv) were stirred at 0° C. The mixture was warmed to 21° C. over 3 h and then stirred at that temperature for 14 h. The mixture was concentrated in vacuo and then 2-propanol was added and it was cooled. The resulting solid was filtered and collected to yield 4.56 g of the disulfide. This disulfide (187 mg, 0.563 mmol, 1.0 equiv) was then dissolved in MeOH (5 mL) and freshly ground magnesium metal shavings (68 mg, 2.81 mmol, 5.0 equiv) was added. The mixture was heated to 40° C. for 14 h. The mixture was filtered through Celite with MeOH to yield 92 mg of product that was used for the subsequent reaction without further purification. MS calcd for $[C_8H_9NOS+H]^+$: 168.05, found 168.17.

Example 96

Preparation of 6-amino-3,4-dihydroquinolin-2(1H)-one

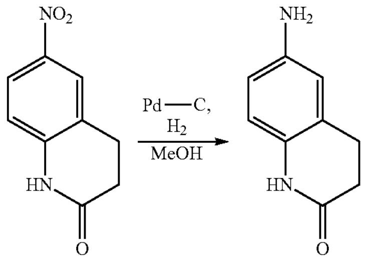

6-Nitro-3,4-dihydroquinolin-2(1H)-one (2.53 g, 13.1 mmol, 1.0 equiv) and palladium on carbon (100 mg) were mixed in EtOH (40 mL). A balloon of hydrogen gas was applied for 8 h, then the mixture was filtered through Celite with DCM and concentrated in vacuo. The resultant brown solid (2.02 g) was used without further purification. This compound does not ionize well, thus there is no product MS peak. $^1H$ NMR (400 MHz, DMSO-d6) δ: 9.65 (s, 1H), 6.54 (d, 1H, J=8.4 Hz), 6.39 (d, 1H, J=2.4 Hz), 6.35 (dd, 1H, J=2.8, 8.4 Hz), 4.73 (bs, 2H), 2.70 (t, 2H, J=8.0 Hz), 2.33 (t, 2H, J=7.2 Hz).

Example 97

Preparation of 1H-pyrrolo[2,3-b]pyridin-5-amine

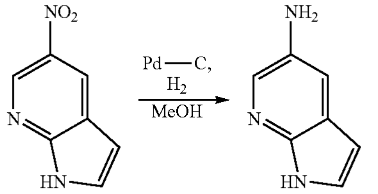

5-Nitro-1H-pyrrolo[2,3-b]pyridine (1.0 g, 6.13 mmol, 1.0 equiv) and palladium on carbon (75 mg) were mixed in EtOAc (20 mL). A balloon of hydrogen gas was applied for 18 h, then the mixture was filtered through Celite with DCM and concentrated in vacuo. The resultant brown solid (800 mg) was used without further purification. MS calcd for $[C_7H_7N_3+H]^+$: 134.07, found 134.16.

Example 98

General Synthetic Scheme for the Preparation of Trisubstituted Pyrimidines

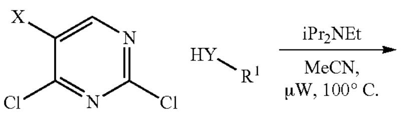

X = $CF_3$, Br, Cl, OMe
Y = NH, O, S

-continued

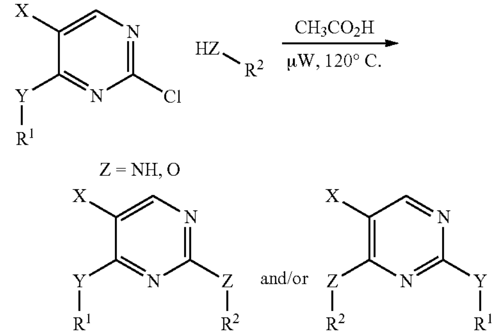

Example 99

Preparation of N-methyl-2-((2-(phenylamino)-5-(trifluoromethyl)pyrimidin-4-yl)oxy)benzamide

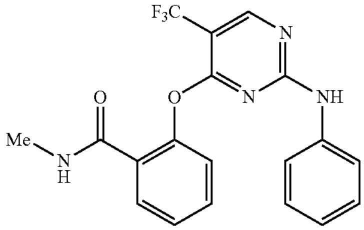 [SMILES: CNC(=O)c1ccccc1Oc1nc(Nc2ccccc2)ncc1C(F)(F)F]

A solution of 2,4-dichloro-5-(trifluoromethyl)pyrimidine (100 mg, 0.461 mmol, 1.0 equiv), 2-hydroxy-N-methylbenzamide (69 mg, 0.461 mmol, 1.0 equiv) and N,N-diisopropyl ethylamine (0.08 mL, 0.461 mmol, 1.0 equiv) in acetonitrile (3 mL) was microwaved at 100° C. for 10 min. The mixture was concentrated in vacuo, then aniline (0.042 mL, 0.461 mmol, 1.0 equiv) and acetic acid (2 mL) were added. This mixture was microwaved at 120° C. for 10 min, then concentrated in vacuo. A fraction of the crude product was purified by reverse phase HPLC to yield the product (13 mg). MS calcd for $[C_{19}H_{15}F_3N_4O_2+H]^+$: 389.12, found 389.32.

Example 100

Preparation of 2((2-((5-bromo-2-methylphenyl) amino)-5-(trifluoromethyl) pyrimidin-4-yl)oxy)-N-methylbenzamide

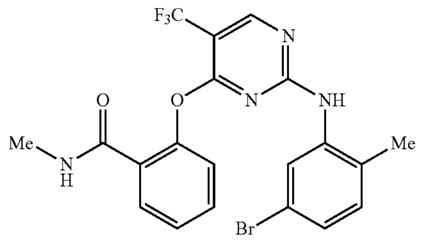 [SMILES: CNC(=O)c1ccccc1Oc1nc(Nc2cc(Br)ccc2C)ncc1C(F)(F)F]

Same procedure as Example 99 using 2,4-dichloro-5-(trifluoromethyl)pyrimidine (100 mg), 2-hydroxy-N-methylbenzamide (69 mg) and N,N-diisopropylethylamine (0.08 mL) in the first step, followed by 5-bromo-2-methylaniline (86 mg) and acetic acid (2 mL) in the second step. 10 mg of product was recovered after reverse phase HPLC. MS calcd for $[C_{20}H_{16}BrF_3N_4O_2+H]^+$: 481.05, found 481.26.

Example 101

Preparation of 2-((2-((5-methoxy-2-methylphenyl) amino)-5-(trifluoromethyl) pyrimidin-4-yl)oxy)-N-methylbenzamide

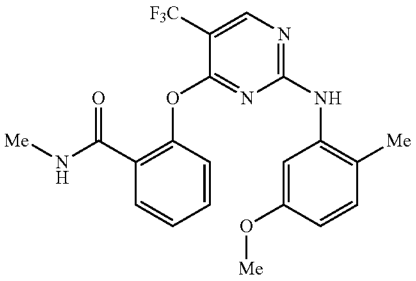 [SMILES: CNC(=O)c1ccccc1Oc1nc(Nc2cc(OC)ccc2C)ncc1C(F)(F)F]

Same procedure as Example 99 using 2,4-dichloro-5-(trifluoromethyl)pyrimidine (100 mg), 2-hydroxy-N-methylbenzamide (69 mg) and N,N-diisopropylethylamine (0.08 mL) in the first step, followed by 5-methoxy-2-methylaniline (63 mg) and acetic acid (2 mL) in the second step. 14 mg of product was recovered after reverse phase HPLC. MS calcd for $[C_{21}H_{19}F_3N_4O_3+H]^+$: 433.15, found 433.41.

Example 102

Preparation of 2-((2-((3-bromo-4-methylphenyl) amino)-5-(trifluoromethyl) pyrimidin-4-yl)oxy)-N-methylbenzamide

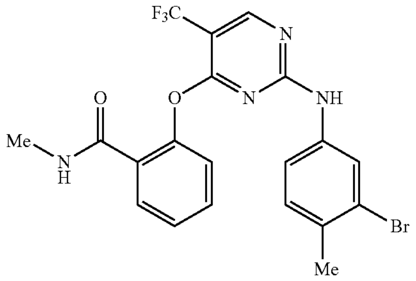

Same procedure as Example 99 using 2,4-dichloro-5-(trifluoromethyl)pyrimidine (100 mg), 2-hydroxy-N-methylbenzamide (69 mg) and N,N-diisopropylethylamine (0.08 mL) in the first step, followed by 3-bromo-4-methylaniline (63 mg) and acetic acid (2 mL) in the second step. 8 mg of product was recovered after reverse phase HPLC. MS calcd for $[C_{20}H_{16}BrF_3N_4O_2+H]^+$: 481.05, found 481.26.

Example 103

Preparation of 2-((2-((2-methoxyphenyl)amino)-5-(trifluoromethyl) pyrimidin-4-yl)oxy)-N-methylbenzamide

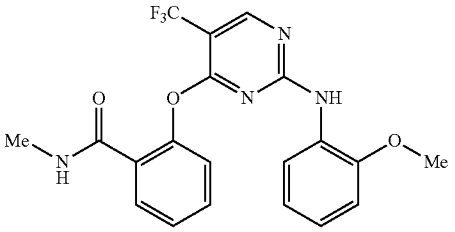 [SMILES: CNC(=O)c1ccccc1Oc1nc(Nc2ccccc2OC)ncc1C(F)(F)F]

Same procedure as Example 99 using 2,4-dichloro-5-(trifluoromethyl)pyrimidine (100 mg), 2-hydroxy-N-methylbenzamide (69 mg) and N,N-diisopropylethylamine (0.08 mL) in the first step, followed by 2-methoxyaniline (57 mg) and acetic acid (2 mL) in the second step. 46 mg of product was recovered after reverse phase HPLC. MS calcd for $[C_{20}H_{17}F_3N_4O_3+H]^+$: 419.13, found 419.35.

Example 104

Preparation of 2-((2-((2,5-dimethylphenyl)amino)-5-(trifluoromethyl) pyrimidin-4-yl)oxy)-N-methylbenzamide

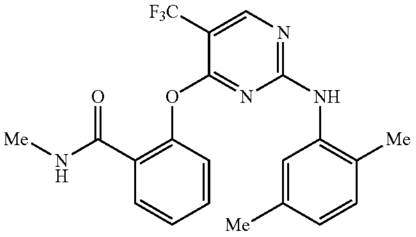 [SMILES: CNC(=O)c1ccccc1Oc1nc(Nc2cc(C)ccc2C)ncc1C(F)(F)F]

Same procedure as Example 99 using 2,4-dichloro-5-(trifluoromethyl)pyrimidine (100 mg), 2-hydroxy-N-methylbenzamide (69 mg) and N,N-diisopropylethylamine (0.08 mL) in the first step, followed by 2,5-dimethylaniline (56 mg) and acetic acid (2 mL) in the second step. 36 mg of product was recovered after reverse phase HPLC. MS calcd for $[C_{21}H_{19}F_3N_4O_2+H]^+$: 417.15, found 417.40.

Example 105

Preparation of 2-((2-((4-methoxyphenyl)amino)-5-(trifluoromethyl) pyrimidin-4-yl)oxy)-N-methylbenzamide and 2-((4-methoxyphenyl)amino)-5-(trifluoromethyl)pyrimidin-4-ol

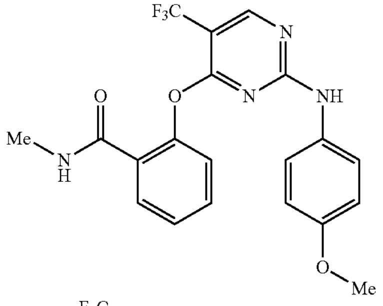

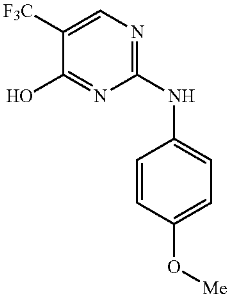

Same procedure as Example 99 using 2,4-dichloro-5-(trifluoromethyl)pyrimidine (150 mg), 2-hydroxy-N-methylbenzamide (104 mg) and N,N-diisopropylethylamine (0.12 mL) in the first step, followed by 4-methoxyaniline (85 mg) and acetic acid (3 mL) in the second step. 10 mg of 2-((2-((4-methoxyphenyl)amino)-5-(trifluoromethyl)pyrimidin-4-yl)oxy)-N-methylbenzamide and 7 mg of 2((4-methoxyphenyl)amino)-5-(trifluoromethyl)pyrimidin-4-ol were recovered after reverse phase HPLC. MS calcd for $[C_{20}H_{17}F_3N_4O_3+H]^+$: 419.13, found 419.35. MS calcd for $[C_{12}H_{10}F_3N_3O_2+H]^+$: 286.08, found 286.25.

Example 106

Preparation of 2-((2-((3,4-dimethylphenyl)amino)-5-(trifluoromethyl) pyrimidin-4-yl)oxy)-N-methylbenzamide

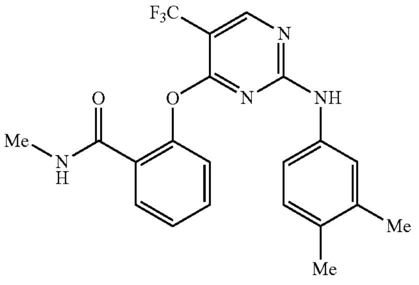 [SMILES: CNC(=O)c1ccccc1Oc1nc(Nc2ccc(C)c(C)c2)ncc1C(F)(F)F]

Same procedure as Example 99 using 2,4-dichloro-5-(trifluoromethyl)pyrimidine (100 mg), 2-hydroxy-N-methylbenzamide (69 mg) and N,N-diisopropylethylamine (0.08 mL) in the first step, followed by 3,4-dimethylaniline (56 mg) and acetic acid (2 mL) in the second step. 13 mg of product was recovered after reverse phase HPLC. MS calcd for $[C_{21}H_{19}F_3N_4O_2+H]^+$: 417.15, found 417.40.

Example 107

Preparation of 2-((2-((2-chloro-4-methylphenyl) amino)-5-(trifluoromethyl) pyrimidin-4-yl)oxy)-N-methylbenzamide

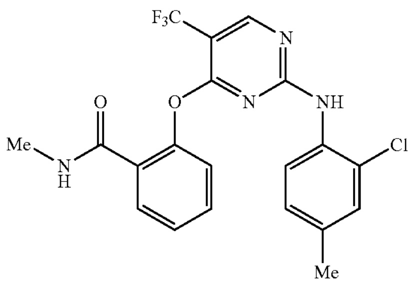 [SMILES: CNC(=O)c1ccccc1Oc1nc(Nc2ccc(C)cc2Cl)ncc1C(F)(F)F]

Same procedure as Example 99 using 2,4-dichloro-5-(trifluoromethyl)pyrimidine (100 mg), 2-hydroxy-N-methylbenzamide (69 mg) and N,N-diisopropylethylamine (0.08 mL) in the first step, followed by 2-chloro-4-methylaniline (65 mg) and acetic acid (2 mL) in the second step. 13 mg of product was recovered after reverse phase HPLC. MS calcd for $[C_{20}H_{16}ClF_3N_4O_2+H]^+$: 437.10, found 437.35.

Example 108

Preparation of 2-((2-((3,4-dichlorophenyl)amino)-5-(trifluoromethyl) pyrimidin-4-yl)oxy)-N-methylbenzamide and 2-((3,4-dichlorophenyl)amino)-5-(trifluoro methyl)pyrimidin-4-ol

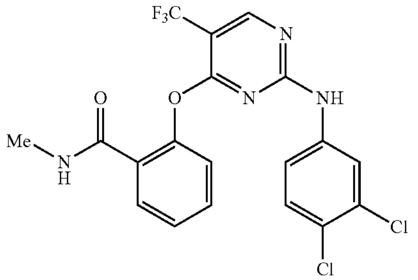

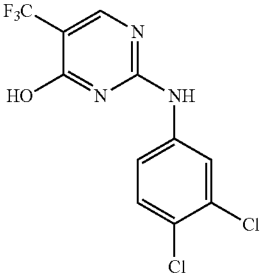

Same procedure as Example 99 using 2,4-dichloro-5-(trifluoromethyl)pyrimidine (100 mg), 2-hydroxy-N-methylbenzamide (70 mg) and N,N-diisopropylethylamine (0.08 mL) in the first step, followed by 4-methoxyaniline (75 mg) and acetic acid (2 mL) in the second step. 27 mg of 2-((2-((3,4-dichlorophenyl)amino)-5-(trifluoromethyl)pyrimidin-4-yl)oxy)-N-methyl benzamide and 14 mg of 2-((3,4-dichlorophenyl)amino)-5-(trifluoromethyl)pyrimidin-4-ol were recovered after reverse phase HPLC. MS calcd for $[C_{19}H_{13}Cl_2F_3N_4O_2+H]^+$: 457.04, found 457.28. MS calcd for $[C_{11}H_6Cl_2F_3N_3O+H]^+$: 323.99, found 323.70.

Example 109

Preparation of 2-((2-((2,5-dimethoxyphenyl)amino)-5-(trifluoromethyl) pyrimidin-4-yl)oxy)-N-methylbenzamide and 2-((2,5-dimethoxyphenyl)amino)-5-(trifluoro methyl)pyrimidin-4-ol

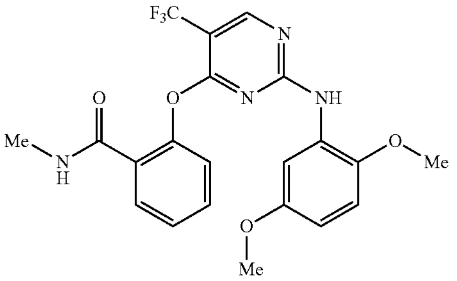

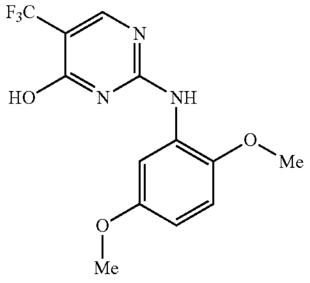

Same procedure as Example 99 using 2,4-dichloro-5-(trifluoromethyl)pyrimidine (100 mg), 2-hydroxy-N-methylbenzamide (70 mg) and N,N-diisopropylethylamine (0.08 mL) in the first step, followed by 2,5-dimethoxyaniline (71 mg) and acetic acid (2 mL) in the second step. 45 mg of 2-((2-((2,5-dimethoxyphenyl)amino)-5-(trifluoromethyl) pyrimidin-4-yl)oxy)-N-methyl benzamide and 6 mg of 2-((2,5-dimethoxyphenyl)amino)-5-(trifluoromethyl)pyrimidin-4-ol were recovered after reverse phase HPLC. MS calcd for $[C_{21}H_{19}F_3N_4O_4+H]^+$: 449.14, found 449.35. MS calcd for $[C_{14}H_{14}F_3N_3O_3+H]^+$: 316.09, found 315.90.

Example 110

Preparation of N-methyl-2-((2-((2-oxo-1,2,3,4-tetrahydroquinolin-6-yl) amino)-5-(trifluoromethyl)pyrimidin-4-yl)oxy)benzamide

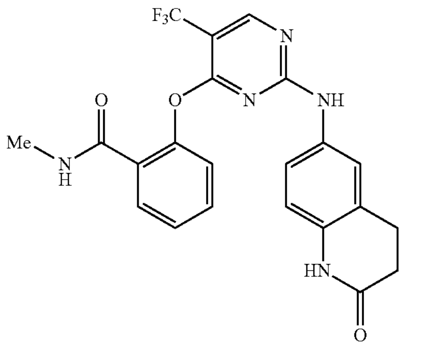 [SMILES: CNC(=O)c1ccccc1Oc1nc(Nc2ccc3c(c2)CCC(=O)N3)ncc1C(F)(F)F]

Same procedure as Example 99 using 2,4-dichloro-5-(trifluoromethyl)pyrimidine (100 mg), 2-hydroxy-N-methylbenzamide (69 mg) and N,N-diisopropylethylamine (0.08 mL) in the first step, followed by 6-amino-3,4-dihydroquinolin-2(1H)-one (75 mg) and acetic acid (2 mL) in the second step. 28 mg of product was recovered after reverse phase HPLC. MS calcd for $[C_{22}H_{18}F_3N_5O_3+H]^+$: 458.14, found 458.40.

Example 111

Preparation of 2-((5-bromo-2-(phenylamino)pyrimidin-4-yl)oxy)-N-methyl benzamide

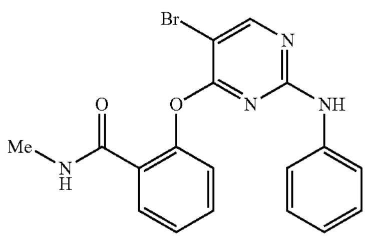 [SMILES: CNC(=O)c1ccccc1Oc1nc(Nc2ccccc2)ncc1Br]

Same procedure as Example 99 using 5-bromo-2,4-dichloropyrimidine (105 mg), 2-hydroxy-N-methylbenzamide (70 mg) and N,N-diisopropylethylamine (0.08 mL) in the first step, followed by aniline (43 mg) and acetic acid (2 mL) in the second step. 12 mg of product was recovered after reverse phase HPLC. MS calcd for $[C_{18}H_{15}BrN_4O_2+H]^+$: 399.05, found 399.29.

Example 112

Preparation of 2-((5-bromo-2-((5-bromo-2-methylphenyl)amino)pyrimidin-4-yl)oxy)-N-methylbenzamide

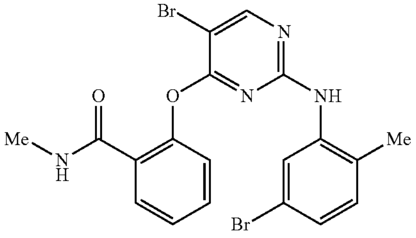 [SMILES: CNC(=O)c1ccccc1Oc1nc(Nc2cc(Br)ccc2C)ncc1Br]

Same procedure as Example 99 using 5-bromo-2,4-dichloropyrimidine (105 mg), 2-hydroxy-N-methylbenzamide (70 mg) and N,N-diisopropylethylamine (0.08 mL) in the first step, followed by 5-bromo-2-methylaniline (86 mg) and acetic acid (2 mL) in the second step. 6 mg of product was recovered after reverse phase HPLC. MS calcd for $[C_{19}H_{16}Br_2N_4O_2+H]^+$: 492.97, found 492.80.

Example 113

Preparation of 2-((2-((2,3-difluorophenyl)amino)-5-(trifluoromethyl) pyrimidin-4-yl)oxy)-N-methylbenzamide

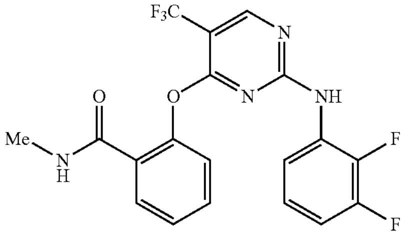 [SMILES: CNC(=O)c1ccccc1Oc1nc(Nc2cccc(F)c2F)ncc1C(F)(F)F]

Same procedure as Example 99 using 2,4-dichloro-5-(trifluoromethyl)pyrimidine (100 mg), 2-hydroxy-N-methylbenzamide (69 mg) and N,N-diisopropylethylamine (0.08 mL) in the first step, followed by 2,3-difluoroaniline (59 mg) and acetic acid (2 mL) in the second step. 32 mg of product was recovered after reverse phase HPLC. MS calcd for $[C_{19}H_{13}F_5N_4O_2+H]^+$: 425.10, found 425.35.

Example 114

Preparation of 5-chloro-$N^2$,$N^4$-diphenylpyrimidine-2,4-diamine

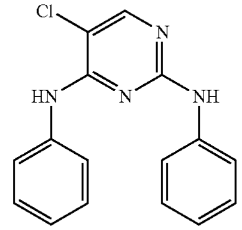 [SMILES: Clc1cnc(Nc2ccccc2)nc1Nc1ccccc1]

Same procedure as Example 99 using 2,4,5-trichloropyrimidine (100 mg), 2-hydroxy-N-methylbenzamide (82 mg) and N,N-diisopropylethylamine (0.095 mL) in the first step, followed by aniline (59 mg) and acetic acid (2 mL) in the second step. 5 mg of the unexpected product was recovered after reverse phase HPLC. MS calcd for $[C_{16}H_{13}ClN_4+H]^+$: 297.09, found 297.30.

Example 115

Preparation of 2-((2-((2,3-dimethoxyphenyl)amino)-5-(trifluoromethyl) pyrimidin-4-yl)oxy)-N-methylbenzamide and 2-((2,3-dimethoxyphenyl)amino)-5-(trifluoromethyl)pyrimidin-4-ol

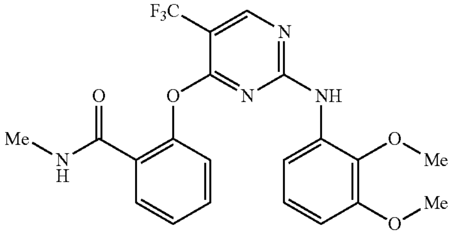

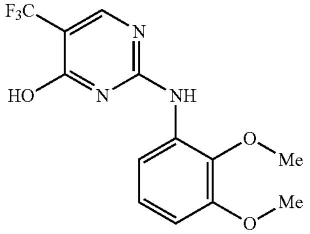

Same procedure as Example 99 using 2,4-dichloro-5-(trifluoromethyl)pyrimidine (100 mg), 2-hydroxy-N-methylbenzamide (70 mg) and N,N-diisopropylethylamine (0.08 mL) in the first step, followed by 2,3-dimethoxyaniline (70 mg) and acetic acid (2 mL) in the second step. 15 mg of 2-((2-((2,3-dimethoxyphenyl)amino)-5-(trifluoromethyl) pyrimidin-4-yl)oxy)-N-methylbenzamide and 6 mg of 2-((2,3-dimethoxyphenyl)amino)-5-(trifluoromethyl)pyrimidin-4-ol were recovered after reverse phase HPLC. MS calcd for $[C_{21}H_{19}F_3N_4O_4+H]^+$: 449.14, found 449.39. MS calcd for $[C_{13}H_{12}F_3N_3O_3+H]^+$: 316.09, found 316.05.

Example 116

Preparation of N-methyl-2-((2-((2-(methylthio)phenyl)amino)-5-(trifluoro methyl)pyrimidin-4-yl)oxy) benzamide and $N^2$,$N^4$-bis(2-(methylthio)phenyl)-5-(trifluoro methyl)pyrimidine-2,4-diamine

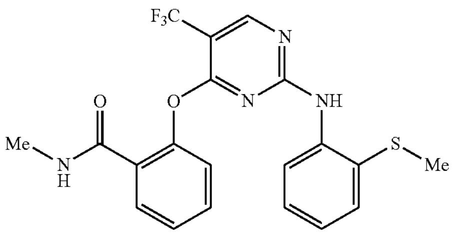

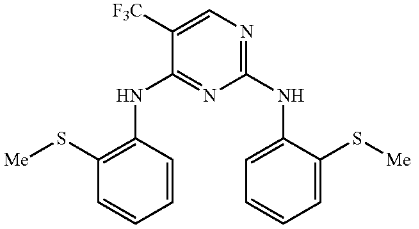

Same procedure as Example 99 using 2,4-dichloro-5-(trifluoromethyl)pyrimidine (100 mg), 2-hydroxy-N-methylbenzamide (70 mg) and N,N-diisopropylethylamine (0.08 mL) in the first step, followed by 2-(methylthio)aniline (78 mg) and acetic acid (2 mL) in the second step. 12 mg of N-methyl-2-((2-((2-(methylthio)phenyl)amino)-5-(trifluoromethyl)pyrimidin-4-yl)oxy)benzamide and 5 mg of $N^2$,$N^4$-bis(2-(methylthio)phenyl)-5-(trifluoromethyl)pyrimidine-2,4-diamine were recovered after reverse phase HPLC. MS calcd for $[C_{20}H_{17}F_3N_4O_2S+H]^+$: 435.11, found 435.36. MS calcd for $[C_{19}H_{17}F_3N_4S_2+H]^+$: 423.09, found 422.95.

Example 117

Preparation of 2-((2-((5-methoxy-2-methylphenyl) amino)-5-(trifluoromethyl) pyrimidin-4-yl)thio)-N-methylbenzamide

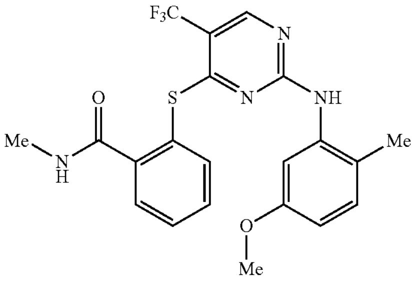

Same procedure as Example 99 using 2,4-dichloro-5-(trifluoromethyl)pyrimidine (100 mg), 2-mercapto-N-methylbenzamide (92 mg) and N,N-diisopropylethylamine (0.08 mL) in the first step, followed by 5-methoxy-2-methylaniline (63 mg) and acetic acid (2 mL) in the second step. 18 mg of product was recovered after reverse phase HPLC. MS calcd for $[C_{21}H_{19}F_3N_4O_2S+H]^+$: 449.13, found 449.38.

Example 118

Preparation of 6-((4-((2-morpholinophenyl)amino)-5-(trifluoromethyl) pyrimidin-2-yl)amino)-3,4-dihydroquinolin-2(1H)-one and 6-((2-((2-morpholinophenyl) amino)-5-(trifluoromethyl)pyrimidin-4-yl) amino)-3,4-dihydroquinolin-2(1H)-one and 4-((2-morpholinophenyl)amino)-5-(trifluoromethyl) pyrimidin-2-ol

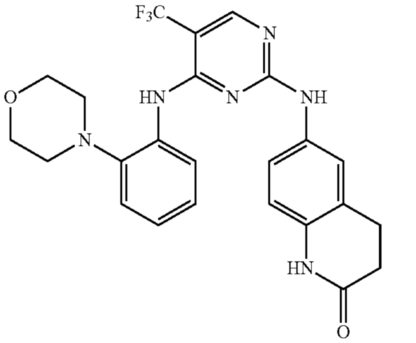

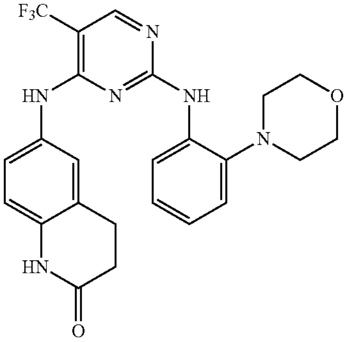

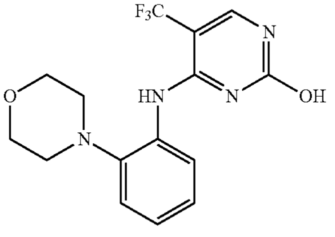

Same procedure as Example 99 using 2,4-dichloro-5-(trifluoromethyl)pyrimidine (100 mg), 2-morpholinoaniline (82 mg) and N,N-diisopropylethylamine (0.08 mL) in the first step, followed by 6-amino-3,4-dihydroquinolin-2(1H)-one (75 mg) and acetic acid (2 mL) in the second step. 13 mg of 6-((4-((2-morpholinophenyl)amino)-5-(trifluoromethyl)pyrimidin-2-yl)amino)-3,4-dihydroquinolin-2(1H)-one, 13 mg of 6-((2-((2-morpholinophenyl)amino)-5-(trifluoromethyl)pyrimidin-4-yl)amino)-3,4-dihydroquinolin-2 (1H)-one and 9 mg of 4-((2-morpholinophenyl)amino)-5-(trifluoromethyl)pyrimidin-2-ol were recovered after reverse phase HPLC. MS calcd for $[C_{24}H_{23}F_3N_6O_2+H]^+$: 485.19, found 485.45. MS calcd for $[C_{24}H_{23}F_3N_6O_2+H]^+$: 485.19, found 485.45. MS calcd for $[C_{15}H_{15}F_3N_4O_2+H]^+$: 341.12, found 341.32.

Example 119

Preparation of 6-((4-((3-methoxyphenyl)amino)-5-(trifluoromethyl) pyrimidin-2-yl)amino)-3,4-dihydroquinolin-2(1H)-one

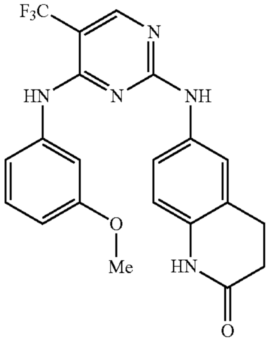

Same procedure as Example 99 using 2,4-dichloro-5-(trifluoromethyl)pyrimidine (100 mg), 3-methoxyaniline (57 mg) and N,N-diisopropylethylamine (0.08 mL) in the first step, followed by 6-amino-3,4-dihydroquinolin-2(1H)-one (75 mg) and acetic acid (2 mL) in the second step. 45 mg of product was recovered after reverse phase HPLC. MS calcd for $[C_{21}H_{18}F_3N_5O_2+H]^+$: 430.15, found 430.43.

Example 120

Preparation of 6-((4-((2-(difluoromethoxy)phenyl) amino)-5-(trifluoromethyl) pyrimidin-2-yl)amino)-3,4-dihydroquinolin-2(1H)-one and $N^2$,$N^4$-bis(2-(difluoromethoxy) phenyl)-5-(trifluoromethyl) pyrimidine-2,4-diamine and 6,6'-((5-(trifluoromethyl) pyrimidine-2,4-diyl)bis(azanediyl)) bis(3,4-dihydroquinolin-2(1H)-one)

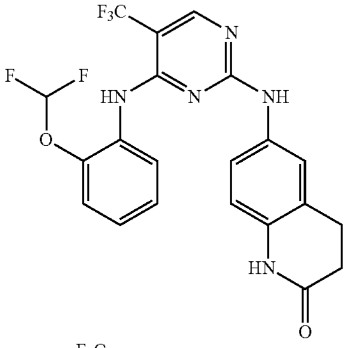

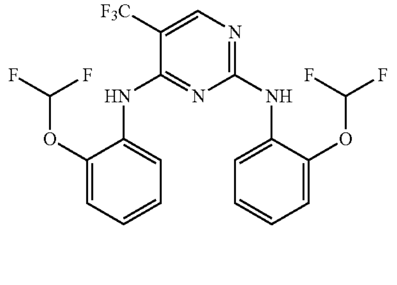

-continued

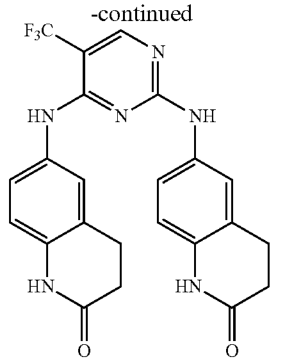

Same procedure as Example 99 using 2,4-dichloro-5-(trifluoromethyl)pyrimidine (100 mg), 2-(difluoromethoxy) aniline (73 mg) and N,N-diisopropylethylamine (0.08 mL) in the first step, followed by 6-amino-3,4-dihydroquinolin-2(1H)-one (75 mg) and acetic acid (2 mL) in the second step. 27 mg of 6-((4(2-(difluoromethoxy)phenyl)amino)-5-(trifluoromethyl)pyrimidin-2-yl)amino)-3,4-dihydroquinolin-2 (1H)-one, 9 mg of $N^2$,$N^4$-bis(2-(difluoromethoxy)phenyl)-5-(trifluoromethyl)pyrimidine-2,4-diamine and 14 mg of 6,6'-((5-(trifluoromethyl)pyrimidine-2,4-diyl)bis (azanediyl))bis(3,4-dihydroquinolin-2(1H)-one) were recovered after reverse phase HPLC. MS calcd for $[C_{21}H_{16}F_5N_5O_2+H]^+$: 466.13, found 466.39. MS calcd for $[C_{19}H_{13}F_7N_4O_2+H]^+$: 463.10, found 463.34. MS calcd for $[C_{23}H_{19}F_3N_6O_2+H]^+$: 469.16, found 469.41.

Example 121

Preparation of 6-((4-((3-(benzyloxy)phenyl)amino)-5-(trifluoromethyl) pyrimidin-2-yl)amino)-3,4-dihydroquinolin-2(1H)-one

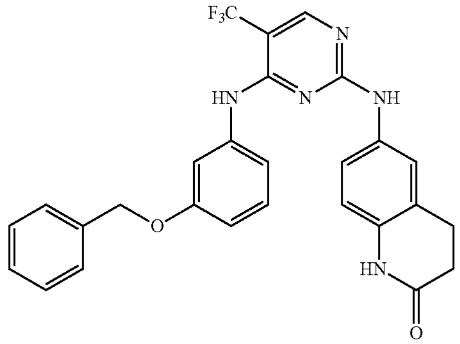 [SMILES: O=C1CCc2cc(Nc3ncc(C(F)(F)F)c(Nc4cccc(OCc5ccccc5)c4)n3)ccc2N1]

Same procedure as Example 99 using 2,4-dichloro-5-(trifluoromethyl)pyrimidine (100 mg), 3-(benzyloxy)aniline (92 mg) and N,N-diisopropylethylamine (0.08 mL) in the first step, followed by 6-amino-3,4-dihydroquinolin-2(1H)-one (75 mg) and acetic acid (2 mL) in the second step. 57 mg of product was recovered after reverse phase HPLC. MS calcd for $[C_{27}H_{22}F_3N_5O_2+H]^+$: 506.18, found 506.47.

Example 122

Preparation of N-methyl-3-((2-((2-oxo-1,2,3,4-tetrahydroquinolin-6-yl) amino)-5-(trifluoromethyl)pyrimidin-4-yl)oxy)benzamide

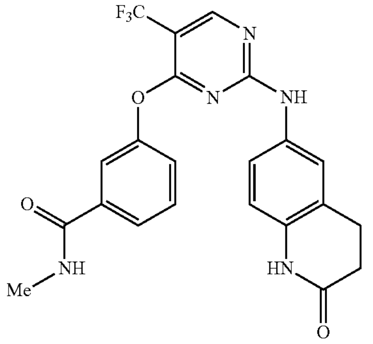 [SMILES: CNC(=O)c1cccc(Oc2nc(Nc3ccc4c(c3)CCC(=O)N4)ncc2C(F)(F)F)c1]

Same procedure as Example 99 using 2,4-dichloro-5-(trifluoromethyl)pyrimidine (100 mg), 3-hydroxy-N-methylbenzamide (70 mg) and N,N-diisopropylethylamine (0.08 mL) in the first step, followed by 6-amino-3,4-dihydroquinolin-2(1H)-one (75 mg) and acetic acid (2 mL) in the second step. 18 mg of product was recovered after reverse phase HPLC. MS calcd for $[C_{22}H_{18}F_3N_5O_3+H]^+$: 458.14, found 458.40.

Example 123

Preparation of 6-((4-((2-methoxy-4-morpholinophenyl)amino)-5-(trifluoromethyl)pyrimidin-2-yl) amino)-3,4-dihydroquinolin-2(1H)-one and 6-((2-((2-methoxy-4-morpholino phenyl)amino)-5-(trifluoromethyl)pyrimidin-4-yl)amino)-3,4-dihydroquinolin-2(1H)-one

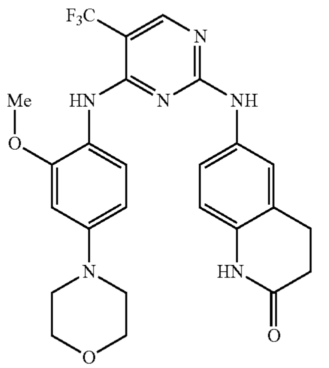

-continued

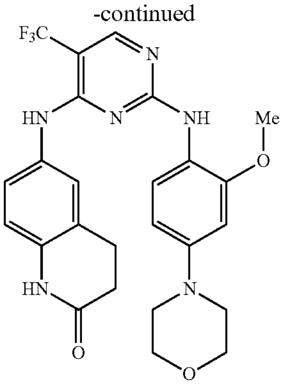

Same procedure as Example 99 using 2,4-dichloro-5-(trifluoromethyl)pyrimidine (100 mg), 2-methoxy-4-morpholinoaniline (96 mg) and N,N-diisopropylethylamine (0.08 mL) in the first step, followed by 6-amino-3,4-dihydroquinolin-2(1H)-one (75 mg) and acetic acid (2 mL) in the second step. 20 mg of 6-((4-((2-methoxy-4-morpholinophenyl)amino)-5-(trifluoromethyl) pyrimidin-2-yl)amino)-3,4-dihydroquinolin-2(1H)-one and 2.7 mg of 6-((2-((2-methoxy-4-morpholinophenyl)amino)-5-(trifluoromethyl) pyrimidin-4-yl)amino)-3,4-dihydroquinolin-2(1H)-one was recovered after reverse phase HPLC. MS calcd for $[C_{25}H_{25}F_3N_6O_3+H]^+$: 515.20, found 515.52. MS calcd for $[C_{25}H_{25}F_3N_6O_3+H]^+$: 515.52, found 515.52.

Example 124

Preparation of 6-((4-(benzo[d][1,3]dioxol-5-ylamino)-5-(trifluoromethyl) pyrimidin-2-yl)amino)-3,4-dihydroquinolin-2(1H)-one and 6-((2-(benzo[d][1,3]dioxol-5-yl amino)-5-(trifluoromethyl) pyrimidin-4-yl)amino)-3,4-dihydroquinolin-2(1H)-one and $N^2$,$N^4$-bis(benzo[d][1,3]dioxol-5-yl)-5-(trifluoromethyl)pyrimidine-2,4-diamine

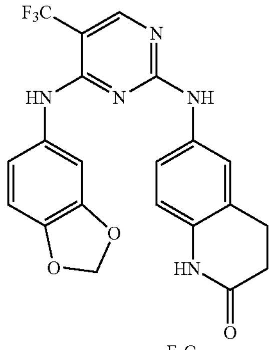

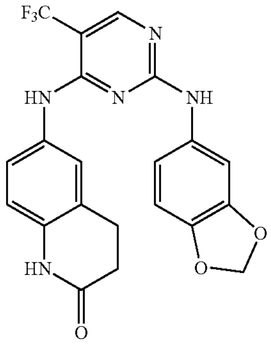

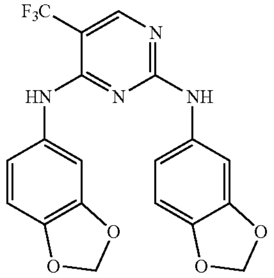

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 6-amino-3,4-dihydroquinolin-2(1H)-one (63 mg) and acetic acid (2 mL) in the second step. 9 mg of a mixture of 6-((4-(benzo[d][1,3]dioxol-5-ylamino)-5-(trifluoromethyl) pyrimidin-2-yl)amino)-3,4-dihydroquinolin-2(1H)-one and 6-((2-(benzo[d][1,3]dioxol-5-yl amino)-5-(trifluoromethyl)pyrimidin-4-yl)amino)-3,4-dihydroquinolin-2(1H)-one and 10 mg of $N^2$,$N^4$-bis(benzo[d][1,3]dioxol-5-yl)-5-(trifluoromethyl)pyrimidine-2,4-diamine was recovered after reverse phase HPLC. MS calcd for $[C_{21}H_{16}F_3N_5O_3+H]^+$: 444.13, found 444.38. MS calcd for $[C_{19}H_{13}F_3N_4O_4+H]^+$: 419.10, found 419.35.

Example 125

Preparation of 6-((4-((3,4-dimethylphenyl)amino)-5-(trifluoromethyl) pyrimidin-2-yl)amino)-3,4-dihydroquinolin-2(1H)-one

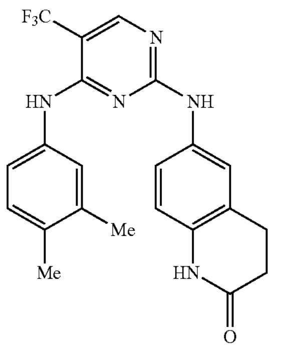 [SMILES: Cc1ccc(Nc2nc(Nc3ccc4c(c3)CCC(=O)N4)ncc2C(F)(F)F)cc1C]

Same procedure as Example 99 using 2,4-dichloro-5-(trifluoromethyl)pyrimidine (100 mg), 3,4-dimethylaniline (47 mg) and N,N-diisopropylethylamine (0.068 mL) in the first step, followed by 6-amino-3,4-dihydroquinolin-2(1H)-one (63 mg) and acetic acid (2 mL) in the second step. 31 mg of product was recovered after reverse phase HPLC. MS calcd for $[C_{22}H_{20}F_3N_5O+H]^+$: 428.17, found 428.44.

Example 126

Preparation of 6-((4-(naphthalen-1-ylamino)-5-(trifluoromethyl)pyrimidin-2-yl)amino)-3,4-dihydroquinolin-2(1H)-one and $N^2$,$N^4$-di(naphthalen-1-yl)-5-(trifluoromethyl) pyrimidine-2,4-diamine

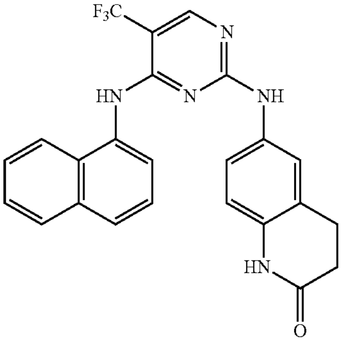

-continued

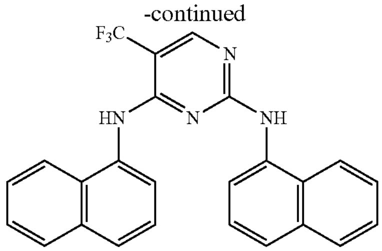

Same procedure as Example 99 using 2,4-dichloro-5-(trifluoromethyl)pyrimidine (85 mg), naphthalen-1-amine (56 mg) and N,N-diisopropylethylamine (0.068 mL) in the first step, followed by 6-amino-3,4-dihydroquinolin-2(1H)-one (63 mg) and acetic acid (2 mL) in the second step. 22 mg of 6-((4-(naphthalen-1-ylamino)-5-(trifluoromethyl)pyrimidin-2-yl)amino)-3,4-dihydroquinolin-2(1H)-one and 4.5 mg of $N^2$,$N^4$-di(naphthalen-1-yl)-5-(trifluoromethyl) pyrimidine-2,4-diamine was recovered after reverse phase HPLC. MS calcd for $[C_{24}H_{18}F_3N_5O+H]^+$: 450.15, found 450.38. MS calcd for $[C_{25}H_{17}F_3N_4+H]^+$: 431.15, found 431.35.

Example 127

Preparation of 6-((4-((5,6,7,8-tetrahydronaphthalen-1-yl)amino)-5-(trifluoromethyl)pyrimidin-2-yl)amino)-3,4-dihydroquinolin-2(1H)-one and 6-((2-((5,6,7,8-tetrahydronaphthalen-1-yl)amino)-5-(trifluoromethyl)pyrimidin-4-yl)amino)-3,4-dihydroquinolin-2(1H)-one

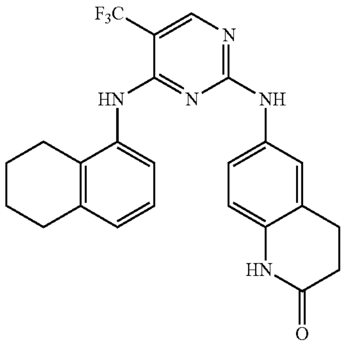

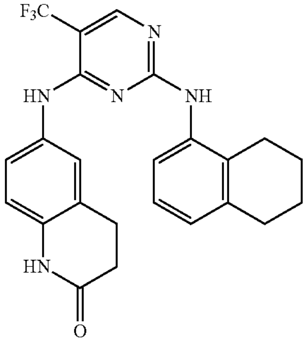

Same procedure as Example 99 using 2,4-dichloro-5-(trifluoromethyl)pyrimidine (85 mg), 5,6,7,8-tetrahydronaphthalen-1-amine (58 mg) and N,N-diisopropylethylamine (0.068 mL) in the first step, followed by 6-amino-3,4-dihydroquinolin-2(1H)-one (63 mg) and acetic acid (2 mL) in the second step. 37 mg of a mixture of 6-((4-((5,6,7,8-tetrahydronaphthalen-1-yl)amino)-5-(trifluoromethyl) pyrimidin-2-yl)amino)-3,4-dihydroquinolin-2(1H)-one and 6-((2-((5,6,7,8-tetrahydronaphthalen-1-yl)amino)-5-(trifluoromethyl)pyrimidin-4-yl)amino)-3,4-dihydroquinolin-2 (1H)-one was recovered after reverse phase HPLC. MS calcd for $[C_{24}H_{22}F_3N_5O+H]^+$: 454.19, found 454.43. MS calcd for $[C_{24}H_{22}F_3N_5O+H]^+$: 454.19, found 4454.43.

Example 128

Preparation of N-methyl-3-((2-((2-oxo-1,2,3,4-tetrahydroquinolin-6-yl) amino)-5-(trifluoromethyl)pyrimidin-4-yl)amino)benzamide

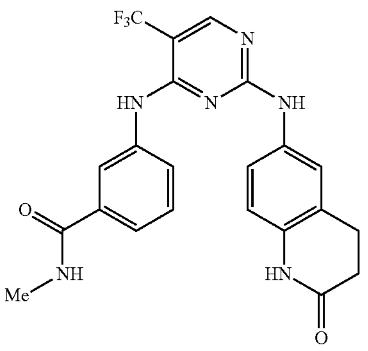 [SMILES: CNC(=O)c1cccc(Nc2nc(Nc3ccc4c(c3)CCC(=O)N4)ncc2C(F)(F)F)c1]

Same procedure as Example 99 using 2,4-dichloro-5-(trifluoromethyl)pyrimidine (85 mg), 3-amino-N-methylbenzamide (58 mg) and N,N-diisopropylethylamine (0.068 mL) in the first step, followed by 6-amino-3,4-dihydroquinolin-2(1H)-one (63 mg) and acetic acid (2 mL) in the second step. 110 mg of product was recovered after reverse phase HPLC. MS calcd for $[C_{22}H_{19}F_3N_6O_2+H]^+$: 457.16, found 457.41.

Example 129

Preparation of 6-((4-((2,3-dihydro-1H-inden-5-yl) amino)-5-(trifluoromethyl) pyrimidin-2-yl)amino)-3,4-dihydroquinolin-2(1H)-one

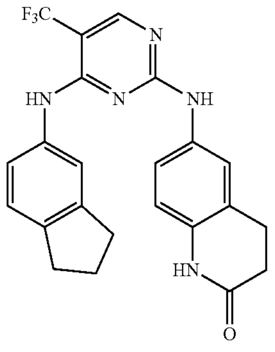 [SMILES: O=C1CCc2cc(Nc3ncc(C(F)(F)F)c(Nc4ccc5c(c4)CCC5)n3)ccc2N1]

Same procedure as Example 99 using 2,4-dichloro-5-(trifluoromethyl)pyrimidine (85 mg), 2,3-dihydro-1H-inden-5-amine (52 mg) and N,N-diisopropylethylamine (0.068 mL) in the first step, followed by 6-amino-3,4-dihydroquinolin-2(1H)-one (63 mg) and acetic acid (2 mL) in the second step. 7 mg of product was recovered after reverse phase HPLC. MS calcd for $[C_{23}H_{20}F_3N_5O+H]^+$: 440.17, found 440.40.

Example 130

Preparation of 6-((4-((2,3-dihydro-1H-inden-2-yl) amino)-5-(trifluoromethyl) pyrimidin-2-yl)amino)-3,4-dihydroquinolin-2(1H)-one and 6-((2-((2,3-dihydro-1H-inden-2-yl)amino)-5-(trifluoromethyl) pyrimidin-4-yl)amino)-3,4-dihydroquinolin-2(1H)-one.

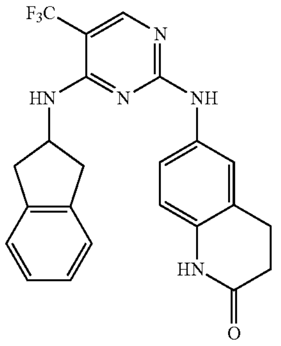
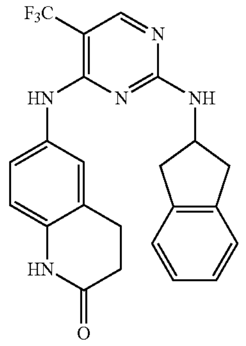

Same procedure as Example 99 using 2,4-dichloro-5-(trifluoromethyl)pyrimidine (85 mg), 2,3-dihydro-1H-inden-2-amine (52 mg) and N,N-diisopropylethylamine (0.068 mL) in the first step, followed by 6-amino-3,4-dihydroquinolin-2(1H)-one (63 mg) and acetic acid (2 mL) in the second step. 8 mg of 6-((4-((2,3-dihydro-1H-inden-2-yl)amino)-5-(trifluoromethyl)pyrimidin-2-yl)amino)-3,4-dihydroquinolin-2(1H)-one and 9 mg of 6-((2-((2,3-dihydro-1H-inden-2-yl)amino)-5-(trifluoromethyl)pyrimidin-4-yl)amino)-3,4-dihydroquinolin-2(1H)-one was recovered after reverse phase HPLC. LRMS calcd for $[C_{23}H_{20}F_3N_5O+H]^+$: 440.17, found 440.40. MS calcd for $[C_{23}H_{20}F_3N_5O+H]^+$: 440.40, found 440.40.

Example 131

Preparation of 6-((4-(cyclopropylamino)-5-(trifluoromethyl)pyrimidin-2-yl) amino)-3,4-dihydroquinolin-2(1H)-one and 6-((2-(cyclopropylamino)-5-(trifluoromethyl) pyrimidin-4-yl)amino)-3,4-dihydroquinolin-2(1H)-one

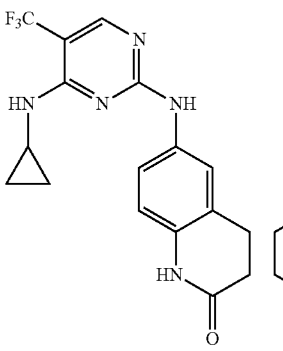
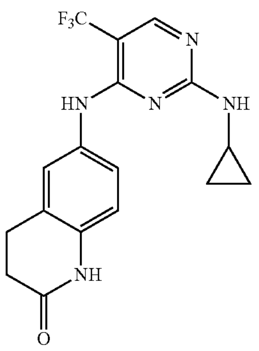

Same procedure as Example 99 using 2,4-dichloro-5-(trifluoromethyl)pyrimidine (85 mg), cyclopropanamine (22 mg) and N,N-diisopropylethylamine (0.068 mL) in the first step, followed by 6-amino-3,4-dihydroquinolin-2(1H)-one (63 mg) and acetic acid (2 mL) in the second step. 12 mg of 6-((4-(cyclopropylamino)-5-(trifluoromethyl)pyrimidin-2-yl)amino)-3,4-dihydroquinolin-2(1H)-one and 15 mg of 6-((2-(cyclopropylamino)-5-(trifluoromethyl)pyrimidin-4-yl)amino)-3,4-dihydroquinolin-2(1H)-one was recovered after reverse phase HPLC. MS calcd for $[C_{17}H_{16}F_3N_5O+H]^+$: 364.14, found 364.36. MS calcd for $[C_{17}H_{16}F_3N_5O+H]^+$: 364.14, found 364.36.

Example 132

Preparation of N-(4-((2-((2-oxo-1,2,3,4-tetrahydroquinolin-6-yl)amino)-5-(trifluoromethyl)pyrimidin-4-yl)amino)phenyl)acetamide

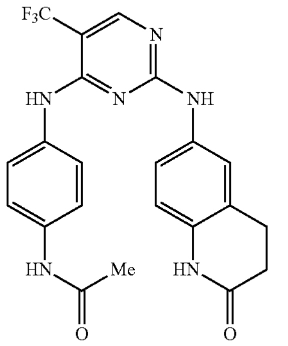 [SMILES: CC(=O)Nc1ccc(Nc2nc(Nc3ccc4c(c3)CCC(=O)N4)ncc2C(F)(F)F)cc1]

Same procedure as Example 99 using 2,4-dichloro-5-(trifluoromethyl)pyrimidine (85 mg), N-(4-aminophenyl)acetamide (59 mg) and N,N-diisopropylethylamine (0.068 mL) in the first step, followed by 6-amino-3,4-dihydroquinolin-2(1H)-one (63 mg) and acetic acid (2 mL) in the second step. 62 mg of product was recovered after reverse phase HPLC. MS calcd for $[C_{22}H_{19}F_3N_6O_2+H]^+$: 457.16, found 457.41.

Example 133

Preparation of $N^2$-(2,3-dihydrobenzo[b][1,4]dioxin-6-yl)-$N^4$-(3-methoxy phenyl)-5-(trifluoromethyl) pyrimidine-2,4-diamine

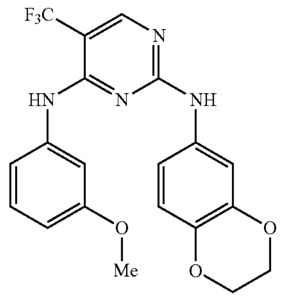 [SMILES: COc1cccc(Nc2nc(Nc3ccc4c(c3)OCCO4)ncc2C(F)(F)F)c1]

Same procedure as Example 99 using 2,4-dichloro-5-(trifluoromethyl)pyrimidine (85 mg), 3-methoxyaniline (48 mg) and N,N-diisopropylethylamine (0.068 mL) in the first step, followed by 2,3-dihydrobenzo[b][1,4]dioxin-6-amine (59 mg) and acetic acid (2 mL) in the second step. 31 mg of product was recovered after reverse phase HPLC. MS calcd for $[C_{20}H_{17}F_3N_4O_3+H]^+$: 419.13, found 419.39.

Example 134

Preparation of 6,6'-((5-chloropyrimidine-2,4-diyl)bis(azanediyl))bis(3,4-dihydroquinolin-2(1H)-one)

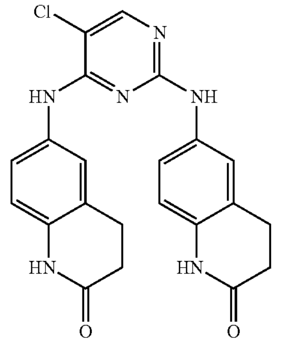

Same procedure as Example 99 using 2,4-dichloro-5-(trifluoromethyl)pyrimidine (46 mg), 6-amino-3,4-dihydroquinolin-2(1H)-one (41 mg) and N,N-diisopropylethylamine (0.044 mL) in the first step, followed by 6-amino-3,4-dihydroquinolin-2(1H)-one (41 mg) and acetic acid (2 mL) in the second step. The crude solid was washed with 10 mL each of acetonitrile, acetone, dichloromethane and ethyl acetate to give 64 mg of semi-pure product which was further washed with 10 mL of methanol to yield 46 mg of product. MS calcd for $[C_{22}H_{19}ClN_6O_2+H]^+$: 435.13, found 435.43.

Example 135

Preparation of 6,6'-((5-methoxypyrimidine-2,4-diyl)bis(azanediyl))bis(3,4-dihydroquinolin-2(1H)-one)

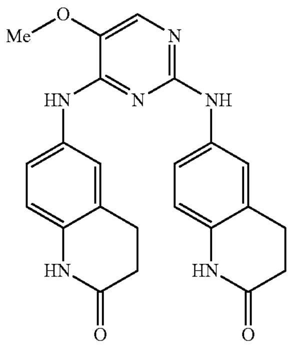 [SMILES: COc1cnc(Nc2ccc3c(c2)CCC(=O)N3)nc1Nc1ccc2c(c1)CCC(=O)N2]

Same procedure as Example 99 using 2,4-dichloro-5-(trifluoromethyl)pyrimidine (46 mg), 6-amino-3,4-dihydroquinolin-2(1H)-one (41 mg) and N,N-diisopropylethylamine (0.068 mL) in the first step, followed by 6-amino-3,4-dihydroquinolin-2(1H)-one (41 mg) and acetic acid (2 mL) in the second step. The crude solid was washed with 10 mL dichloromethane to give 11 mg of pure product. A further 11 mg of product was recovered after reverse phase HPLC purification of the above filtrate. MS calcd for $[C_{23}H_{22}N_6O_3+H]^+$: 431.18, found 431.42.

Example 136

Preparation of $N^2$-(3-chloro-4-(trifluoromethoxy) phenyl)-$N^4$-(3-methoxy phenyl)-5-(trifluoromethyl) pyrimidine-2,4-diamine and $N^4$-(3-chloro-4-(trifluoromethoxy) phenyl)-$N^2$-(3-methoxyphenyl)-5-(trifluoromethyl)pyrimidine-2,4-diamine

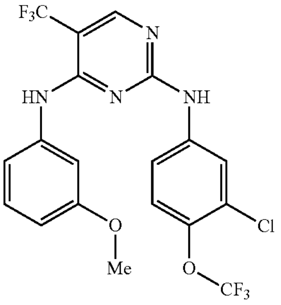

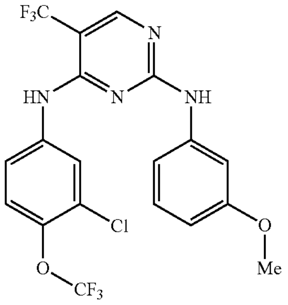

Same procedure as Example 99 using 2,4-dichloro-5-(trifluoromethyl)pyrimidine (85 mg), 3-methoxyaniline (48 mg) and N,N-diisopropylethylamine (0.068 mL) in the first step, followed by 3-chloro-4-(trifluoromethoxy)aniline (83 mg) and acetic acid (2 mL) in the second step. 26 mg of a mixture of $N^2$-(3-chloro-4-(trifluoromethoxy)phenyl)-$N^4$-(3-methoxyphenyl)-5-(trifluoromethyl)pyrimidine-2,4-diamine and $N^4$-(3-chloro-4-(trifluoromethoxy)phenyl)-$N^2$-(3-methoxyphenyl)-5-(trifluoromethyl)pyrimidine-2,4-diamine was recovered after reverse phase HPLC. MS calcd for $[C_{19}H_{13}ClF_6N_4O_2+H]^+$: 479.07, found 479.35. MS calcd for $[C_{19}H_{13}ClF_6N_4O_2+H]^+$: 479.07, found 479.35.

Example 137

Preparation of 3-((4-((3-methoxyphenyl)amino)-5-(trifluoromethyl) pyrimidin-2-yl)amino)naphthalen-2-ol and 3-((2-((3-methoxyphenyl)amino)-5-(trifluoromethyl)pyrimidin-4-yl)amino)naphthalen-2-ol

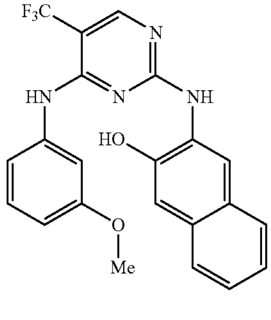 [SMILES: COc1cccc(Nc2nc(Nc3cc4ccccc4cc3O)ncc2C(F)(F)F)c1]

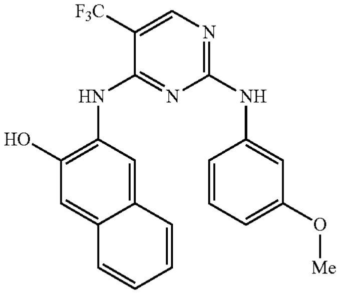 [SMILES: COc1cccc(Nc2ncc(C(F)(F)F)c(Nc3cc4ccccc4cc3O)n2)c1]

Same procedure as Example 99 using 2,4-dichloro-5-(trifluoromethyl)pyrimidine (85 mg), 3-methoxyaniline (48 mg) and N,N-diisopropylethylamine (0.068 mL) in the first step, followed by 3-aminonaphthalen-2-ol (62 mg) and acetic acid (2 mL) in the second step. 25 mg of a mixture of 3-((4-((3-methoxyphenyl)amino)-5-(trifluoromethyl)pyrimidin-2-yl)amino)naphthalen-2-ol and 3-((2-((3-methoxyphenyl)amino)-5-(trifluoromethyl)pyrimidin-4-yl)amino) naphthalen-2-ol was recovered after reverse phase HPLC. MS calcd for $[C_{22}H_{17}F_3N_4O_2+H]^+$: 427.14, found 427.44. MS calcd for $[C_{22}H_{17}F_3N_4O_2+H]^+$: 427.14, found 427.44.

Example 138

Preparation of 3-((4-(benzo[d][1,3]dioxol-5-ylamino)-5-(trifluoromethyl) pyrimidin-2-yl)amino) benzamide and 3-((2-(benzo[d][1,3]dioxol-5-ylamino)-5-(trifluoromethyl) pyrimidin-4-yl)amino) benzamide

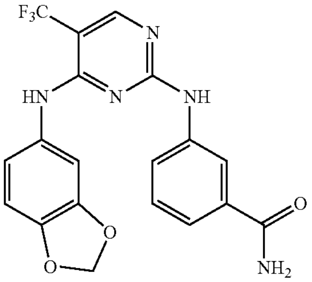

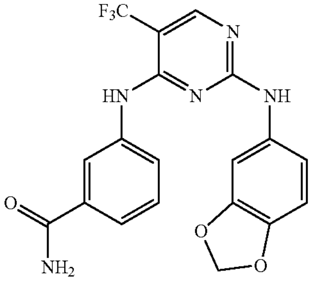

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 3-aminobenzamide (53 mg) and acetic acid (2 mL) in the second step. 34 mg of a mixture of 3-((4-(benzo[d][1,3]dioxol-5-ylamino)-5-(trifluoromethyl)pyrimidin-2-yl)amino)benzamide and 3-((2-(benzo[d][1,3]dioxol-5-ylamino)-5-(trifluoromethyl)pyrimidin-4-yl)amino)benzamide was recovered after reverse phase HPLC. MS calcd for $[C_{19}H_{14}F_3N_5O_3+H]^+$: 418.11, found 418.36. MS calcd for $[C_{19}H_{14}F_3N_5O_3+H]^+$: 418.11, found 418.36.

Example 139

Preparation of $N^2$-(4-(1H-pyrrol-1-yl)phenyl)-$N^4$-(benzo[d][1,3]dioxol-5-yl)-5-(trifluoromethyl)pyrimidine-2,4-diamine and $N^4$-(4-(1H-pyrrol-1-yl)phenyl)-$N^2$-(benzo [d][1,3]dioxol-5-yl)-5-(trifluoromethyl)pyrimidine-2,4-diamine

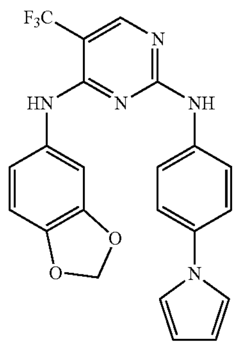 [SMILES: FC(F)(F)c1cnc(Nc2ccc(-n3cccc3)cc2)nc1Nc1ccc2c(c1)OCO2]

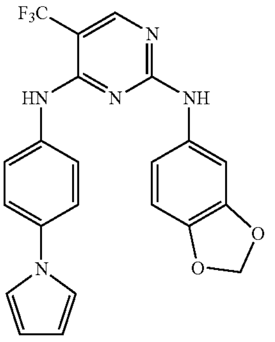 [SMILES: FC(F)(F)c1cnc(Nc2ccc3c(c2)OCO3)nc1Nc1ccc(-n2cccc2)cc1]

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 4-(1H-pyrrol-1-yl)aniline (62 mg) and acetic acid (2 mL) in the second step. 22 mg of a mixture of $N^2$-(4-(1H-pyrrol-1-yl)phenyl)-$N^4$-(benzo[d][1,3]dioxol-5-yl)-5-(trifluoromethyl)pyrimidine-2,4-diamine and $N^4$-(4-(1H-pyrrol-1-yl)phenyl)-$N^2$-(benzo[d][1,3]dioxol-5-yl)-5-(trifluoromethyl)pyrimidine-2,4-diamine was recovered after reverse phase HPLC. MS calcd for $[C_{22}H_{16}F_3N_5O_2+H]^+$: 440.13, found 440.40. MS calcd for $[C_{22}H_{16}F_3N_5O_2+H]^+$: 440.13, found 440.40.

Example 140

Preparation of $N^4$-(benzo[d][1,3]dioxol-5-yl)-$N^2$-(2,3-dihydro-1H-inden-5-yl)-5-(trifluoromethyl)pyrimidine-2,4-diamine and $N^2$-(benzo[d][1,3]dioxol-5-yl)-$N^4$-(2,3-dihydro-1H-inden-5-yl)-5-(trifluoromethyl)pyrimidine-2,4-diamine

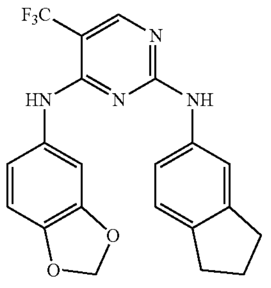
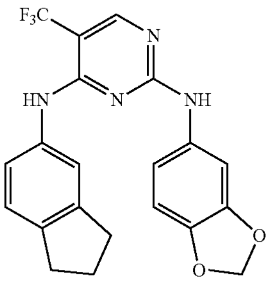

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 2,3-dihydro-1H-inden-5-amine (52 mg) and acetic acid (2 mL) in the second step. 7 mg of a mixture of $N^4$-(benzo[d][1,3]dioxol-5-yl)-$N^2$-(2,3-dihydro-1H-inden-5-yl)-5-(trifluoromethyl)pyrimidine-2,4-diamine and $N^2$-(benzo[d][1,3]dioxol-5-yl)-$N^4$-(2,3-dihydro-1H-inden-5-yl)-5-(trifluoromethyl)pyrimidine-2,4-diamine was recovered after reverse phase HPLC. MS calcd for $[C_{21}H_{17}F_3N_4O_2+H]^+$: 415.14, found 415.41. MS calcd for $[C_{21}H_{17}F_3N_4O_2+H]^+$: 415.14, found 415.41.

Example 141

Preparation of $N^4$-(benzo[d][1,3]dioxol-5-yl)-$N^2$-(2-fluoro-3-(trifluoromethyl) phenyl)-5-(trifluoromethyl)pyrimidine-2,4-diamine and $N^2$-(benzo[d][1,3]dioxol-5-yl)-$N^4$-(2-fluoro-3-(trifluoromethyl)phenyl)-5-(trifluoromethyl)pyrimidine-2,4-diamine

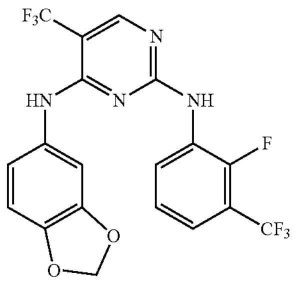

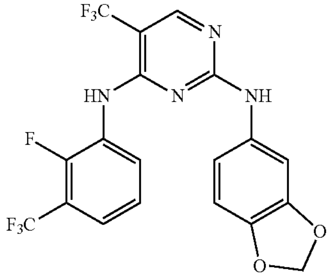

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 2-fluoro-3-(trifluoromethyl)aniline (70 mg) and acetic acid (2 mL) in the second step. 14 mg of $N^4$-(benzo[d][1,3]dioxol-5-yl)-$N^2$-(2-fluoro-3-(trifluoromethyl)phenyl)-5-(trifluoromethyl)pyrimidine-2,4-diamine and 6 mg of $N^2$-(benzo[d][1,3]dioxol-5-yl)-$N^4$-(2-fluoro-3-(trifluoromethyl)phenyl)-5-(trifluoromethyl) pyrimidine-2,4-diamine was recovered after reverse phase HPLC. MS calcd for $[C_{19}H_{11}F_7N_4O_2+H]^+$: 461.08, found 461.38. MS calcd for $[C_{19}H_{11}F_7N_4O_2+H]^+$: 461.08, found 461.38.

Example 142

Preparation of 6-((5-bromo-4-((3-methoxyphenyl) amino)pyrimidin-2-yl)amino)-3,4-dihydroquinolin-2 (1H)-one

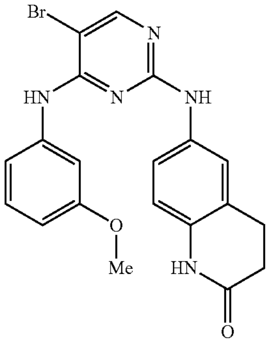

Same procedure as Example 99 using 5-bromo-2,4-dichloropyrimidine (93 mg), 3-methoxyaniline (50 mg) and N,N-diisopropylethylamine (0.071 mL) in the first step, followed by 6-amino-3,4-dihydroquinolin-2(1H)-one (66 mg) and acetic acid (2 mL) in the second step. 15 mg of product was recovered after reverse phase HPLC. MS calcd for $[C_{20}H_{18}BrN_5O_2+H]^+$: 440.07, found 440.33.

Example 143

Preparation of 6-((5-chloro-4-((3-methoxyphenyl) amino)pyrimidin-2-yl)amino)-3,4-dihydroquinolin-2 (1H)-one and 5-chloro-$N^2$,$N^4$-bis(3-methoxyphenyl) pyrimidine-2,4-diamine

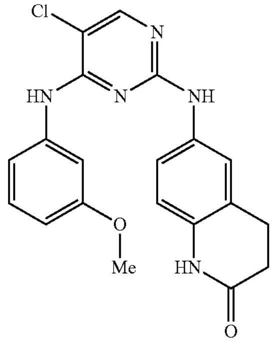 [SMILES: COc1cccc(Nc2nc(Nc3ccc4c(c3)CCC(=O)N4)ncc2Br)c1]

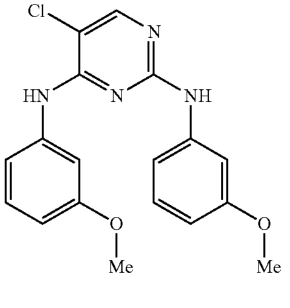

Same procedure as Example 99 using 2,4,5-trichloropyrimidine (74 mg), 3-methoxyaniline (50 mg) and N,N-diisopropylethylamine (0.077 mL) in the first step, followed by 6-amino-3,4-dihydroquinolin-2(1H)-one (59 mg) and acetic acid (2 mL) in the second step. 18 mg of 6-((5-chloro-4-((3-methoxyphenyl)amino)pyrimidin-2-yl)amino)-3,4-dihydroquinolin-2(1H)-one and 1.2 mg of 5-chloro-$N^2$,$N^4$-bis (3-methoxyphenyl)pyrimidine-2,4-diamine was recovered after reverse phase HPLC. MS calcd for $[C_{20}H_{18}ClN_5O_2+H]^+$: 396.12, found 396.34. MS calcd for $[C_{18}H_{17}ClN_4O_2+H]^+$: 357.11, found 357.33.

Example 144

Preparation of $N^4$-(benzo[d][1,3]dioxol-5-yl)-$N^2$(4-methoxyphenyl)-5-(trifluoromethyl)pyrimidine-2,4-diamine and $N^2$-(benzo[d][1,3]dioxol-5-yl)-$N^4$-(4-methoxy phenyl)-5-(trifluoromethyl)pyrimidine-2,4-diamine

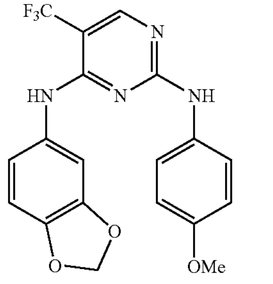

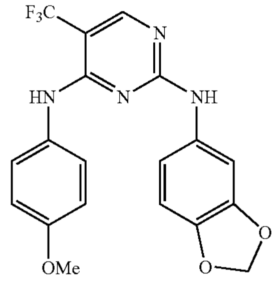

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 4-methoxyaniline (48 mg) and acetic acid (2 mL) in the second step. 29 mg of a mixture of $N^4$-(benzo[d][1,3]dioxol-5-yl)-$N^2$-(4-methoxyphenyl)-5-(trifluoromethyl) pyrimidine-2,4-diamine and $N^2$-(benzo[d] [1,3]dioxol-5-yl)-$N^4$-(4-methoxyphenyl)-5-(trifluoro methyl)pyrimidine-2,4-diamine was recovered after reverse phase HPLC. MS calcd for $[C_{19}H_{15}F_3N_4O_3+H]^+$: 405.12, found 405.36. MS calcd for $[C_{19}H_{15}F_3N_4O_3+H]^+$: 405.12, found 405.36.

Example 145

Preparation of $N^4$-(benzo[d][1,3]dioxol-5-yl)-$N^2$-(5-methoxy-2-methylphenyl)-5-(trifluoromethyl)pyrimidine-2,4-diamine and $N^2$-(benzo[d][1,3]dioxol-5-yl)-$N^4$-(5-methoxy-2-methylphenyl)-5-(trifluoromethyl)pyrimidine-2,4-diamine

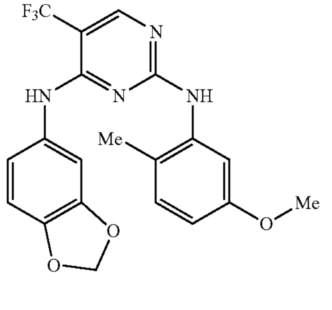

-continued

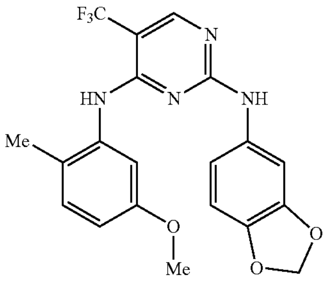

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 5-methoxy-2-methylaniline (53 mg) and acetic acid (2 mL) in the second step. 25 mg of a mixture of $N^4$-(benzo[d][1,3]dioxol-5-yl)-$N^2$-(5-methoxy-2-methylphenyl)-5-(trifluoromethyl)pyrimidine-2,4-diamine and $N^2$-(benzo[d][1,3]dioxol-5-yl)-$N^4$-(5-methoxy-2-methylphenyl)-5-(trifluoromethyl)pyrimidine-2,4-diamine was recovered after reverse phase HPLC. MS calcd for $[C_{20}H_{17}F_3N_4O_3+H]^+$: 419.13, found 419.39. MS calcd for $[C_{20}H_{17}F_3N_4O_3+H]^+$: 419.13, found 419.39.

Example 146

Preparation of $N^4$-(benzo[d][1,3]dioxol-5-yl)-$N^2$-(3,4-dimethylphenyl)-5-(trifluoromethyl)pyrimidine-2,4-diamine and $N^2$-(benzo[d][1,3]dioxol-5-yl)-$N^4$-(3,4-dimethylphenyl)-5-(trifluoromethyl)pyrimidine-2,4-diamine

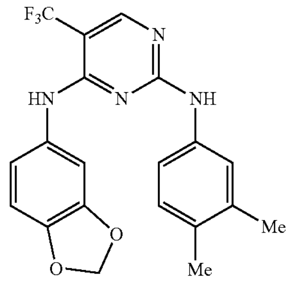 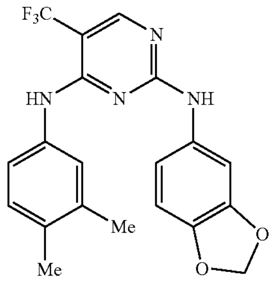

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 3,4-dimethylaniline (47 mg) and acetic acid (2 mL) in the second step. 9 mg of a mixture of $N^4$-(benzo[d][1,3]dioxol-5-yl)-$N^2$-(3,4-dimethylphenyl)-5-(trifluoromethyl)pyrimidine-2,4-diamine and $N^2$-(benzo[d][1,3]dioxol-5-yl)-$N^4$-(3,4-dimethylphenyl)-5-(trifluoromethyl)pyrimidine-2,4-diamine was recovered after reverse phase HPLC. MS calcd for $[C_{20}H_{17}F_3N_4O_2+H]^+$: 403.14, found 403.37.

Example 147

Preparation of $N^4$-(benzo[d][1,3]dioxol-5-yl)-$N^2$-(2,3-dichlorophenyl)-5-(trifluoromethyl)pyrimidine-2,4-diamine and $N^2$-(benzo[d][1,3]dioxol-5-yl)-$N^4$-(2,3-dichlorophenyl)-5-(trifluoromethyl)pyrimidine-2,4-diamine

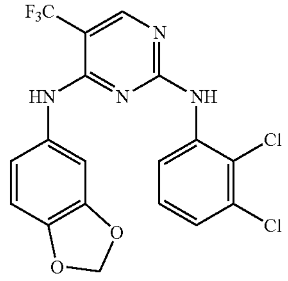 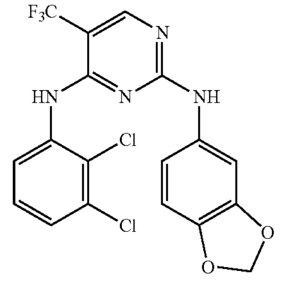

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 2,3-dichloroaniline (63 mg) and acetic acid (2 mL) in the second step. 12 mg of a mixture of $N^4$-(benzo[d][1,3]dioxol-5-yl)-$N^2$-(2,3-dichlorophenyl)-5-(trifluoromethyl)pyrimidine-2,4-diamine and $N^2$-(benzo[d][1,3]dioxol-5-yl)-$N^4$-(2,3-dichlorophenyl)-5-(trifluoromethyl)pyrimidine-2,4-diamine was recovered after reverse phase HPLC. MS calcd for $[C_{18}H_{11}Cl_2F_3N_4O_2+H]^+$: 443.03, found 443.28. MS calcd for $[C_{18}H_{11}Cl_2F_3N_4O_2+H]^+$: 443.03, found 443.28.

Example 148

Preparation of $N^4$-(benzo[d][1,3]dioxol-5-yl)-$N^2$-(3-chloro-4-fluorophenyl)-5-(trifluoromethyl)pyrimidine-2,4-diamine and $N^2$-(benzo[d][1,3]dioxol-5-yl)-$N^4$-(3-chloro-4-fluorophenyl)-5-(trifluoromethyl)pyrimidine-2,4-diamine

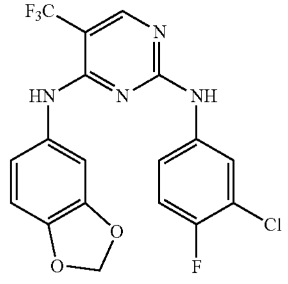 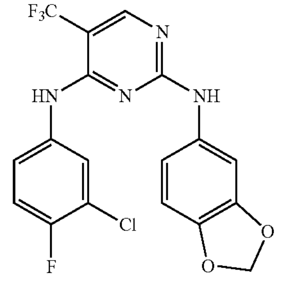

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 3-chloro-4-fluoroaniline (57 mg) and acetic acid (2 mL) in the second step. 36 mg of a mixture of $N^4$-(benzo[d][1,3]dioxol-5-yl)-$N^2$-(3-chloro-4-fluorophenyl)-5-(trifluoromethyl)pyrimidine-2,4-diamine and $N^2$-(benzo[d][1,3]dioxol-5-yl)-$N^4$-(3-chloro-4-fluorophenyl)-5-(trifluoromethyl)pyrimidine-2,4-diamine was recovered after reverse phase HPLC. MS calcd for $[C_{18}H_{11}ClF_4N_4O_2+H]^+$: 427.06, found 427.30. MS calcd for $[C_{18}H_{11}ClF_4N_4O_2+H]^+$: 427.06, found 427.30.

Example 149

Preparation of $N^4$-(benzo[d][1,3]dioxol-5-yl)-$N^2$-(3-phenoxyphenyl)-5-(trifluoromethyl)pyrimidine-2,4-diamine and $N^2$-(benzo[d][1,3]dioxol-5-yl)-$N^4$-(3-phenoxyphenyl)-5-(trifluoromethyl)pyrimidine-2,4-diamine

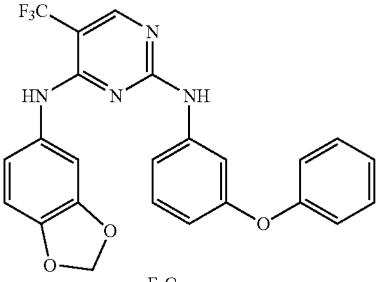

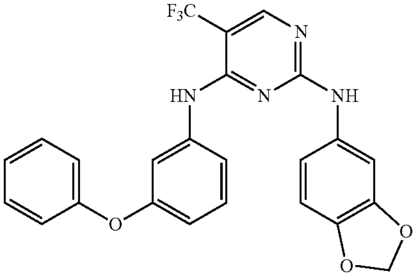

Same procedure as Example 99 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by 3-phenoxyaniline (73 mg) and acetic acid (2 mL) in the second step. 36 mg of a mixture of $N^4$-(benzo[d][1,3]dioxol-5-yl)-$N^2$-(3-phenoxyphenyl)-5-(trifluoromethyl)pyrimidine-2,4-diamine and $N^2$-(benzo[d][1,3]dioxol-5-yl)-$N^4$-(3-phenoxyphenyl)-5-(trifluoromethyl)pyrimidine-2,4-diamine was recovered after reverse phase HPLC. MS calcd for $[C_{24}H_{17}F_3N_4O_3+H]^+$: 467.13, found 467.41. MS calcd for $[C_{24}H_{17}F_3N_4O_3+H]^+$: 467.13, found 467.41.

Example 150

Preparation of 6-((4-(cyclobutylamino)-5-(trifluoromethyl)pyrimidin-2-yl)amino)-3,4-dihydroquinolin-2(1H)-one and 6-((2-(cyclobutylamino)-5-(trifluoromethyl)pyrimidin-4-yl)amino)-3,4-dihydroquinolin-2(1H)-one

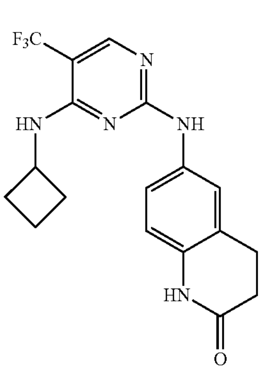

-continued

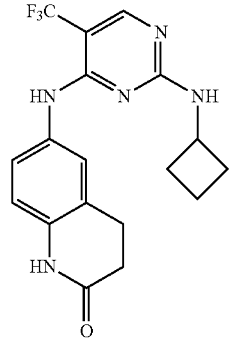

Same procedure as Example 99 using 2,4-dichloro-5-(trifluoromethyl)pyrimidine (70 mg), cyclobutanamine (23 mg) and N,N-diisopropylethylamine (0.056 mL) in the first step, followed by 6-amino-3,4-dihydroquinolin-2(1H)-one (52 mg) and acetic acid (2 mL) in the second step. 12 mg of 6-((4-(cyclobutylamino)-5-(trifluoromethyl)pyrimidin-2-yl)amino)-3,4-dihydroquinolin-2(1H)-one and 18 mg of 6-((2-(cyclobutylamino)-5-(trifluoromethyl)pyrimidin-4-yl)amino)-3,4-dihydroquinolin-2(1H)-one were recovered after reverse phase HPLC. MS calcd for $[C_{18}H_{18}F_3N_5O+H]^+$: 378.15, found 378.35.

Example 151

Preparation of 6-((4-((2-methoxyethyl)amino)-5-(trifluoromethyl)pyrimidin-2-yl)amino)-3,4-dihydroquinolin-2(1H)-one and 6-((2-((2-methoxyethyl)amino)-5-(trifluoromethyl)pyrimidin-4-yl)amino)-3,4-dihydroquinolin-2(1H)-one

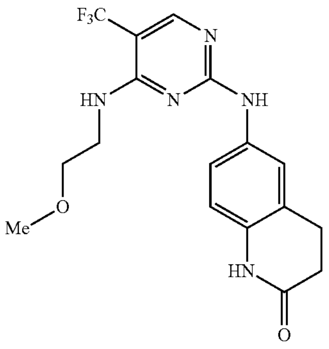

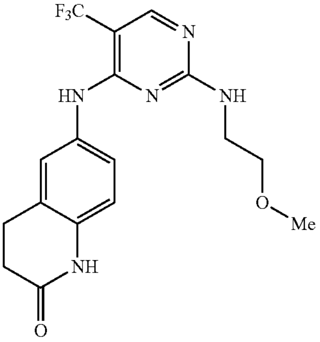

Same procedure as Example 99 using 2,4-dichloro-5-(trifluoromethyl)pyrimidine (70 mg), 2-methoxyethan-1- amine (24 mg) and N,N-diisopropylethylamine (0.062 mL) in the first step, followed by 6-amino-3,4-dihydroquinolin-2(1H)-one (52 mg) and acetic acid (2 mL) in the second step. 11 mg of 6-((4-((2-methoxyethyl)amino)-5-(trifluoromethyl)pyrimidin-2-yl)amino)-3,4-dihydroquinolin-2(1H)-one and 20 mg of 6-((2-((2-methoxyethyl)amino)-5-(trifluoromethyl) pyrimidin-4-yl)amino)-3,4-dihydroquinolin-2(1H)-one was recovered after reverse phase HPLC. LRMS calcd for $[C_{17}H_{18}F_3N_5O_2+H]^+$: 382.15, found 382.33. MS calcd for $[C_{17}H_{18}F_3N_5O_2+H]^+$: 382.15, found 382.33.

Example 152

Preparation of $N^4$-cyclopropyl-$N^2$-(1H-pyrrolo[2,3-b]pyridin-5-yl)-5-(trifluoromethyl)pyrimidine-2,4-diamine and $N^2$-cyclopropyl-$N^4$-(1H-pyrrolo[2,3-b] pyridin-5-yl)-5-(trifluoromethyl)pyrimidine-2,4-diamine

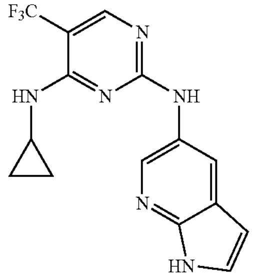

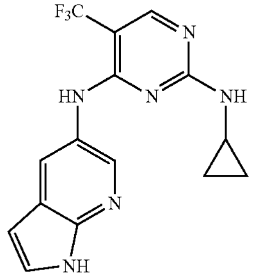

Same procedure as Example 99 using 2,4-dichloro-5-(trifluoromethyl)pyrimidine (85 mg), cyclopropanamine (22 mg) and N,N-diisopropylethylamine (0.068 mL) in the first step, followed by 1H-pyrrolo[2,3-b]pyridin-5-amine (52 mg) and acetic acid (2 mL) in the second step. 13 mg of $N^4$-cyclopropyl-$N^2$-(1H-pyrrolo[2,3-b]pyridin-5-yl)-5-(trifluoromethyl)pyramidine-2,4-diamine and 9 mg of $N^2$-cyclopropyl-$N^4$-(1H-pyrrolo[2,3-b]pyridin-5-yl)-5-(trifluoromethyl)pyrimidine-2,4-diamine was recovered after reverse phase HPLC. MS calcd for $[C_{15}H_{13}F_3N_6+H]^+$: 335.12, found 335.25. MS calcd for $[C_{15}H_{13}F_3N_6+H]^+$: 335.12, found 335.25.

Example 153

Preparation of 5-bromo-$N^2$-(1H-indol-5-yl)-$N^4$-(3-(methylsulfonyl)benzyl) pyrimidine-2,4-diamine

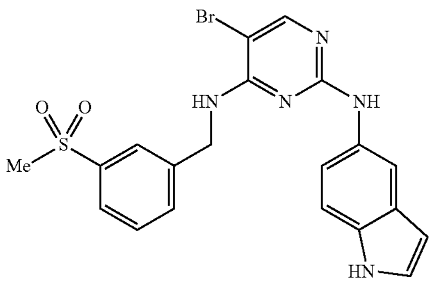 [SMILES: CS(=O)(=O)c1cccc(CNc2nc(Nc3ccc4[nH]ccc4c3)ncc2Br)c1]

Same procedure as Example 99 using 5-bromo-2,4-dichloropyrimidine (150 mg), (3-(methylsulfonyl)phenyl) methanamine, HCl salt (50 mg) and N,N-diisopropylethylamine (0.229 mL) in the first step, followed by 1H-indol-5-amine (87 mg) and acetic acid (2 mL) in the second step. 41 mg of product was recovered after flash chromatography using reverse phase C18 silica gel. MS calcd for $[C_{20}H_{18}BrN_5O_2S+H]^+$: 472.04, found 472.25.

Example 154

Preparation of 5-bromo-$N^2$-(1H-indol-5-yl)-$N^4$-(pyridin-2-yl)pyrimidine-2,4-diamine

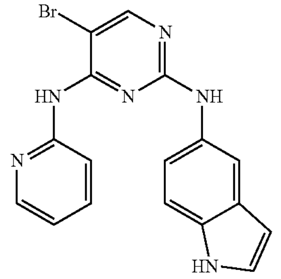 [SMILES: Brc1cnc(Nc2ccc3[nH]ccc3c2)nc1Nc1ccccn1]

Same procedure as Example 99 using 5-bromo-2,4-dichloropyrimidine (150 mg), pyridin-2-amine (62 mg) and N,N-diisopropylethylamine (0.117 mL) in the first step, followed by 1H-indol-5-amine (87 mg) and acetic acid (2 mL) in the second step. 14 mg of product was recovered after flash chromatography using reverse phase C18 silica gel. MS calcd for $[C_{17}H_{13}BrN_6+H]^+$: 381.05, found 381.19.

Example 155

Preparation of 6-((5-bromo-4-(pyridin-2-ylamino) pyrimidin-2-yl)amino)-3,4-dihydroquinolin-2(1H)-one

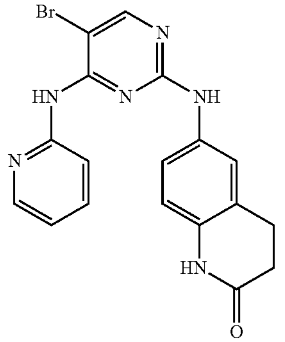 [SMILES: O=C1CCc2cc(Nc3ncc(Br)c(Nc4ccccn4)n3)ccc2N1]

Same procedure as Example 99 using 5-bromo-2,4-dichloropyrimidine (150 mg), pyridin-2-amine (62 mg) and N,N-diisopropylethylamine (0.117 mL) in the first step, followed by 6-amino-3,4-dihydroquinolin-2(1H)-one (107 mg) and acetic acid (2 mL) in the second step. 12 mg of product was recovered after flash chromatography using reverse phase C18 silica gel. MS calcd for $[C_{18}H_{15}BrN_6O+H]^+$: 411.06, found 411.22.

Example 156

Preparation of 6-((5-bromo-4-((6-methoxypyridin-3-yl)amino)pyrimidin-2-yl)amino)-3,4-dihydroquinolin-2(1H)-one

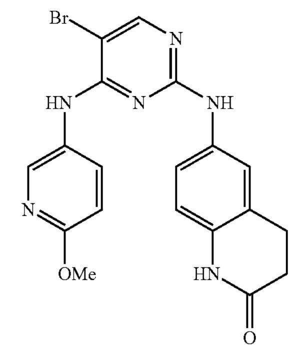 [SMILES: COc1ccc(Nc2nc(Nc3ccc4c(c3)CCC(=O)N4)ncc2Br)cn1]

Same procedure as Example 99 using 5-bromo-2,4-dichloropyrimidine (150 mg), 6-methoxypyridin-3-amine (82 mg) and N,N-diisopropylethylamine (0.117 mL) in the first step, followed by 6-amino-3,4-dihydroquinolin-2(1H)-one (107 mg) and acetic acid (2 mL) in the second step. 8 mg of product was recovered after flash chromatography using reverse phase C18 silica gel. MS calcd for $[C_{19}H_{17}BrN_6O_2+H]^+$: 441.07, found 441.15.

Example 157

Preparation of 6-((4-(phenylamino)-5-(trifluoromethyl)pyrimidin -2-yl) amino)-3,4-dihydroquinolin-2 (1H)-one and 6-((2-(phenylamino)-5-(trifluoromethyl) pyrimidin-4-yl)amino)-3,4-dihydroquinolin-2 (1H)-one

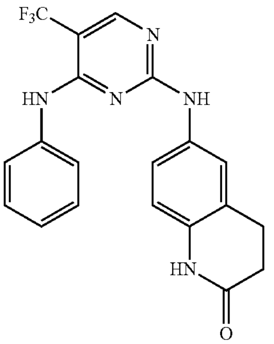

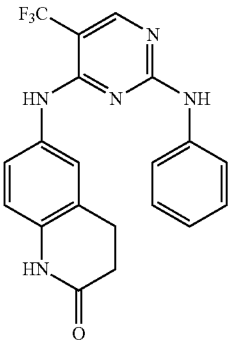

Same procedure as Example 99 using 2,4-dichloro-5-(trifluoromethyl)pyrimidine (85 mg), aniline (36 mg) and N,N-diisopropylethylamine (0.068 mL) in the first step, followed by 6-amino-3,4-dihydroquinolin-2(1H)-one (64 mg) and acetic acid (2 mL) in the second step. 23 mg of a mixture of 6-((4-(phenylamino)-5-(trifluoromethyl)pyrimidin-2-yl)amino)-3,4-dihydroquinolin-2(1H)-one and 6-((2-(phenylamino)-5-(trifluoromethyl)pyrimidin-4-yl)amino)-3,4-dihydroquinolin-2(1H)-one was recovered after reverse phase HPLC. MS calcd for $[C_{20}H_{16}F_3N_5O+H]^+$: 400.14, found 400.36. MS calcd for $[C_{20}H_{16}F_3N_5O+H]^+$: 400.14, found 400.36.

Example 158

Preparation of $N^4$-cyclopropyl-$N^2$-(2,3-dihydrobenzo[b][1,4]dioxin-6-yl)-5-(trifluoromethyl)pyrimidine-2,4-diamine and $N^2$-cyclopropyl-$N^4$-(2,3-dihydro benzo[b][1,4]dioxin-6-yl)-5-(trifluoromethyl)pyrimidine-2,4-diamine

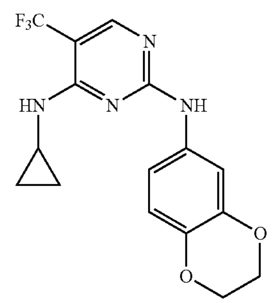

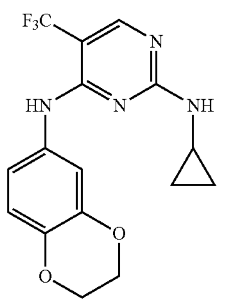

Same procedure as Example 99 using 2,4-dichloro-5-(trifluoromethyl)pyrimidine (85 mg), cyclopropanamine (22 mg) and N,N-diisopropylethylamine (0.068 mL) in the first step, followed by 2,3-dihydrobenzo[b][1,4]dioxin-6-amine (59 mg) and acetic acid (2 mL) in the second step. 15 mg of $N^4$-cyclopropyl-$N^2$-(2,3-dihydrobenzo[b][1,4]dioxin-6-yl)-5-(trifluoromethyl)pyrimidine-2,4-diamine and 8 mg of $N^2$-cyclopropyl-$N^4$-(2,3-dihydrobenzo[b][1,4]dioxin-6-yl)-5-(trifluoromethyl)pyrimidine-2,4-diamine was recovered after reverse phase HPLC. MS calcd for $[C_{16}H_{15}F_3N_4O_2+H]^+$: 353.12, found 353.31. MS calcd for $[C_{16}H_{15}F_3N_4O_2+H]^+$: 353.12, found 353.31.

Example 159

Preparation of 6-((5-bromo-4-(cyclopropylamino) pyrimidin-2-yl)amino)-3,4-dihydroquinolin-2(1H)-one

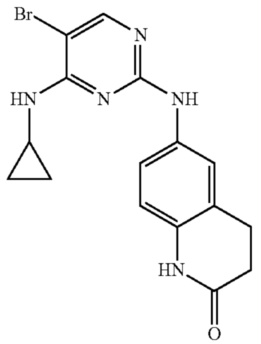 [SMILES: O=C1CCc2cc(Nc3ncc(Br)c(NC4CC4)n3)ccc2N1]

Same procedure as Example 99 using 5-bromo-2,4-dichloropyrimidine (80 mg), cyclopropanamine (26 mg) and N,N-diisopropylethylamine (0.092 mL) in the first step, followed by 6-amino-3,4-dihydroquinolin-2(1H)-one (57 mg) and acetic acid (2 mL) in the second step. 10 mg of product was isolated by filtration of the crude solid and rinsing with acetonitrile. MS calcd for $[C_{16}H_{16}BrN_5O+H]^+$: 374.06, found 374.26.

Example 160

Preparation of 6-((4-(cyclopentylamino)-5-(trifluoromethyl)pyrimidin-2-yl)amino)-3,4-dihydroquinolin-2(1H)-one and 6-((2-(cyclopentylamino)-5-(trifluoromethyl)pyrimidin-4-yl)amino)-3,4-dihydroquinolin-2(1H)-one

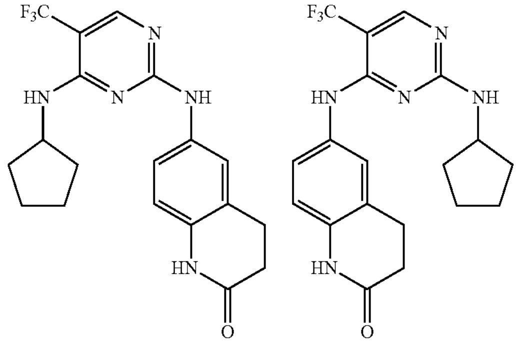

Same procedure as Example 99 using 2,4-dichloro-5-(trifluoromethyl)pyrimidine (120 mg), cyclopentanamine (47 mg) and N,N-diisopropylethylamine (0.096 mL) in the first step, followed by 6-amino-3,4-dihydroquinolin-2(1H)-one (90 mg) and acetic acid (2 mL) in the second step. 65 mg of 6-((4-(cyclopentylamino)-5-(trifluoromethyl)pyrimidin-2-yl)amino)-3,4-dihydroquinolin-2(1H)-one and 86 mg of 6-((2-(cyclopentylamino)-5-(trifluoromethyl)pyrimidin-4-yl)amino)-3,4-dihydroquinolin-2(1H)-one was recovered after reverse phase HPLC. MS calcd for $[C_{19}H_{20}F_3N_5O+H]^+$: 392.17, found 392.40. MS calcd for $[C_{19}H_{20}F_3N_5O+H]^+$: 392.17, found 392.35.

Example 161

Preparation of $N^4$-cyclobutyl-$N^2$-(1H-pyrrolo[2,3-b]pyridin-5-yl)-5-(trifluoromethyl)pyrimidine-2,4-diamine and $N^2$-cyclobutyl-$N^4$-(1H-pyrrolo[2,3-b]pyridin-5-yl)-5-(trifluoromethyl)pyrimidine-2,4-diamine

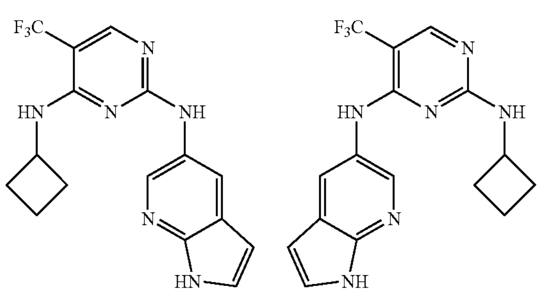

Same procedure as Example 99 using 2,4-dichloro-5-(trifluoromethyl)pyrimidine (120 mg), cyclobutanamine (49 mg) and N,N-diisopropylethylamine (0.120 mL) in the first step, followed by 1H-pyrrolo[2,3-b]pyridin-5-amine (92 mg) and acetic acid (3 mL) in the second step. 50 mg of a $N^4$-cyclobutyl-$N^2$-(1H-pyrrolo[2,3-b]pyridin-5-yl)-5-(trifluoromethyl)pyrimidine-2,4-diamine and 60 mg of a mixture of $N^2$-cyclobutyl-$N^4$-(1H-pyrrolo[2,3-b]pyridin-5-yl)-5-(trifluoromethyl)pyrimidine-2,4-diamine and its regioisomer (60:40 ratio) was recovered after reverse phase HPLC. MS calcd for $[C_{16}H_{15}F_3N_6+H]^+$: 349.14, found 349.35. MS calcd for $[C_{16}H_{15}F_3N_6+H]^+$: 349.14, found 349.25.

Example 162

General Synthetic Scheme for the Preparation of Trisubstituted Pyrimidines Described Below

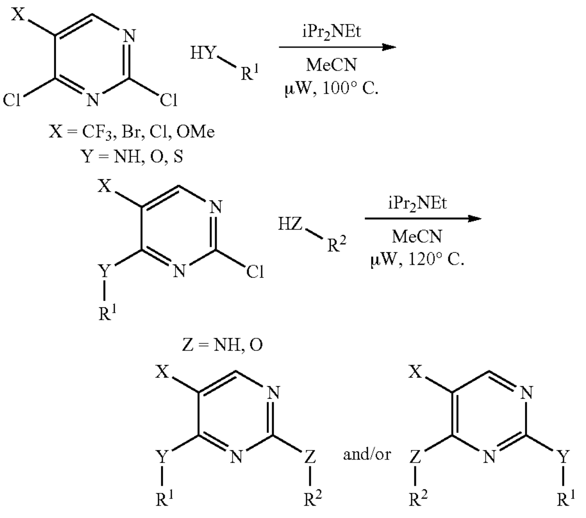

Example 163

Preparation of $N^4$-(benzo[d][1,3]dioxol-5-yl)-$N^2$-(2,3-dihydro-1H-inden-2-yl)-5-(trifluoromethyl)pyrimidine-2,4-diamine and $N^2$-(benzo [d] [1,3]dioxol-5-yl)-$N^4$-(2,3-dihydro-1H-inden-2-yl)-5-(trifluoromethyl)pyrimidine-2,4-diamine

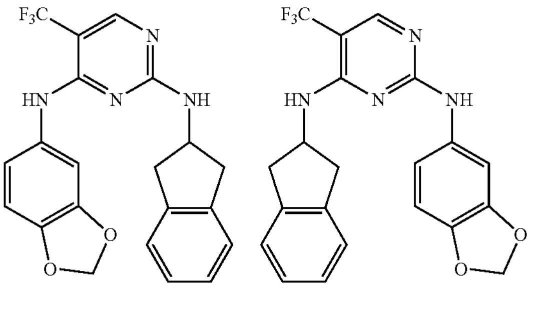

A solution of 2,4-dichloro-5-(trifluoromethyl)pyrimidine (85 mg, 0.392 mmol, 1.0 equiv), benzo[d][1,3]dioxol-5-amine (54 mg, 0.392 mmol, 1.0 equiv) and N,N-diisopropylethylamine (0.068 mL, 0.392 mmol, 1.0 equiv) in acetonitrile (3 mL) was microwaved at 100° C. for 10 min. Then 2,3-dihydro-1H-inden-2-amine (52 mg, 0.392 mmol, 1.0 equiv) and N,N-diisopropylethyl amine (0.068 mL, 0.392 mmol, 1.0 equiv) were added. This mixture was microwaved at 100° C. for 10 min, then concentrated in vacuo. A fraction of the crude product was purified by reverse phase HPLC to yield 5.3 mg of $N^4$-(benzo[d][1,3]dioxol-5-yl)-$N^2$-(2,3-dihydro-1H-inden-2-yl)-5-(trifluoromethyl)pyrimidine-2,4-diamine and 3.5 mg of $N^2$-(benzo[d][1,3]dioxol-5-yl)-$N^4$-(2,3-dihydro-1H-inden-2-yl)-5-(trifluoromethyl)pyrimidine-2,4-diamine. MS calcd for $[C_{21}H_{17}F_3N_4O_2+H]^+$: 415.14, found 415.34. MS calcd for $[C_{21}H_{17}F_3N_4O_2+H]^+$: 415.14, found 415.34.

Example 164

Preparation of N-(benzo[d][1,3]dioxol-5-yl)-2-(pyrrolidin-1-yl)-5-(trifluoromethyl)pyrimidin-4-amine and N-(benzo[d][1,3]dioxol-5-yl)-4-(pyrrolidin-1-yl)-5-(trifluoromethyl)pyrimidin-2-amine

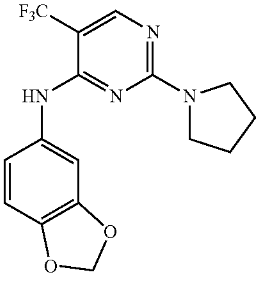

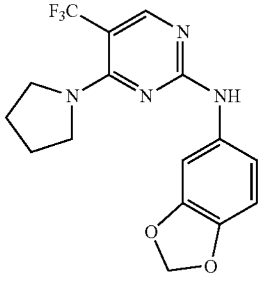

Same procedure as Example 163 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by pyrrolidine (28 mg) and N,N-diisopropylethylamine (0.068 mL) in the second step. 2 mg of N-(benzo[d][1,3]dioxol-5-yl)-2-(pyrrolidin-1-yl)-5-(trifluoromethyl) pyrimidin-4-amine and 1.4 mg of N-(benzo[d][1,3]dioxol-5-yl)-4-(pyrrolidin-1-yl)-5-(trifluoro methyl)pyrimidin-2-amine was recovered after reverse phase HPLC. MS calcd for $[C_{16}H_{15}F_3N_4O_2+H]^+$: 353.12, found 353.33. MS calcd for $[C_{16}H_{15}F_3N_4O_2+H]^+$: 353.12, found 353.34.

Example 165

Preparation of $N^4$-(benzo[d][1,3]dioxol-5-yl)-5-(trifluoromethyl)pyrimidine-2,4-diamine and $N^2$-(benzo[d][1,3]dioxol-5-yl)-5-(trifluoromethyl)pyrimidine-2,4-diamine

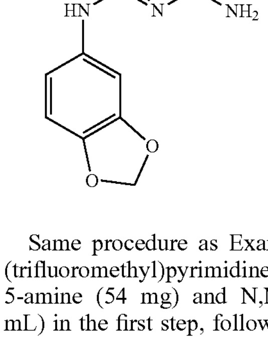

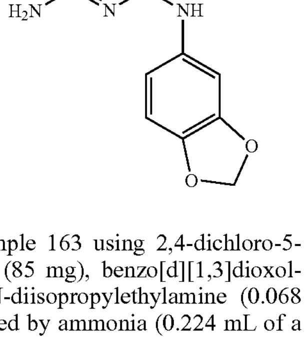

Same procedure as Example 163 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by ammonia (0.224 mL of a 7 M solution in MeOH) and N,N-diisopropyl ethylamine (0.068 mL) in the second step. 15 mg of $N^4$-(benzo[d][1,3]dioxol-5-yl)-5-(trifluoromethyl)pyrimidine-2,4-diamine and 15 mg of $N^2$-(benzo[d][1,3]dioxol-5-yl)-5-(trifluoromethyl)pyrimidine-2,4-diamine was recovered after reverse phase HPLC. MS calcd for $[C_{12}H_9F_3N_4O_2+H]^+$: 299.08, found 299.28. MS calcd for $[C_{12}H_9F_3N_4O_2+H]^+$: 299.08, found 299.28.

Example 166

Preparation of 2-(azetidin-1-yl)-N-(benzo[d][1,3]dioxol-5-yl)-5-(trifluoro methyl)pyrimidin-4-amine and 4-(azetidin-1-yl)-N-(benzo[d][1,3]dioxol-5-yl)-5-(trifluoromethyl)pyrimidin-2-amine

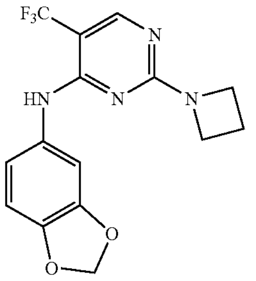

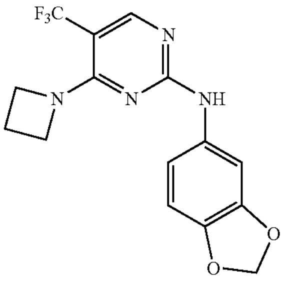

Same procedure as Example 163 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by azetidine, HCl salt (37 mg) and N,N-diisopropylethylamine (0.137 mL) in the second step. 2.5 mg of 2-(azetidin-1-yl)-N-(benzo[d][1,3]dioxol-5-yl)-5-(trifluoromethyl)pyrimidin-4-amine and 1.4 mg of 4-(azetidin-1-yl)-N-(benzo[d][1,3]dioxol-5-yl)-5-(trifluoromethyl)pyrimidin-2-amine was recovered after reverse phase HPLC. MS calcd for $[C_{15}H_{13}F_3N_4O_2+H]^+$: 339.11, found 339.29. MS calcd for $[C_{15}H_{13}F_3N_4O_2+H]^+$: 339.11, found 339.29.

Example 167

Preparation of $N^4$-(benzo[d][1,3]dioxol-5-yl)-$N^2$-(cyclopropylmethyl)-5-(trifluoromethyl)pyrimidine-2,4-diamine and $N^2$-(benzo[d][1,3]dioxol-5-yl)-$N^4$-(cyclopropylmethyl)-5-(trifluoromethyl)pyrimidine-2,4-diamine.

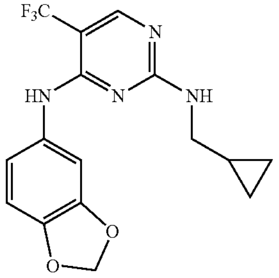

-continued

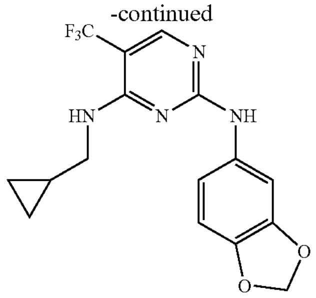

Same procedure as Example 163 using 2,4-dichloro-5-(trifluoromethyl)pyrimidine (85 mg), benzo[d][1,3]dioxol-5-amine (54 mg) and N,N-diisopropylethylamine (0.068 mL) in the first step, followed by cyclopropylmethanamine (56 mg) and N,N-diisopropylethylamine (0.068 mL) in the second step. 10 mg of $N^4$-(benzo[d][1,3]dioxol-5-yl)-$N^2$-(cyclopropylmethyl)-5-(trifluoromethyl)pyrimidine-2,4-diamine and 10 mg of $N^2$-(benzo[d][1,3]dioxol-5-yl)-$N^4$-(cyclopropylmethyl)-5-(trifluoromethyl)pyrimidine-2,4-diamine was recovered after reverse phase HPLC. MS calcd for $[C_{16}H_{15}F_3N_4O_2+H]^+$: 353.12, found 353.32. MS calcd for $[C_{16}H_{15}F_3N_4O_2+H]^+$: 353.12, found 353.32.

Example 168

Preparation of $N^4$-(benzo[d][1,3]dioxol-5-yl)-$N^2$-cyclobutyl-5-(trifluoromethyl)pyrimidine-2,4-diamine, $N^2$-(benzo[d][1,3]dioxol-5-yl)-$N^4$-cyclobutyl-5-(trifluoromethyl)pyrimidine-2,4-diamine and $N^2$,$N^4$-dicyclobutyl-5-(trifluoromethyl) pyrimidine-2,4-diamine

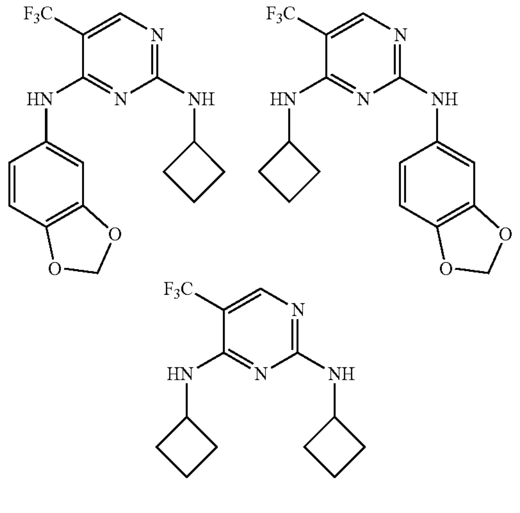

Same procedure as Example 163 using 2,4-dichloro-5-(trifluoromethyl)pyrimidine (85 mg), benzo[d][1,3]dioxol-5-amine (48 mg, 0.89 equiv.) and N,N-diisopropylethylamine (0.068 mL) in the first step, followed by cyclobutanamine (56 mg, 2 equiv) and N,N-diisopropylethylamine (0.068 mL) in the second step. 13 mg of $N^4$-(benzo[d][1,3]dioxol-5-yl)-$N^2$-cyclobutyl-5-(trifluoromethyl)pyrimidine-2,4-diamine, 18 mg of $N^2$-(benzo[d][1,3]dioxol-5-yl)-$N^4$-cyclobutyl-5-(trifluoromethyl)pyrimidine-2,4-diamine and 4.5 mg of $N^2$,$N^4$-dicyclobutyl-5-(trifluoromethyl)pyrimidine-2,4-diamine was recovered after reverse phase HPLC. LRMS calcd for $[C_{16}H_{15}F_3N_4O_2+H]^+$: 353.12, found 353.32. MS calcd for $[C_{16}H_{15}F_3N_4O_2+H]^+$: 353.12, found 353.32. MS calcd for $[C_{13}H_{17}F_3N_4+H]^+$: 287.15, found 287.32.

Example 169

Preparation of $N^2$,$N^4$-dicyclopropyl-5-(trifluoromethyl)pyrimidine-2,4-diamine

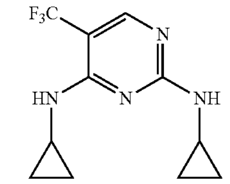 [SMILES: FC(F)(F)c1cnc(NC2CC2)nc1NC1CC1]

Same procedure as Example 163 using 2,4-dichloro-5-(trifluoromethyl)pyrimidine (60 mg), cyclopropanamine (16 mg) and N,N-diisopropylethylamine (0.035 mL) in the first step, followed by cyclopropanamine (16 mg) and N,N-diisopropylethylamine (0.035 mL) in the second step. 29 mg of $N^2$,$N^4$-dicyclopropyl-5-(trifluoromethyl)pyrimidine-2,4-diamine was recovered after reverse phase HPLC. MS calcd for $[C_{11}H_{13}F_3N_4+H]^+$: 259.12, found 259.24.

Example 170

Preparation of 2-((5-bromo-2-((5-methoxy-2-methylphenyl)amino)pyrimidin-4-yl)oxy)-N-methylbenzamide

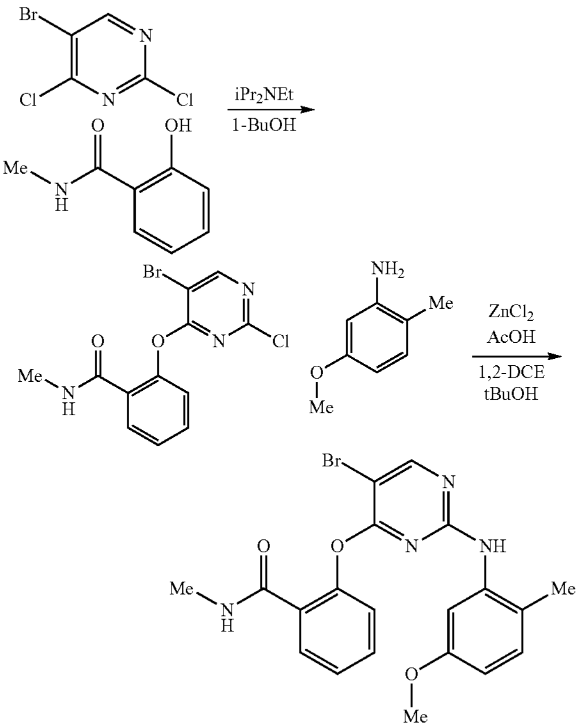

A solution of 5-bromo-2,4-dichloropyrimidine (53 mg, 0.232 mmol, 1.0 equiv), 2-hydroxy-N-methylbenzamide (35 mg, 0.232 mmol, 1.0 equiv) and N,N -diisopropylethylamine (0.048 mL, 0.276 mmol, 1.2 equiv) in 1-butanol (3 mL) was stirred at 0° C. for 20 min, then at 21° C. for 16 h. The mixture was concentrated in vacuo, then 5-methoxy-2-methylaniline (32 mg, 0.232 mmol, 1.0 equiv), zinc chloride (1 M solution in ether, 0.232 mL, 0.232 mmol, 1 equiv) and acetic acid (2 mL) were added. This mixture was microwaved at 120° C. for 10 min, then concentrated in vacuo. The crude product was purified by reverse phase HPLC to yield 8 mg of 2-((5-bromo-2-((5-methoxy-2-methylphenyl)amino)pyrimidin-4-yl)oxy)-N-methylbenzamide. MS calcd for $[C_{20}H_{19}BrN_4O_3+H]^+$: 443.07, found 443.35.

Example 171

Preparation of 2-((5-bromo-2-((3,4,5-trimethoxyphenyl)amino)pyrimidin-4-yl)oxy)-N-methylbenzamide and N-(5-bromo-2-((3,4,5-trimethoxyphenyl)amino)pyrimidin-4-yl)-2-hydroxy-N-methylbenzamide

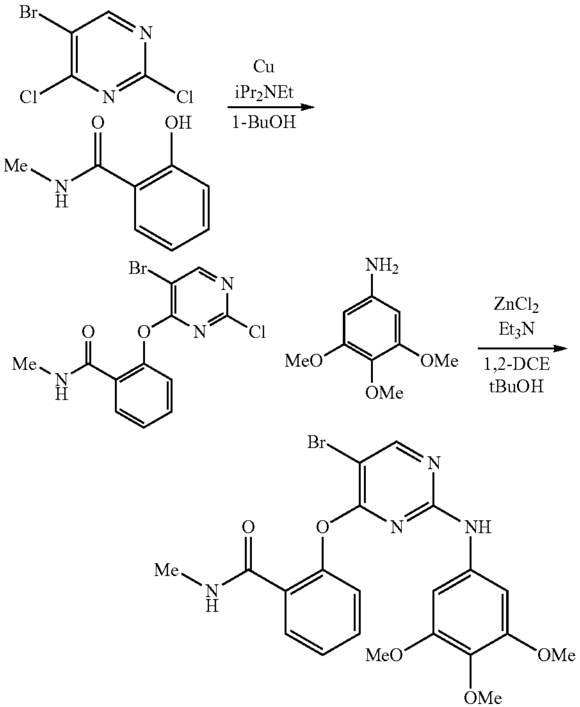

A solution of 5-bromo-2,4-dichloropyrimidine (1.809 g, 7.94 mmol, 1.0 equiv), 2-hydroxy-N-methylbenzamide (1.2 g, 7.94 mmol, 1.0 equiv), copper metal powder (50 mg, 0.794 mmol, 0.1 equiv) and N,N-diisopropylethylamine (1.383 mL, 7.94 mmol, 1.0 equiv) in DMF (10 mL) was heated to 50° C. for 2 h. Added EtOAc (100 mL) and washed with brine (4×50 mL), then water (3×50 mL), dried organics over sodium sulfate and concentrated in vacuo to give 2-((5-bromo-2-chloropyrimidin-4-yl)oxy)-N-methylbenzamide. Reagent amounts were calculated for the next step assuming an 80% yield of the intermediate product. Next, to the crude intermediate in 1,2-DCE (15 mL) and t-butanol (15 mL) was added zinc chloride (1.05 g, 7.71 mmol, 1.2 equiv). This mixture was sonicated to promote solubility of reagents. 3,4,5-Trimethox yaniline (1.177 g, 6.42 mmol, 1.0 equiv) and triethylamine (1.074 mL, 7.71 mmol, 1.2 equiv) were added and the mixture was heated to 45° C. for 7 h, then concentrated in vacuo. To the crude product was added DCM (300 mL) and it was washed with water (1×50 mL) and brine (6×30 mL), dried over sodium sulfate and concentrated in vacuo. The crude product was purified by C18 reverse phase flash chromatography (water/MeCN gradient, 22% to 44% MeCN over 40 min) to yield 560 mg of 2-((5-bromo-2-((3,4,5-trimethoxyphenyl)amino)pyrimidin-4-yl)oxy)-N-methylbenzamide and 64 mg of N-(5-bromo-2-((3,4,5-trimethoxyphenyl) amino)pyrimidin-4-yl)-2-hydroxy-N-methylbenzamide. MS calcd for $[C_{21}H_{21}BrN_4O_5+H]^+$: 489.08, found 489.37.

Example 172

Preparation of 5-bromo-N-(2-fluoro-3-(trifluoromethyl)phenyl)-4-methoxy pyrimidin-2-amine

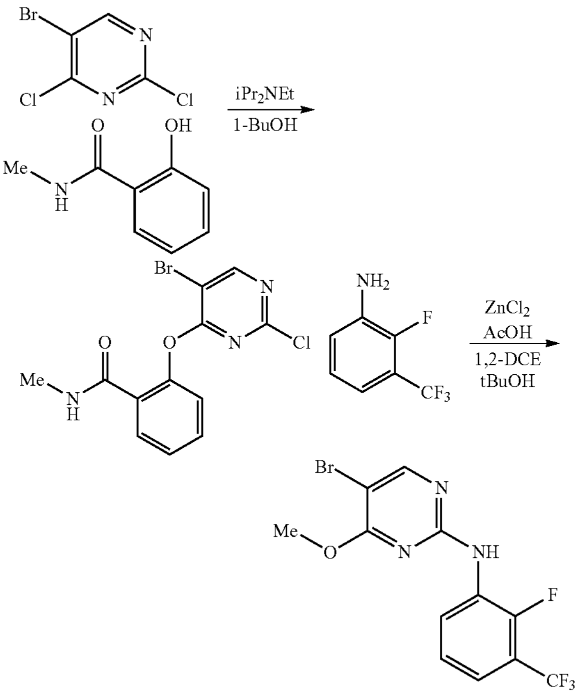

A solution of 5-bromo-2,4-dichloropyrimidine (105 mg, 0.461 mmol, 1.0 equiv), 2-hydroxy-N-methylbenzamide (70 mg, 0.461 mmol, 1.0 equiv) and N,N-diisopropylethylamine (0.096 mL, 0.553 mmol, 1.2 equiv) in 1-butanol (3 mL) was stirred at 0° C. for 20 min, then at 21° C. for 16 h. The mixture was concentrated in vacuo, then 2-fluoro-3-(trifluoromethyl)aniline (82 mg, 0.461 mmol, 1.0 equiv), zinc chloride (1 M solution in ether, 0.461 mL, 0.461 mmol, 1 equiv) and acetic acid (2 mL) were added. This mixture was microwaved at 120° C. for 10 min, then concentrated in vacuo. The crude product was purified by reverse phase HPLC (water/MeOH eluent) to yield 6 mg of 5-bromo-N-(2-fluoro-3-(trifluoromethyl)phenyl)-4-methoxypyrimidin-2-amine. MS calcd for $[C_{12}H_9BrF_4N_3O+H]^+$: 365.99, found 365.25.

Example 173

Preparation of 5-bromo-4-butoxy-N-(3,4,5-trimethoxyphenyl)pyrimidin-2-amine

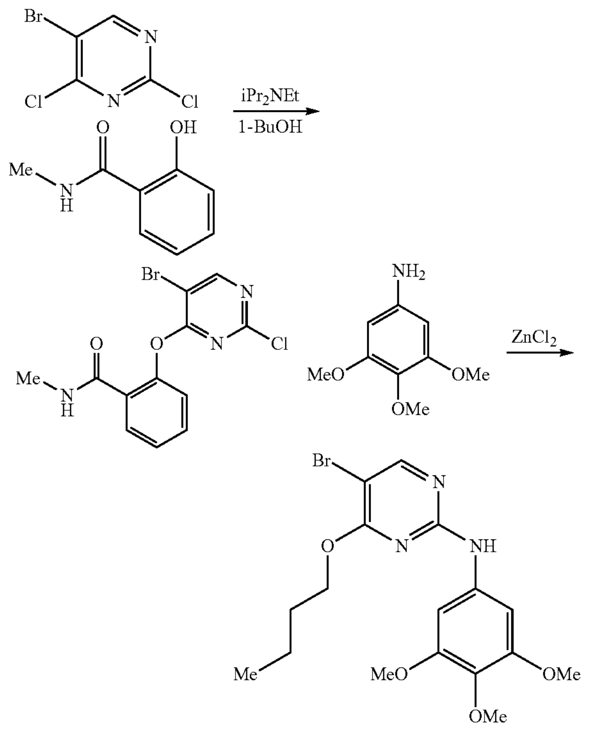

A solution of 5-bromo-2,4-dichloropyrimidine (170 mg, 0.748 mmol, 1.0 equiv), 2-hydroxy-N-methylbenzamide (113 mg, 0.748 mmol, 1.0 equiv) and N,N-diisopropylethylamine (0.130 mL, 0.748 mmol, 1.0 equiv) in 1-butanol (6 mL) was stirred at 21° C. for 22 h. Then 3,4,5-trimethoxyaniline (137 mg, 0.748 mmol, 1.0 equiv), zinc chloride (1 M solution in ether, 0.748 mL, 0.748 mmol, 1 equiv) were dded. This mixture was microwaved at 100° C. for 10 min, then concentrated in vacuo. The crude white solid was filtered and washed with MeCN (20 mL) to yield 80 mg of 2-((5-bromo-2-((3,4,5-trimethoxyphenyl)amino)pyrimidin-4-yl)oxy)-N-methylbenzamide. MS calcd for $[C_{17}H_{22}BrN_3O_4+H]^+$: 412.09, found 412.32.

Example 174

Preparation of 5-bromo-N4-cyclopropyl-N2-(1H-pyrrolo[2,3-b]pyridin-5-yl)pyrimidine-2,4-diamine

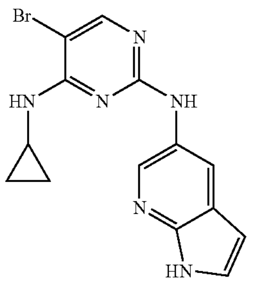 [SMILES: Brc1cnc(Nc2cnc3[nH]ccc3c2)nc1NC1CC1]

Same procedure as Example 99 using 5-bromo-2,4-dichloropyrimidine (200 mg), cyclopropanamine (50 mg) and N,N-diisopropylethylamine (0.153 mL) in the first step, followed by 1H-pyrrolo[2,3-b]pyridin-5-amine (117 mg) and acetic acid (4 mL) in the second step. 54 mg of product was isolated after automated reverse phase chromatography (water-MeCN eluent). MS calcd for $[C_{14}H_{13}BrN_6+H]^+$: 345.05, found 344.80.

Example 175

Preparation of 6-((4-cyclobutoxy-5-(trifluoromethyl)pyrimidin-2-yl)amino)-3,4-dihydroquinolin-2(1H)-one

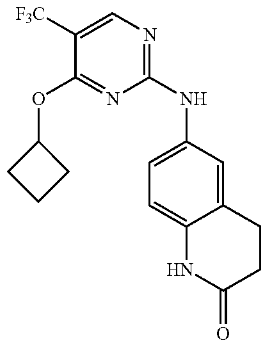 [SMILES: O=C1CCc2cc(Nc3ncc(C(F)(F)F)c(OC4CCC4)n3)ccc2N1]

Same procedure as Example 99 using 2,4-dichloro-5-(trifluoromethyl)pyrimidine (100 mg), cyclobutanol (33 mg) and N,N-diisopropylethylamine (0.080 mL) in the first step, followed by 6-amino-3,4-dihydroquinolin-2(1H)-one (75 mg) and acetic acid (3 mL) in the second step. 14 mg of 6-((4-cyclobutoxy-5-(trifluoromethyl)pyrimidin-2-yl)amino)-3,4-dihydroquinolin-2(1H)-one was isolated after automated reverse phase chromatography (water-MeCN eluent). MS calcd for $[C_{18}H_{17}F_3N_4O_2+H]^+$: 379.14, found 379.10.

Example 176

Preparation of N-(4-chloro-5-(trifluoromethyl)pyrimidin-2-yl)-1H-pyrrolo[2,3-b]pyridin-5-amine and N-(2-chloro-5-(trifluoromethyl)pyrimidin-4-yl)-1H-pyrrolo[2,3-b]pyridin-5-amine

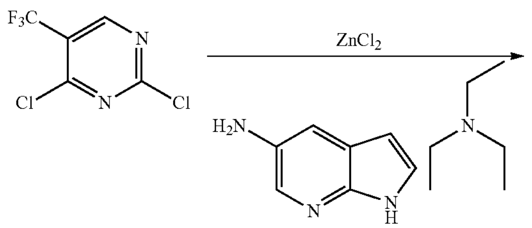

-continued

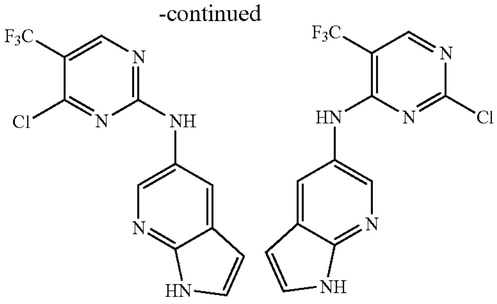

To 2,4-dichloro-5-(trifluoromethyl)pyrimidine (0.4 g, 1.844 mmol) in Dichloromethane (5 ml) and t-Butanol (5.00 ml) at −10° C. under nitrogen was added zinc(II) chloride (0.502 g, 3.69 mmol). Kept at −10 to 0° C. for 1 h. 1H-pyrrolo[2,3-b]pyridin-5-amine (0.245 g, 1.844 mmol) and triethylamine (0.283 ml, 2.028 mmol) were then added. Let the cold bath warm to 21° C. Concentrated to remove DCM, then filtered solid and washed with water. 620 mg of a 70:30 mix of isomers (N-(4-chloro-5-(trifluoromethyl) pyrimidin-2-yl)-1H-pyrrolo[2,3-b]pyridin-5-amine major) was isolated. MS calcd for $[C_{12}H_7ClF_3N_5+H]^+$: 314.04, found 313.80.

Example 177

Preparation of N4-(benzo[d][1,3]dioxol-5-yl)-N2-(1H-pyrrolo[2,3-b]pyridin-5-yl)-5-(trifluoromethyl) pyrimidine-2,4-diamine

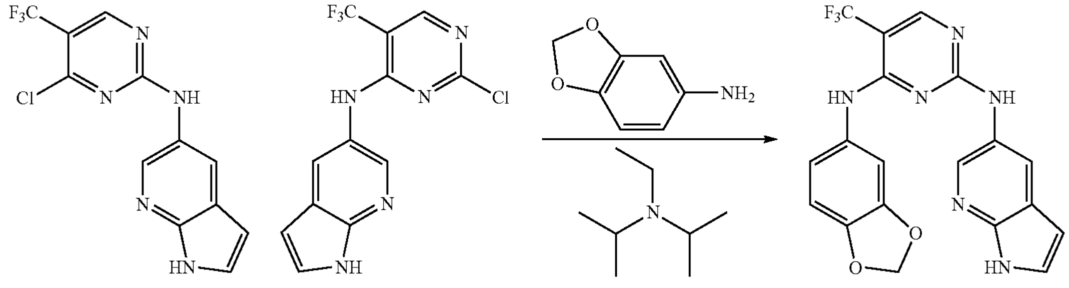

70:30

N-(4-chloro-5-(trifluoromethyl)pyrimidin-2-yl)-1H-pyrrolo[2,3-b]pyridin-5-amine (0.100 g, 0.319 mmol, contains 30% of the regioisomer), benzo[d][1,3]dioxol-5-amine (0.044 g, 0.319 mmol) and N-ethyl-N-isopropylpropan-2-amine (0.111 ml, 0.638 mmol) were mixed in DMF (3 mL). The mixture was microwaved at 130° C. for 30 minutes and then concentrated. 5 mg of the product was isolated after automated reverse phase chromatography (water-MeCN eluent). MS calcd for $[C_{19}H_{13}F_3N_6O_2+H]^+$: 415.12, found 415.20.

Example 178

Preparation of 6-((4-((2,2-difluorobenzo[d][1,3] dioxol-5-yl)amino)-5-(trifluoromethyl)pyrimidin-2-yl)amino)-3,4-dihydroquinolin-2(1H)-one and 6-((2-((2,2-difluorobenzo[d][1,3]dioxol-5-yl)amino)-5-(trifluoromethyl)pyrimidin-4-yl)amino)-3,4-dihydroquinolin-2(1H)-one

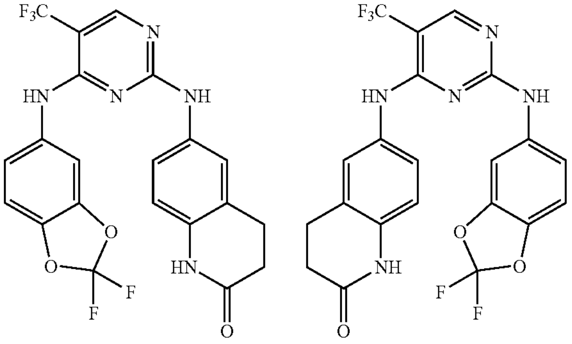

Same procedure as Example 99 using 2,4-dichloro-5-(trifluoromethyl)pyrimidine (100 mg), 2,2-difluorobenzo[d] [1,3]dioxol-5-amine (80 mg) and N,N-diisopropylethylamine (0.08 mL) in the first step, followed by 6-amino-3,4-dihydroquinolin-2(1H)-one (60 mg) and acetic acid (2 mL) in the second step. 24 mg of 6-((4-((2,2-difluorobenzo[d][1,3]dioxol-5-yl)amino)-5-(trifluoromethyl)pyrimidin-2-yl) amino)-3,4-dihydroquinolin-2(1H)-one and 94 mg of 6-((2-((2,2-difluorobenzo[d][1,3]dioxol-5-yl)amino)-5-(trifluoromethyl)pyrimidin-4-yl)amino)-3,4-dihydroquinolin-2(1H)-one were recovered after automated reverse phase chromatography (water-MeCN eluent). MS calcd for $[C_{21}H_{14}F_5N_5O_3+H]^+$: 480.11, found 480.35.

Example 179

Preparation of N4-(2-methoxyethyl)-N2-(1H-pyrrolo[2,3-b]pyridin-5-yl)-5-(trifluoromethyl)pyrimidine-2,4-diamine

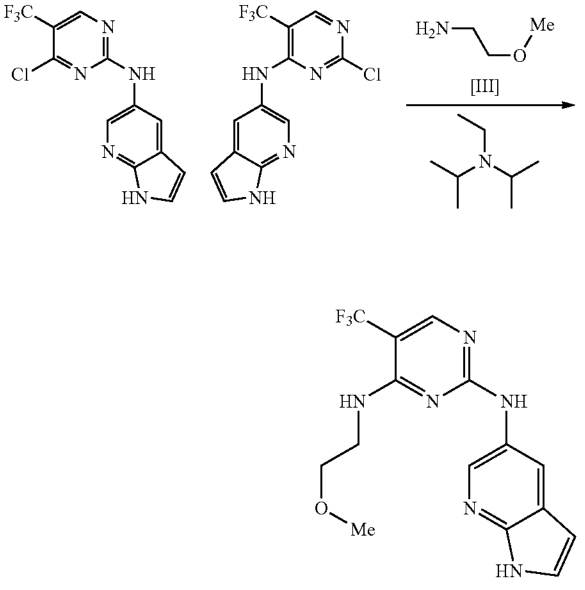

N-(4-chloro-5-(trifluoromethyl)pyrimidin-2-yl)-1H-pyrrolo[2,3-b]pyridin-5-amine (0.100 g, 0.319 mmol, contains 30% of the regioisomer), 2-methoxyethan-1-amine (24 mg) and N,N-diisopropylethylamine (0.111 mL) were mixed in DMF (2 mL). The mixture was microwaved at 100° C. for 10 minutes and then concentrated. 13 mg of N4-(2-methoxyethyl)-N2-(1H-pyrrolo[2,3-b]pyridin-5-yl)-5-(trifluoromethyl)pyrimidine-2,4-diamine was recovered after automated reverse phase chromatography (water-MeCN eluent). MS calcd for $[C_{15}H_{15}F_3N_6O+H]^+$: 353.14, found 353.25.

Example 180

Preparation of N4-(2-methoxyethyl)-N2-(1H-pyrrolo[2,3-b]pyridin-5-yl)-5-(trifluoromethyl)pyrimidine-2,4-diamine

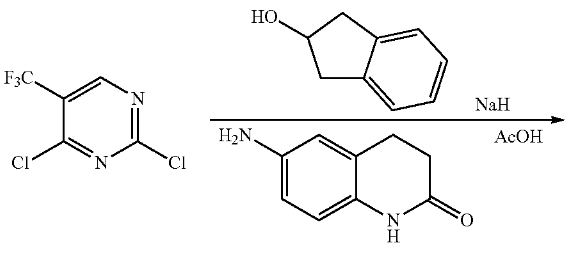

-continued

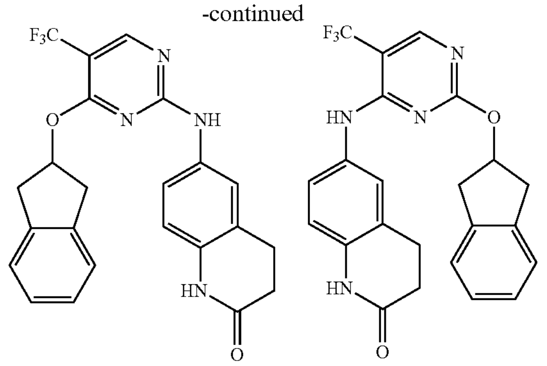

2,4-dichloro-5-(trifluoromethyl)pyrimidine (0.100 g, 0.461 mmol), 2,3-dihydro-1H-inden-2-ol (0.065 g, 0.484 mmol) and sodium hydride (0.028 g, 0.691 mmol) were mixed in acetonitrile (2 ml). The mixture was microwaved at 120° C. for 20 minutes. Concentrated and then added 6-amino-3,4-dihydroquinolin-2(1H)-one (0.075 g, 0.461 mmol) and acetic acid (0.527 ml, 9.22 mmol). The mixture was microwaved at 120° C. for 10 minutes and then concentrated. 15 mg of 6-((4-((2,3-dihydro-1H-inden-2-yl)oxy)-5-(trifluoromethyl)pyrimidin-2-yl)amino)-3,4-dihydroquinolin-2(1H)-one and 9 mg of 6-((2-((2,3-dihydro-1H-inden-2-yl)oxy)-5-(trifluoromethyl)pyrimidin-4-yl)amino)-3,4-dihydroquinolin-2(1H)-one were recovered after automated reverse phase chromatography (water-MeCN eluent). MS calcd for $[C_{23}H_{19}F_3N_4O_2+H]^+$: 441.16, found 441.15.

Example 181

Preparation of N4-phenyl-N2-(1H-pyrrolo[2,3-b]pyridin-5-yl)-5-(trifluoromethyl)pyrimidine-2,4-diamine and N4-(1H-pyrrolo[2,3-b]pyridin-5-yl)-5-(trifluoromethyl)pyrimidine-2,4-diamine

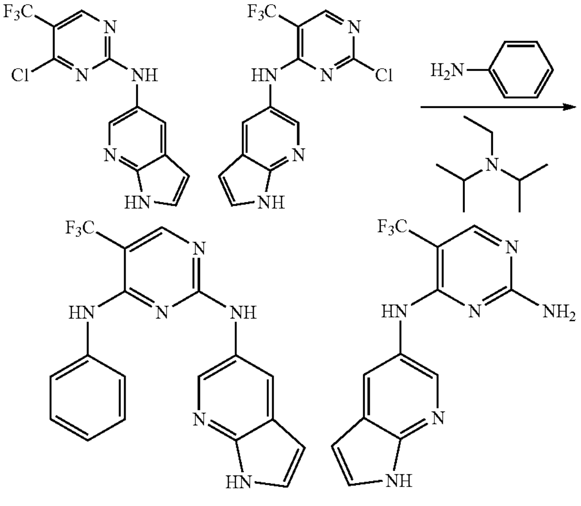

N-(4-chloro-5-(trifluoromethyl)pyrimidin-2-yl)-1H-pyrrolo[2,3-b]pyridin-5-amine (0.100 g, 0.319 mmol, contains 30% of the regioisomer), aniline (0.029 ml, 0.319 mmol) and N-ethyl-N-isopropylpropan-2-amine (0.111 ml, 0.638 mmol) were mixed in Acetonitrile (2 ml). The mixture was microwaved at 130° C. for 20 minutes and then concentrated. In order to degrade the unreacted minor starting material regioisomer, ammonia (455 mL, 7M in MeOH), was added and the mixture was microwaved at 120° C. for 20 minutes. 19 mg of N4-phenyl-N2-(1H-pyrrolo[2,3-b]pyridin-5-yl)-5-(trifluoromethyl)pyrimidine-2,4-diamine and 15 mg of N4-(1H-pyrrolo[2,3-b]pyridin-5-yl)-5-(trifluoromethyl)pyrimidine-2,4-diamine were recovered after automated reverse phase chromatography (water-MeCN eluent). MS calcd for $[C_{18}H_{13}F_3N_6+H]^+$: 371.13, found 371.10. MS calcd for $[C_{12}H_9F_3N_6+H]^+$: 295.09, found 294.85.

Example 182

Preparation of N4-methyl-N2-(1H-pyrrolo[2,3-b]pyridin-5-yl)-5-(trifluoromethyl)pyrimidine-2,4-diamine and N2-methyl-N4-(1H-pyrrolo[2,3-b]pyridin-5-yl)-5-(trifluoromethyl)pyrimidine-2,4-diamine

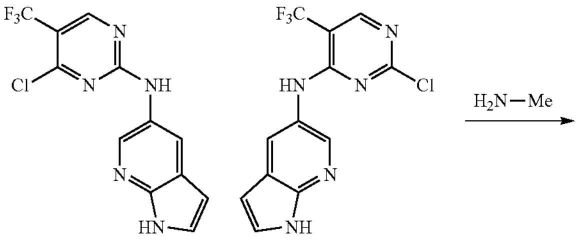

-continued

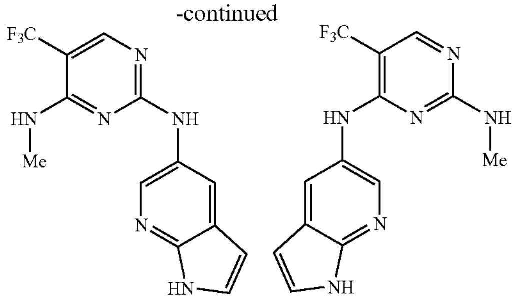

N-(4-chloro-5-(trifluoromethyl)pyrimidin-2-yl)-1H-pyrrolo[2,3-b]pyridin-5-amine (0.100 g, 0.319 mmol, contains 30% of the regioisomer) and methanamine (0.119 ml, 0.956 mmol) were mixed in DMF (2 mL). The mixture was microwaved at 100° C. for 20 minutes and then concentrated. 20 mg of N4-methyl-N2-(1H-pyrrolo[2,3-b]pyridin-5-yl)-5-(trifluoromethyl)pyrimidine-2,4-diamine and 11 mg of N2-methyl-N4-(1H-pyrrolo[2,3-b]pyridin-5-yl)-5-(trifluoromethyl)pyrimidine-2,4-diamine were recovered after automated reverse phase chromatography (water-MeCN eluent). MS calcd for $[C_{13}H_{11}F_3N_6+H]^+$: 309.11, found 308.95.

Example 183

Preparation of 6-((4-(2-methylaziridin-1-yl)-5-(trifluoromethyl)pyrimidin-2-yl)amino)-3,4-dihydroquinolin-2(1H)-one and 6-((4-((2-chloropropyl)amino)-5-(trifluoromethyl)pyrimidin-2-yl)amino)-3,4-dihydroquinolin-2(1H)-one and 6-((4-((1-chloropropan-2-yl)amino)-5-(trifluoromethyl)pyrimidin-2-yl)amino)-3,4-dihydroquinolin-2(1H)-one

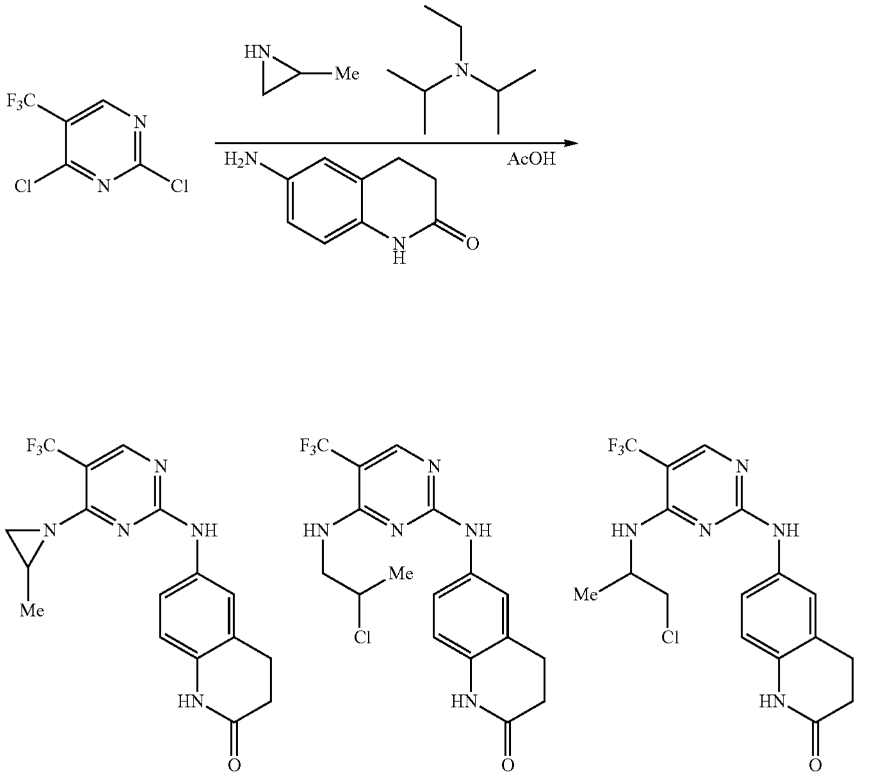

2,4-dichloro-5-(trifluoromethyl)pyrimidine (0.100 g, 0.461 mmol), 2-methylaziridine (0.033 ml, 0.461 mmol) and N-ethyl-N-isopropylpropan-2-amine (0.060 g, 0.461 mmol) were mixed in Acetonitrile (2 ml). The mixture was microwaved at 70° C. for 10 minutes. Concentrated and added 6-amino-3,4-dihydroquinolin-2(1H)-one (0.071 g, 0.438 mmol) and acetic acid (2 mL). The mixture was microwaved at 120° C. for 10 minutes and then concentrated. 16 mg of 6-((4-(2-methylaziridin-1-yl)-5-(trifluoromethyl)pyrimidin-2-yl)amino)-3,4-dihydroquinolin-2(1H)-one, 10 mg of 6-((4-((2-chloropropyl)amino)-5-(trifluoromethyl)pyrimidin-2-yl)amino)-3,4-dihydroquinolin-2(1H)-one and 12 mg of 6-((4-((1-chloropropan-2-yl)amino)-5-(trifluoromethyl)pyrimidin-2-yl)amino)-3,4-dihydroquinolin-2(1H)-one were recovered after automated reverse phase chromatography (water-MeCN eluent). MS calcd for $[C_{17}H_{16}F_3N_5O+H]^+$: 364.14, found 364.05. MS calcd for $[C_{17}H_{17}ClF_3N_5O+H]^+$: 400.12, found 400.10.

Example 184

Preparation of 6-((4-(methyl(phenyl)amino)-5-(trifluoromethyl)pyrimidin-2-yl)amino)-3,4-dihydroquinolin-2(1H)-one and 6-((2-(methyl(phenyl)amino)-5-(trifluoro methyl)pyrimidin-4-yl)amino)-3,4-dihydroquinolin-2(1H)-one

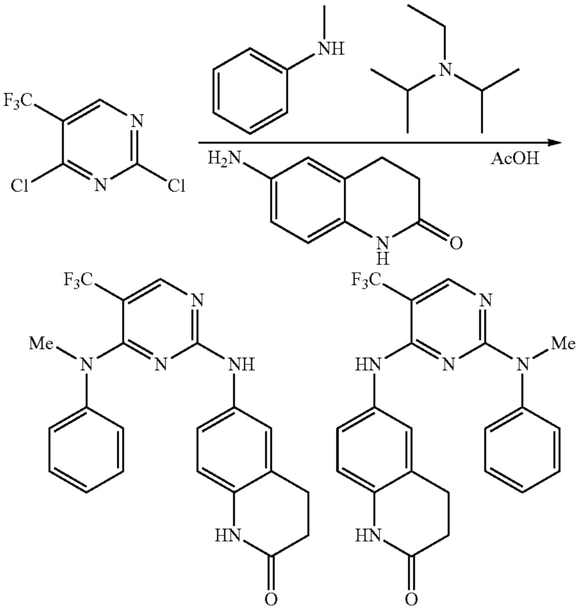

2,4-dichloro-5-(trifluoromethyl)pyrimidine (0.100 g, 0.461 mmol), N-methylaniline (0.050 ml, 0.461 mmol) and N-ethyl-N-isopropylpropan-2-amine (0.080 ml, 0.461 mmol) were mixed in Acetonitrile (2 ml). The mixture was microwaved at 90° C. for 10 minutes and then concentrated. Added 6-amino-3,4-dihydroquinolin-2(1H)-one (0.075 g, 0.461 mmol) and acetic acid (2 mL). The mixture was microwaved at 120° C. for 10 minutes and then concentrated. 48 mg of 6-((4-(methyl(phenyl)amino)-5-(trifluoromethyl)pyrimidin-2-yl)amino)-3,4-dihydro quinolin-2(1H)-one and 30 mg of 6-((2-(methyl(phenyl)amino)-5-(trifluoromethyl) pyrimidin-4-yl)amino)-3,4-dihydroquinolin-2(1H)-one were recovered after automated reverse phase chromatography (water-MeCN eluent). MS calcd for $[C_{21}H_{18}F_3N_5O+H]^+$: 414.16, found 414.35.

Example 185

Preparation of 6-((4-((1H-indazol-5-yl)amino)-5 (trifluoromethyl)pyrimidin-2-yl)amino)-3,4-dihydroquinolin-2(1H)-one

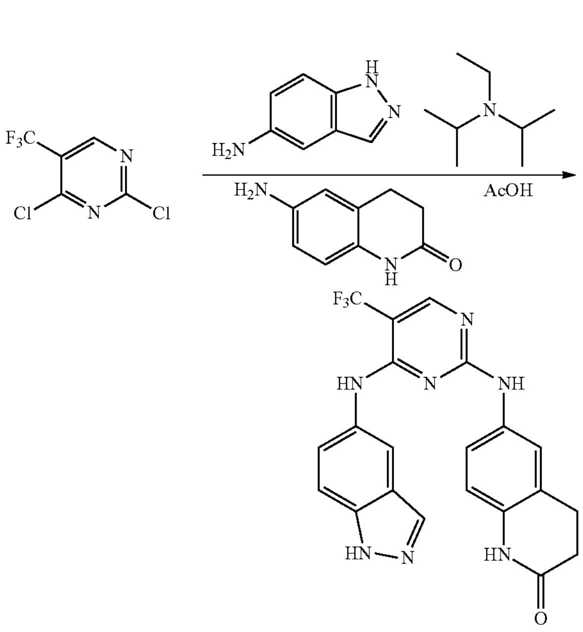

2,4-dichloro-5-(trifluoromethyl)pyrimidine (0.100 g, 0.461 mmol), 1H-indazol-5-amine (0.061 g, 0.461 mmol) and N-ethyl-N-isopropylpropan-2-amine (0.080 ml, 0.461 mmol) were mixed in Acetonitrile (2 ml). The mixture was microwaved at 90° C. for 10 minutes and then concentrated. 6-amino-3,4-dihydroquinolin-2(1H)-one (0.075 g, 0.461 mmol) and acetic acid (2 mL) were added. The mixture was microwaved at 120° C. for 10 minutes and then concentrated. 30 mg of 6-((4-(1H-indazol-5-yl)amino)-5-(trifluoromethyl)pyrimidin-2-yl)amino)-3,4-dihydroquinolin-2 (1H)-one was recovered after automated reverse phase chromatography (water-ethanol eluent). MS calcd for $[C_{21}H_{16}F_3N_7O+H]^+$: 440.15, found 440.20.

Example 186

Preparation of 5-bromo-N4-cyclopropyl-N2-(3,4,5-trimethoxyphenyl)pyrimidine-2,4-diamine

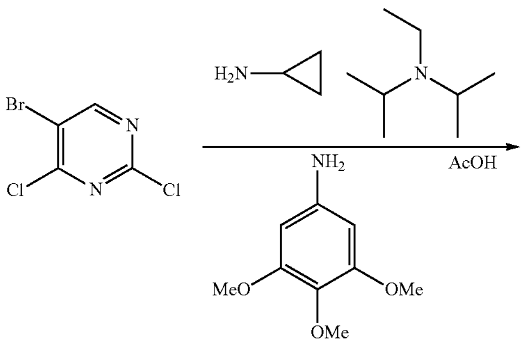

-continued

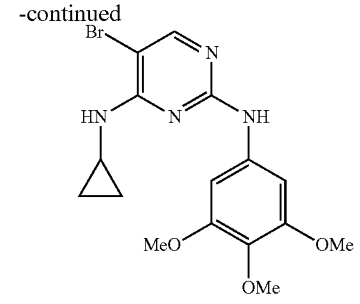

5-bromo-2,4-dichloropyrimidine (0.125 g, 0.549 mmol) and cyclopropanamine (0.038 ml, 0.549 mmol) were mixed in Acetonitrile (2 ml) at 5° C. After 2 min, added N-ethyl-N-isopropylpropan-2-amine (0.096 ml, 0.549 mmol) and warmed to 21° C. The mixture was microwaved at 70° C. for 10 minutes and then concentrated. 3,4,5-trimethoxyaniline (0.100 g, 0.549 mmol) and Acetic Acid (2 ml) were added. The mixture was microwaved at 100° C. for 10 minutes and then concentrated. Added acetone and filtered the solid to give 120 mg of 5-bromo-N4-cyclopropyl-N2-(3,4,5-trimethoxyphenyl)pyrimidine-2,4-diamine. MS calcd for $[C_{16}H_{19}BrN_4O_3+H]^+$: 395.07, found 394.90.

Example 187

Preparation of 5-bromo-N4-cyclopropyl-N2-(3,4,5-trimethoxyphenyl)pyrimidine-2,4-diamine

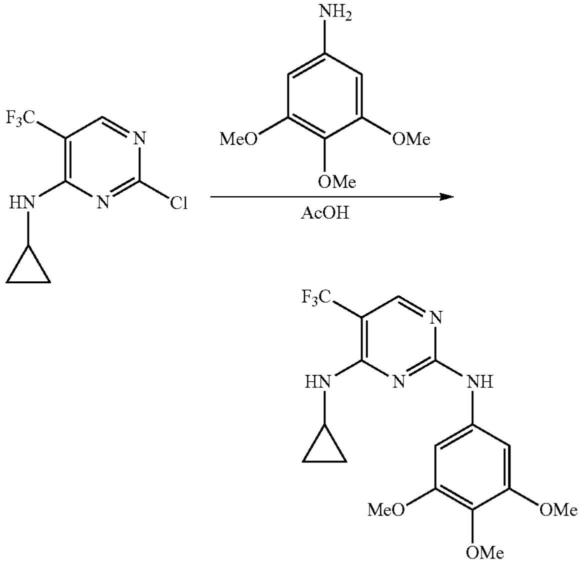

2-chloro-N-cyclopropyl-5-(trifluoromethyl)pyrimidin-4-amine (0.090 g, 0.379 mmol) and 3,4,5-trimethoxyaniline (0.069 g, 0.379 mmol) were mixed in Acetic Acid (2 ml). The mixture was microwaved at 100° C. for 10 minutes and then concentrated. Added acetone and filtered the white solid to give 80 mg of 5-bromo-N4-cyclopropyl-N2-(3,4,5-trimethoxyphenyl)pyrimidine-2,4-diamine. MS calcd for $[C_{17}H_{19}F_3N_4O_3+H]^+$: 385.15, found 385.40.

Example 188

Preparation of N2-(1H-benzo[d][1,2,3]triazol-6-yl)-N4-cyclopropyl-5-(trifluoromethyl)pyrimidine-2,4-diamine

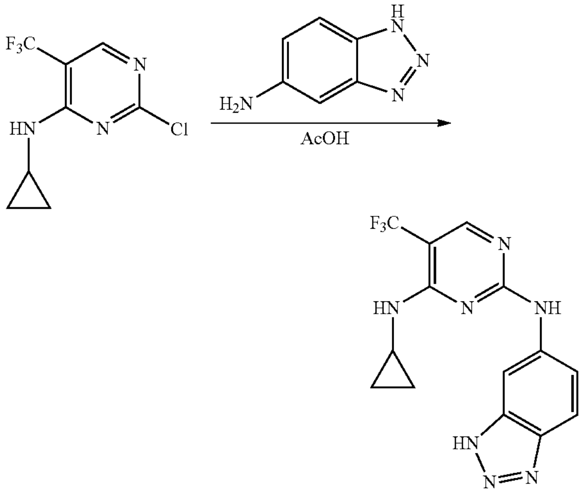

2-chloro-N-cyclopropyl-5-(trifluoromethyl)pyrimidin-4-amine (0.090 g, 0.379 mmol) and 1H-benzo[d][1,2,3]triazol-5-amine (0.051 g, 0.379 mmol) were mixed in Acetic Acid (2 ml). The mixture was microwaved at 110° C. for 10 minutes and then concentrated. Added acetone and filtered the white solid to give 97 mg of N2-(1H-benzo[d][1,2,3]triazol-6-yl)-N4-cyclopropyl-5-(trifluoromethyl)pyrimidine-2,4-diamine. MS calcd for $[C_{14}H_{12}F_3N_7+H]^+$: 336.12, found 336.20.

Example 189

Preparation of 4-(cyclopropylamino)-5-(trifluoromethyl)pyrimidin-2-ol

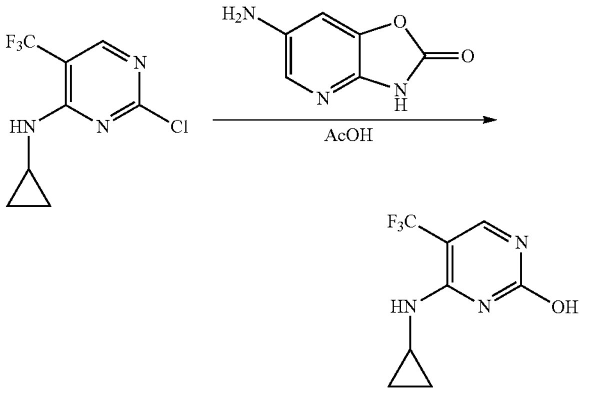

2-chloro-N-cyclopropyl-5-(trifluoromethyl)pyrimidin-4-amine (0.099 g, 0.417 mmol) and 6-aminooxazolo[4,5-b]pyridin-2(3H)-one (0.063 g, 0.417 mmol) were mixed in Acetic Acid (2 ml). The mixture was microwaved at 120° C. for 10 minutes and then concentrated. The desired product did not form. 4-(cyclopropylamino)-5-(trifluoromethyl)pyrimidin-2-ol was recovered after automated reverse phase chromatography (water-MeCN eluent). MS calcd for $[C_8H_8F_3N_3O+H]^+$: 220.07, found 219.85.

Example 190

Preparation of N4-cyclopropyl-N2-(3,4-dihydro-2H-benzo[b][1,4]dioxepin-7-yl)-5-(trifluoromethyl)pyrimidine-2,4-diamine

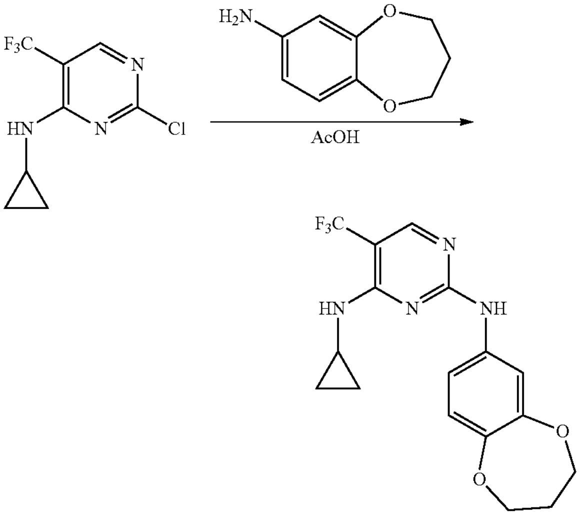

2-chloro-N-cyclopropyl-5-(trifluoromethyl)pyrimidin-4-amine (0.080 g, 0.337 mmol) and 3,4-dihydro-2H-benzo[b][1,4]dioxepin-7-amine (0.056 g, 0.337 mmol) were mixed in Acetic Acid (2 ml). The mixture was microwaved at 110° C. for 10 minutes and then concentrated. The product was recovered after automated reverse phase chromatography (water-MeCN eluent). MS calcd for $[C_{17}H_{17}F_3N_4O_2+H]^+$: 367.14, found 367.30.

Example 191

Preparation of 6-aminooxazolo[4,5-b]pyridin-2(3H)-one

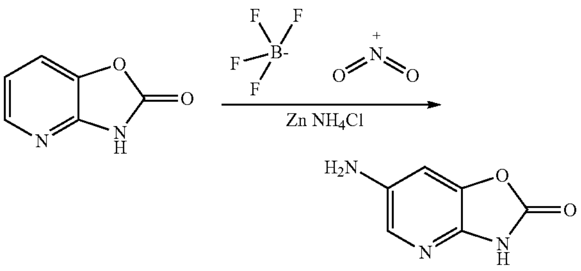

Oxazolo[4,5-b]pyridin-2(3H)-one (1.0 g, 7.35 mmol) and nitronium tetrafluoroborate (1.464 g, 11.02 mmol) were mixed in sulfolane (4 ml). Heated to 100° C. for 14 h. The crude mixture was flushed through a short silica column with a 50:40:10 DCM/EtOAc/MeOH solvent mixture. The product was concentrated, with sulfolane still remaining. Then zinc (1.083 g, 16.56 mmol) and ammonium chloride (1.184 g, 16.56 mmol) were added. Filtered through Celite with EtOAc and MeOH (1:1), then concentrated. The product was recovered after automated reverse phase chromatography (water-MeCN eluent). Sulfolane coelutes and so a yield calculation was not possible. The material was used as-is. Due to poor ionization, the product mass could not be observed by LCMS.

Example 192

Preparation of 6-((5-bromo-2-((2,3-dihydrobenzo[b][1,4]dioxin-6-yl)amino)pyrimidin-4-yl)amino)oxazolo[4,5-b]pyridin-2(3H)-one

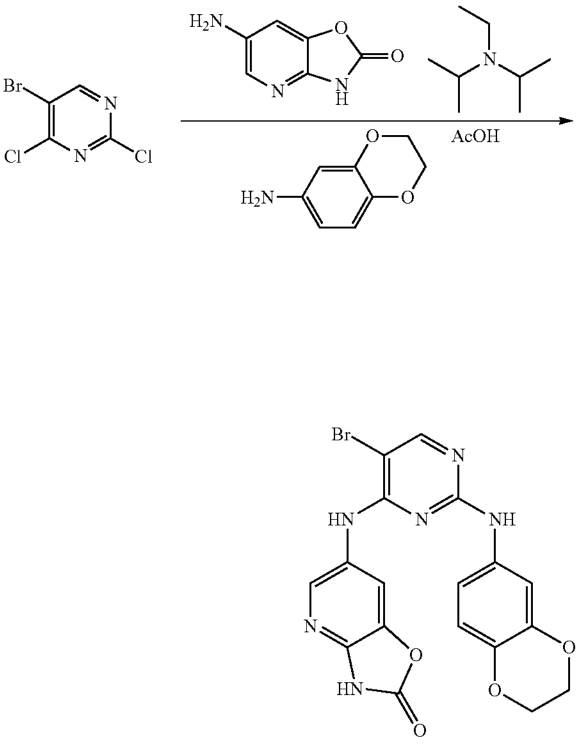

5-Bromo-2,4-dichloropyrimidine (0.040 g, 0.176 mmol), 6-aminooxazolo[4,5-b]pyridin-2(3H)-one (0.027 g, 0.176 mmol) and N-ethyl-N-isopropylpropan-2-amine (0.031 ml, 0.176 mmol) were mixed in sulfolane (2 ml). The mixture was microwaved at 100° C. for 10 minutes. Then 2,3-dihydrobenzo[b][1,4]dioxin-6-amine (0.022 ml, 0.176 mmol) and acetic acid (1 mL) were added. The mixture was microwaved at 120° C. for 10 minutes and then concentrated (sulfolane remains). 12 mg of product was recovered after automated reverse phase chromatography (water-MeCN eluent). MS calcd for $[C_{18}H_{13}BrN_6O_4+H]^+$: 457.03, found 456.90.

Example 193

Preparation of 6-((4-(oxetan-3-ylamino)-5-(trifluoromethyl)pyrimidin-2-yl)amino)-3,4-dihydroquinolin-2(1H)-one

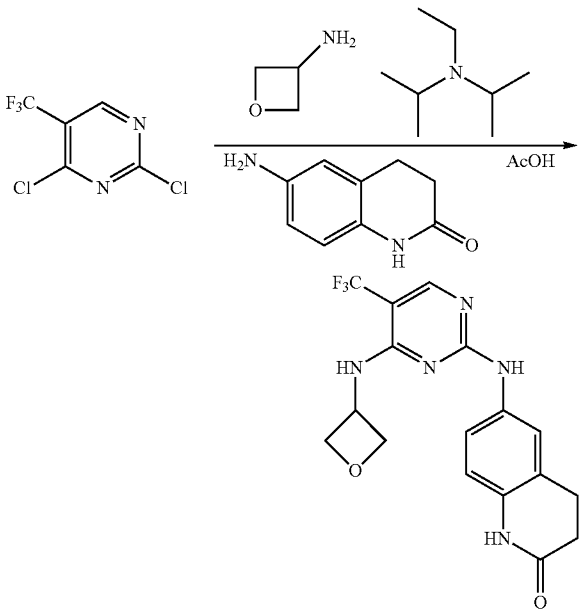

2,4-dichloro-5-(trifluoromethyl)pyrimidine (0.090 g, 0.415 mmol), oxetan-3-amine (0.030 g, 0.415 mmol) and N-ethyl-N-isopropylpropan-2-amine (0.072 ml, 0.415 mmol) were mixed in Acetonitrile (1 ml). The mixture was microwaved at 70° C. for 10 minutes and then concentrated. 6-amino-3,4-dihydroquinolin-2(1H)-one (0.067 g, 0.415 mmol) and acetic acid (2 mL) were added. The mixture was microwaved at 100° C. for 10 minutes and then concentrated. 14 mg of product was recovered after automated reverse phase chromatography (water-MeCN eluent). MS calcd for $[C_{17}H_{16}F_3N_5O_2+H]^+$: 380.14, found 379.90.

Example 194

Preparation of N4-(oxetan-3-yl)-N2-(1H-pyrrolo[2,3-b]pyridin-5-yl)-5-(trifluoromethyl)pyrimidine-2,4-diamine

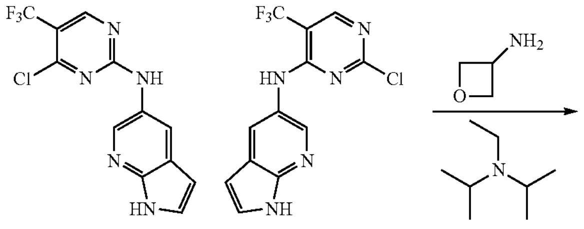

-continued

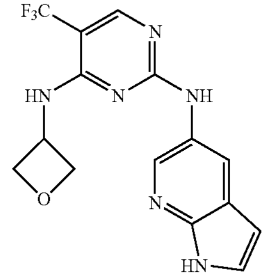

N-(4-chloro-5-(trifluoromethyl)pyrimidin-2-yl)-1H-pyrrolo[2,3-b]pyridin-5-amine (0.100 g, 0.319 mmol, contains 30% of the regioisomer), oxetan-3-amine (0.016 g, 0.223 mmol) and N-ethyl-N-isopropylpropan-2-amine (0.039 ml, 0.223 mmol) were mixed in DMF (1 ml). The mixture was microwaved at 100° C. for 10 minutes and then concentrated. 13 mg of product was recovered after automated reverse phase chromatography (water-MeCN eluent). MS calcd for $[C_{15}H_{13}F_3N_6O+H]^+$: 351.12, found 350.95.

Example 195

Preparation of N4-cyclopropyl-N2-(1H-indazol-5-yl)-5-(trifluoromethyl) pyrimidine-2,4-diamine

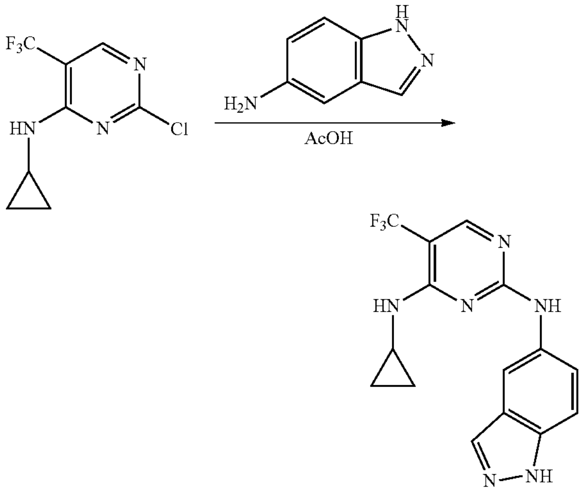

2-Chloro-N-cyclopropyl-5-(trifluoromethyl)pyrimidin-4-amine (0.080 g, 0.337 mmol) and 1H-indazol-5-amine (0.045 g, 0.337 mmol) were mixed in Acetic Acid (1 ml). The mixture was microwaved at 110° C. for 10 minutes and then concentrated. Added acetone and filtered solid to give 70 mg of product. MS calcd for $[C_{15}H_{13}F_3N_6+H]^+$: 335.13, found 335.15.

Example 196

Preparation of N4-cyclopropyl-N2-(pyridin-3-yl)-5-(trifluoromethyl) pyrimidine-2,4-diamine

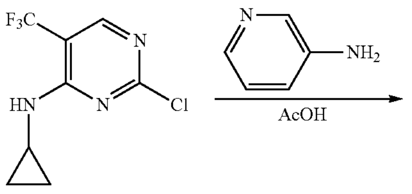

-continued

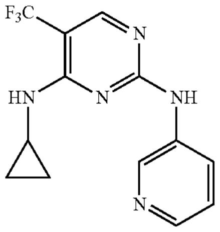

2-Chloro-N-cyclopropyl-5-(trifluoromethyl)pyrimidin-4-amine (0.080 g, 0.337 mmol) and pyridin-3-amine (0.032 g, 0.337 mmol) were mixed in Acetic Acid (1 ml). The mixture was microwaved at 110° C. for 10 minutes and then concentrated. 27 mg of product was recovered after automated reverse phase chromatography (water-MeCN eluent). MS calcd for $[C_{13}H_{12}F_3N_5+H]^+$: 296.11, found 295.95.

Example 197

Preparation of 6-((4-((2-hydroxyethyl)amino)-5-(trifluoromethyl)pyrimidin-2-yl)amino)-3,4-dihydroquinolin-2(1H)-one

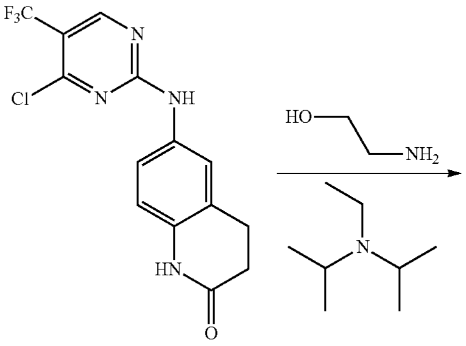

-continued

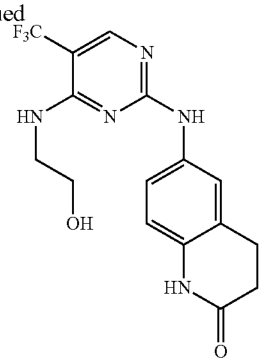

6-((4-chloro-5-(trifluoromethyl)pyrimidin-2-yl)amino)-3,4-dihydroquinolin-2(1H)-one (0.070 g, 0.204 mmol), 2-aminoethan-1-ol (0.012 g, 0.204 mmol) and N-ethyl-N-isopropylpropan-2-amine (0.036 ml, 0.204 mmol) were mixed in Acetonitrile (1 ml). The mixture was microwaved at 100° C. for 10 minutes and then concentrated. Added acetone and filtered solid to give 53 mg of product. MS calcd for $[C_{16}H_{16}F_3N_5O_2+H]^+$: 368.14, found 368.10.

Example 198

Preparation of 6-((4-(azetidin-3-ylamino)-5-(trifluoromethyl)pyrimidin-2-yl)amino)-3,4-dihydroquinolin-2(1H)-one and 6-((4-(3-((2-((2-oxo-1,2,3,4-tetrahydroquinolin-6-yl)amino)-5-(trifluoromethyl)pyrimidin-4-yl)amino)azetidin-1-yl)-5-(trifluoromethyl)pyrimidin-2-yl)amino)-3,4-dihydroquinolin-2(1H)-one

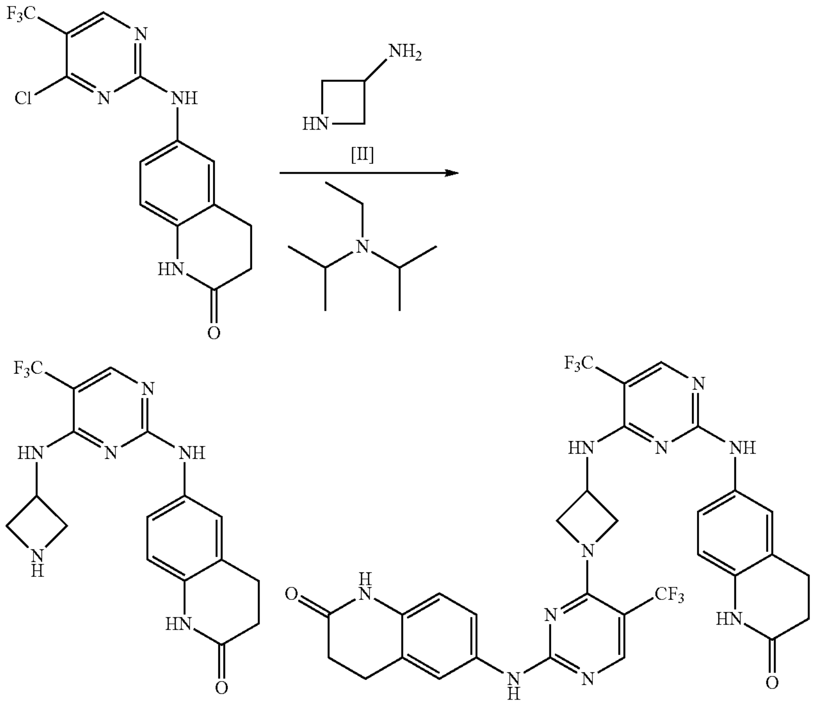

6-((4-Chloro-5-(trifluoromethyl)pyrimidin-2-yl)amino)-3,4--dihydroquinolin-2(1H)-one (0.070 g, 0.204 mmol), azetidin-3-amine.2HCl (0.030 g, 0.204 mmol) and N-ethyl-N-isopropyl propan-2-amine (0.107 ml, 0.613 mmol) were mixed in DMF (1 ml). The mixture was microwaved at 90° C. for 30 minutes, then concentrated. Added water and MeCN and filtered the solid (side product) and washed with methanol and acetone to give 41 mg of 6-((4-(3-((2-((2-oxo-1,2,3,4-tetrahydroquinolin-6-yl)amino)-5-(trifluoromethyl) pyrimidin-4-yl)amino)azetidin-1-yl)-5-(trifluoromethyl)pyrimidin-2-yl)amino)-3,4-dihydroquinolin-2(1H)-one. 30 mg of 6-((4-(azetidin-3-ylamino)-5-(trifluoromethyl)pyrimidin-2-yl)amino)-3,4-dihydroquinolin-2(1H)-one was recovered after automated reverse phase chromatography (water-MeCN eluent). MS calcd for $[C_{17}H_{17}F_3N_6O+H]^+$: 379.15, found 379.05. MS calcd for $[C_{31}H_{26}F_6N_{10}O_2+H]^+$: 685.22, found 685.40.

Example 199

Preparation of 6-((4-(2-ethylhydrazinyl)-5-(trifluoromethyl)pyrimidin-2-yl)amino)-3,4-dihydroquinolin-2(1H)-one

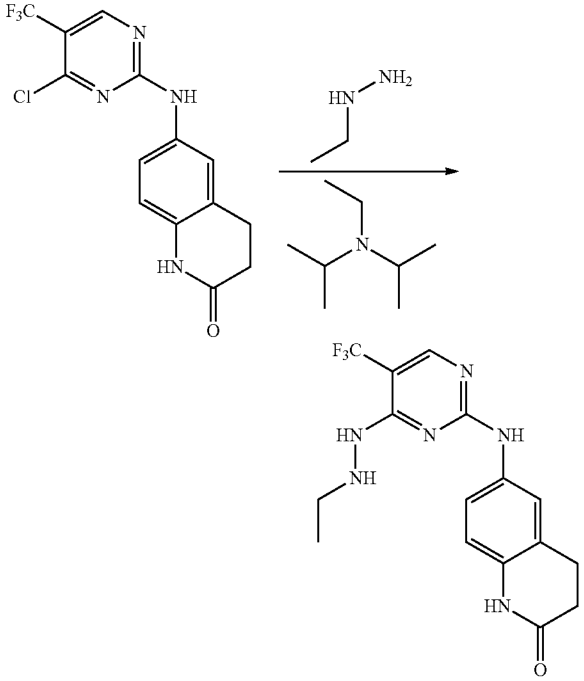

6-((4-Chloro-5-(trifluoromethyl)pyrimidin-2-yl)amino)-3,4-dihydroquinolin-2(1H)-one (0.070 g, 0.204 mmol), ethylhydrazine.oxalic acid (0.031 g, 0.204 mmol) and N-ethyl-N-isopropylpropan-2-amine (0.107 ml, 0.613 mmol) were mixed in Acetonitrile (1 ml). The mixture was microwaved at 100° C. for 10 minutes and then concentrated. Added acetone and filtered solid to give 61 mg of product. MS calcd for $[C_{16}H_{17}F_3N_6O+H]^+$: 367.15, found 367.30.

Example 200

Preparation of 6-((4-(2-ethylhydrazinyl)-5-(trifluoromethyl)pyrimidin-2-yl)amino)-3,4-dihydroquinolin-2(1H)-one

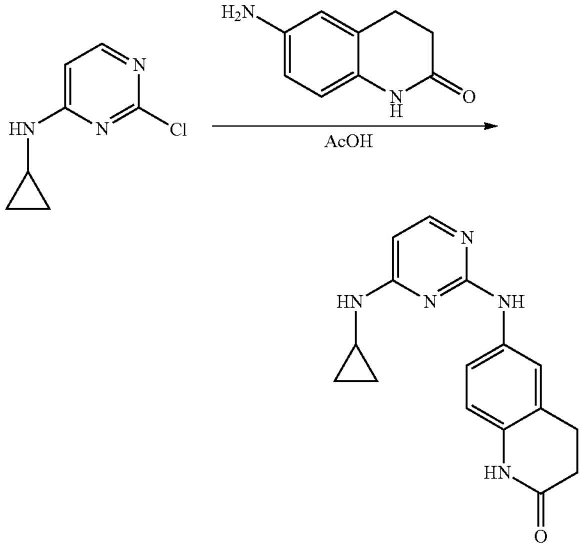

2-Chloro-N-cyclopropylpyrimidin-4-amine (0.060 g, 0.354 mmol) and 6-amino-3,4-dihydroquinolin-2(1H)-one (0.057 g, 0.354 mmol) were mixed in Acetic Acid (1 ml). The mixture was microwaved at 110° C. for 10 minutes and then concentrated. 85 mg of product was recovered after automated reverse phase chromatography (water-MeCN eluent). MS calcd for $[C_{16}H_{17}N_5O+H]^+$: 296.15, found 296.00.

Example 201

Preparation of 2-((2((1H-pyrrolo[2,3-b]pyridin-5-yl) amino)-5-(trifluoro methyl) pyrimidin-4-yl)amino)-N-methylbenzamide

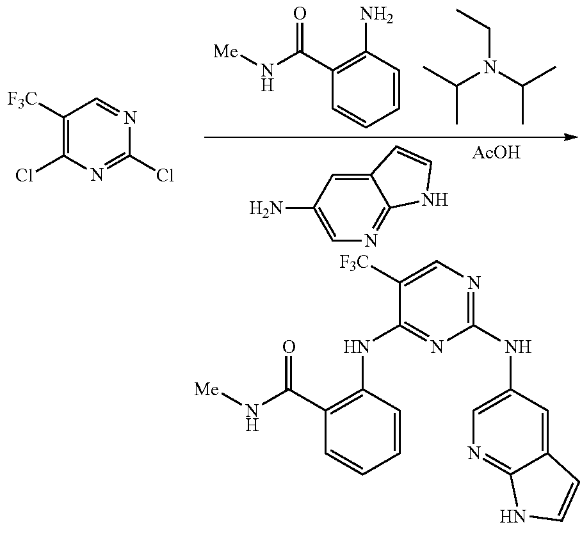

2,4-Dichloro-5-(trifluoromethyl)pyrimidine (0.085 g, 0.392 mmol), 2-amino-N-methylbenzamide (0.059 g, 0.392 mmol) and N-ethyl-N-isopropylpropan-2-amine (0.068 ml, 0.392 mmol) were mixed in Acetonitrile (1 ml). The mixture was microwaved at 90° C. for 10 minutes and then concentrated. 1H-pyrrolo[2,3-b]pyridin-5-amine (0.052 g, 0.392 mmol) and acetic acid (0.024 g, 0.392 mmol) were added. The mixture was microwaved at 110° C. for 10 minutes and then concentrated. Added methanol and filtered the solid, then washed with THF. 34 mg of product was isolated. MS calcd for $[C_{20}H_{16}F_3N_7O+H]^+$: 428.15, found 428.15.

Example 202

Preparation of 6-((4-(cyclopropyl(methyl)amino)-5-(trifluoromethyl) pyrimidin-2-yl)amino)-3,4-dihydroquinolin-2(1H)-one

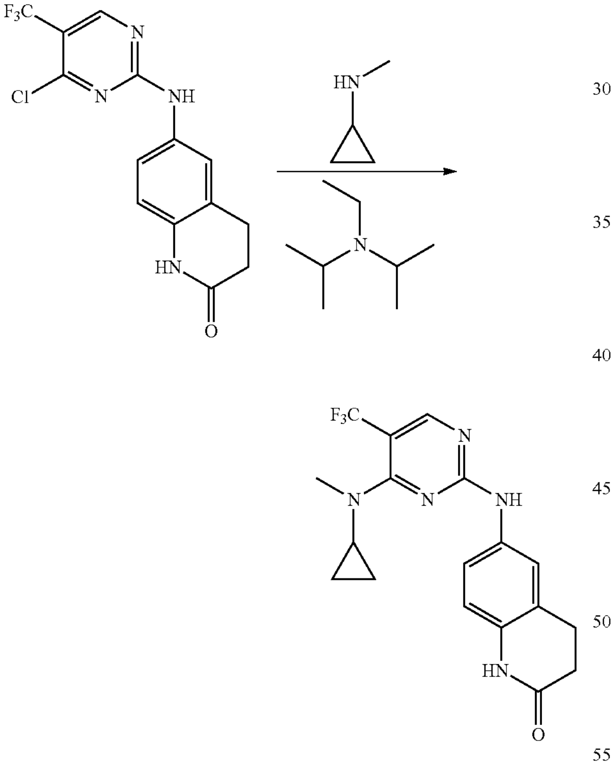

6-((4-Chloro-5-(trifluoromethyl)pyrimidin-2-yl)amino)-3,4-dihydroquinolin-2(1H)-one (0.075 g, 0.219 mmol), N-methylcyclopropanamine.HCl (0.024 g, 0.219 mmol) and N-ethyl-N-isopropylpropan-2-amine (0.076 ml, 0.438 mmol) were mixed in Acetonitrile (1 ml). The mixture was microwaved at 90° C. for 10 minutes and then concentrated. Added EtOAc and filtered the solid. MS calcd for $[C_{18}H_{18}F_3N_5O+H]^+$: 378.16, found 378.30.

Example 203

Preparation of N4-cyclopropyl-N2-(pyrimidin-5-yl)-5-(trifluoromethyl) pyrimidine-2,4-diamine

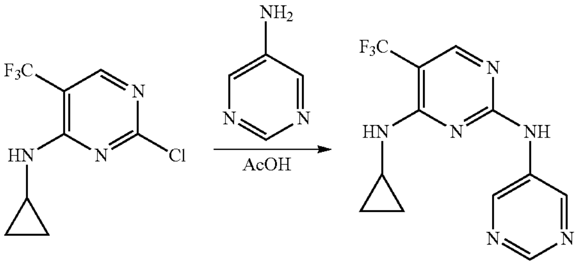 [SMILES: "AcOH" ; FC(F)(F)c1cnc(Cl)nc1NC1CC1 ; Nc1cncnc1 ; FC(F)(F)c1cnc(Nc2cncnc2)nc1NC1CC1]

2-Chloro-N-cyclopropyl-5-(trifluoromethyl)pyrimidin-4-amine (0.070 g, 0.295 mmol) and pyrimidin-5-amine (0.028 g, 0.295 mmol) were mixed in Acetic Acid (1 ml). The mixture was microwaved at 120° C. for 10 minutes and then concentrated. 3 mg of product was recovered after automated reverse phase chromatography (water-MeCN eluent). MS calcd for $[C_{12}H_{11}F_3N_6+H]^+$: 297.11, found 296.90.

Example 204

Preparation of N4-cyclopropyl-N2-(1H-pyrrolo[2,3-b]pyridin-5-yl)pyrimidine-2,4-diamine

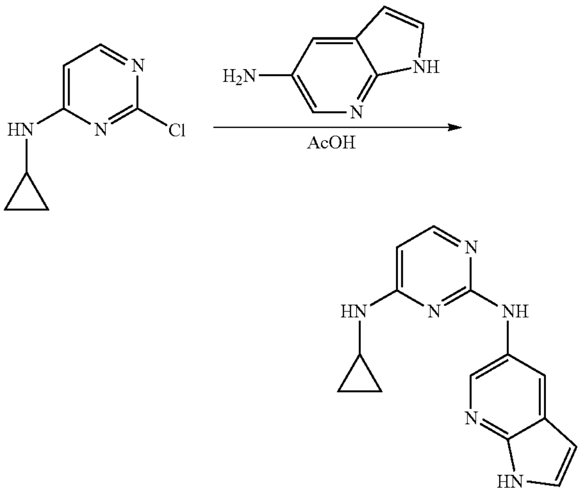

2-Chloro-N-cyclopropylpyrimidin-4-amine (0.070 g, 0.413 mmol) and 1H -pyrrolo[2,3-b]pyridin-5-amine (0.055 g, 0.413 mmol) were mixed in Acetic Acid (1 ml). The mixture was microwaved at 120° C. for 10 minutes and then concentrated. 18 mg of product was recovered after automated reverse phase chromatography (water-MeCN eluent). MS calcd for $[C_{14}H_{14}N_6+H]^+$: 267.14, found 266.80.

Example 205

Preparation of N4-cyclopropyl-N2-(pyrazin-2-yl)-5-(trifluoromethyl) pyrimidine-2,4-diamine

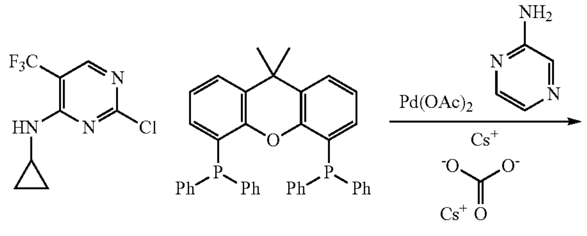

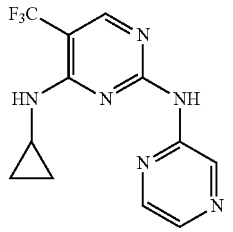

Flame dried the flask; also bubbled nitrogen through reagents and solvents prior to heating. 2-Chloro-N-cyclopropyl-5-(trifluoromethyl)pyrimidin-4-amine (0.075 g, Example 206

Preparation of N4-cyclopropyl-N2-(1H-indol-5-yl)-5-(trifluoromethyl) pyrimidine-2,4-diamine

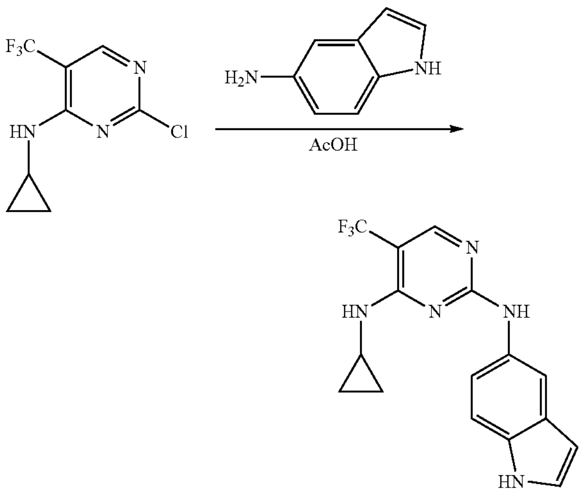

2-chloro-N-cyclopropyl-5-(trifluoromethyl)pyrimidin-4-amine (0.070 g, 0.295 mmol), 1H-indol-5-amine (0.039 g, 0.295 mmol) and acetic acid (0.017 ml, 0.295 mmol) were mixed in Acetic Acid (1 ml). The mixture was microwaved at 110° C. for 10 minutes and then concentrated to give 72 mg of product. MS calcd for $[C_{16}H_{14}F_3N_5+H]^+$: 334.13, found 334.15.

Example 207

Preparation of N2-(2-aminopyridin-3-yl)-N4-cyclopropyl-5-(trifluoromethyl)pyrimidine-2,4-diamine

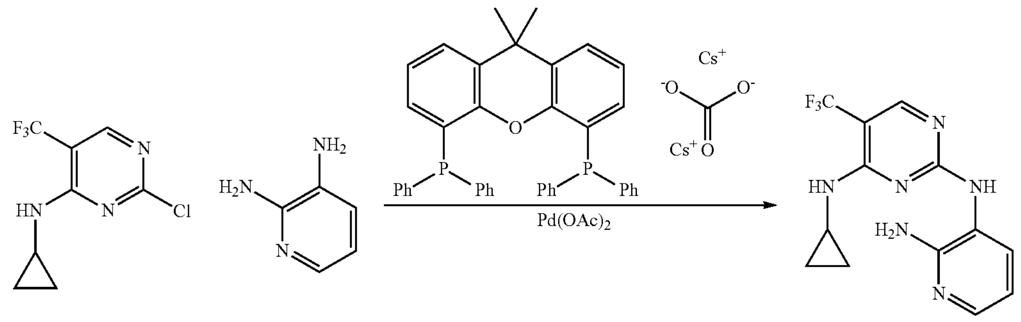

0.316 mmol), (9,9-dimethyl-9H-xanthene-4,5-diyl)bis(diphenylphosphane) (0.018 g, 0.032 mmol), diacetoxypalladium (3.54 mg, 0.016 mmol), pyrazin-2-amine (0.030 g, 0.316 mmol) and CESIUM CARBONATE (0.206 g, 0.631 mmol) were mixed in 1,4-Dioxane (1 ml). The mixture was microwaved at 160° C. for 40 minutes. Filtered through celite with methanol. Concentrated. Added 2:1 water/MeCN and filtered the solid. Once again added MeCN to the solid and filtered the resulting solid to give 33 mg of product. MS calcd for $[C_{12}H_{11}F_3N_6+H]^+$: 297.11, found 296.95.

Flame dried the flask; also bubbled nitrogen through reagents and solvents prior to heating. 2-Chloro-N-cyclopropyl-5-(trifluoromethyl)pyrimidin-4-amine (0.075 g, 0.316 mmol), pyridine-2,3-diamine (0.034 g, 0.316 mmol), (9,9-dimethyl-9H-xanthene-4,5-diyl)bis(diphenylphosphane) (0.018 g, 0.032 mmol), CESIUM CARBONATE (0.206 g, 0.631 mmol) and diacetoxypalladium (3.54 mg, 0.016 mmol) were mixed in 1,4-Dioxane (1 ml). The mixture was microwaved at 140° C. for 20 minutes. Filtered through Celite with MeOH and then concentrated. Added MeCN to crude and filtered solid. 19 mg of product was recovered after automated reverse phase chromatography (water-MeCN eluent). MS calcd for $[C_{13}H_{13}F_3N_6+H]^+$: 311.13, found 310.80.

Example 208

Preparation of N2-(benzo[d]oxazol-6-yl)-N4-cyclopropyl-5-(trifluoromethyl) pyrimidine-2,4-diamine and 6-((4-(cyclopropylamino)-5-(trifluoromethyl) pyrimidin-2-yl) amino)-2,3-dihydrobenzo[d]oxazol-2-ol

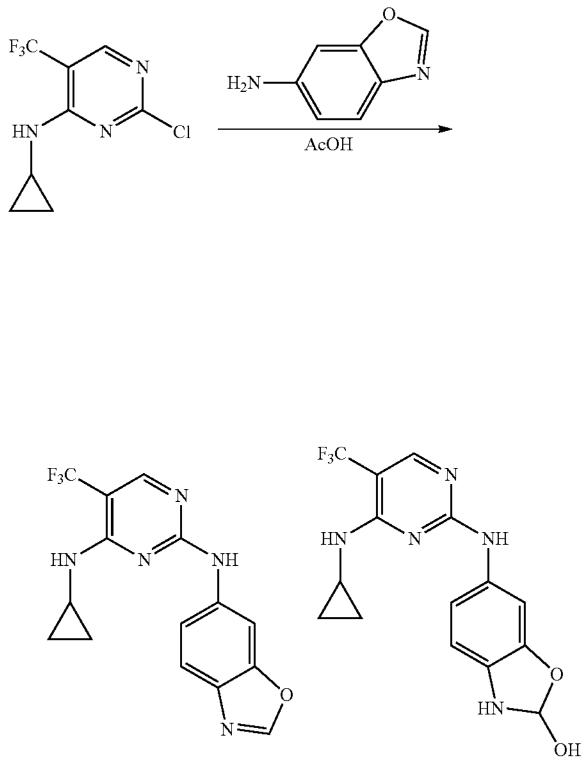

2-Chloro-N-cyclopropyl-5-(trifluoromethyl)pyrimidin-4-amine (0.065 g, 0.274 mmol) and benzo[d]oxazol-6-amine (0.037 g, 0.274 mmol) were mixed in Acetic Acid (1 ml). The mixture was microwaved at 130° C. for 20 minutes and then concentrated. Added acetone and filtered the solid. 4 mg of N2-(benzo[d]oxazol-6-yl)-N4-cyclopropyl-5-(trifluoromethyl)pyrimidine-2,4-diamine and 14 mg of 6-((4-(cyclopropylamino)-5-(trifluoromethyl)pyrimidin-2-yl)amino)-2,3-dihydrobenzo[d]oxazol-2-ol were recovered after automated reverse phase chromatography (water-MeCN eluent) on the filtrate. MS calcd for $[C_{15}H_{12}F_3N_5O+H]^+$: 336.11, found 335.95. MS calcd for $[C_{15}H_{14}F_3N_5O_2+H]^+$: 354.12, found 353.90.

Example 209

Preparation of 6-((4-amino-5-(trifluoromethyl)pyrimidin-2-yl)amino)-3,4-dihydroquinolin-2(1H)-one

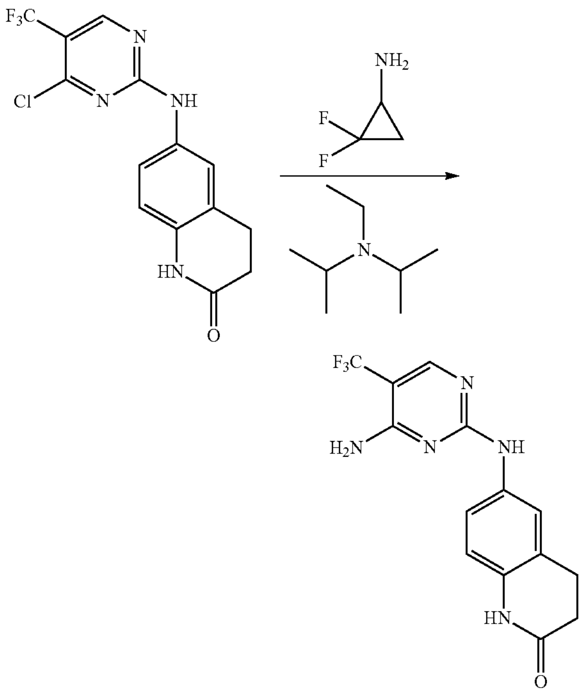

6-((4-Chloro-5-(trifluoromethyl)pyrimidin-2-yl)amino)-3,4-dihydroquinolin-2(1H)-one (0.070 g, 0.204 mmol), 2,2-difluorocyclopropan-1-amine.HCl (0.026 g, 0.204 mmol) and N-ethyl-N-isopropylpropan-2-amine (0.036 ml, 0.204 mmol) were mixed in Acetonitrile (1 ml). The mixture was microwaved at 100° C. for 10 minutes. Added 10% Pd—C (~20 mg) and the mixture was microwaved at 140° C. for 20 minutes. Added MeOH and filtered the solid. 12 mg of the side product was recovered after automated reverse phase chromatography (water-MeOH eluent). MS calcd for $[C_{14}H_{12}F_3N_5O+H]^+$: 324.11, found 323.80.

Example 210

Preparation of N2-(4-aminopyridin-3-yl)-N4-cyclopropyl-5-(trifluoromethyl) pyrimidine-2,4-diamine

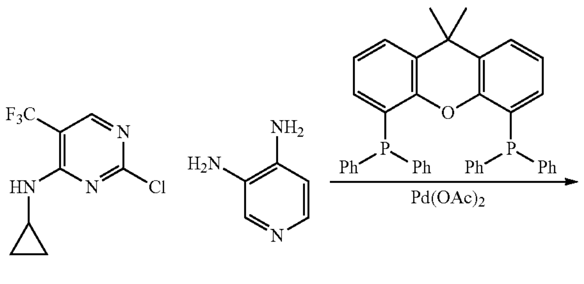

-continued

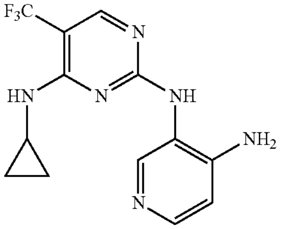

Flame dried flask. Bubbled nitrogen through reagents and solvents prior to heating. 2-chloro-N-cyclopropyl-5-(trifluoromethyl)pyrimidin-4-amine (0.070 g, 0.295 mmol), pyridine-3,4-diamine (0.032 g, 0.295 mmol), (9,9-dimethyl-9H-xanthene-4,5-diyl)bis(diphenylphosphane) (0.017 g, 0.029 mmol) and diacetoxypalladium (3.31 mg, 0.015 mmol) were mixed in 1,4-Dioxane (1 ml). The mixture was microwaved at 140° C. for 20 minutes. Filtered through Celite with MeOH and then concentrated. 16 mg of product was recovered after automated reverse phase chromatography (water-MeCN eluent). MS calcd for $[C_{13}H_{13}F_3N_6+H]^+$: 311.13, found 310.90.

Example 211

Preparation of N2-(1H-benzo[d]imidazol-6-yl)-N4-cyclopropyl-5-(trifluoromethyl)pyrimidine-2,4-diamine

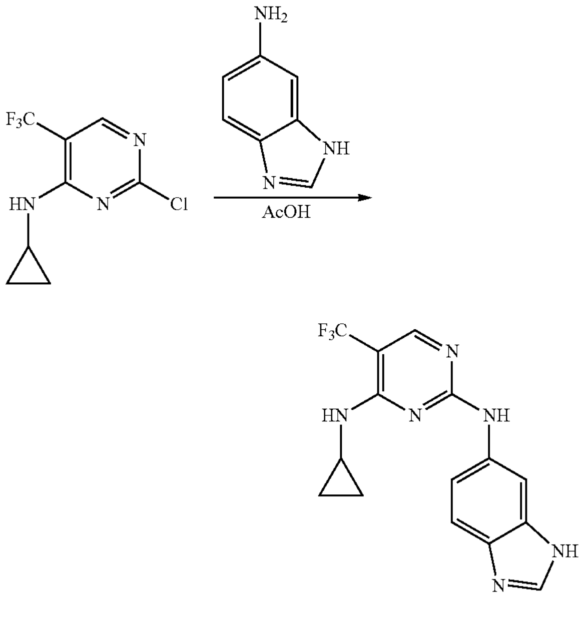

2-Chloro-N-cyclopropyl-5-(trifluoromethyl)pyrimidin-4-amine (0.065 g, 0.274 mmol) and 1H-benzo[d]imidazol-6-amine (0.036 g, 0.274 mmol) were mixed in Acetic Acid (1 ml). The mixture was microwaved at 130° C. for 20 minutes and then concentrated. 41 mg of product was recovered after automated reverse phase chromatography (water-MeOH eluent). MS calcd for $[C_{15}H_{13}F_3N_6+H]^+$: 335.13, found 335.00.

Example 212

Preparation of 6-((4-(bis(2-hydroxyethyl)amino)-5-(trifluoromethyl) pyrimidin-2-yl)amino)-3,4-dihydroquinolin-2(1H)-one and 6-((4-(2-((2-hydroxyethyl)amino)ethoxy)-5-(trifluoromethyl)pyrimidin-2-yl)amino)-3,4-dihydroquinolin-2(1H)-one

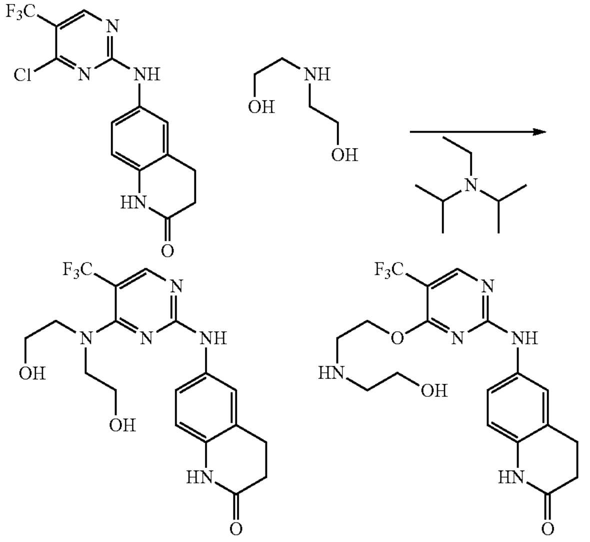

6-((4-Chloro-5-(trifluoromethyl)pyrimidin-2-yl)amino)-3,4-dihydroquinolin -2(1H)-one (0.070 g, 0.204 mmol), 2,2'-azanediylbis(ethan-1-ol) (0.020 ml, 0.204 mmol) and N-ethyl-N-isopropylpropan-2-amine (0.036 ml, 0.204 mmol) were mixed in Acetonitrile (1 ml). The mixture was microwaved at 110° C. for 10 minutes and then concentrated. 18 mg of 6-((4-(bis(2-hydroxyethyl)amino)-5-(trifluoromethyl)pyrimidin-2-yl)amino)-3,4-dihydroquinolin-2 (1H)-one and 20 mg of 6-((4-(2-((2-hydroxyethyl)amino) ethoxy)-5-(trifluoromethyl)pyrimidin-2-yl)amino)-3,4-dihydroquinolin-2(1H)-one were recovered after automated reverse phase chromatography (water-MeOH eluent). MS calcd for $[C_{18}H_{20}F_3N_5O_3+H]^+$: 412.16, found 412.10.

Example 213

Preparation of N2-(benzo[d][1,3]dioxol-5-yl)-N4-cyclopropyl-5-(trifluoromethyl)pyrimidine-2,4-diamine

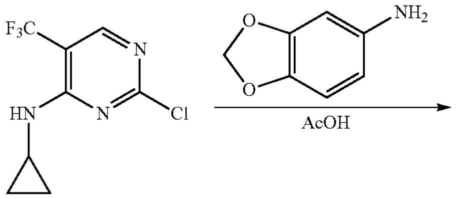

-continued

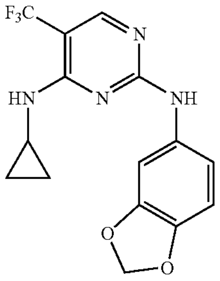

2-Chloro-N-cyclopropyl-5-(trifluoromethyl)pyrimidin-4-amine (0.060 g, 0.253 mmol) and benzo[d][1,3]dioxol-5-amine (0.035 g, 0.253 mmol) were mixed in Acetic Acid (1 ml). The mixture was microwaved at 110° C. for 10 minutes. 56 mg of product was recovered after automated reverse phase chromatography (water-MeCN eluent). MS calcd for $[C_{15}H_{13}F_3N_4O_2+H]^+$: 339.11, found 339.00.

Example 214

Preparation of N4-cyclopropyl-N2-(isoxazol-3-yl)-5-(trifluoromethyl) pyrimidine-2,4-diamine and N-cyclopropyl-2-(3-iminoisoxazol-2(3H)-yl)-5-(trifluoromethyl)pyrimidin-4-amine

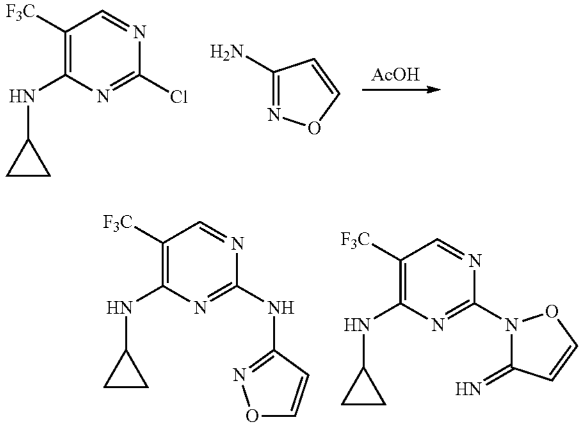

2-Chloro-N-cyclopropyl-5-(trifluoromethyl)pyrimidin-4-amine (0.070 g, 0.295 mmol) and isoxazol-3-amine (0.025 g, 0.295 mmol) were mixed in Acetic Acid (1 ml). The mixture was microwaved at 120° C. for 10 minutes and then concentrated. 3 mg of N4-cyclopropyl-N2-(isoxazol-3-yl)-5-(trifluoromethyl)pyrimidine-2,4-diamine and 3 mg of N-cyclopropyl-2-(3-iminoisoxazol-2(3H)-yl)-5-(trifluoromethyl)pyrimidin-4-amine were recovered after automated reverse phase chromatography (water-MeCN eluent). MS calcd for $[C_{11}H_{10}F_3N_5O+H]^+$: 286.09, found 285.85.

Example 215

Preparation of 6-((4-(3,3-difluoroazetidin-1-yl)-5-(trifluoromethyl) pyrimidin-2-yl)amino)-3,4-dihydroquinolin-2(1H)-one

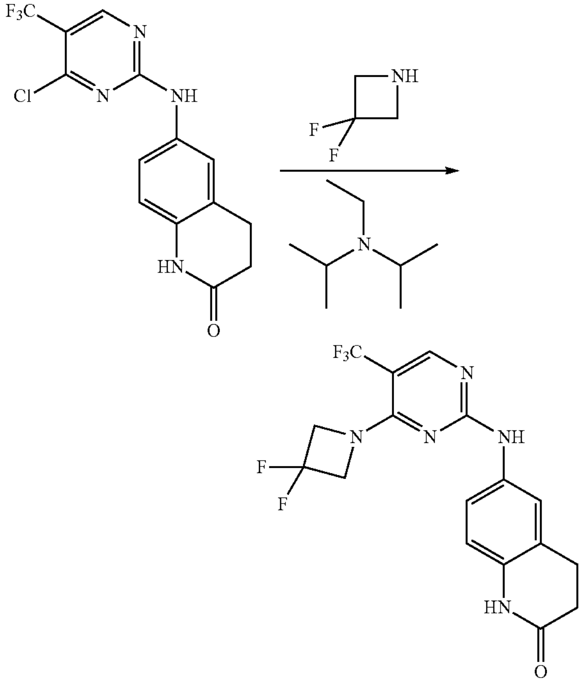

6-((4-Chloro-5-(trifluoromethyl)pyrimidin-2-yl)amino)-3,4-dihydroquinolin-2(1H)-one (0.070 g, 0.204 mmol), 3,3-difluoroazetidine, HCl (0.026 g, 0.204 mmol) and N-ethyl-N-isopropylpropan-2-amine (0.071 ml, 0.409 mmol) were mixed in Acetonitrile (1 ml). The mixture was microwaved at 100° C. for 10 minutes and then concentrated. Added acetone and filtered the solid to give 62 mg of product. MS calcd for $[C_{17}H_{14}F_5N_5O+H]^+$: 400.12, found 400.20.

Example 216

Preparation of 6-((4-((cyclopropylmethyl)amino)-5-(trifluoromethyl) pyrimidin-2-yl)amino)-3,4-dihydroquinolin-2(1H)-one

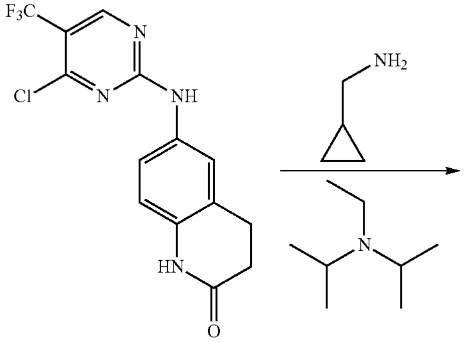

-continued

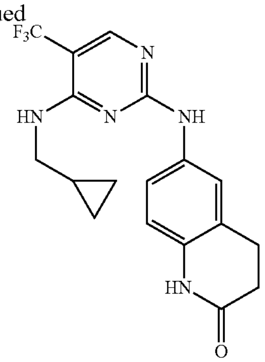

6-((4-Chloro-5-(trifluoromethyl)pyrimidin-2-yl)amino)-3,4-dihydroquinolin-2(1H)-one (0.070 g, 0.204 mmol), cyclopropylmethanamine (0.015 g, 0.204 mmol) and N-ethyl-N-isopropylpropan-2-amine (0.036 ml, 0.204 mmol) were mixed in Acetonitrile (1 ml). The mixture was microwaved at 110° C. for 10 minutes and then concentrated. Added MeCN and filtered the solid. Rinsed with acetone as well to give 57 mg of product. MS calcd for $[C_{18}H_{18}F_3N_5O+H]^+$: 378.16, found 378.30.

Example 217

Preparation of N2-(1H-pyrrolo[2,3-b]pyridin-5-yl)-5-(trifluoromethyl) pyrimidine-2,4-diamine

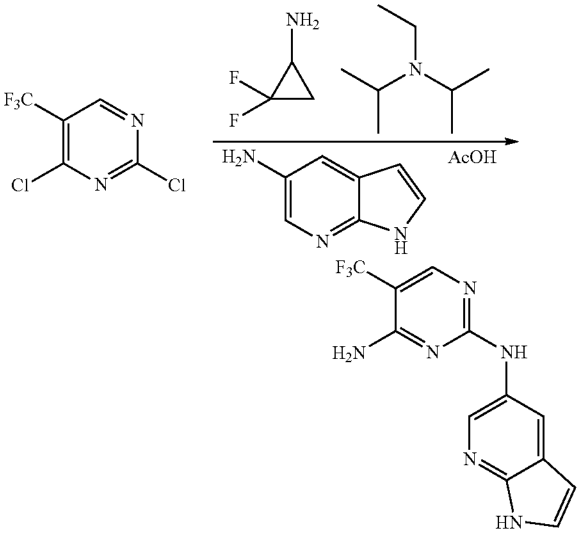

2,4-Dichloro-5-(trifluoromethyl)pyrimidine (0.060 g, 0.277 mmol), 2,2-difluorocyclopropan-1-amine.HCl (0.036 g, 0.277 mmol) and N-ethyl-N-isopropylpropan-2-amine (0.096 ml, 0.553 mmol) were mixed in Acetonitrile (1 ml). The mixture was microwaved at 70° C. for 10 minutes and then concentrated. 1H-pyrrolo[2,3-b]pyridin-5-amine (0.037 g, 0.277 mmol) and acetic acid (0.016 ml, 0.277 mmol) were added. The mixture was microwaved at 120° C. for 20 minutes and then concentrated. 9 mg of side product was recovered after automated reverse phase chromatography (water-MeCN eluent). MS calcd for $[C_{12}H_9F_3N_6+H]^+$: 295.09, found 294.90.

Example 218

Preparation of methyl (2-((2-oxo-1,2,3,4-tetrahydroquinolin-6-yl)amino)-5-(trifluoromethyl)pyrimidin-4-yl)glycinate

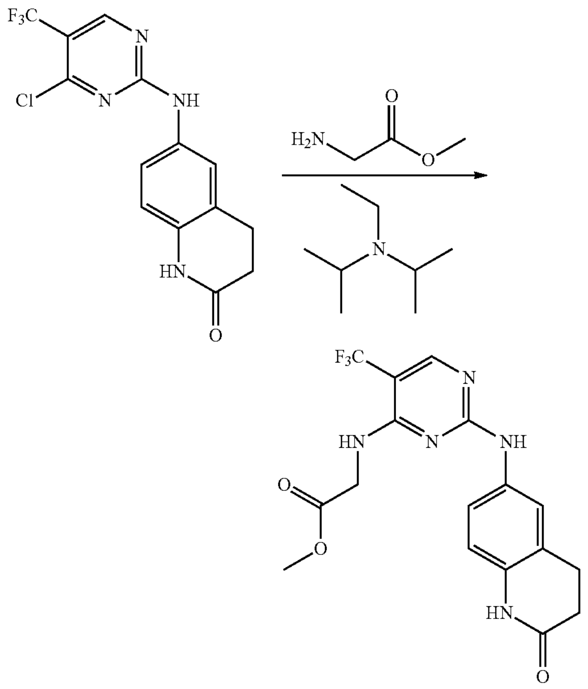

6-((4-Chloro-5-(trifluoromethyl)pyrimidin-2-yl)amino)-3,4-dihydroquinolin-2(1H)-one (0.070 g, 0.204 mmol), methyl glycinate.HCl (0.026 g, 0.204 mmol) and N-ethyl-N-isopropylpropan-2-amine (0.071 ml, 0.409 mmol) were mixed in DMF (1 ml). The mixture was microwaved at 130° C. for 30 minutes and then concentrated. Added MeCN and filtered to give 38 mg of the product as a solid. MS calcd for $[C_{17}H_{16}F_3N_5O_3+H]^+$: 396.13, found 396.05.

Example 219

Preparation of 6-((4-(ethoxyamino)-5-(trifluoromethyl)pyrimidin-2-yl)amino)-3,4-dihydroquinolin-2(1H)-one

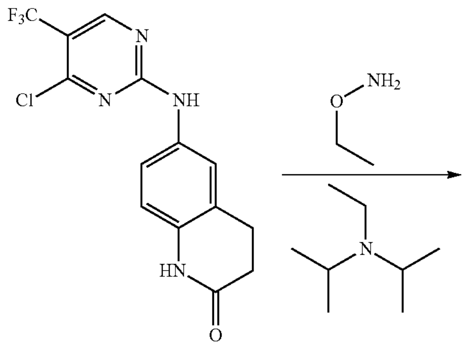

-continued

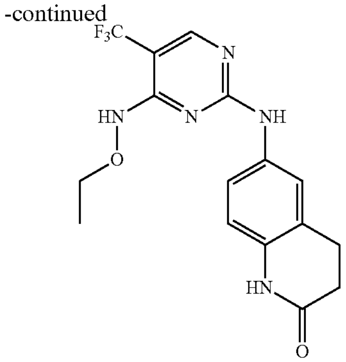

6-((4-Chloro-5-(trifluoromethyl)pyrimidin-2-yl)amino)-3,4-dihydroquinolin-2(1H)-one (0.070 g, 0.204 mmol), O-ethylhydroxylamine.HCl (0.020 g, 0.204 mmol) and N-ethyl-N-isopropylpropan-2-amine (0.071 ml, 0.409 mmol) were mixed in DMF (1 ml). The mixture was microwaved at 130° C. for 30 minutes and then concentrated. 29 mg of product was recovered after automated reverse phase chromatography (water-MeCN eluent). MS calcd for $[C_{16}H_{16}F_3N_5O_2+H]^+$: 368.14, found 368.05.

Example 220

Preparation of 6-((4-((3-methyloxetan-3-yl)amino)-5-(trifluoromethyl) pyrimidin-2-yl)amino)-3,4-dihydroquinolin-2(1H)-one, 6-((4-(dimethylamino)-5-(trifluoromethyl)pyrimidin-2-yl)amino)-3,4-dihydroquinolin-2(1H)-one and 6-((4-((2-(dimethylamino)-1-methoxypropan-2-yl)amino)-5-(trifluoromethyl)pyrimidin-2-yl)amino)-3,4-dihydroquinolin-2(1H)-one 6-((4-Chloro-5-(trifluoromethyl)pyrimidin-2-yl)amino)-3,4-dihydroquinolin-2(1H)-one (0.070 g, 0.204 mmol), 3-methyloxetan-3-amine (0.018 g, 0.204 mmol) and N-ethyl-N-isopropylpropan-2-amine (0.036 ml, 0.204 mmol) were mixed in DMF (1 nil). The mixture was microwaved at 130° C. for 30 minutes and then concentrated. Added MeOH-water and filtered off the solid. Ran two separate reverse phase columns with the solid and the filtrate (water-MeCN eluent). 8 mg of 6-((4-((3-methyloxetan-3-yl)amino)-5-(trifluoromethyl)pyrimidin-2-yl) amino)-3,4-dihydroquinolin-2(1H)-one, 3 mg of 6-((4-(dimethylamino)-5-(trifluoromethyl)pyrimidin-2-yl)amino)-3,4-dihydroquinolin-2(1H)-one and 3 mg of 6-((4-((2-(dimethylamino)-1-methoxypropan-2-yl)amino)-5-(trifluoromethyl)pyrimidin-2-yl)amino)-3,4-dihydroquinolin-2(1H)-one were recovered after automated reverse phase chromatography (water-MeCN eluent). MS calcd for $[C_{18}H_{18}F_3N_5O_2+H]^+$: 394.15, found 394.10. MS calcd for $[C_{16}H_{16}F_3N_5O+H]^+$: 352.14, found 352.25. MS calcd for $[C_{20}H_{25}F_3N_6O_2+H]^+$: 439.21, found 439.00.

Example 221

Preparation of N4-cyclopropyl-N2-(pyridazin-4-yl)-5-(trifluoromethyl) pyrimidine-2,4-diamine and N4-cyclopropyl-N2-(4-(cyclopropylamino)-5-(trifluoromethyl) pyrimidin-2-yl)-N2-(pyridazin-4-yl)-5-(trifluoromethyl)pyrimidine-2,4-diamine

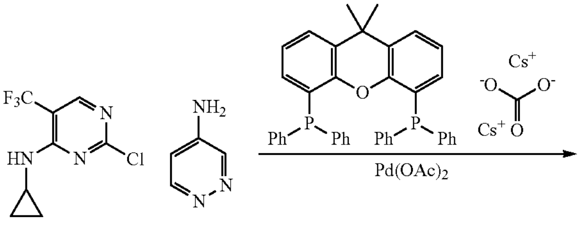

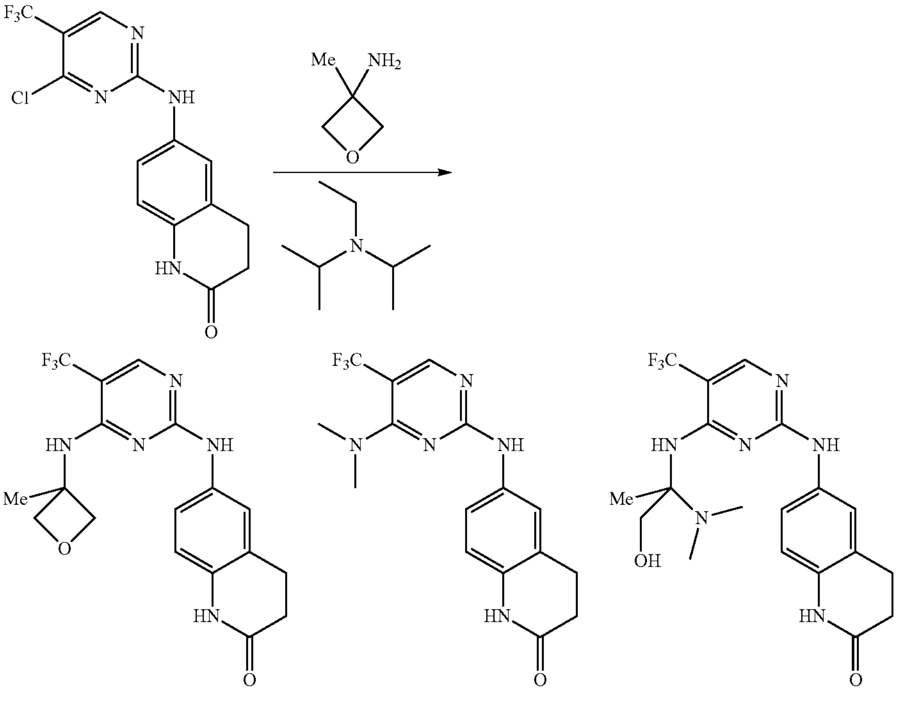

-continued

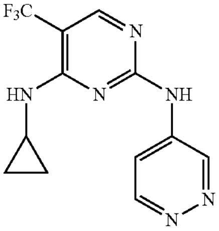

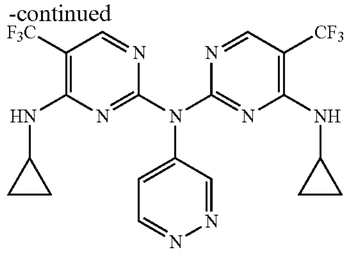

Flame dried flask and stir bar. Bubbled nitrogen through reagents and solvents prior to heating. 2-Chloro-N-cyclopropyl-5-(trifluoromethyl)pyrimidin-4-amine (0.070 g, 0.295 mmol), pyridazin-4-amine (0.028 g, 0.295 mmol), (9,9-dimethyl-9H-xanthene-4,5-diyl)bis(diphenyl phosphane) (0.017 g, 0.029 mmol), diacetoxypalladium (3.31 mg, 0.015 mmol) and cesium carbonate (0.192 g, 0.589 mmol) were mixed in 1,4-Dioxane (1 ml). The mixture was microwaved at 140° C. for 20 minutes. Filtered through Celite with methanol and concentrated. 5 mg of N4-cyclopropyl-N2-(pyridazin-4-yl)-5-(trifluoromethyl)pyrimidine-2,4-diamine and 6 mg of N4-cyclopropyl-N2-(4-(cyclopropylamino)-5-(trifluoromethyl)pyrimidin-2-yl)-N2-(pyridazin-4-yl)-5-(trifluoromethyl)pyrimidine-2,4-diamine were recovered after automated reverse phase chromatography (water-MeCN eluent). MS calcd for $[C_{12}H_{11}F_3N_6+H]^+$: 297.11, found 296.75. MS calcd for $[C_{20}H_{17}F_6N_9+H]^+$: 498.16, found 498.35.

Example 222

Preparation of 6-((4-((2,2,2-trifluoroethyl)amino)-5-(trifluoromethyl) pyrimidin-2-yl)amino)-3,4-dihydroquinolin-2(1H)-one

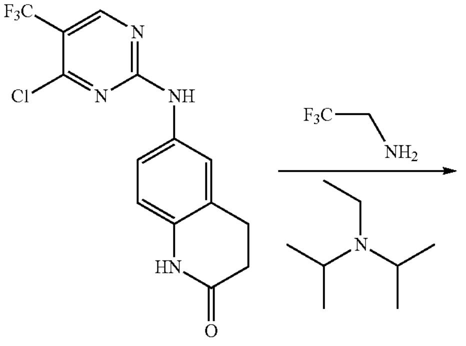

-continued

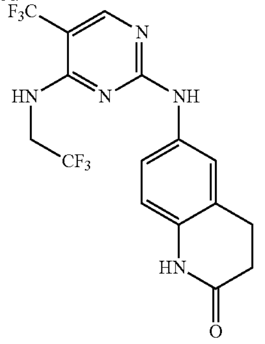

6-((4-Chloro-5-(trifluoromethyl)pyrimidin-2-yl)amino)-3,4-dihydroquinolin-2(1H)-one (0.070 g, 0.204 mmol), 2,2,2-trifluoroethan-1-amine.HCl (0.028 g, 0.204 mmol) and N-ethyl-N-isopropylpropan-2-amine (0.071 ml, 0.409 mmol) were mixed in DMF (1 ml). The mixture was microwaved at 130° C. for 20 minutes and then concentrated. 22 mg of product was recovered after automated reverse phase chromatography (water-10% THF in MeCN eluent). MS calcd for $[C_{16}H_{13}F_6N_5O+H]^+$: 406.11, found 406.30.

Example 223

Preparation of N-(2-((2-oxo-1,2,3,4-tetrahydroquinolin-6-yl)amino)-5-(trifluoromethyl)pyrimidin-4-yl) acetamide

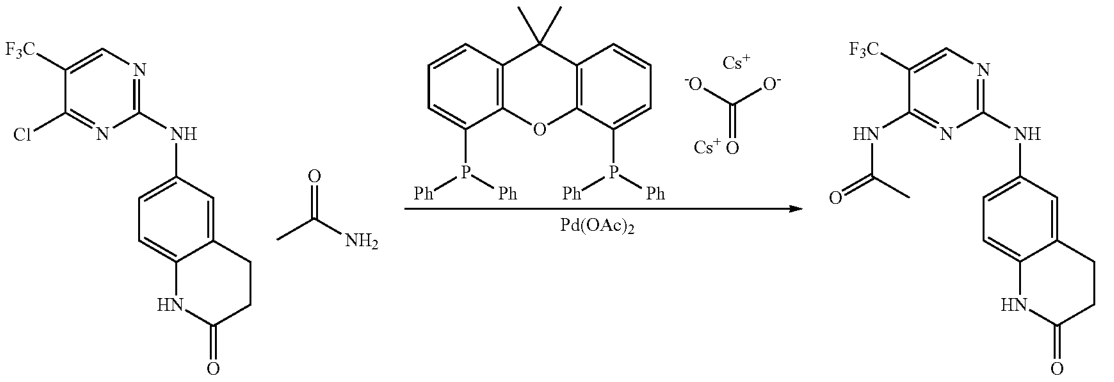

Flame dried flask and stir bar. Bubbled nitrogen through reagents and solvents prior to heating. 6-((4-Chloro-5-(trifluoromethyl)pyrimidin-2-yl)amino)-3,4-dihydroquinolin-2(1H)-one (0.070 g, 0.204 mmol), acetamide (0.012 g, 0.204 mmol), (9,9-dimethyl-9H-xanthene-4,5-diyl)bis (diphenylphosphane) (0.012 g, 0.020 mmol), diacetoxypalladium (2.293 mg, 10.21 μmol) and CESIUM CARBONATE (0.100 g, 0.306 mmol) were mixed in DMF (1 ml). The mixture was microwaved at 140° C. for 20 minutes. Filtered through Celite with methanol and then concentrated. Automated reverse phase chromatography was run (water-MeOH eluent). 1 mg of product was isolated after further purification using prep TLC. MS calcd for $[C_{16}H_{14}F_3N_5O_2+H]^+$: 366.12, found 366.00.

Example 224

Preparation of N4-cyclopropyl-N2-(2,3-dihydrobenzo[b][1,4]dioxin-6-yl)pyrimidine-2,4-diamine

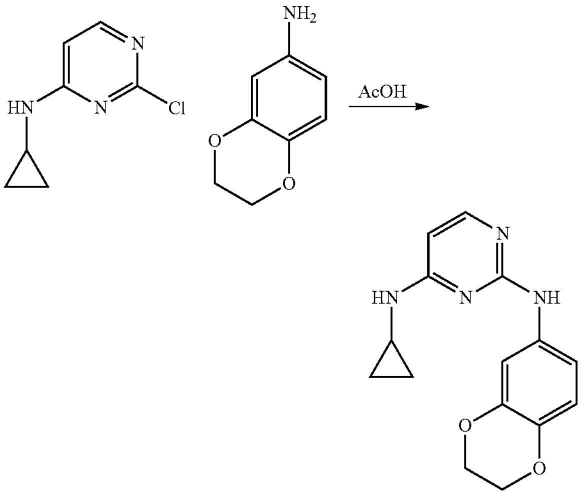

2-Chloro-N-cyclopropylpyrimidin-4-amine (0.060 g, 0.354 mmol) and 2,3-dihydro benzo[b][1,4]dioxin-6-amine (0.053 g, 0.354 mmol) were mixed in Acetic Acid (1 ml). The mixture was microwaved at 130° C. for 10 minutes and then concentrated. 64 mg of product was recovered after automated reverse phase chromatography (water-MeOH eluent). MS calcd for $[C_{15}H_{16}N_4O_2+H]^+$: 285.14, found 284.90.

Example 225

Preparation of 6-((4-(cyclopropylamino)-1,3,5-triazin-2-yl)amino)-3,4-dihydroquinolin-2(1H)-one

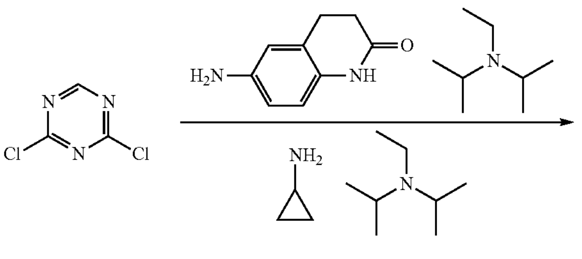

-continued

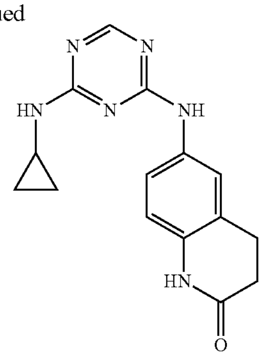

2,4-Dichloro-1,3,5-triazine (0.055 g, 0.367 mmol), 6-amino-3,4-dihydroquinolin-2(1H)-one (0.059 g, 0.367 mmol) and N-ethyl-N-isopropylpropan-2-amine (0.064 ml, 0.367 mmol) were mixed in DMF (1 ml). The mixture was microwaved at 120° C. for 10 minutes. Added MeOH and filtered solid. Concentrated the filtrate which contains product. 7 mg of product was recovered after automated reverse phase chromatography (water-2% DMF in MeOH eluent). MS calcd for $[C_{15}H_{16}N_6O+H]^+$: 297.15, found 296.90.

Example 226

Preparation of N-(2-((2-oxo-1,2,3,4-tetrahydroquinolin-6-yl)amino)-5-(trifluoromethyl)pyrimidin-4-yl)methanesulfonamide

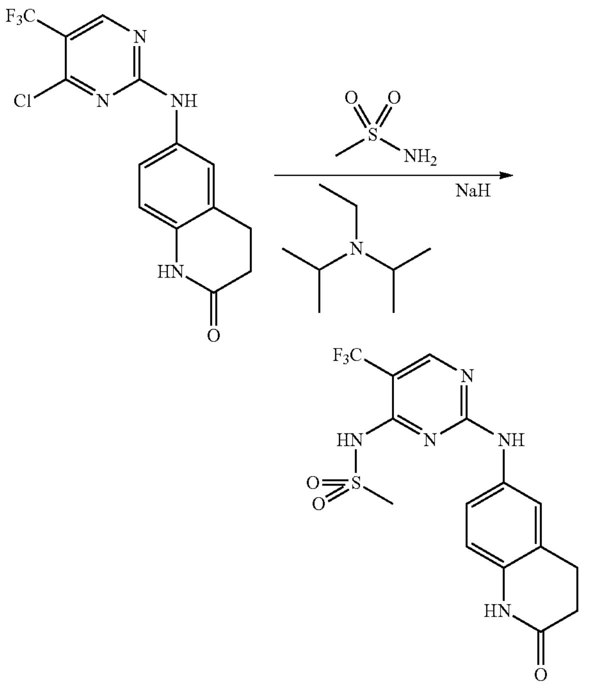

6-((4-Chloro-5-(trifluoromethyl)pyrimidin-2-yl)amino)-3,4-dihydroquinolin-2(1H)-one (0.070 g, 0.204 mmol), methanesulfonamide (0.019 g, 0.204 mmol) and SODIUM HYDRIDE (0.016 g, 0.409 mmol) were mixed in DMF (1 ml). The mixture was microwaved at 130° C. for 20 minutes and then concentrated. Automated reverse phase chromatography (water-2% DMF in MeOH eluent) was used to obtain semipure product. After concentration, the solid was washed with ethanol to give 2 mg of the product. MS calcd for $[C_{15}H_{14}F_3N_5O_3S+H]^+$: 402.09, found 402.10.

Example 227

Preparation of methyl (2-((2-oxo-1,2,3,4-tetrahydroquinolin-6-yl)amino)-5-(trifluoromethyl)pyrimidin-4-yl)-L-prolinate

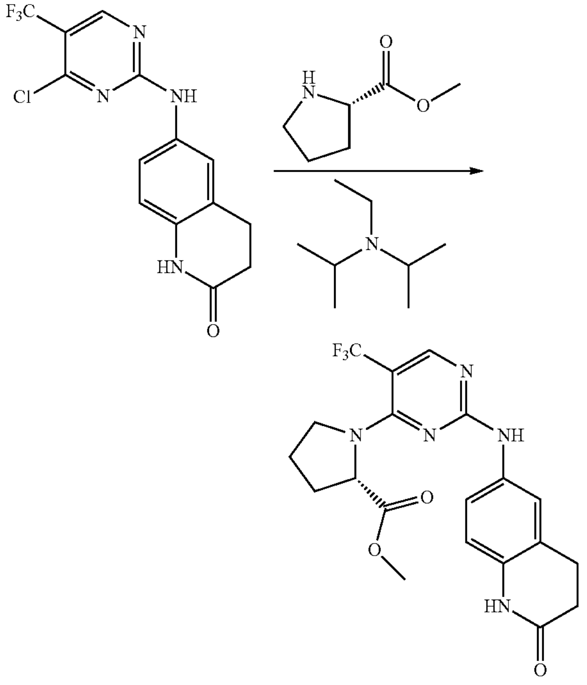

6-((4-Chloro-5-(trifluoromethyl)pyrimidin-2-yl)amino)-3,4-dihydroquinolin-2(1H)-one (0.070 g, 0.204 mmol), methyl L-prolinate.HCl (0.034 g, 0.204 mmol) and N-ethyl-N-isopropyl propan-2-amine (0.071 ml, 0.409 mmol) were mixed in DMF (1 ml). The mixture was microwaved at 100° C. for 20 minutes and then concentrated. Automated reverse phase chromatography (water-10% THF in MeCN eluent) was used to obtain semipure product. After concentration, the material was further purified by normal phase chromatography on silica gel (3% MeOH/DCM eluent) to give 18 mg of product. MS calcd for $[C_{20}H_{20}F_3N_5O_3+H]^+$: 436.16, found 436.15.

Example 228

Preparation of N-cyclopropyl-2-(2-(pyridin-3-yl)pyrrolidin-1-yl)-5-(trifluoromethyl)pyrimidin-4-amine

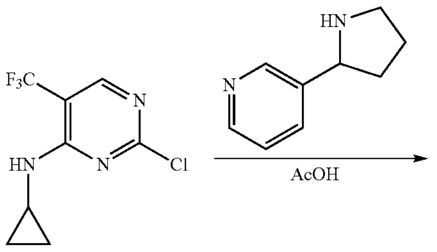

-continued

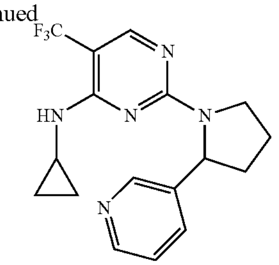

2-Chloro-N-cyclopropyl-5-(trifluoromethyl)pyrimidin-4-amine (0.064 g, 0.269 mmol) and 3-(pyrrolidin-2-yl)pyridine (0.040 g, 0.269 mmol) were mixed in Acetic Acid (1 ml). The mixture was microwaved at 110° C. for 10 minutes and then concentrated. 3 mg of product was recovered after automated reverse phase chromatography (water-MeCN eluent). MS calcd for $[C_{17}H_{18}F_3N_6+H]^+$: 350.16, found 349.90.

Example 229

Preparation of N4-cyclopropyl-N2-(6-methoxypyridin-2-yl)-5-(trifluoromethyl)pyrimidine-2,4-diamine

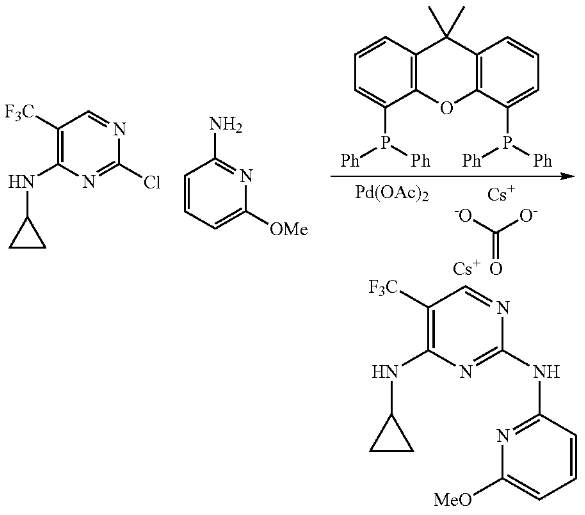

Flame dried flask and stir bar. Bubbled nitrogen through reagents and solvents prior to heating. 2-Chloro-N-cyclopropyl-5-(trifluoromethyl)pyrimidin-4-amine (0.065 g, 0.274 mmol), 6-methoxypyridin-2-amine (0.034 g, 0.274 mmol), (9,9-dimethyl-9H-xanthene-4,5-diyl)bis(diphenylphosphane) (0.016 g, 0.027 mmol), diacetoxypalladium (3.07 mg, 0.014 mmol) and CESIUM CARBONATE (0.134 g, 0.410 mmol) were mixed in 1,4-Dioxane (1 ml). The mixture was microwaved at 140° C. for 20 minutes. Filtered through Celite with MeOH and concentrated. 9 mg of product was recovered after automated reverse phase chromatography (water-10% THF in MeCN eluent). MS calcd for $[C_{14}H_{14}F_3N_5O+H]^+$: 326.13, found 326.10.

Example 230

Preparation of N4-cyclopropyl-N2-(5-methoxypyridin-3-yl)-5-(trifluoromethyl) pyrimidine-2,4-diamine

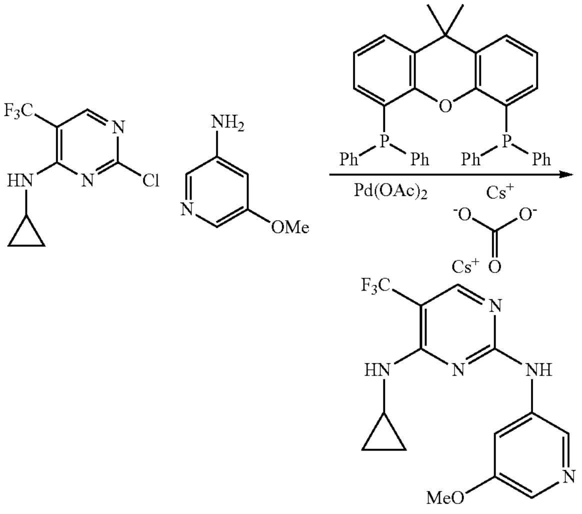

Flame dried flask and stir bar. Bubbled nitrogen through reagents and solvents prior to heating. 2-Chloro-N-cyclopropyl-5-(trifluoromethyl)pyrimidin-4-amine (0.065 g, 0.274 mmol), 5-methoxypyridin-3-amine (0.034 g, 0.274 mmol), (9,9-dimethyl-9H-xanthene-4,5-diyl)bis(diphenylphosphane) (0.016 g, 0.027 mmol), diacetoxypalladium (3.07 mg, 0.014 mmol) and CESIUM CARBONATE (0.134 g, 0.410 mmol) were mixed in 1,4-Dioxane (1 ml). The mixture was microwaved at 140° C. for 20 minutes. Filtered through Celite with MeOH and concentrated. 9 mg of product was recovered after automated reverse phase chromatography (water-MeCN eluent). MS calcd for $[C_{14}H_{14}F_3N_5O+H]^+$: 326.13, found 325.90.

Example 231

Preparation of 6-((4-(oxetan-3-yloxy)-5-(trifluoromethyl)pyrimidin-2-yl)amino)-3,4-dihydroquinolin-2(1H)-one and 6-((4-hydroxy-5-(trifluoromethyl) pyrimidin-2-yl)amino)-3,4-dihydroquinolin-2(1H)-one

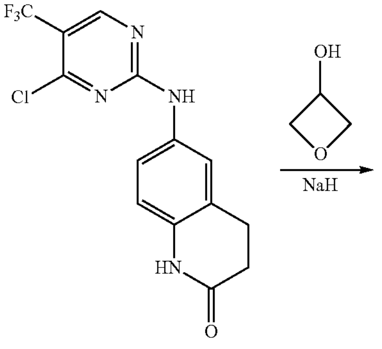

-continued

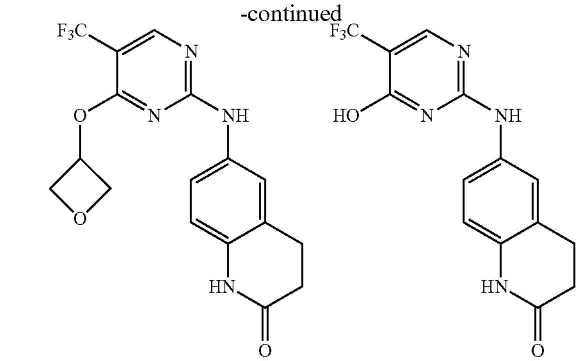

The reaction flask and stir bar were flame-dried. 6-((4-chloro-5-(trifluoromethyl) pyrimidin-2-yl)amino)-3,4-dihydroquinolin-2(1H)-one (0.070 g, 0.204 mmol), oxetan-3-ol (0.015 g, 0.204 mmol) and sodium hydride (6.37 mg, 0.266 mmol) were mixed in DMF (1 ml). The mixture was microwaved at 120° C. for 20 minutes and then concentrated. 11 mg of 6-((4-(oxetan-3-yloxy)-5-(trifluoromethyl) pyrimidin-2-yl)amino)-3,4-dihydroquinolin-2(1H)-one and 2 mg of 6-((4-hydroxy-5-(trifluoromethyl)pyrimidin-2-yl) amino)-3,4-dihydroquinolin-2(1H)-one were recovered after automated reverse phase chromatography (water-MeCN eluent). MS calcd for $[C_{17}H_{15}F_3N_4O_3+H]^+$: 381.12, found 381.00. MS calcd for $[C_{14}H_{11}F_3N_4O_2+H]^+$: 325.09, found 324.80.

Example 232

Preparation of 5-((4-(cyclopropylamino)pyrimidin-2-yl)amino)-1,3-dihydro-2H-benzo[d]imidazol-2-one

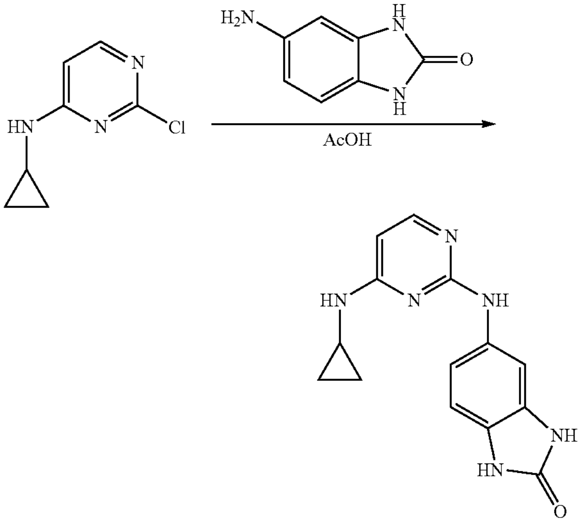

The reaction flask and stir bar were flame-dried. 2-chloro-N-cyclopropylpyrimidin-4-amine (0.060 g, 0.354 mmol) and 5-amino-1,3-dihydro-2H-benzo[d]imidazol-2-one (0.053 g, 0.354 mmol) were mixed in Acetic Acid (1 ml). The mixture was microwaved at 110° C. for 10 minutes and then concentrated. Added acetone and filtered the solid to give 67 mg of product. MS calcd for $[C_{14}H_{14}N_6O+H]^+$: 283.13, found 282.85.

Example 233

Preparation of 5,5'-((5-bromopyrimidine-2,4-diyl) bis(azanediyl))bis(1,3-dihydro-2H-benzo[d]imidazol-2-one)

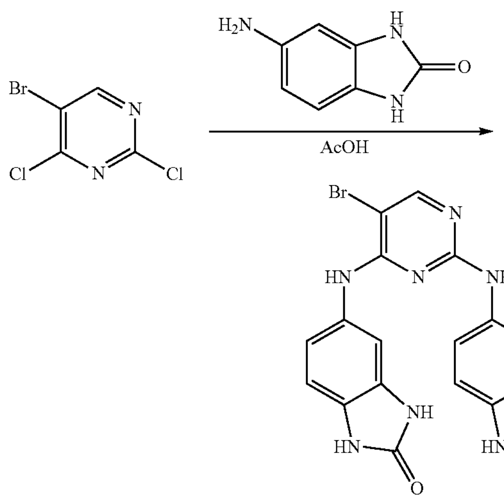

The reaction flask and stir bar were flame-dried. 5-bromo-2,4-dichloropyrimidine (0.100 g, 0.439 mmol) and 5-amino-1,3-dihydro-2H-benzo[d]imidazol-2-one (0.065 g, 0.439 mmol) were mixed in Acetic Acid (1 ml). The mixture was microwaved at 110° C. for 20 minutes and then concentrated. Acetonitrile was added and the solid filtered to give 40 mg of product. MS calcd for $[C_{18}H_{13}BrN_8O_2+H]^+$: 453.04, found 452.90.

Example 234

Preparation of 2-((5-chloro-2-((3,4,5-trimethoxyphenyl)amino)pyrimidin-4-yl)oxy)-N-methylbenzamide and N-(5-chloro-2-((3,4,5-trimethoxyphenyl)amino) pyrimidin-4-yl)-2-hydroxy-N-methylbenzamide

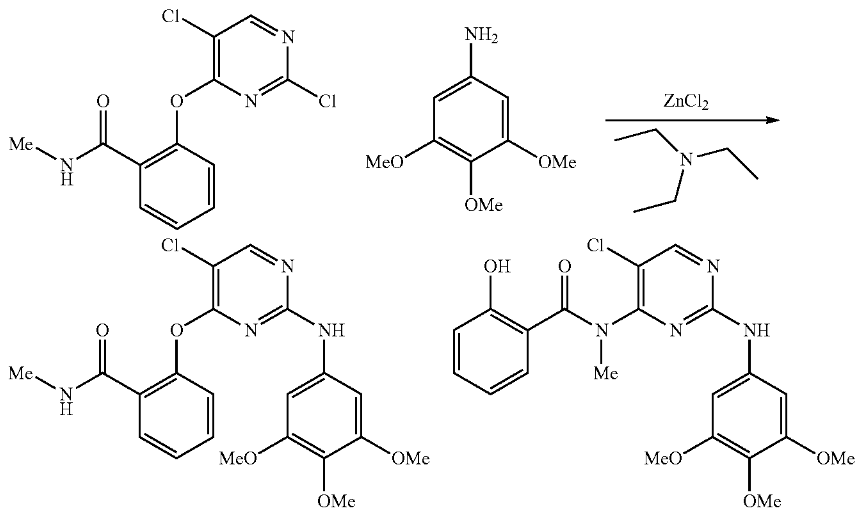

2-((2,5-Dichloropyrimidin-4-yl)oxy)-N-methylbenzamide (0.325 g, 1.090 mmol), 3,4,5-trimethoxyaniline (0.200 g, 1.090 mmol), zinc(II) chloride (0.178 g, 1.308 mmol) and triethylamine (0.280 ml, 1.308 mmol) were mixed in 1,2-Dichloroethane (2 ml) and t-Butanol (2 mL). Heated to 60° C. for 8 h, then the mixture was microwaved at 100° C. for 10 minutes and then concentrated. 10 mg of 2-((5-chloro-2-((3,4,5-trimethoxyphenyl)amino)pyrimidin-4-yl)oxy)-N-methylbenzamide and 5 mg of N-(5-chloro-2-((3,4,5-trimethoxyphenyl)amino)pyrimidin-4-yl)-2-hydroxy-N-methylbenzamide were recovered after automated reverse phase chromatography (water-MeCN eluent). MS calcd for $[C_{21}H_{21}ClN_4O_5+H]^+$: 445.13, found 445.25.

Example 235

Preparation of 6-((4-(1H-pyrrol-1-yl)-5-(trifluoromethyl)pyrimidin-2-yl)amino)-3,4-dihydroquinolin-2 (1H)-one

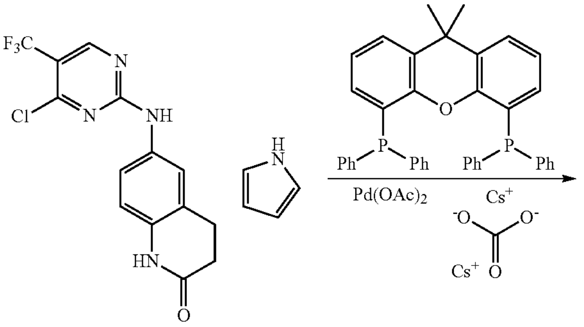

-continued

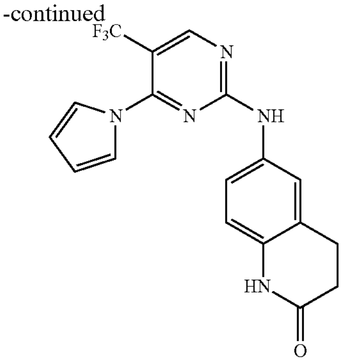

Flame dried flask and stir bar. Bubbled nitrogen through reagents and solvents prior to heating. 6-((4-Chloro-5-(trifluoromethyl)pyrimidin-2-yl)amino)-3,4-dihydroquinolin-2(1H)-one (0.070 g, 0.204 mmol), 1H-pyrrole (0.015 g, 0.225 mmol), (9,9-dimethyl-9H-xanthene-4,5-diyl)bis(diphenylphosphane) (7.09 mg, 0.012 mmol), diacetoxypalladium (1.376 mg, 6.13 μmol) and cesium carbonate (0.087 g, 0.266 mmol) were mixed in DMF (1 ml). The mixture was microwaved at 140° C. for 20 minutes. Added MeCN and filtered the solid. The filtrate was concentrated and 2 mg of product was recovered after automated reverse phase chromatography (water-MeCN eluent). MS calcd for $[C_{18}H_{14}F_3N_5O+H]^+$: 374.13, found 373.85.

Example 236

Preparation of 5-((5-bromo-4-(cyclopropylamino)pyrimidin-2-yl)amino)-1,3-dihydro-2H-benzo[d]imidazol-2-one

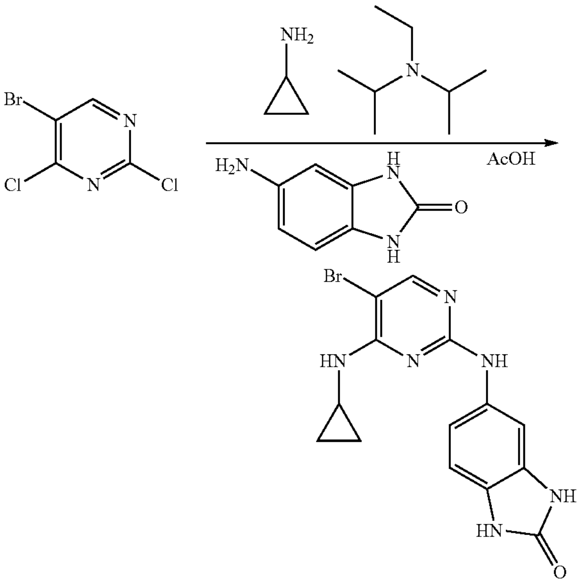

The reaction flask and stir bar were flame-dried. 5-bromo-2,4-dichloropyrimidine (0.100 g, 0.439 mmol), cyclopropanamine (0.030 ml, 0.439 mmol) and N-ethyl-N-isopropylpropan-2-amine (0.076 ml, 0.439 mmol) were mixed in Acetonitrile (2 ml). The mixture was microwaved at 60° C. for 10 minutes and then concentrated. 5-amino-1,3-dihydro-2H-benzo[d]imidazol-2-one (0.065 g, 0.439 mmol) was added. The mixture was microwaved at 120° C. for 20 minutes and then concentrated. Added MeCN and filtered the solid to give 112 mg of product. MS calcd for $[C_{14}H_{13}BrN_6O+H]^+$: 361.04, found 360.80.

Example 237

Preparation of 2-((5-bromo-2-((3,4,5-trimethoxyphenyl)amino)pyrimidin-4-yl)amino)-N-methylbenzenesulfonamide

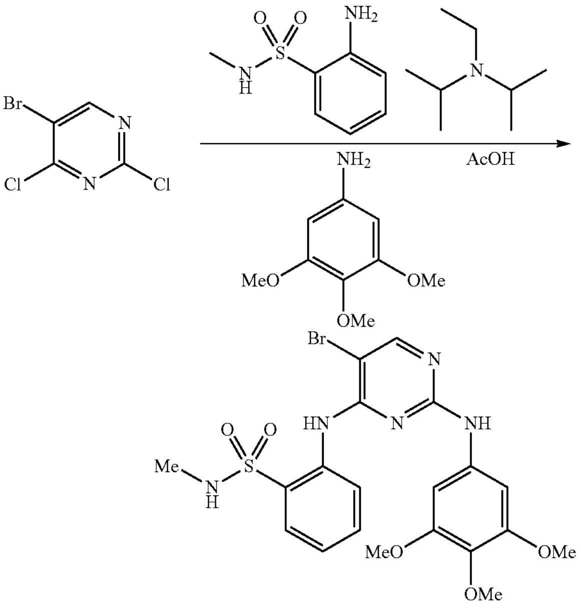

The reaction flask and stir bar were flame-dried. 5-bromo-2,4-dichloropyrimidine (0.080 g, 0.351 mmol), 2-amino-N-methylbenzenesulfonamide (0.065 g, 0.351 mmol) and N-ethyl-N-isopropylpropan-2-amine (0.061 ml, 0.351 mmol) were mixed in Acetonitrile (2 ml). The mixture was microwaved at 120° C. for 20 minutes and then concentrated. Added 3,4,5-trimethoxyaniline (0.064 g, 0.351 mmol) and acetic acid (0.021 g, 0.351 mmol). The mixture was microwaved at 120° C. for 20 minutes and then concentrated. 31 mg of product was recovered after automated reverse phase chromatography (water-MeCN eluent). MS calcd for $[C_{20}H_{22}BrN_5O_5S+H]^+$: 524.06, found 524.30.

Example 238

Preparation of 2-((2-chloropyrimidin-4-yl)oxy)-N-methylbenzamide

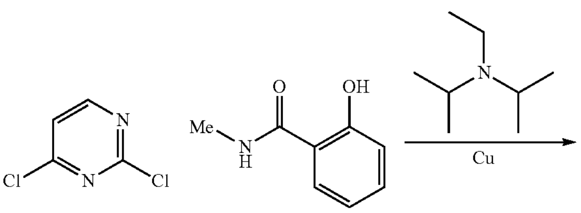

-continued

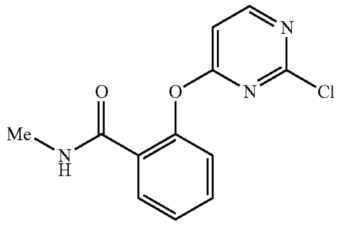

2,4-Dichloropyrimidine (1 g, 6.71 mmol), 2-hydroxy-N-methylbenzamide (1.015 g, 6.71 mmol), N-ethyl-N-isopropylpropan-2-amine (1.169 ml, 6.71 mmol) and copper (0.043 g, 0.671 mmol) were mixed in DMF (10 ml). The mixture was microwaved, reaching 140° C. at 7 min, and then the run was canceled. The mixture was concentrated and used as-is. MS calcd for $[C_{12}H_{10}ClN_3O_2+H]^+$: 264.06, found 263.70.

Example 239

Preparation of N-methyl-2-((2-((3,4,5-trimethoxyphenyl)amino)pyrimidin-4-yl)oxy)benzamide

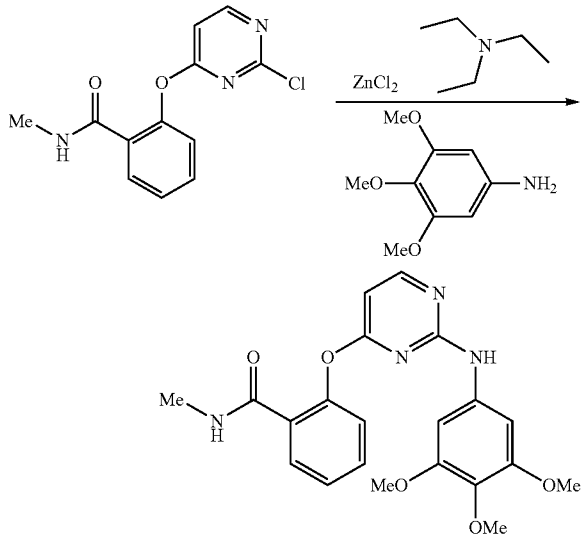

2-((2-Chloropyrimidin-4-yl)oxy)-N-methylbenzamide (1.529 g, 5.8 mmol), and zinc(II) chloride (0.790 g, 5.80 mmol) were mixed in 1,2-dichloroethane (4 mL) and t-butanol (4 mL). Stirred for 1 h and then added 3,4,5-trimethoxyaniline (1.063 g, 5.80 mmol) and triethylamine (0.808 mL, 5.80 mmol). Microwaved in a sealed tube at 100° C. for 20 min. Transferred to a flask and heated in an oil batch to 80° C. for a total of 24 h and then concentrated. 74 mg of product was recovered after automated reverse phase chromatography (water-MeCN eluent). MS calcd for $[C_{21}H_{22}N_4O_5+H]^+$: 411.17, found 411.20.

Example 240

Preparation of 5-((4-(cyclopropylamino)-5-(trifluoromethyl)pyrimidin-2-yl)amino)indolin-2-one

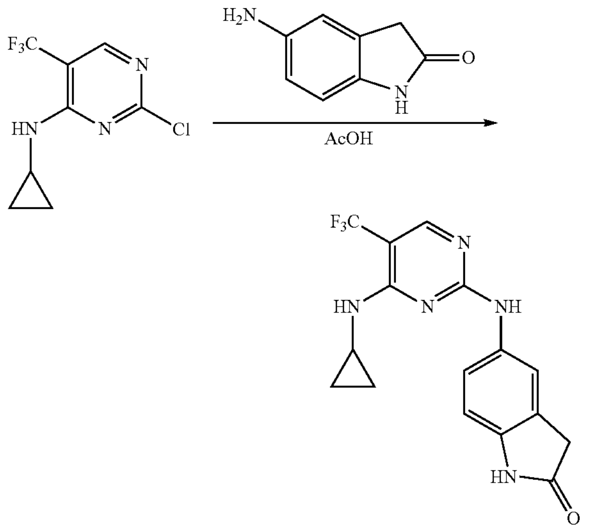

2-Chloro-N-cyclopropyl-5-(trifluoromethyl)pyrimidin-4-amine (0.060 g, 0.253 mmol) and 5-aminoindolin-2-one (0.037 g, 0.253 mmol) were mixed in acetic acid (1 ml). The mixture was microwaved at 110° C. for 10 min. Filtered the solid and washed with acetonitrile to give 18 mg of product. MS calcd for $[C_{16}H_{14}F_3N_5O+H]^+$: 350.13, found 350.10.

Example 241

Preparation of 3-((5-bromo-2-chloropyrimidin-4-yl)oxy)-N-methylbenzamide

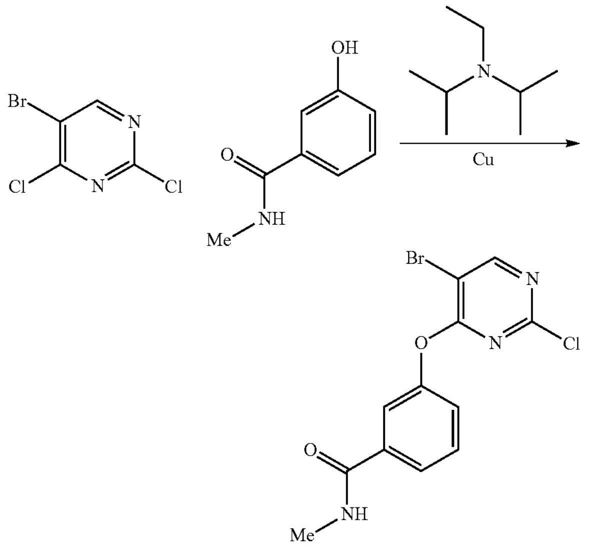

5-Bromo-2,4-dichloropyrimidine (0.100 g, 0.439 mmol), 3-hydroxy-N-methylbenzamide (0.066 g, 0.439 mmol), N-ethyl-N-isopropylpropan-2-amine (0.076 ml, 0.439 mmol) and copper (2.79 mg, 0.044 mmol) were mixed in DMF (2 ml). The mixture was microwaved at 80° C. for 20 min and then concentrated. It was used as-is. MS calcd for $[C_{12}H_9BrClN_3O_2+H]^+$: 341.97, found 341.65.

Example 242

Preparation of 3-((5-bromo-2-((3,4,5-trimethoxyphenyl)amino)pyrimidin-4-yl)oxy)-N-methylbenzamide

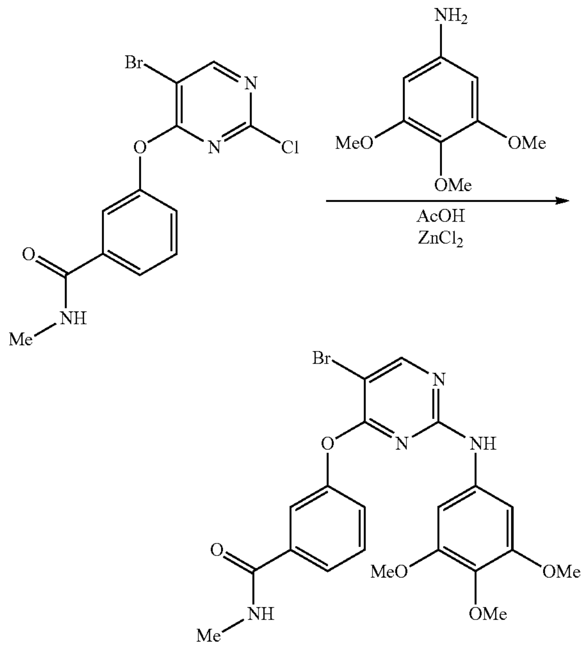

3-((5-Bromo-2-chloropyrimidin-4-yl)oxy)-N-methylbenzamide (0.147 g, 0.43 mmol) and 3,4,5-trimethoxyaniline (0.079 g, 0.430 mmol) were mixed in acetic acid (1 ml). The mixture was microwaved at 110° C. for 10 min. zinc(II) chloride (0.059 g, 0.430 mmol) was added. The mixture was microwaved at 120° C. for 20 min and then concentrated. 13 mg of product was recovered after automated reverse phase chromatography (water-MeCN eluent). MS calcd for $[C_{21}H_{21}BrN_4O_5+H]^+$: 489.08, found 488.95.

Example 243

Preparation of 6-((4-((3-amino-1H-1,2,4-triazol-5-yl)amino)-5-(trifluoro methyl)pyrimidin-2-yl)amino)-3,4-dihydroquinolin-2(1H)-one

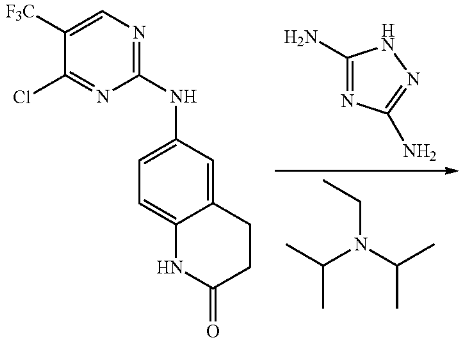

-continued

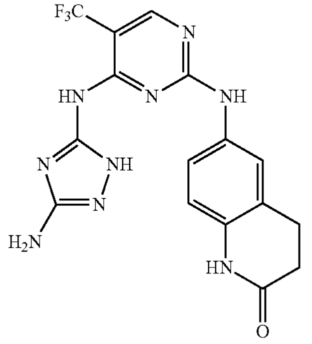

6-((4-Chloro-5-(trifluoromethyl)pyrimidin-2-yl)amino)-3,4-dihydroquinolin-2(1H)-one (0.072 g, 0.210 mmol), 1H-1,2,4-triazole-3,5-diamine (0.021 g, 0.210 mmol) and N-ethyl-N-isopropylpropan-2-amine (0.037 ml, 0.210 mmol) were mixed in DMF (2 ml). The mixture was microwaved at 110° C. for 20 min. Added copper (6.68 mg, 0.105 mmol) and more base and the mixture was microwaved at 130° C. for 20 min and then concentrated. 7 mg of product was recovered after automated reverse phase chromatography (water-3% DMF in MeCN eluent). MS calcd for $[C_{16}H_{14}F_3N_9O+H]^+$: 406.14, found 406.10.

Example 244

Preparation of 2-((5-bromo-2-chloropyrimidin-4-yl)oxy)-N,N-dimethyl benzamide

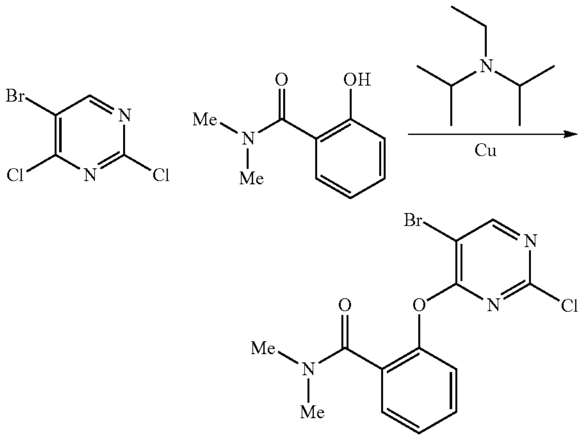

5-Bromo-2,4-dichloropyrimidine (0.150 g, 0.658 mmol), 2-hydroxy-N,N-dimethylbenzamide (0.109 g, 0.658 mmol), N-ethyl-N-isopropylpropan-2-amine (0.115 ml, 0.658 mmol) and copper (4.18 mg, 0.066 mmol) were mixed in DMF (3 ml). The mixture was microwaved at 60° C. for 20 min and then concentrated and used as-is. MS calcd for $[C_{13}H_{11}BrClN_3O_2+H]^+$: 355.98, found 355.70.

Example 245

Preparation of 2-((5-bromo-2-((3,4,5-trimethoxyphenyl)amino)pyrimidin-4-yl)oxy)-N,N-dimethylbenzamide

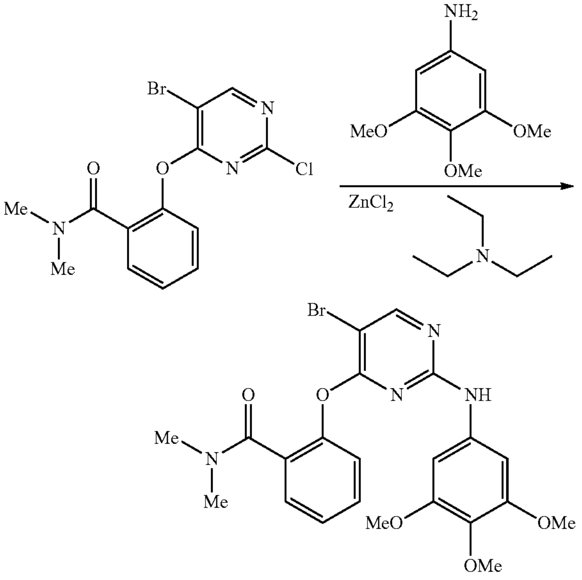

2-((5-Bromo-2-chloropyrimidin-4-yl)oxy)-N,N-dimethylbenzamide (0.203 g, 0.57 mmol) and zinc(II) chloride (0.078 g, 0.570 mmol) were mixed in 1,2-dichloroethane (2 ml) and t-butanol (2.000 ml). Stirred for 15 min, then 3,4,5-trimethoxyaniline (0.104 g, 0.570 mmol) and triethylamine (0.079 ml, 0.570 mmol) were added. The mixture was microwaved at 80° C. for 20 min and then concentrated. 29 mg of product was recovered after automated reverse phase chromatography (water-MeCN eluent). MS calcd for $[C_{22}H_{23}BrN_4O_5+H]^+$: 503.10, found 503.00.

Example 246

Preparation of 4-(2-((4-(cyclopropylamino)-5-(trifluoromethyl)pyrimidin-2-yl)amino)ethyl)phenol

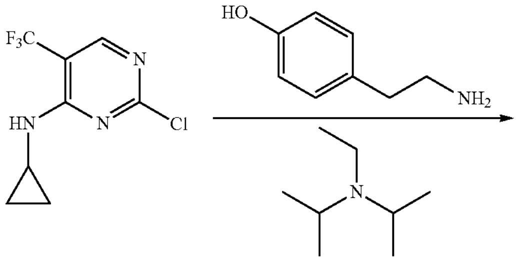

-continued

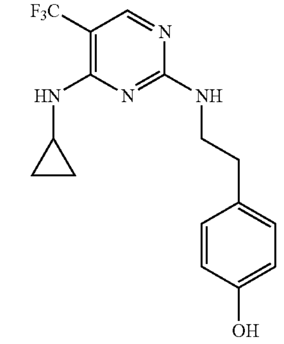

2-Chloro-N-cyclopropyl-5-(trifluoromethyl)pyrimidin-4-amine (0.055 g, 0.231 mmol), 4-(2-aminoethyl)phenol (0.032 g, 0.231 mmol) and N-ethyl-N-isopropylpropan-2-amine (0.040 ml, 0.231 mmol) were mixed in DMF (1 ml). The mixture was microwaved at 120° C. for 20 min and then concentrated. Added acetone and filtered through Celite. Concentrated the filtrate to give 60 mg of product. MS calcd for $[C_{16}H_{17}F_3N_4O+H]^+$: 339.15, found 339.20.

Example 247

Preparation of (R)-6-((4-(3-methylmorpholino)-5-(trifluoromethyl)pyrimidin-2-yl)amino)-3,4-dihydroquinolin-2(1H)-one

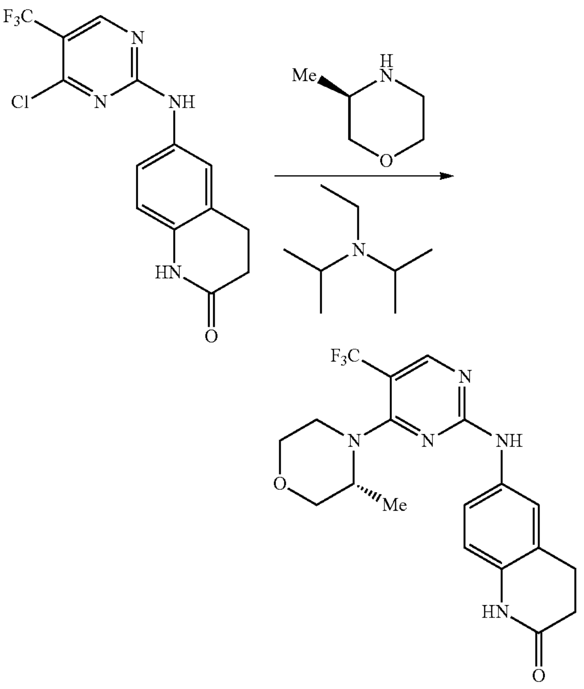

6-((4-Chloro-5-(trifluoromethyl)pyrimidin-2-yl)amino)-3,4-dihydroquinolin-2(1H)-one (0.055 g, 0.160 mmol), (R)-3-methylmorpholine (0.016 g, 0.160 mmol) and N-ethyl-N-isopropylpropan-2-amine (0.028 ml, 0.160 mmol) were mixed in DMF (1 ml). The mixture was microwaved at 130° C. for 20 min and then concentrated. 6 mg of product was recovered after automated reverse phase chromatography (water-MeOH eluent). MS calcd for $[C_{19}H_{20}F_3N_5O_2+H]^+$: 408.17, found 408.35.

Example 248

Preparation of 2-((5-bromo-2-chloropyrimidin-4-yl) oxy)-N-methoxy benzamide

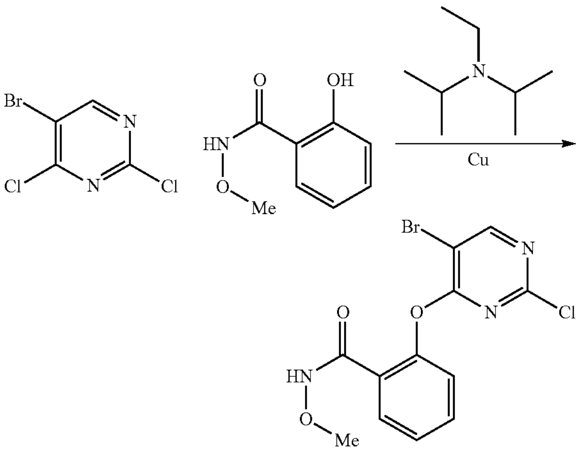

5-Bromo-2,4-dichloropyrimidine (0.150 g, 0.658 mmol), 2-hydroxy-N-methoxy benzamide (0.110 g, 0.658 mmol), N-ethyl-N-isopropylpropan-2-amine (0.115 ml, 0.658 mmol) and copper (4.18 mg, 0.066 mmol) were mixed in DMF (3 ml). The mixture was microwaved at 60° C. for 20 min and then concentrated and used as-is. MS calcd for $[C_{12}H_9BrClN_3O_3+H]^+$: 357.96, found 357.70.

Example 249

Preparation of 2-((5-bromo-2-((3,4,5-trimethoxyphenyl)amino)pyrimidin-4-yl)oxy)benzamide

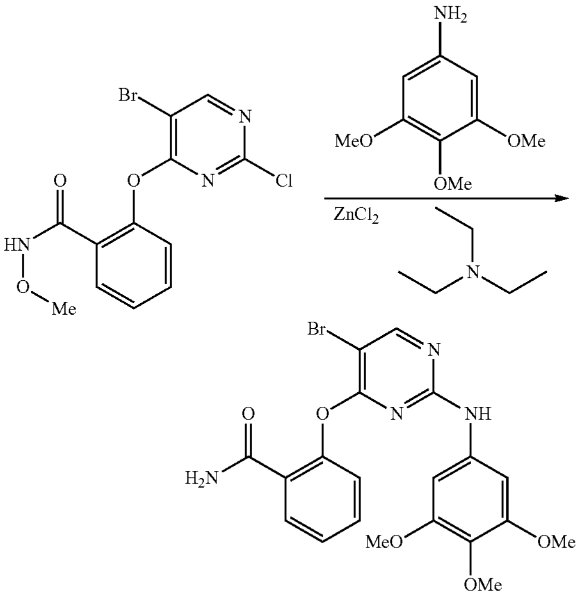

2-((5-Bromo-2-chloropyrimidin-4-yl)oxy)-N-methoxybenzamide (0.179 g, 0.500 mmol) and zinc(II) chloride (0.075 g, 0.550 mmol) were mixed in 1,2-dichloroethane (1 ml) and t-butanol (1.000 ml). After 1 h, added 3,4,5-trimethoxyaniline (0.092 g, 0.500 mmol) and triethylamine (0.070 ml, 0.500 mmol) and microwaved at 80° C. for 20 min and then concentrated. 19 mg of side product was recovered after automated reverse phase chromatography (water-MeCN eluent). MS calcd for $[C_{20}H_{19}BrN_4O_5+H]^+$: 475.06, found 474.90.

Example 250

Preparation of N4-cyclopropyl-N2-(pyrimidin-4-yl)-5-(trifluoromethyl) pyrimidine-2,4-diamine

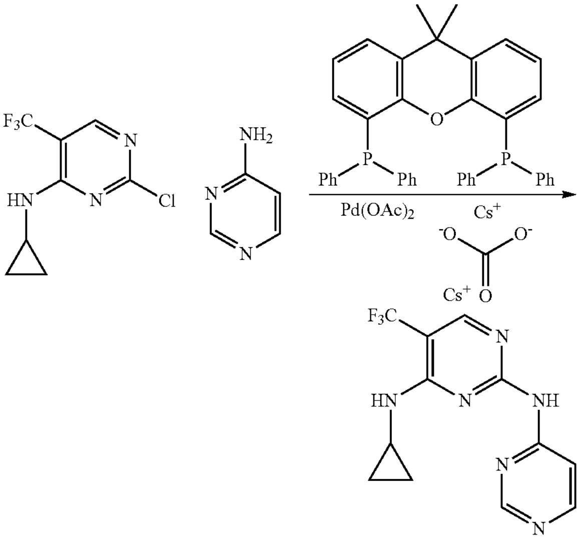

Flame dried flask and stir bar. Bubbled nitrogen through reagents and solvents prior to heating. 2-Chloro-N-cyclopropyl-5-(trifluoromethyl)pyrimidin-4-amine (0.070 g, 0.295 mmol), pyrimidin-4-amine (0.028 g, 0.295 mmol), (9,9-dimethyl-9H-xanthene-4,5-diyl)bis(diphenylphosphane) (0.017 g, 0.029 mmol), diacetoxypalladium (3.31 mg, 0.015 mmol) and cesium carbonate (0.144 g, 0.442 mmol) were mixed in 1,4-dioxane (2 ml). The mixture was microwaved at 140° C. for 20 min. Filtered through Celite with MeOH and then concentrated. 13 mg of product was recovered after automated reverse phase chromatography (water-MeOH eluent). MS calcd for $[C_{12}H_{11}F_3N_6+H]^+$: 297.11, found 297.05.

Example 251

Preparation of 2-((5-bromo-2-chloropyrimidin-4-yl) oxy)-3-methoxy-N-methylbenzamide

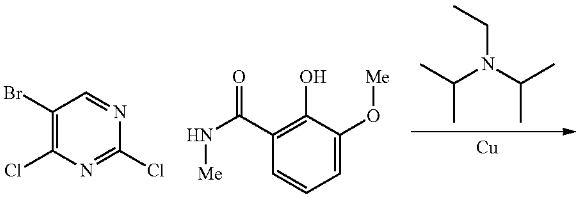

-continued

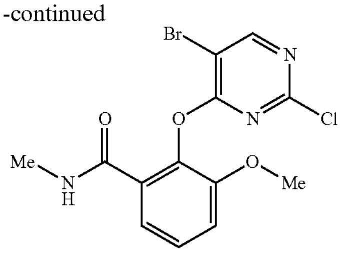

5-Bromo-2,4-dichloropyrimidine (0.150 g, 0.658 mmol), 2-hydroxy-3-methoxy-N-methylbenzamide (0.119 g, 0.658 mmol), N-ethyl-N-isopropylpropan-2-amine (0.115 ml, 0.658 mmol) and copper (4.18 mg, 0.066 mmol) were mixed in DMF (3 ml). The mixture was microwaved at 60° C. for 20 min and then concentrated and used as-is. MS calcd for $[C_{13}H_{11}BrClN_3O_3+H]^+$: 371.98, found 371.70.

Example 252

Preparation of 2-((5-bromo-2-((3,4,5-trimethoxyphenyl)amino)pyrimidin-4-yl)oxy)-3-methoxy-N-methylbenzamide

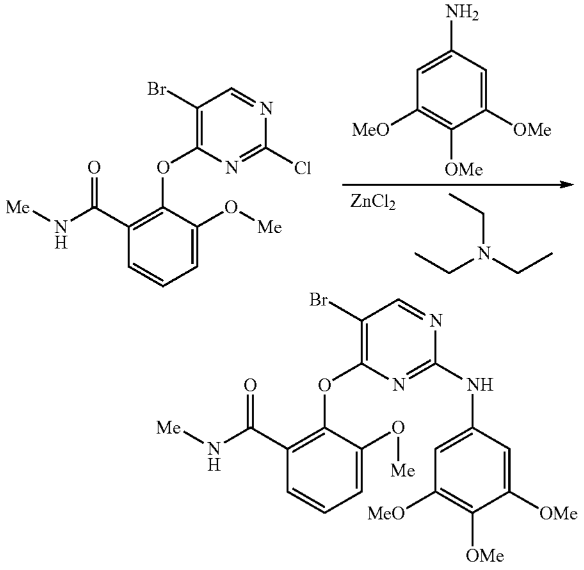

2-((5-Bromo-2-chloropyrimidin-4-yl)oxy)-3-methoxy-N-methylbenzamide (0.220 g, 0.590 mmol) and zinc(II) chloride (0.080 g, 0.590 mmol) were mixed in 1,2-dichloroethane (2 ml) and t-butanol (2.000 ml). After 90 min, 3,4,5-trimethoxyaniline (0.108 g, 0.590 mmol) and triethylamine (0.082 ml, 0.590 mmol) were added. The mixture was microwaved at 120° C. for 20 min and then concentrated. 57 mg of product was recovered after automated reverse phase chromatography (water-MeCN eluent). MS calcd for $[C_{22}H_{23}BrN_4O_6+H]^+$: 519.09, found 519.05.

Example 253

Preparation of N-(2-((5-bromo-2-chloropyrimidin-4-yl)oxy)phenyl)acetamide

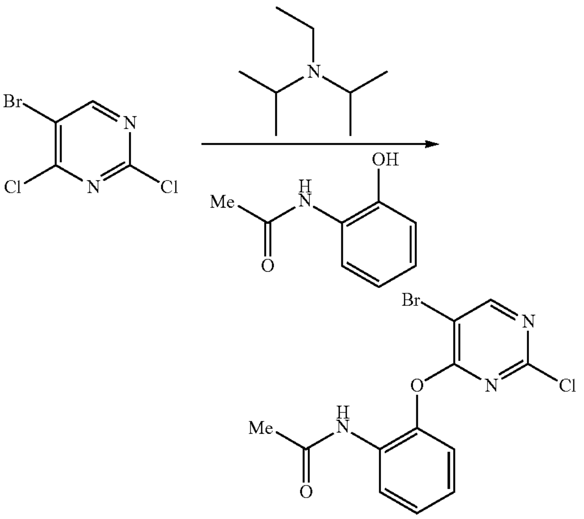

5-Bromo-2,4-dichloropyrimidine (0.150 g, 0.658 mmol), N-ethyl-N-isopropylpropan-2-amine (0.117 ml, 0.658 mmol) and N-(2-hydroxyphenyl)acetamide (0.100 g, 0.658 mmol) were mixed in acetonitrile (3 ml). The mixture was microwaved at 100° C. for 10 min and then concentrated and used as-is. MS calcd for $[C_{12}H_9BrClN_3O_2+H]^+$: 341.97, found 341.60.

Example 254

Preparation of N-(2-((5-bromo-2-((3,4,5-trimethoxyphenyl)amino)pyrimidin-4-yl)oxy)phenyl)acetamide and 4-(2-aminophenoxy)-5-bromo-N-(3,4,5-trimethoxyphenyl) pyrimidin-2-amine

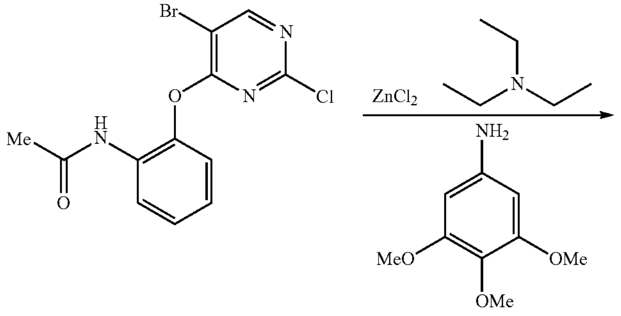

-continued

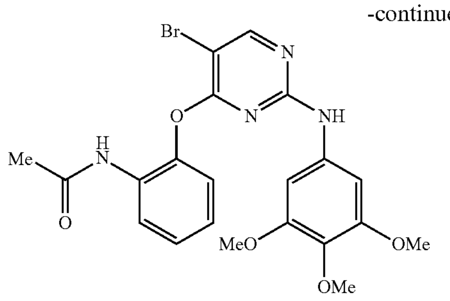

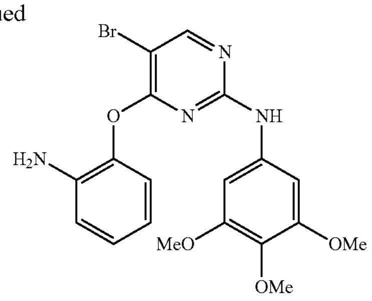

N-(2-((5-Bromo-2-chloropyrimidin-4-yl)oxy)phenyl)acetamide (0.220 g, 0.642 mmol) and zinc(II) chloride (0.088 g, 0.642 mmol) were mixed in 1,2-dichloroethane (2 ml) and t-butanol (2.000 ml). Stirred for 1 h. triethylamine (0.090 ml, 0.642 mmol) and 3,4,5-trimethoxyaniline (0.118 g, 0.642 mmol) were added. The mixture was microwaved at 100° C. for 20 min and then concentrated and purified first by normal phase chromatography on silica gel (DCM-EtOAc), then by automated reverse phase chromatography (water-MeCN eluent) to give 43 mg of N-(2-((5-bromo-2-((3,4,5-trimethoxyphenyl)amino)pyrimidin-4-yl)oxy)phenyl)acetamide and 39 mg of 4-(2-aminophenoxy)-5-bromo-N-(3,4,5-trimethoxyphenyl)pyrimidin-2-amine. MS calcd for $[C_{21}H_{21}BrN_4O_5+H]^+$: 489.08, found 488.95. MS calcd for $[C_{19}H_{19}BrN_4O_4+H]^+$: 447.07, found 446.90.

Example 255

Preparation of 2-((4-(cyclopropylamino)-5-(trifluoromethyl)pyrimidin-2-yl)amino)phenol

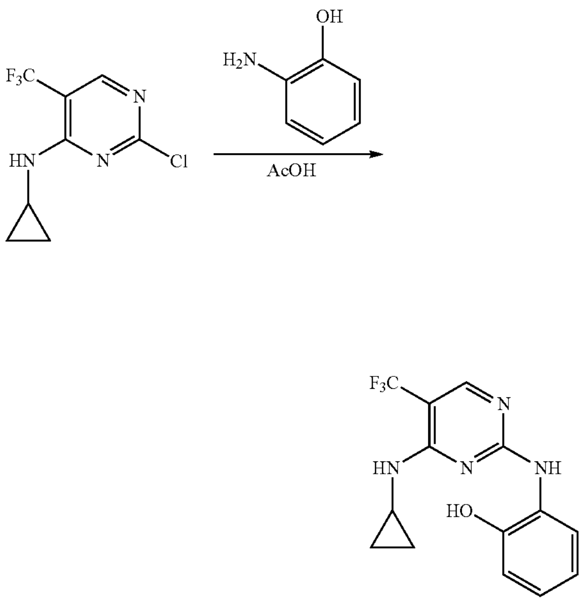

2-Chloro-N-cyclopropyl-5-(trifluoromethyl)pyrimidin-4-amine (0.060 g, 0.253 mmol) and 2-aminophenol (0.028 g, 0.253 mmol) were mixed in acetic acid (1 ml). The mixture was microwaved at 110° C. for 20 min and then concentrated. Added EtOAc and filtered the solid to give 57 mg of product. MS calcd for $[C_{14}H_{13}F_3N_4O+H]^+$: 311.11, found 311.15.

Example 256

Preparation of 2-((5-bromo-2-chloropyrimidin-4-yl)oxy)-6-hydroxy-N-methylbenzamide

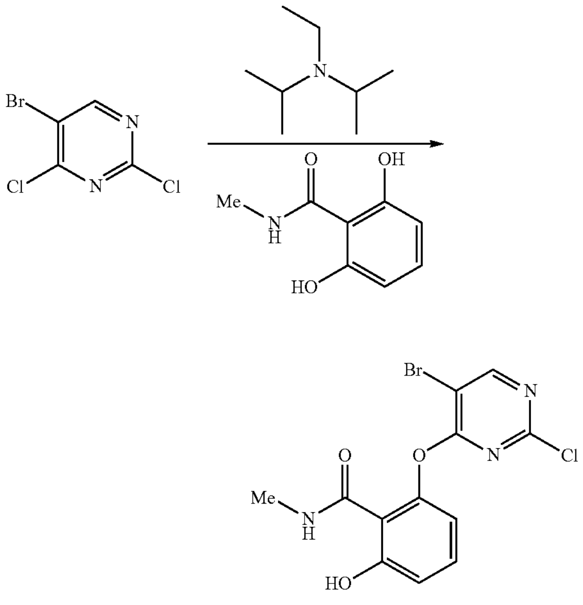

5-Bromo-2,4-dichloropyrimidine (0.150 g, 0.658 mmol), N-ethyl-N-isopropylpropan-2-amine (0.115 ml, 0.658 mmol) and 2,6-dihydroxy-N-methylbenzamide (0.110 g, 0.658 mmol) were mixed in acetonitrile (2 ml). The mixture was microwaved at 100° C. for 10 min and then concentrated and used as-is. MS calcd for $[C_{12}H_9BrClN_3O_3+H]^+$: 357.96, found 357.70.

Example 257

Preparation of 2-((5-bromo-2-((3,4,5-trimethoxyphenyl)amino)pyrimidin-4-yl)oxy)-6-hydroxy-N-methylbenzamide

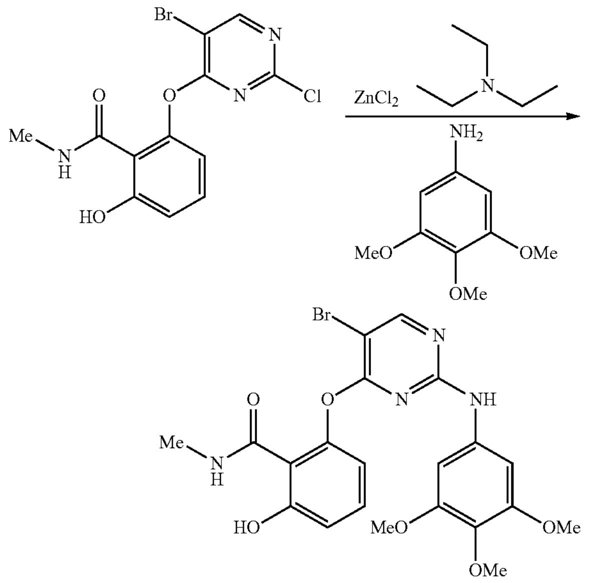

2-((5-Bromo-2-chloropyrimidin-4-yl)oxy)-6-hydroxy-N-methylbenzamide (0.143 g, 0.400 mmol) and zinc(II) chloride (0.055 g, 0.400 mmol) were mixed in 1,2-dichloroethane (1 ml) and t-butanol (1.000 ml). After 1 h, triethylamine (0.056 ml, 0.400 mmol) and 3,4,5-trimethoxyaniline (0.073 g, 0.400 mmol) were added. The mixture was microwaved at 100° C. for 10 min and then concentrated and purified first by normal phase chromatography on silica gel (DCM-EtOAc), then by automated reverse phase chromatography (water-10% THF in MeCN) to give 41 mg of product. MS calcd for $[C_{21}H_{21}BrN_4O_6+H]^+$: 505.07, found 504.95.

Example 258

Preparation of N4-cyclopropyl-N2-(2,2-difluorobenzo[d][1,3]dioxol-5-yl)-5-(trifluoromethyl)pyrimidine-2,4-diamine

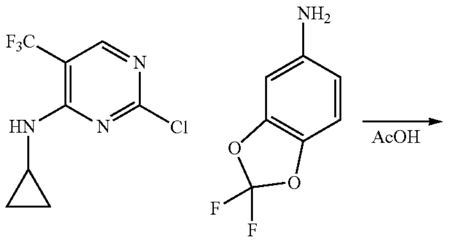

-continued

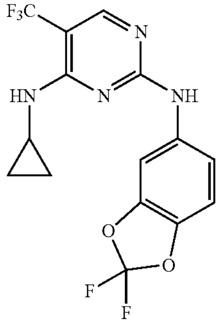

2-Chloro-N-cyclopropyl-5-(trifluoromethyl)pyrimidin-4-amine (0.050 g, 0.210 mmol) and 2,2-difluorobenzo[d][1,3]dioxol-5-amine (0.036 g, 0.210 mmol) were mixed in acetic acid (1 ml). The mixture was microwaved at 110° C. for 10 min and then concentrated. 35 mg of product was recovered after normal phase chromatography on silica gel (DCM). MS calcd for $[C_{15}H_{11}F_4N_4O_2+H]^+$: 375.09, found 375.20.

Example 259

Preparation of 1-(2-((5-bromo-2-chloropyrimidin-4-yl)oxy)phenyl)propan-1-one

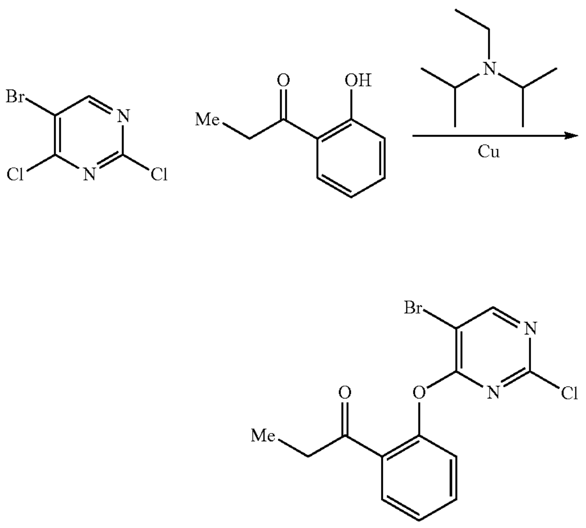

5-Bromo-2,4-dichloropyrimidine (0.150 g, 0.658 mmol), 1-(2-hydroxyphenyl)propan-1-one (0.099 g, 0.658 mmol), N-ethyl-N-isopropylpropan-2-amine (0.115 ml, 0.658 mmol) and copper (4.18 mg, 0.066 mmol) were mixed in DMF (3 ml). The mixture was microwaved at 80° C. for 10 min and then concentrated and used as-is. MS calcd for $[C_{13}H_{10}BrClN_2O_2+H]^+$: 340.97, found 340.65.

Example 260

Preparation of 1-(2-((5-bromo-2-((3,4,5-trimethoxyphenyl)amino)pyrimidin-4-yl)oxy)phenyl)propan-1-one

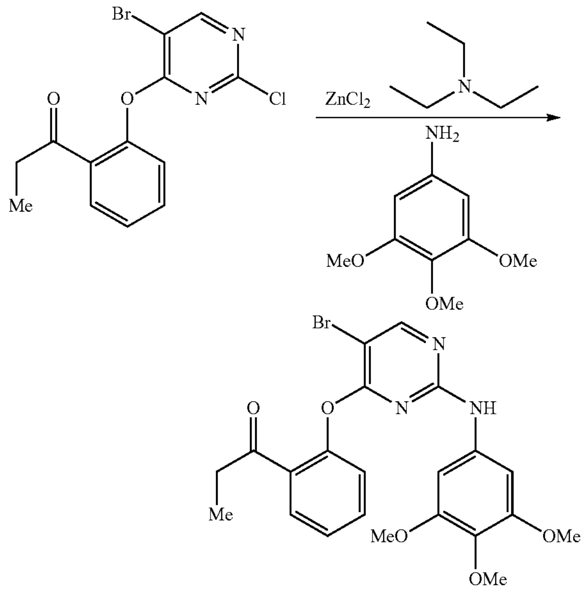

1-(2-((5-Bromo-2-chloropyrimidin-4-yl)oxy)phenyl)propan-1-one (0.200 g, 0.585 mmol) and zinc(II) chloride (0.080 g, 0.585 mmol) were mixed in 1,2-dichloroethane (2 ml) and t-butanol (1 ml). The mixture was microwaved at 100° C. for 10 min. 34 mg of product was recovered after automated reverse phase chromatography (water-10% THF/MeCN). MS calcd for $[C_{22}H_{22}BrN_3O_5+H]^+$: 488.08 found 487.90.

Example 261

Preparation of benzyl (2-((2-((2-oxo-1,2,3,4-tetrahydroquinolin-6-yl)amino)-5-(trifluoromethyl)pyrimidin-4-yl)oxy)ethyl)carbamate

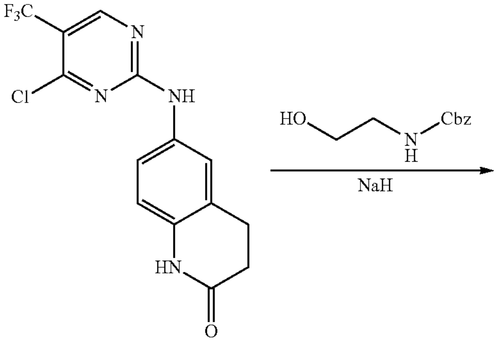

-continued

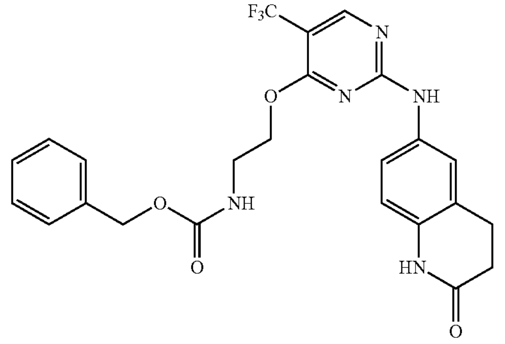

6-((4-Chloro-5-(trifluoromethyl)pyrimidin-2-yl)amino)-3,4-dihydroquinolin-2(1H)-one (0.120 g, 0.350 mmol), benzyl (2-hydroxyethyl)carbamate (0.068 g, 0.350 mmol) and sodium hydride (0.017 g, 0.420 mmol) were mixed in DMF (2 ml). The mixture was microwaved at 100° C. for 10 min and then concentrated. 4 mg of product was recovered after reverse phase HPLC (water-MeCN). MS calcd for $[C_{24}H_{22}F_3N_5O_4+H]^+$: 502.17 found 502.30.

Example 262

Preparation of N4-cyclopropyl-N2-(naphthalen-1-ylmethyl)-5-(trifluoromethyl)pyrimidine-2,4-diamine

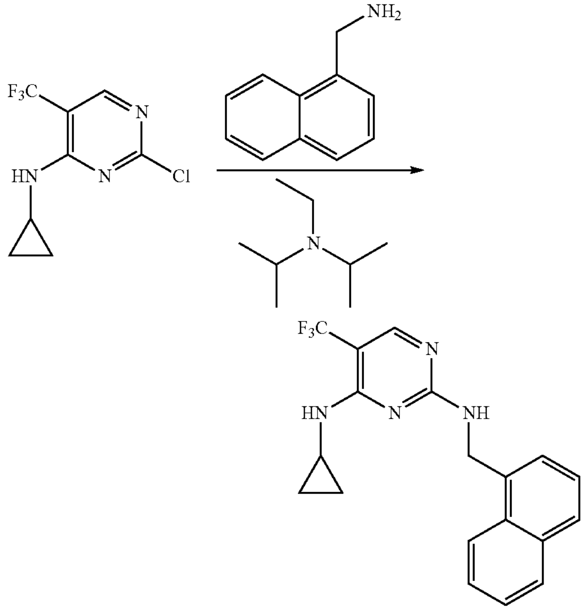

2-Chloro-N-cyclopropyl-5-(trifluoromethyl)pyrimidin-4-amine (0.055 g, 0.231 mmol), naphthalen-1-ylmethanamine (0.036 g, 0.231 mmol) and N-ethyl-N-isopropylpropan-2-amine (0.044 ml, 0.255 mmol) were mixed in DMF (2 ml). The mixture was microwaved at 130° C. for 20 min and then concentrated. Added 50% MeCN in water and filtered the solid to give 32 mg of product. MS calcd for $[C_{19}H_{17}F_3N_4+H]^+$: 359.15 found 359.40.

Example 263

Preparation of 6-((4-(cyclopropylamino)quinazolin-2-yl)amino)-3,4-dihydroquinolin-2(1H)-one

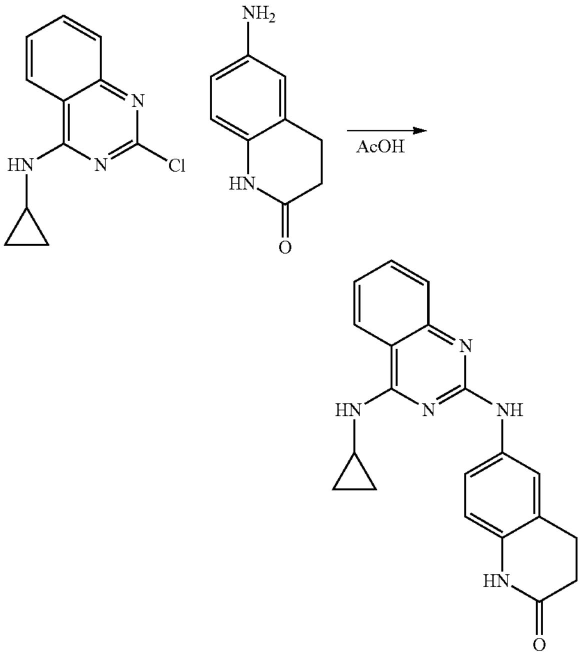

2-Chloro-N-cyclopropylquinazolin-4-amine (0.055 g, 0.250 mmol) and 6-amino-3,4-dihydroquinolin-2(1H)-one (0.041 g, 0.250 mmol) were mixed in acetic acid (1 ml). The mixture was microwaved at 110° C. for 10 min and then concentrated. Added acetone and filtered the solid to give 80 mg of product. MS calcd for $[C_{20}H_{19}N_5O+H]^+$: 346.17 found 346.30.

Example 264

Preparation of N4-cyclopropyl-N2-(quinolin-6-yl)-5-(trifluoromethyl) pyrimidine-2,4-diamine

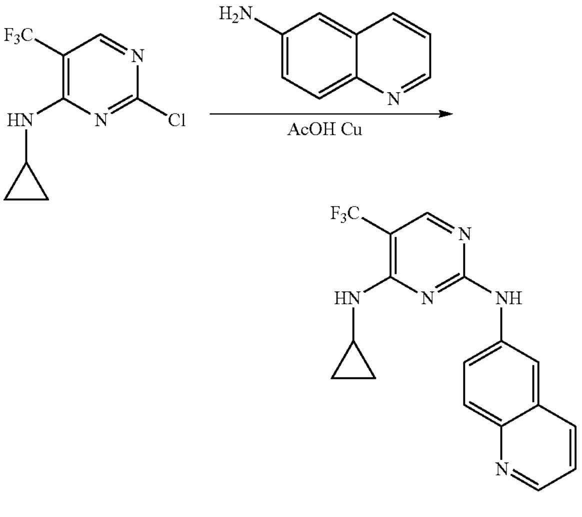

2-Chloro-N-cyclopropyl-5-(trifluoromethyl)pyrimidin-4-amine (0.060 g, 0.253 mmol), copper (1.605 mg, 0.025 mmol) and quinolin-6-amine (0.036 g, 0.253 mmol) were mixed in acetic acid (2 ml). The mixture was microwaved at 120° C. for 10 min and then concentrated. Added acetone and filtered the solid. 7 mg of product was recovered after automated reverse phase chromatography (water-MeCN) on the filtrate. MS calcd for $[C_{17}H_{14}F_3N_5+H]^+$: 346.13 found 345.95.

Example 265

Preparation of 5-bromo-2-chloro-4-phenoxypyrimidine

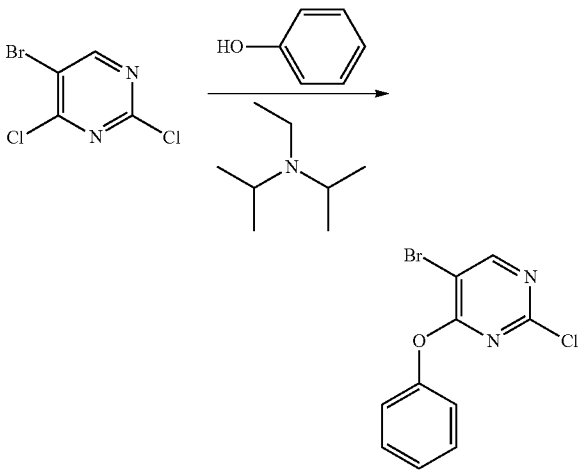

5-Bromo-2,4-dichloropyrimidine (0.150 g, 0.658 mmol), phenol (0.062 g, 0.658 mmol) and N-ethyl-N-isopropylpropan-2-amine (0.126 ml, 0.724 mmol) were mixed in DMF (3 ml). The mixture was microwaved at 100° C. for 10 min and then concentrated and used as-is. MS calcd for $[C_{10}H_6BrClN_2O+H]^+$: 284.95 found 284.50.

Example 266

Preparation of 5-bromo-4-phenoxy-N-(3,4,5-trimethoxyphenyl)pyrimidin-2-amine

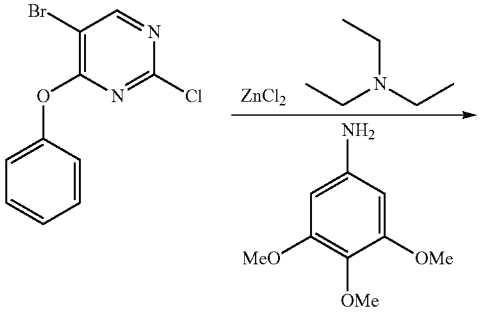

-continued

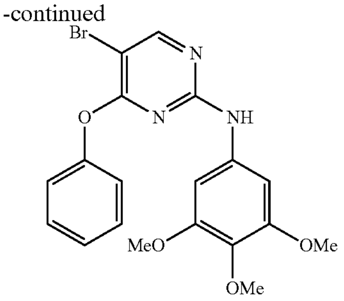

5-Bromo-2-chloro-4-phenoxypyrimidine (0.180 g, 0.630 mmol) and zinc(II) chloride (0.086 g, 0.630 mmol) were mixed in 1,2-dichloroethane (2 ml) and t-butanol (1 ml). After 40 min, triethylamine (0.097 ml, 0.693 mmol) and 3,4,5-trimethoxyaniline (0.115 g, 0.630 mmol) were added. The mixture was microwaved at 100° C. for 10 min and then concentrated. 78 mg of product was recovered after normal phase chromatography on silica gel (EtOAc-DCM). MS calcd for $[C_{19}H_{18}BrN_3O_4+H]^+$: 432.06, found 431.90.

Example 267

Preparation of 3-((5-bromo-2-chloropyrimidin-4-yl)oxy)-N-methylbenzamide

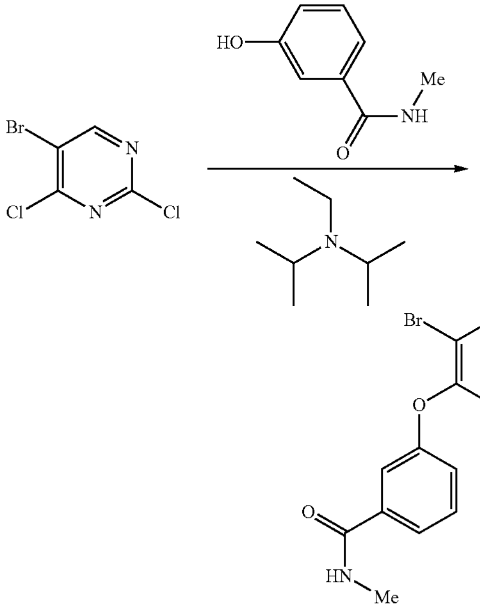

5-Bromo-2,4-dichloropyrimidine (0.150 g, 0.658 mmol), 3-hydroxy-N-methylbenzamide (0.100 g, 0.658 mmol) and N-ethyl-N-isopropylpropan-2-amine (0.126 ml, 0.724 mmol) were mixed in acetonitrile (3 ml). The mixture was microwaved at 100° C. for 10 min and then concentrated and used as-is. MS calcd for $[C_{12}H_9BrClN_3O_2+H]^+$: 341.97, found 341.70.

Example 268

Preparation of 3-((5-bromo-2-((2-oxo-1,2,3,4-tetrahydroquinolin-6-yl)amino)pyrimidin-4-yl)oxy)-N-methylbenzamide

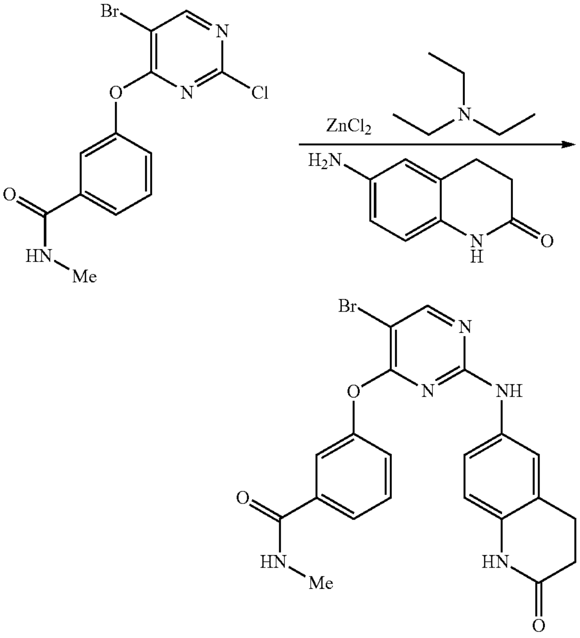

3-((5-Bromo-2-chloropyrimidin-4-yl)oxy)-N-methylbenzamide (0.075 g, 0.219 mmol) and zinc(II) chloride (0.030 g, 0.219 mmol) were mixed in 1,2-dichloroethane (4 ml) and t-butanol (1 ml). After 30 min, triethylamine (0.034 ml, 0.241 mmol) and 6-amino-3,4-dihydro quinolin-2(1H)-one (0.036 g, 0.219 mmol) were added. The mixture was microwaved at 140° C. for 20 min and then concentrated. 11 mg of product was recovered after automated reverse phase chromatography (water-MeCN). MS calcd for $[C_{21}H_{18}BrN_5O_3+H]^+$: 468.07 found 467.90.

Example 269

Preparation of 2-((5-bromo-2-chloropyrimidin-4-yl)oxy)-N-cyclopropyl benzamide

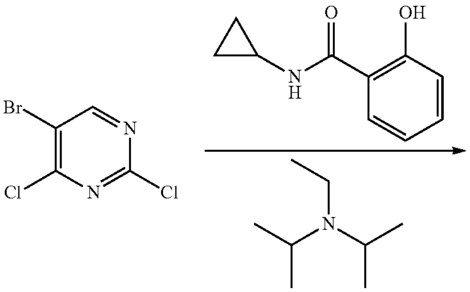

-continued

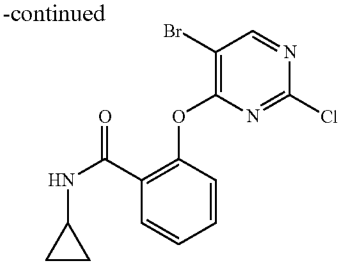

5-Bromo-2,4-dichloropyrimidine (0.150 g, 0.658 mmol), N-cyclopropyl-2-hydroxy benzamide (0.117 g, 0.658 mmol) and N-ethyl-N-isopropylpropan-2-amine (0.126 ml, 0.724 mmol) were mixed in acetonitrile (3 ml). The mixture was microwaved at 100° C. for 10 min and then concentrated and used as-is. MS calcd for $[C_{14}H_{11}BrClN_3O_2+H]^+$: 367.98 found 367.70.

Example 270

Preparation of 2-((5-bromo-2-((3,4,5-trimethoxyphenyl)amino)pyrimidin-4-yl)oxy)-N-cyclopropylbenzamide

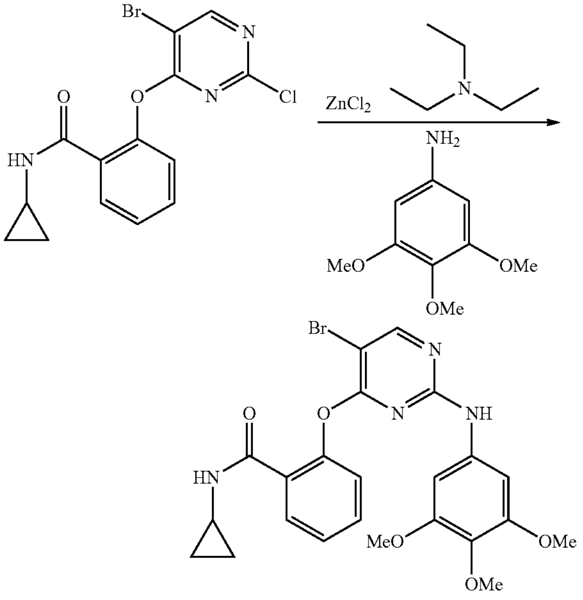

2-((5-Bromo-2-chloropyrimidin-4-yl)oxy)-N-cyclopropylbenzamide (0.230 g, 0.624 mmol) and zinc(II) chloride (0.085 g, 0.624 mmol) were mixed in 1,2-dichloroethane (3 ml) and t-butanol (0.5 ml). triethylamine (0.096 ml, 0.686 mmol) and 3,4,5-trimethoxyaniline (0.114 g, 0.624 mmol) were added. The mixture was microwaved at 120° C. for 20 min and then concentrated. 67 mg of product was recovered after automated reverse phase chromatography (water-MeCN). MS calcd for $[C_{23}H_{23}BrN_4O_5+H]^+$: 515.10 found 515.05.

Example 271

Preparation of 6-((4-((5-cyclobutyl-1H-pyrazol-3-yl)amino)-5-(trifluoromethyl)pyrimidin-2-yl)amino)-3,4-dihydroquinolin-2(1H)-one

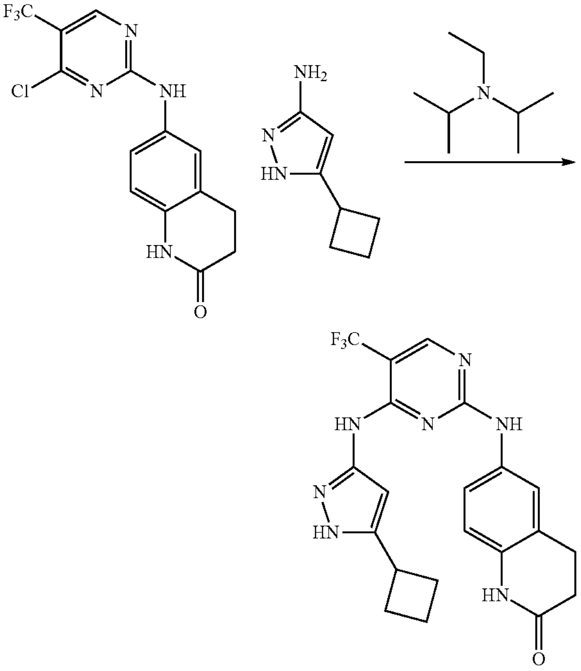

6-((4-Chloro-5-(trifluoromethyl)pyrimidin-2-yl)amino)-3,4-dihydroquinolin-2(1H)-one (0.060 g, 0.175 mmol), 5-cyclobutyl-1H-pyrazol-3-amine (0.024 g, 0.175 mmol) and N-ethyl-N-isopropylpropan-2-amine (0.034 ml, 0.193 mmol) were mixed in DMF (2 ml). The mixture was microwaved at 130° C. for 30 min and then concentrated. 14 mg of product was recovered after automated reverse phase chromatography (water-10% THF in MeCN). MS calcd for $[C_{21}H_{20}F_3N_7O+H]^+$: 444.18 found 444.15.

Example 272

Preparation of 5-bromo-4-chloro-N-(3,4,5-trimethoxyphenyl)pyrimidin-2-amine

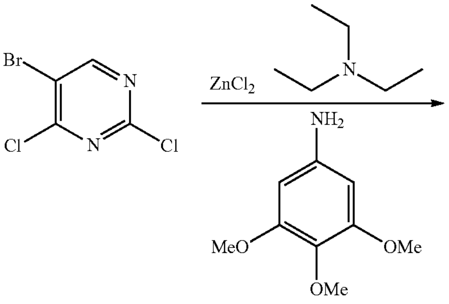

-continued

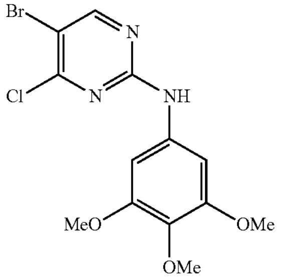

5-Bromo-2,4-dichloropyrimidine (1.5 g, 6.58 mmol) and zinc(II) chloride (0.897 g, 6.58 mmol) were mixed in 1,2-dichloroethane (8 ml) and t-butanol (2 ml). After 30 min, triethylamine (1.009 ml, 7.24 mmol) and 3,4,5-trimethoxyaniline (1.206 g, 6.58 mmol) were added. The mixture was microwaved at 80° C. for 10 min and then concentrated and used as-is. MS calcd for $[C_{13}H_{13}BrClN_3O_3+H]^+$: 373.99, found 373.75.

Example 273

Preparation of 5-bromo-2-chloro-4-(2-(methoxymethyl)phenoxy)pyrimidine

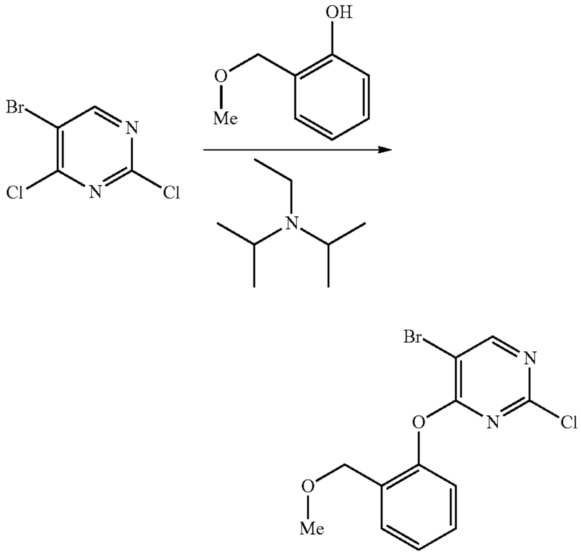

5-Bromo-2,4-dichloropyrimidine (0.150 g, 0.658 mmol), 2-(methoxymethyl)phenol (0.091 g, 0.658 mmol) and N-ethyl-N-isopropylpropan-2-amine (0.115 ml, 0.658 mmol) were mixed in acetonitrile (3 ml). The mixture was microwaved at 80° C. for 10 min and then concentrated and used as-is. MS calcd for $[C_{12}H_{10}BrClN_2O_2+H]^+$: 328.97, found 328.70.

Example 274

Preparation of 5-bromo-4-(2-(methoxymethyl)phenoxy)-N-(3,4,5-trimethoxyphenyl)pyrimidin-2-amine

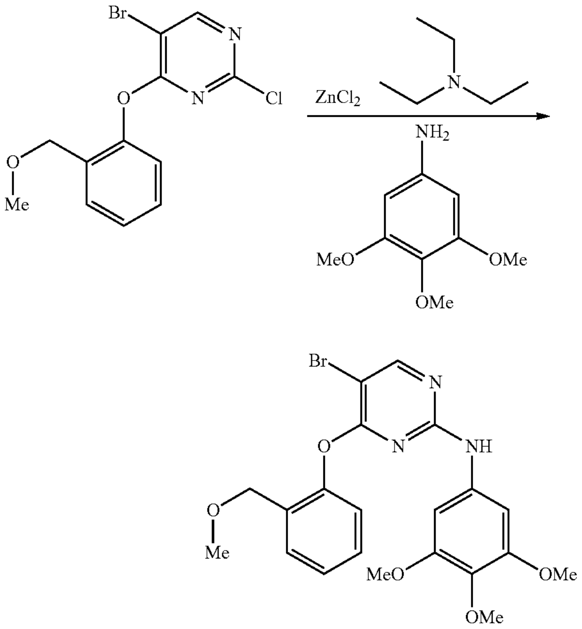

5-Bromo-2-chloro-4-(2-(methoxymethyl)phenoxy)pyrimidine (0.200 g, 0.607 mmol) and zinc(II) chloride (0.083 g, 0.607 mmol) were mixed in 1,2-dichloroethane (3 ml) and t-butanol (1.00 ml). After 15 min, triethylamine (0.093 ml, 0.668 mmol) and 3,4,5-trimethoxyaniline (0.111 g, 0.607 mmol) were added. The mixture was microwaved at 120° C. for 20 min and then concentrated. 27 mg of product was recovered after automated reverse phase chromatography (water-10% THF in MeCN). MS calcd for $[C_{21}H_{22}BrN_3O_5+H]^+$: 476.08 found 475.95.

Example 275

Preparation of N4-cyclopropyl-N2-(quinolin-3-yl)-5-(trifluoromethyl) pyrimidine-2,4-diamine

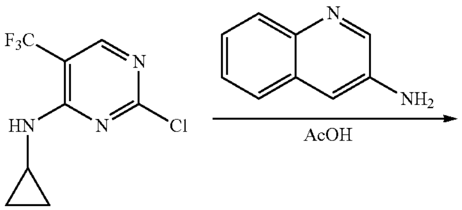

-continued

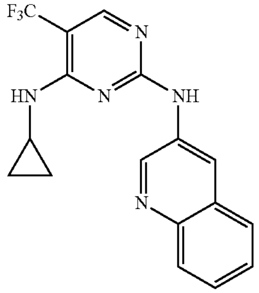

2-Chloro-N-cyclopropyl-5-(trifluoromethyl)pyrimidin-4-amine (0.060 g, 0.253 mmol) and quinolin-3-amine (0.036 g, 0.253 mmol) were mixed in acetic acid (1 ml). The mixture was microwaved at 120° C. for 20 min and then concentrated. Added acetone and filtered solid impurity. 8 mg of product was recovered after automated reverse phase chromatography (water-MeCN) on the filtrate. MS calcd for $[C_{17}H_{14}FN_5+H]^+$: 346.13 found 345.80.

Example 276

Preparation of (2-((5-bromo-2-chloropyrimidin-4-yl)oxy)phenyl)(pyrrolidin-1-yl)methanone

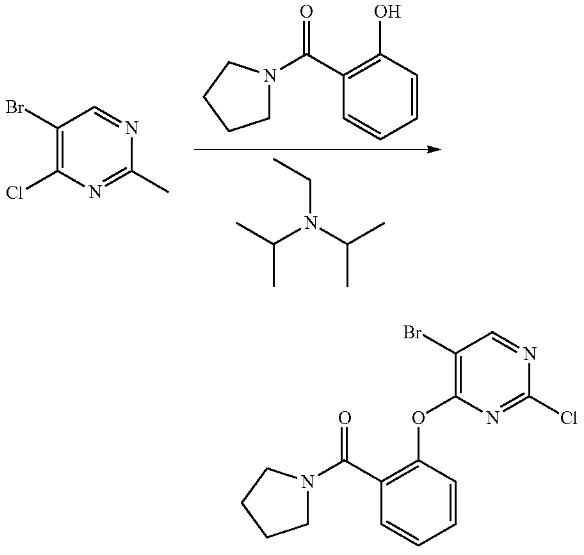

5-Bromo-2,4-dichloropyrimidine (0.150 g, 0.658 mmol), (2-hydroxyphenyl)(pyrrolidin-1-yl)methanone (0.126 g, 0.658 mmol) and N-ethyl-N-isopropylpropan-2-amine (0.126 ml, 0.724 mmol) were mixed in acetonitrile (3 ml). The mixture was microwaved at 100° C. for 20 min and then concentrated and used as-is. MS calcd for $[C_{15}H_{13}BrClN_3O_2+H]^+$: 382.00, found 381.70.

Example 277

Preparation of (2-((5-bromo-2-((3,4,5-trimethoxyphenyl)amino)pyrimidin-4-yl)oxy)phenyl)(pyrrolidin-1-yl)methanone

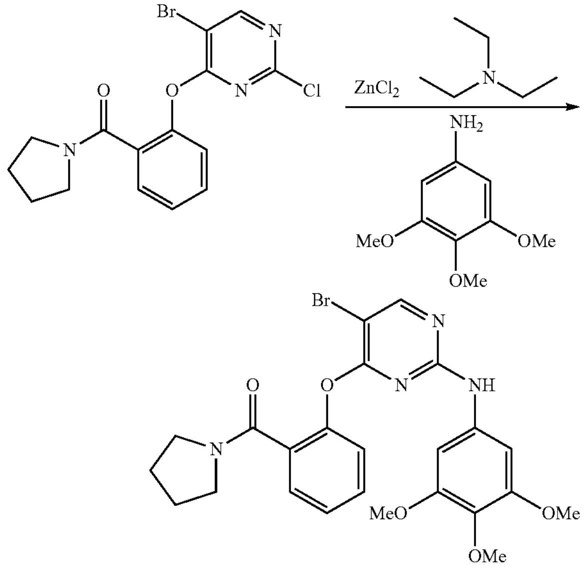

(2-((5-Bromo-2-chloropyrimidin-4-yl)oxy)phenyl)(pyrrolidin-1-yl)methanone (0.200 g, 0.523 mmol) and zinc(II) chloride (0.071 g, 0.523 mmol) were mixed in 1,2-dichloroethane (3 ml) and t-butanol (1 ml). triethylamine (0.080 ml, 0.575 mmol) and 3,4,5-trimethoxyaniline (0.096 g, 0.523 mmol) were added. The mixture was microwaved at 120° C. for 20 min and then concentrated. 66 mg of product was recovered after automated reverse phase chromatography (water-MeCN). MS calcd for $[C_{24}H_{25}BrN_4O_5+H]^+$: 529.11 found 529.00.

Example 278

Preparation of N4-cyclopropyl-N2-(quinolin-5-yl)-5-(trifluoromethyl) pyrimidine-2,4-diamine

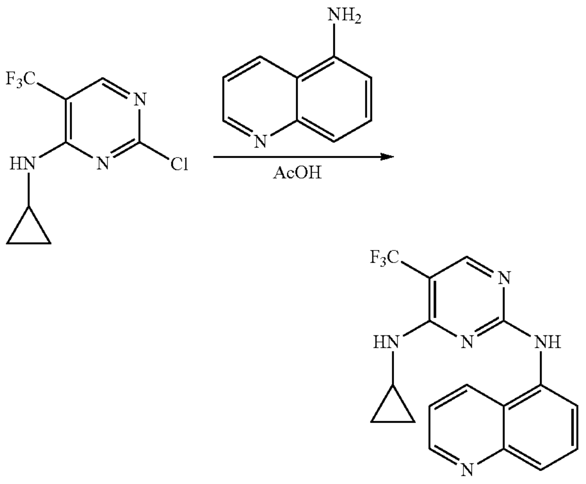

2-Chloro-N-cyclopropyl-5-(trifluoromethyl)pyrimidin-4-amine (0.060 g, 0.253 mmol), quinolin-5-amine (0.036 g, 0.253 mmol) and acetic acid (0.015 g, 0.253 mmol) were mixed in acetic acid (1 ml). The mixture was microwaved at 120° C. for 20 min and then concentrated. Added acetone and filtered the solid to give 42 mg of product. MS calcd for $[C_{17}H_{14}F_3N_5+H]^+$: 346.13 found 345.80.

Example 279

Preparation of N-(2-hydroxyphenyl)cyclopropanecarboxamide

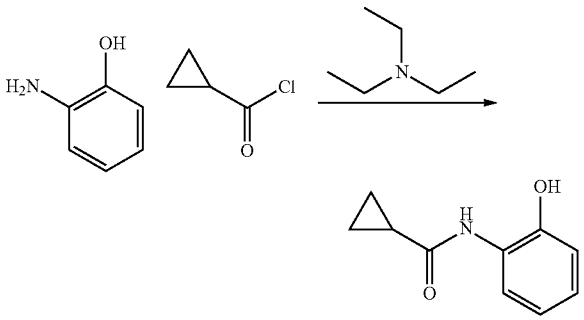

2-Aminophenol (3 g, 27.5 mmol), cyclopropanecarbonyl chloride (2.87 g, 27.5 mmol) and triethylamine (4.21 ml, 30.2 mmol) were mixed in tetrahydrofuran (30 ml). Heated to 40° C. for 8 h and then concentrated. Flash chromatography on silica gel (hexanes-EtOAc/DCM) was used to purify the material. The doubly acylated compound (245 amu) contaminated the desired product after purification. The material was used despite this impurity. MS calcd for $[C_{10}H_{11}NO_2+H]^+$: 178.09 found 177.85.

Example 280

Preparation of N-(2-((5-bromo-2-chloropyrimidin-4-yl)oxy)phenyl) cyclopropanecarboxamide

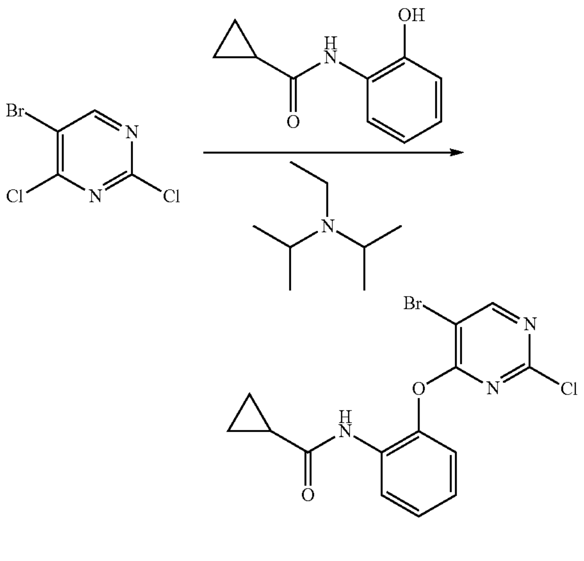

5-Bromo-2,4-dichloropyrimidine (0.150 g, 0.658 mmol), N-(2-hydroxyphenyl) cyclopropanecarboxamide (0.117 g, 0.658 mmol) and N-ethyl-N-isopropylpropan-2-amine (0.126 ml, 0.724 mmol) were mixed in acetonitrile (3 ml). The mixture was microwaved at 100° C. for 20 min and then concentrated and used as-is. MS calcd for $[C_{14}H_{11}BrClN_3O_2+H]^+$: 367.98 found 367.70.

Example 281

Preparation of N-(2-((5-bromo-2-((3,4,5-trimethoxyphenyl)amino)pyrimidin-4-yl)oxy)phenyl)cyclopropanecarboxamide

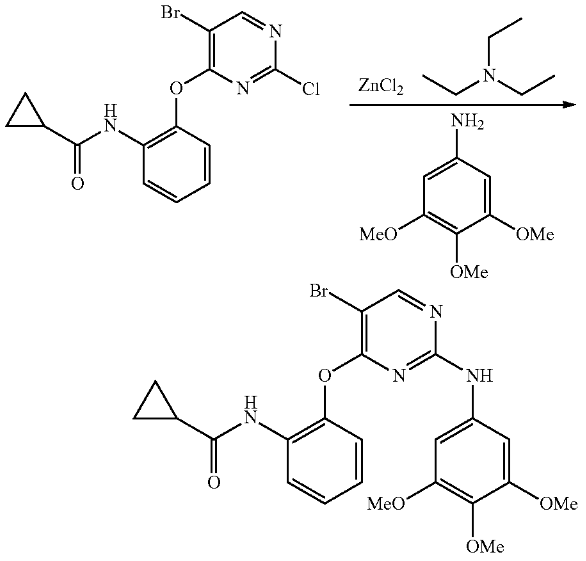

N-(2-((5-Bromo-2-chloropyrimidin-4-yl)oxy)phenyl)cyclopropanecarboxamide (0.220 g, 0.597 mmol) and zinc(II) chloride (0.081 g, 0.597 mmol) were mixed in 1,2-dichloroethane (3 ml) and t-butanol (1 ml). After 2 h, triethylamine (0.092 ml, 0.657 mmol) and 3,4,5-trimethoxy aniline (0.109 g, 0.597 mmol) were added. The mixture was microwaved at 130° C. for 20 min and then concentrated. MS calcd for $[C_{23}H_{23}BrN_4O_5+H]^+$: 515.10 found 515.00.

Example 282

Preparation of 1-(2-((5-bromo-2-chloropyrimidin-4-yl)oxy)phenyl)-N,N-dimethylmethanamine

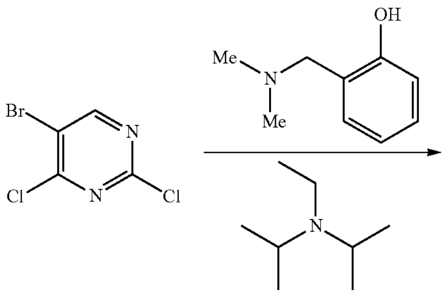

-continued

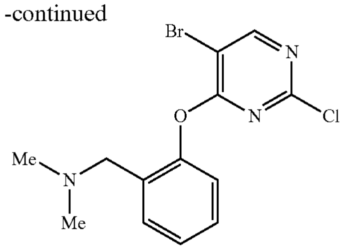

5-Bromo-2,4-dichloropyrimidine (0.150 g, 0.658 mmol), 2-((dimethylamino)methyl) phenol (0.100 g, 0.658 mmol) and N-ethyl-N-isopropylpropan-2-amine (0.126 ml, 0.724 mmol) were mixed in acetonitrile (3 ml). The mixture was microwaved at 70° C. for 10 min and then concentrated and used as-is. MS calcd for $[C_{13}H_{13}BrClN_3O+H]^+$: 342.00 found 341.65.

Example 283

Preparation of 5-bromo-4-(2-((dimethylamino) methyl)phenoxy)-N-(3,4,5-trimethoxyphenyl)pyrimidin-2-amine

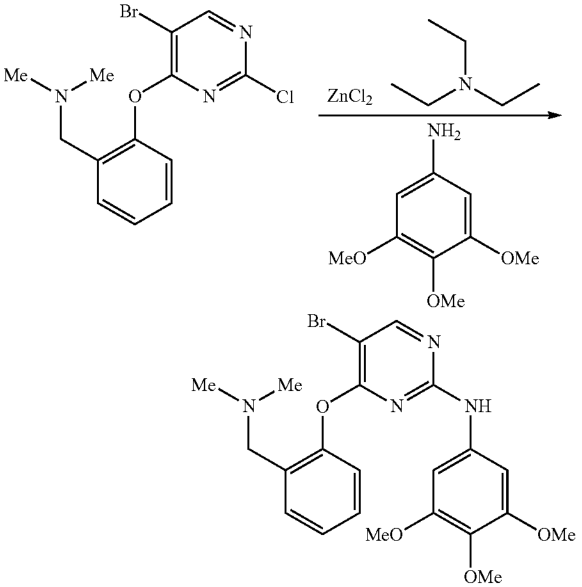

1-(2-((5-Bromo-2-chloropyrimidin-4-yl)oxy)phenyl)-N, N-dimethylmethanamine (0.170 g, 0.496 mmol) and zinc(II) chloride (0.068 g, 0.496 mmol) were mixed in 1,2-dichloroethane (3 ml) and t-butanol (1 ml). After 20 min, triethylamine (0.076 ml, 0.546 mmol) and 3,4,5-trimethoxyaniline (0.091 g, 0.496 mmol) were added. The mixture was microwaved at 120° C. for 20 min and then concentrated. Flash chromatography on silica gel (DCM) was used first to partially purify the material, then 5 mg were recovered after automated reverse phase chromatography (water-MeCN) on that semipure material. MS calcd for $[C_{24}H_{25}BrN_4O_5+H]^+$: 529.11 found 529.00.

Example 284

Preparation of 5-bromo-4-ethoxy-N-(3,4,5-trimethoxyphenyl)pyrimidin-2-amine

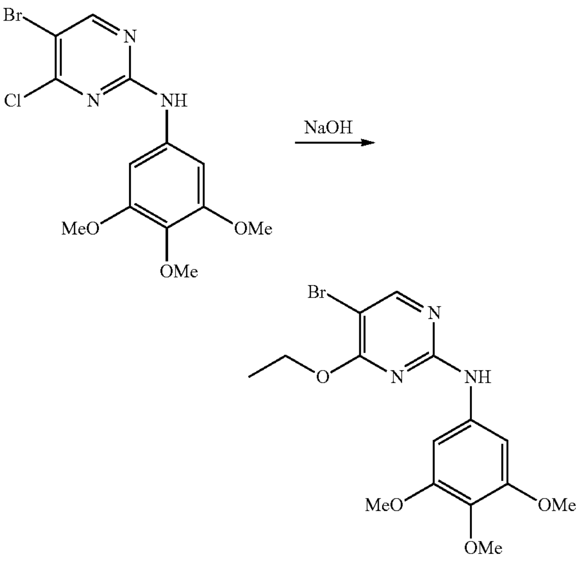

5-Bromo-4-chloro-N-(3,4,5-trimethoxyphenyl)pyrimidin-2-amine (2.3 g, 6.14 mmol) and sodium hydroxide (10.23 mL, 30.7 mmol) were mixed in water (1 mL) and ethanol (10 ml). Heated to 100° C. for 8 h, then kept at 23° C. for 6 d. Added ammonium chloride solution to neutralize, then removed organic solvent by rotovap. Filtered solid and washed with water. 60 mg of the solid was purified by flash chromatography on silica gel (DCM-EtOAc) to give 41 mg of product. MS calcd for $[C_{15}H_{18}BrN_3O_4+H]^+$: 384.06 found 383.90.

Example 285

Preparation of 2-chloro-4-(cyclopropylamino)pyrimidine-5-carboxylic acid

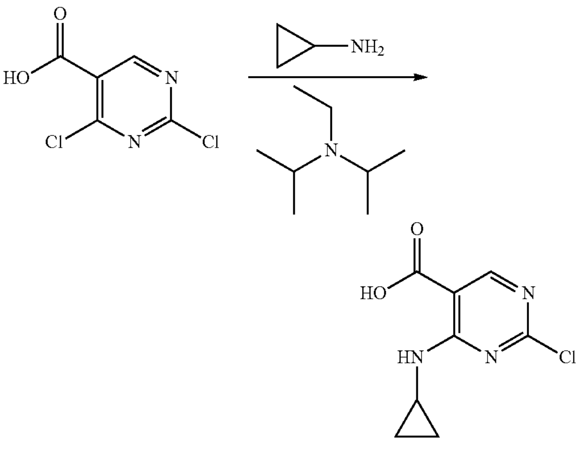

2,4-Dichloropyrimidine-5-carboxylic acid (0.100 g, 0.518 mmol), cyclopropanamine (0.036 ml, 0.518 mmol) and N-ethyl-N-isopropylpropan-2-amine (0.099 ml, 0.570 mmol) were mixed in DMF (2 ml). The mixture was microwaved at 70° C. for 10 min and then concentrated and used as-is. MS calcd for $[C_8H_8ClN_3O_2+H]^+$: 214.04 found 213.65.

Example 286

Preparation of 4-(cyclopropylamino)-2-((2-oxo-1,2,3,4-tetrahydroquinolin-6-yl)amino)pyrimidine-5-carboxylic acid

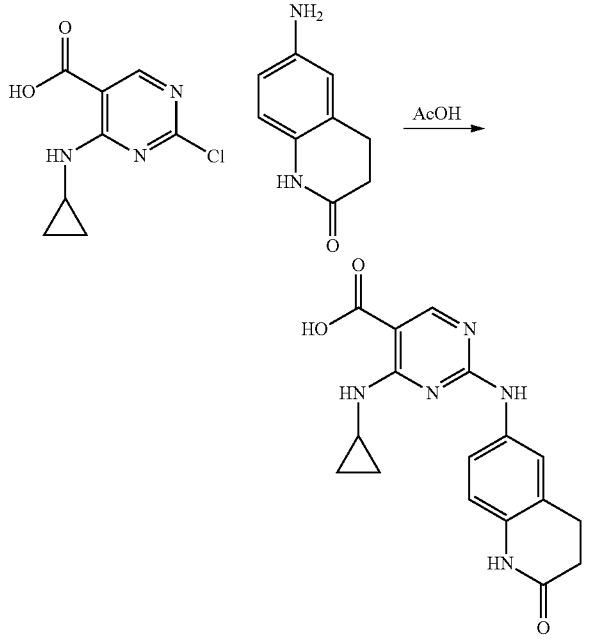

2-Chloro-4-(cyclopropylamino)pyrimidine-5-carboxylic acid (0.100 g, 0.468 mmol) and 6-amino-3,4-dihydroquinolin-2(1H)-one (0.076 g, 0.468 mmol) were mixed in acetic acid (1 ml). The mixture was microwaved at 120° C. for 20 min and then concentrated. Added acetone and filtered the solid. Added MeOH to the previous solid and filtered to give 74 mg of final product. MS calcd for $[C_{17}H_{17}N_5O_3+H]^+$: 340.14 found 340.00.

Example 287

Preparation of 4-(cyclopropylamino)-2-((2-oxo-1,2,3,4-tetrahydroquinolin-6-yl)amino)pyrimidine-5-carbonitrile and 2-(cyclopropylamino)-4-((2-oxo-1,2,3,4-tetrahydroquinolin-6-yl)amino)pyrimidine-5-carbonitrile

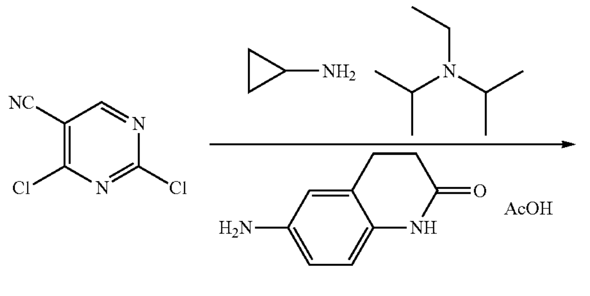

-continued

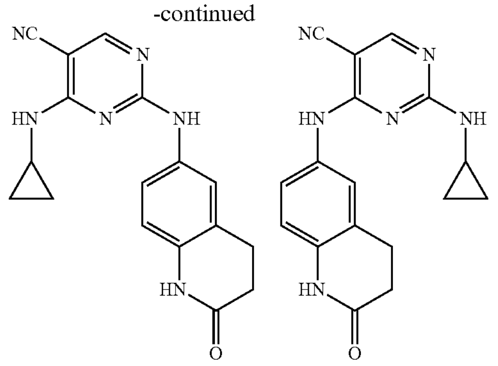

2,4-Dichloropyrimidine-5-carbonitrile (0.100 g, 0.575 mmol), cyclopropanamine (0.040 ml, 0.575 mmol) and N-ethyl-N-isopropylpropan-2-amine (0.110 ml, 0.632 mmol) were mixed in acetonitrile (2 ml). The mixture was microwaved at 70° C. for 10 min and then concentrated. 6-amino-3,4-dihydroquinolin-2(1H)-one (0.093 g, 0.575 mmol) and acetic acid (0.035 g, 0.575 mmol) were added. The mixture was microwaved at 110° C. for 20 min and then concentrated. 14 mg of 4-(cyclopropylamino)-2-((2-oxo-1,2,3,4-tetrahydroquinolin-6-yl)amino)pyrimidine-5-carbonitrile and 14 mg of 2-(cyclopropylamino)-4-((2-oxo-1,2,3,4-tetrahydroquinolin-6-yl)amino)pyrimidine-5-carbonitrile were recovered after automated reverse phase chromatography (water-MeCN). MS calcd for $[C_{17}H_{16}N_6O+H]^+$: 321.15 found 321.00.

Example 288

Preparation of N2-(1H-benzo[d]imidazol-2-yl)-N4-cyclopropyl-5-(trifluoromethyl)pyrimidine-2,4-diamine

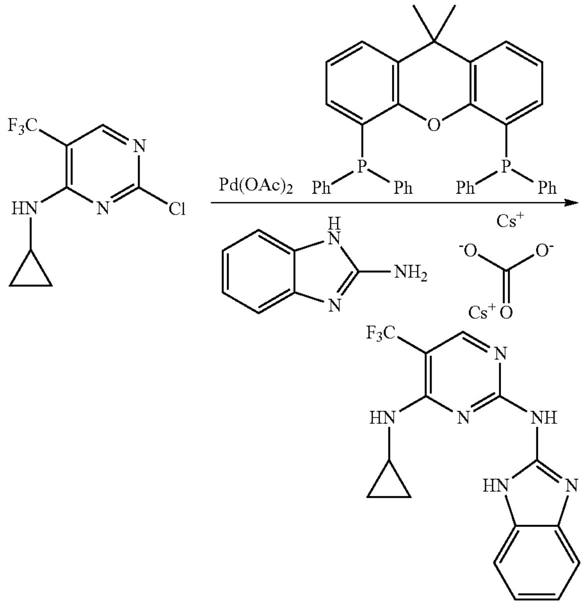

Flame dried flask and stir bar. Bubbled nitrogen through reagents and solvents prior to heating. 2-chloro-N-cyclopropyl-5-(trifluoromethyl)pyrimidin-4-amine (0.065 g, 0.274 mmol), (9,9-dimethyl-9H-xanthene-4,5-diyl)bis(diphenylphosphane) (0.016 g, 0.027 mmol), diacetoxypalladium (3.07 mg, 0.014 mmol), 1H-benzo[d]imidazol-2-amine (0.036 g, 0.274 mmol) and cesium carbonate (0.107 g, 0.328 mmol) were mixed in 1,4-dioxane (2 ml). The mixture was microwaved at 140° C. for 20 min. Filtered through Celite with MeOH and then concentrated. Added acetone and filtered the solid to give 13 mg of product. MS calcd for $[C_{15}H_{13}FN_6+H]^+$: 335.13 found 335.10.

Example 289

Preparation of 2-(2-((5-bromo-2-chloropyrimidin-4-yl)oxy)phenyl)-4-methyloxazole

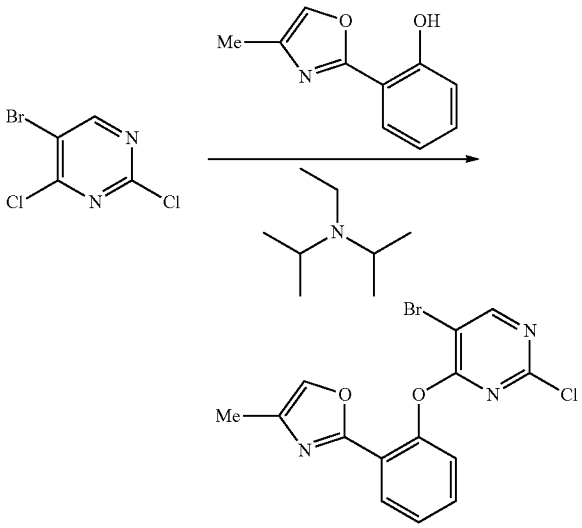

5-Bromo-2,4-dichloropyrimidine (0.150 g, 0.658 mmol), 2-(4-methyloxazol-2-yl)phenol (0.115 g, 0.658 mmol) and N-ethyl-N-isopropylpropan-2-amine (0.126 ml, 0.724 mmol) were mixed in acetonitrile (2 ml). The mixture was microwaved at 120° C. for 20 min and then concentrated and used as-is. MS calcd for $[C_{14}H_9BrClN_3O_2+H]^+$: 365.97 found 365.70.

Example 290

Preparation of 5-bromo-4-(2-(4-methyloxazol-2-yl)phenoxy)-N-(3,4,5-trimethoxyphenyl)pyrimidin-2-amine

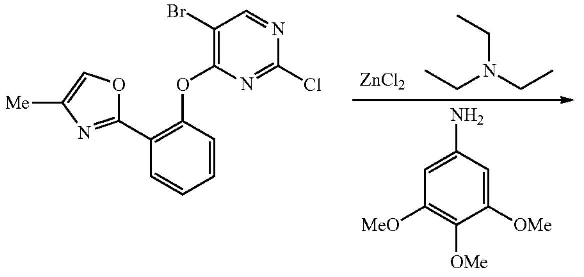

-continued

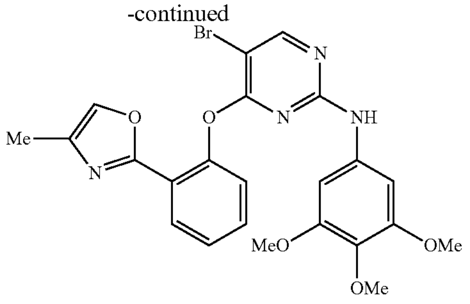

2-(2-((5-Bromo-2-chloropyrimidin-4-yl)oxy)phenyl)-4-methyloxazole (0.230 g, 0.627 mmol) and zinc(II) chloride (0.094 g, 0.690 mmol) were mixed in 1,2-dichloroethane (3 ml). After 30 min, triethylamine (0.105 ml, 0.753 mmol) and 3,4,5-trimethoxyaniline (0.115 g, 0.627 mmol) were added. The mixture was microwaved at 120° C. for 10 min and then concentrated. Flash chromatography on silica gel (DCM) was used to isolate a semipure product. 18 mg of product was recovered after automated reverse phase chromatography (water-10% THF in MeCN). MS calcd for $[C_{23}H_{21}BrN_4O_5+H]^+$: 513.08 found 512.95.

Example 291

Preparation of 6-((4-(cyclopropylamino)-5-nitropyrimidin-2-yl)amino)-3,4-dihydroquinolin-2(1H)-one and N2,N4-dicyclopropyl-5-nitropyrimidine-2,4-diamine

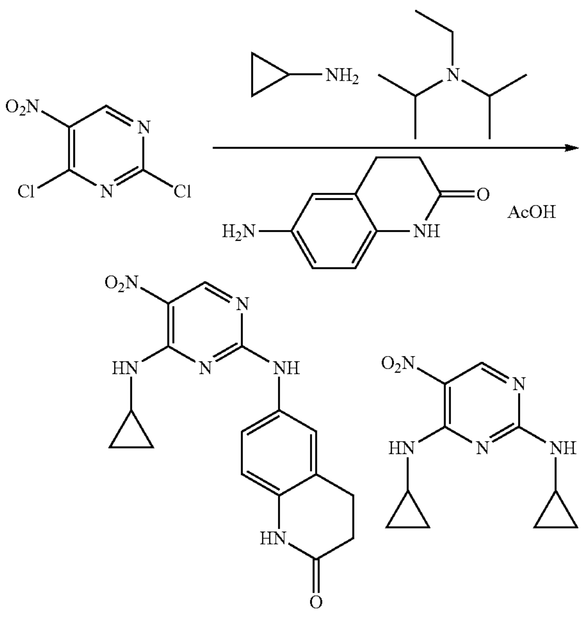

To 2,4-dichloro-5-nitropyrimidine (0.070 g, 0.361 mmol) in acetonitrile (2 ml) at 0° C. was added cyclopropanamine (0.025 ml, 0.361 mmol). After 5 min, N-ethyl-N-isopropylpropan-2-amine (0.069 ml, 0.397 mmol) was added. The mixture was microwaved at 60° C. for 10 min and then concentrated. 6-amino-3,4-dihydroquinolin-2(1H)-one (0.059 g, 0.361 mmol) and acetic acid (0.022 g, 0.361 mmol) were added. The mixture was microwaved at 100° C. for 10 min and then concentrated. Added acetone and filtered the solid to give 17 mg of 6-((4-(cyclopropylamino)-5-nitropyrimidin-2-yl)amino)-3,4-dihydroquinolin-2(1H)-one, with the filtrate containing 20 mg of N2,N4-dicyclopropyl-5-nitropyrimidine-2,4-diamine after concentration. MS calcd for $[C_{16}H_{16}N_6O_3+H]^+$: 341.14 found 341.00. MS calcd for $[C_{10}H_{13}N_5O_2+H]^+$: 236.12 found 236.00.

Example 292

Preparation of 5-bromo-2-chloro-N-phenylpyrimidin-4-amine

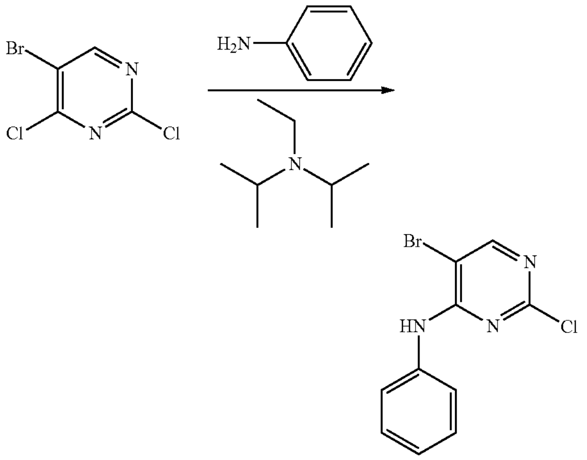

5-Bromo-2,4-dichloropyrimidine (0.150 g, 0.658 mmol), aniline (0.060 ml, 0.658 mmol) and N-ethyl-N-isopropylpropan-2-amine (0.126 ml, 0.724 mmol) were mixed in acetonitrile (2 ml). The mixture was microwaved at 100° C. for 10 min and then concentrated and used as-is. MS calcd for $[C_{10}H_7BrClN_3+H]^+$: 283.96 found 283.55.

Example 293

Preparation of 5-bromo-N4-phenyl-N2-(3,4,5-trimethoxyphenyl)pyrimidine-2,4-diamine

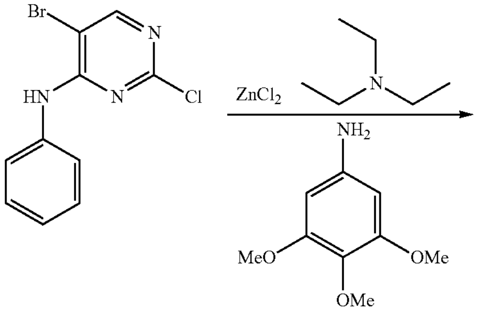

-continued

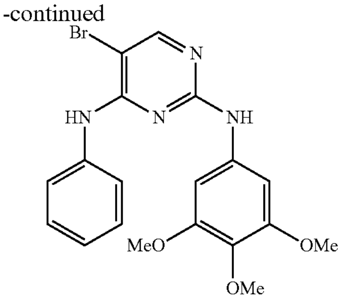

5-Bromo-2-chloro-N-phenylpyrimidin-4-amine (0.175 g, 0.615 mmol) and zinc(II) chloride (0.101 g, 0.738 mmol) were mixed in 1,2-dichloroethane (3 ml). After 30 min, the mixture was microwaved at 140° C. for 20 min. Added ammonia in methanol (200 μL, 7 M). The mixture was microwaved at 140° C. for 20 min to consume starting material and simplify purification. Flash chromagography on silica gel (DCM) was used to give semipure material, then 40 mg of product was recovered after automated reverse phase chromatography (water-10% THF in MeCN). MS calcd for $[C_{19}H_{19}BrN_4O_3+H]^+$: 431.07 found 430.90.

Example 294

Preparation of 6-((4-((1H-1,2,4-triazol-3-yl)amino)-5-(trifluoromethyl) pyrimidin-2-yl)amino)-3,4-dihydroquinolin-2(1H)-one

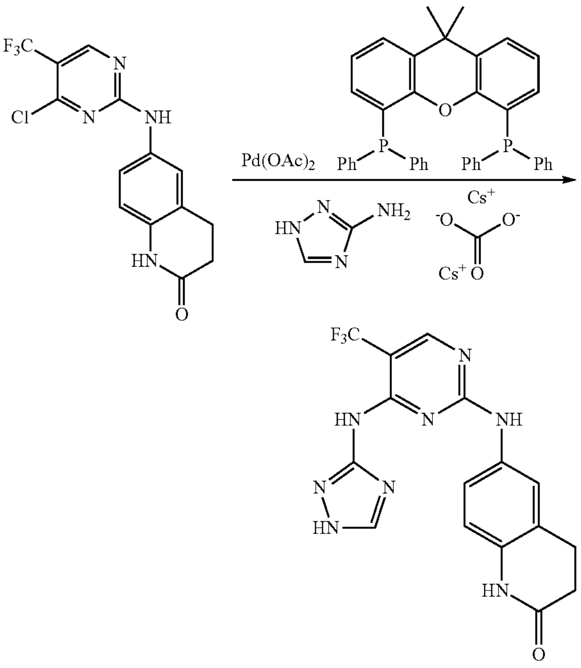

Flame dried flask and stir bar. Bubbled nitrogen through reagents and solvents prior to heating. 6-((4-Chloro-5-(trifluoromethyl)pyrimidin-2-yl)amino)-3,4-dihydroquinolin-2(1H)-one (0.085 g, 0.248 mmol), diacetoxypalladium (1.671 mg, 7.44 μmol), 1H-1,2,4-triazol-3-amine (0.023 g, 0.273 mmol) and cesium carbonate (0.105 g, 0.322 mmol) were mixed in DMF (2 ml). The mixture was microwaved at 140°

C. for 20 min. Filtered through Celite with MeOH and then concentrated. Added MeOH and filtered the yellow solid. Washed with acetone and DCM to remove nonpolar impurities and give 35 mg of product. MS calcd for $[C_{16}H_{13}F_3N_8O+H]^+$: 391.13 found 391.00.

Example 295

Preparation of methyl (2-((5-bromo-2-chloropyrimidin-4-yl)oxy)phenyl) carbamate

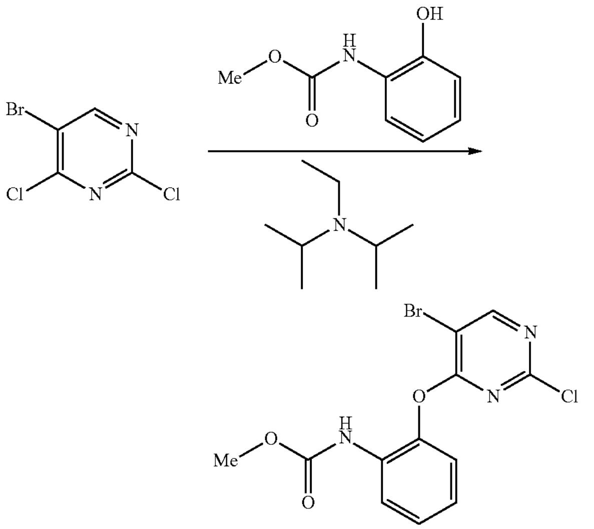

5-Bromo-2,4-dichloropyrimidine (0.150 g, 0.658 mmol), methyl (2-hydroxyphenyl) carbamate (0.110 g, 0.658 mmol) and N-ethyl-N-isopropylpropan-2-amine (0.126 ml, 0.724 mmol) were mixed in acetonitrile (2 ml). The mixture was microwaved at 120° C. for 20 min and then concentrated and used as-is. MS calcd for $[C_{12}H_9BrClN_3O_3+H]^+$: 357.96 found 357.70.

Example 296

Preparation of methyl (2-((5-bromo-2-((3,4,5-trimethoxyphenyl)amino) pyrimidin-4-yl)oxy)phenyl)carbamate

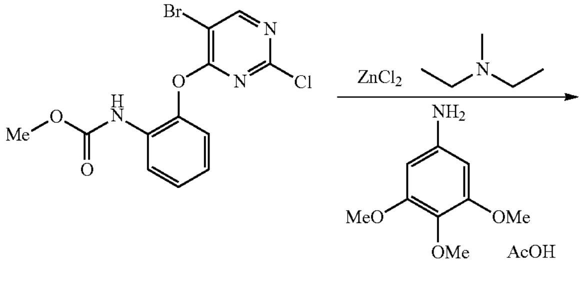

-continued

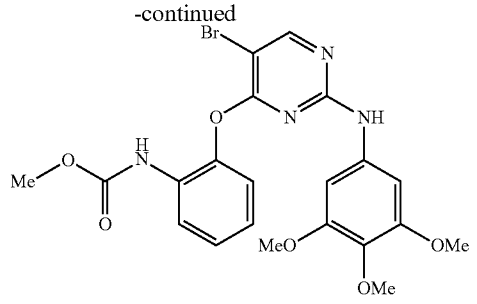

Methyl (2((5-bromo-2-chloropyrimidin-4-yl)oxy)phenyl) carbamate (0.220 g, 0.614 mmol) and zinc(II) chloride (0.100 g, 0.736 mmol) were mixed in 1,2-dichloroethane (3 ml). After 1 h, triethylamine (0.103 ml, 0.736 mmol) and 3,4,5-trimethoxyaniline (0.112 g, 0.614 mmol) were added. The mixture was microwaved at 120° C. for 20 min. acetic acid (0.037 g, 0.614 mmol) and 3,4,5-trimethoxyaniline (0.112 g, 0.614 mmol) were added. The mixture was microwaved at 130° C. for 10 min and then concentrated. Flash chromagography on silica gel (DCM-EtOAc) was used to give semipure material, then 36 mg of product was recovered after automated reverse phase chromatography (water-10% THF in MeCN). MS calcd for $[C_{21}H_{21}BrN_4O_6+H]^+$: 505.07, found 504.95.

Example 297

Preparation of N2-(1H-benzo[d]imidazol-6-yl)-N4-(5-cyclobutyl-1H-pyrazol-3-yl)-5-(trifluoromethyl) pyrimidine-2,4-diamine

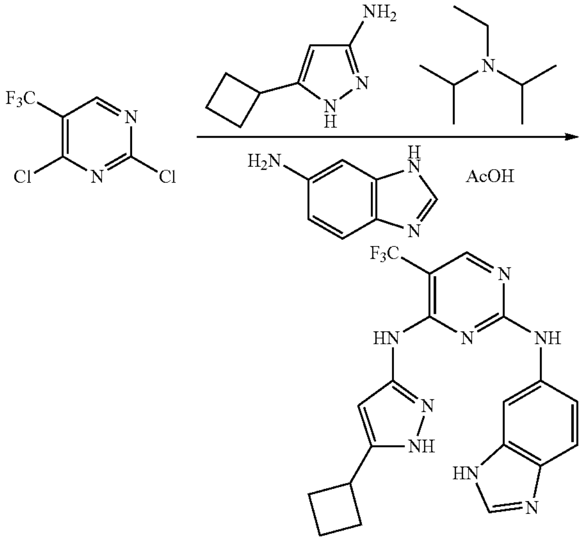

2,4-Dichloro-5-(trifluoromethyl)pyrimidine (0.087 g, 0.401 mmol), 5-cyclobutyl-1H-pyrazol-3-amine (0.055 g, 0.401 mmol) and N-ethyl-N-isopropylpropan-2-amine (0.077 ml, 0.441 mmol) were mixed in acetonitrile (2 ml). The mixture was microwaved at 80° C. for 20 min and then concentrated. 1H-benzo[d]imidazol-6-amine (0.053 g, 0.401 mmol) and acetic acid (0.024 g, 0.401 mmol) were added. The mixture was microwaved at 110° C. for 20 min and then concentrated. 14 mg of product was recovered after automated reverse phase chromatography (water-MeCN). MS calcd for $[C_{19}H_{17}F_3N_8+H]^+$: 415.16, found 415.20.

Example 298

Preparation of 5-bromo-2-chloro-4-(2-(trifluoromethyl)phenoxy)pyrimidine

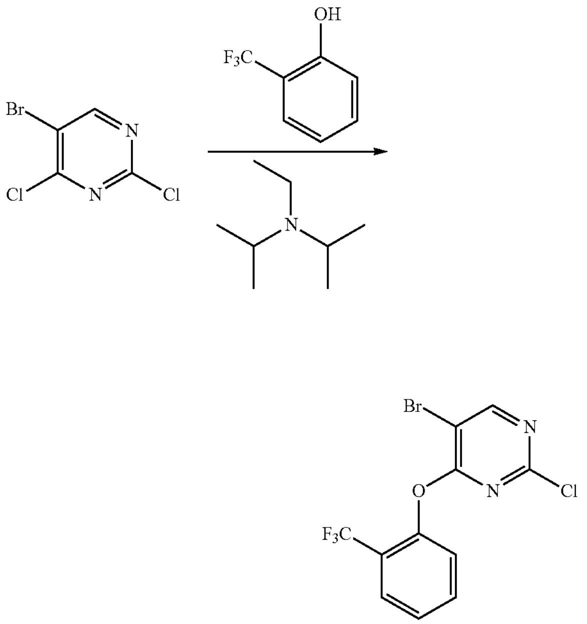

5-Bromo-2,4-dichloropyrimidine (0.150 g, 0.658 mmol), 2-(trifluoromethyl)phenol (0.117 g, 0.724 mmol) and N-ethyl-N-isopropylpropan-2-amine (0.138 ml, 0.790 mmol) were mixed in acetonitrile (3 ml). The mixture was microwaved at 120° C. for 20 min and then concentrated and used as-is. MS calcd for $[C_{11}H_5BrClF_3N_2O+H]^+$: 352.93, found 352.60.

Example 299

Preparation of 5-bromo-4-(2-(trifluoromethyl)phenoxy)-N-(3,4,5-trimethoxyphenyl)pyrimidin-2-amine

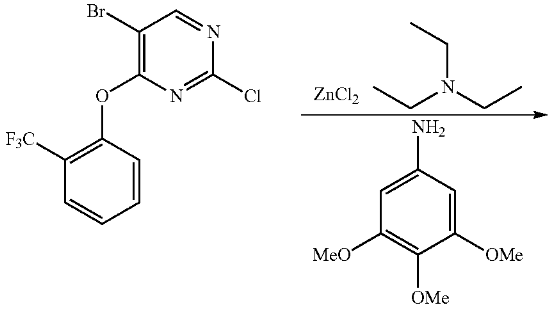

-continued

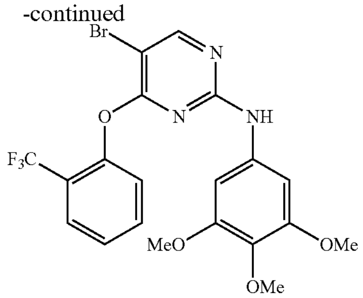

5-Bromo-2-chloro-4-(2-(trifluoromethyl)phenoxy)pyrimidine (0.220 g, 0.622 mmol) and zinc(II) chloride (0.110 g, 0.809 mmol) were mixed in 1,2-dichloroethane (3 ml). After 30 min, triethylamine (0.121 ml, 0.871 mmol) and 3,4,5-trimethoxyaniline (0.114 g, 0.622 mmol) were added. The mixture was microwaved at 120° C. for 20 min and then concentrated. 45 mg of product was recovered after flash chromatography on silica gel (DCM-EtOAc). MS calcd for $[C_{20}H_{17}BrF_3N_3O_4+H]^+$: 500.05, found 500.00.

Example 300

Preparation of 6-((4-phenoxy-5-(trifluoromethyl)pyrimidin-2-yl)amino)-3,4-dihydroquinolin-2(1H)-one and 6-((2-phenoxy-5-(trifluoromethyl)pyrimidin-4-yl)amino)-3,4-dihydroquinolin-2(1H)-one

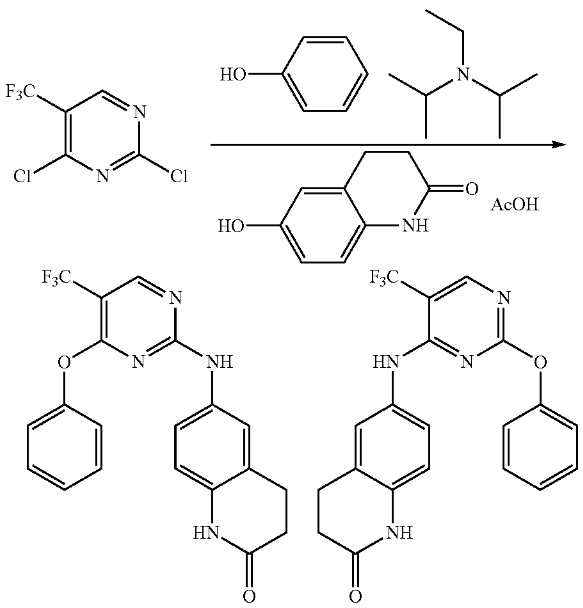

2,4-Dichloro-5-(trifluoromethyl)pyrimidine (0.080 g, 0.369 mmol), phenol (0.035 g, 0.369 mmol) and N-ethyl-N-isopropylpropan-2-amine (0.071 ml, 0.406 mmol) were mixed in acetonitrile (2 ml). The mixture was microwaved at 100° C. for 10 min and then concentrated. 6-amino-3,4-dihydroquinolin-2(1H)-one (0.060 g, 0.369 mmol) and acetic acid (0.022 g, 0.369 mmol) were added. The mixture was microwaved at 110° C. for 20 min and then concentrated. Added 50:50 MeCN-water mixture and filtered the solid. To this solid was added acetone and that solid was filtered to give the 23 mg of 6-((4-phenoxy-5-(trifluoromethyl)pyrimidin-2-yl)amino)-3,4-dihydroquinolin-2(1H)-one. The MeCN-water filtrate from above was purified using automated reverse phase chromatography (water-MeCN) to give 8 mg of 6-((2-phenoxy-5-(trifluoromethyl)pyrimidin-4-yl) amino)-3,4-dihydroquinolin-2(1H)-one. MS calcd for $[C_{20}H_{15}F_3N_4O_2+H]^+$: 401.12, found 401.20.

Example 301

Preparation of 6-((4-(cyclopropylamino)-5-(trifluoromethyl)pyrimidin-2-yl)amino)-3,4-dihydronaphthalen-1(2H)-one

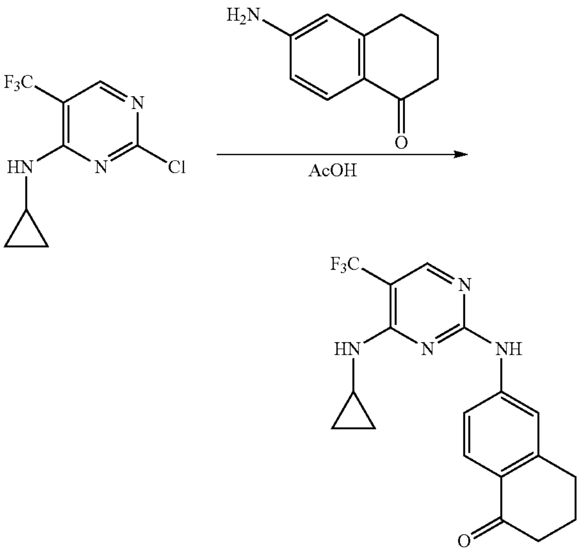

2-Chloro-N-cyclopropyl-5-(trifluoromethyl)pyrimidin-4-amine (0.060 g, 0.253 mmol) and 6-amino-3,4-dihydronaphthalen-1(2H)-one (0.041 g, 0.253 mmol) were mixed in acetic acid (1 ml). The mixture was microwaved at 110° C. for 20 min and then concentrated. Added DCM-EtOAc and filtered the solid to give 61 mg of product. MS calcd for $[C_{18}H_{17}F_3N_4O+H]^+$: 363.15, found 363.15.

Example 302

Preparation of (2-((5-bromo-2-chloropyrimidin-4-yl) amino)phenyl)methanol

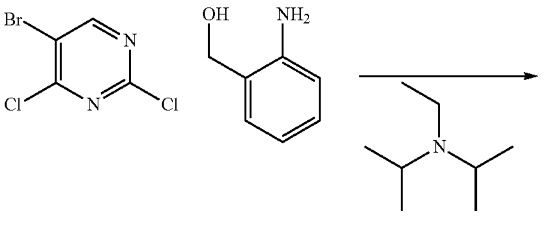

-continued

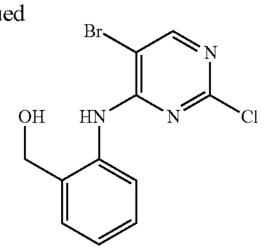

5-Bromo-2,4-dichloropyrimidine (0.100 g, 0.439 mmol), (2-aminophenyl)methanol (0.054 g, 0.439 mmol) and N-ethyl-N-isopropylpropan-2-amine (0.084 ml, 0.483 mmol) were mixed in acetonitrile (2 ml). The mixture was microwaved at 100° C. for 20 min and then concentrated and used as-is. MS calcd for $[C_{11}H_9BrClN_3O+H]^+$: 313.97, found 313.60.

Example 303

Preparation of (2-((5-bromo-2-((3,4,5-trimethoxyphenyl)amino)pyrimidin-4-yl)amino)phenyl)methanol

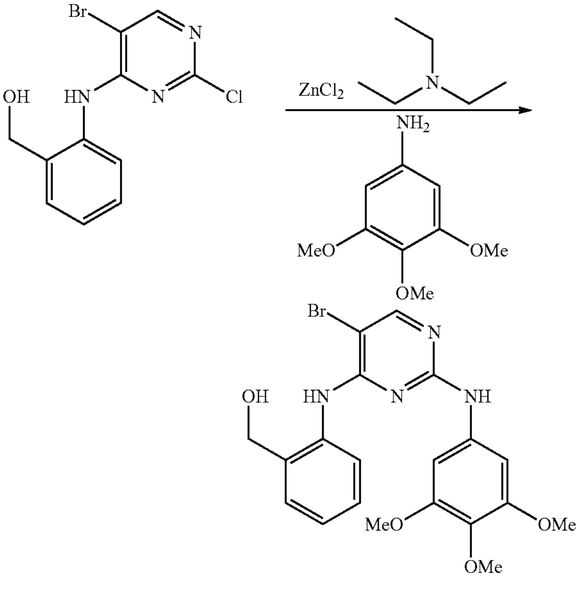

(2-((5-Bromo-2-chloropyrimidin-4-yl)amino)phenyl) methanol (0.125 g, 0.397 mmol) and zinc(II) chloride (0.065 g, 0.477 mmol) were mixed in 1,2-dichloroethane (2 ml). After 30 min, triethylamine (0.072 ml, 0.517 mmol) and 3,4,5-trimethoxyaniline (0.073 g, 0.397 mmol) were added. The mixture was microwaved at 140° C. for 20 min and then concentrated. The material was purified using automated reverse phase chromatography (water-10% THF in MeCN) to give semipure material. It was further purified by flash chromatgraphy on silica gel (DCM-EtOAc) to give 22 mg of product. MS calcd for $[C_{20}H_{21}BrN_4O_4+H]^+$: 461.08, found 460.90.

Example 304

Preparation of N2-(4-aminophenyl)-N4-cyclopropyl-5-(trifluoromethyl) pyrimidine-2,4-diamine and N2,N2'-(1,4-phenylene)bis(N4-cyclopropyl-5-(trifluoromethyl) pyrimidine-2,4-diamine)

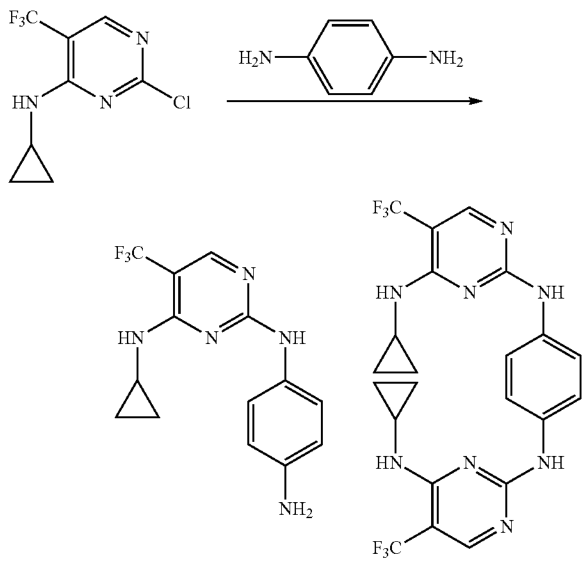

2-Chloro-N-cyclopropyl-5-(trifluoromethyl)pyrimidin-4-amine (0.060 g, 0.253 mmol) and benzene-1,4-diamine (0.055 g, 0.505 mmol) were mixed in butan-1-ol (1 ml). The mixture was microwaved at 120° C. for 20 min and then concentrated. Added acetone and filtered the solid to give 36 mg of N2,N2'-(1,4-phenylene)bis(N4-cyclopropyl-5-(trifluoromethyl)pyrimidine-2,4-diamine). The filtrate was concentrated to give 92 mg of N2-(4-aminophenyl)-N4-cyclopropyl-5-(trifluoromethyl)pyrimidine-2,4-diamine. MS calcd for $[C_{14}H_{14}F_3N_5+H]^+$: 310.13, found 310.00. MS calcd for $[C_{22}H_{20}F_6N_8+H]^+$: 511.18, found 511.30.

Example 305

Preparation of N4-cyclopropyl-N2-(quinoxalin-6-yl)-5-(trifluoromethyl) pyrimidine-2,4-diamine

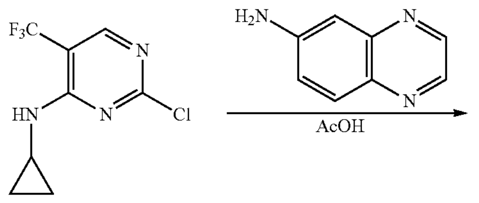

-continued

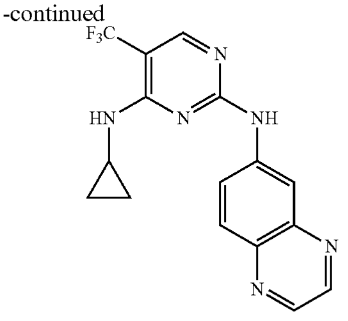

2-Chloro-N-cyclopropyl-5-(trifluoromethyl)pyrimidin-4-amine (0.060 g, 0.253 mmol) and quinoxalin-6-amine (0.037 g, 0.253 mmol) were mixed in acetic acid (1 ml). The mixture was microwaved at 120° C. for 20 min and then concentrated. 17 mg of product was recovered after automated reverse phase chromatography (water-MeCN). MS calcd for $[C_{16}H_{13}F_3N_6+H]^+$: 347.13, found 347.10.

Example 306

Preparation of 6-((4-(cyclopropylamino)-6-(trifluoromethyl)pyrimidin-2-yl)amino)-3,4-dihydroquinolin-2(1H)-one

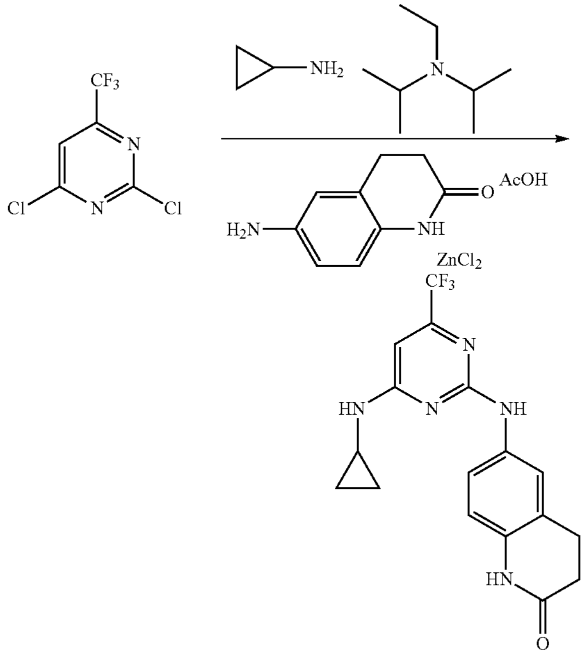

2,4-Dichloro-6-(trifluoromethyl)pyrimidine (0.110 g, 0.507 mmol), cyclopropanamine (0.035 ml, 0.507 mmol) and N-ethyl-N-isopropylpropan-2-amine (0.088 ml, 0.507 mmol) were mixed in ethanol (3 ml). Stirred at 23° C. for 3 h and then concentrated. 6-amino-3,4-dihydroquinolin-2(1H)-one (0.082 g, 0.507 mmol) and acetic acid (0.030 g, 0.507 mmol) were added. The mixture was microwaved at 130° C. for 20 min. The intermediate was still present. Concentrated the reaction mixture and added 1,2-dichloroethane (4 mL) and zinc(II) chloride (0.069 g, 0.507 mmol). The mixture was microwaved at 110° C. for 20 min and then concentrated. 20 mg of product were isolated after flash chromatgraphy on silica gel (DCM-EtOAc). MS calcd for $[C_{17}H_{16}F_3N_5O+H]^+$: 364.14, found 364.20.

Example 307

Preparation of N-(2-((2-oxo-1,2,3,4-tetrahydroquinolin-6-yl)amino)-5-(trifluoromethyl)pyrimidin-4-yl) cyclopropanecarboxamide

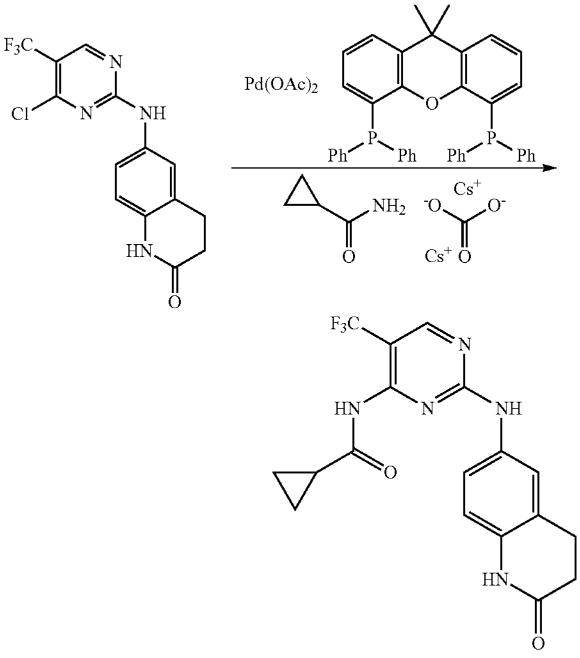

Flame dried flask and stir bar. Bubbled nitrogen through reagents and solvents prior to heating. 6-((4-Chloro-5-(trifluoromethyl)pyrimidin-2-yl)amino)-3,4-dihydroquinolin-2(1H)-one (0.080 g, 0.233 mmol), diacetoxypalladium (1.572 mg, 7.00 μmol), cyclopropanecarboxamide (0.022 g, 0.257 mmol) and cesium carbonate (0.099 g, 0.303 mmol) were mixed in DMF (2 ml). The mixture was microwaved at 130° C. for 20 min. Filtered through Celite with MeOH and then concentrated. 4 mg of product was isolated after automated reverse phase chromatography (water-MeCN). MS calcd for $[C_{18}H_{16}F_3N_5O_2+H]^+$: 392.14, found 392.05.

Example 308

Preparation of tert-butyl 6-((4-(cyclopropylamino)-5-(trifluoromethyl) pyrimidin-2-yl)amino)-3,4-dihydroisoquinoline-2(1H)-carboxylate

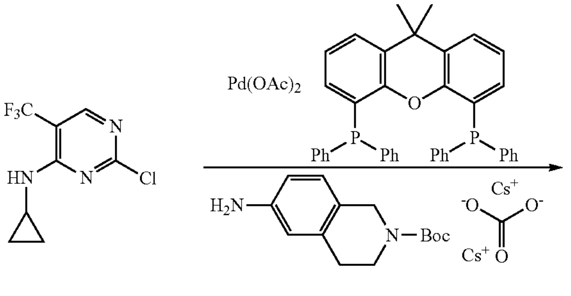

-continued

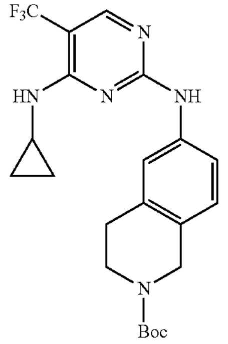

Flame dried flask and stir bar. Bubbled nitrogen through reagents and solvents prior to heating. 2-chloro-N-cyclopropyl-5-(trifluoromethyl)pyrimidin-4-amine (0.100 g, 0.421 mmol), diacetoxypalladium (2.83 mg, 0.013 mmol), tert-butyl 6-amino-3,4-dihydroisoquinoline-2(1H)-carboxylate (0.115 g, 0.463 mmol) and cesium carbonate (0.178 g, 0.547 mmol) were mixed in 1,4-dioxane (2 ml). The mixture was microwaved at 130° C. for 20 min. Filtered through Celite with MeOH and then concentrated. Added acetone and filtered the solid; product is in the filtrate, which was concentrated. 166 mg of product were isolated after flash chromatgraphy on silica gel (DCM-EtOAc). MS calcd for $[C_{22}H_{26}F_3N_5O_2+H]^+$: 450.21, found 450.55.

Example 309

Preparation of N4-cyclopropyl-N2-(1,2,3,4-tetrahydroisoquinolin-6-yl)-5-(trifluoromethyl)pyrimidine-2,4-diamine HCl

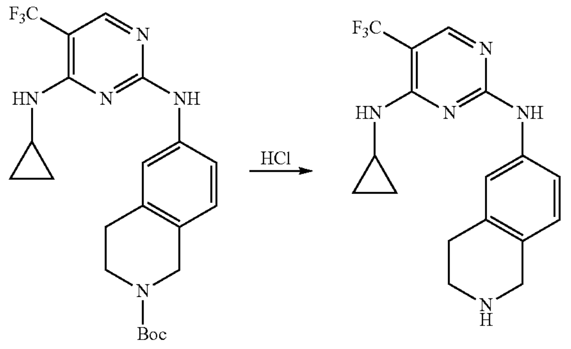 [SMILES: CC(C)(C)OC(=O)N1CCc2cc(Nc3ncc(C(F)(F)F)c(NC4CC4)n3)ccc2C1 ; Cl ; FC(F)(F)c1cnc(Nc2ccc3c(c2)CCNC3)nc1NC1CC1]

tert-Butyl 6-((4-(cyclopropylamino)-5-(trifluoromethyl) pyrimidin-2-yl)amino)-3,4-dihydroisoquinoline-2(1H)-carboxylate (0.132 g, 0.294 mmol) and hydrogen chloride in water (0.489 ml, 1.468 mmol, 3M in water) were mixed in methanol (1 ml). Heated to 60° C. for 16 h and then concentrated. The solid was washed with DCM to give 109 mg of product. MS calcd for $[C_{17}H_{18}F_3N_5+H]^+$: 350.16, found 350.05.

Example 310

Preparation of tert-butyl (3-((2-((2-oxo-1,2,3,4-tetrahydroquinolin-6-yl)amino)-5-(trifluoromethyl) pyrimidin-4-yl)amino)propyl)carbamate

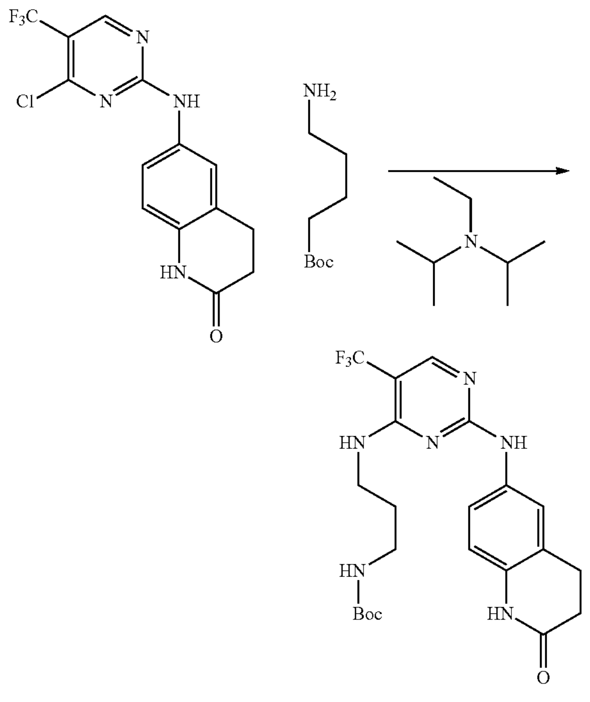

6-((4-Chloro-5-(trifluoromethyl)pyrimidin-2-yl)amino)-3,4-dihydroquinolin-2(1H)-one (0.200 g, 0.584 mmol), tert-butyl 5-aminopentanoate (0.101 g, 0.584 mmol) and N-ethyl-N-isopropylpropan-2-amine (0.102 ml, 0.584 mmol) were mixed in DMF (5 ml). The mixture was microwaved at 100° C. for 20 min and then concentrated. 242 mg of product was isolated after flash chromatgraphy on silica gel (DCM-MeOH). MS calcd for $[C_{22}H_{27}F_3N_6O_3+H]^+$: 481.22, found 481.55.

Example 311

Preparation of N-(cyclopropanecarbonyl)-N-(4-((4-(cyclopropylamino)-5-(trifluoromethyl)pyrimidin-2-yl)amino)phenyl)cyclopropanecarboxamide

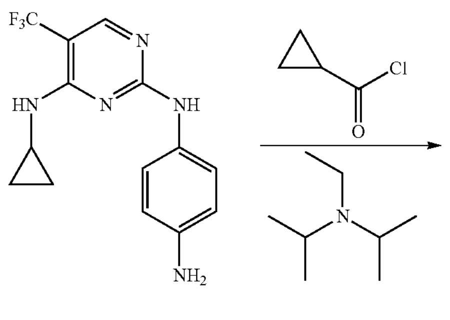

-continued

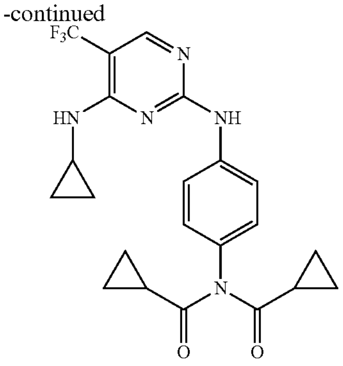

N2-(4-Aminophenyl)-N4-cyclopropyl-5-(trifluoromethyl)pyrimidine-2,4-diamine (0.043 g, 0.139 mmol), cyclopropanecarbonyl chloride (0.016 g, 0.153 mmol) and N-ethyl-N-isopropyl propan-2-amine (0.029 ml, 0.167 mmol) were mixed in DMF (1 ml). The mixture was microwaved at 60° C. for 10 min. Added more cyclopropanecarbonyl chloride (0.016 g, 0.153 mmol). The mixture was microwaved at 60° C. for 10 min. 10 mg of product was isolated after automated reverse phase chromatography (water-MeCN). MS calcd for $[C_{22}H_{22}F_3N_5O_2+H]^+$: 446.18, found 446.35.

Example 312

Preparation of N-(4-((4-(cyclopropylamino)-5-(trifluoromethyl)pyrimidin-2-yl)amino)phenyl)cyclopropanecarboxamide

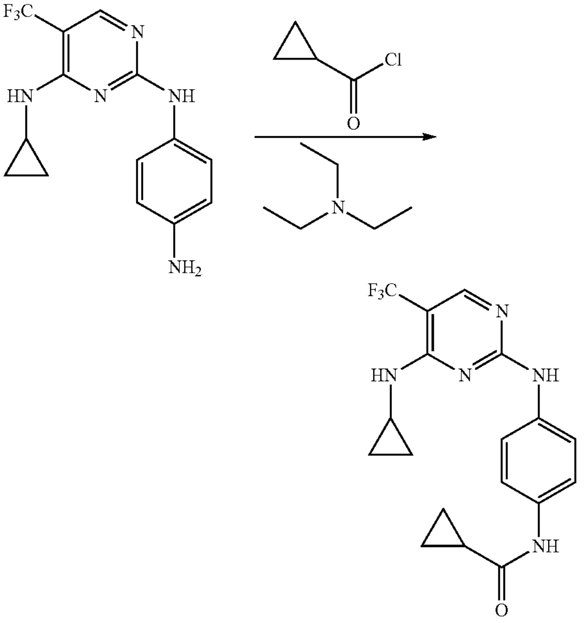

N2-(4-Aminophenyl)-N4-cyclopropyl-5-(trifluoromethyl)pyrimidine-2,4-diamine (0.020 g, 0.065 mmol), cyclopropanecarbonyl chloride (6.16 µl, 0.068 mmol) and triethylamine (0.012 ml, 0.084 mmol) were mixed in DMF (1 ml). The mixture was microwaved at 60° C. for 10 min and then concentrated. 3 mg of product was isolated after automated reverse phase chromatography (water-MeCN). MS calcd for $[C_{18}H_{18}F_3N_5O+H]^+$: 378.16, found 378.00.

Example 313

Preparation of 6-((4-((3-aminopropyl)amino)-5-(trifluoromethyl)pyrimidin-2-yl)amino)-3,4-dihydroquinolin-2(1H)-one.HCl

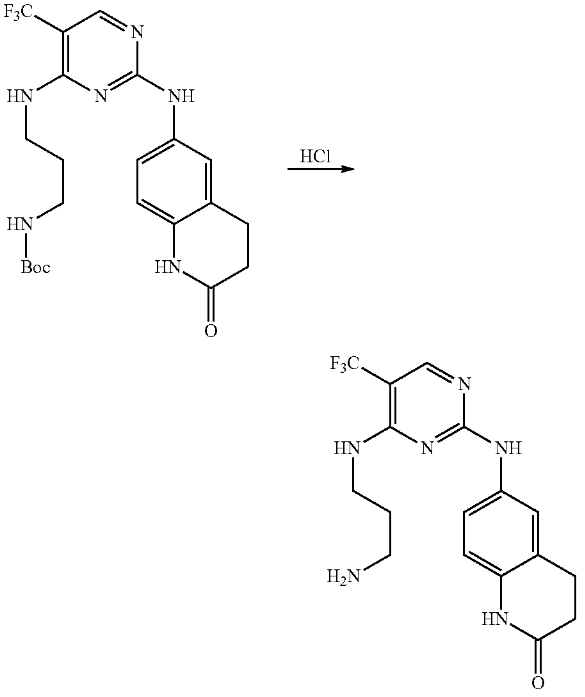

tert-Butyl (3-((2-((2-oxo-1,2,3,4-tetrahydroquinolin-6-yl)amino)-5-(trifluoromethyl) pyrimidin-4-yl)amino)propyl) carbamate (0.232 g, 0.483 mmol) and hydrogen chloride, $H_2O$ (0.644 ml, 1.931 mmol) were mixed in methanol (2 ml). Concentrated to give 195 mg of product. MS calcd for $[C_{17}H_{19}F_3N_6O+H]^+$: 381.17, found 381.10.

Example 314

Preparation of 5-((4-(cyclopropylamino)-5-(trifluoromethyl)pyrimidin-2-yl)amino)isoindoline-1,3-dione

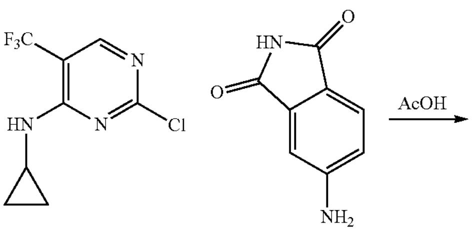

-continued

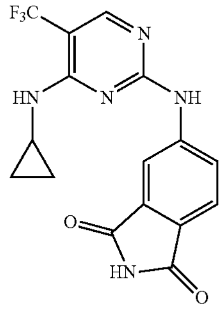

2-Chloro-N-cyclopropyl-5-(trifluoromethyl)pyrimidin-4-amine (0.060 g, 0.253 mmol) and 5-aminoisoindoline-1,3-dione (0.041 g, 0.253 mmol) were mixed in acetic acid (2 ml). The mixture was microwaved at 120° C. for 20 min and then concentrated. 1 mg of product was isolated after automated reverse phase chromatography (water-3% DMF in MeCN). MS calcd for $[C_{16}H_{12}F_3N_5O_2+H]^+$: 364.10, found 364.00.

Example 315

Preparation of 3-((5-bromo-2-chloropyrimidin-4-yl)oxy)-N-methyl propanamide

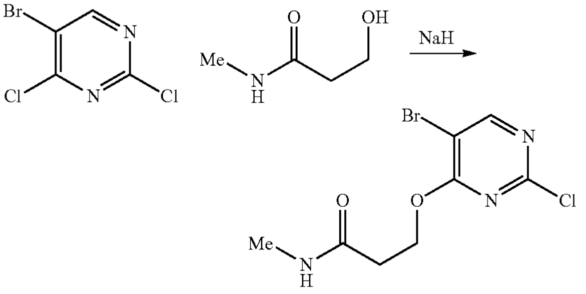

3-Hydroxy-N-methylpropanamide (0.068 g, 0.658 mmol) and sodium hydride (0.026 g, 0.658 mmol) were mixed in DMF (1 ml). The mixture was microwaved at 80° C. for 20 min and then concentrated and used as-is. MS calcd for $[C_8H_9BrClN_3O_2+H]^+$: 293.97, found 293.60.

Example 316

Preparation of 3-((5-bromo-2-((3,4,5-trimethoxyphenyl)amino)pyrimidin-4-yl)oxy)-N-methylpropanamide

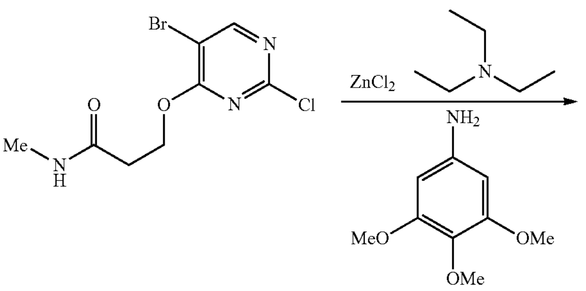

-continued

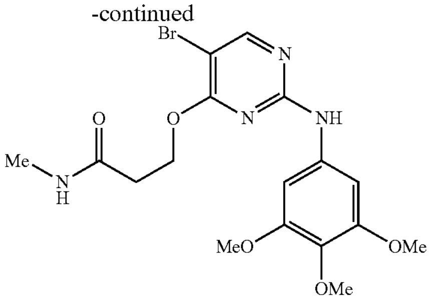

3-((5-Bromo-2-chloropyrimidin-4-yl)oxy)-N-methylpropanamide (0.175 g, 0.594 mmol) and zinc(II) chloride (0.105 g, 0.772 mmol) were mixed in 1,2-dichloroethane (3 ml). After 30 min, triethylamine (0.083 ml, 0.594 mmol) and 3,4,5-trimethoxyaniline (0.109 g, 0.594 mmol) were added. The mixture was microwaved at 120° C. for 20 min and then concentrated. 31 mg of product was isolated after automated reverse phase chromatography (water-MeCN). MS calcd for $[C_{17}H_{21}BrN_4O_5+H]^+$: 441.08, found 440.85.

Example 317

Preparation of 2-((5-bromo-2-((3,4,5-trimethoxyphenyl)amino)pyrimidin-4-yl)amino)phenol

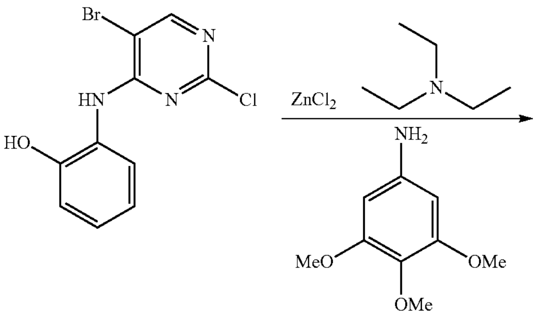

-continued

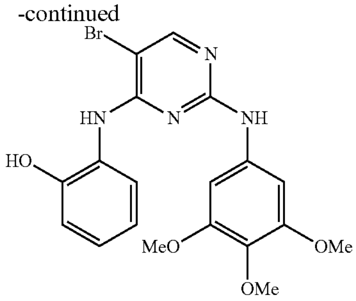

2-((5-Bromo-2-chloropyrimidin-4-yl)amino)phenol (0.180 g, 0.599 mmol) and zinc(II) chloride (0.098 g, 0.719 mmol) were mixed in 1,2-dichloroethane (4 ml). triethylamine (0.100 ml, 0.719 mmol) and 3,4,5-trimethoxyaniline (0.110 g, 0.599 mmol) were added. The mixture was microwaved at 130° C. for 20 min and then concentrated. Flash chromagography on silica gel (DCM-EtOAc) was used to give semipure material, then 19 mg of product was recovered after automated reverse phase chromatography (water-10% THF in MeCN). MS calcd for $[C_{19}H_{19}BrN_4O_4+H]^+$: 447.07, found 446.85.

Example 318

Preparation of 2-((5-bromo-2-((3,4,5-trimethoxyphenyl)amino)pyrimidin-4-yl)oxy)-4-methoxy-N-methylbenzamide and 2-((5-bromo-4-((3,4,5-trimethoxyphenyl)amino)pyrimidin-2-yl)oxy)-4-methoxy-N-methylbenzamide

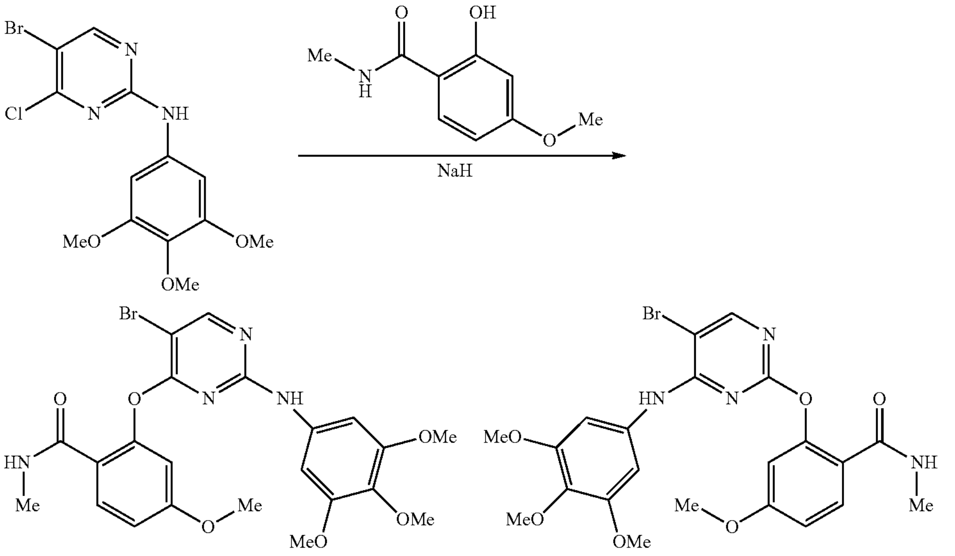

2-hydroxy-4-methoxy-N-methylbenzamide (0.048 g, 0.267 mmol) and sodium hydride (0.014 g, 0.347 mmol) were mixed in DMF (3 ml). Then 5-bromo-4-chloro-N-(3,4,5-trimethoxy phenyl)pyrimidin-2-amine (0.100 g, 0.267 mmol) was added. The mixture was microwaved at 110° C. for 10 min, and then concentrated ammonium chloride solution was added. The organics were extracted with DCM, dried over sodium sulfate and concentrated. 12 mg of 2-((5-bromo-2-((3,4,5-trimethoxyphenyl)amino)pyrimidin-4-yl)oxy)-4-methoxy-N-methylbenzamide and 6 mg of 2-((5-bromo-4-((3,4,5-trimethoxyphenyl)amino)pyrimidin-2-yl)oxy)-4-methoxy-N-methylbenzamide were recovered after automated reverse phase chromatography (water-10% THF in MeCN). MS calcd for $[C_{22}H_{23}BrN_4O_6+H]^+$: 519.09, found 519.05.

Example 319

Preparation of N-(2-hydroxyphenyl)pivalamide

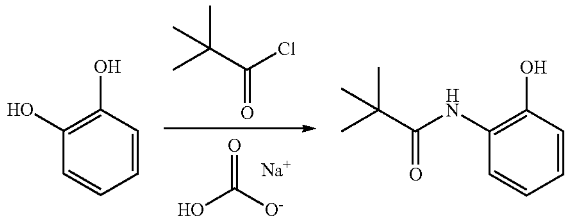

2-aminophenol (2 g, 18.33 mmol), pivaloyl chloride (2.483 ml, 20.16 mmol) and sodium hydrogen carbonate (4.62 g, 55.0 mmol) were mixed in water (60 ml) and ethyl acetate (50 ml). Added 1 M HCl and extracted once with EtOAc and once with DCM. The mixture was dried over sodium sulfate, filtered and concentrated in vacuo. The doubly acylated product also forms. Washed with hexane to remove impurity and used as-is. MS calcd for $[C_{11}H_{15}NO_2+H]^+$: 194.12, found 194.00.

Example 320

Preparation of N-(2-((5-bromo-2-((3,4,5-trimethoxyphenyl)amino)pyrimidin-4-yl)oxy)phenyl)pivalamide

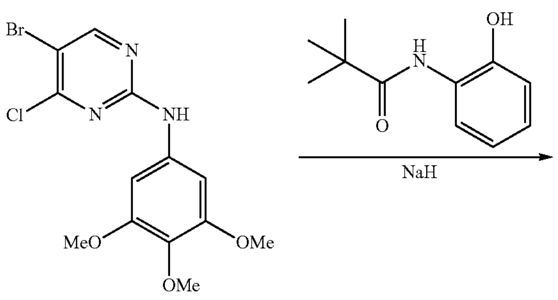

-continued

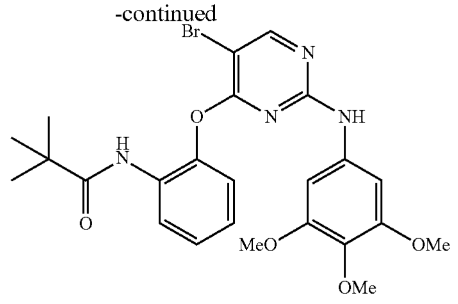

N-(2-Hydroxyphenyl)pivalamide (0.062 g, 0.320 mmol) and sodium hydride (9.99 mg, 0.416 mmol) were mixed in DMF (3 ml). Then 5-bromo-4-chloro-N-(3,4,5-trimethoxyphenyl) pyrimidin-2-amine (0.120 g, 0.320 mmol) was added. The mixture was microwaved at 110° C. for 10 min and then concentrated. 16 mg of product was recovered after automated reverse phase chromatography (water-10% THF in MeCN). MS calcd for $[C_{24}H_{27}BrN_4O_5+H]^+$: 531.13, found 531.05.

Example 321

Preparation of N-(2-((2-(benzo[d][1,3]dioxol-5-ylamino)-5-bromopyrimidin-4-yl)oxy)phenyl)acetamide and 4-(2-aminophenoxy)-N-(benzo[d][1,3]dioxol-5-yl)-5-bromopyrimidin-2-amine

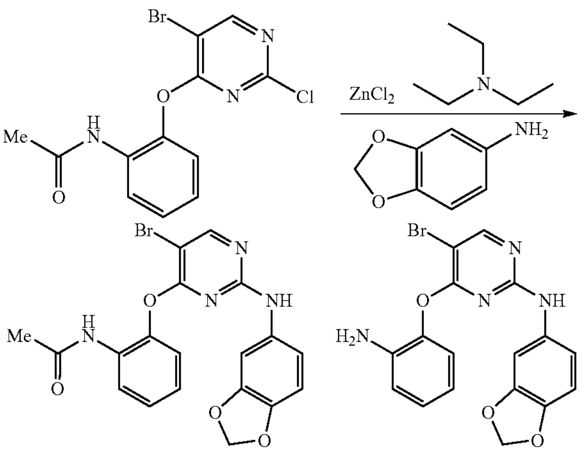

N-(2-((5-Bromo-2-chloropyrimidin-4-yl)oxy)phenyl)acetamide (0.170 g, 0.496 mmol) and zinc(II) chloride (0.081 g, 0.595 mmol) were mixed in 1,2-dichloroethane (3 ml). After 15 min, triethylamine (0.069 ml, 0.496 mmol) and benzo[d][1,3]dioxol-5-amine (0.068 g, 0.496 mmol) were added. The mixture was microwaved at 120° C. for 20 min and then concentrated. 8 mg of N-(2-((2-(benzo[d][1,3]dioxol-5-ylamino)-5-bromopyrimidin-4-yl)oxy)phenyl)acetamide and 26 mg of 4-(2-aminophenoxy)-N-(benzo[d][1,3]dioxol-5-yl)-5-bromopyrimidin-2-amine were recovered after automated reverse phase chromatography (water-10% THF in MeCN). MS calcd for $[C_{19}H_{15}BrN_4O_4+H]^+$: 443.04, found 442.85. MS calcd for $[C_{17}H_{13}BrN_4O_3+H]^+$: 401.03, found 400.80.

Example 322

Preparation of 2-((2,5-dichloropyrimidin-4-yl)oxy)-N-methylbenzamide

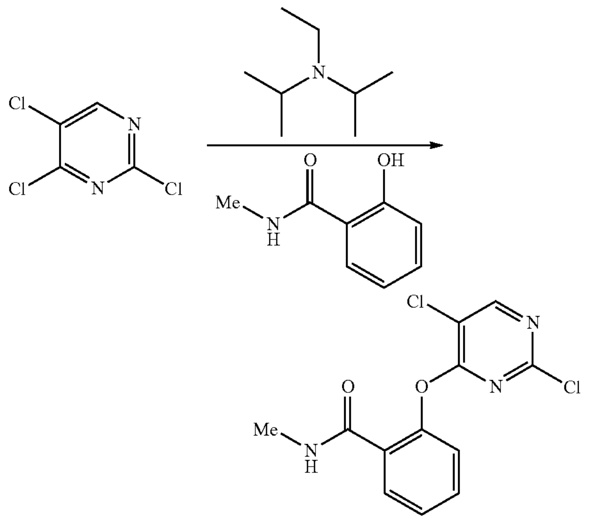

Mixed 2,4,5-trichloropyrimidine (0.170 g, 0.927 mmol), N-ethyl-N-isopropylpropan-2-amine (0.161 ml, 0.927 mmol) and 2-hydroxy-N-methylbenzamide (0.140 g, 0.927 mmol) in n-Butanol (5 ml). Heated to 60° C. for 16 h and then concentrated and used as-is. MS calcd for $[C_{12}H_9Cl_2N_3O_2+H]^+$: 298.02, found 297.65.

Example 323

Preparation of N-(2-((5-bromo-2-((3,4,5-trimethoxyphenyl)amino)pyrimidin-4-yl)oxy)phenyl)-2,2,2-trifluoroacetamide

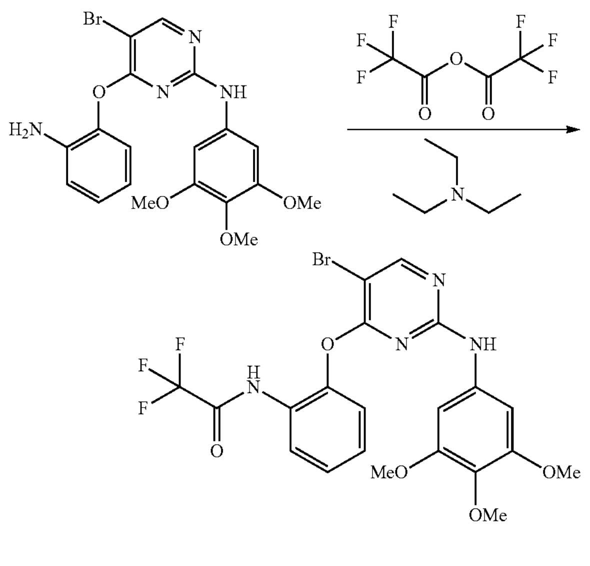

4-(2-Aminophenoxy)-5-bromo-N-(3,4,5-trimethoxyphenyl)pyrimidin-2-amine (0.190 g, 0.425 mmol), triethylamine (0.065 ml, 0.467 mmol) and 2,2,2-trifluoroacetic anhydride (0.059 ml, 0.425 mmol) were mixed in acetonitrile (4.00 ml). The mixture was microwaved at 130° C. for 10 min and then concentrated. 10 mg of product was recovered after flash chromatography on silica gel (DCM). MS calcd for $[C_{19}H_{15}BrN_4O_4+H]^+$: 443.04, found 442.85. MS calcd for $[C_{21}H_{18}BrF_3N_4O_5+H]^+$: 543.05, found 543.00.

Example 324

Preparation of 5-bromo-4-(quinolin-8-yloxy)-N-(3,4,5-trimethoxyphenyl) pyrimidin-2-amine and 5-bromo-2-(quinolin-8-yloxy)-N-(3,4,5-trimethoxyphenyl) pyrimidin-4-amine

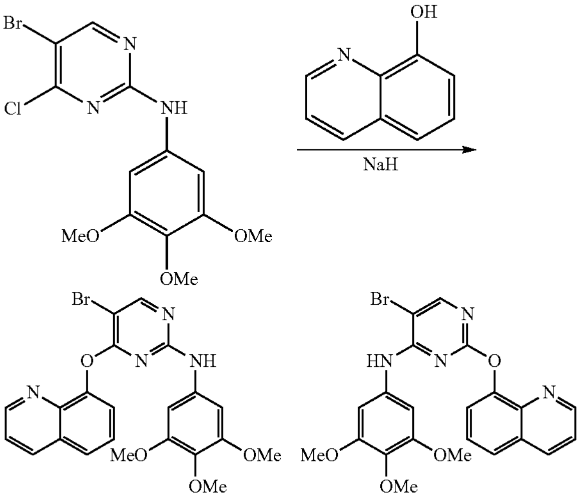

Quinolin-8-ol (0.046 g, 0.320 mmol) and sodium hydride (0.017 g, 0.416 mmol) were mixed in DMF (2 ml). Then 5-bromo-4-chloro-N-(3,4,5-trimethoxyphenyl)pyrimidin-2-amine (0.120 g, 0.320 mmol) was added. The mixture was microwaved at 120° C. for 20 min and then concentrated. 28 mg of 5-bromo-4-(quinolin-8-yloxy)-N-(3,4,5-trimethoxyphenyl)pyrimidin-2-amine and 24 mg of 5-bromo-2-(quinolin-8-yloxy)-N-(3,4,5-trimethoxyphenyl)pyrimidin-4-amine were recovered after automated reverse phase chromatography (water-10% THF in MeCN). MS calcd for $[C_{22}H_{19}BrN_4O_4+H]^+$: 483.07, found 482.90.

Example 325

Preparation of 2-((5-bromo-2-((2-oxo-1,2,3,4-tetrahydroquinolin-6-yl)amino)pyrimidin-4-yl)oxy)-N-methylbenzamide

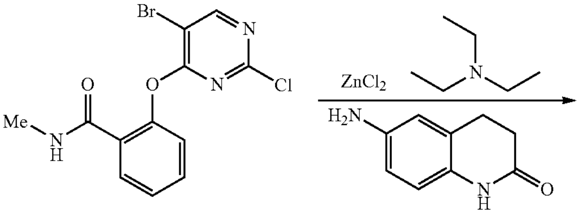

-continued

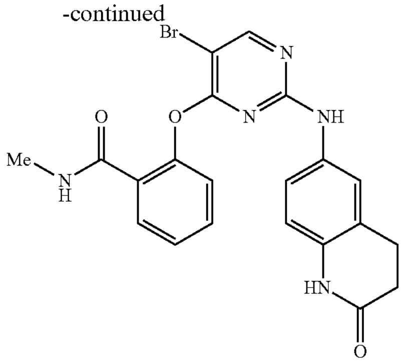

2-((5-Bromo-2-chloropyrimidin-4-yl)oxy)-N-methylbenzamide (0.140 g, 0.409 mmol), which was prepared as above, and zinc(II) chloride (0.067 g, 0.490 mmol) were mixed in 1,2-dichloroethane (3 ml). After 30 min, triethylamine (0.063 ml, 0.450 mmol) and 6-amino-3,4-dihydroquinolin-2(1H)-one (0.066 g, 0.409 mmol) were added. The mixture was microwaved at 130° C. for 10 min and then concentrated. 32 mg of product was recovered after automated reverse phase chromatography (water-10% THF in MeCN). MS calcd for $[C_{21}H_{18}BrN_5O_3+H]^+$: 468.07, found 467.95.

Example 326

Preparation of 2-((1H-pyrrolo[2,3-b]pyridin-5-yl)amino)-5-(trifluoromethyl) pyrimidin-4-ol

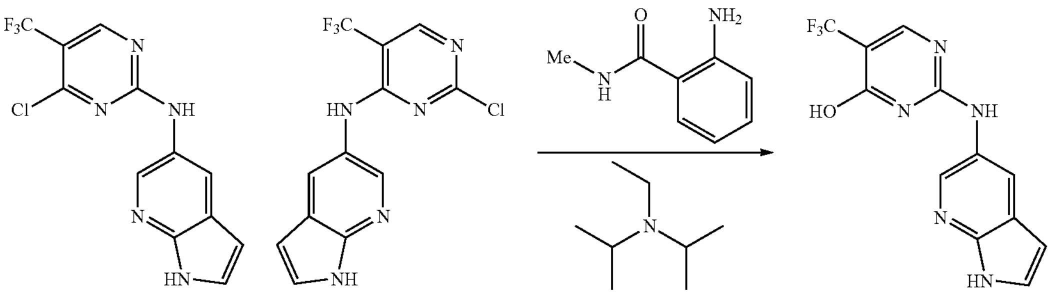

N-(4-Chloro-5-(trifluoromethyl)pyrimidin-2-yl)-1H-pyrrolo [2,3-b]pyridin-5-amine (0.102 g, 0.325 mmol), 2-amino-N-methylbenzamide (0.029 g, 0.195 mmol) and N-ethyl-N-isopropylpropan-2-amine (0.057 ml, 0.325 mmol) were mixed in DMF (1 ml). The mixture was microwaved at 120° C. for 20 min and then concentrated. Added 2:1 water/MeCN to precipitate a solid, which was filtered. The filtrate was concentrated and 20 mg of side product was recovered after automated reverse phase chromatography (water-MeCN). MS calcd for $[C_{12}H_8F_3N_5O+H]^+$: 296.08, found 295.85.

Example 327

Preparation of 2-(2-((5-bromo-2-((3,4,5-trimethoxyphenyl)amino)pyrimidin-4-yl)oxy)phenyl)-N-methylacetamide

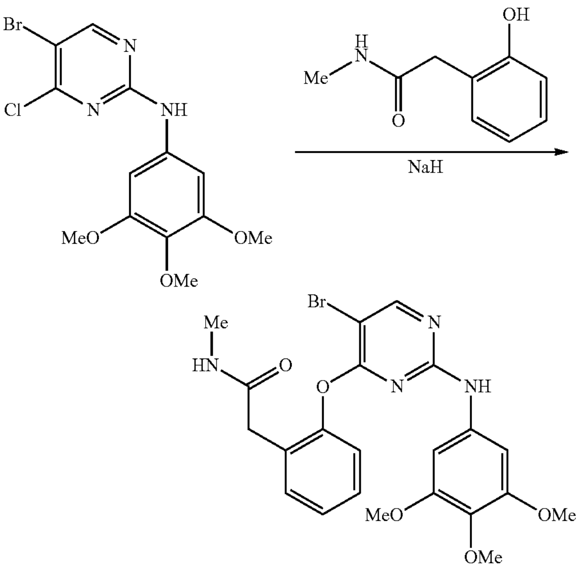

2-(2-Hydroxyphenyl)-N-methylacetamide (0.044 g, 0.267 mmol) and sodium hydride (8.33 mg, 0.347 mmol) were mixed in DMF (2 ml). After 5 min, 5-bromo-4-chloro-N-(3,4,5-trimethoxyphenyl)pyrimidin-2-amine (0.100 g, 0.267 mmol) was added. The mixture was microwaved at 120° C. for 20 min and then concentrated. 50 mg of product was recovered after automated reverse phase chromatography (water-10% THF in MeCN). MS calcd for $[C_{22}H_{23}BrN_4O_5+H]^+$: 503.10, found 503.00.

Example 328

Preparation of N-(2-((5-bromo-2-((3,4,5-trimethoxyphenyl)amino)pyrimidin-4-yl)oxy)benzyl)acetamide

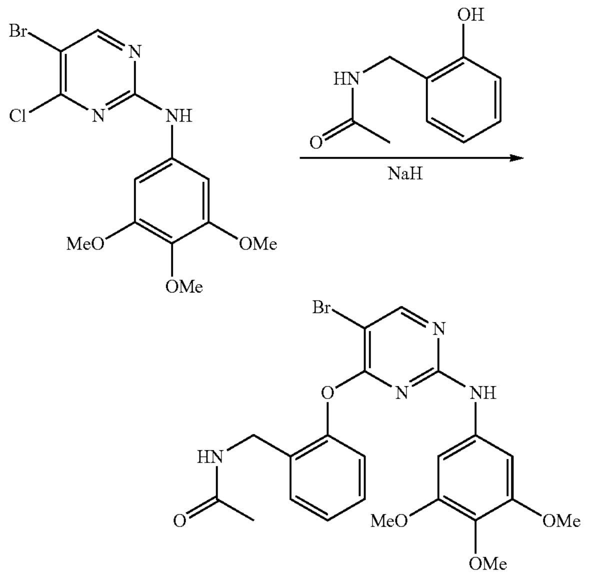

5-Bromo-4-chloro-N-(3,4,5-trimethoxyphenyl)pyrimidin-2-amine (0.110 g, 0.294 mmol), N-(2-hydroxybenzyl) acetamide (0.049 g, 0.294 mmol) and sodium hydride (0.015 g, 0.382 mmol) were mixed in DMF (2 ml). The mixture was microwaved at 120° C. for 20 min and then concentrated. 31 mg of product was recovered after automated reverse phase chromatography (water-10% THF in MeCN). MS calcd for $[C_{22}H_{23}BrN_4O_5+H]^+$: 503.10, found 503.05.

Example 329

Preparation of 4-((1H-indol-7-yl)oxy)-5-bromo-N-(3,4,5-trimethoxyphenyl) pyrimidin-2-amine and 2-((1H-indol-7-yl)oxy)-5-bromo-N-(3,4,5-trimethoxyphenyl) pyrimidin-4-amine

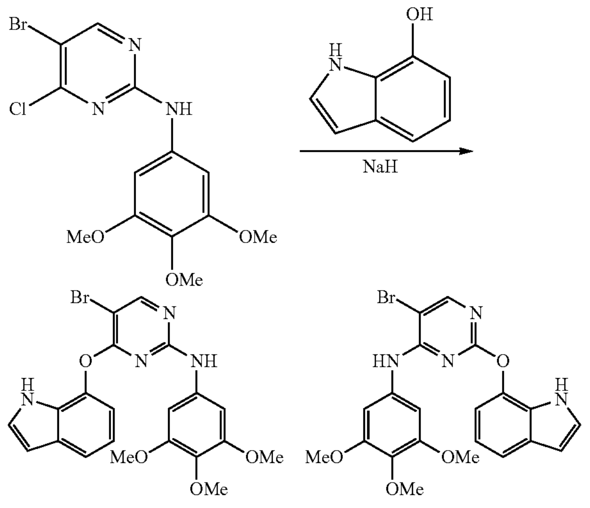

1H-Indol-7-ol (0.039 g, 0.294 mmol) and sodium hydride (0.015 g, 0.382 mmol) were mixed in DMF (3 ml). Then 5-bromo-4-chloro-N-(3,4,5-trimethoxyphenyl)pyrimidin-2-amine (0.110 g, 0.294 mmol) was added. The mixture was microwaved at 120° C. for 20 min and then concentrated. 44 mg of 4-((1H-indol-7-yl)oxy)-5-bromo-N-(3,4,5-trimethoxyphenyl)pyrimidin-2-amine and 6 mg of 2-((1H-indol-7-yl)oxy)-5-bromo-N-(3,4,5-trimethoxyphenyl)pyrimidin-4-amine were recovered after automated reverse phase chromatography (water-10% THF in MeCN). MS calcd for $[C_{21}H_{19}BrN_4O_4+H]^+$: 471.07, found 470.95.

Example 330

Preparation of 5-bromo-4-((5,6,7,8-tetrahydronaphthalen-1-yl)oxy)-N-(3,4,5-trimethoxyphenyl)pyrimidin-2-amine and 5-bromo-2-((5,6,7,8-tetrahydronaphthalen-1-yl)oxy)-N-(3,4,5-trimethoxyphenyl) pyrimidin-4-amine

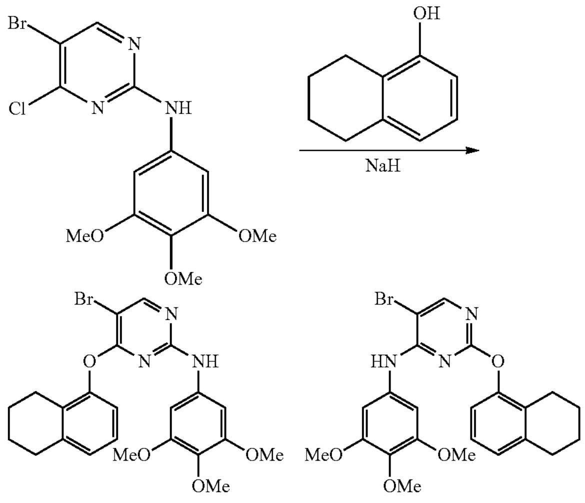

5,6,7,8-Tetrahydronaphthalen-1-ol (0.044 g, 0.294 mmol) and sodium hydride (0.015 g, 0.382 mmol) were mixed in DMF (3 ml). After 5 min, 5-bromo-4-chloro-N-(3,4,5-trimethoxyphenyl)pyrimidin-2-amine (0.110 g, 0.294 mmol) was added. The mixture was microwaved at 120° C. for 20 min and then concentrated. 66 mg of 5-bromo-4-((5,6,7,8-tetrahydronaphthalen-1-yl)oxy)-N-(3,4,5-trimethoxyphenyl)pyrimidin-2-amine and 14 mg of 5-bromo-2-((5,6,7,8-tetrahydronaphthalen-1-yl)oxy)-N-(3,4,5-trimethoxyphenyl)pyrimidin-4-amine were recovered after automated reverse phase chromatography (water-10% THF in MeCN). MS calcd for $[C_{23}H_{24}BrN_3O_4+H]^+$: 486.11, found 486.05.

Example 331

Preparation of 4-(1H-benzo[d][1,2,3]triazol-1-yl)-5-bromo-N-(3,4,5-trimethoxyphenyl)pyrimidin-2-amine and 2-(1H-benzo[d][1,2,3]triazol-1-yl)-5-bromo-N-(3,4,5-trimethoxyphenyl)pyrimidin-4-amine

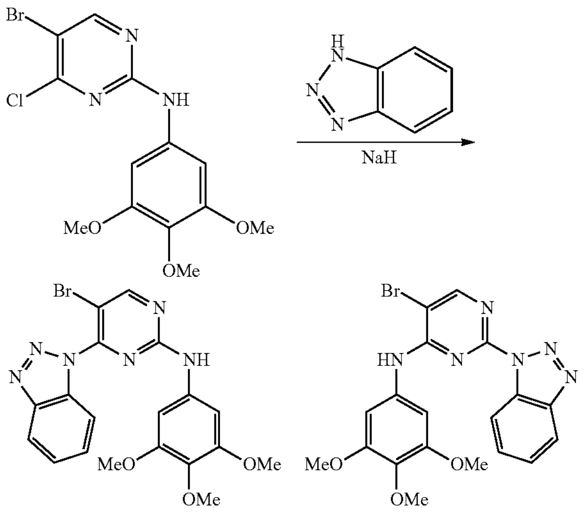

1H-Benzo[d][1,2,3]triazole (0.035 g, 0.294 mmol) and sodium hydride (0.015 g, 0.382 mmol) were mixed in DMF (3 ml). After 5 min, 5-bromo-4-chloro-N-(3,4,5-trimethoxyphenyl)pyrimidin-2-amine (0.110 g, 0.294 mmol) was added. The mixture was microwaved at 120° C. for 20 min and then concentrated. 70 mg of 4-(1H-benzo[d][1,2,3]triazol-1-yl)-5-bromo-N-(3,4,5-trimethoxyphenyl)pyrimidin-2-amine and 28 mg of 2-(1H-benzo[d][1,2,3]triazol-1-yl)-5-bromo-N-(3,4,5-trimethoxyphenyl)pyrimidin-4-amine were recovered after flash chromatography on silica gel (DCM-EtOAc). MS calcd for $[C_{23}H_{24}BrN_3O_4+H]^+$: 486.11, found 486.05.

Example 332

Preparation of cyclopropyl(6-((4-(cyclopropylamino)-5-(trifluoromethyl) pyrimidin-2-yl)amino)-3,4-dihydroisoquinolin-2(1H)-yl)methanone

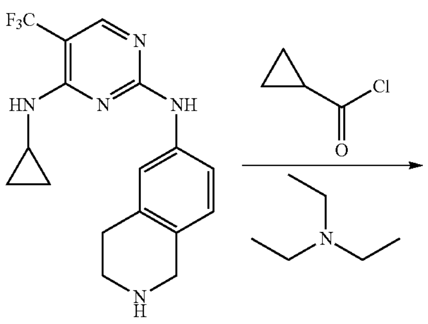

-continued

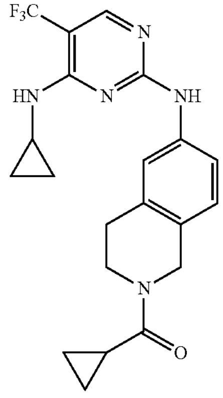

N4-Cyclopropyl-N2-(1,2,3,4-tetrahydroisoquinolin-6-yl)-5-(trifluoromethyl)pyrimidine-2,4-diamine.HCl (0.018 g, 0.047 mmol), cyclopropanecarbonyl chloride (4.23 μl, 0.047 mmol) and triethylamine (0.026 ml, 0.187 mmol) were mixed in DMF (3 ml). Heated to 60° C. for 8 h. Added MeOH and concentrated. 8 mg of product was recovered after flash chromatography on silica gel (DCM-EtOAc). MS calcd for $[C_{21}H_{22}F_3N_5O+H]^+$: 418.19, found 418.00.

Example 333

Preparation of N-(3-((2-((2-oxo-1,2,3,4-tetrahydroquinolin-6-yl)amino)-5-(trifluoromethyl)pyrimidin-4-yl)amino)propyl)cyclopropanecarboxamide

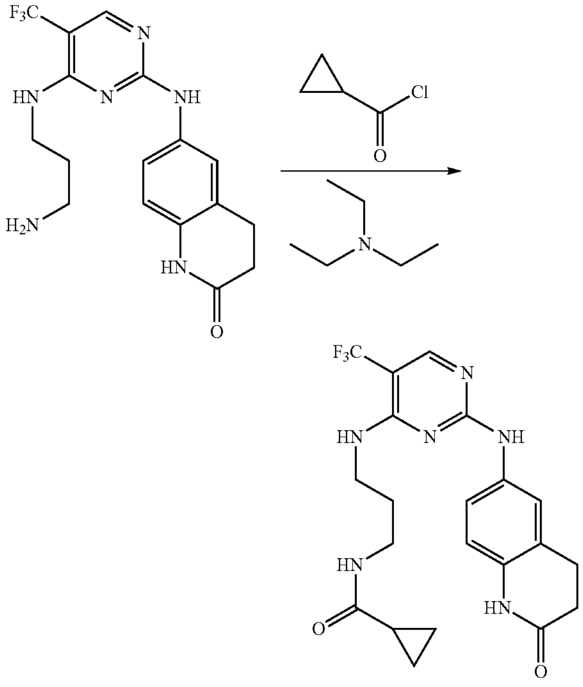

6-((4-((3-Aminopropyl)amino)-5-(trifluoromethyl)pyrimidin-2-yl)amino)-3,4-dihydro quinolin-2(1H)-one.HCl (0.024 g, 0.058 mmol), cyclopropanecarbonyl chloride (5.22 μl, 0.058 mmol) and triethylamine (0.020 ml, 0.144 mmol) were mixed in DMF (1 ml). Added MeOH and stirred for 1 h, then concentrated. 19 mg of product was recovered after flash chromatography on silica gel (DCM-MeOH). MS calcd for $[C_{21}H_{23}F_3N_6O_2+H]^+$: 449.19, found 449.00.

Example 334

Preparation of 6-((4-(cyclopropylamino)-5-(trifluoromethyl)pyrimidin-2-yl)amino)-2,3-dihydrophthalazine-1,4-dione

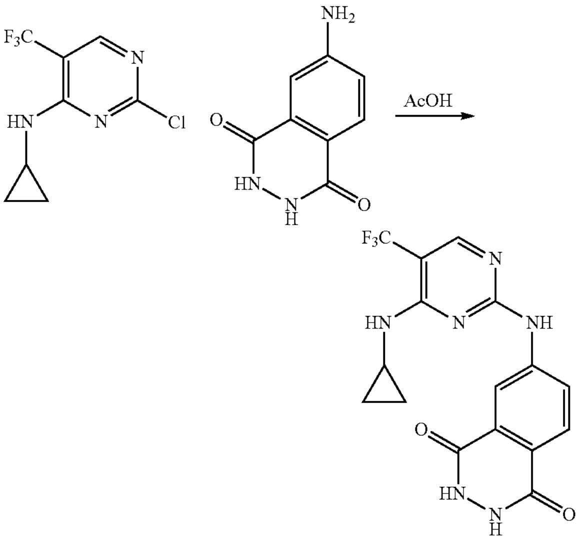

2-Chloro-N-cyclopropyl-5-(trifluoromethyl)pyrimidin-4-amine (0.055 g, 0.231 mmol) and 6-amino-2,3-dihydrophthalazine-1,4-dione (0.041 g, 0.231 mmol) were mixed in acetic acid (2 ml). The mixture was microwaved at 110° C. for 20 min and then concentrated. Added MeOH and 5% DMF and filtered the solid to give 35 mg of product. MS calcd for $[C_{16}H_{13}F_3N_6O_2+H]^+$: 379.12, found 379.00.

Example 335

Preparation of 1-(8-((5-bromo-2-((3,4,5-trimethoxyphenyl)amino)pyrimidin-4-yl)oxy)-3,4-dihydroquinolin-1(2H)-yl)ethan-1-one and 1-(8-((5-bromo-4-((3,4,5-trimethoxyphenyl)amino)pyrimidin-2-yl)oxy)-3,4-dihydroquinolin-1(2H)-yl)ethan-1-one

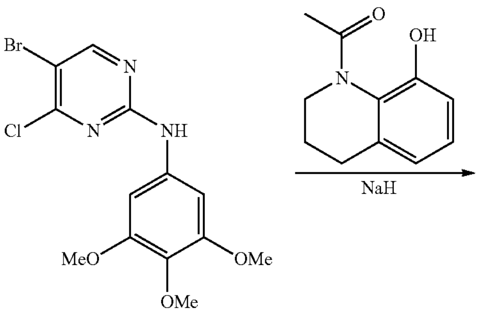

-continued

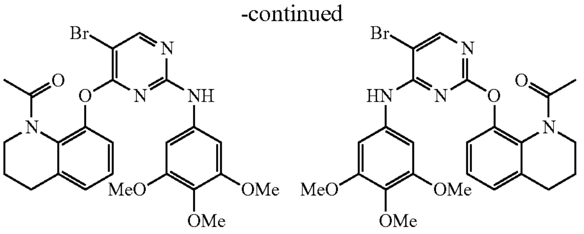

5-Bromo-4-chloro-N-(3,4,5-trimethoxyphenyl)pyrimidin-2-amine (0.100 g, 0.267 mmol), 1-(8-hydroxy-3,4-dihydroquinolin-1(2H)-yl)ethan-1-one (0.051 g, 0.267 mmol) and sodium hydride (0.014 g, 0.347 mmol) were mixed in DMF (2 ml). The mixture was microwaved at 120° C. for 20 min and then concentrated. 52 mg of 1-(8-((5-bromo-2-((3,4,5-trimethoxyphenyl)amino)pyrimidin-4-yl)oxy)-3,4-dihydroquinolin-1(2H)-yl)ethan-1-one and 36 mg of 1-(8-((5-bromo-4-((3,4,5-trimethoxyphenyl)amino)pyrimidin-2-yl)oxy)-3,4-dihydroquinolin-1(2H)-yl)ethan-1-one were recovered after automated reverse phase chromatography (water-10% THF in MeCN). MS calcd for $[C_{24}H_{25}BrN_4O_5+H]^+$: 529.11, found 529.10.

Example 336

Preparation of 2-((5-bromo-2-((3,4,5-trimethoxyphenyl)amino)pyrimidin-4-yl)oxy)phenol

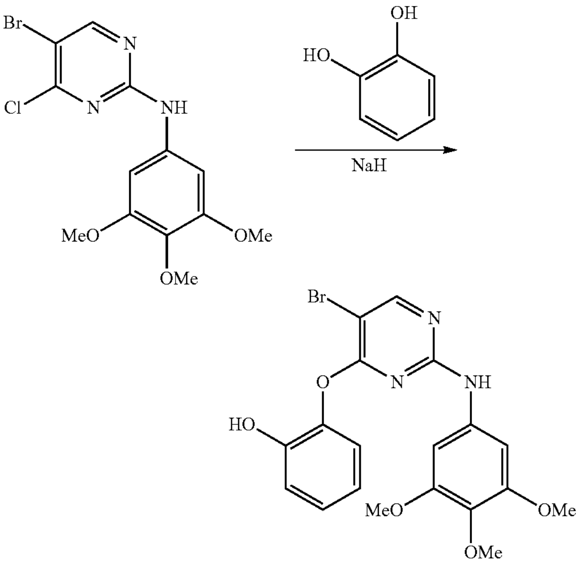

Pyrocatechol (0.032 g, 0.294 mmol) and sodium hydride (0.015 g, 0.382 mmol) were mixed in DMF (2 ml). Then 5-bromo-4-chloro-N-(3,4,5-trimethoxyphenyl)pyrimidin-2-amine (0.110 g, 0.294 mmol) was added. The mixture was microwaved at 120° C. for 10 min and then concentrated. 31 mg of product was recovered after automated reverse phase chromatography (water-10% THF in MeCN). MS calcd for $[C_{19}H_{18}BrN_3O_5+H]^+$: 448.05, found 447.95.

Example 337

Preparation of 2-(hydroxymethyl)-N-methylbenzamide

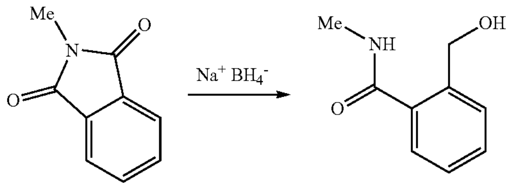 [SMILES: "Na+ BH4-" ; CN1C(=O)c2ccccc2C1=O ; CNC(=O)c1ccccc1CO]

2-Methylisoindoline-1,3-dione (1.08 g, 6.70 mmol) and SODIUM BOROHYDRIDE (0.761 g, 20.10 mmol) were mixed in 2-propanol (15 ml), toluene (2.500 ml) and water (2.500 ml). Added 1 M HCl to quench reagent, then concentrated to remove 2-propanol. Extracted twice with EtOAc, dried over sodium sulfate and concentrated and the product was used as-is. Data matched those reported in Tetrahedron Letters 39, (1998), 5017-5018.

Example 338

Preparation of 2-(((5-bromo-2-((3,4,5-trimethoxyphenyl)amino)pyrimidin-4-yl)oxy)methyl)-N-methylbenzamide

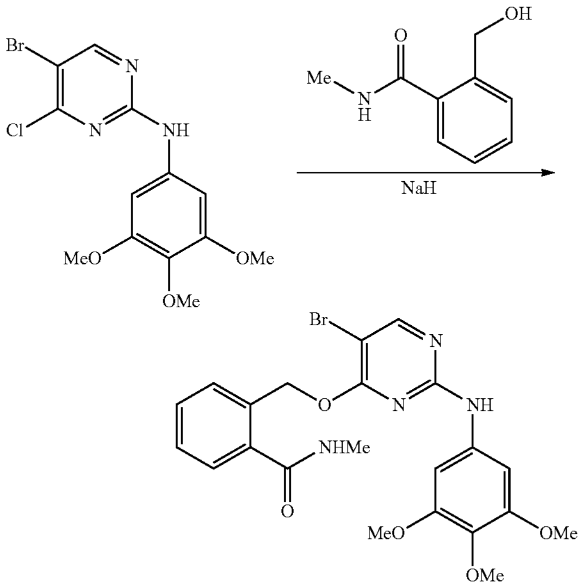

2-(Hydroxymethyl)-N-methylbenzamide (0.044 g, 0.267 mmol) and sodium hydride (0.014 g, 0.347 mmol) were mixed in DMF (3 ml). Then 5-bromo-4-chloro-N-(3,4,5-trimethoxyphenyl)pyrimidin-2-amine (0.100 g, 0.267 mmol) was added. The mixture was microwaved at 150° C. for 10 min and then concentrated. The material was subjected to flash chromatography on silica gel (DCM-MeOH) to give a semipure solid, which was then washed with acetone to give 18 mg of product. MS calcd for $[C_{22}H_{23}BrN_4O_5+H]^+$: 503.10, found 503.00.

Example 339

Preparation of 5-Chloro-N2-(5-methoxy-2-methylphenyl)-N4-(2-(5-methyl-1,2,4-oxadiazol-3-yl)phenyl)pyrimidine-2,4-diamine

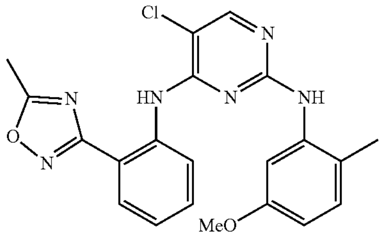

2,5-Dichloro-N-(2-(5-methyl-1,2,4-oxadiazol-3-yl)phenyl)pyrimidin-4-amine (0.161 g, 0.5 mmol) and 5-methoxy-2-methylaniline (0.137 g, 1 mmol) were taken in $^n$BuOH (5 mL) and processed according to General method 1b. Pale yellow solid (0.122 g, 58%). LCMS calcd for $C_{21}H_{19}ClN_6O_2$ [M+H]+: 423.13. Found: 423.00.

Example 340

Preparation of 2-((3-bromo-5-nitropyridin-2-yl)(ethyl)amino)ethan-1-ol

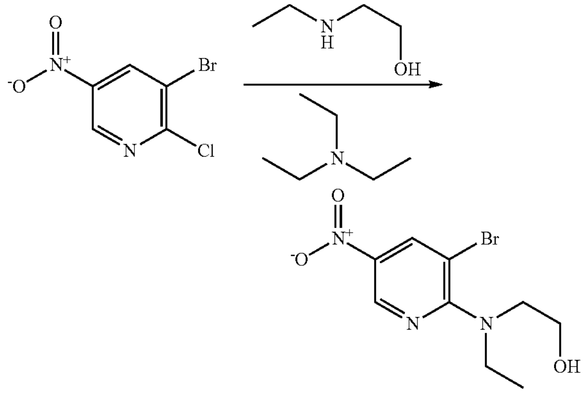

3-Bromo-2-chloro-5-nitropyridine (2 g, 8.42 mmol), triethylamine (1.174 ml, 8.42 mmol) and 2-(ethylamino)ethan-1-ol (0.751 g, 8.42 mmol) were mixed in Acetonitrile (30 ml). Heated to 80° C. for 14 h and then concentrated. 1.76 g of product was recovered after automated chromatography on silica gel (DCM-EtOAc).

Example 341

Preparation of 4-ethyl-7-nitro-3,4-dihydro-2H-pyrido[3,2-b][1,4]oxazine

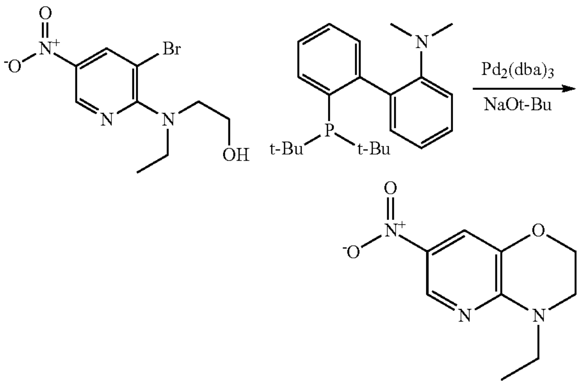

2-((3-Bromo-5-nitropyridin-2-yl)(ethyl)amino)ethan-1-ol (0.182 g, 0.627 mmol), 2'-(di-tert-butylphosphanyl)-N,N-dimethyl-[1,1'-biphenyl]-2-amine (0.013 g, 0.038 mmol), Pd2(dba)3 (0.017 g, 0.019 mmol) and sodium 2-methylpropan-2-olate (0.090 g, 0.941 mmol) were mixed in Toluene (5 ml). Heated to 100° C. for 16 h and then concentrated. Added water and extracted three times with DCM and once with EtOAc. Dried over sodium sulfate and concentrated. The material was subjected to flash chromatography on alumina (DCM) to give 51 mg of the product. LCMS calcd for $[C_9H_{11}N_3O_3+H]^+$: 210.09, found: 210.21.

Example 342

Preparation of 4-ethyl-3,4-dihydro-2H-pyrido[3,2-b][1,4]oxazin-7-amine

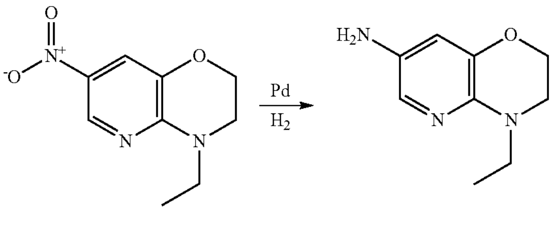

4-Ethyl-7-nitro-3,4-dihydro-2H-pyrido[3,2-b][1,4]oxazine (0.051 g, 0.244 mmol) and palladium (2.59 mg, 0.024 mmol) were mixed in Methanol (3 ml). Added hydrogen balloon and stirred for 2 d, then filtered through Celite with DCM and MeOH and concentrated to give 47 mg of product that was used as-is. LCMS calcd for $[C_9H_{11}N_3O_3+H]^+$: 210.09, found: 210.21.

Example 343

Preparation of 6-((5-bromo-4-((4-ethyl-3,4-dihydro-2H-pyrido[3,2-b][1,4]oxazin-7-yl)amino)pyrimidin-2-yl)amino)-3,4-dihydroquinolin-2(1H)-one

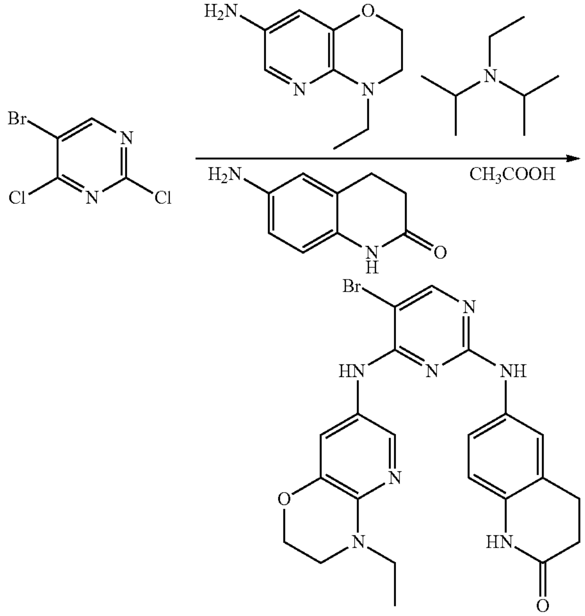

5-Bromo-2,4-dichloropyrimidine (0.051 g, 0.223 mmol), 4-ethyl-3,4-dihydro-2H-pyrido[3,2-b][1,4]oxazin-7-amine (0.04 g, 0.223 mmol) and N-ethyl-N-isopropylpropan-2-amine (0.039 ml, 0.223 mmol) were mixed in Acetonitrile (2 ml). The mixture was microwaved at 100° C. for 10 minutes and then concentrated. 6-amino-3,4-dihydroquinolin-2(1H)-one (0.032 g, 0.200 mmol) was added along with Acetic Acid (1 ml). The mixture was microwaved at 120° C. for 20 minutes and then concentrated. 5 mg of product was recovered after reverse phase HPLC (water-MeCN). MS calcd for $[C_{22}H_{22}BrN_7O_2+H]^+$: 496.11, found 496.32.

Example 344

Preparation of N4-cyclopropyl-N2-(4-ethyl-3,4-dihydro-2H-pyrido[3,2-b][1,4]oxazin-7-yl)-5-(trifluoromethyl)pyrimidine-2,4-diamine

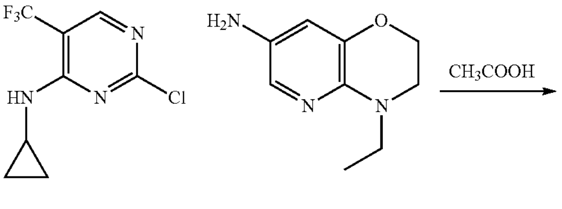

-continued

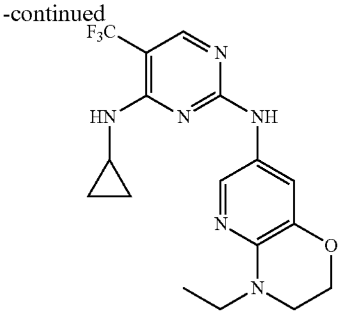

2-Chloro-N-cyclopropyl-5-(trifluoromethyl)pyrimidin-4-amine (0.120 g, 0.505 mmol) and 4-ethyl-3,4-dihydro-2H-pyrido[3,2-b][1,4]oxazin-7-amine (0.091 g, 0.505 mmol) were mixed in Acetic Acid (2 ml). The mixture was microwaved at 110° C. for 10 minutes and then concentrated. 76 mg of product was recovered after automated reverse phase chromatography (water-MeCN). MS calcd for $[C_{17}H_{19}F_3N_6O+H]^+$: 381.17, found 381.33.

Additional Examples are provided herein:

| Example | Structure | Formula |
|---|---|---|
| 345 | 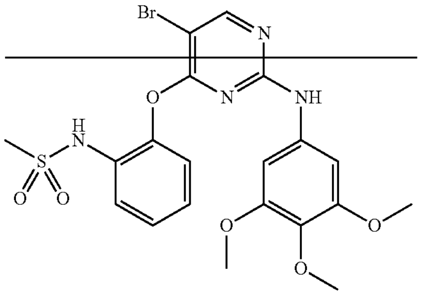 | $C_{20}H_{21}BrN_4O_6S$ |
| 346 | 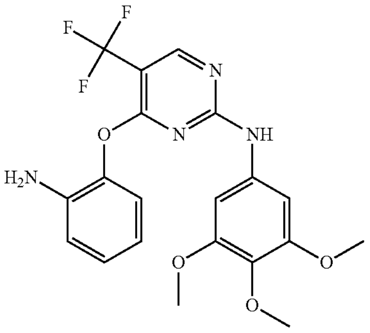 [SMILES: COc1cc(Nc2ncc(C(F)(F)F)c(Oc3ccccc3N)n2)cc(OC)c1OC] | $C_{20}H_{19}F_3N_4O_4$ |
| 347 | 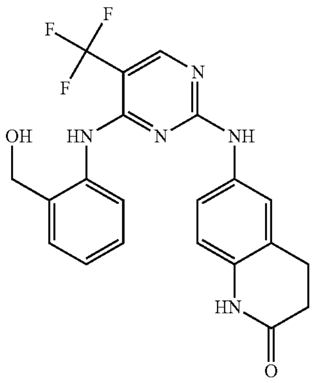 [SMILES: O=C1CCc2cc(Nc3ncc(C(F)(F)F)c(Nc4ccccc4CO)n3)ccc2N1] | $C_{21}H_{18}F_3N_5O_2$ |

-continued
| Example | Structure | Formula |
| --- | --- | --- |
| 348 | 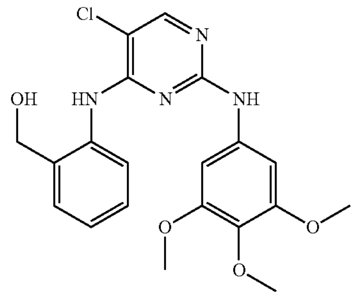 [SMILES: COc1cc(Nc2ncc(Cl)c(Nc3ccccc3CO)n2)cc(OC)c1OC] | $C_{20}H_{21}ClN_4O_4$ |
| 349 | 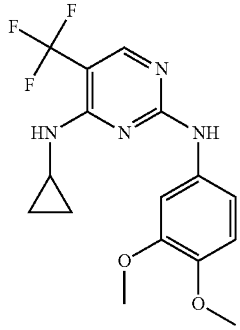 [SMILES: COc1ccc(Nc2ncc(C(F)(F)F)c(NC3CC3)n2)cc1OC] | $C_{16}H_{17}F_3N_4O_2$ |
| 350 | 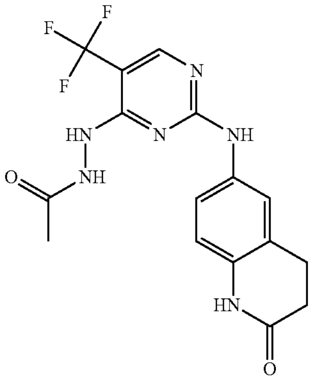 [SMILES: CC(=O)NNc1nc(Nc2ccc3c(c2)CCC(=O)N3)ncc1C(F)(F)F] | $C_{16}H_{15}F_3N_6O_2$ |
| 351 | 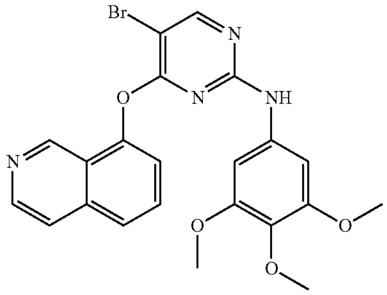 [SMILES: COc1cc(Nc2ncc(Br)c(Oc3cccc4ccncc34)n2)cc(OC)c1OC] | $C_{22}H_{19}BrN_4O_4$ |

-continued
| Example | Structure | Formula |
|---|---|---|
| 352 | 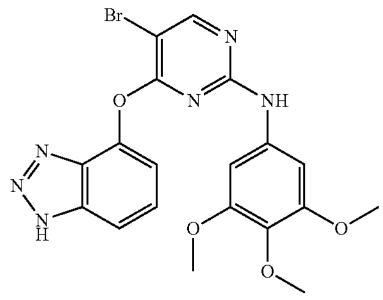 [SMILES: COc1cc(Nc2ncc(Br)c(Oc3cccc4[nH]nnc34)n2)cc(OC)c1OC] | $C_{19}H_{17}BrN_6O_4$ |
| 353 | 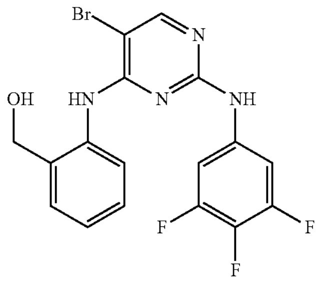 [SMILES: OCc1ccccc1Nc1nc(Nc2cc(F)c(F)c(F)c2)ncc1Br] | $C_{17}H_{12}BrF_3N_4O$ |
| 354 | 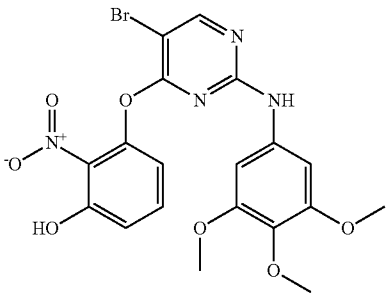 | $C_{19}H_{17}BrN_4O_7$ |
| 355 | 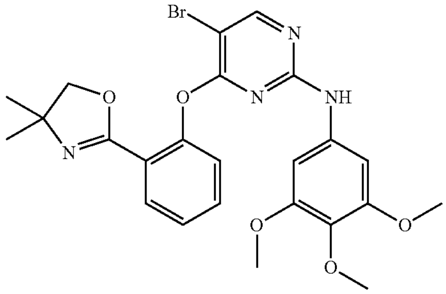 | $C_{24}H_{25}BrN_4O_5$ |
| 356 | 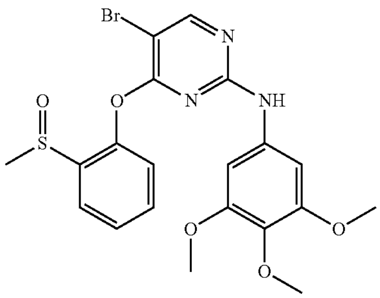 | $C_{20}H_{20}BrN_3O_5S$ |

Example 357

Methods

Plasmids

The cDNA encoding human Atg13 (KIAA0652/AB014552) was obtained from Kazusa DNA Research Institute in Japan. The cDNAs for human FIP200, mouse ULK1, and mouse ULK2 constructs were obtained from Open Biosystems (clones 3908134, 6834534, and 5709559 respectively). Human Atg101, human VPS34, human Ambra1 and human Beclin-1 were obtained from Invitrogen. The cDNA for mouse Syntenin-1 was cloned from a cDNA library prepared from mouse embryonic fibroblasts (MEFs) and sequence verified to match the sequence of the transcript variant 1 of mouse Syntenin-1 (NM_001098227.1).

The Flag tag and attL1 sites (for BP reaction) were PCR amplified using the standard procedure. cDNAs were subcloned into pDONR221 with BP clonase (Invitrogen), and site-directed mutagenesis was performed using QuikChange II XL (Stratagene). Kinase dead ULK1 was achieved by a K46I mutation. Kinase dead VPS34 was achieved by D747N/N748K double mutation. Wild type and mutant alleles in pDONR221 were sequenced in their entirety to verify no additional mutations were introduced during PCR or mutagenesis steps and then put into either pcDNA3 Myc or Flag mammalian expression vector, or pcDNA6.2 V5 dest (Invitrogen), or pQCXIN retroviral destination vector (Addgene 17399) by LR reaction (Invitrogen). pMXspuro-GFP-DFCP1 was a kind gift from Noboru Mizushima and pEGFP-p40PX was a kind gift from Seth Field (UCSD).

Antibodies and Reagents

Cell Signaling Antibodies used: total 4EBP-1 (#9452), total Beclin (#3495), Parp (#9542), total Atg13 (#6940), pAMPK Thr172 (#2535), total AMPK alpha1 (#2532), pACC Ser79 (#3661), total ACC (#4190), pAurora (#2914), pRaptor Ser792 (#2083), total raptor (#4978), phospho ULK1 ser555 (#5869), pS6 (#4858), Myc (#2278), LC3B (#3868), total VPS34 (#4263), pJak2 (#4406). Phospho VPS34 ser249 antibody was developed in collaboration with Gary Kasof at Cell Signaling Technology.

Abgent antibodies used: gabarap (PM037). pFAK Y397 from Abcam (ab4803). Total FAK from Epitomics (2146-1). Sigma antibodies used: Total ULK1(A7481) tubulin (T5168), and Flag polyclonal (F7425). Guinea pig anti p62 sequestosome antibody from Progen, Heidelberg Germany (03-GPP62-C). pBeclin-1 ser15 from Abbiotec (254515).

EBSS (14155-063) and Glucose-free media (11966-025) from Gibco/Life Technologies. Chloroquine from Sigma. AZD-8055 (A-1008) from Active Biochem. Annexin V-PE Apoptosis Detection Kit from BD Biosciences. Phos-Tag™ AAL-107 from NARD (#304-93521). Ad5-CMV-Cre purchased from University of Iowa adenoviral core.

Cell Culture, Transient Transfections, Cell Lysis and Phos-tag™ Mobility Shift Analysis HEK293T, U87MG, PC3, A549 and SV40 immortalized wild-type mouse embryonic fibroblast (MEF) cells were cultured in DMEM (Mediatech, Manassas, Va.) containing 10% fetal bovine serum (Hyclone, Thermo Scientific) and penicillin/streptomycin at 37° C. in 10% $CO_2$ FAK MEs were a kind gift from David Schlaepfer (UCSD), ULK1 KO and ULK1/2 DKO MEFs from Craig Thompson (MSKCC) VPS34$^{flox/flox}$ MEFs from Wei-Xing Zong (SUNYSB) and Atg5 MEFs from Jay Debnath (UCSF).

For transient expression in HEK293T cells were transfected with 2 ug each DNA plasmid per 6 cm dish using Lipofectamine 2000 (Invitrogen) following the manufacturer's protocol. Cells were harvested 24 hours after transfection and rinsed once with ice-cold PBS and lysed in boiling SDS lysis buffer (10 mM Tris pH7.5, 100 mM NaCl, 1% SDS). After trituration, lysates were equilibrated for protein levels using the BCA method (Pierce) and resolved on 8 to 15% SDS-PAGE Phos-Tag™ gels according to the manufacturer's instructions. Briefly, Phos-Tag™ AAL-107 (HARD #304-93521) was added to SDS-PAGE acryamide mixture at a final concentration of 50 μM along with $MnCl_2$ at a final concentration of 100 μM. Prior to transfer, the gel is soaked in transfer buffer containing 1 mmol/L EDTA for 30 min with gentle agitation to eliminate the manganese ions from the gel. The gel is transferred to PVDF membrane and probed with indicated antibodies according to the manufacturers instructions.

Lenti- and Retro-viral Preparation and Viral Infection

Lentiviral shRNA transduction and retroviral gene expression was performed as described previously. Briefly, the pQCXIN Flag ULK1 construct was transfected along with the ampho packaging plasmid into growing 293 Ts. Virus-containing supernatants were collected 48 hours after transfection, filtered to eliminate cells and target ULK1−/− MEFs or A549s were infected in the presence of polybrene. 24 hours later, cells were selected with neomcyin. The pLKO shRNA vectors encoding shRNAs were transfected into HEK293T cells with lentiviral packaging plasmids vsvg, GAG/pol, and REV using Lipofectamine 2000. Viruses were collected 48 hours after transfection, and MEFs (shRNA #93 against mULK2) and U2OS (shRNA #8 and #91 against hULK1 and hULK2 respectively) already stably expressing Myc ULK1 were infected with the collected viruses for 4 h in the presence of polybrene to knock down the endogenous human protein, but not Myc ULK1, which is mouse.

ULK1 Kinase Assays

Gamma-$^{32}$P assays to measure ULK1 kinase activity were performed as previously described. Briefly, Flag ULK1 was transfected into HEK293T cells and 20 hours later treated as indicated. The immmunoprecipitate was washed in IP buffer 3 times, and washed in kinase buffer (25 mM MOPS, pH 7.5, 1 mM EGTA, 0.1 mM $Na_3VO_4$, 15 mM $MgCl_2$,). Hot and cold ATP were added at a 100 μM final concentration. As substrates, GST or the recombinant protein GST-Atg101 purified from *E. coli* were used at 1 μg for each reaction. Reactions were boiled, run out on SDS page gel. The gel was dried, and imaged using PhosphoImager software. For cold assays to asses ULK1, Flag ULK1 which was transiently overexpressed and immunoprecipited from HEK293T cells. Reactions were then run out on SDS page gel, transferred to PVDF membrane and blotted for total levels Fluorescence Microscopy Vps34$^{flox/flox}$ MEFs were reconstituted with Flag-VPS34 and either p40FX or GFP-DFCP1. 48 hours post infection with adenovirus expressing Cre recombinase (MOI of 100), cells were plated on glass coverslips at a density of $3\times10^5$ cells per well in 6-well tissue culture plates. 18 h later, cells were fixed in 4% PFA in PBS for 10 minutes and permeabilized in 0.2% Triton in PBS for 10 minutes. The following primary antibodies were used: mouse anti-Myc epitope and LC3B XP antibody (2276 and 3868 respectively, Cell Signaling Technologies). Secondary antibodies were anti-rabbit Alexa488 and anti-mouse Alexa594 (Molecular Probes, 1:1000. Cells were then fixed and counter stained with DAPI. Coverslips were mounted in FluoromountG (SouthernBiothech). Images were acquired on a Zeiss Axioplan2 epifluorescence microscope coupled to the Openlab software. Confocal images of mitotracker were taken on Zeiss LSM 710 laser scanning confocal microscope. 10 random fields per condition were acquired using the 100× objective and representative images shown. Glass coverslips were mounted directly on plate with FluoromountG and images taken on Zeiss Axioplan2 epifluorescence microscope.

Peptide Library Screening

Peptide mixtures (50 mM) were incubated 2 hours at 30° C. in multiwell plates in the presence of the indicated kinase in 50 mM HEPES, pH 7.4, 25 mM MgCl2, 0.25 mM DTT, 12.5 mM b-glycerophosphate, 5 mM EGTA, 2 mM EDTA, 0.1% Tween 20, and 50 mM ATP (0.03 mCi/ml). Aliquots of each reaction were transferred to streptavidin-coated membrane (Promega), which was quenched, washed and dried as described previously. Membranes were exposed to a phosphor imager screen to quantify radiolabel incorporation. Heat maps were generated using Microsoft Excel.

Mass Spectrometry

Myc ULK1 overexpressed in 293T cells was treated with either vehicle, A769662, or phenformin, IP'd with anti Myc antibody (Cell Signaling), run out on SDS page gel and coomassie stained. Bands on the gel corresponding to ULK1 were cut out and subjected to reduction with dithiothreitol, alkylation with iodoacetamide, and in-gel digestion with trypsin or chymotrypsin overnight at pH 8.3, followed by reversed-phase microcapillary/tandem mass spectrometry (LC/MS/MS). LC/MS/MS was performed using an Easy-nLC nanoflow HPLC (Proxeon Biosciences) with a self-packed 75 μm id×15 cm $C_{18}$ column coupled to a LTQ-Orbitrap XL mass spectrometer (Thermo Scientific) in the data-dependent acquisition and positive ion mode at 300 nL/min. Peptide ions from AMPK predicted phosphorylation sites were also targeted in MS/MS mode for quantitative analyses. MS/MS spectra collected via collision induced dissociation in the ion trap were searched against the concatenated target and decoy (reversed) single entry ULK1 and full Swiss-Prot protein databases using Sequest (Proteomics Browser Software, Thermo Scientific) with differential modifications for Ser/Thr/Tyr phosphorylation (+79.97) and the sample processing artifacts Met oxidation (+15.99), deamidation of Asn and Gln (+0.984) and Cys alkylation (+57.02). Phosphorylated and unphosphorylated peptide sequences were identified if they initially passed the following Sequest scoring thresholds against the target database: 1+ ions, Xcorr≥2.0 Sf≥0.4, P≥5; 2+ ions, Xcorr≥2.0, Sf≥0.4, P≥5; 3+ ions, Xcorr≥2.60, Sf≥0.4, P≥5 against the target protein database. Passing MS/MS spectra were manually inspected to be sure that all b- and y-fragment ions aligned with the assigned sequence and modification sites. Determination of the exact sites of phosphorylation was aided using FuzzyIons and GraphMod and phosphorylation site maps were created using ProteinReport software (Proteomics Browser Software suite, Thermo Scientific). False discovery rates (FDR) of peptide hits (phosphorylated and unphosphorylated) were estimated below 1.5% based on reversed database hits.

Apoptosis Analysis—Western Blot and Flow Cytometry

A549 cells (ATCC #CCL185) and MEFs were seeded at a concentration of $2.5\times10^5$ cells/mL (i.e., 750,000 cells per 6 cm dish), grown overnight (18 hrs) and treated as indicted in the figure legends. Unless otherwise indicated, "starvation" is EBSS and "control" is DMEM with full serum for indicated timepoints. Samples for western blot were washed once in 1× ice cold PBS and lysed in boiling SDS lysis buffer (10 mM Tris p17.5, 100 mM NaCl, 1% SDS). After trituration, lysates were equilibrated for protein levels using the BCA method (Pierce) and resolved on 8 to 15% SDS-PAGE gels, depending on the size of the protein. PVDF membranes were probed with indicated antibodies overnight according to the manufacturers instructions.

For flow cytometry analysis, cells were collected at the appropriate time point, washed once in PBS, trypsinized and pelleted. For Annexin V staining, cells were washed in 1× Annexin V buffer and treated as described by the Annexin V staining protocol (BD Pharmingen, San Diego, Calif.). Briefly, cells were resuspended in Annexin V buffer to a concentration of one million per mL, 100,000 cells were then stained with 5 μL of phycoerythrin (PE)-conjugated Annexin V antibody (BD Pharmingen, San Diego, Calif.) and 5 μL of 7-amino-actinomycin D (7AAD) and then incubated at room temperature for 15 minutes. 400 μL of Annexin V buffer was then added to each sample with gentle mixing. Stained cells were analyzed using a FACScan flow cytometer (Becton Dickinson, San Jose, Calif.). Flow cytometry data was analyzed using FlowJo 8.6 software (Tree Star Inc., Ashland, Oreg.).

Selectivity Profiling

Kinase inhibitor specificity profiling assays were first carried out using DiscoveRx KINOMEscan competition binding assay against a panel of 456 kinases (www dot discoverx dot corn) using 1 μM compound 14. Kinases that potentially interacted with compound 14 (inhibited to less than 10% DMSO control) were then tested in classic in vitro kinase assays with a dose curve of compound 14 to monitor enzymatic activity and determine $IC_{50}$ curves using Reaction Biology.

Discussion

Determination of the ULK1 Kinase Consensus Phosphorylation Site

To identify novel substrates of ULK1 that may be important for its function, we identified an optimal ULK1 phosphorylation site consensus motif using arrayed degenerate peptide libraries, as we have done previously for AMPK. To generate active ULK1 for these experiments, epitope-tagged ULK1 was co-expressed with its subunits FIP200 and Atg13 in HEK293T cells and peptide eluted from affinity resin. Previous studies have demonstrated that association of FIP200 and Atg13 is required for proper ULK1 activity. To examine the in vitro kinase activity of our immunoprecipitated ULK1/FIP200/Atg13 complexes, we utilized Atg13 as an in vitro kinase substrate, as it is a conserved ULK1 substrate across evolution, and one of the earliest ULK1 substrates reported in mammalian cells. The purified ULK1 complex exhibited robust kinase activity towards Atg13 in a dose-response fashion. This source of purified ULK1 complex was subjected to in vitro kinase assays on arrayed degenerate peptide libraries, revealing selective transfer of $^{32}\gamma$-ATP to specific peptide libraries reflecting the sequence preferences of ULK1 towards its substrates.

Figure 4A:
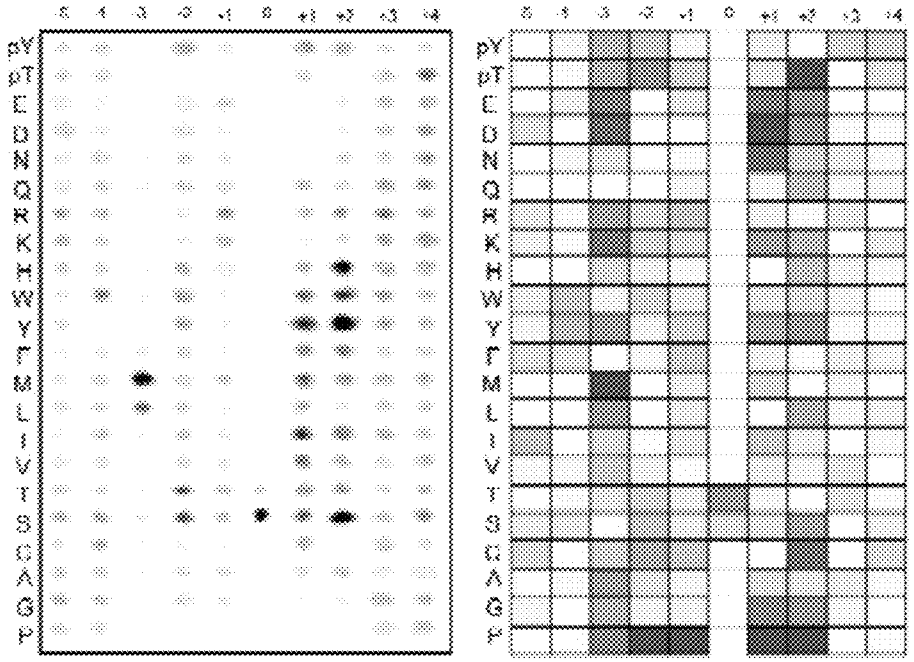
FIG. 4A is a set of images illustrating ULK1 substrate motif sequence specificity.
Figure 4B:
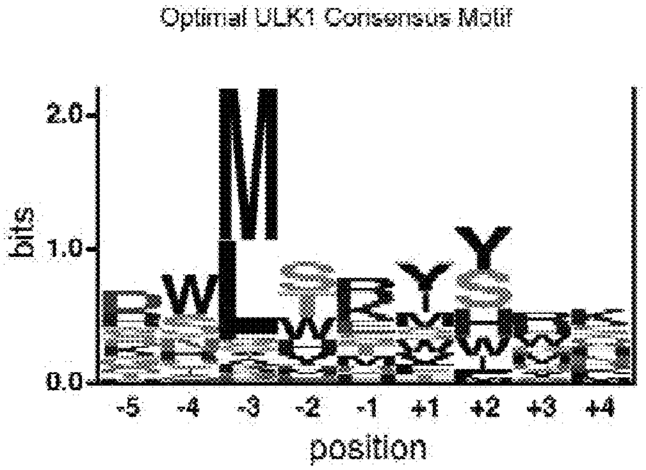
FIG. 4B is a matrix illustrating position-specific selectivities for ULK1.
Figure 4C:
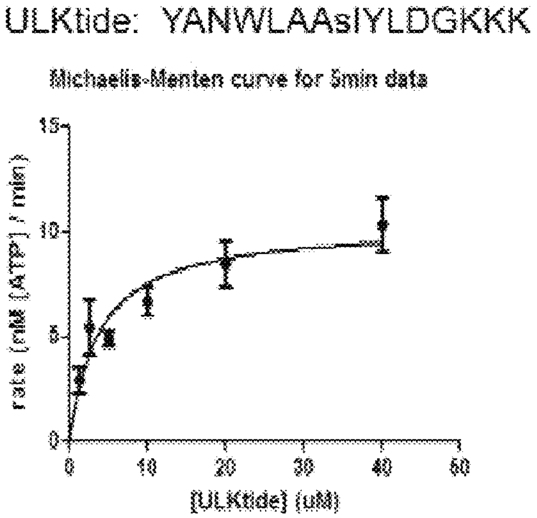
FIG. 4C is a graph illustrating ULK1 kinase activity in vitro (ULKtide is SEQ ID NO: 1).
Figure 4D:
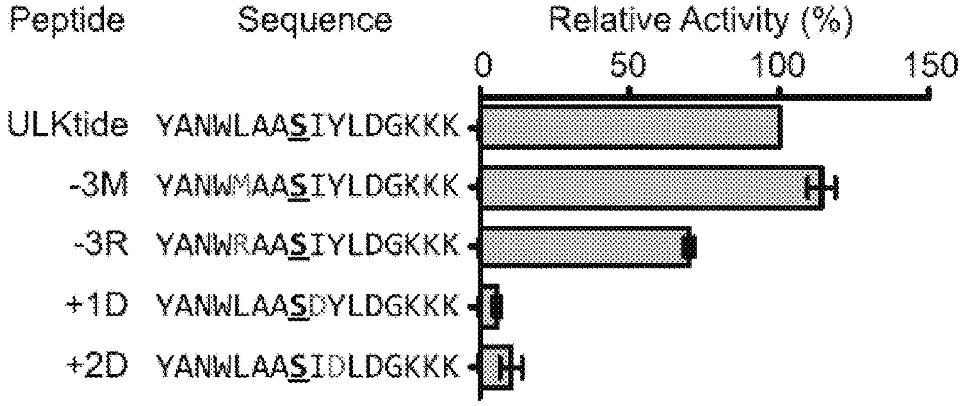
FIG. 4D is a graph illustrating residue substitutions (−7E, +5K, −3M, −3R, +1D and +2D are, respectively, SEQ ID NOs: 2-7).

The ULK1 substrate motif sequence specificity we determined (FIG. 4A) matches extremely well with recent data on the yeast ortholog of ULK1, Atg1, but is quite unique compared to most kinases studied to date. In particular, ULK1 prefers hydrophobic residues at position −3, particularly methionine and leucine. In addition, hydrophobic residues, especially bulky resides like phenylalanine and tyrosine are enriched in the +1 position, correlating well with the Atg1 optimal motif (FIG. 4B). We generated an optimal peptide, Ulktide, based on the optimal ULK1 substrate consensus sequence, validating its efficient use as a surrogate for ULK1 kinase activity in vitro (FIG. 4B). Starting with this peptide, substitutions in key residues including the −3 and +1 positions were tested for activity as a substrate in an in vitro kinase assays revealing that both positions are important for optimal sequence specificity (FIG. 4D).

Identification of Novel ULK1 Substrates

A matrix of the position-specific selectivities of ULK1 (FIG. 4B) was used to bioinformatically search the human proteome for sites closely matching the ULK1 substrate consensus. We chose to focus first on those candidate substrates with well-established highly conserved roles in autophagy. To define ULK1 phosphorylation sites in vivo, we took advantage of the fact that wild-type ULK1 is constitutively active when overexpressed, thus we compared global phosphorylation events on epitope-tagged candidate targets when co-expressed with wild-type, or kinase-dead, ULK1 in HEK293T cells. Using mass spectrometry to determine all phospho-peptides in candidate proteins under these conditions revealed that several candidate proteins bearing multiple ULK1 consensus sites contained peptides which were highly phosphorylated in the presence of wild-type but not kinase-dead ULK1. Focusing on the core autophagy proteins bearing a consensus candidate ULK1 phosphorylation site, it was notable that none of the downstream ATG components contained this consensus (e.g. ATG5, ATG7, ATG3, ATG12), yet many of the upstream components (FIP200, ATG13, ATG14, Beclin) did bear such sequences. We first focused on the components of the ULK1 kinase complex itself, including FIP200, ATG13, and ATG101.

Figure 10A:
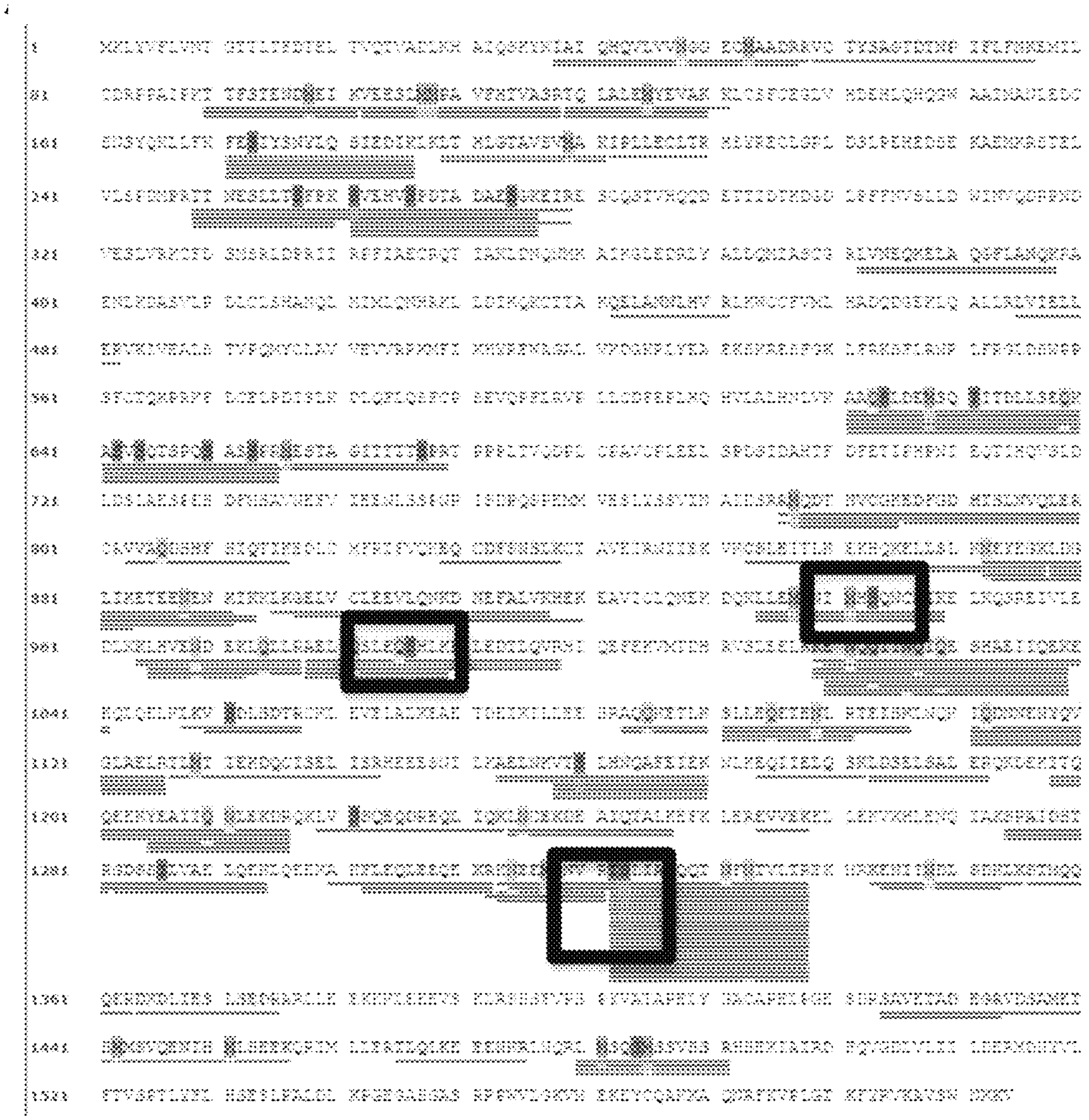
FIGS. 10A-10C are a series of sequence alignmnets illustrating the discovery of multiple serine sites in FIP200 and Atg13 bearing the ULK1 substrate consensus whose phosphorylation was induced by overexpressed ULK1 in vivo.
Figure 10A:
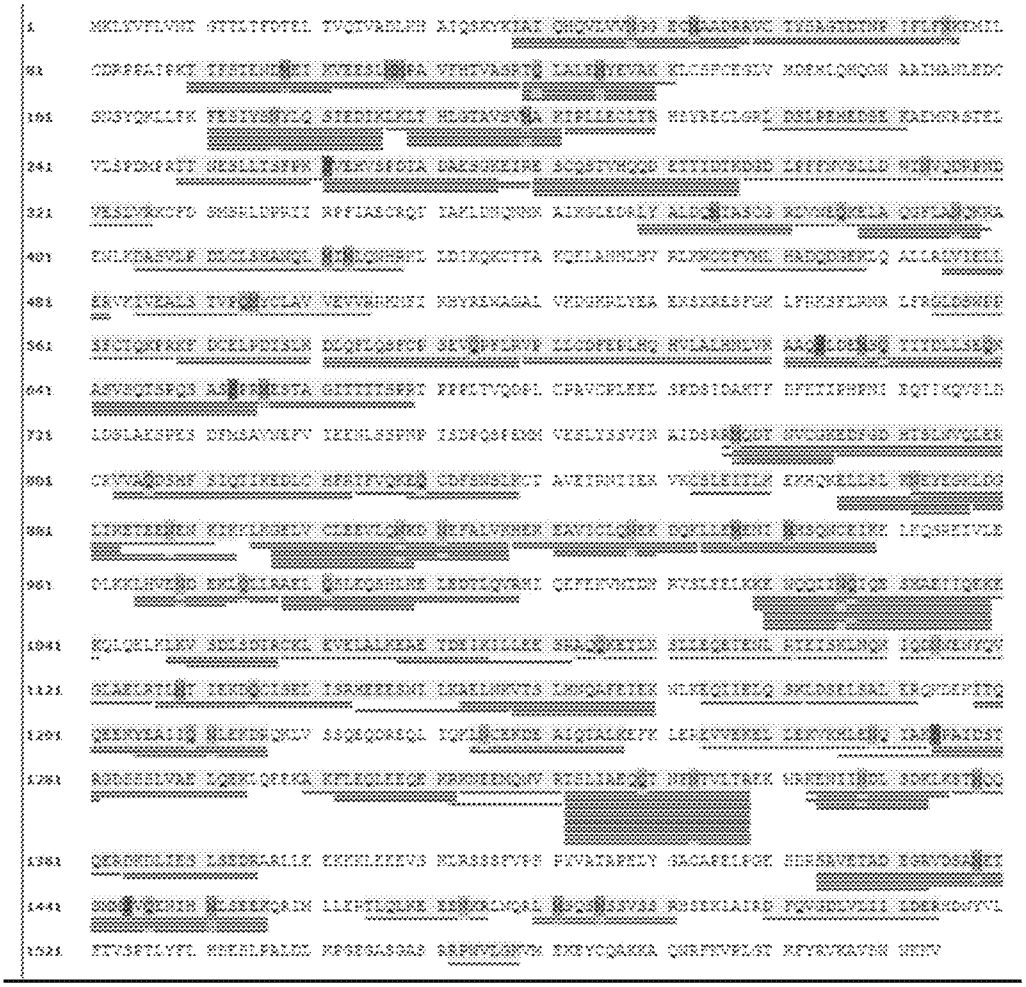
Figure 10B:
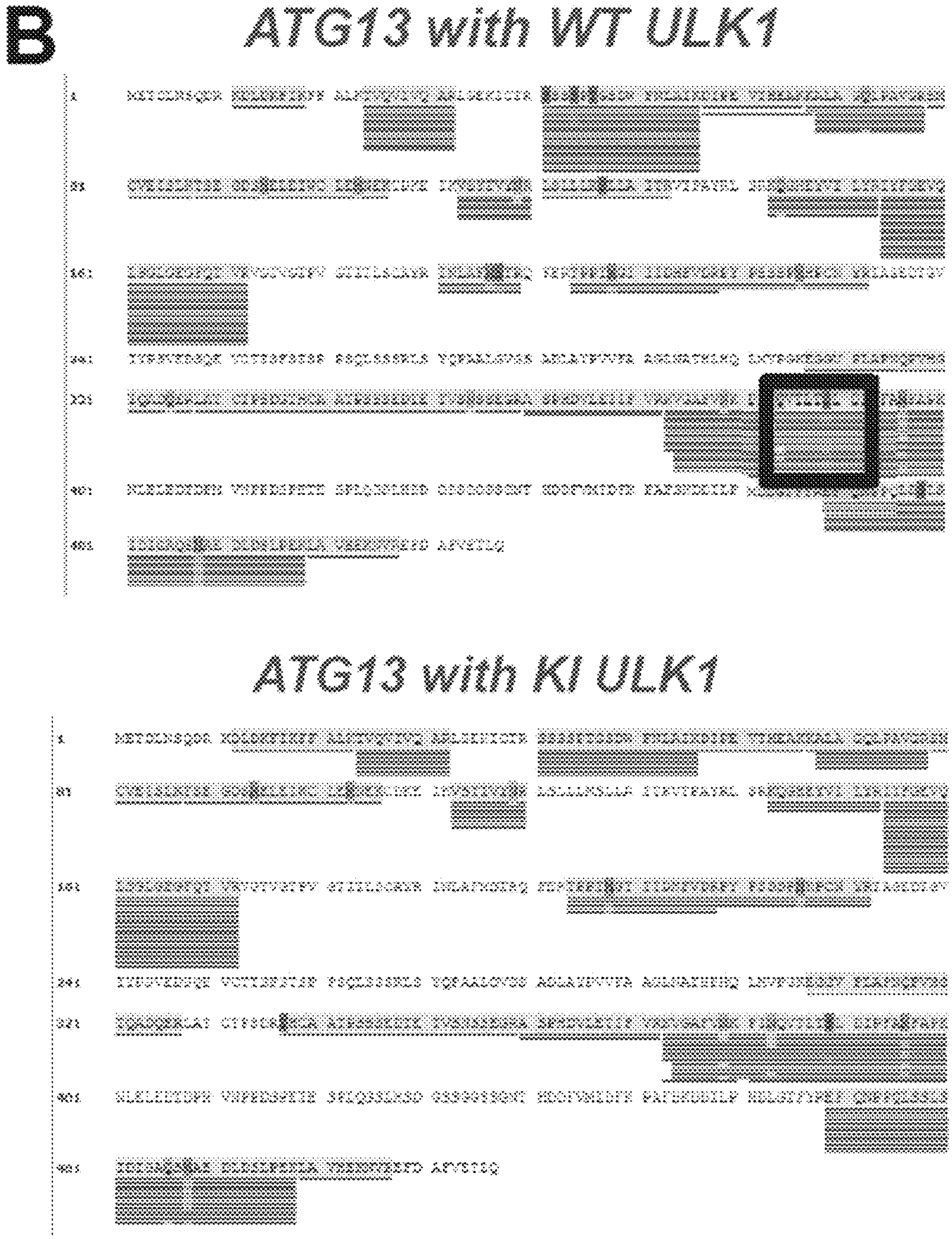
Figure 10C:
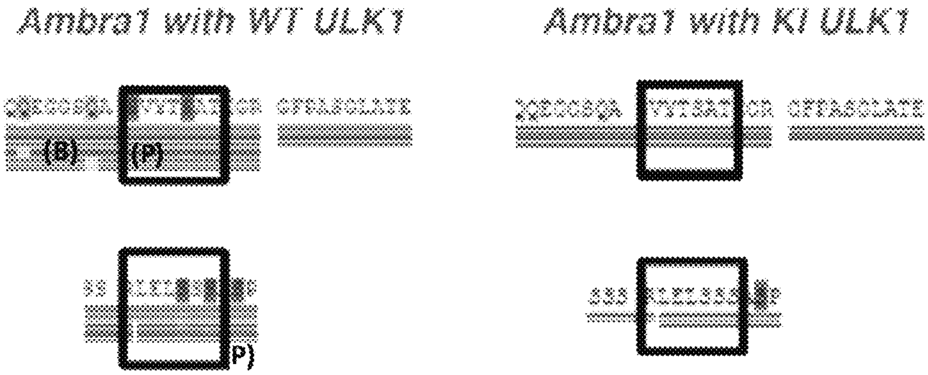

Atg101 was first identified by mass spectrometry on ULK1 and found to encode a highly conserved integral component of the ULK1-AT13-FIP200 complex in mammalian cells immunoprecipitations. ATG101 was found to bind directly to Atg13, and is critical for Atg13 stabilization and its resultant stimulation of ULK1 kinase activity. To map potential ULK1-dependent phosphorylation events in Atg101, we co-expressed FLAG-tagged ATG101 with wild-type or kinase-dead ULK1 and performed MS/MS analysis of total peptide in the FLAG-Atg101 immunoprecipitates to map total phosphorylation sites in Atg101 under the two conditions. We observed that two specific serine sites (Ser11, Ser203) within human Atg101 were stoichiometrically phosphorylated in cells bearing a wild-type ULK1 but not in cells co-expressing kinase-dead ULK1 (FIG. 5A). Notably these two ULK1-dependent phosphorylation sites conform well to the optimal ULK1 substrate motif, suggesting they may be direct ULK1 substrates in vivo. To further explore ULK1 phosphorylation in vivo, we examined its migration on a Phos-tag SDS-PAGE gel, which uses a phosphate binding dinuclear metal complex to accentuate mobility shifts on proteins containing phosphorylation events. Comparing the pattern of ATG101 on a Phostag containing gel when overexpressed in HEK293 cells with wild-type or kinase-dead ULK1 or vector controls, revealed a robust mobility change indicative of phosphorylation (FIG. 5A, bottom panel). Mutation of ATG101 Ser11 abolished a large extent of the mobility change, which was further enhanced in a Ser11/Ser203 double mutant, thus corroborating their identification as potential ULK1-dependent sits by mass spectrometry. We next performed similar analysis of FIP200 and ATG13 phosphorylation events, discovering multiple serine sites in FIP200 and Atg13 bearing the ULK1 substrate consensus whose phosphorylation was induced by overexpressed ULK1 in vivo. (FIGS. 10A-10C)

Next we examined components of the Beclin/Vps34 complex which lies downstream of the ULK1 complex in autophagy initiation. Here we identified multiple serines in Beclin which conform to the optimal Ulk1 consensus and contribute to Beclin mobility change on Phostag gels (FIG. 5C). One of these sites, Ser15, was recently discovered and reported to play a conserved role in autophagy induction. Our data examining Beclin mobility on Phostag gels suggests that when co-expressed with active ULK1, only when three serines are abolished (Ser15, Ser30, Ser337), does one reduce the mobility back to control levels. Examination of another component of the Beclin complex, Ambra1 revealed multiple ULK1-dependent phosphorylation events in vivo, suggesting many components of the Beclin-Vps34 complex may be targeted by ULK1. (FIG. 10C) Finally, we examined a known ULK1 interactor, Syntenin-1, which was also recently reported as a ULK1 substrate. Here we find the previously reported in vitro phosphorylation site, Ser6, along with a second site Ser61, are responsible for altered mobility of Syntenin-1 in the presence of ULK1 in vivo (FIG. 5E). Notably, both of these sites match the ULK1 consensus we defined using peptide libraries.

In contrast to all of these substrates which contain between 2 and 4 ULK1-dependent phosphorylation sites, we only found a single protein with an apparent single site regulated: Vps34. The highly conserved Ser249 of Vps34 was stoichiometrically phosphorylated in HEK293 cells when co-expressed with wild-type but not kinase dead ULK1 (FIG. 6A-6B). In vitro kinase assays using kinase-dead Vps34 as a substrate revealed that a single serine-to-alanine substitution at Ser249 abolished in vitro phosphorylation of Vps34 by ULK1 (FIG. 6C), which was paralleled by abolition of a significant mobility shift of Vps34 protein with the Ser249Ala mutant even on a regular SDS-PAGE gel when co-expressed with ULK1 (FIG. 6D).

We explored the potential function for Vps34 phosphorylation by ULK1 by introducing non-phosphorylatable (Ser249Ala) or phospho-mimetic (Ser49Asp) mutants into conditional Vps34 foxed murine embryonic fibroblasts. After first corroborating the requirement of Vps34 for proper autophagy and ultimate cell viability, we tested the effects of the mutants in four assays of Vps34 function in autophagy: LC3 and p62 turnover in MEF following starvation, PI3P production in vivo as detected by p40FX-GFP immunolocalization, autophagosome formation as detected by GFP-DFCP1 immunolocalization in vivo, cell viability following starvation, and EGFR turnover as a measure of general Vps34 function independent of autophagy. Vps34 Ser249 did not appear to control any of these activities under the conditions we examined. Given that ULK1 is also regulating multiple phosphorylation events in Beclin and Ambra1 at the same time it is inducing Ser249, this suggests that the sum effects of Ulk1 on the different Beclin-Vps34 subcomplexes will be a highly regulated series of events requiring further study.

Figure 6F:
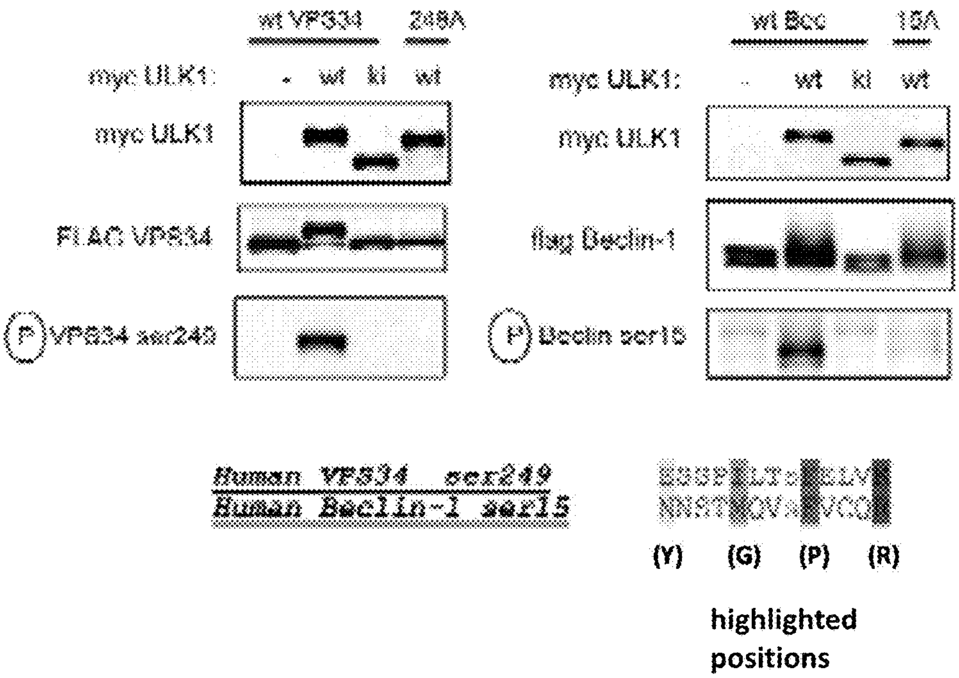

We next developed a phospho-specific antibody to Vps34 Ser249, whose signal was increased when ULK1 or ULK2, but not ULK3, was co-expressed with a wild-type but not Ser-249Ala mutant in HEK293T cells (FIG. 6E). Using this phosphor-Ser249 Vps34 antibody, we next directly compared its sensitivity to a commercial available phospho-Ser15 Beclin antibody, demonstrating parallel induction of each site when wild-type but not kinase ULK1 was co-expressed in HEK293T cells (FIG. 6F). Notably, the residues flanking Ser15 of Beclin and Ser249 of Vps34 share extensive sequence homology, beyond the ULK1 selective sites at −3 and +1 (FIG. 6F).

Development of Novel ATP-competitive Inhibitors of ULK1

Figure 7A:
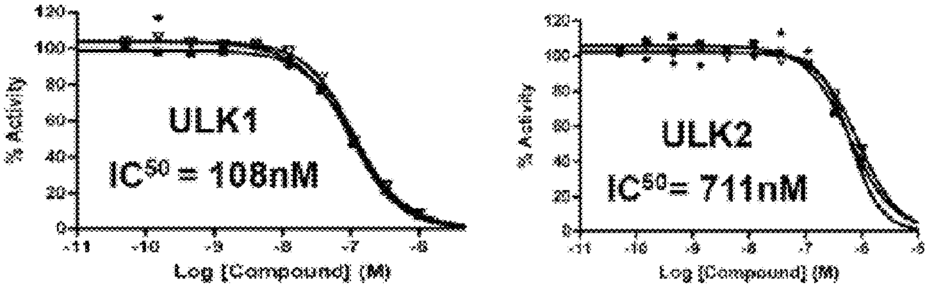
FIGS. 7A-7F illustrate in cellulo screen identification of compound 14 as a potent ULK1 kinase inhibitor against its downstream substrate phosphorylation sites.
Figure 7A:
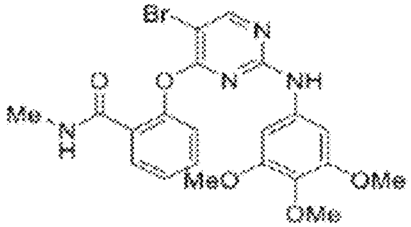
Figure 7B:
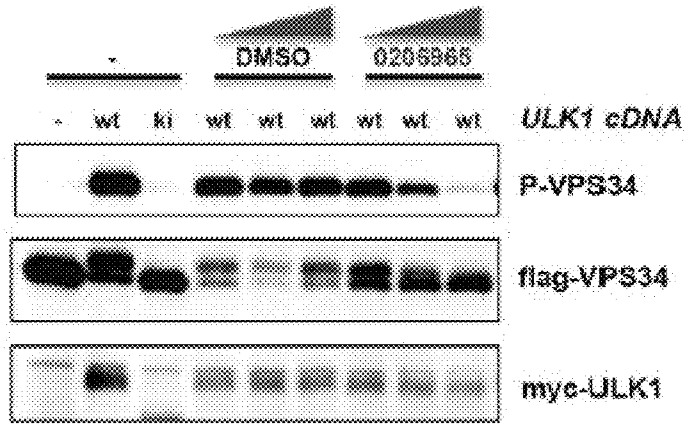
Figure 7C:
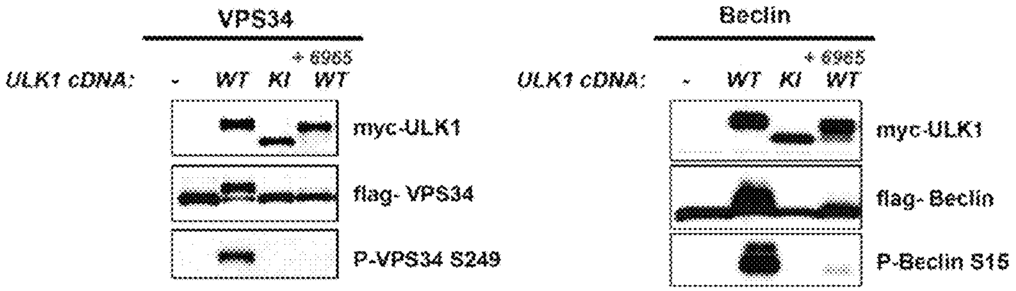
Figures 11A, 11B:
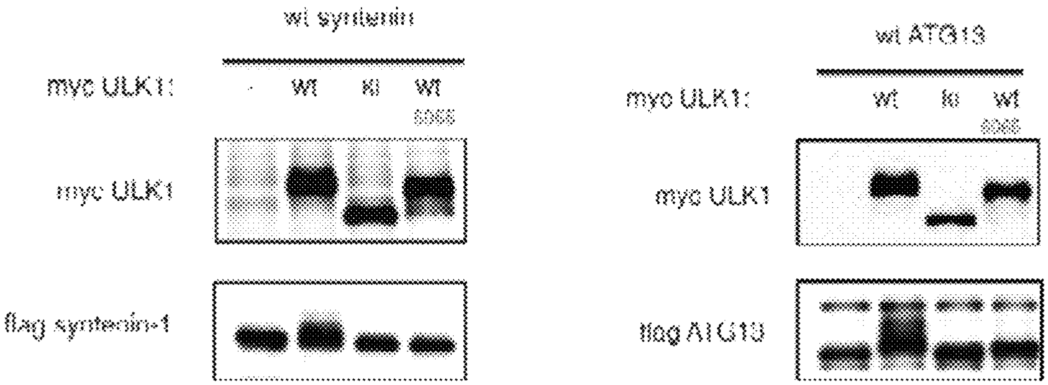
FIG. 11A shows that in HEK293 Ts, compound 14 collapsed the bandshift that overexpressed syntenin-1 and Atg13 undergo when co-expressed with wild-type ULK1.
FIG. 11B illustrates that the S(35) selectivity index of compound 14=0.123 where S(35) is (number of non-mutant kinases with % Ctrl <35)/(number of non-mutant kinases tested), as measured by the % of the kinome inhibited below 35% of control.

To further examine how ULK1 regulates autophagy, we sought to identify small molecule ATP competitive kinase inhibitors of ULK1. Screening a library of chemical compounds for inhibitors of ULK1 kinase activity in vitro, we identified a lead compound that was further elaborated through a medicinal chemistry effort to produce compound 14. Dose-response analysis of compound 14 revealed an in vitro $IC_{50}$ of 107 nM for ULK1 and 711 nM for ULK2 kinase activity (FIG. 7A). To further characterize the ability of compound 14 and related derivatives to inhibit ULK1 in cells, we tested the ability of these compounds to inhibit the phosphorylation of Vps34 Ser249 when epitope-tagged Vps34 was co-expressed in HEK293T cells with a wild-type ULK1 cDNA. Screening 40 compounds, we found compound 14 inhibited P-Vps34 on overexpressed Vps34 when used at ~5 μM (FIG. 7B). We next examined the sensitivity of phosphorylation of Vps34 Serine 249 versus Beclin Serine 15 to two structurally distinct ULK1 inhibitors, when cDNAs bearing each were introduced into HEK293T cells. We found that in HEK293 Ts, compound 14 inhibited Beclin Ser15 and Vps34 Ser249 to comparable extents (FIG. 7C), as well collapsing the bandshift that overexpressed syntenin-1 and Atg13 undergo when co-expressed with wild-type ULK1. (FIG. 11A).

Figure 7D:
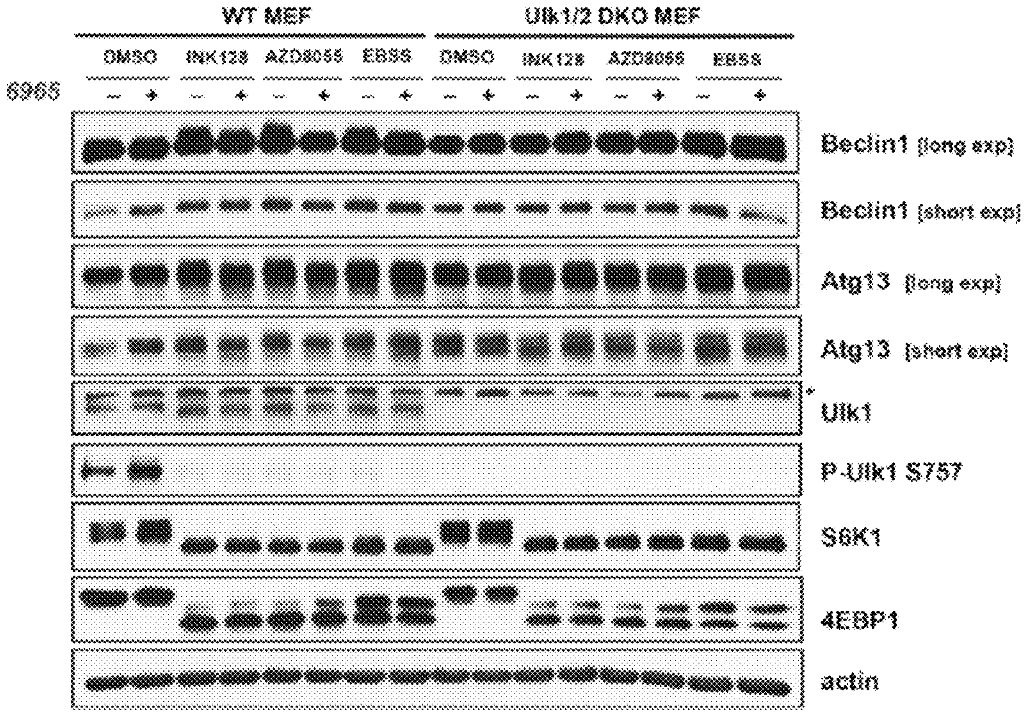
Figure 7E:
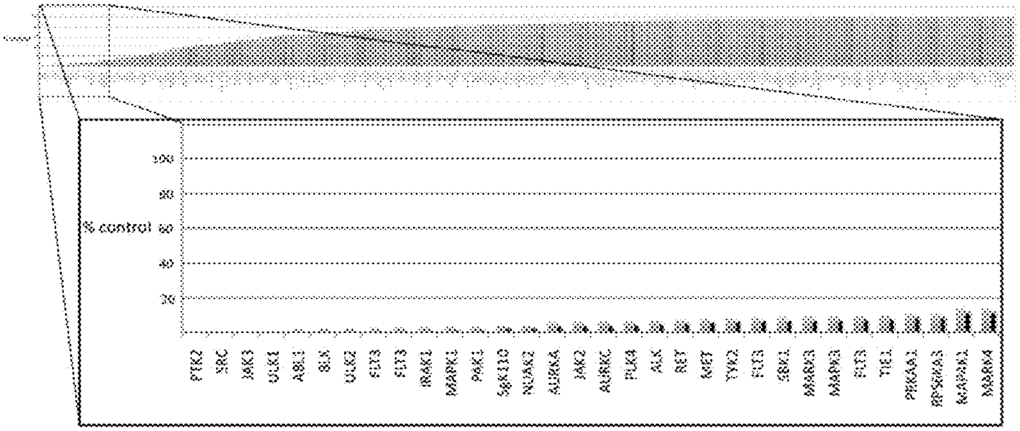
Figure 7F:
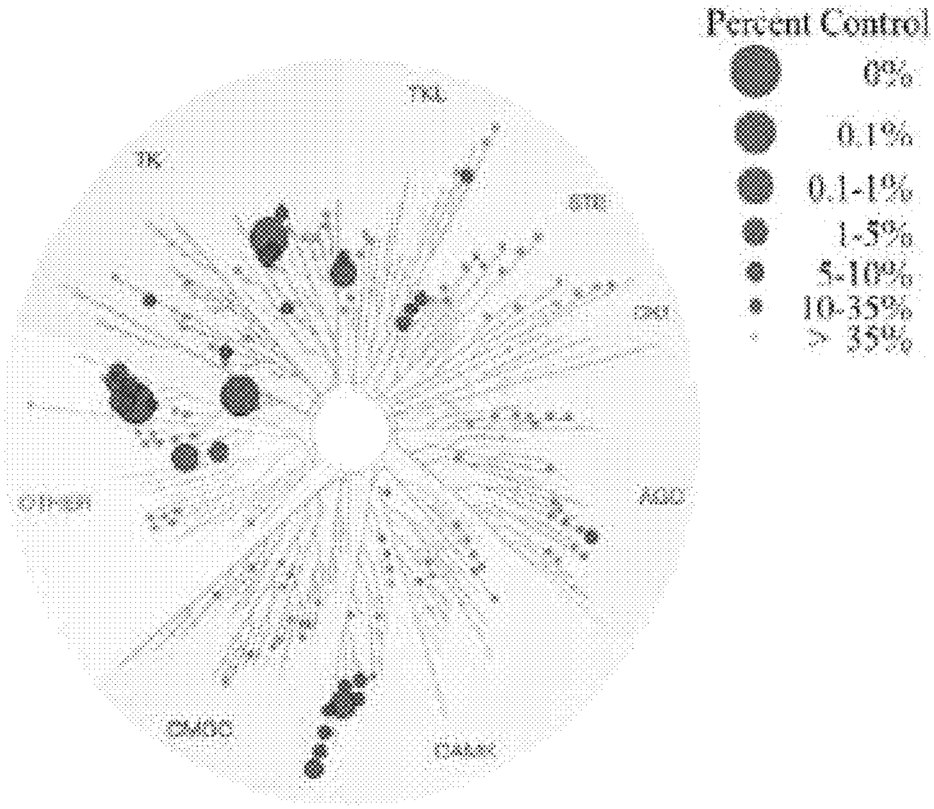

We next examined whether compound 14 inhibits endogenous ULK1 activity. To activate endogenous ULK1, we treated MEFs with either amino acid starvation media (Earle's balanced salt solution [EBSS]) or the mTOR ATP-competitive inhibitors INK128 or AZD8055. In WT MEFs, we observed a mobility shift in endogenous Beclin1 and Atg13 in response to EBSS starvation media or the mTOR catalytic inhibitors, which was abolished in Ulk1/2-deficient MEFs (FIG. 7D). The EBSS and mTOR-inhibitor induced mobility shift in Beclin1 and Atg13 was inhibited by 6965 co-treatment in WT MEFs (FIG. 7D). Neither Beclin1 nor Atg13 underwent a mobility shift upon treatment with either EBSS or the mTOR catalytic inhibitors in Ulk1/2-deficient MEFs, and no further decrease in their basal mobility was observed with 6965 co-treatment. In certain embodiments, the mobility shifts observed in endogenous Beclin1 and Atg13 induced by mTOR inhibitors and starvation media reflect phosphorylation of endogenous Beclin1/Atg13 by endogenous ULK1/2 as they only occur in WT but not Ulk1/2-deficient MEFs.

Compound 14 is a Highly Selective ULK1 Inhibitor

We next examined the specificity of compound 14 using the DiscoveRx KINOMEscan panel of 456 purified human kinases and subsequent competition binding assay. As seen in FIG. 7D, compound 14 was a very selective, only inhibiting 8 kinases >95% and 19 kinases >90% when tested at 10 μM. The S(35) selectivity index of compound 14=0.123 where S(35)=(number of non-mutant kinases with % Ctrl <35)/(number of non-mutant kinases tested), as measured by the % of the kinome inhibited below 35% of control (FIG. 11B), which is comparable to several kinase inhibitors in widespread use in clinical oncology, including Gleevac and Lapatinib and more selective than several other kinase inhibitors in clinical oncology use including Erlotinib, Sorafenib, and Dasatinib. Notably, by this ATP binding pocket competition assay, compound 14 inhibited FAK, Src, Abl, and Jak3 with similar IC50 to Ulk1 (FIG. 7D), which is notable as other than ULK1, all of the other kinases hit by the compound act on tyrosine residues.

To use a more well-established measure of the selectivity of compound 14 against its top binding kinases, we examined dose-response curves for its inhibition of these kinases in a classic in vitro kinase assays. Here we tested the ten kinases most suppressed by compound 14 by the ATP binding assay. From this analysis, ULK1, FAK, JAK2, and AuroraA kinase emerged as being equivalently inhibited by compound 14. It is important to note that even though compound 14 inhibits these 4 kinase quite equivalently across all of the different assays we have examined, this is still greater selectivity than all but a handful of widely used ATP-competitive kinases inhibitors widely used in clinical oncology today. We next examined the ability of compound 14 to suppress signaling downstream of various kinases in cells in culture. We found that at 1 μM, compound 14 reduced FAK and AuroraA kinase signaling to an extent comparable to inhibition of Ulk1 in HEK293 cells. Similarly, compound 14 inhibited FAK and AuroraA comparably to ULK1 in MEFs as well.

Figure 9E:
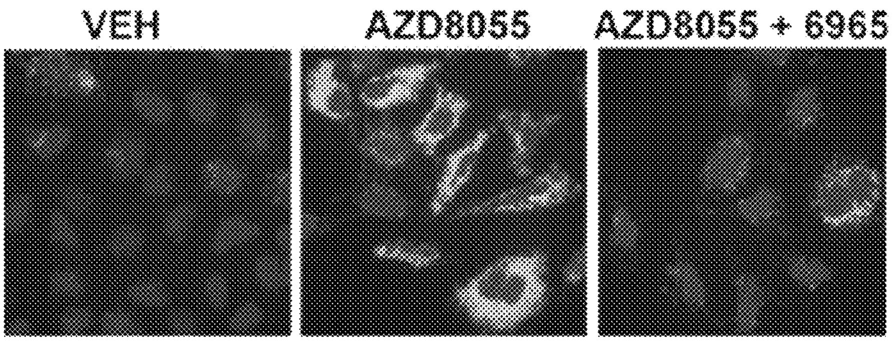
FIG. 9E is an immunoflourescence imaging of A549 cells treated in the presence or absence of 5 μM compound 14 for 2 hr followed by 4 μM of the mTOR catalytic inhibitor AZD8055 for 24 hr. Autophagic vacuoles were detected using the Cyto-ID autophagy detection kit and are visualized in green, while cell nuclei were counterstained by DAPI and are visualized in blue.
Figure 9F:
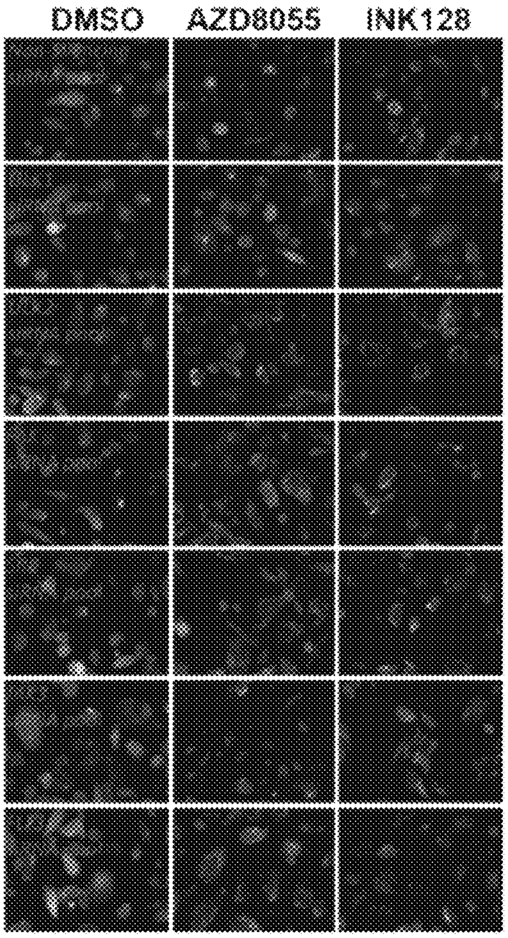
FIG. 9F are representative immunofluorescence images for the data shown in FIG. 9D. GFP-LC3 puncta are visualized in green and cell nuclei, which were counterstained with DAPI, are visualized in blue.

SBI-0206965 Suppresses Autophagy Induced by mTOR Inhibition, and this is Phenocopied by ULK1 siRNA To test the ability of compound 14 to block autophagy and cell survival, initial studies were performed in A549 lung cancer cells, which are highly sensitive to mTOR inhibition. We observed that the catalytic ATP-competitive mTOR kinase inhibitor AZD8055 induced robust autophagy as visualized by accumulation of the Cyto-ID autophagy dye, and this effect was strongly suppressed by treatment with 5-μM 6965 (FIG. 9E). Next, we genetically assessed the requirement for ULK1 versus other kinases inhibited by compound 14 to induce autophagy after pharmacological mTOR inhibition. A robust high-throughput microscopy method for quantifying GFP-LC3 puncta was established using a PC3 prostate-cancer cell line stably expressing a GFP-LC3 construct. Using this assay, we performed a focused RNAi analysis of the top 20 kinases identified in the DiscovRx screen as best binding to compound 14. Quantitative measurement on wells of cells transfected with control siRNAs revealed a consistent 2-fold induction in GFP-LC3 puncta formation after treatment with either of the mTOR catalytic inhibitors INK128 or AZD8055 (FIGS. 9D and 9F). Strikingly, of the 18 kinases tested, only one kinase siRNA, ULK1, nearly fully abolished the LC3 puncta induced by the mTOR inhibitors (FIG. 9D). The ability of ULK1 siRNA to nearly fully ablate the autophagic response induced by mTOR inhibition suggests that, in this cell line at least, ULK1 is essential for stimulating autophagy in response to mTOR suppression.

Figure 8A:
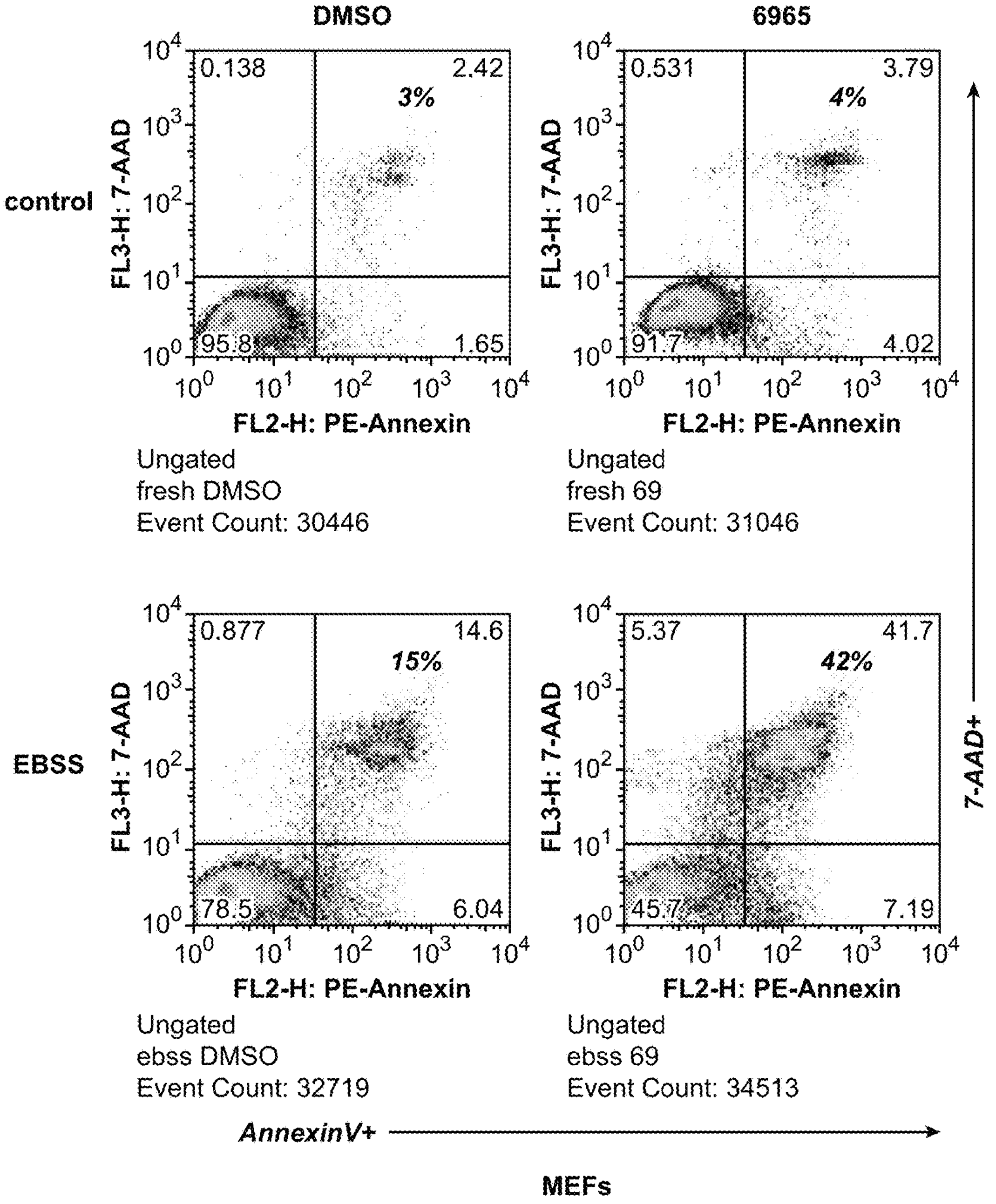
FIG. 8A is a set of images that show that at 24 h after amino-acid deprivation, 20% of the vehicle treated MEFs were positive for AnnexinV, a classic apoptotic marker, whereas 50% of the compound 14 treated cells were AnnexinV positive.
Figure 8C:
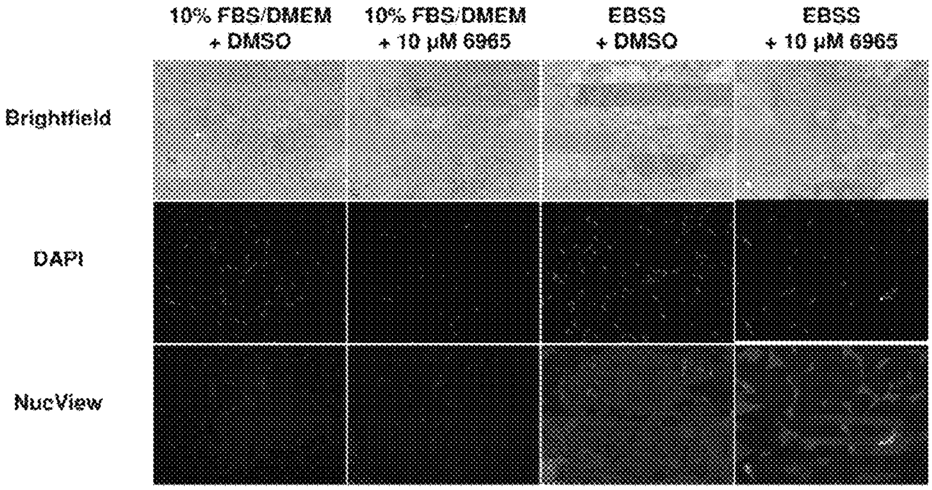
FIG. 8C is a set of images that show bright field, DAPI, and NucView staining by immunocytochemistry.

Compound 14 Following Nutrient Deprivation Prevents ULK1-Dependent Cell Survival One of the best-established functions of autophagy is to promote cell survival under conditions of nutrient deprivation. For example, genetic removal of ATG5 in MEFs has no effect on cell survival of cells in normal media conditions, but when such cells are placed into starvation media, they undergo apoptosis at a greatly accelerated rate compared to control cells. Similarly, we previously demonstrated that RNAi to ULK1 and ULK2 phenocopied RNAi to ATG5 in the loss of cell viability under nutrient deprived conditions. To examine whether our small molecule ULK1 inhibitor would similarly control cell survival under nutrient deprived conditions, we treated MEFs with compound 14 in the context of normal media, amino-acid deprived media, or glucose-deprived media. At 24 h after amino-acid deprivation, 20% of the vehicle treated MEFs were positive for AnnexinV, a classic apoptotic marker (FIG. 8A), whereas 50% of the compound 14 treated cells were AnnexinV positive. Similar effects were also seen in glucose-deprived MEFs, where compound 14 also promoted cell death. An immunoblot timecourse analysis of amino-acid starved cells revealed that active cleaved caspase-3 and the cleavage of its target PARP was observed only appreciably in starved, compound 14 co-treated cells (FIG. 8B), which was paralleled by apoptotic markers by immunocytochemistry (FIG. 8C). Interestingly, the immunoblot analysis revealed that compound 14 treatment induced loss of ULK1 and Atg13 protein levels, but only in nutrient-deprived, and not nutrient replete, conditions. Perhaps only in this context when ULK1 is activated, does the direct binding of compound 14 stimulate ULK1 turnover (FIG. 8B).

Small Molecule ULK1 Inhibitor Converts the Cytostatic Response to Catalytic mTOR Inhibitors into a Cytotoxic Response There has been great interest in the role of autophagy in the survival of tumor cells, particular tumor cells faced with metabolic stress from chemotherapies or targeted therapeutics. We next examined whether compound 14 would promote apoptosis in tumor cells similar to the MEFs, selectively under conditions in which autophagy is actively engaged. In U87MG glioblastoma cells and murine Kras p53 lung carcinoma cells, compound 14 promoted apoptosis (AnnexinV+ cells) selectively in the nutrient-starved state (FIG. 9A). Given that mTOR activity is a dominant regulator of ULK1 activity, and we previously noted that treatment of cells with mTOR catalytic inhibitors was sufficient to induce ULK1 activity, we examined the effect of adding in the ULK1 inhibitor in the context of treatment with mTOR catalytic inhibitors. Using a cell line well-established to be sensitive to mTORC1 inhibition, A549 lung cancer cells, we treated with escalating doses of ULK1 inhibitor while keeping a constant cytostatic growth arrest-inducing 1 micromolar dose of the mTOR catalytic inhibitor AZD8055. We observed that 5 μM compound 14 in combination with AZD8055 triggered apoptosis in 22% of A549 cells compared to 9% of the 5 μM compound 14 alone or 6% of those cells treated with AZD8055 alone. The induction of Annexin-V+ apoptotic A549 cells was even more dramatically heightened at 10 or 20 μM dosing of compound 14 (FIG. 9C). As observed in MEFs with nutrient deprivation combined with the ULK1 inhibitor, immunoblot analysis revealed that only the combination of ULK1 and mTOR inhibitors triggered caspase activation in A549 cells, paralleling the FACS analysis of cell death (FIG. 9B). Degradation of total ULK1 levels and Atg13 levels was observed as before, only in the presence of the autophagy activating stimulus (AZD8055) and the ULK1 inhibitor.

Figure 3A:
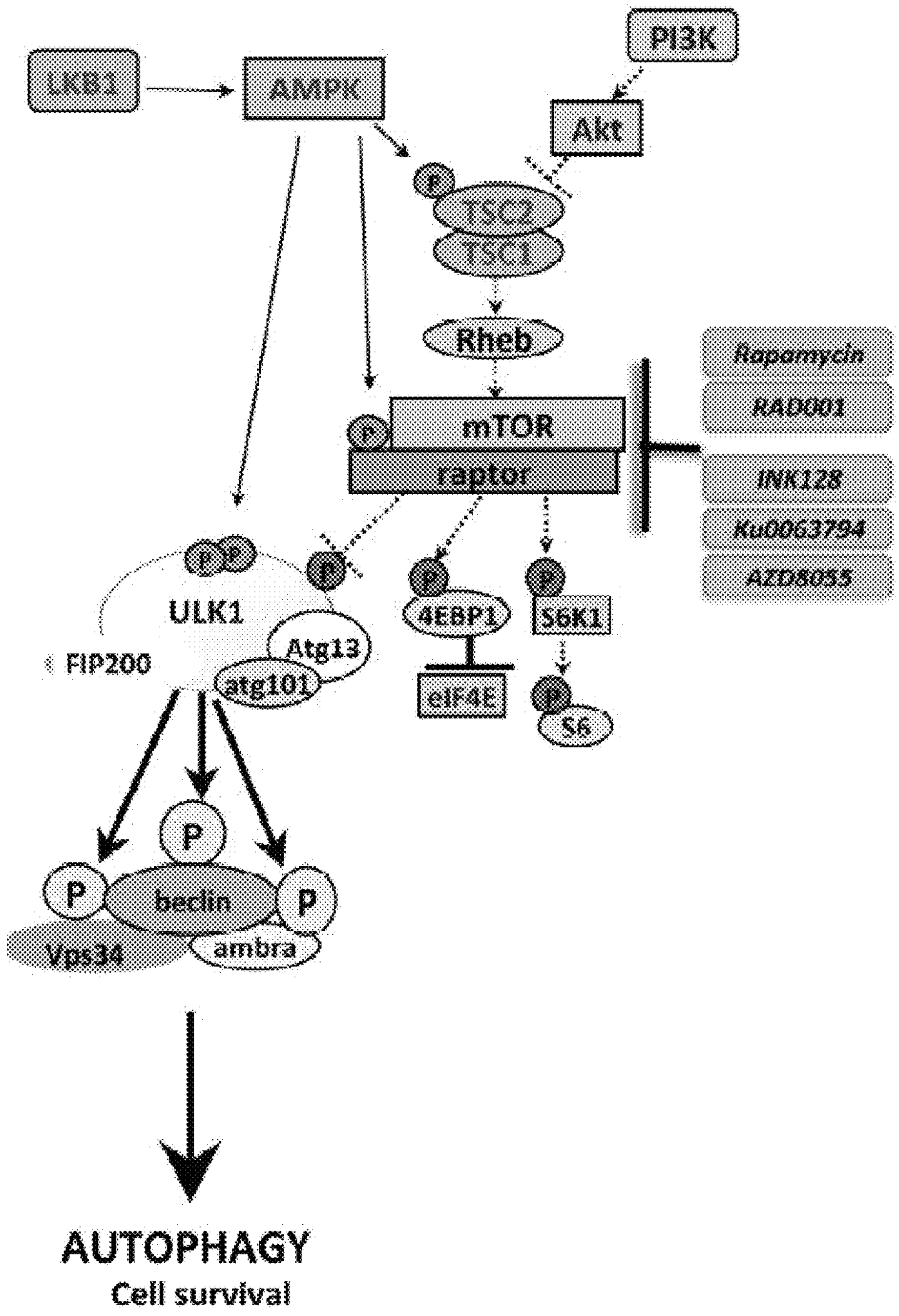
FIGS. 3A-3B illustrate cascades for exemplary use of ULK1 inhibitors.
Figure 3B:
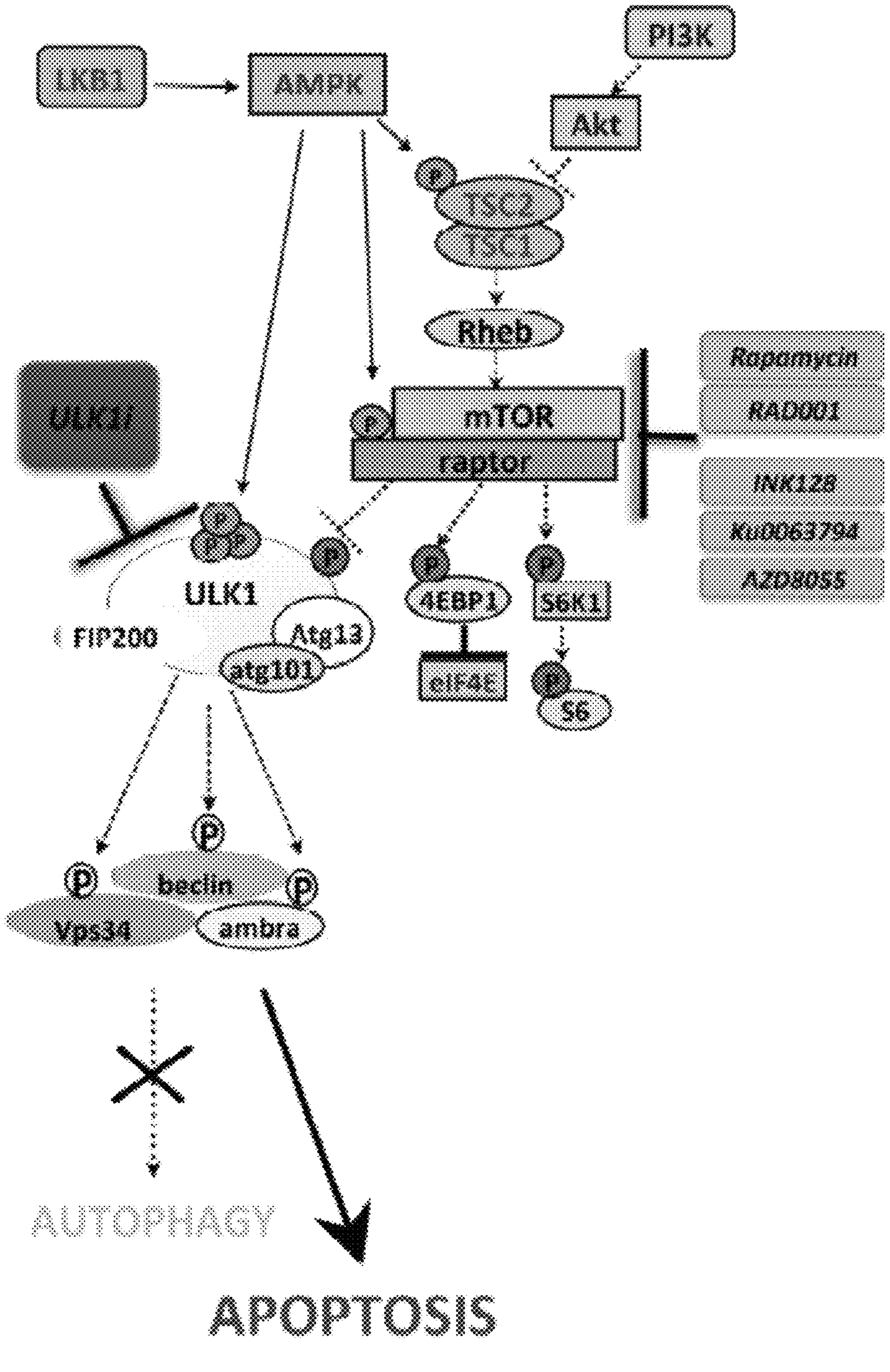

As another examination to demonstrate that ULK1 is the critical target of compound 14 mediating its effects following mTOR inhibition, we examined the ability of RNAi mediated suppression of each of the top 5 kinase targets of compound 14 to regulate LC3 puncta formation after treatment with the mTOR inhibitor AZD8055. As seen in FIG. 9D, RNAi to ULK1 completely ablated the ability of AZD8055 to induce LC3 puncta, whereas RNAi to FAK, Src, AuroraA or JAK3 had no effect. These findings support our hypothesis that tumor cells reliant on mTOR for cell growth will induce ULK1 upon mTOR inhibition, which acts a cell survival mechanism. If one pre-treats tumor cells with a ULK1 inhibitor, one prevents the mTOR-dependent activation of ULK1 and attendant survival benefit. We expect ULK1 small molecular inhibitors to be most effective in tumors addicted to high levels of mTOR activity (FIG. 3).

In view of the many possible embodiments to which the principles of the disclosed compounds, compositions and methods may be applied, it should be recognized that the illustrated embodiments are only preferred examples of the invention and should not be taken as limiting the scope of the invention.

What is claimed is:
1. A compound, or a pharmaceutically acceptable salt thereof, selected from the group consisting of:
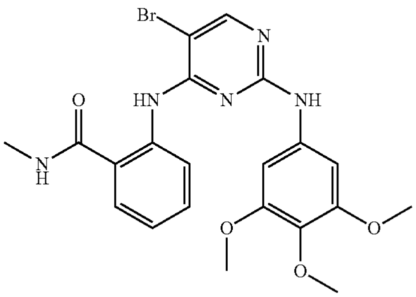,
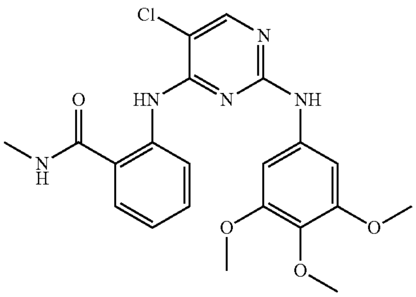,
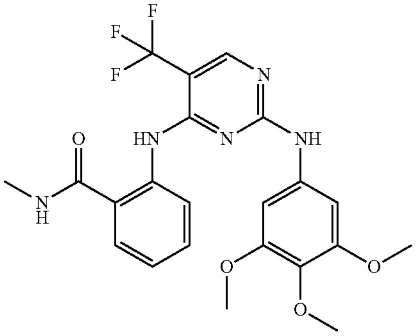,
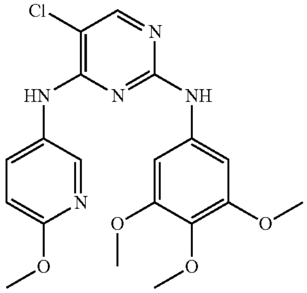,
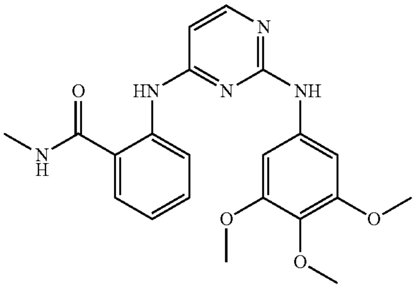,
-continued
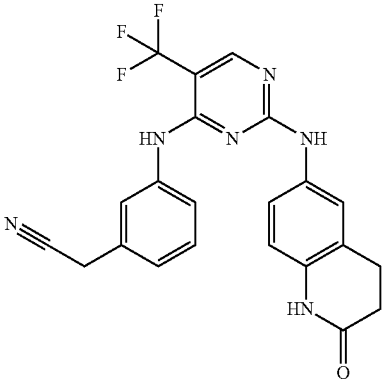,
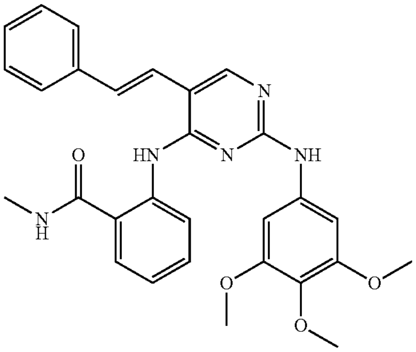,
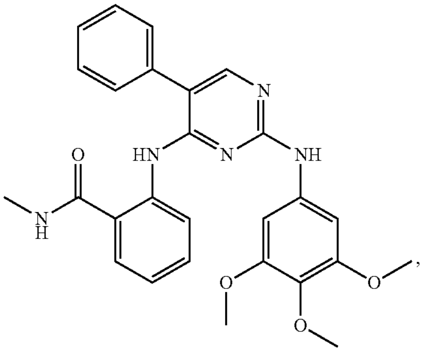,
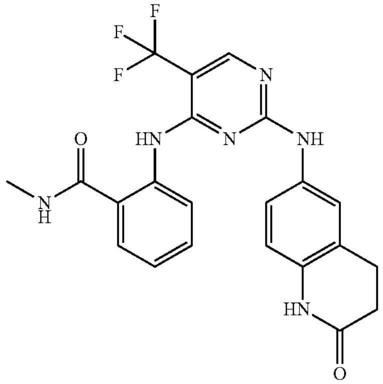,

-continued
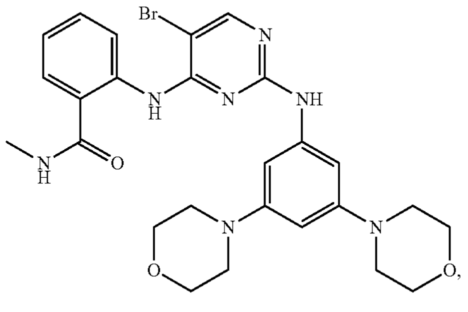
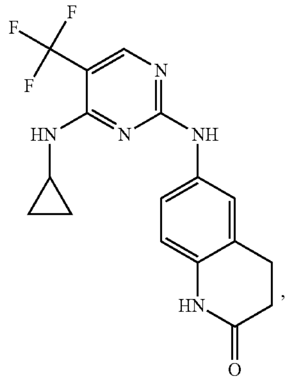
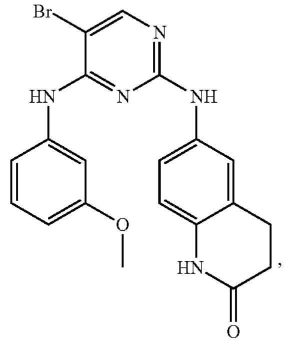
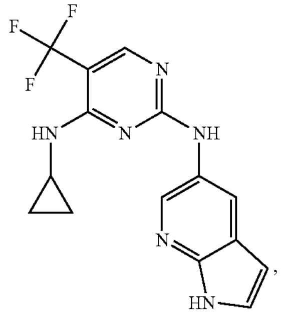
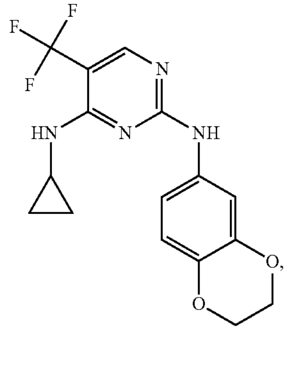
-continued
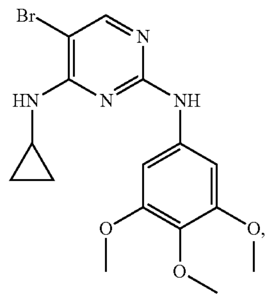
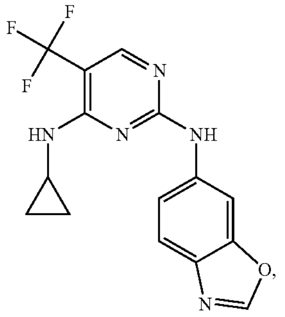
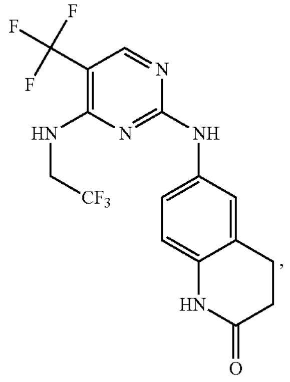
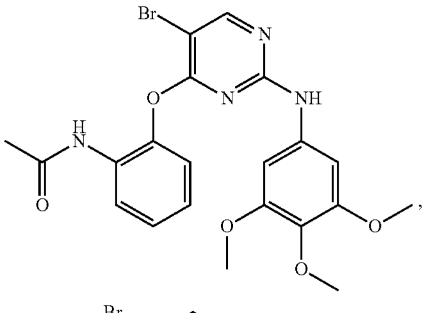
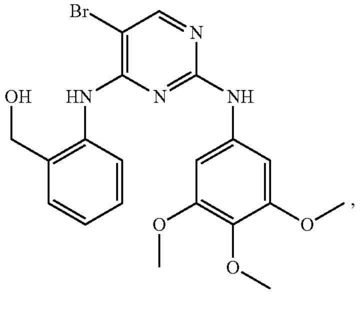

-continued
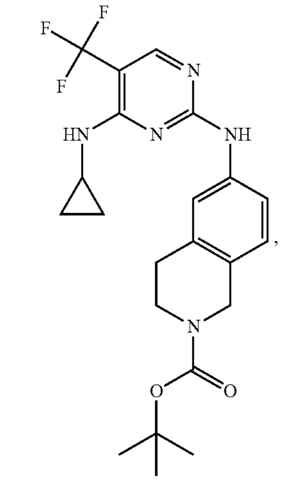
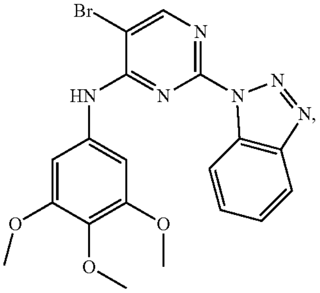
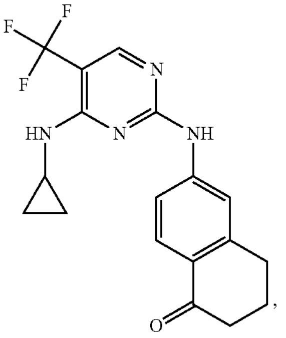
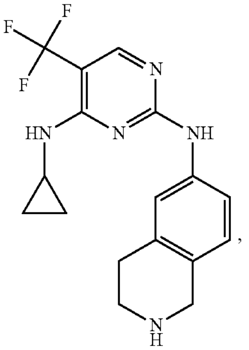
-continued
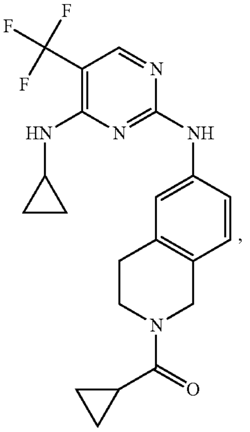
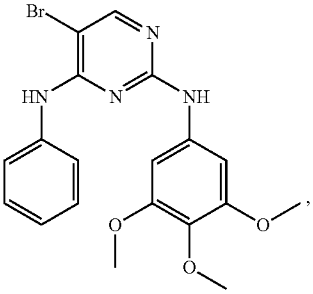
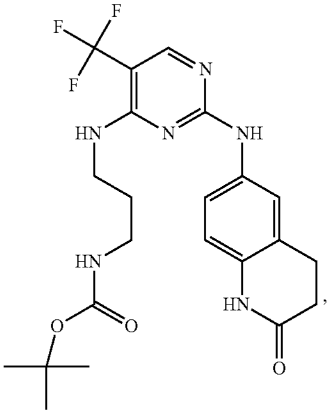
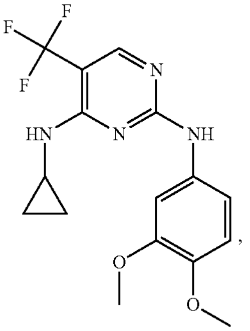

-continued

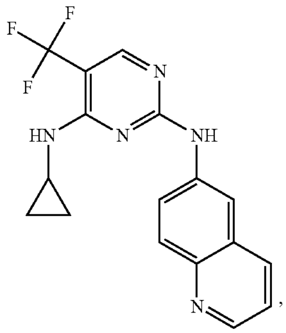

,

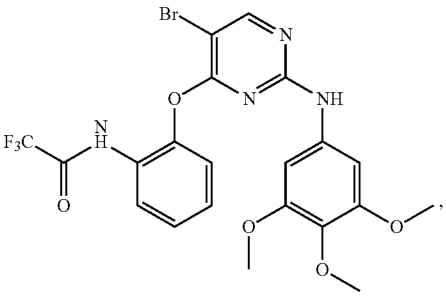

, and

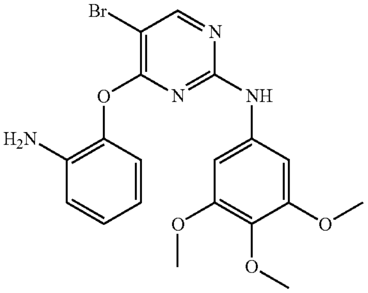

.

2. The compound or pharmaceutically acceptable salt thereof of claim 1, having the structure:

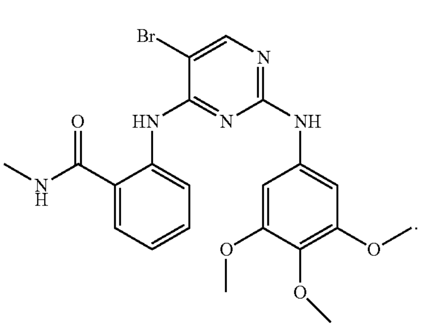

.

3. The compound or pharmaceutically acceptable salt thereof of claim 1, having the structure:

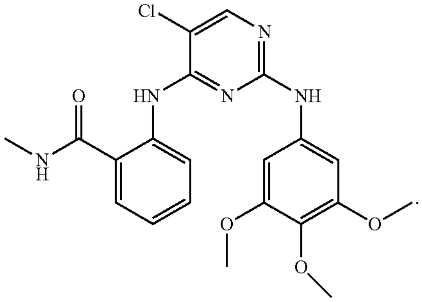

.

4. The compound or pharmaceutically acceptable salt thereof of claim 1, having the structure:

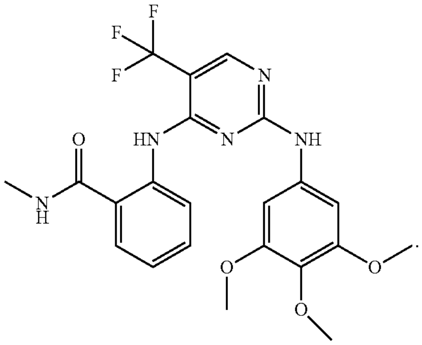

.

5. The compound or pharmaceutically acceptable salt thereof of claim 1, having the structure:

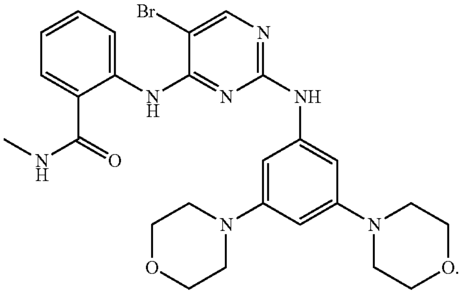 [SMILES: CNC(=O)c1ccccc1Nc1nc(Nc2cc(N3CCOCC3)cc(N3CCOCC3)c2)ncc1Br]

.

6. The compound or pharmaceutically acceptable salt thereof of claim 1, having the structure:

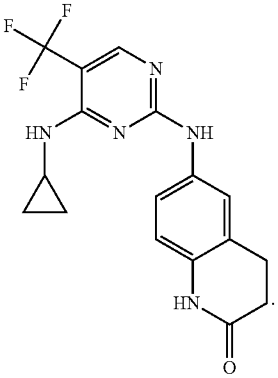 [SMILES: O=C1CCc2cc(Nc3ncc(C(F)(F)F)c(NC4CC4)n3)ccc2N1]

.

7. The compound or pharmaceutically acceptable salt thereof of claim 1, having the structure:

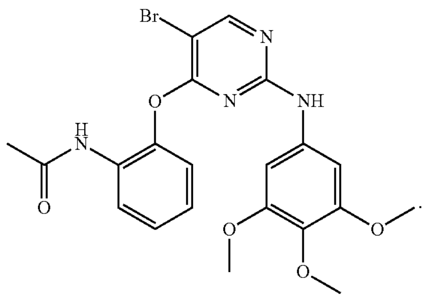 [SMILES: COc1cc(Nc2ncc(Br)c(Oc3ccccc3NC(C)=O)n2)cc(OC)c1OC]

8. The compound or pharmaceutically acceptable salt thereof of claim 1, having the structure:

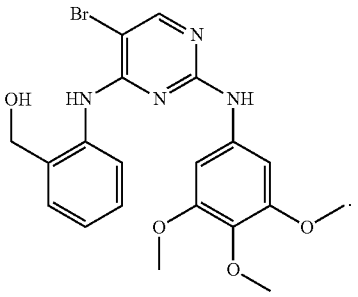 [SMILES: COc1cc(Nc2ncc(Br)c(Nc3ccccc3CO)n2)cc(OC)c1OC]

9. The compound or pharmaceutically acceptable salt thereof of claim 1, having the structure:

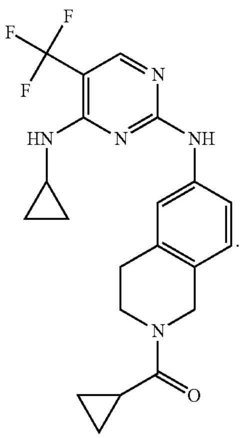 [SMILES: O=C(C1CC1)N1CCc2cc(Nc3ncc(C(F)(F)F)c(NC4CC4)n3)ccc2C1]

10. The compound or pharmaceutically acceptable salt thereof of claim 1, having the structure:

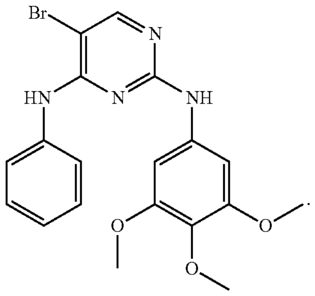 [SMILES: COc1cc(Nc2ncc(Br)c(Nc3ccccc3)n2)cc(OC)c1OC]

11. The compound or pharmaceutically acceptable salt thereof of claim 1, having the structure:

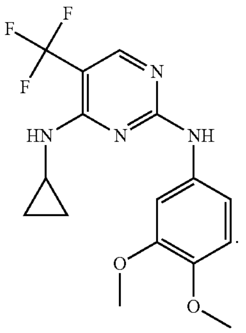 [SMILES: COc1ccc(Nc2ncc(C(F)(F)F)c(NC3CC3)n2)cc1OC]

12. The compound or pharmaceutically acceptable salt thereof of claim 1, having the structure:

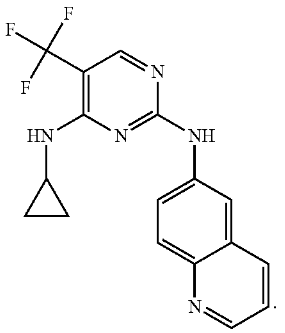 [SMILES: FC(F)(F)c1cnc(Nc2ccc3ncccc3c2)nc1NC1CC1]

13. A compound or a pharmaceutically acceptable salt thereof having the structure:

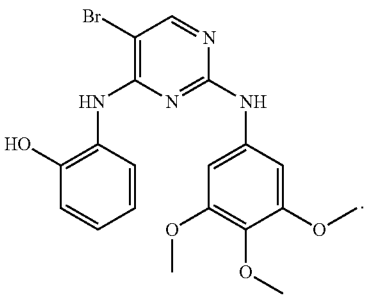 [SMILES: COc1cc(Nc2ncc(Br)c(Nc3ccccc3O)n2)cc(OC)c1OC]

14. A pharmaceutical composition comprising a compound or a pharmaceutically acceptable salt thereof selected from the group consisting of:
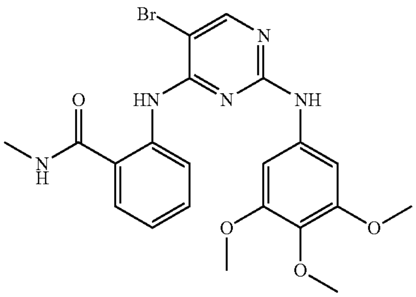
,
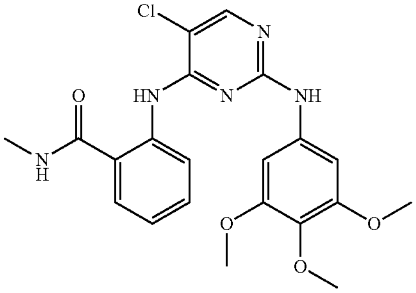
,
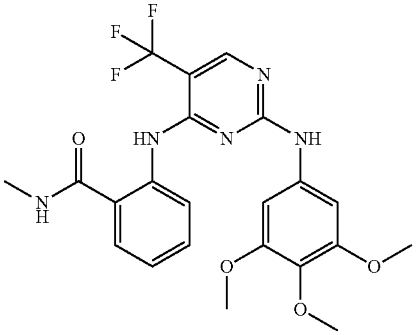
,
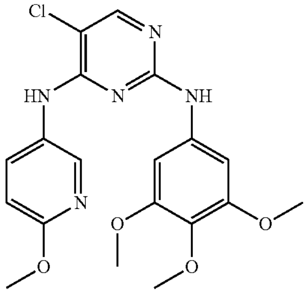
,
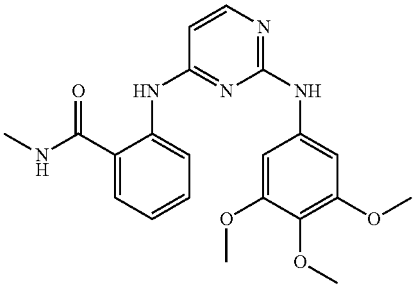
,
-continued
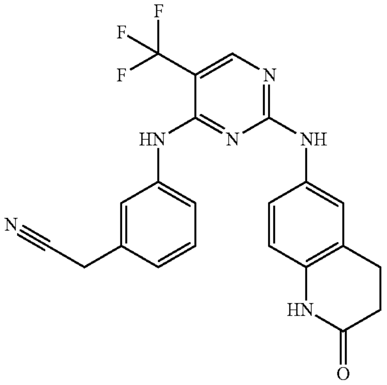
,
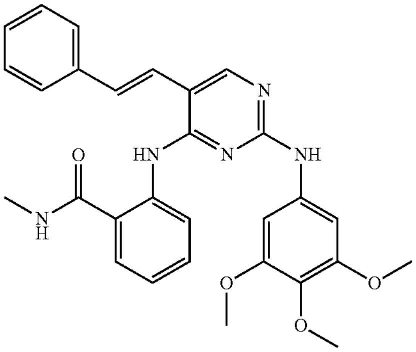
,
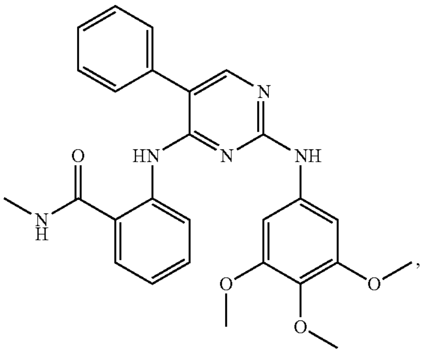
,
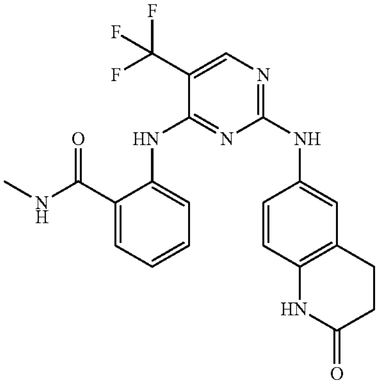
, -continued
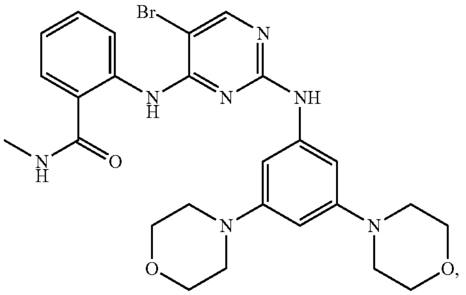
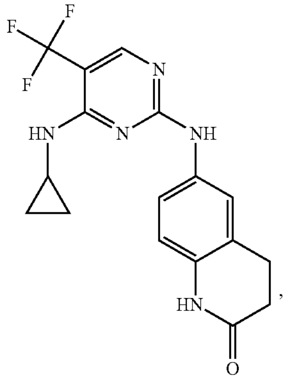
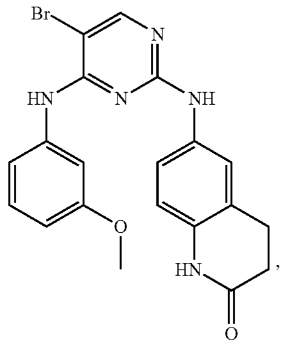
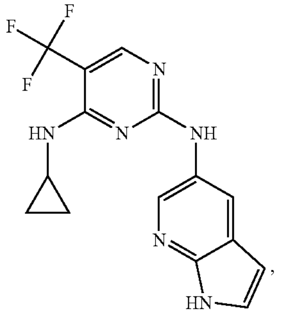
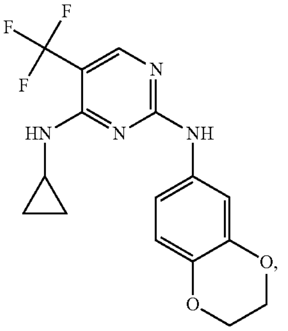
-continued
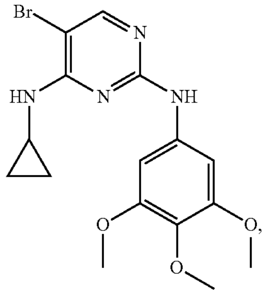
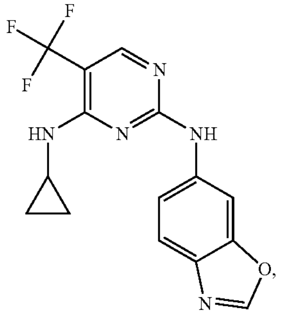
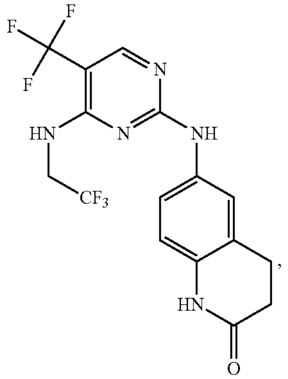
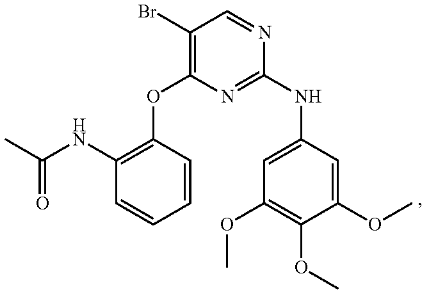
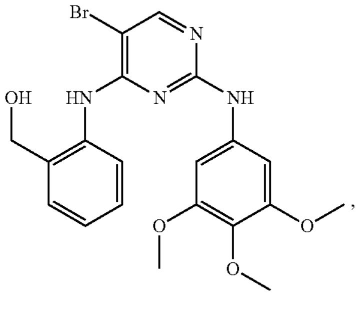

-continued
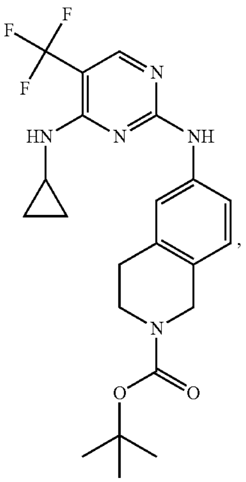
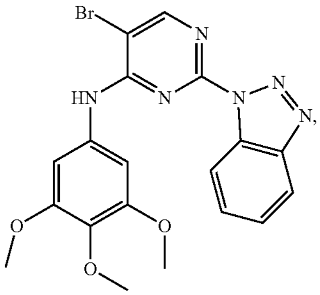
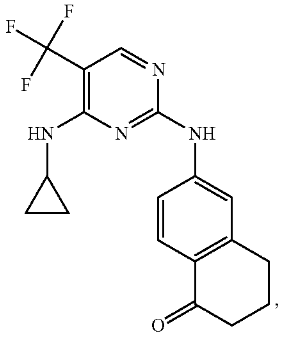
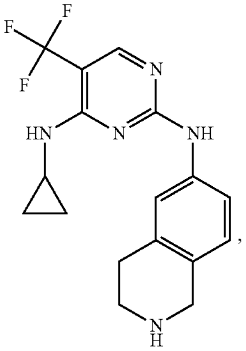
-continued
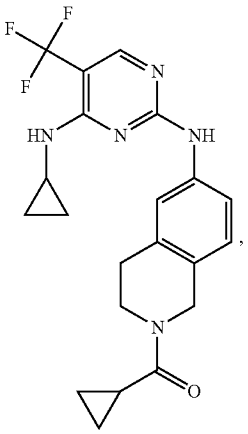
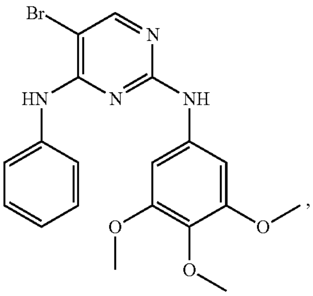
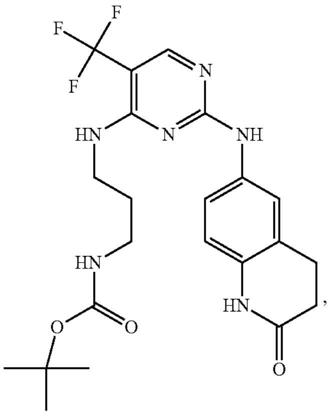
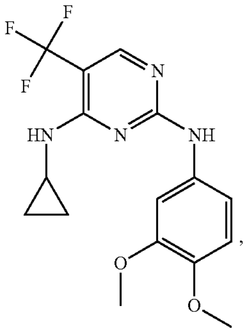

-continued

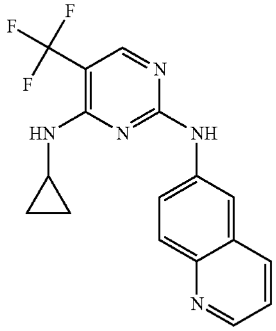

,

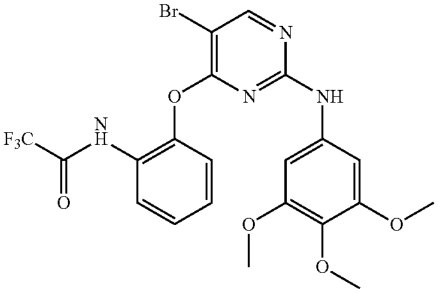

, and

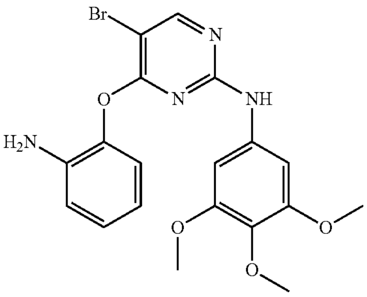

;

and at least one pharmaceutically acceptable additive.

15. The pharmaceutical composition of claim 14, wherein the compound or the pharmaceutically acceptable salt thereof is selected from the group consisting of:

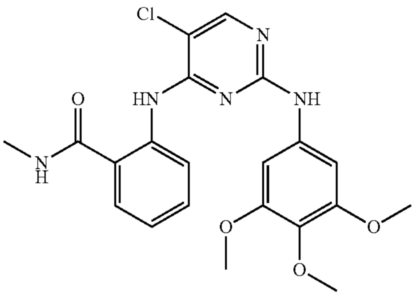

and

-continued

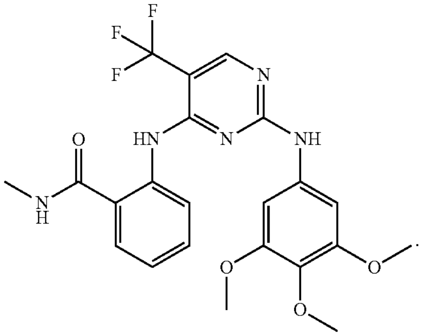

.

16. The pharmaceutical composition of claim 14, wherein the compound or the pharmaceutically acceptable salt thereof is selected from the group consisting of:

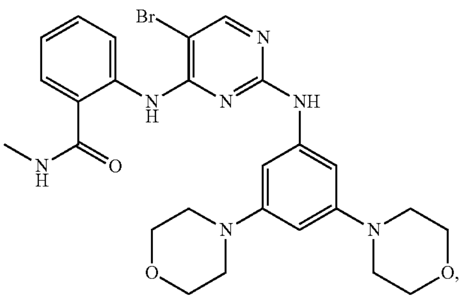

,

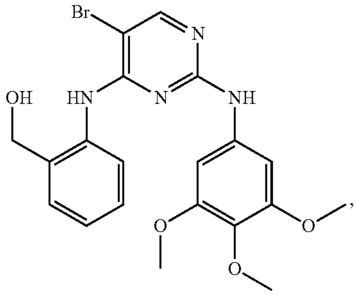

, and

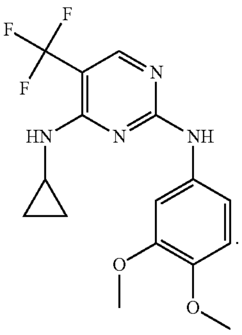

.

17. The pharmaceutical composition of claim 14, wherein the compound or the pharmaceutically acceptable salt thereof is selected from the group consisting of:

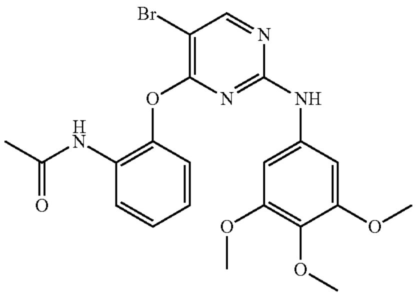

and

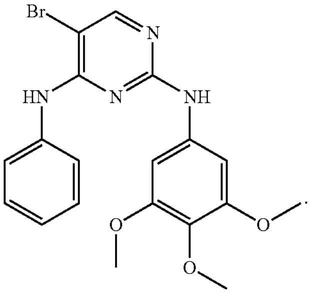

18. The pharmaceutical composition of claim 14, wherein the compound or the pharmaceutically acceptable salt thereof is selected from the group consisting of:

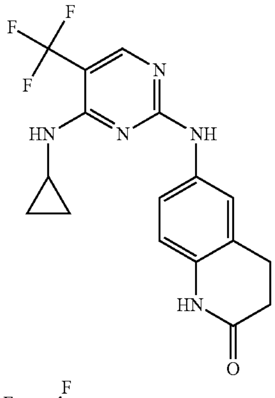

,

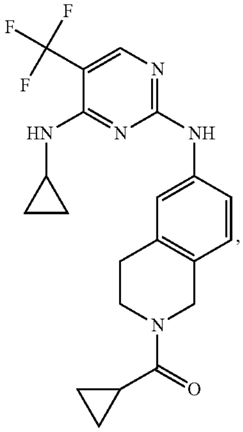

, and

-continued

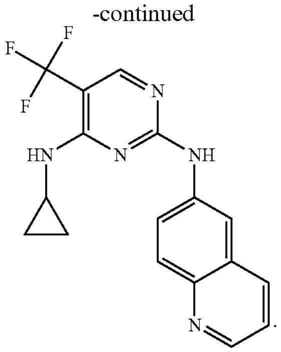

19. The pharmaceutical composition of claim 14, wherein the compound or the pharmaceutically acceptable salt thereof has the structure:

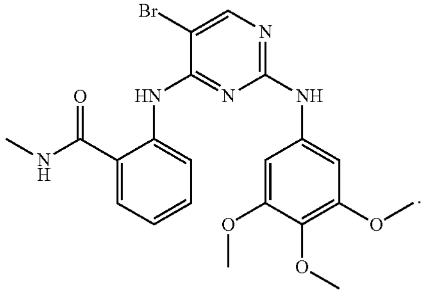

20. A pharmaceutical composition comprising:

a compound or a pharmaceutically acceptable salt thereof having the structure:

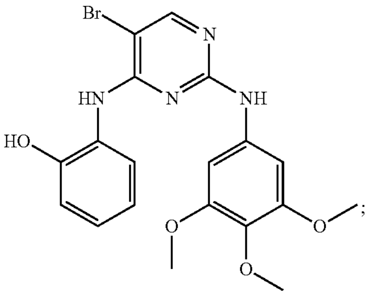 [SMILES: COc1cc(Nc2ncc(Br)c(Nc3ccccc3O)n2)cc(OC)c1OC]

and at least one pharmaceutically acceptable additive.

* * * * *

SEQUENCE LISTING

```
<160> NUMBER OF SEQ ID NOS: 7

<210> SEQ ID NO 1
<211> LENGTH: 16
<212> TYPE: PRT
<213> ORGANISM: Artificial Sequence
<220> FEATURE:
<223> OTHER INFORMATION: Synthetic peptide

<400> SEQUENCE: 1

Tyr Ala Asn Trp Leu Ala Ala Ser Ile Tyr Leu Asp Gly Lys Lys Lys
1               5                   10                  15


<210> SEQ ID NO 2
<211> LENGTH: 16
<212> TYPE: PRT
<213> ORGANISM: Artificial Sequence
<220> FEATURE:
<223> OTHER INFORMATION: Synthetic peptide

<400> SEQUENCE: 2
```

-continued

Glu Ala Asn Trp Leu Ala Ala Ser Ile Tyr Leu Asp Gly Lys Lys Lys
1 5 10 15

<210> SEQ ID NO 3
<211> LENGTH: 16
<212> TYPE: PRT
<213> ORGANISM: Artificial Sequence
<220> FEATURE:
<223> OTHER INFORMATION: Synthetic peptide

<400> SEQUENCE: 3

Tyr Ala Asn Trp Leu Ala Ala Ser Ile Tyr Leu Asp Lys Lys Lys Lys
1 5 10 15

<210> SEQ ID NO 4
<211> LENGTH: 16
<212> TYPE: PRT
<213> ORGANISM: Artificial Sequence
<220> FEATURE:
<223> OTHER INFORMATION: Synthetic peptide

<400> SEQUENCE: 4

Tyr Ala Asn Trp Met Ala Ala Ser Ile Tyr Leu Asp Gly Lys Lys Lys
1 5 10 15

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Tyr Ala Asn Trp Arg Ala Ala Ser Ile Tyr Leu Asp Gly Lys Lys Lys
1 5 10 15

<210> SEQ ID NO 6
<211> LENGTH: 16
<212> TYPE: PRT
<213> ORGANISM: Artificial Sequence
<220> FEATURE:
<223> OTHER INFORMATION: Synthetic peptide

<400> SEQUENCE: 6

Tyr Ala Asn Trp Leu Ala Ala Ser Asp Tyr Leu Asp Gly Lys Lys Lys
1 5 10 15

<210> SEQ ID NO 7
<211> LENGTH: 16
<212> TYPE: PRT
<213> ORGANISM: Artificial Sequence
<220> FEATURE:
<223> OTHER INFORMATION: Synthetic peptide

<400> SEQUENCE: 7

Tyr Ala Asn Trp Leu Ala Ala Ser Ile Asp Leu Asp Gly Lys Lys Lys
1 5 10 15